(12) United States Patent
Matsunaga et al.

(10) Patent No.: US 8,461,348 B2
(45) Date of Patent: Jun. 11, 2013

(54) HETEROCYCLIC DERIVATIVE AND USE THEREOF

(75) Inventors: Nobuyuki Matsunaga, Osaka (JP);
Yoshihisa Nakada, Osaka (JP); Yusuke Ohba, Osaka (JP); Hideyuki Nakagawa, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 71 days.

(21) Appl. No.: 12/936,291

(22) PCT Filed: Apr. 3, 2009

(86) PCT No.: PCT/JP2009/056994
§ 371 (c)(1),
(2), (4) Date: Oct. 4, 2010

(87) PCT Pub. No.: WO2009/123316
PCT Pub. Date: Oct. 8, 2009

(65) Prior Publication Data
US 2011/0028493 A1 Feb. 3, 2011

(30) Foreign Application Priority Data
Apr. 4, 2008 (JP) ................................ 2008-098622

(51) Int. Cl.
*C07D 277/20* (2006.01)
*C07D 277/62* (2006.01)
*A61K 31/425* (2006.01)

(52) U.S. Cl.
USPC ............ 548/202; 548/152; 514/365; 514/367

(58) Field of Classification Search
None
See application file for complete search history.

(56) References Cited

U.S. PATENT DOCUMENTS

| | | | |
|---|---|---|---|
| 5,342,851 A | 8/1994 | Sanfilippo et al. | |
| 6,335,334 B1 | 1/2002 | Schindler et al. | |
| 6,660,465 B2 | 12/2003 | Uehira et al. | |
| 7,087,644 B1 | 8/2006 | Alonso-Alija et al. | |
| 2003/0104324 A1 | 6/2003 | Uehira et al. | |
| 2005/0065196 A1 | 3/2005 | Inaba et al. | |
| 2006/0122181 A1 | 6/2006 | Ikemoto et al. | |
| 2007/0179139 A1 | 8/2007 | Alonso-Alija et al. | |
| 2008/0058314 A1 | 3/2008 | Alonso-Alija et al. | |
| 2008/0319012 A1 | 12/2008 | Kim et al. | |
| 2009/0209556 A1 | 8/2009 | Bittner et al. | |
| 2009/0270359 A1* | 10/2009 | Ito et al. ................... | 514/210.18 |

FOREIGN PATENT DOCUMENTS

| | | |
|---|---|---|
| DE | 198 34 110 | 2/2000 |
| EP | 1 854 793 | 11/2007 |
| JP | 4-154773 | 5/1992 |
| JP | 11-302277 | 11/1999 |
| JP | 2003-231679 | 8/2003 |
| WO | 92/16527 | 10/1992 |
| WO | 00/27394 | 5/2000 |
| WO | 03/002062 | 1/2003 |
| WO | 03/076408 | 9/2003 |
| WO | 2004/056815 | 7/2004 |
| WO | 2006/097625 | 9/2006 |
| WO | 2007/055941 | 5/2007 |
| WO | 2009/032249 | 3/2009 |
| WO | 2009/068652 | 6/2009 |
| WO | 2009/071504 | 6/2009 |
| WO | 2010/015652 | 2/2010 |
| WO | 2010/015653 | 2/2010 |

OTHER PUBLICATIONS

Harris et al. J. Med. Chem. (2008) 51, pp. 3788-3803.*
International Search Report issued Jun. 23, 2009 in International (PCT) Application No. PCT/JP2009/056994.
P. J. Sanfilippo et al., "Novel Thiazole-Based Heterocycles as Selective Inhibitors of Fibrinogen-Mediated Platelet Aggregation", J. Med. Chem., vol. 38, pp. 34-41, 1995.

* cited by examiner

*Primary Examiner* — Joseph K. McKane
*Assistant Examiner* — Nyeemah A Grazier
(74) *Attorney, Agent, or Firm* — Wenderoth, Lind & Ponack, L.L.P.

(57) ABSTRACT

The present invention aims to provide a compound having superior pharmacological action, physicochemical properties and the like and useful as an sGC activation drug, or an agent for the prophylaxis and/or treatment of diseases such as hypertension, ischemic cardiac disease, cardiac failure, kidney disease, arteriosclerotic disease, atrial fibrillation, pulmonary hypertension, diabetes, diabetic complications, metabolic syndrome, peripheral arterial obstruction, erectile dysfunction and the like.
An sGC activation drug containing a compound represented by the formula (II):

$$D_2 - Y_2 - B_2 - X_2 - N\underset{R_2}{\overset{N}{\diagdown A_2}}\quad (II)$$

wherein each symbol is as defined in the specification, or a salt thereof, as an active ingredient.

22 Claims, No Drawings

HETEROCYCLIC DERIVATIVE AND USE THEREOF

This application is a U.S. national stage of International Application No. PCT/W2009/056994 filed Apr. 3, 2009.

TECHNICAL FIELD

The present invention relates to a compound having a particular structure, which exhibits a soluble guanylate cyclase (sometimes to be abbreviated as sGC in the present specification) activating action, and is useful for the prophylaxis or treatment of hypertension, ischemic cardiac disease, cardiac failure, kidney disease, arteriosclerotic disease (cerebral apoplexy and the like), atrial fibrillation, pulmonary hypertension, diabetes, diabetic complications, metabolic syndrome, peripheral arterial obstruction, erectile dysfunction and the like, or a salt thereof, or prodrugs thereof, as well as a production method and use thereof and the like.

BACKGROUND OF THE INVENTION sGC is a heterodimer heme protein present in the cytoplasm, which is an enzyme that catalyzes biosynthesis of cyclic guanosine monophosphate (cGMP) from guanosine triphosphate (GTP). sGC activating substances present in the body are nitric oxide (NO) and analogous molecular species thereof (carbon monoxide and the like). cGMP is an important cellular transmitter substance in mammalian cells, which shows various biological responses via regulation by cGMP-dependent protein kinase, cGMP-dependent ion channel and cGMP-dependent phosphodiesterase and the like. For example, smooth muscle relaxation, natriuresis, suppression of platelet activation, suppression of cell proliferation, suppression of leukocyte adhesion, promotion of sugar uptake by tissues, and the like can be mentioned. Under pathologic conditions, decrease of sGC or attenuation of sGC activating ability leads to, for example, elevation of blood pressure, platelet activation, increased cell proliferation and cell adhesion, elevation of blood glucose, and decline of kidney function. As a result, hypertension, endothelial dysfunction, atherosclerosis, stable or unstable angina pectoris, thrombosis, myocardial infarction, erectile dysfunction, nephropathy, nephritis, diabetes, metabolic syndrome and the like are developed. A compound having an sGC activating action normalizes them and provides a treatment or prophylactic effect.

In hypertension, diabetes and various diseases related thereto, attenuation of blood vessel endothelial functions (for example, endothelial-dependent vasorelaxation, suppression of platelet activation, suppression of cell proliferation, suppression of inflammatory cell infiltration, suppression of phlogogenic substance production and the like) plays an important role in causing such diseases. Attenuation of endothelial function occurs due to the decreased production of nitric oxide, which is an endogenous sGC activating substance, and attenuation of sGC activation ability. Therefore, sGC activation normalizes the functions of blood vessel endothelium and blood vessel smooth muscle, recovers circulation to the peripheral tissues and metabolic function, protects tissues from organ disorders, and achieves progression and prophylaxis of pathology.

By sGC activation, cGMP is produced, and blood vessel smooth muscle is relaxed via reduction of intracellular calcium, various protein phosphorylation and the like. Thus, a compound having an sGC activating action exhibits a hypotensive action in the hypertension pathology. In addition, in ischemic cardiac diseases, it increases coronary blood flow, and shows an anti-angina pectoris action, a myocardial infarction onset-preventive and myocardial infarction prognosis-improving effects.

In diseases such as hypertension, cardiac disease, kidney disease, diabetes, metabolic syndrome and the like, insulin resistance is deeply involved in the progression of pathology and tissue disorder. Insulin causes various biological responses via NO-cGMP signal, but the insulin signal is attenuated in the above pathology. sGC activation leads to normalization of insulin signal, promoted transfer of glucose transporter to cellular membrane and the like. A compound having an sGC activating action shows a prophylactic effect on the onset and progression of the above-mentioned diseases via improvement of insulin resistance, improvement of metabolic function by promotion of sugar uptake by peripheral tissues, correction of hyperglycemia, normalization of lipid abnormality, pancreas protective action, and the like.

In diseases such as hypertension, cardiac disease, kidney disease, obesity, diabetes and the like, decreased sGC function is involved in the attenuation of diuretic action in the kidney due to the elevation of blood pressure. As a reaction to the elevation of blood pressure, NO is produced in the body due to the shear stress caused by increased kidney perfusion pressure, cGMP is produced by activation of sGC, reabsorption of sodium in the renal tubule decreases, and natriuresis is induced to lower the blood pressure. In the pathology mentioned earlier, NO-cGMP signal is attenuated. Therefore, in these pathologies, natriuresis is promoted by sGC activation, and hypotension and decrease of intrarenal glomerular pressure occur, whereby a kidney protection action is expected.

Accordingly, a compound having an sGC activating action is extremely useful for the prophylaxis or treatment of hypertension, ischemic cardiac disease, cardiac failure, kidney disease, arteriosclerotic diseases (including atherosclerosis, cerebral apoplexy, peripheral arterial obstruction and the like), atrial fibrillation, diabetes, diabetic complications and cardiovascular or metabolic disease related to metabolic syndrome and the like.

U.S. Pat. No. 6,335,334 describes a compound represented by the formula

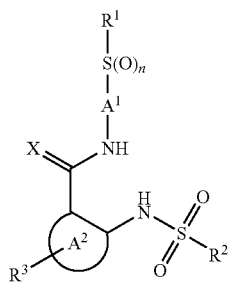

wherein $A^1$ is a divalent residue selected from the group consisting of phenylene, naphthylene and heteroarylene, each of which is optionally substituted;

ring $A^2$ is a benzene ring, a naphthalene ring, a saturated or partially unsaturated 3-membered to 7-membered carbon ring, a saturated or partially unsaturated or aromatic monocyclic 5-membered or 7-membered heterocycle, or a saturated or partially unsaturated or aromatic bicyclic 8-membered to 10-membered heterocycle;

$R^1$ is aryl, heterocyclyl or optionally substituted alkyl and the like;

$R^2$ is optionally substituted alkyl;

$R^3$ is hydrogen, halogen, $CF_3$, OH, —O-alkyl and the like;

N is 0, 1 or 2; and

X is O or NH and the like, and a physiologically acceptable salt thereof, and describes that the compound has a soluble guanylate cyclase activation action, and is useful as an agent for the prophylaxis or treatment of cardiovascular diseases, hypertension, myocardial infarction, cardiac failure and the like. Moreover, a compound represented by the following formula

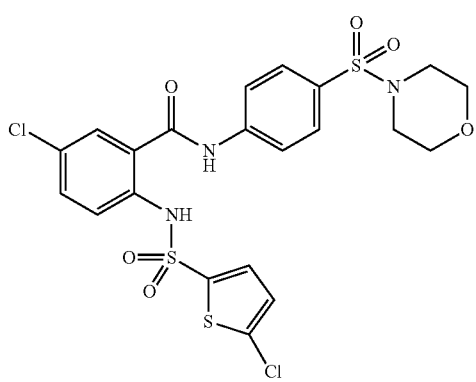 [SMILES: O=C(Nc1ccc(S(=O)(=O)N2CCOCC2)cc1)c1cc(Cl)ccc1NS(=O)(=O)c1ccc(Cl)s1]

(HMR-1766) is disclosed in Example 129 (see patent document 1).

U.S. Pat. No. 7,087,644 describes a compound represented by the formula

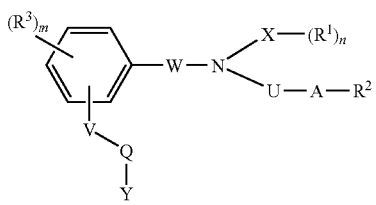

wherein V is void, O, $NR^4$, $NR^4CONR^4$ ($R^4$ is alkyl, cycloalkyl and the like) and the like; Q is void, alkylene, alkenediyl, alkynediyl and the like; Y is hydrogen, $NR^8R^9$ ($R^8$ and $R^9$ are each independently hydrogen, alkyl, alkenyl, aryl, aromatic heterocycle, cycloalkyl and the like), aryl, aromatic or saturated heterocycle, cycloalkyl and the like; $R^3$ is hydrogen, halogen, alkyl, halogenoalkyl and the like; m is an integer of 1-4; W is alkylene, alkenediyl and the like; U is alkyl; A is aryl, aromatic heterocycle and the like; $R^2$ is tetrazolyl, $COOR^{24}$, $CONR^{25}R^{26}$ ($R^{24}$ is hydrogen, alkyl or cycloalkyl, $R^{25}$ and $R^{26}$ are each independently hydrogen, alkyl, cycloalkyl and the like) and the like; X is alkylene, alkenediyl and the like; n is 1 or 2; $R^1$ is tetrazolyl, $COOR^{30}$ or $CONR^{31}R^{32}$ ($R^{30}$ is hydrogen, alkyl or cycloalkyl, $R^{31}$ and $R^{32}$ are each independently hydrogen, alkyl, cycloalkyl and the like) and the like, a stereoisomer thereof and a salt thereof, and describes that the compound has a soluble guanylate cyclase activating action and is useful as an agent for the prophylaxis or treatment of cardiovascular diseases, hypertension, thrombosis and the like. Moreover, a compound represented by the following formula

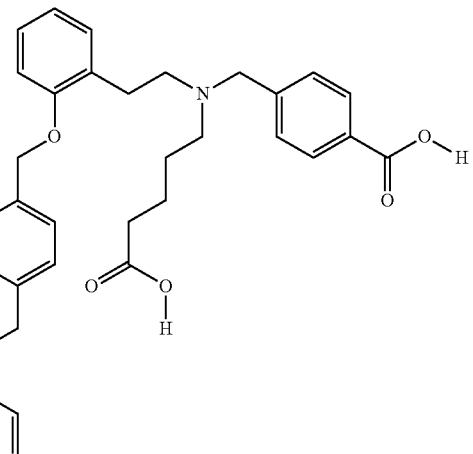

(BAY58-2667) is disclosed in Example 8 (see patent document 2).

US-A-2007/0179139 describes a compound represented by the formula

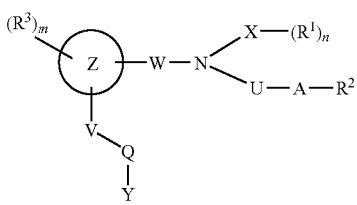

wherein Z is a phenyl ring condensed with a hetero ring, a carbon ring or heterocycle and the like; V is void, O, $NR^4$, $NR^4CONR^4$ ($R^4$ is alkyl, cycloalkyl and the like) and the like; Q is void, alkylene, alkenediyl, alkynediyl and the like; Y is hydrogen, $NR^8R^9$ ($R^8$ and $R^9$ are each independently hydrogen, alkyl, alkenyl, aryl, aromatic heterocycle, cycloalkyl and the like), aryl, aromatic or saturated heterocycle, cycloalkyl and the like; $R^3$ is hydrogen, halogen, alkyl, haloalkyl and the like; m is an integer of 1-4; W is alkylene, alkenediyl and the like; U is alkylene; A is aryl, aromatic heterocycle and the like; $R^2$ is tetrazolyl, $COOR^{24}$, $CONR^{25}R^{26}$ ($R^{24}$ is hydrogen, alkyl or cycloalkyl, $R^{25}$ and $R^{26}$ are each independently hydrogen, alkyl, cycloalkyl and the like) and the like; X is alkylene, alkenediyl and the like; n is 1 or 2; $R^1$ is tetrazolyl, $COOR^{30}$ or $CONR^{31}R^{32}$ ($R^{30}$ is hydrogen, alkyl or cycloalkyl, $R^{31}$ and $R^{32}$ are each independently hydrogen, alkyl, cycloalkyl and the like) and the like, a stereoisomer thereof and a salt thereof, and describes that the compound has a soluble guanylate cyclase activating action and is useful as an agent for the prophylaxis or treatment of cardiovascular diseases, hypertension, thrombosis and the like. Moreover, a compound represented by the following formula

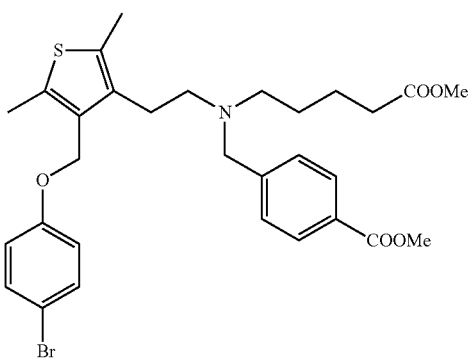 [SMILES: COC(=O)CCCCN(CCc1c(C)sc(C)c1COc1ccc(Br)cc1)Cc1ccc(C(=O)OC)cc1]

is disclosed in Example 1 (see patent document 3).

US-A-2008/0058314 describes a compound represented by the formula

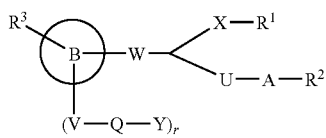

wherein B is aryl or aromatic heterocycle; r is 0 or 1; V is void, O, $NR^4$, $NR^4CONR^4$, $NR^4CO$ ($R^4$ is alkyl, cycloalkyl and the like) and the like; Q is void, alkylene, alkenediyl, alkynediyl and the like; Y is hydrogen, $NR^6R^7$ ($R^6$ and $R^7$ are each independently hydrogen, alkyl, alkoxy, alkyloxyalkyl, cycloalkyl, aryl and the like), aryl, aromatic or saturated heterocycle, cycloalkyl and the like; $R^3$ is hydrogen, halogen, alkyl, halogenoalkyl, alkoxy, halogenoalkoxy and the like; W is alkylene, alkenediyl and the like; U is alkylene, O, NH, S, SO or $SO_2$; A is void, aryl, aromatic heterocycle and the like; $R^2$ is CN, tetrazolyl, $COOR^{26}$ or $CONR^{27}R^{28}$ ($R^{26}$ is hydrogen, alkyl or cycloalkyl, $R^{27}$ and $R^{28}$ are each independently hydrogen, alkyl, cycloalkyl and the like) and the like; X is alkylene, alkenediyl and the like; $R^1$ is CN, tetrazolyl, $COOR^{35}$ or $CONR^{36}R^{37}$ ($R^{35}$ is hydrogen, alkyl, cycloalkyl and the like, $R^{36}$ and $R^{37}$ are each independently hydrogen, alkyl, cycloalkyl and the like) and the like, stereoisomers thereof and salts thereof, and describes that the compound has a soluble guanylate cyclase activating action and is useful as an agent for the prophylaxis or treatment of cardiovascular diseases, hypertension, cardiac failure, angina pectoris and the like. Moreover, a compound represented by the following formula

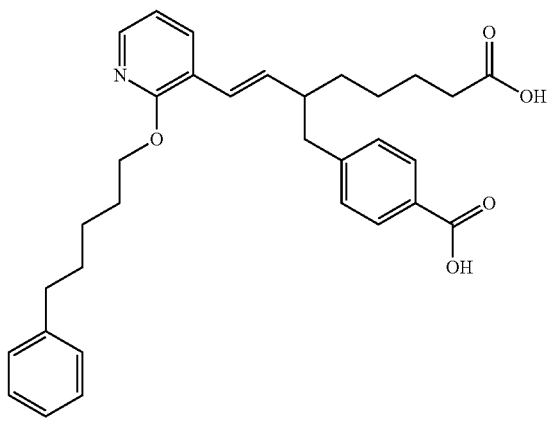 [SMILES: O=C(O)CCCCC(/C=C/c1cccnc1OCCCCCc1ccccc1)Cc1ccc(C(=O)O)cc1]

is disclosed in Example 34 (see patent document 4).

WO2009/032249 describes a compound represented by the formula

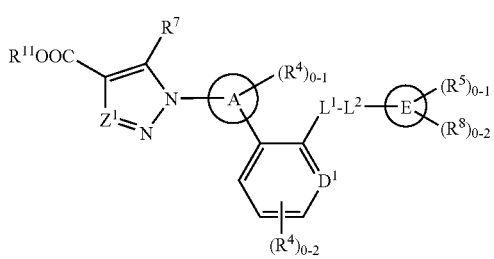

wherein $Z^1$ is CH or N; ring A is a benzene ring, a pyridine ring and the like; $D^1$ is CH, N and the like; $R^7$ is a hydrogen atom, a $C_{1-6}$ alkyl group and the like; $L^1$ is O, S and the like; $L^2$ is a $C_{2-4}$ alkylene group and the like; ring E is a 6- to 10-membered aryl ring and the like; $R^4$ is a halogen atom, a $C_{1-6}$ alkyl group and the like; $R^5$ is a $C_{1-6}$ alkyl group, a $C_{2-6}$ alkenyl group and the like; $R^8$ is a $C_{1-4}$ alkyl group, a $C_{2-4}$ alkenyl group and the like; $R^{11}$ is a hydrogen atom or a $C_{1-6}$ alkyl group, and a pharmaceutically acceptable salt thereof, and describes that the compound has a soluble guanylate cyclase activating action and is useful as an agent for the prophylaxis or treatment of cardiovascular diseases, hypertension, cardiac failure, angina pectoris and the like (see patent document 5).

WO2004/056815 describes a compound represented by the formula

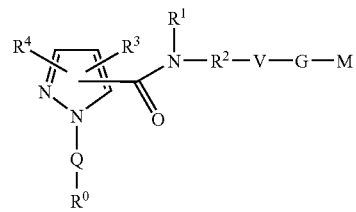

wherein $R^0$ is a 4- to 15-membered monocycle or fused ring (containing 1-4 hetero atoms) optionally substituted by $R^8$ ($R^8$ is a 6- to 14-membered aromatic hydrocarbon ring (monocyclic or fused ring) optionally substituted by a halogen atom or alkoxy, etc.) and the like; $R^3$ and $R^4$ are each alkyl, carboxyl and the like; $R^1$ is $C_{1-4}$ alkyl and the like; $R^2$ is a bond, $C_{1-4}$ alkyl and the like; V is a 3- to 7-membered ring; M is $C_{1-8}$ alkyl etc., and describes that the compound has a FXa or VIIIa inhibitory activity (see patent document 6).

US-A-2006/122181 describes a compound represented by the formula

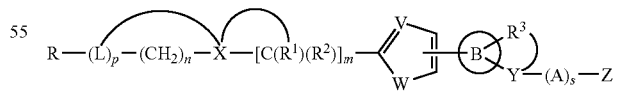

wherein V is N or CH; W is S or O; m is 0, 1 or 2; n is 0, or an integer of 1-4; $R^1$ and $R^2$ are each H or $C_{1-4}$ alkyl; X is pyrazole and the like; $R^3$ is a hydrogen atom, a halogen atom, trihalomethyl and the like; R is carboxyl and the like; L is methylene, arylene and the like; p is 0 or 1; A is alkylene; s is 0 or 1; Z is aryl etc., and describes that the compound has a protein tyrosine phosphatase 1B inhibitory activity and is useful for the treatment of diabetes, hyperlipidemia and the like (see patent document 7).

US-A-2003/104324 describes a compound represented by the formula

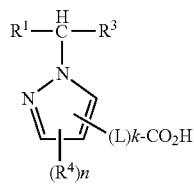

wherein $R^1$ and $R^3$ are each an aryl group optionally having substituent, a hetero ring residue and the like; $R^4$ is a halogen atom, an alkyl group and the like; n is an integer of not less than 0 and not more than 2; k is an integer of not less than 0; L is a divalent linking group, and describes that the compound is useful as a color photographic sensitizer (see patent document 8).

US-A-2005/65196 describes a compound represented by the formula

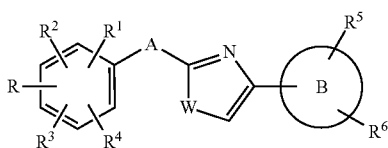

wherein W is S or O; R is —COOR$^7$, —X$^1$-A$^1$-COOR$^7$ (R$^7$ is H or alkyl; A$^1$ is lower alkylene) or tetrazolyl; $R^1$, $R^2$, $R^3$ and $R^4$ are each H and the like; A is —(CH$_2$)$_m$—X— (m is an integer of 0 or 1-3; X is —N(R$^8$)—, —C(R$^9$)(R$^{10}$) CO— or —CO—N(R$^8$)— (R$^8$ is H and the like; $R^9$ and $R^{10}$ are each H and the like); B is aryl or an aromatic heterocyclic group; $R^5$ is H and the like; $R^6$ is —(Y)$_{s1}$-(A$^2$)$_s$—Z (s1 is 0 or 1; s is 0 or 1; Y is —O—, —S(O)$_t$— (t is 0, 1 or 2), —N(R$^{13}$)— (R$^{13}$ is H etc.), —N(R$^{14}$)—CO—, —N(R$^{14}$)—SO$_2$—, —SO$_2$—N (R$^{14}$ is H or lower alkyl) and the like, A$^2$ is alkylene, Z is cycloalkyl, aryl, an aromatic heterocyclic group, indanyl, piperazinyl etc.), and describes that the compound has a protein tyrosine phosphatase 1B inhibitory activity and is useful for the treatment of diabetes, hyperlipidemia and the like (see patent document 9).

JP-A-4-154773 describes a compound represented by the formula

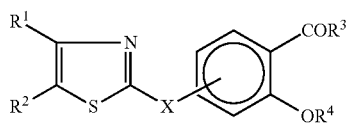

wherein $R^1$ and $R^2$ are each phenyl and the like; $R^3$ is a hydroxyl group and the like; $R^4$ is a hydrogen atom and the like; X is alkylene etc., and describes that the compound has an anti-inflammatory action (see patent document 10).

US-A-2006/205731 describes a compound represented by the formula

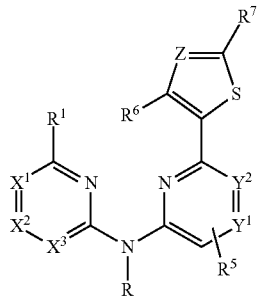

wherein $X^1$, $X^2$, $X^3$, Z, $Y^1$ and $Y^2$ are each a carbon atom or a nitrogen atom; R, $R^1$, $R^5$ and $R^6$ are each a hydrogen atom, an alkyl group and the like; $R^7$ is a hydrogen atom, a halogen atom, a nitro group, a cyano group, a 5- to 6-membered saturated heterocyclic group, an aromatic heterocyclic group etc., and describes that the compound has an SyK (Spleen tyrosine kinase) inhibitory action and is useful for diseases derived from immediate allergic reaction and delayed inflammatory reaction, diseases involving antibody, diseases involving eosinophilic inflammation or platelet activation and the like (see patent document 11).

WO92/16527 describes a compound represented by the formula

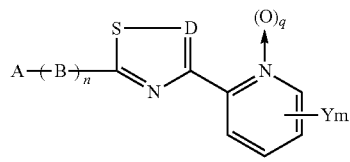

wherein A is aryl and the like; B is an oxygen atom and the like; n is 0 or 1; D is —C(R)=, N and the like (R is a hydrogen atom, a halogen atom etc.); m is 0, 1 or 2; q is 0 or 1; Y is lower alkyl etc., and describes use as a bactericide agent for agriculture and horticulture (see patent document 12).

PRIOR ART DOCUMENTS

Patent Documents patent document 1: U.S. Pat. No. 6,335,334
patent document 2: U.S. Pat. No. 7,087,644
patent document 3: US-A-2007/0179139
patent document 4: US-A-2008/0058314
patent document 5: WO2009/032249
patent document 6: WO2004/056815
patent document 7: US-A-2006/122181
patent document 8: US-A-2003/104324
patent document 9: US-A-2005/65196
patent document 10: JP-A-4-154773
patent document 11: US-A-2006/205731
patent document 12: WO92/16527

SUMMARY OF THE INVENTION

Problems to be Solved by the Invention

An object of the present invention is to provide a compound useful for the prophylaxis or treatment of cardiovascular or metabolic diseases relating to hypertension, ischemic cardiac diseases, cardiac failure, kidney disease, arteriosclerotic diseases (including atherosclerosis, cerebral apoplexy, peripheral arterial obstruction and the like), atrial fibrillation, pulmonary hypertension, diabetes, diabetic complications, metabolic syndrome, and the like, which has a superior pharmacological action, superior physicochemical properties and the like.

Means of Solving the Problems

The present inventors have first found that a compound represented by the following formula (I) has a soluble guanylate cyclase (sGC) activating action, and is useful for the prophylaxis or treatment of cardiovascular or metabolic diseases relating to hypertension, ischemic cardiac diseases, cardiac failure, kidney disease, arteriosclerotic diseases (including atherosclerosis, cerebral apoplexy, peripheral arterial obstruction and the like), atrial fibrillation, pulmonary hypertension, diabetes, diabetic complications, metabolic syndrome, and the like. Based on these findings, the present inventors have conducted intensive studies and completed the present invention.

Accordingly, the present invention provides the following.
[1] An sGC activating agent comprising a compound represented by the formula (I):

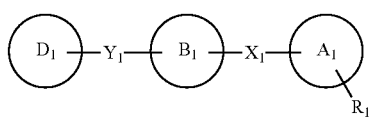

wherein
ring $A_1$ is an aromatic hydrocarbon ring optionally further substituted or a 5- or 6-membered aromatic heterocycle optionally further substituted;
ring $B_1$ is an optionally substituted 5-membered aromatic heterocycle, or an optionally substituted fused heterocycle wherein 5-membered aromatic heterocycle is fused with a 5- or 6-membered hydrocarbon ring or heterocycle;
ring $D_1$ is an optionally substituted aromatic hydrocarbon ring, or optionally substituted aromatic heterocycle;
$R_1$ is a carboxyl group, a tetrazolyl group, an oxooxadiazolyl group, or a group represented by —C(=O)NH—S(=O)$_2$R$_{11}$ wherein R$_{11}$ is an optionally substituted lower alkyl group, an acyl group, an optionally substituted aromatic hydrocarbon ring group, or an optionally substituted 5-membered or 6-membered aromatic heterocyclic group;
$X^1$ is a bond or an optionally substituted lower alkylene group;
$Y_1$ is a bond, optionally substituted lower alkylene group, or a group represented by L$_{1a}$-E$_1$-L$_{1b}$ wherein L$_{1a}$ and L$_{1b}$ are the same or different and each is a bond or an optionally substituted lower alkylene group, E$_1$ is O, S, SO, SO$_2$, NR$_{12}$, C(=O), C(=O)NR$_{13}$, NR$_{13}$—C(=O), S(=O)$_2$NR$_{13}$, or NR$_{13}$—S(=O)$_2$ wherein R$_{12}$ is a hydrogen atom, an optionally substituted lower alkyl group, an acyl group, an optionally substituted aromatic hydrocarbon ring group, or an optionally substituted 5-membered or 6-membered aromatic heterocyclic group, R$_{13}$ is a hydrogen atom, an is optionally substituted lower alkyl group, an optionally substituted aromatic hydrocarbon ring group, or an optionally substituted 5- or 6-membered aromatic heterocyclic group, provided that when both $X_1$ and $Y_1$ are bonds, the substituent of the optionally substituted aromatic hydrocarbon ring or the substituent of the optionally substituted 5- or 6-membered aromatic heterocycle for ring $D_1$ is not a group represented by the following formula (i)

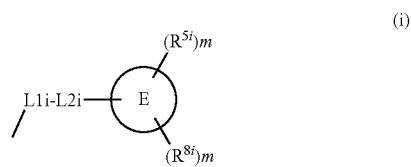

[wherein
m is 0 or 1;
n is an integer of 0-2;
L1i is selected from the group consisting of O, S, C(R$^{12i}$)$_2$ and CF$_2$;
L2i is selected from the group consisting of a C$_{2-4}$ alkylene group, —C(R$^{12i}$)$_2$, —CF$_2$O and S (when L1i is O or S, L2i is not O or S);
R$^{12i}$ is independently selected from the group consisting of a hydrogen atom and a C$_{1-3}$ alkyl group optionally substituted by 1 to 3 fluorine atoms;
E is a ring selected from the group consisting of
1) a 6- to 10-membered aryl ring,
2) a 5-10-membered heteroaryl ring having 1, 2 or 3 hetero atoms selected from the group consisting of 0, 1, 2 or 3 N atoms, 0 or 10 atom, and 0 or 1 S atom, and
3) a C$_{3-8}$ cycloalkyl ring;
when the above-mentioned aryl ring, heteroaryl ring and cycloalkyl ring are substituted by 0 or 1 R$^{5i}$ or 0, 1 or 2 R$^{8i}$, R$^{5i}$ is a group selected from the group consisting of
1) R$^{6i}$,
2) —OR$^{6i}$,
3) a C$_{1-6}$ alkyl group optionally substituted by 1 to 3 fluorine atoms and optionally monosubstituted by a group selected from the group consisting of a C$_{3-6}$ cycloalkyl group, a —O—C$_{1-4}$ alkyl group, OH, =O, an S(O)$_n$C$_{1-4}$ alkyl group wherein n' is an integer of 0-2, —OR$^{6i}$ and R$^{6i}$,
4) a C$_{2-6}$ alkenyl group optionally substituted by 1 to 3 fluorine atoms, and optionally monosubstituted by a group selected from the group consisting of a —O—C$_{1-4}$ alkyl group, OH, =O, an S(O)$_n$C$_{1-4}$ alkyl group wherein n' is an integer of 0-2, —OR$^6$ and R$^6$,
5) a —O—C$_{1-6}$ alkyl group (the alkyl group is optionally substituted by 1 to 3 fluorine atoms, and optionally monosubstituted by a group selected from the group consisting of C$_{3-6}$ cycloalkyl group and R$^6$),
6) a —S—C$_{1-6}$ alkyl group,
7) a C$_{3-8}$ cycloalkyl group optionally substituted by 1 to 3 substituents independently selected from the group consisting of fluoro and C$_{1-4}$ alkyl group, and optionally monosubstituted by a group selected from the group consisting of a C$_{1-4}$ alkyl group (the alkyl group is optionally substituted by 1 to 3 fluorine atoms), a —O—C$_{1-4}$ alkyl group, OH, =O, an S(O)$_n$C$_{1-4}$ alkyl group wherein n' is an integer of 0-2, —OR$^{6i}$, R$^{6i}$ and NR$^{9i}$R$^{10i}$,
8) a C$_{5-8}$ cycloalkenyl group optionally substituted by 1 to 3 substituents independently selected from the group consisting of fluoro and C$_{1-4}$ alkyl group, and optionally monosubstituted by a group selected from the group consisting of a C$_{1-4}$ alkyl group (the alkyl group is optionally substituted by 1 to 3 fluorine atoms), a —O—C$_{1-4}$ alkyl group, OH, =O, an S(O)$_n$C$_{1-4}$ alkyl group wherein n' is an integer of 0-2, and R$^{6i}$,
9) a 5- or 6-membered heterocyclic group having 1 or 2 hetero atoms selected from the group consisting of N, O and S, and optionally monosubstituted by a group selected from the group consisting of a $C_{1-4}$ alkyl group (the alkyl group is optionally substituted by 1 to 3 fluorine atoms), a —O—$C_{1-4}$ alkyl group, and =O, and 10) a halogen atom;

$R^{6i}$ is a group selected from the group consisting of 1) phenyl optionally substituted by a group selected from the group consisting of halogen, OH, CN, a $C_{1-4}$ alkyl group (the alkyl group is optionally substituted by 1 to 3 fluorine atoms), a —O—$C_{1-4}$ alkyl group (the alkyl group is optionally substituted by 1 to 3 fluorine atoms), $NO_2$, an $S(O)_n C_{1-4}$ alkyl group wherein n' is an integer of 0-2, a $C_{2-4}$ alkenyl group, a —O—$C_{2-4}$ alkenyl group, $NR^{9i}R^{10i}$ wherein $R^{9i}$ and $R^{10i}$ are each a group independently selected from the group consisting of a hydrogen atom and a $C_{1-6}$ alkyl group), and COOH, and 2) a 5- or 6-membered aromatic heterocyclic group having 1 or 2 hetero atoms selected from the group consisting of N, O and S, and optionally substituted by a group selected from the group consisting of halogen, OH, CN, a $C_{1-4}$ alkyl group (the alkyl group is optionally substituted by 1 to 3 fluorine atoms), a —O—$C_{1-4}$ alkyl group (the alkyl group is optionally substituted by 1 to 3 fluorine atoms), $NO_2$, an $S(O)_n C_{1-4}$ alkyl group wherein n' is an integer of 0-2, an $S(O)_{n'}$ aryl group wherein n' is an integer of 0-2, a $C_{2-6}$ alkenyl group, a —O—$C_{2-6}$ alkenyl group, $NR^{9i}R^{10i}$ wherein $R^{9i}$ and $R^{10i}$ are each a group independently selected from the group consisting of a hydrogen atom and $C_{1-6}$ alkyl group), and COON;

$R^{8i}$ is a group selected from the group consisting of a $C_{1-4}$ alkyl group (the alkyl group is optionally substituted by 1 to 3 fluorine atoms), a $C_{2-4}$ alkenyl group, a halogen atom, a $C_{3-6}$ cycloalkyl group (the cycloalkyl group is optionally substituted by 1 to 3 fluorine atoms), a —O—$C_{1-4}$ alkyl group (the alkyl group is optionally substituted by 1 to 3 fluorine atoms), a —O—$C_{2-4}$ alkenyl group, $NO_2$ an $S(O)_n C_{1-4}$ alkyl group wherein n' is an integer of 0-2, and CN], or a salt thereof, or a prodrug thereof as an active ingredient.

[2] The sGC activating agent of the above-mentioned [1], wherein, in the formula [I], when both $X_1$ and $Y_1$ are bonds, the substituent of the optionally substituted aromatic hydrocarbon ring or the substituent of the optionally substituted 5- or 6-membered aromatic heterocycle for ring $D_1$ is selected from the group consisting of a halogen atom, an alkyl group substituted by a halogen atom, and an alkoxy group substituted by a halogen atom.

[1-1] The sGC activating agent of the above-mentioned [1], wherein the $A_1$ ring is an optionally further substituted 5- or 6-membered aromatic heterocycle.

[1-2] The sGC activating agent of the above-mentioned [1], wherein the $A_1$ ring is an optionally further substituted 5-membered aromatic heterocycle.

[1-3] The sGC activating agent of the above-mentioned [1], wherein the $A_1$ ring is an optionally further substituted pyrazole ring.

[1-4] The sGC activating agent of the above-mentioned [1], wherein the $A_1$ ring is a pyrazole ring optionally substituted by a substituent selected from the group consisting of (1) a $C_{1-6}$ alkyl group optionally substituted by a halogen atom or a $C_{1-6}$ alkoxy group, (2) a cycloalkyl group, and (3) a $C_{1-6}$ alkoxy group.

[1-5] The sGC activating agent of the above-mentioned [1], wherein the $A_1$ ring is an optionally further substituted 6-membered aromatic hydrocarbon ring.

[1-6] The sGC activating agent of the above-mentioned [1], wherein the $A_1$ ring is an optionally further substituted benzene ring.

[1-7] The sGC activating agent of the above-mentioned [1], wherein the $A_1$ ring is a benzene ring optionally further substituted by a substituent selected from the group consisting of (1) a halogen atom, (2) a $C_{1-6}$ alkyl group, (3) a $C_{1-6}$ alkoxy group, (4) an amino group, (5) an oxo group, (6) a $C_{1-6}$ alkyl-carbonylamino group and (7) a sulfonylamino group.

[1-8] The sGC activating agent of the above-mentioned [1], wherein the ring $B_1$ is an optionally substituted 5-membered aromatic heterocycle.

[1-9] The sGC activating agent of the above-mentioned [1], wherein the ring $B_1$ is an optionally substituted thiazole ring, an optionally substituted isoxazole ring, an optionally substituted oxazole ring, an optionally substituted furan ring, an optionally substituted thiophene ring, an optionally substituted oxadiazole ring, or an optionally substituted thiadiazole ring.

[1-10] The sGC activating agent of the above-mentioned [1], wherein the ring $B_1$ is an optionally substituted thiazole ring.

[1-11] The sGC activating agent of the above-mentioned [1], wherein the ring $B_1$ is a thiazole ring optionally substituted by a substituent selected from the group consisting of (1) a halogen atom, (2) a $C_{3-6}$ cycloalkyl group, (3) a $C_{2-6}$ alkenyl group, and (4) a $C_{1-6}$ alkyl group optionally substituted by a halogen atom.

[1-12] The sGC activating agent of the above-mentioned [1], wherein the ring $B_1$ is a thiazole ring optionally substituted by a $C_{1-6}$ alkyl group.

[1-13] The sGC activating agent of the above-mentioned [1], wherein the ring $D_1$ is an optionally substituted $C_{6-14}$ arene.

[1-14] The sGC activating agent of the above-mentioned [1], wherein the ring $D_1$ is an optionally substituted benzene ring.

[1-15] The sGC activating agent of the above-mentioned [1], wherein the ring $D_1$ is an optionally substituted 5- to 7-membered monocyclic aromatic heterocycle.

[1-16] The sGC activating agent of the above-mentioned [1], wherein the ring $D_1$ is a benzene ring optionally substituted by substituent(s) selected from the group consisting of (1) a halogen atom, (2) a $C_{1-6}$ alkyl group optionally substituted by (i) a halogen atom, (ii) a hydroxy group, (iii) an aryloxy group, (iv) an aryl group or (v) a 3- to 8-membered nitrogen-containing heterocyclic group optionally having substituents and optionally containing, besides a carbon atom and one nitrogen atom, 1-3 hetero atoms selected from a nitrogen atom, an oxygen atom and a sulfur atom, (3) a $C_{1-6}$ alkoxy group optionally substituted by (i) a halogen atom, (ii) a cycloalkyl group, (iii) a $C_{1-6}$ alkoxy group, (iv) a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom, (v) a mono-$C_{1-6}$ alkylamino group optionally having substituents, (vi) an arylthio group or (vii) an aryl group, (4) an amino group, (5) a nitro group, (6) a $C_{1-6}$ alkyl-carbonylamino group optionally substituted by a hydroxy group or a $C_{1-6}$ alkoxy group, (7) a $C_{1-6}$ alkyl-carbonyl group, (8) $C_{2-6}$ alkenyl group optionally substituted by an aryl group or a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom, (9) a $C_{1-6}$ alkylamino group, (10) a $C_{1-6}$ alkylsulfonyl group, (11) an aryl group, (12) a cyano group, (13) a cycloalkyl group, (14) an aralkyloxy group optionally substituted by a halogen atom, (15) a $C_{2-6}$ alkynyl group optionally substituted by a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom, (16) a carbonylamino-$C_{1-6}$ alkyl group optionally substituted by a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom, (17) an aralkyl group optionally substituted by a $C_{1-6}$ alkyl-carbonyl group, and (18) a cycloalkyloxy group.

[1-17] The sGC activating agent of the above-mentioned [1], wherein the ring $D_1$ is a benzene ring substituted by the same or different, 1 to 3 substituents selected from the group consisting of a halogen atom and a $C_{1-6}$ alkyl group optionally substituted by a halogen atom.

[1-18] The sGC activating agent of the above-mentioned [1], wherein the ring $D_1$ is a benzene ring substituted by the same or different, 1 to 3 substituents selected from the group consisting of a halogen atom and a trihalo($C_{1-6}$)alkyl group.

[1-19] The sGC activating agent of the above-mentioned [1], wherein the ring $D_1$ is an optionally further substituted benzene ring substituted by a trihalo($C_{1-6}$)alkyl group.

[1-20] The sGC activating agent of the above-mentioned [1], wherein the ring $D_1$ is a benzene ring substituted by a trihalo ($C_{1-6}$)alkyl group, which is optionally further substituted by a halogen atom.

[1-21] The sGC activating agent of the above-mentioned [1], wherein the ring $D_1$ is a benzene ring substituted by the same or different, 1 or 2 halogen atoms.

[1-22] The sGC activating agent of the above-mentioned [1], wherein $R_1$ is a carboxyl group, a tetrazolyl group, an oxooxadiazolyl group, or —C(=O)NH—S(=O)$_2$R$_{11}$, and R$_{11}$ is an optionally substituted $C_{1-6}$ alkyl group.

[1-23] The sGC activating agent of the above-mentioned [1], wherein $R_1$ is a carboxyl group.

[1-24] The sGC activating agent of the above-mentioned [1], wherein $X_1$ is a bond, or an optionally substituted $C_{1-6}$ alkylene group.

[1-25] The sGC activating agent of the above-mentioned [1], wherein $Y_1$ is a bond, an optionally substituted $C_{1-6}$ alkylene group, or
$L_{1a'}$-$E_1'$-$L_{1b'}$ wherein $L_{1a'}$ is a bond or a $C_{1-6}$ alkylene group, $E_1'$ is C(=O)NH, O, S, or NH, and $L_{1b'}$ is a bond or a $C_{1-6}$ alkylene group.

[1-26] The sGC activating agent of the above-mentioned [1], wherein $Y_1$ is a $C_{1-6}$ alkylene group.

[3] A compound represented by the formula (II):

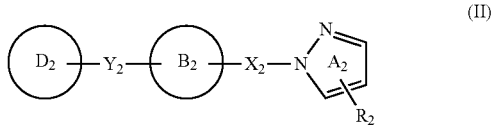

wherein
ring $A_2$ is an optionally further substituted pyrazole ring;
ring $B_2$ is an optionally substituted 5-membered aromatic heterocycle, or an optionally substituted fused heterocycle wherein a 5-membered aromatic heterocycle is fused with a 5- or 6-membered hydrocarbon ring or heterocycle;

ring $D_2$ is an optionally substituted aromatic hydrocarbon ring, or an optionally substituted aromatic heterocycle;
$R_2$ is a carboxyl group, a tetrazolyl group, an oxooxadiazolyl group, or a group represented by —C(=O)NH—S(=O)$_2$R$_{21}$ wherein R$_{21}$ is an optionally substituted lower alkyl group, an acyl group, an optionally substituted aromatic hydrocarbon ring group, or an optionally substituted 5- or 6-membered aromatic heterocyclic group;
$X_2$ is an optionally substituted lower alkylene group;
$Y_2$ is a bond, an optionally substituted lower alkylene group, or $L_{2a}$-$E_2$-$L_{2b}$ wherein $L_{2a}$ and $L_{2b}$ are the same or different and each is a bond or an optionally substituted lower alkylene group, and $E_2$ is a group represented by O, S, SO, SO$_2$, NR$_{22}$, C(=O)C(=O)NR$_{23}$, NR$_{23}$—C(=O), S(=O)$_2$NR$_{23}$, or NR$_{23}$—S(=O)$_2$ wherein R$_{22}$ is a hydrogen atom, an optionally substituted lower alkyl group, an acyl group, an optionally substituted aromatic hydrocarbon ring group, or an optionally substituted 5- or 6-membered aromatic heterocyclic group, R$_{23}$ is a hydrogen atom, an optionally substituted lower alkyl group, an optionally substituted aromatic hydrocarbon ring group, or an optionally substituted 5- or 6-membered aromatic heterocyclic group, provided that
$B_2$ is not an isoxazole ring;
the substituent of ring $D_2$ is not a [4-(1-propylbutyl)phenoxy] methyl group when ring $B_2$ is a thiazole ring and ring $D_2$ is a benzene ring;
and $X_2$ is not a substituted oxoethylene group when ring $B_2$ is a pyrrole ring or an indole ring,
or a salt thereof,
excluding 1-[(5-phenyl-2H-tetrazol-2-yl)methyl]-1H-pyrazole-3-carboxylic acid.

[4] The compound of the above-mentioned [3], wherein the ring $A_2$ is a pyrazole ring optionally further substituted by a substituent selected from the group consisting of
a $C_{1-6}$ alkyl group optionally substituted by a halogen atom, and a $C_{1-6}$ alkoxy group.

[4-1] The compound of the above-mentioned [3], wherein the ring $A_2$ is a pyrazole ring optionally further substituted by the same or different 1-3 substituents selected from the group consisting of a $C_{1-6}$ alkyl group optionally substituted by a halogen atom and a $C_{1-6}$ alkoxy group.

[5] The compound of the above-mentioned [3], wherein the ring $A_2$ is pyrazole.

[6] The compound of the above-mentioned [3], wherein the ring $B_2$ is an optionally substituted 5-membered aromatic heterocycle.

[7] The compound of the above-mentioned [3], wherein the ring $B_2$ is an optionally substituted thiazole ring, an optionally substituted oxazole ring, an optionally substituted furan ring, an optionally substituted thiophene ring, an optionally substituted oxadiazole ring or an optionally substituted thiadiazole ring.

[7-1] The compound of the above-mentioned [3], wherein the ring $B_2$ is a thiazole ring optionally substituted by a halogen atom, a $C_{3-6}$ cycloalkyl group, a $C_{2-6}$ alkenyl group, or a $C_{1-6}$ alkyl group optionally substituted by a halogen atom;
an oxazole ring optionally substituted by a halogen atom, a $C_{3-6}$ cycloalkyl group, a $C_{2-6}$ alkenyl group, or a $C_{1-6}$ alkyl group optionally substituted by a halogen atom;
a furan ring optionally substituted by a halogen atom, a $C_{3-6}$ cycloalkyl group, a $C_{2-6}$ alkenyl group, or a $C_{1-6}$ alkyl group optionally substituted by a halogen atom;
a thiophene ring optionally substituted by a halogen atom, a $C_{3-6}$ cycloalkyl group, a $C_{2-6}$ alkenyl group, or a $C_{1-6}$ alkyl group optionally substituted by a halogen atom;

an oxadiazole ring optionally substituted by a halogen atom, a $C_{3-6}$ cycloalkyl group, a $C_{2-6}$ alkenyl group, or a $C_{1-6}$ alkyl group optionally substituted by a halogen atom; or a thiodiazole ring optionally substituted by a halogen atom, a $C_{3-6}$ cycloalkyl group, a $C_{2-6}$ alkenyl group, or a $C_{1-6}$ alkyl group optionally substituted by a halogen atom.

[8] The compound of the above-mentioned [3], wherein the ring $B_2$ is an optionally substituted thiazole ring.

[8-1] The compound of the above-mentioned [3], wherein the ring $B_2$ is a thiazole ring optionally substituted by a substituent selected from the group consisting of a $C_{1-6}$ alkyl group optionally substituted by a halogen atom, a $C_{2-6}$ alkenyl group, a halogen atom and a $C_{3-6}$ cycloalkyl group.

[8-2] The compound of the above-mentioned [3], wherein the ring $B_2$ is a thiazole ring optionally substituted by a $C_{1-6}$ alkyl group.

[8-3] The compound of the above-mentioned [3], wherein the ring $B_2$ is a thiazole ring optionally substituted by a methyl group.

[9] The compound of the above-mentioned [3], wherein the ring $D_2$ is an optionally substituted aromatic hydrocarbon ring.

[9-1] The compound of the above-mentioned [3], wherein the ring $D_2$ is an optionally substituted $C_{6-14}$ arene.

[9-2] The compound of the above-mentioned [3], wherein the ring $D_2$ is an optionally substituted aromatic heterocycle.

[9-3] The compound of the above-mentioned [3], wherein the ring $D_2$ is an optionally substituted 5- to 7-membered monocyclic aromatic heterocycle.

[10] The compound of the above-mentioned [3], wherein the ring $D_2$ is an optionally substituted benzene ring.

[10-1] The compound of the above-mentioned [3], wherein the ring $D_2$ is a benzene ring optionally substituted by substituent(s) selected from the group consisting of (1) a halogen atom, (2) a $C_{1-6}$ alkyl group optionally substituted by a halogen atom or an aryl group, (3) a $C_{1-6}$ alkoxy group optionally substituted by a halogen atom, (4) a nitro group, (5) a $C_{1-6}$ alkyl-carbonylamino group optionally substituted by a $C_{1-6}$ alkoxy group, (7) a $C_{1-6}$ alkyl-carbonyl group, and (8) a $C_{2-6}$ alkenyl group optionally substituted by an aryl group.

[10-2] The compound of the above-mentioned [3], wherein the ring $D_2$ is a benzene ring substituted by substituent(s) selected from the group consisting of (1) an optionally substituted $C_{1-6}$ alkyl group, (2) an optionally substituted $C_{2-6}$ alkynyl group, (3) an optionally substituted $C_{2-6}$ alkenyl group, (4) an optionally substituted cycloalkyl group, (5) an optionally substituted $C_{1-6}$ alkoxy group, (6) an optionally substituted cycloalkyloxy group, (7) an optionally substituted amino group, (8) an optionally substituted cyano group, and (9) an optionally substituted sulfonyl group.

[10-3] The compound of the above-mentioned [3], wherein the ring $D_2$ is a benzene ring optionally substituted by substituent(s) selected from the group consisting of (1) a halogen atom, (2) an optionally substituted $C_{1-6}$ alkyl group, (3) an optionally substituted $C_{3-6}$ cycloalkyl group, (4) an optionally substituted $C_{1-6}$ alkoxy group, and (5) an optionally substituted amino group.

[11] The compound of the above-mentioned [3], wherein the ring $D_2$ is an optionally further substituted benzene ring substituted by a $C_{1-6}$ alkyl group optionally substituted by a halogen atom.

[12] The compound of the above-mentioned [3], wherein the ring $D_2$ is a benzene ring substituted by (preferably 1 or 2, more preferably 2) substituents selected from a halogen atom and a $C_{1-6}$ alkyl group optionally substituted by a halogen atom.

[13] The compound of the above-mentioned [3], wherein $R_2$ is a carboxyl group.

[13-1] The compound of the above-mentioned [3], wherein $R_2$ is a carboxyl group, a tetrazolyl group, an oxooxadiazolyl group, or a group represented by —C(=O)NH—S(=O)$_2$R$_{21'}$, wherein R$_{21'}$ is an optionally substituted $C_{1-6}$ alkyl group, an acyl group, an optionally substituted aromatic hydrocarbon ring group, or an optionally substituted 5- or 6-membered aromatic heterocyclic group.

[13-2] The compound of the above-mentioned [3], wherein $R_2$ is a carboxyl group, a tetrazolyl group, an oxooxadiazolyl group, or —C(=O)NH—S(=O)$_2$R$_{21''}$, wherein R$_{21''}$ is an optionally substituted $C_{1-6}$ alkyl group.

[14] The compound of the above-mentioned [3], wherein $R_2$ is present at the 4-position on the pyrazole ring.

[15] The compound of the above-mentioned [3], wherein $X_2$ is a $C_{1-6}$ alkylene group.

[15-1] The compound of the above-mentioned [3], wherein $X_2$ is a methylene group optionally substituted by a $C_{1-6}$ alkyl group optionally substituted by a carboxyl group.

[15-2] The compound of the above-mentioned [3], wherein $X_2$ is methylene optionally substituted by 1 or 2 methyl.

[16] The compound of the above-mentioned [3], wherein $Y_2$ is a bond or an optionally substituted $C_{1-6}$ alkylene group.

[17] The compound of the above-mentioned [3], wherein $Y_2$ is a bond.

[17-1] The compound of the above-mentioned [3], wherein $Y_2$ is an optionally substituted $C_{1-6}$ alkylene group.

[18] The compound of the above-mentioned [3], wherein the ring $A_2$ is a pyrazole ring optionally further substituted by a substituent selected from the group consisting of a $C_{1-6}$ alkyl group optionally substituted by a halogen atom, and a $C_{1-6}$ alkoxy group;

$R_2$ is a carboxyl group;

ring $D_2$ is a benzene ring substituted by a halogen atom, and a $C_{1-6}$ alkyl group optionally substituted by a halogen atom.

[18-1] The compound of the above-mentioned [3], wherein the ring $A_2$ is a pyrazole ring;

ring $B_2$ is a thiazole ring optionally substituted by a $C_{1-6}$ alkyl group;

ring $D_2$ is a benzene ring optionally substituted by substituent(s) selected from the group consisting of a halogen atom, and a $C_{1-6}$ alkyl group optionally substituted by a halogen atom;

$R_2$ is a carboxyl group;

$X_2$ is a $C_{1-6}$ alkylene group; and $Y_2$ is a bond.

[19] 1-({4-[3-(Trifluoromethyl)phenyl]-1,3-thiazol-2-yl}methyl)-1H-pyrazole-4-carboxylic acid or a salt thereof.

[20] 1-({4-[2-Fluoro-3-(trifluoromethyl)phenyl]-1,3-thiazol-2-yl}methyl)-1H-pyrazole-4-carboxylic acid or a salt thereof.

[21] 1-({2-[2-Fluoro-3-(trifluoromethyl)phenyl]-5-methyl-1,3-thiazol-4-yl}methyl)-1H-pyrazole-4-carboxylic acid or a salt thereof.

[22] 1-({2-[3-Chloro-5-(trifluoromethyl)phenyl]-5-methyl-1,3-thiazol-4-yl}methyl)-1H-pyrazole-4-carboxylic acid or a salt thereof.

[23] A compound represented by the formula (III):

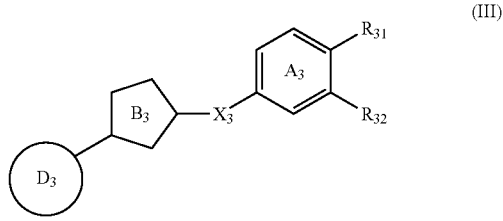

wherein
ring $A_3$ is an optionally further substituted benzene ring;
ring $B_3$ is an optionally substituted thiazole ring, an optionally substituted oxazole ring, an optionally substituted furan ring, an optionally substituted thiophene ring, an optionally substituted oxadiazole ring or an optionally substituted thiadiazole ring;
ring $D_3$ is a benzene ring substituted by a halogen atom, a benzene ring substituted by a $C_{1-6}$ alkoxy group or an optionally further substituted benzene ring substituted by a $C_{1-6}$ alkyl group substituted by a halogen atom;
one of $R_{31}$ and $R_{32}$ is a carboxyl group, a tetrazolyl group, an oxooxadiazolyl group, or a group represented by —C(=O)NH—S(=O)$_2$1$R_{33}$ wherein $R_{33}$ is an optionally substituted $C_{1-6}$ alkyl group, an acyl group, an optionally substituted aromatic hydrocarbon group, or an optionally substituted 5- or 6-membered aromatic heterocyclic group, and the other is a hydrogen atom or a halogen atom; and
$X_3$ is optionally substituted methylene,
or a salt thereof.
[24] The compound of the above-mentioned [23], wherein the ring $A_3$ is a benzene ring optionally further substituted by a halogen atom.
[24-1] The compound of the above-mentioned [23], wherein the ring $A_3$ is a benzene ring optionally further substituted by the same or different, 1 to 3 substituents selected from the group consisting of a $C_{1-6}$ alkyl group optionally substituted by a halogen atom, and a $C_{1-6}$ alkoxy group.
[25] The compound of the above-mentioned [23], wherein the ring $A_3$ is a benzene ring.
[26] The compound of the above-mentioned [23], wherein the ring $B_3$ is an optionally substituted thiazole ring.
[26-1] The compound of the above-mentioned [23], wherein the ring $B_3$ is a thiazole ring optionally substituted by a $C_{1-6}$ alkyl group.
[27] The compound of the above-mentioned [23], wherein the ring $D_3$ is an optionally further substituted benzene ring substituted by a trihalo($C_{1-6}$)alkyl group.
[27-1] The compound of the above-mentioned [23], wherein the ring $D_3$ is a benzene ring substituted by the same or different, 1 to 3 substituents selected from the group consisting of a halogen atom, and a $C_{1-6}$ alkyl group optionally substituted by a halogen atom.
[27-2] The compound of the above-mentioned [23], wherein the ring $D_3$ is a benzene ring substituted by the same or different, 1 to 3 substituents selected from a halogen atom and a trihalo($C_{1-6}$)alkyl group.
[27-3] The compound of the above-mentioned [23], wherein the ring $D_3$ is a benzene ring substituted by a trihalo($C_{1-6}$) alkyl group, which ring is optionally further substituted by halogen atom.
[27-4] The compound of the above-mentioned [23], wherein the ring $D_3$ is a benzene ring substituted by the same or different, 1 or 2 halogen atoms.
[28] The compound of the above-mentioned [23], wherein $R_{31}$ is a carboxyl group, $R_{32}$ is a hydrogen atom or a halogen atom.
[29] The compound of the above-mentioned [23], wherein $X_3$ is methylene.
[28-1] The compound of the above-mentioned [23], wherein
the
ring $A_3$ is a benzene ring;
ring $B_3$ is a thiazole ring optionally substituted by a $C_{1-6}$ alkyl group;
ring $D_3$ is an optionally further substituted benzene ring substituted by a trihalo($C_{1-6}$)alkyl group;
$R_{31}$ is a carboxyl group;
$R_{32}$ is a hydrogen atom or halogen atom; and
$X_3$ is a $C_{1-6}$ alkylene group.
[30] 4-({4-[3-(Trifluoromethyl)phenyl]-1,3-thiazol-2-yl}methyl)benzoic acid or a salt thereof.
[31] 4-{[4-(3,4-Dichlorophenyl)-1,3-thiazol-2-yl]methyl}benzoic acid or a salt thereof.
[32] 4-({4-[2-Fluoro-3-(trifluoromethyl)phenyl]-1,3-thiazol-2-yl}methyl)benzoic acid or a salt thereof.
[33] A prodrug of the compound of any of the above-mentioned [2] to [32].
[34] A medicament comprising the compound of any of the above-mentioned [2] to [32] or a prodrug thereof as an active ingredient.
[35] The medicament of the above-mentioned [34], which is an sGC activating agent.
[36] The medicament of the above-mentioned [34], which is an agent for the prophylaxis or treatment of at least one kind selected from the group consisting of hypertension, ischemic cardiac diseases, cardiac failure, kidney disease, arteriosclerotic diseases, atrial fibrillation, pulmonary hypertension, diabetes, diabetic complications, metabolic syndrome, peripheral arterial obstruction and erectile dysfunction.
[37] Use of the compound of any of the above-mentioned [3] to [33] or a prodrug thereof for the production of an agent for the prophylaxis or treatment of at least one kind selected from the group consisting of hypertension, ischemic cardiac diseases, cardiac failure, kidney disease, arteriosclerotic diseases, atrial fibrillation, pulmonary hypertension, diabetes, diabetic complications, metabolic syndrome, peripheral arterial obstruction and erectile dysfunction.
[38] The compound of any of the above-mentioned [3] to [33] or a prodrug thereof, which is used as an agent for the prophylaxis or treatment of at least one kind selected from the group consisting of hypertension, ischemic cardiac diseases, cardiac failure, kidney disease, arteriosclerotic diseases, atrial fibrillation, pulmonary hypertension, diabetes, diabetic complications, metabolic syndrome, peripheral arterial obstruction and erectile dysfunction.
[39] A method for the prophylaxis or treatment of at least one kind selected from the group consisting of hypertension, ischemic cardiac diseases, cardiac failure, kidney disease, arteriosclerotic diseases, atrial fibrillation, pulmonary hypertension, diabetes, diabetic complications, metabolic syndrome, peripheral arterial obstruction and erectile dysfunction in a mammal, comprising administering an effective amount of the compound of any of the above-mentioned [3] to [33] or a prodrug thereof to the mammal.

Effect of the Invention

Since the compound of the present invention shows an sGC activating action, it is highly useful as an sGC activating agent, or an agent for the prophylaxis or treatment of a disease such as hypertension, ischemic cardiac diseases, cardiac failure, kidney disease, arteriosclerotic diseases, atrial fibrillation, pulmonary hypertension, diabetes, diabetic complications, metabolic syndrome, peripheral arterial obstruction and erectile dysfunction and the like.

DETAILED DESCRIPTION OF THE INVENTION

The definition of each symbol used in the present specification is described in detail in the following.

As the "aromatic hydrocarbon ring" of the "optionally substituted aromatic hydrocarbon ring" used in the present specification, $C_{6-14}$ arene (e.g., benzene, naphthalene and the like) is preferable, $C_{6-10}$ arene is more preferable, and benzene is particularly preferable.

As the "substituent" of the "optionally substituted aromatic hydrocarbon ring", a substituent selected from the group consisting of (1) a halogen atom (e.g., fluorine, chlorine, bromine, iodine; preferably fluorine),
(2) a lower alkyl group (e.g., a $C_{1-6}$ alkyl group such as methyl, ethyl, propyl, isopropyl, butyl, isobutyl, sec-butyl, tert-butyl, pentyl, hexyl and the like, and the like),
(3) a cycloalkyl group (e.g., a $C_{3-6}$ cycloalkyl group such as cyclopropyl, cyclobutyl, cyclopentyl, cyclohexyl and the like, and the like),
(4) a lower alkynyl group (e.g., a $C_{2-6}$ alkynyl group such as ethynyl, 1-propynyl, propargyl and the like, and the like),
(5) a lower alkenyl group (e.g., a $C_{2-6}$ alkenyl group such as vinyl, allyl, isopropenyl, butenyl, isobutenyl and the like, and the like),
(6) an aralkyl group (e.g., a $C_{7-12}$ aralkyl group such as benzyl, α-methylbenzyl, phenethyl and the like, and the like),
(7) an aryl group (e.g., a $C_{6-10}$ aryl group such as phenyl, naphthyl and the like, and the like, preferably phenyl group),
(8) a lower alkoxy group (e.g., a $C_{1-6}$ alkoxy group such as methoxy, ethoxy, propoxy, isopropoxy, butoxy, isobutoxy, sec-butoxy, tert-butoxy and the like, and the like),
(9) an aryloxy group (e.g., a $C_{6-10}$ aryloxy group such as phenoxy and the like, and the like),
(10) a formyl group or lower alkanoyl group (e.g., a $C_{1-6}$ alkyl-carbonyl group such as acetyl, propionyl, butyryl, isobutyryl and the like, and the like),
(11) an arylcarbonyl group (e.g., a $C_{6-10}$ aryl-carbonyl group such as benzoyl, naphthoyl and the like, and the like),
(12) a formyloxy group or lower alkanoyloxy group (e.g., a $C_{1-6}$ alkyl-carbonyloxy group such as acetyloxy, propionyloxy, butyryloxy, isobutyryloxy and the like, and the like),
(13) an arylcarbonyloxy group (e.g., a $C_{6-10}$ aryl-carbonyloxy group such as benzoyloxy, naphthoyloxy and the like, and the like),
(14) a carboxyl group,
(15) a lower alkoxycarbonyl group (e.g., a $C_{1-6}$ alkoxy-carbonyl group such as methoxycarbonyl, ethoxycarbonyl, propoxycarbonyl, isopropoxycarbonyl, butoxycarbonyl, isobutoxycarbonyl, tert-butoxycarbonyl and the like, and the like),
(16) an aralkyloxycarbonyl group (e.g., a $C_{7-12}$ aralkyloxycarbonyl group such as benzyloxycarbonyl and the like, and the like),
(17) a carbamoyl group,
(18) a mono-, di- or tri-halogeno-lower alkyl group (e.g., a mono-, di- or tri-halogeno-$C_{1-6}$ alkyl group such as chloromethyl, dichloromethyl, trifluoromethyl, 2,2,2-trifluoroethyl and the like, and the like),
(19) an oxo group,
(20) an amidino group,
(21) an imino group,
(22) an amino group,
(23) a mono-lower alkylamino group optionally having substituent (e.g., a mono-$C_{1-6}$ alkylamino group optionally substituted by a $C_{6-10}$ aryl group; methylamino, ethylamino, propylamino, isopropylamino, butylamino and the like),
(24) a di-lower alkylamino group (e.g., a di-$C_{1-6}$ alkylamino group such as dimethylamino, diethylamino, dipropylamino, diisopropylamino, dibutylamino, N-ethyl-N-methylamino and the like, and the like),
(25) a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom (e.g., a 3- to 8-membered nitrogen-containing heterocyclic group optionally having 1-5 substituents selected from a halogen atom, a nitro group, a cyano group, a hydroxy group, an oxo group, an optionally halogenated $C_{1-6}$ alkyl group, an optionally halogenated $C_{1-6}$ alkoxy group, an amino group, a mono-$C_{1-6}$ alkylamino group, a di-$C_{1-6}$ alkylamino group, a carboxyl group, a $C_{1-6}$ alkyl-carbonyl group, a $C_{1-6}$ alkoxy-carbonyl group, a carbamoyl group, a mono-$C_{1-6}$ alkyl-carbamoyl group, a di-$C_{1-6}$ alkyl-carbamoyl group, a $C_{6-10}$ aryl-carbamoyl group, a $C_{6-10}$ aryl group, a $C_{7-12}$ aralkyl group, a $C_{6-10}$ aryloxy group, and an optionally halogenated $C_{1-6}$ alkyl-carbonylamino group, an oxo group and the like, and optionally containing, besides a carbon atom and one nitrogen atom, 1-3 hetero atoms selected from a nitrogen atom, an oxygen atom and a sulfur atom; for example, aziridinyl, azetidinyl, pyrrolidinyl, pyridyl, pyrrolinyl, pyrrolyl, imidazolyl, pyrazolyl, imidazolidinyl, piperidyl, oxadiazolyl, isoxazolyl, morpholinyl, dihydropyridyl, tetrahydropyridyl, piperazinyl, N-methylpiperazinyl, N-ethylpiperazinyl and the like),
(26) an alkylenedioxy group (e.g., a $C_{1-3}$ alkylenedioxy group such as methylenedioxy, ethylenedioxy and the like, and the like),
(27) a hydroxy group,
(28) a nitro group,
(29) a cyano group,
(30) a mercapto group,
(31) a sulfo group,
(32) a sulfino group,
(33) a phosphono group,
(34) a sulfamoyl group,
(35) a mono-lower alkylsulfamoyl group (e.g., a mono-$C_{1-6}$ alkylsulfamoyl group such as N-methylsulfamoyl, N-ethylsulfamoyl, N-propylsulfamoyl, N-isopropylsulfamoyl, N-butylsulfamoyl and the like, and the like),
(36) a di-lower alkylsulfamoyl group (e.g., a di-$C_{1-6}$ alkylsulfamoyl group such as N,N-dimethylsulfamoyl, N,N-diethylsulfamoyl, N,N-dipropylsulfamoyl, N,N-dibutylsulfamoyl and the like, and the like),
(37) a lower alkylthio group (e.g., a $C_{1-6}$ alkylthio group such as methylthio, ethylthio, propylthio, isopropylthio, butylthio, sec-butylthio, tert-butylthio and the like, and the like),
(38) an arylthio group (e.g., a $C_{6-10}$ arylthio group such as phenylthio, naphthylthio and the like, and the like),
(39) a lower alkylsulfinyl group (e.g., a $C_{1-6}$ alkylsulfinyl group such as methylsulfinyl, ethylsulfinyl, propylsulfinyl, butylsulfinyl and the like, and the like),
(40) an arylsulfinyl group (e.g., a $C_{6-10}$ arylsulfinyl group such as phenylsulfinyl, naphthylsulfinyl and the like, and the like),
(41) a lower alkylsulfonyl group (e.g., a $C_{1-6}$ alkylsulfonyl group such as methylsulfonyl, ethylsulfonyl, propylsulfonyl, butylsulfonyl and the like, and the like),

(42) an arylsulfonyl group (e.g., a $C_{6-10}$ arylsulfonyl group such as phenylsulfonyl, naphthylsulfonyl and the like, and the like),
(43) a lower alkyl-carbonylamino group (e.g., a $C_{1-6}$ alkyl-carbonylamino group such as methylcarbonylamino and the like, and the like),
(44) a lower alkoxy-carbonylamino group (e.g., a $C_{1-6}$ alkoxy-carbonylamino group such as methoxycarbonylamino, ethoxycarbonylamino and the like, and the like),
(45) a carbonylamino group-lower alkyl group (e.g., a carbonylamino-$C_{1-6}$ alkyl group such as carbonylaminomethyl and the like, and the like),
(46) an aralkyloxy group (e.g., a $C_{7-12}$ aralkyloxy group such as benzyloxy and the like, and the like),
(47) a cycloalkyloxy group (e.g., a $C_{3-6}$ cycloalkyloxy group such as cyclopropyloxy, cyclobutyloxy, cyclopentyloxy, cyclohexyloxy and the like, and the like), and the like (to be referred to as substituent group (a) in the present specification) is used.

The "aromatic hydrocarbon ring" of the "optionally substituted aromatic hydrocarbon ring" may have 1-5, preferably 1-3, substituents mentioned above at the substitutable position(s) of the aromatic hydrocarbon ring. When the number of the substituents is two or more, the respective substituents may be the same or different. Furthermore, these substituents are optionally substituted by substituent group (a).

As the "aromatic hydrocarbon ring group" of the "optionally substituted aromatic hydrocarbon ring group" used in the present specification, $C_{6-14}$ aryl (e.g., phenyl, naphthyl and the like) is preferable, $C_{6-10}$ aryl is more preferable, and phenyl is particularly preferable.

As the "substituent" of the "optionally substituted aromatic hydrocarbon ring group", those exemplified in the above-mentioned substituent group (a) can be mentioned.

The "hydrocarbon ring group" of the "optionally substituted aromatic hydrocarbon ring group" may have 1-5, preferably 1-3, substituents mentioned above at the substitutable position(s) of the aromatic hydrocarbon ring group. When the number of the substituents is two or more, the respective substituents may be the same or different. Furthermore, these substituents are optionally substituted by substituent group (a).

As the "optionally substituted aromatic heterocycle" used in the present specification, a 5- to 7-membered monocyclic aromatic heterocycle or condensed aromatic heterocycle containing, as a ring-constituting atom besides carbon atom, 1 to 4 hetero atoms selected from an oxygen atom, a sulfur atom and a nitrogen atom can be mentioned. As the condensed aromatic heterocycle, a group resulting from condensation of such 5- to 7-membered monocyclic aromatic heterocycle and a 6-membered ring containing 1 or 2 nitrogen atoms, a benzene ring or a 5-membered ring containing one sulfur atom and the like can be mentioned.

Preferable examples of the "aromatic heterocycle" include 5- to 7-membered monocyclic aromatic heterocycles such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like; 8- to 16-membered (preferably, 8- to 12-membered) condensed aromatic heterocycle (preferably, heterocycle resulting from condensation of one or two (preferably one) 5- to 7-membered monocyclic aromatic heterocycles mentioned above and one or two (preferably one) benzene rings, or heterocycle resulting from condensation of 2-3 (preferably 2), the same or different heterocycles of the aforementioned 5- to 7-membered monocyclic aromatic heterocycle) such as benzofuran, isobenzofuran, benzo[b]thiophene, benzo[c]thiophene, indole, isoindole, 1H-indazole, benzimidazole, benzoxazole, 1,2-benzisoxazole, benzothiazole, 1,2-benzisothiazole, 1H-benzotriazole, quinoline, isoquinoline, cinnoline, quinazoline, quinoxaline, phthalazine, naphthyridine, purine, pteridine, carbazole, α-carboline, β-carboline, γ-carboline, acridine, phenoxazine, phenothiazine, phenazine, phenoxathiine, thianthrene, phenanthridine, phenanthrolin, indolizine, pyrrolopyridine, pyrrolo[1,2-b]pyridazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine, 1,2,4-triazolo[4,3-b]pyridazine and the like, and the like.

As the "substituent" of the "optionally substituted aromatic heterocycle", those exemplified in the above-mentioned substituent group (a) can be mentioned.

The "aromatic heterocycle" of the "optionally substituted aromatic heterocycle" optionally has 1-5, preferably 1-3, substituents mentioned above at the substitutable position(s) of the ring. When the number of the substituents is two or more, the respective substituents may be the same or different. Furthermore, these substituents are optionally substituted by substituent group (a).

Examples of the "optionally substituted 5- or 6-membered aromatic heterocycle" used in the present specification include 5- or 6-membered ones from among the above-mentioned "optionally substituted aromatic heterocycles". Preferable examples of the "5- or 6-membered aromatic heterocycle" include 5- or 6-membered monocyclic aromatic heterocycles such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like.

As the "substituent" of the "optionally substituted 5- or 6-membered aromatic heterocycle", those exemplified in the above-mentioned substituent group (a) can be mentioned.

The "5- or 6-membered aromatic heterocycle" of the "optionally substituted 5- or 6-membered aromatic heterocycle" optionally has 1-5, preferably 1-3, substituents mentioned above at the substitutable position(s) of the ring. When the number of the substituents is two or more, the respective substituents may be the same or different. Furthermore, these substituents are optionally substituted by substituent group (a).

Examples of the "optionally substituted 5- or 6-membered aromatic heterocyclic group" used in the present specification include a group derived from 5- or 6-membered ones from among the above-mentioned "optionally substituted aromatic heterocycles". Preferable examples of the "5- or 6-membered aromatic heterocyclic group" include 5- or 6-membered monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazol-1-yl, 1,2,4-triazol-3-yl) and the like.

As the "substituent" of the "optionally substituted 5- or 6-membered aromatic heterocyclic group", those exemplified in the above-mentioned substituent group (a) can be mentioned.

The "5- or 6-membered aromatic heterocyclic group" of the "optionally substituted 5- or 6-membered aromatic heterocyclic group" optionally has 1-5, preferably 1-3, substituents mentioned above at the substitutable position(s) of the ring. When the number of the substituents is two or more, the respective substituents may be the same or different. Furthermore, these substituents are optionally substituted by substituent group (a).

Examples of the "optionally substituted 5-membered aromatic heterocycle" used in the present specification include 5-membered ones from among the above-mentioned "optionally substituted aromatic heterocycle". Preferable examples of the "5-membered aromatic heterocycle" include 5-membered monocyclic aromatic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole and the like.

Examples of the "optionally substituted fused heterocycle wherein 5-membered aromatic heterocycle is fused with a 5- or 6-membered hydrocarbon ring or heterocycle" used in the present specification include the following.
(i) optionally substituted fused heterocycle wherein 5-membered aromatic heterocycle is condensed with 5- or 6-membered hydrocarbon ring Examples of the "5-membered aromatic heterocycle" include those similar to the "5-membered aromatic heterocycle" of the above-mentioned "optionally substituted 5-membered aromatic heterocycle". Examples of the "5- or 6-membered hydrocarbon ring" include a 6-membered aromatic hydrocarbon ring (i.e., benzene), and a 5- or 6-membered nonaromatic hydrocarbon ring. Examples of the "5- or 6-membered nonaromatic hydrocarbon ring" include 5- or 6-membered cycloalkane, cycloalkene, cycloalkadiene and the like can be mentioned, specifically, cyclopentane, cyclohexane, cyclopentene, cyclohexene, cyclopentadiene, and cyclohexadiene.

As the "substituent" of the "optionally substituted fused heterocycle wherein a 5-membered aromatic heterocycle is condensed with a 5- or 6-membered hydrocarbon ring", those exemplified in the above-mentioned substituent group (a) can be mentioned.

The fused heterocycle optionally has 1-5, preferably 1-3, substituents mentioned above at the substitutable position(s) of the ring. When the number of the substituents is two or more, the respective substituents may be the same or different. Furthermore, these substituents are optionally substituted by substituent group (a).
(ii) optionally substituted fused heterocycle wherein 5-membered aromatic heterocycle is condensed with 5- or 6-membered heterocycle Here, as the "5-membered aromatic heterocycle", those similar to the "5-membered aromatic heterocycle" of the above-mentioned "optionally substituted 5-membered aromatic heterocycle" can be mentioned. As the "5- or 6-membered heterocycle", 5- or 6-membered aromatic heterocycle and 5- or 6-membered non-aromatic heterocycle can be mentioned. As the "5- or 6-membered aromatic heterocycle", those similar to the "5- or 6-membered aromatic heterocycle" of the above-mentioned "optionally substituted 5- or 6-membered aromatic heterocycle" can be mentioned. As the "5- or 6-membered non-aromatic heterocycle", 5- or 6-membered saturated or unsaturated (preferably unsaturated) non-aromatic heterocycle and the like can be mentioned, specifically, pyrrolidine, tetrahydrofuran, thioran, piperidine, tetrahydropyran, thiane, morpholine, thiomorpholine, piperazine and the like can be mentioned.

As the "substituent" of the "optionally substituted fused heterocycle wherein a 5-membered aromatic heterocycle is condensed with a 5- or 6-membered heterocycle", those exemplified in the above-mentioned substituent group (a) can be mentioned.

The fused heterocycle optionally has 1-5, preferably 1-3, substituents mentioned above at the substitutable position(s) of the ring. When the number of the substituents is two or more, the respective substituents may be the same or different. Furthermore, these substituents are optionally substituted by substituent group (a).

Examples of the "lower alkyl group" of the "optionally substituted lower alkyl group" used in the present specification include a straight chain or branched chain $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, 2,2-dimethylbutyl, 3,3-dimethylbutyl, 2-ethylbutyl, heptyl, octyl and the like, with preference given to a $C_{1-6}$ alkyl group.

As the "substituent" of the "optionally substituted lower alkyl group", those exemplified in the above-mentioned substituent group (a) can be mentioned.

The "lower alkyl group" of the "optionally substituted lower alkyl group" has 1-5, preferably 1-3, substituents mentioned above at substitutable position(s). When the number of the substituents is two or more, the respective substituents may be the same or different. Furthermore, these substituents are optionally substituted by substituent group (a).

Examples of the "acyl group" used in the present specification include an optionally substituted hydrocarbon group-carbonyl group, an optionally substituted heterocyclic group-carbonyl group, an optionally substituted hydrocarbon group-sulfonyl group, an optionally substituted heterocyclic group-sulfonyl group and the like.

Examples of the "optionally substituted hydrocarbon group" of the "optionally substituted hydrocarbon group-carbonyl group" and "optionally substituted hydrocarbon group-sulfonyl group" include an aliphatic hydrocarbon group, a monocyclic saturated hydrocarbon group and an aromatic hydrocarbon group and the like, with preference given to those having a carbon number of 1-16. Specifically, for example, an alkyl group, an alkenyl group, an alkynyl group, a cycloalkyl group and an aryl group and the like can be used.

As the "alkyl group", for example, a $C_{1-6}$ alkyl group and the like are preferable and, for example, methyl, ethyl, propyl, isopropyl, butyl, isobutyl, sec-butyl, tert-butyl, pentyl, hexyl and the like are widely used.

As the "alkenyl group", for example, a $C_{2-6}$ alkenyl group and the like are preferable and, for example, vinyl, 1-propenyl, allyl, isopropenyl, butenyl, isobutenyl and the like are widely used.

As the "alkynyl group", for example, a $C_{2-6}$ alkynyl group and the like are preferable and, for example, ethynyl, propargyl, 1-propynyl and the like are widely used.

As the "cycloalkyl group", for example, a $C_{3-6}$ cycloalkyl group and the like are preferable and, for example, cyclopropyl, cyclobutyl, cyclopentyl and cyclohexyl are widely used.

As the "aryl group", for example, $C_{6-14}$ aryl group such as phenyl, 1-naphthyl, 2-naphthyl, biphenylyl, 2-anthryl and the like are preferable and, a $C_{6-10}$ aryl group is more preferable, for example, phenyl group and the like are widely used.

As the "substituent" of the "optionally substituted hydrocarbon group", those exemplified in the above-mentioned substituent group (a) can be mentioned.

The "hydrocarbon group" of the "optionally substituted hydrocarbon group" has 1-5, preferably 1-3, substituents mentioned above at substitutable position(s). When the number of the substituents is two or more, the respective substituents may be the same or different. Furthermore, these substituents are optionally substituted by substituent group (a).

As the "optionally substituted heterocyclic group" of the "optionally substituted heterocyclic group-carbonyl group" and "optionally substituted heterocyclic group-sulfonyl group", an aromatic heterocyclic group and a nonaromatic heterocyclic group can be mentioned.

As the aromatic heterocyclic group, for example, a 5- to 7-membered monocyclic aromatic heterocyclic group and a condensed aromatic heterocyclic group containing, as a ring-constituting atom besides carbon atom, 1 to 4 hetero atoms selected from an oxygen atom, a sulfur atom and a nitrogen atom, can be mentioned. As the condensed aromatic heterocyclic group, a group wherein such 5- to 7-membered monocyclic aromatic heterocyclic group is condensed with one or two 5- or 6-membered rings containing 1 or 2 nitrogen atoms, 5-membered rings containing one sulfur atom or benzene rings and the like, and the like can be mentioned.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazol-1-yl, 1,2,4-triazol-3-yl) and the like; condensed aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzoisooxazolyl (e.g., 7-benzoisooxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,5-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like.

As the nonaromatic heterocyclic group, for example, a 5- to 7-membered monocyclic nonaromatic heterocyclic group and a condensed nonaromatic heterocyclic group containing, as a ring-constituting atom besides carbon atom, 1 to 4 hetero atoms selected from an oxygen atom, a sulfur atom and a nitrogen atom, can be mentioned. As the condensed nonaromatic heterocyclic group, a group wherein such 5- to 7-membered monocyclic nonaromatic heterocyclic group is condensed with one or two 5- or 6-membered rings containing 1 or 2 nitrogen atoms, 5-membered rings containing one sulfur atom or benzene rings and the like, and the like can be mentioned.

Preferable examples of the nonaromatic heterocyclic group include
monocyclic nonaromatic heterocyclic groups such as pyrrolidinyl (e.g., 1-pyrrolidinyl), piperidinyl (e.g., piperidino), morpholinyl (e.g., morpholino), thiomorpholinyl (e.g., thiomorpholino), piperazinyl (e.g., 1-piperazinyl), hexamethyleniminyl (e.g., hexamethylenimine-1-yl), oxazolidinyl (e.g., oxazolidin-3-yl), thiazolidinyl (e.g., thiazolidin-3-yl), imidazolidinyl (e.g., imidazolidin-3-yl), dioxolyl (e.g., 1,3-dioxol-4-yl), dioxolanyl (e.g., 1,3-dioxolan-4-yl), dihydroooxadiazolyl (e.g., 4,5-dihydro-1,2,4-oxadiazol-3-yl), 2-thioxo-1,3-oxazolidin-5-yl, tetrahydropyranyl (e.g., 4-tetrahydropyranyl) and the like; condensed nonaromatic heterocyclic groups such as dihydroisoindolyl (e.g., 1,3-dihydro-2H-isoindol-2-yl), 4,5,6,7-tetrahydro-1-benzofuranyl (e.g., 4,5,6,7-tetrahydro-1-benzofuran-3-yl), 4,5,6,7-tetrahydro-1-benzothienyl (e.g., 4,5,6,7-tetrahydro-1-benzothiophen-3-yl), indanyl (e.g., indan-5-yl), chromenyl (e.g., 4H-chromen-2-yl, 2H-chromen-3-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), pyrazolidinyl (e.g., pyrazolidin-1-yl), tetrahydroquinolinyl (e.g., 1,2,3,4-tetrahydroquinolin-4-yl) and the like; and the like.

As the "substituent" of the "optionally substituted heterocyclic group", those exemplified in the above-mentioned substituent group (a) can be mentioned.

The "heterocyclic group" of the "optionally substituted heterocyclic group" has 1-5, preferably 1-3, substituents mentioned above at substitutable position(s). When the number of the substituents is two or more, the respective substituents may be the same or different. Furthermore, these substituents are optionally substituted by substituent group (a).

As the "optionally substituted lower alkylene group" used in the present specification, a straight chain or branched chain $C_{1-6}$ alkylene group such as methylene, ethylene, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$— and the like can be mentioned.

As the "substituent" of the "optionally substituted lower alkylene group", those exemplified in the above-mentioned substituent group (a) can be mentioned.

The "lower alkylene group" of the "optionally substituted lower alkylene group" has 1-5, preferably 1-3, substituents mentioned above at substitutable position(s). When the number of the substituents is two or more, the respective substituents may be the same or different. Furthermore, these substituents are optionally substituted by substituent group (a).

The present invention provides an sGC activating agent containing a compound represented by the formula (I) or a salt thereof (hereinafter compound and a salt thereof are also referred to simply as compound of the formula (I)) as an active ingredient. The compound of the formula (I) is explained in the following. Unless otherwise specified, the definition of each group is as defined above.

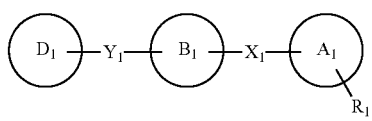

(I)

In the formula (I), $A_1$ ring is an aromatic hydrocarbon ring optionally further substituted or a 5- or 6-membered aromatic heterocycle optionally further substituted. Here, the "optionally further substituted by" means that $A_1$ ring is optionally substituted by a substituent other than $R_1$. That is, the substituent of the "aromatic hydrocarbon ring optionally further substituted" and the "5- or 6-membered aromatic heterocycle optionally further substituted" is a substituent other than $R_1$ on the $A_1$ ring.

$A_1$ ring is preferably "a 5- or 6-membered aromatic heterocycle optionally further substituted", particularly preferably "an optionally further substituted 5-membered aromatic heterocycle". Further preferably, $A_1$ ring is an "optionally further substituted pyrazole ring". As the "substituent" of the "optionally substituted pyrazole ring" as preferable $A_1$ ring, those exemplified in the above-mentioned substituent group (a) can be mentioned, which substituent is preferably selected from the group consisting of (1) a lower alkyl group (e.g., $C_{1-6}$ alkyl group) optionally substituted by a halogen atom or a lower alkoxy group (e.g., $C_{1-6}$ alkoxy group), (2) a cycloalkyl group, and (3) a lower alkoxy group (e.g., $C_{1-6}$ alkoxy group), particularly preferably selected from the group consisting of a lower alkyl group (e.g., $C_{1-6}$ alkyl group) optionally substituted by a halogen atom, and a lower alkoxy group (e.g., $C_{1-6}$ alkoxy group).

$A_1$ ring is also preferably an optionally further substituted benzene ring. As the "substituent" of the "optionally further substituted benzene ring" as preferable $A_1$ ring, those exemplified in the above-mentioned substituent group (a) can be mentioned, which substituent is preferably selected from the group consisting of (1) a halogen atom, (2) a $C_{1-6}$ alkyl group, (3) a $C_{1-6}$ alkoxy group, (4) an amino group, (5) an oxo group, (6) a $C_{1-6}$ alkyl-carbonylamino group and (7) a sulfonylamino group, more preferably selected from the group consisting of a halogen atom, a $C_{1-6}$ alkyl group optionally substituted by a halogen atom, and a $C_{1-6}$ alkoxy group, and particularly preferably a halogen atom.

The definition of each group exemplified as a preferable substituent is the same as for each group referred to in substituent group (a). The number of the substituents is 1 or 2, preferably 1. When the number of the substituents is 2, each substituent may be the same or different.

Particularly preferred as $A_1$ ring is a pyrazole ring free of a substituent besides $R_1$ or a benzene ring free of a substituent besides $R_1$.

In the formula (I), ring $B_1$ is an optionally substituted 5-membered aromatic heterocycle, or an optionally substituted fused heterocycle wherein 5-membered aromatic heterocycle is fused with a 5- or 6-membered hydrocarbon ring or heterocycle. Preferably, ring $B_1$ is an optionally substituted 5-membered aromatic heterocycle. Particularly preferably, ring $B_1$ is an optionally substituted thiazole ring, an optionally substituted oxazole ring, an optionally substituted furan ring, an optionally substituted thiophene ring, an optionally substituted oxadiazole ring or an optionally substituted thiadiazole ring. As the "substituent" of the "optionally substituted thiazole ring", "optionally substituted oxazole ring", "optionally substituted furan ring", "optionally substituted thiophene ring", "optionally substituted oxadiazole ring" and "optionally substituted thiadiazole ring" for preferable ring $B_1$, those exemplified in the above-mentioned substituent group (a) can be mentioned, which is preferably selected from the group consisting of (1) a $C_{1-6}$ alkyl group optionally substituted by a halogen atom, (2) a $C_{2-6}$ alkenyl group, (3) a halogen atom and (4) a $C_{3-6}$ cycloalkyl group. The definition of each group exemplified as a preferable substituent is the same as for each group referred to in substituent group (a). The number of the substituents is 1-3, preferably 1. When the number of the substituents is 2 or more, the respective substituents may be the same or different.

Preferably, ring $B_1$ is an optionally substituted thiazole ring, more preferably, a thiazole ring optionally substituted by a substituent selected from the group consisting of (1) a $C_{1-6}$ alkyl group optionally substituted by a halogen atom, (2) a $C_{2-6}$ alkenyl group, (3) a halogen atom and (4) a $C_{3-6}$ cycloalkyl group, with particularly preference given to unsubstituted thiazole ring.

In the formula (I), ring $D_1$ is an optionally substituted aromatic hydrocarbon ring (preferably optionally substituted $C_{6-14}$ arene (e.g., benzene, naphthalene and the like; particularly preferably benzene)) or optionally substituted aromatic heterocycle (preferably optionally substituted 5- to 7-membered monocyclic aromatic heterocycle). Preferably, ring $D_1$ is an optionally substituted aromatic hydrocarbon ring, and particularly preferably an optionally substituted benzene ring. As the substituent on the ring $D_1$, those exemplified in the above-mentioned substituent group (a) can be mentioned, which is preferably selected from the group consisting of
(1) a halogen atom,
(2) a $C_{1-6}$ alkyl group optionally substituted by (i) a halogen atom, (ii) a hydroxy group, (iii) an aryloxy group, (iv) an aryl group or (v) a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom,
(3) a $C_{1-6}$ alkoxy group optionally substituted by (i) a halogen atom, (ii) a cycloalkyl group, (iii) a $C_{1-6}$ alkoxy group, (iv) a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom, (v) a mono-$C_{1-6}$ alkylamino group optionally having substituents, (vi) an arylthio group or (vii) an aryl group,
(4) an amino group,
(5) a nitro group,
(6) a $C_{1-6}$ alkyl-carbonylamino group optionally substituted by a hydroxy group or a $C_{1-6}$ alkoxy group,
(7) a $C_{1-6}$ alkyl-carbonyl group,
(8) a $C_{2-6}$ alkenyl group optionally substituted by an aryl group, or a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom,
(9) a $C_{1-6}$ alkylamino group,
(10) a $C_{1-6}$ alkylsulfonyl group,
(11) an aryl group,
(12) a cyano group,
(13) a cycloalkyl group,
(14) an aralkyloxy group optionally substituted by a halogen atom,

(15) a $C_{2-6}$ alkynyl group optionally substituted by a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom,
(16) a carbonylamino-$C_{1-6}$ alkyl group optionally substituted by a 3- to 8-membered nitrogen-containing heterocyclic group optionally having substituents, and optionally containing, besides a carbon atom and one nitrogen atom, 1-3 hetero atoms selected from a nitrogen atom, an oxygen atom and a sulfur atom,
(17) an aralkyl group optionally substituted by a $C_{1-6}$ alkyl-carbonyl group, and
(18) a cycloalkyloxy group,
particularly preferably selected from the group consisting of a halogen atom, and a lower alkyl group (e.g., $C_{1-6}$ alkyl group) optionally substituted by a halogen atom (e.g., trihalo ($C_{1-6}$)alkyl group). The number of the substituents is 1-5, preferably 1 or 2. When the number of the substituents is two or more, the respective substituents may be the same or different. For example, a benzene ring substituted by a trihalo ($C_{1-6}$)alkyl group, which is optionally further substituted by a halogen atom etc., is preferable for ring $D_1$.

The definition of each group exemplified as a preferable substituent is the same as for each group referred to in substituent group (a).

In the formula (I), $R_1$ is a carboxyl group, a tetrazolyl group, an oxooxadiazolyl group, or —C(=O)NH—S(=O)$_2$R$_{11}$. Here, $R_{11}$ is an optionally substituted lower alkyl group (e.g., $C_{1-6}$ alkyl group), an acyl group, an optionally substituted aromatic hydrocarbon ring group, or an optionally substituted 5- or 6-membered aromatic heterocyclic group, and preferably, $R_{11}$ is an optionally substituted lower alkyl group (e.g., $C_{1-6}$ alkyl group).

As $R_1$, a carboxyl group is particularly preferable.

In the formula (I), $X_1$ is a bond or an optionally substituted lower alkylene group (preferably a $C_{1-6}$ alkylene group such as methylene group, ethylene group and the like). Here, as the "substituent" of the "optionally substituted lower alkylene group", those exemplified in the above-mentioned substituent group (a) can be mentioned, with preference given to a lower alkyl group (e.g., $C_{1-6}$ alkyl group) optionally substituted by a carboxyl group or an equivalent thereof (tetrazolyl group, oxooxadiazolyl group and the like). The number of the substituents is 1-5, preferably 1 or 2. When the number of the substituents is two or more, the respective substituents may be the same or different.

The definition of each group exemplified as a preferable substituent is the same as for each group referred to in substituent group (a).

In the formula (I), $Y_1$ is a bond, an optionally substituted lower alkylene group (e.g., $C_{1-6}$ alkylene group), or $L_{1a}$-$E_1$*$L_{1b}$. Here, $L_{1a}$ and $L_{1b}$ are the same or different and each is a bond or an optionally substituted lower alkylene group (e.g., $C_{1-6}$ alkylene group); $E_1$ is O, S, SO, SO$_2$, NR$_{12}$, O(=O), C(=O)NR$_{13}$, NR$^{13}$—C(=O)S(=O)$_2$NR$_{13}$, or NR$_{13}$—S(=O)$_2$ wherein R$_{12}$ is a hydrogen atom, an optionally substituted lower alkyl group (e.g., $C_{1-6}$ alkyl group), an acyl group, an optionally substituted aromatic hydrocarbon ring group, or an optionally substituted 5- or 6-membered aromatic heterocyclic group; R$_{13}$ is a hydrogen atom, an optionally substituted lower alkyl group, an optionally substituted aromatic hydrocarbon ring, or an optionally substituted 5- or 6-membered aromatic heterocyclic group. The "optionally substituted lower alkylene group" for $Y_1$ is preferably an unsubstituted lower alkylene group (e.g., $C_{1-6}$ alkylene group). As $L_{1a}$-$E_1$-$L_{1b}$, $L_{1a'}$ ($L_{1a'}$ is a bond or an unsubstituted lower alkylene group (e.g., $C_{1-6}$ alkylene group))-$E_{1'}$ ($E_{1'}$ is C(=O)NH, O, S or NH)-$L_{1b'}$ ($L_{1b'}$ is a bond or an unsubstituted lower alkylene group (e.g., $C_{1-6}$ alkylene group)) is preferable.

As $Y_1$, a bond or unsubstituted lower alkylene (e.g., $C_{1-6}$ alkylene group) is particularly preferable.

In the formula [I], when both $X_1$ and $Y_1$ are bonds, the substituent of the optionally substituted aromatic hydrocarbon ring, or the substituent of the optionally substituted 5- or 6-membered aromatic heterocycle, for ring $D_1$ is not a group represented by the following formula (i)

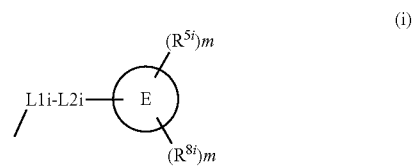

wherein
m is 0 or 1;
n is an integer of 0-2;
L1i is selected from the group consisting of O, S, C(R$^{12i}$)$_2$ and CF$_2$;
L2i is selected from the group consisting of a $C_{2-4}$ alkylene group, —C(R$^{12i}$)$_2$, —CF$_2$O and S (when L1i is O or S, L2i is not O or S);
R$^{12i}$ is independently selected from the group consisting of a hydrogen atom and a $C_{1-3}$ alkyl group (the $C_{1-3}$ alkyl group is optionally substituted by 1 to 3 fluorine atoms);
E is a ring selected from the group consisting of
1) a 6-10-membered aryl ring,
2) a 5- to 10-membered heteroaryl ring having 1, 2 or 3 hetero atoms independently selected from the group consisting of 0, 1, 2 or 3 N atoms, 0 or 1 O atom, and 0 or 1 S atom, and
3) a $C_{3-6}$ cycloalkyl ring;
when the above-mentioned aryl ring, heteroaryl ring and cycloalkyl ring are substituted by 0 or 1 R$^{5i}$, or 0, 1 or 2 R$^{8i}$, R$^{5i}$ is a group selected from the group consisting of
1) R$^{6i}$
2) —OR$^{6i}$,
3) a $C_{1-6}$ alkyl group optionally substituted by 1 to 3 fluorine atoms, and optionally monosubstituted by a group selected from the group consisting of a $C_{3-6}$ cycloalkyl group, an —O—$C_{1-4}$ alkyl group, OH, =O, an S(O)$_n$,$C_{1-4}$ alkyl group wherein n' is an integer of 0-2, —OR$^{6i}$ and R$^{6i}$,
4) a $C_{2-6}$ alkenyl group optionally substituted by 1 to 3 fluorine atoms, and optionally monosubstituted by a group selected from the group consisting of a —O—$C_{1-4}$ alkyl group, OH, =O, an S(O)$_n$,$C_{1-4}$ alkyl group wherein n' is an integer of 0-2, —OR$^6$ and R$^6$,
5) an —O—$C_{1-6}$ alkyl group (the alkyl group is optionally substituted by 1 to 3 fluorine atoms, and optionally monosubstituted by a group selected from the group consisting of a $C_{3-6}$ cycloalkyl group and R$^6$),
6) an —S—$C_{1-6}$ alkyl group,
7) a $C_{3-8}$ cycloalkyl group optionally substituted by 1 to 3 substituents independently selected from the group consisting of fluoro and a $C_{1-4}$ alkyl group, and optionally monosubstituted by a group selected from the group consisting of a $C_{1-4}$ alkyl group (the alkyl group is optionally substituted by 1 to 3 fluorine atoms), a —O—$C_{1-4}$ alkyl group, OH, =O, an S(O)$_n$,$C_{1-4}$ alkyl group wherein n' is an integer of 0-2, —OR$^{6i}$, R$^{6i}$ and NR$^{9i}$R$^{10i}$, 8) a $C_{5-8}$ cycloalkenyl group optionally substituted by 1 to 3 substituents independently selected from the group consisting of fluoro and a $C_{1-4}$ alkyl group, and optionally monosubstituted by a group selected from the group consisting of a $C_{1-4}$ alkyl group (the alkyl group is optionally substituted by 1 to 3 fluorine atoms), an $-O-C_{1-4}$ alkyl group, OH, =O, an $S(O)_{n'}C_{1-4}$ alkyl group wherein n' is an integer of 0-2, and $R^{6i}$, 9) a 5- or 6-membered heterocyclic group having 1 or 2 hetero atoms selected from the group consisting of N, O and S, and optionally monosubstituted by a group selected from the group consisting of a $C_{1-4}$ alkyl group (the alkyl group is optionally substituted by 1 to 3 fluorine atoms), an $-O-C_{1-4}$ alkyl group, and =O, and 10) a halogen atom;

$R^{6i}$ is a group selected from the group consisting of 1) phenyl optionally substituted by a group selected from the group consisting of halogen, OH, CN, a $C_{1-4}$ alkyl group (the alkyl group is optionally substituted by 1 to 3 fluorine atoms), a $-O-C_{1-4}$ alkyl group (the alkyl group is optionally substituted by 1 to 3 fluorine atoms), $NO_2$, an $S(O)_{n'}C_{1-4}$ alkyl group wherein n' is an integer of 0-2, a $C_{2-4}$ alkenyl group, an $-O-C_{2-4}$ alkenyl group, $NR^{9i}R^{10i}$ wherein $R^{9i}$ and $R^{10i}$ are each a group independently selected from the group consisting of a hydrogen atom and a $C_{1-6}$ alkyl group), and COOH, and 2) a 5- or 6-membered aromatic heterocyclic group having 1 or 2 hetero atoms selected from the group consisting of N, O and S and optionally substituted by a group selected from the group consisting of halogen, OH, CN, a $C_{1-4}$ alkyl group (the alkyl group is optionally substituted by 1 to 3 fluorine atoms), an $-O-C_{1-4}$ alkyl group (the alkyl group is optionally substituted by 1 to 3 fluorine atoms), $NO_2$, an $S(O)_{n'}C_{1-4}$ alkyl group wherein n' is an integer of 0-2, an $S(O)_{n'}$ aryl group wherein n' is an integer of 0-2, a $C_{2-6}$ alkenyl group, an $-O-C_{2-6}$ alkenyl group, $NR^{9i}R^{10i}$ wherein $R^{9i}$ and $R^{10i}$ are each a group independently selected from the group consisting of a hydrogen atom and a $C_{1-6}$ alkyl group, and COOH;

$R^{8i}$ is a group selected from the group consisting of a $C_{1-4}$ alkyl group (the alkyl group is optionally substituted by 1 to 3 fluorine atoms), a $C_{2-4}$ alkenyl group, a halogen atom, a $C_{3-6}$ cycloalkyl group (the cycloalkyl group is optionally substituted by 1 to 3 fluorine atoms), an $-O-C_{1-4}$ alkyl group (the alkyl group is optionally substituted by 1 to 3 fluorine atoms), an $-O-C_{2-4}$ alkenyl group, $NO_2$, an $S(O)_{n'}C_{1-4}$ alkyl group wherein n' is an integer of 0-2, and CN.

In the definitions of the formula (i), as the $C_{1-6}$ alkyl group, methyl, ethyl, propyl, isopropyl, butyl, isobutyl, sec-butyl, tert-butyl, pentyl, hexyl and the like can be mentioned. As the $C_{1-4}$ alkyl group and $C_{1-3}$ alkyl group, those exemplified as the above-mentioned $C_{1-6}$ alkyl group, which have a carbon number of 1-4 and 1-3, respectively, can be mentioned. As the $C_{3-8}$ cycloalkyl ring, cyclopropane, cyclobutane, cyclopentane, cyclohexane, cycloheptane, cyclooctane and the like can be mentioned. As the $C_{3-8}$ cycloalkyl group and $C_{3-6}$ cycloalkyl group, monovalent groups induced from the above-mentioned $C_{3-8}$ cycloalkyl ring, which have a carbon number of 3-8 and 3-6, respectively, can be mentioned. As the $C_{2-6}$ alkenyl group, vinyl, allyl, isopropenyl, butenyl, isobutenyl and the like can be mentioned. As the $C_{2-4}$ alkenyl group, those exemplified as the above-mentioned $C_{2-6}$ alkenyl group, which have a carbon number of 2-4, can be mentioned. As the $C_{5-8}$ cycloalkenyl group, cyclopentenyl, cyclohexenyl, cycloheptenyl, cyclooctenyl and the like can be mentioned. As the 6- to 10 membered aryl ring, $C_{5-10}$ arene exemplified as the above-mentioned "aromatic hydrocarbon ring" can be mentioned. As the 5-10-membered heteroaryl ring, those specifically exemplified as the above-mentioned "aromatic heterocycle", which have 1, 2 or 3 hetero atoms independently selected from the group consisting of 0, 1, 2 or 3 N atoms, 0 or 1 O atom, and 0 or 1 S atom, can be mentioned. As the 5- or 6-membered heterocyclic group, those exemplified as the "heterocyclic group" of the above-mentioned "optionally substituted heterocyclic group", which are 5- or 6-membered, can be mentioned.

Other groups are as defined for the aforementioned groups.

In the formula [I], when both $X_1$ and $Y_1$ are bonds, the substituent of the optionally substituted aromatic hydrocarbon ring, or the substituent of the optionally substituted 5- or 6-membered aromatic heterocycle for ring $D_1$ is preferably selected from a halogen atom, an alkyl group substituted by a halogen atom, and an alkoxy group substituted by a halogen atom.

In the formula (I), a compound represented by the following formula (II) is a novel compound, and the present invention provides a compound represented by the following formula (II) or a salt thereof (hereinafter to be also referred to as compound (II)). In the following, compound (II) is explained. Unless otherwise specified, the definition of each group is as defined above.

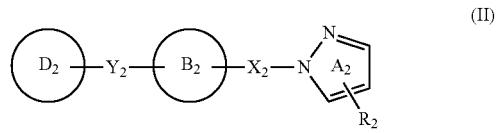

(II)

In the formula (II), ring $A_2$ is an optionally further substituted pyrazole ring. Here, the substituent of the "optionally further substituted pyrazole ring" means the substituents other than $R_2$ on ring $A_2$. As the "substituent" the "optionally further substituted pyrazole ring", those exemplified in the above-mentioned substituent group (a) can be mentioned, which is preferably selected from the group consisting of (i) a lower alkyl group optionally substituted by a halogen atom, and (ii) a lower alkoxy group, and particularly preferably selected from the group consisting of a $C_{1-6}$ alkyl group optionally substituted by a halogen atom, and a $C_{1-6}$ alkoxy group. The number of the substituents is 1-3, preferably 1 or 2. When the number of the substituents is two or more, the respective substituents may be the same or different.

The definition of each group exemplified as a preferable substituent is the same as for each group referred to in substituent group (a).

In the formula (II), ring $B_2$ is an optionally substituted 5-membered aromatic heterocycle, or an optionally substituted fused heterocycle wherein 5-membered aromatic heterocycle is fused with a 5- or 6-membered hydrocarbon ring or heterocycle. Preferably, ring $B_2$ is an optionally substituted 5-membered aromatic heterocycle. Particularly preferably, ring $B_2$ is an optionally substituted thiazole ring, an optionally substituted oxazole ring, an optionally substituted furan ring, an optionally substituted thiophene ring, an optionally substituted oxadiazole ring or an optionally substituted thiadiazole ring. As the substituent on each ring, those exemplified in the above-mentioned substituent group (a) can be mentioned, which is preferably selected from the group consisting of (1) a halogen atom, (2) a $C_{3-6}$ cycloalkyl group, (3) a $C_{2-6}$ alkenyl group and (4) a $C_{1-6}$ alkyl group optionally substituted by a halogen atom. Particularly preferably, ring $B_2$ is an optionally substituted thiazole ring, and as the substituent on ring $B_2$, those exemplified in the above-mentioned substituent group (a) can be mentioned, which is preferably selected from the group consisting of (1) a halogen atom, (2) a $C_{3-6}$ cycloalkyl group, (3) a $C_{2-6}$ alkenyl group and (4) a $C_{1-6}$ alkyl group optionally substituted by a halogen atom. Particularly preferably, the substituent is a $C_{1-6}$ alkyl group, more preferably methyl.

In the formula (II), ring $D_2$ is an optionally substituted aromatic hydrocarbon ring (preferably optionally substituted $C_{6-14}$ arene (e.g., benzene, naphthalene and the like; particularly preferably benzene)) or optionally substituted aromatic heterocycle (preferably optionally substituted 5- to 7-membered monocyclic aromatic heterocycle). Preferably, ring $D_2$ is an optionally substituted benzene ring. As the substituent on the ring $D_2$, those exemplified in the above-mentioned substituent group (a) can be mentioned, which is preferably selected from the group consisting of
(1) a halogen atom, (2) a lower alkyl group (e.g., $C_{1-6}$ alkyl group) optionally substituted by a halogen atom or an aryl group, (3) a lower alkoxy group (e.g., $C_{1-6}$ alkoxy group) optionally substituted by a halogen atom, (4) a nitro group, (5) a lower alkyl-carbonylamino group (e.g., a $C_{1-6}$ alkyl-carbonylamino group) optionally substituted by a lower alkoxy group (e.g., $C_{1-6}$ alkoxy group), (6) a lower alkanoyl group (e.g., $C_{1-6}$ alkyl-carbonyl group), and (7) a lower alkenyl group (e.g., a $C_{2-6}$ alkenyl group) optionally substituted by an aryl group.

The substituent on the ring $D_2$ is preferably selected from the group consisting of (1) an optionally substituted $C_{1-6}$ alkyl group, (2) an optionally substituted $C_{2-6}$ alkynyl group, (3) an optionally substituted $C_{2-6}$ alkenyl group, (4) an optionally substituted cycloalkyl group, (5) an optionally substituted $C_{1-6}$ alkoxy group, (6) an optionally substituted cycloalkyloxy group, (7) an optionally substituted amino group, (8) an optionally substituted cyano group, and (9) an optionally substituted sulfonyl group.

The substituent on the ring $D_2$ is particularly preferably selected from the group consisting of (1) a halogen atom, (2) an optionally substituted $C_{1-6}$ alkyl group, (3) an optionally substituted $C_{3-6}$ cycloalkyl group, (4) an optionally substituted $C_{1-6}$ alkoxy group, and (5) an optionally substituted amino group.

The number of the substituents is 1-3, preferably 1 or 2. When the number of the substituents is two or more, the respective substituents may be the same or different.

For example, as ring $D_2$, a benzene ring substituted by a $C_{1-6}$ alkyl group optionally substituted by a halogen atom and optionally further substituted by a halogen atom etc. is preferable.

As the "optionally substituted $C_{1-6}$ alkyl group", the above-mentioned "optionally substituted lower alkyl group", which has a carbon number of 1-6, can be mentioned.

As the "$C_{2-6}$ alkynyl group" of the "optionally substituted $C_{2-6}$ alkynyl group", those exemplified as the "lower alkynyl group" in the above-mentioned substituent group (a), which have a carbon number of 2-6, can be mentioned. As the "substituent" of the "optionally substituted $C_{2-6}$ alkynyl group", those exemplified for the above-mentioned substituent group (a) can be mentioned.

As the "optionally substituted $C_{2-6}$ alkenyl group", the above-mentioned "optionally substituted lower alkenyl group", which has a carbon number of 2-6, can be mentioned. As the "substituent" of the "optionally substituted $C_{2-6}$ alkenyl group", those exemplified for the above-mentioned substituent group (a) can be mentioned.

As the "cycloalkyl group" of the "optionally substituted cycloalkyl group", those exemplified as the "cycloalkyl group" in the above-mentioned substituent group (a) can be mentioned. As the "substituent" of the "optionally substituted cycloalkyl group", those exemplified for the above-mentioned substituent group (a) can be mentioned.

As the "$C_{1-6}$ alkoxy group" of the "optionally substituted $C_{1-6}$ alkoxy group", those exemplified as the "lower alkoxy group" in the above-mentioned substituent group (a), which have a carbon number of 1-6, can be mentioned. As the "substituent" of the "optionally substituted lower alkoxy group", those exemplified for the above-mentioned substituent group (a) can be mentioned.

As the "cycloalkyloxy group" of the "optionally substituted cycloalkyloxy group", those exemplified as the "cycloalkyloxy group" in the above-mentioned substituent group (a) can be mentioned. As the "substituent" of the "optionally substituted cycloalkyloxy group", those exemplified for the above-mentioned substituent group (a) can be mentioned.

As the "substituent" of the "optionally substituted amino group", those exemplified for the above-mentioned substituent group (a) can be mentioned. As the "optionally substituted amino group", specifically, $C_{1-6}$ alkoxy-$C_{1-6}$ alkyl-carbonylamino (e.g., methoxymethylcarbonylamino, ethoxymethylcarbonylamino and the like), hydroxy-$C_{1-6}$ alkyl-carbonylamino (e.g., hydroxymethylcarbonylamino and the like) and the like can be mentioned.

As the "substituent" of the "optionally substituted cyano group", those exemplified for those exemplified for the above-mentioned substituent group (a) can be mentioned.

As the "substituent" of the "optionally substituted sulfonyl group", those exemplified for the above-mentioned substituent group (a) can be mentioned.

In the formula (II), $R_2$ is a carboxyl group, a tetrazolyl group, an oxooxadiazolyl group, or —C(=O)NH—S(=O)$_2R_{21}$. Here, $R_{21}$ is an optionally substituted lower alkyl group (e.g., $C_{1-6}$ alkyl group), an acyl group, an optionally substituted aromatic hydrocarbon ring group, or an optionally substituted 5- or 6-membered aromatic heterocyclic group, and preferably, $R_{21}$ is an optionally substituted lower alkyl group (e.g., $C_{1-6}$ alkyl group).

As $R_2$, a carboxyl group is preferable.

$R_2$ is preferably present at the 4-position of the "optionally further substituted pyrazole ring" for ring $A_2$.

In the formula (II), $X_2$ is an optionally substituted lower alkylene group (e.g., $C_{1-6}$ alkylene group), preferably an optionally substituted methylene group. As the "substituent", those exemplified in the above-mentioned substituent group (a) can be mentioned, with preference given to a lower alkyl group (e.g., $C_{1-6}$ alkyl group) optionally substituted by a carboxyl group.

For example, a methylene group optionally substituted by 1 or 2 methyl is preferable as $X_2$.

The definition of each group exemplified as a preferable substituent is the same as for each group referred to in substituent group (a).

In the formula (II), $Y_2$ is a bond, an optionally substituted lower alkylene group (e.g., $C_{1-6}$ alkylene group), or $L_{2a}$-$E_2$-$L_{2b}$. Here, $L_{2a}$ and $L_{2b}$ are the same or different and each is a bond or an optionally substituted lower alkylene group (e.g., $C_{1-6}$ alkylene group); $E_2$ is O, S, SO, SO$_2$, NR$_{22}$, C(=O), C(=O)NR$_{23}$, NR$_{23}$—C(=O) S(=O)$_2$NR$_{23}$, or NR$_{23}$—S(=O)$_2$ wherein $R_{22}$ is a hydrogen atom, an optionally substituted lower alkyl group (e.g., $C_{1-6}$ alkyl group), an acyl group, an optionally substituted aromatic hydrocarbon ring group, or an optionally substituted 5- or 6-membered aromatic heterocyclic group; $R_{23}$ is a hydrogen atom, an optionally substituted lower alkyl group (e.g., $C_{1-6}$ alkyl group), an optionally substituted aromatic hydrocarbon ring, or an optionally substituted 5- or 6-membered aromatic heterocyclic group. $Y_2$ is preferably an optionally substituted lower alkylene group (e.g., $C_{1-6}$ alkylene group). $Y_2$ is preferably a bond.

In compound (II), the substituent of ring $D_2$ when ring $B_2$ is not an isoxazole ring, ring $B_2$ is a thiazole ring and ring $D_2$ is a benzene ring is not a [4-(1-propylbutyl)phenoxy]methyl group, and when ring $B_2$ is a pyrrole ring or indole ring, $X_2$ is not a substituted oxoethylene group.

In addition, 1-[(5-phenyl-2H-tetrazol-2-yl)methyl]-1H-pyrazole-3-carboxylic acid is not included in compound (II).

In the formula (II),
a compound wherein ring $A_2$ is a pyrazole ring optionally further substituted by a substituent selected from the group consisting of a $C_{1-6}$ alkyl group optionally substituted by a halogen atom and a $C_{1-6}$ alkoxy group; $R_2$ is a carboxyl group; and ring $D_2$ is a benzene ring substituted by a halogen atom, and a $C_{1-6}$ alkyl group optionally substituted by a halogen atom, and
a compound wherein ring $A_2$ is a pyrazole ring; ring $B_2$ is a thiazole ring optionally substituted by a $C_{1-6}$ alkyl group; ring $D_2$ is a benzene ring optionally substituted by substituent(s) selected from the group consisting of a halogen atom, and a $C_{1-6}$ alkyl group optionally substituted by a halogen atom; $R_2$ is a carboxyl group; $X_2$ is a $C_{1-6}$ alkylene group; and $Y_2$ is a bond are preferable as compound (II).

Particularly, as compound (II), 1-({4-[3-(trifluoromethyl)phenyl]-1,3-thiazol-2-yl}methyl)-1H-pyrazole-4-carboxylic acid, 1-({4-[2-fluoro-3-(trifluoromethyl)phenyl]-1,3-thiazol-2-yl}methyl)-1H-pyrazole-4-carboxylic acid, 1-({2-[2-fluoro-3-(trifluoromethyl)phenyl]-5-methyl-1,3-thiazol-4-yl}methyl)-1H-pyrazole-4-carboxylic acid, 1-({2-[3-chloro-5-(trifluoromethyl)phenyl]-5-methyl-1,3-thiazol-4-yl}methyl)-1H-pyrazole-4-carboxylic acid or a salt thereof is preferable.

In the formula (I), a compound represented by the following formula (III) is also a novel compound, the present invention provides a compound represented by the following formula (III) or a salt thereof (hereinafter to be also referred to as compound (III)). In the following, compound (III) is explained. Unless otherwise specified, the definition of each group is as defined above.

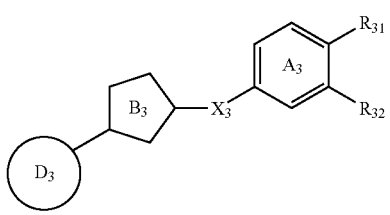

(III)

In the formula (III), ring $A_3$ is an optionally further substituted benzene ring. Here, the substituent of the "optionally further substituted benzene ring" means the substituents other than $R_{31}$ and $R_{32}$ on ring $A_3$. As the "substituent" of the "optionally further substituted benzene ring", those exemplified in the above-mentioned substituent group (a) can be mentioned, which is preferably selected from the group consisting of (i) a lower alkyl group (e.g., $C_{1-6}$ alkyl group) optionally substituted by a halogen atom, and (ii) a lower alkoxy group (e.g., $C_{1-6}$ alkoxy group). As the "substituent" of the "optionally further substituted benzene ring", halogen atom is also preferable. The number of the substituents is 1-3, preferably 1 or 2. When the number of the substituents is two or more, the respective substituents may be the same or different.

For example, $A_3$ is preferably an unsubstituted benzene ring.

The definition of each group exemplified as a preferable substituent is the same as for each group referred to in substituent group (a).

In the formula (III), ring $B_3$ is an optionally substituted thiazole ring, an optionally substituted oxazole ring, an optionally substituted furan ring, an optionally substituted thiophene ring, an optionally substituted oxadiazole ring or an optionally substituted thiadiazole ring. As the substituent on each ring, those exemplified in the above-mentioned substituent group (a) can be mentioned. As ring $B_2$, a thiazole ring optionally substituted by a $C_{1-6}$ alkyl group is preferable.

In the formula (III), ring $D_3$ is a benzene ring substituted by a halogen atom, a benzene ring substituted by a $C_{1-6}$ alkoxy group, or an optionally further substituted benzene ring substituted by a $C_{1-6}$ alkyl group substituted by a halogen atom.

Preferably, ring $D_3$ is an optionally further substituted benzene ring substituted by a trihalo($C_{1-6}$)alkyl group; a benzene ring substituted by the same or different 1 to 3 substituents selected from the group consisting of a halogen atom, and a $C_{1-6}$ alkyl group optionally substituted by a halogen atom; a benzene ring substituted by the same or different, 1 to 3 substituents selected from a halogen atom and a trihalo ($C_{1-6}$)alkyl group; a benzene ring optionally further substituted by a halogen atom, and substituted by a trihalo($C_{1-6}$) alkyl group; and a benzene ring substituted by the same or different, 1 or 2 halogen atoms. As the substituent that the "benzene ring substituted by a $C_{1-6}$ alkyl group substituted by a halogen atom" or "benzene ring substituted by a trihalo($C_{1-6}$)alkyl group" optionally has, those exemplified in the above-mentioned substituent group (a) can be mentioned, with preference given to a halogen atom.

The definition of each group exemplified as a preferable substituent is the same as for each group referred to in substituent group (a).

In the formula (III), one of $R_{31}$ and $R_{32}$ is a carboxyl group, a tetrazolyl group, an oxooxadiazolyl group, or a group represented by $-C(=O)NH-S(=O)_2R_{33}$ wherein $R_{33}$ is an optionally substituted $C_{1-6}$ alkyl group, an acyl group, an optionally substituted aromatic hydrocarbon group, or an optionally substituted 5- or 6-membered aromatic heterocyclic group, and the other is a hydrogen atom or a halogen atom.

$R_{31}$ is preferably a carboxyl group.

$R_{32}$ is preferably a hydrogen atom or a halogen atom.

In the formula (III), $X_3$ is an optionally substituted methylene group. As the "substituent" of the "optionally substituted methylene group", those exemplified in the above-mentioned substituent group (a) can be mentioned. $X_3$ is preferably an unsubstituted methylene group.

In the formula (III), a compound wherein ring $A_3$ is a benzene ring; ring $B_3$ is a thiazole ring optionally substituted by a $C_{1-6}$ alkyl group; ring $D_3$ is an optionally further substituted benzene ring substituted by a trihalo($C_{1-6}$)alkyl group; $R_{31}$ is a carboxyl group; $R_{32}$ is a hydrogen atom or a halogen atom; and $X_3$ is a $C_{1-6}$ alkylene group is preferable as compound (III).

Particularly, as compound (III), 4-({4-[3-(trifluoromethyl)phenyl]-1,3-thiazol-2-yl}methyl)benzoic acid; 4-{[4-(3,4- dichlorophenyl)-1,3-thiazol-2-yl]methyl}benzoic acid; 4-({4-[2-fluoro-3-(trifluoromethyl)phenyl]-1,3-thiazol-2-yl}methyl)benzoic acid or a salt thereof is preferable.

Moreover, the present invention provides a compound represented by the following formula (IA) or a salt thereof (hereinafter to be also referred to as compound (IA)) in a preferable embodiment. In the following, compound (IA) is explained. Unless otherwise specified, the definition of each group is as defined above.

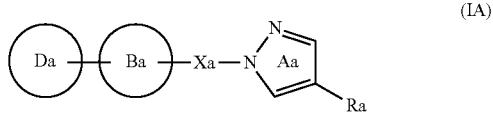

(IA)

In the formula (IA), ring $A_3$ is an optionally further substituted pyrazole ring. Here, the substituent of the "optionally further substituted pyrazole ring" means the substituents other than $R_a$ on ring $A_a$. As the "substituent" of the "optionally further substituted pyrazole ring", those exemplified in the above-mentioned substituent group (a) can be mentioned, which is preferably a lower alkyl group optionally substituted by a halogen atom. The definition of each group exemplified as a preferable substituent is the same as for each group referred to in substituent group (a).

In the formula (IA), ring $B_a$ is an optionally substituted 5-membered aromatic heterocycle, or an optionally substituted fused heterocycle wherein 5-membered aromatic heterocycle is fused with a 5- or 6-membered hydrocarbon ring or heterocycle. Preferably, ring $B_a$ is an optionally substituted 5-membered aromatic heterocycle. Particularly preferably, ring $B_a$ is an optionally substituted thiazole ring.

In the formula (IA), ring $D_a$ is an optionally substituted aromatic hydrocarbon ring (preferably optionally substituted $C_{6-14}$ arene (e.g., benzene, naphthalene and the like; particularly preferably benzene)) or optionally substituted 5- or 6-membered aromatic heterocycle. Preferably, ring $D_a$ is $C_{6-14}$-arene. As the substituent on the ring $D_a$, those exemplified in the above-mentioned substituent group (a) can be mentioned, which is preferably selected from the group consisting of (1) a halogen atom and (2) a lower alkyl group optionally substituted by a halogen atom (e.g., $C_{1-6}$ alkyl group). The definition of each group exemplified as a preferable substituent is the same as for each group referred to in substituent group (a).

In the formula (IA), $R_a$ is a carboxyl group, a tetrazolyl group, an oxooxadiazolyl group, or —C(=O)NH—S(=O)$_2R_{a1}$. Here, $R_{a1}$ is an optionally substituted lower alkyl group, an acyl group, an optionally substituted aromatic hydrocarbon ring group, or an optionally substituted 5- or 6-membered aromatic heterocyclic group. As $R_a$, a carboxyl group is preferable.

In the formula (IA), Xa is an optionally substituted lower alkylene group (e.g., $C_{1-6}$ alkylene group), preferably an optionally substituted methylene group. As the "substituent", those exemplified in the above-mentioned substituent group (a) can be mentioned, with preference given to a lower alkyl group (e.g., $C_{1-6}$ alkyl group) optionally substituted by a carboxyl group.

For example, an unsubstituted methylene group is preferable as Xa.

In the present specification, unless otherwise specified, compound (I) is a concept including compound (II) and compound (III) as well as compound (Ia). These compounds are also generally referred to as the compound of the present invention for convenience.

In the present invention of this application, examples of the salt of a compound represented by each formula (formula (I), formula (II), formula (III) and formula (IA)) include a pharmacologically acceptable salt and the like. Examples thereof include acid addition salt with an acid such as trifluoroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid and the like; salt with a metal salt such as sodium, potassium, magnesium, calcium and the like; salt with an organic base such as trimethylamine, triethylamine, pyridine, picoline, N-methylpyrrolidine, N-methylpiperidine, N-methylmorpholine and the like, and the like.

In the present invention, the compound of the present invention is provided and can be used as a prodrug. The prodrug means a compound which is converted to the compound of the present invention under the physiological condition in the living body by a reaction with an enzyme, a gastric acid, or the like, that is, by enzymatic oxidation, reduction, hydrolysis, etc.; by hydrolysis with gastric acid, etc. The prodrug of the present invention includes a compound wherein the amino group of the compound of the present invention is modified with acyl, alkyl or phosphoric acid (e.g., a compound wherein the amino group of the compound of the present invention is modified with eicosanoyl, alanyl, pentylaminocarbonyl, (5-methyl-2-oxo-1,3-dioxol-4-yl)methoxycarbonyl, tetrahydrofuranyl, pyrrolidylmethyl, pivaloyloxymethyl or t-butyl, etc.); a compound wherein the hydroxy group of the compound of the present invention is modified with acyl, alkyl, phosphoric acid or boric acid (e.g., a compound wherein the hydroxy group of compound (I) is modified with acetyl, palmitoyl, propanoyl, pivaloyl, succinyl, fumaryl, alanyl or dimethylaminomethylcarbonyl, etc.); a compound wherein a carboxyl group of the compound of the present invention is modified to ester or amide (e.g., compound wherein a carboxyl group of the compound of the present invention is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These prodrugs can be produced from the compound of the present invention by a method known per se.

In addition, the prodrug of the compound of the present invention may be a compound, which is converted into the compound of the present invention under the physiological conditions, as described in "Pharmaceutical Research and Development", Vol. 7 (Drug Design), pp. 163-198 (1990), published by Hirokawa Publishing Co.

When the compound of the present invention has isomers such as optical isomer, stereoisomer, positional isomer, rotational isomer and the like, any isomers and mixture of isomers are encompassed in the compound of the present invention. For example, when the compound of the present invention has an optical isomer, an optical isomer resolved from a racemate is also encompassed in the compound of the present invention. These isomers can be obtained as independent products by a synthesis means or a separation means (e.g., concentration, solvent extraction, column chromatography, recrystallization and the like) known per se.

The compound of the present invention may be a crystal or an amorphous form. When the compound of the present invention is a crystal, both a single crystal and crystal mixtures are encompassed in the compound of the present invention. Crystals can be produced by crystallization according to crystallization methods known per se.

The compound of the present invention may be a solvate (e.g., hydrate etc.) or a non-solvate, both of which are encompassed in the compound of the present invention.

The compound of the present invention may be labeled with an isotope (e.g., $^3H$, $^{14}C$, $^{35}S$, $^{125}I$ and the like) and the like.

Since the compound of the present invention has a strong sGC activating action, the compound of the present invention is useful as a prophylactic or therapeutic agent for diseases developed (or whose onset is promoted) in a mammal (e.g., human, monkey, cat, swine, horse, bovine, mouse, rat, guinea pig, dog, rabbit etc.) by decreased tissue blood flow due to vasoconstriction, cell proliferation or organ disorder expressed via attenuation of sGC action, or a factor induced by active oxygen or in the presence of active oxygen.

Examples of such disease include hypertension, blood pressure circadian rhythm abnormality, heart diseases (e.g., cardiac hypertrophy, acute heart failure, chronic heart failure including congestive failure, impaired vasodilation, cardiac myopathy, angina pectoris, myocarditis, atrial fibrillation, arrhythmia, tachycardia, myocardial infarction etc.), cerebrovascular disorders (e.g., asymptomatic cerebrovascular disorder, transient cerebral ischemia, cerebral apoplexy, cerebrovascular dementia, hypertensive encephalopathy, cerebral infarction etc.), cerebral edema, cerebral circulatory disorder, recurrence and sequela of cerebrovascular disorders (e.g., neurotic symptom, psychic symptom, subjective symptom, disorder in daily living activities etc.), ischemic peripheral circulation disorder, myocardial ischemia, venous insufficiency, progression of cardiac insufficiency after myocardial infarction, renal diseases (e.g., nephritis, glomerulonephritis, glomerulosclerosis, renal failure, thrombotic vasculopathy, complication of dialysis, organ dysfunction including nephropathy by radiation damage etc.), erectile dysfunction, arteriosclerosis including atherosclerosis (e.g., aneurysm, coronary sclerosis, cerebral arteriosclerosis, peripheral arterial sclerosis etc.), vascular hypertrophy, vascular hypertrophy or obliteration and organ disorders after intervention (e.g., percutaneous transluminal coronary angioplasty, stenting, coronary angioscopy, intravascular ultrasound, intracoronary thrombolysis etc.), vascular re-obliteration and restenosis after bypass, polycythemia, hypertension, organ disorder and vascular hypertrophy after transplantation, rejection after transplantation, ocular diseases (e.g., glaucoma, ocular hypertension etc.), thrombosis, multiple organ disorder, endothelial dysfunction, hypertensive tinnitus, other cardiovascular diseases (e.g., deep vein thrombosis, obstructive peripheral circulatory disorder, arteriosclerosis obliterans, thromboangiitis obliterans, ischemic cerebral circulatory disorder, Raynaud's disease, Buerger's disease etc.), metabolic and/or nutritional disorders (e.g., obesity, hyperlipidemia, hypercholesterolemia, hyperuricacidemia, hyperkalemia, hypernatremia etc.), nerve degeneration diseases (e.g., Alzheimer's disease, Parkinson's disease, amyotrophic lateral sclerosis, AIDS encephalopathy etc.), central nervous system disorders (e.g., disorders such as cerebral hemorrhage, cerebral infarction etc., and their sequela and complication, head injury, spinal injury, cerebral edema, sensory malfunction, sensory functional disorder, autonomic nervous system disorder, autonomic nervous system malfunction, multiple sclerosis etc.), dementia, defects of memory, disorder of consciousness, amnesia, anxiety symptom, catatonic symptom, discomfort mental state, psychopathies (e.g., depression, epilepsy, alcoholism etc.), inflammatory diseases (e.g., arthritis such as rheumatoid arthritis, osteoarthritis, rheumatoid myelitis, periostitis etc.; inflammation after operation and injury; remission of swelling; pharyngitis; cystitis; pneumonia; atopic dermatitis; inflammatory intestinal diseases such as Crohn's disease, ulcerative colitis etc.; meningitis; inflammatory ocular disease; inflammatory pulmonary diseases such as pneumonia, pulmonary silicosis, pulmonary sarcoidosis, pulmonary tuberculosis etc.), allergic diseases (e.g., allergic rhinitis, conjunctivitis, gastrointestinal allergy, pollinosis, anaphylaxis etc.), chronic obstructive pulmonary disease, interstitial pneumonia, pneumocytis carinni pneumonia, collagen diseases (e.g., systemic lupus erythematosus, scleroderma, polyarteritis etc.), hepatic diseases (e.g., hepatitis including chronic hepatitis, hepatic cirrhosis etc.), portal hypertension, digestive system disorders (e.g., gastritis, gastric ulcer, gastric cancer, gastric disorder after operation, dyspepsia, esophageal ulcer, pancreatitis, colon polyp, cholelithiasis, hemorrhoidal disease, varices ruptures of esophagus and stomach etc.), blood and/or myelopoietic diseases (e.g., erythrocytosis, vascular purpura, autoimmune hemolytic anemia, disseminated intravascular coagulation syndrome, multiple myelopathy etc.), bone diseases (e.g., fracture, refracture, osteoporosis, osteomalacia, bone Paget's disease, sclerosing myelitis, rheumatoid arthritis, osteoarthritis of the knee and joint tissue destruction and the like caused by diseases similar to these etc.), solid tumor, tumors (e.g., malignant melanoma, malignant lymphoma, cancer of digestive organs (e.g., stomach, intestine etc.) etc.), cancer and cachexia following cancer, metastasis cancer, endocrinopathy (e.g., Addison's disease, Cushing's syndrome, pheochromocytoma, primary aldosteronism etc.), Creutzfeldt-Jakob disease, urinary organ and/or male genital diseases (e.g., cystitis, prostatic hypertrophy, prostatic cancer, sex infectious disease etc.), female disorders (e.g., climacteric disorder, gestosis, endometriosis, hysteromyoma, ovarian disease, breast disease, sex infectious disease etc.), disease relating to environment and occupational factors (e.g., radiation hazard, hazard by ultraviolet, infrared or laser beam, altitude sickness etc.), respiratory diseases (e.g., cold syndrome, pneumonia, asthma, pulmonary hypertension, pulmonary thrombosis and pulmonary embolism etc.), infectious diseases (e.g., viral infectious diseases with cytomegalovirus, influenza virus, herpes virus etc., rickettsiosis, bacterial infectious disease etc.), toxemias (e.g., sepsis, septic shock, endotoxin shock, Gram-negative sepsis, toxic shock syndrome etc.), otorhinolaryngological diseases (e.g., Meniere's syndrome, tinnitus, dysgeusia, vertigo, disequilibrium, dysphagia etc.), skin diseases (e.g., keloid, hemangioma, psoriasis etc.), intradialytic hypotension, myasthenia gravis, systemic diseases such as chronic fatigue syndrome and the like.

In addition, since the compound of the present invention activates sGC in a sustained manner for a long time, it improves or suppresses progression of a disorder or abnormality in the biological function and physiological activity, which causes various diseases associated with adult diseases, aging and the like, and can primarily and secondarily prevent or suppress progression of a disease or pathology caused thereby. Examples of the disorder or abnormality in the biological function and physiological activity include a disorder or abnormality in the brain circulation or kidney circulation autoregulation, a circulatory disorders (e.g., peripheral, brain, microcirculatory etc.), cerebral blood barrier disorder, sodium chloride sensitivity, coagulation or fibrinolytic system abnormality, abnormality in the property of blood or blood cell components (e.g., enhancement in platelet aggregation, abnormality in red blood cell deformability, enhancement in leukocyte adhesiveness, increased blood viscosity etc.), production and promoted activity of growth factor or cytokine (e.g., PDGF, VEGF, FGF, interleukin, TNF-α, MCP-1 etc.), production and promoted infiltration of inflammatory system cell, promoted production of free radical, promotion of fatty deposition, endothelial dysfunction, endothelial, cell and organ disorder, edema, altered morphology of cell in smooth muscle and the like (altered morphology into proliferative form etc.), production and promoted function of vasoactive substance or thrombus-induced substance (e.g., endothelin, thromboxane $A_2$ etc.), abnormal coarctation of blood vessel and the like, abnormal metabolism (e.g., serum lipid abnormality, blood glucose abnormality etc.), abnormal growth of cells and the like, angiogenesis (including abnormal vasculogenesis in abnormal capillary net formation of atherosclerosis focal adventitia) and the like. Particularly, the compound of the present invention can be used as a primary or a secondary agent for the prophylaxis or treatment of organ disorder associated with various diseases (e.g., cerebrovascular disorder and organ disorders associated therewith, organ disorder associated with circulatory diseases, organ disorder associated with diabetes, organ disorder after intervention etc.). Especially, since the compound of the present invention has osmotic diuretic action and natriuretic action, it can be used as a kidney protector. Hence, the compound of the present invention can be advantageously used even when patients with insulin resistance, impaired glucose tolerance, diabetes or hyperinsulinemia have concomitantly developed the above-mentioned disease or pathology.

The compound of the present invention can be used as an insulin resistance improving agent, insulin sensitizer. The compound of the present invention has a hypoglycemic action, a hypolipidemic action, an insulin resistance improving activity, an insulin sensitivity enhancing action. The compound of the present invention normalizes the intracellular insulin signal transduction mechanism, which mainly causes insulin resistance, thereby reducing insulin resistance and enhancing insulin activity, and has a glucose tolerance improvement activity. Therefore, the compound or a salt thereof or a prodrug thereof in the present invention (including the compound of the present invention) can be used for mammals (e.g., human, monkey, cat, pig, horse, bovine, mouse, rat, guinea pig, dog, rabbit etc.) as an improving agent or an agent for the prophylaxis and/or treatment of the diseases in which insulin resistance is involved. Examples of such diseases include an agent for the prophylaxis or treatment of diabetes (e.g., type 1 diabetes, type 2 diabetes, gestational diabetes, obese diabetes); an agent for the prophylaxis or treatment of hyperlipidemia (e.g., hypertriglyceridemia, hypercholesterolemia, hypoHDL-emia, postprandial hyperlipemia); an insulin tolerance improving agent; an insulin sensitizer; an agent for the prophylaxis or treatment of impaired glucose tolerance (IGT); or an agent for preventing progression of impaired glucose tolerance to diabetes. In addition, the compound of the present invention can be used as, for example, an agent for the prophylaxis or treatment of hyperinsulinemia or hypertension associated with insulin resistance, hypertension associated with impaired glucose tolerance, hypertension associated with diabetes (e.g., type 2 diabetes etc.), hypertension associated with hyperinsulinemia, insulin resistance occurring in association with hypertension, impaired glucose tolerance occurring in association with hypertension, diabetes occurring in association with hypertension or hyperinsulinemia occurring in association with hypertension. Moreover, the compound or a salt thereof or a prodrug thereof in the present invention can also be used for the treatment of patients with high normal blood pressure who has developed diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia hypacusis, hypacusis, cerebrovascular disorder, peripheral blood circulation disorder], obesity, osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, hypertension, polycystic ovary syndrome, renal diseases (e.g., diabetic nephropathy, glomerulonephritis, glomerulosclerosis, nephrosis syndrome, hypertensive nephrosclerosis, end-stage renal disorder), muscular dystrophy, myocardial infarction, angina pectoris; cerebrovascular disorders (e.g., cerebral infarction, cerebral apoplexy), insulin resistance syndrome, syndrome X, metabolic syndrome (pathology having 3 or more selected from hyper-triglycerid (TG)emia, low HDL cholesteremia (HDL-C), hypertension, abdomen obesity and impaired glucose tolerance), hyperinsulinemia, perception disorder in hyperinsulinemia, tumor (e.g., leukemia, breast cancer, prostate cancer, skin cancer), irritable bowel syndrome, acute or chronic diarrhea, inflammatory diseases (e.g., arteriosclerosis (e.g., atherosclerosis etc.), rheumatoid arthritis, spondylitis deformans, osteoarthritis, lumbago, gout, post-surgical or posttraumatic inflammation, swelling, neuralgia, pharyngolaryngitis, cystitis, hepatitis (including nonalcoholic steatohepatitis), pneumonia, pancreatitis, inflammatory colitis, ulcerative colitis), visceral obesity syndrome and the like.

The compound of the present invention has an apoptosis suppressive activity and is also used as an agent for the prophylaxis or treatment of diseases involving promoted apoptosis. Here, examples of the disease involving promoted apoptosis include virus diseases (e.g., AIDS, fulminant hepatitis), neurodegenerative diseases (e.g., Alzheimer's disease, Parkinson's disease, amyotrophic lateral sclerosis, pigmentosa, cerebellar degeneration), myelodysplasia (e.g., aplastic anemia), ischemic diseases (e.g., myocardial infarction, cerebral apoplexy), hepatic diseases (e.g., alcoholic hepatitis, Hepatitis B, Hepatitis C), articular diseases (e.g., osteoarthritis), atherosclerosis and the like.

The compound of the present invention can be used for reducing visceral fats, inhibiting accumulation of visceral fats, ameliorating glycometabolism, ameliorating lipid metabolism, ameliorating insulin resistance, inhibiting oxidized LDL production, ameliorating lipoprotein metabolism, ameliorating coronary artery metabolism, preventing or treating cardiovascular complications, preventing or treating heart failure complications, lowering blood remnant, preventing or treating anovulation, preventing or treating hirsutism, preventing or treating hyperandrogenism, and the like.

The compound of the present invention is also used for the secondary prevention of various diseases mentioned above (e.g., cardiovascular event such as myocardial infarction etc.) and suppression of progression thereof.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/di is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can also be used as an agent for improving or the prophylaxis or treatment of diabetes, borderline type, impaired glucose tolerance, IFG (Impaired Fasting Glucose) and IFG (Impaired Fasting Glycemia), as determined according to the new diagnostic criteria, or further, as an agent for treating hypertension of hypertensive patients having not less than the above-mentioned diagnostic criteria (e.g., fasting blood sugar level of 126 mg/dl). Moreover, the compound of the present invention can prevent progression of borderline type, impaired glucose tolerance, IFG (Impaired Fasting Glucose) or IFG (Impaired Fasting Glycemia) into diabetes.

The compound of the present invention is effective as an agent for the suppression or improvement of cardiac hypofunction, progression of cardiac remodeling and aggravation of conditions in, or an agent for the suppression of decreased survival rate of, cardiac patients (e.g., cardiac hypertrophy, acute cardiac failure, chronic cardiac failure including congestive cardiac failure, impaired vasodilation, cardiomyopathy, angina pectoris, myocarditis, atrial fibrillation, arrhythmia, tachycardia, myocardial infarction and the like) with diabetes. In addition, it is effective for the prevention of the onset of cardiac diseases (e.g., cardiac hypertrophy, acute cardiac failure, chronic cardiac failure including congestive cardiac failure, impaired vasodilation, cardiomyopathy, angina pectoris, myocarditis, atrial fibrillation, arrhythmia, tachycardia, myocardial infarction and the like) and cerebrovascular disorders (e.g., asymptomatic cerebrovascular disorder, transient cerebral ischemic attack, cerebral apoplexy, cerebrovascular dementia, hypertensive encephalopathia, cerebral infarction and the like) in diabetic patients.

The compound of the present invention is useful as an agent for the prophylaxis or treatment of metabolic syndrome. Since patients with metabolic syndrome have an extreme high incidence of cardiovascular diseases as compared to patients with single lifestyle-related diseases, the prophylaxis or treatment of metabolic syndrome is quite important to prevent cardiovascular diseases.

The compound of the present invention can be used for the treatment of hypertension patients who have developed metabolic syndrome. Since patients with metabolic syndrome show markedly high onset rates of cardiovascular diseases as compared to those who have developed a single lifestyle-related disease, it is extremely important to prevent or treat metabolic syndrome for preventing cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in the United States, patients with at least three of abdominal obesity, hypertriglyceridemia, hypo-HDL cholesterolemia, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can be used for treating patients of hypertension with metabolic syndrome.

Since the compound of the present invention has an anti-inflammatory activity, it can be used as an anti-inflammatory agent for preventing or treating inflammatory diseases. Examples of the inflammatory diseases include inflammatory diseases due to various diseases such as arthritis (e.g. rheumatoid arthritis, osteoarthritis, rheumatoid myelitis, gouty arthritis, synovitis), asthma, allergic diseases, arteriosclerosis including atherosclerosis (aneurysm, coronary sclerosis, cerebral arterial sclerosis, peripheral arterial sclerosis, atrial fibrillation etc.), digestive tract diseases such as inflammatory intestine disease (e.g. Crohn's disease, ulcerative colitis), diabetic complications (diabetic neuropathy, diabetic vascular disorder), atopic dermatitis, chronic obstructive pulmonary disease, systemic lupus erythematosus, visceral inflammatory diseases (nephritic, hepatitis), autoimmune hemolytic anemia, psoriasis, nervous degenerative diseases (e.g. Alzheimer's disease, Parkinson's diseases, amyotrophic lateral sclerosis, AIDS encephalopathy), central nervous disorders (e.g. cerebrovascular disorders such as cerebral hemorrhage, cerebral infarct etc., head trauma, spinal damage, cerebral edema, multiple sclerosis etc.), meningitis, angina pectoris, cardiac infarct, congestive cardiac failure, vascular hypertrophy or occlusion and organ disorder after intervention (percutaneous transluminal coronary angioplasty, stenting, coronary angioscopy, intravascular ultrasound, intracoronary thrombolysis etc.), vascular reocclusion or restenosis after bypass operation, endothelial functional disorder, other circulatory diseases (intermittent claudication, obstructive peripheral circulatory disorder, arteriosclerosis obliterans, thromboangiitis obliterans, ischemic cerebral circulatory disorder, Raynaud's disease, Buerger's disease etc.), inflammatory ocular disease, inflammatory pulmonary diseases (e.g. chronic pneumonia, silicosis, pulmonary sarcoidosis, pulmonary tuberculosis), endometritis, toxemia (e.g. sepsis, septic shock, endotoxin shock, gram negative sepsis, toxin shock syndrome), cachexia (e.g. cachexia due to infection, carcinomatous cachexia, cachexia due to acquired immunodeficiency syndrome), cancer, Addison's disease, Creutzfeldt-Jakob disease, virus infection (e.g. infection of virus such as cytomegalovirus, influenza virus, herpes virus etc.), disseminated intravascular coagulation and the like.

The content of the compound of the present invention in a pharmaceutical composition is generally about 0.01-about 99.9 wt %, preferably about 0.1-about 50 wt %, relative to the entire preparation.

The dose of the compound of the present invention is determined in consideration of age, body weight, general health condition, sex, diet, administration time, administration method, clearance rate, combination of agents, the level of disease for which the patient is under treatment then, and other factors.

While the dose varies depending on the target disease, symptom, subject of administration, administration method and the like, for oral administration of the compound in the present invention as a therapeutic agent for adult essential hypertension, for example, it is preferably about 0.1-600 mg once to 3 times a day.

In addition, since the compound of the present invention shows superior safety, it can be administered for a long period.

The compound of the present invention can be used in combination with medicaments such as a therapeutic agent for diabetes, a therapeutic agent for diabetic complications, an anti-hyperlipidemia agent, an anti-arteriosclerotic agent, an anti-hypertensive agent, an antiobestic agent, a diuretic, an antigout agent, an antithrombotic agent, an anti-inflammatory agent, a chemotherapeutic agent, an immunotherapeutic agent, a therapeutic agent for osteoporosis, an anti-dementia agent, an erectile dysfunction amelioration agent, a therapeutic agent for urinary incontinence/urinary frequency and the like (hereinafter to be abbreviated as a concomitant agent). These concomitant agents may be low-molecular-weight compounds, high-molecular-weight proteins, polypeptides, antibodies, vaccines and the like. In this case, the timing of administration of the compound of the present invention and a combination agent is not limited, and the compound of the present invention and a combination agent only need to be combined at the time of administration. Examples of such administration mode include the following: (1) administration of a single preparation obtained by simultaneously processing the compound of the present invention and the concomitant agent, (2) simultaneous administration of two kinds of preparations of the compound of the present invention and the concomitant agent, which have been separately produced, by the same administration route, (3) administration of two kinds of preparations of the compound of the present invention and the concomitant agent, which have been separately produced, by the same administration route in a staggered manner, (4) simultaneous administration of two kinds of preparations of the compound of the present invention and the concomitant agent, which have been separately produced, by different administration routes, (5) administration of two kinds of preparations of the compound of the present invention and the concomitant agent, which have been separately produced, by different administration routes in a staggered manner (e.g., administration in the order of the compound of the present invention and the concomitant agent, or in the reverse order) and the like. The dose of the concomitant agent can be appropriately determined based on the dose clinically employed. The mixing ratio of the compound of the present invention and the concomitant agent can be appropriately selected according to the administration subject, administration route, target disease, condition, combination, and other factors. In cases where the administration subject is human, for example, the concomitant agent may be used in an amount of 0.01 to 100 parts by weight per part by weight of the compound of the present invention.

Examples of the therapeutic agents for diabetes include insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1), oral insulin preparation), insulin resistance improving agents (e.g., pioglitazone or a salt thereof (preferably hydrochloride), rosiglitazone or a salt thereof (preferably maleate), Netoglitazone (MCC-555), Rivoglitazone (CS-011), FK-614, a compound described in WO01/38325, Tesaglitazar (AZ-242), Ragaglitazar (N,N-622), Muraglitazar (BMS-298585), Edaglitazone (BM-13-1258), Metaglidasen (MBX-102), Naveglitazar (LY-519818), MX-6054, LY-510929, AMG131 (T-131) or a salt thereof, THR-0921), α-glucosidase inhibitors (e.g., voglibose, acarbose, miglitol, emiglitate), biguanides (e.g., phenformin, metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Vidagliptin (LAF237), P32/98, Sitagliptin (MK-431), P93/01, PT-100, Saxagliptin (BMS-477118), T-6666, TS-021), β3 agonists (e.g., AJ-9677), GPR40 agonists, GLP-1 receptor agonists [e.g., GLP-1, GLP-1MR agent, N,N-2211, AC-2993 (exendin-4), BIM-51077, Aib(8,35)hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095), 11β-hydroxysteroid dehydrogenase inhibitors (e.g., BVT-3498), adiponectin or agonists thereof, IKK inhibitors (e.g., AS-2868), leptin resistance improving drugs, somatostatin receptor agonists (compounds etc. described in WO01/25228, WO03/42204, WO98/44921, WO98/45285, WO99/22735), glucokinase activators (e.g., Ro-28-1675), ACC2 (acetyl-CoA carboxylase 2) inhibitor and the like.

Examples of the therapeutic agents for diabetic complications include aldose reductase inhibitors (e.g., tolrestat, epalrestat, zenarestat, zopolrestat, minalrestat, fidarestat, CT-112, ranirestat (AS-3201)), neurotrophic factors and enhancers thereof (e.g., NGF, NT-3, BDNF, neurotrophin production/secretion promoting agents described in WO01/14372 (e.g., 4-(4-chlorophenyl)-2-(2-methyl-1-imidazolyl)-5-[3-(2-methylphenoxy)propyl]oxazole)), PKC inhibitors (e.g., ruboxistaurin mesylate), AGE inhibitors (e.g., ALT946, pimagedine, N-phenacylthiazolium bromide (ALT766), EXO-226, Pyridorin, pyridoxamine), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitors and the like.

Examples of the anti-hyperlipidemia agents include statin compounds which are cholesterol synthesis inhibitors (e.g., cerivastatin, pravastatin, simvastatin, lovastatin, atorvastatin, fluvastatin, itavastatin or salts thereof (e.g., sodium salt etc.) etc.), squalene synthetase inhibitors (e.g., TAK-475 etc.) or fibrate compounds having a triglyceride lowering effect (e.g., bezafibrate, clofibrate, simfibrate, clinofibrate etc.), cholesterol absorption inhibitors (e.g., zechia), anion exchange resins (e.g., colestyramine), probucol, nicotinic acid drugs (e.g., nicomol, niceritrol), phytosterols (e.g., soysterol, γ-oryzanol), EPA, DHA and the like.

Examples of the anti-arteriosclerotic agent include acyl-coenzyme A cholesterol acyltransferase (ACAT) inhibitor (e.g., melinamide, (e.g., Avasimibe, Eflucimibe and the like), Lipid-rich plaques regressing agent (e.g., compounds described in WO02/06264, WO03/059900 and the like, and the like) and the like.

Examples of the antihypertensive agent include angiotensin converting enzyme inhibitor (e.g., captopril, enalapril, delapril and the like), angiotensin II antagonist (e.g., candesartan cilexetil, candesartan, losartan, losartan potassium, eprosartan, valsartan, telmisartan, irbesartan, tasosartan, olmesartan, olmesartan medoxomil and the like), calcium antagonist (e.g., manidipine, nifedipine, amlodipine, efonidipine, nicardipine and the like), β blocker (e.g., metoprolol, atenolol, propranolol, carvedilol, pindolol and the like), clonidine and the like.

Examples of the antiobesity agent include central-acting antiobesity agent (e.g., dexfenfluramine, fenfluramine, phentermine, sibutramine, amfepramone, dexamphetamine, mazindol, phenylpropanolamine, clobenzorex and the like), MCH receptor antagonists (e.g., SB-568849; SNAP-7941; compounds described in WO01/82925 and WO01/87834); neuropeptide γ antagonist (e.g., CP-422935); cannabinoid receptor antagonists (e.g., SR-141716, SR-147778); ghrelin antagonist; 11β-hydroxysteroid dehydrogenase inhibitor (e.g., BVT-3498)), pancreatic lipase inhibitors (e.g., orlistat and the like), β3 agonist (e.g., CL-316243, SR-58611-A, UL-TG-307, SB-226552, AJ-9677, BMS-196085, AZ40140 and the like), anorectic peptides (e.g., leptin, CNTF (ciliary neurotrophic factor) and the like), cholecystokinin agonist (e.g., lintitript, FPL-15849 and the like), anorexigenic agent (e.g., P-57) and the like.

Examples of the diuretics include xanthine derivatives (e.g., theobromine sodium salicylate, theobromine calcium salicylate etc.), thiazide preparations (e.g., ethiazide, cyclopenthiazide, trichloromethiazide, hydrochlorothiazide, hydroflumethiazide, benzylhydrochlorothiazide, penfluthiazide, poly5 thiazide, methyclothiazide etc.), antialdosterone preparations (e.g., spironolactone, triamterene etc.), carbonate dehydratase inhibitors (e.g., acetazolamide etc.), chlorobenzenesulfonamide preparations (e.g., chlortalidone, mefruside, indapamide etc.), azosemide, isosorbide, etacrynic acid, piretanide, bumetanide, furosemide and the like.

Examples of the antigout agents include allopurinol, probenecid, colchicine, benzbromarone, febuxostat, citrate and the like.

Examples of the antithrombotic agent include anticoagulant [e.g., heparin sodium, heparin calcium, warfarincalcium (warfarin), anti-thrombin drug (e.g., argatroban), activated blood coagulation factor X inhibitor (e.g., compound described in WO2004/048363, and the like) and the like], thrombolytic agent [e.g., tPA, urokinase], antiplatelet agent [e.g., aspirin, sulfinpyrazone (anturan), dipyridamole (persantin), ticlopidine (panaldine), cilostazol (pletal), GPIIb/IIIa antagonist (e.g., reopro and the like), clopidogrel and the like] and the like.

Examples of the anti-inflammatory agents include non-steroidal anti-inflammatory agents such as acetaminophen, fenasetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizol, tiaramide hydrochloride, zaltoprofen, gabexate mesylate, camostat mesylate, ulinastatin, colchicine, probenecid, sulfinpyrazone, benzbromarone, allopurinol, sodium gold thiomalate, sodium hyaluronate, sodium salicylate, morphine hydrochloride, salicylic acid, atropine, scopolamine, morphine, pethidine, levorphanol, ketoprofen, naproxen, oxymorphone and salts thereof etc., and the like.

Examples of the chemotherapeutic agents include alkylating agents (e.g., cyclophosphamide, ifosfamide etc.), metabolic antagonists (e.g., methotrexate, 5-fluorouracil etc.), anticancer antibiotics (e.g., mitomycin, adriamycin etc.), plant-derived anticancer agents (e.g., vincristine, vindesine, Taxol etc.), cisplatin, carboplatin, etoposide and the like. Of these, Furtulon or NeoFurtulon, which are 5 fluorouracil derivatives, and the like are preferable.

Examples of the immunotherapeutic agents include microorganism or bacterial components (e.g., muramyl dipeptide derivative, Picibanil etc.), polysaccharides having immunity potentiating activity (e.g., lentinan, schizophyllan, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to IL-1, IL-2, IL-12 and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium and the like.

Examples of the anti-dementia agents include tacrine, donepezil, rivastigmine, galanthamine and the like.

Examples of the erectile dysfunction amelioration agents include apomorphine, PDE5 (phosphodiesterase 5) inhibitor (e.g., sildenafil citrate) and the like.

Examples of the therapeutic agents for urinary incontinence frequency include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving activity established in animal models and clinical situations, such as cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentanoic acid etc.) [British Journal of Cancer, Vol. 68, pages 314-318, 1993], growth hormones, IGF-1, or antibodies to a cachexia-inducing factor such as TNF-α, LIF, IL-6, oncostatin M, production suppressants thereof and the like, can be used in combination with the compound of the present invention.

Furthermore, examples of the concomitant agent include nerve regeneration promoting drugs (e.g., Y-128, VX853, prosaptide), antidepressants (e.g., desipramine, amitriptyline, imipramine), antiepileptics (e.g., lamotrigine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin), α2 receptor agonists (e.g., clonidine), local analgesics (e.g., capsaicin), antianxiety drugs (e.g., benzodiazepines), dopamine agonists (e.g., apomorphine), midazolam, ketoconazole and the like.

The concomitant agent preferably includes diuretic, insulin preparation, insulin resistance improving agent, α-glucosidase inhibitor, biguanide, insulin secretagogue (preferably, sulfonylurea) and the like. Particularly, diuretic such as hydrochlorothiazide and the like, insulin resistance improving agent such as pioglitazone hydrochloride and the like are preferable.

The above-mentioned concomitant agent may be a combination of two or more kinds thereof combined at appropriate ratios.

When the compound of the present invention is used in combination with a concomitant agent, the amount of each drug can be reduced within a safe range in consideration of the opposite effect of these drugs. Particularly, the dose of the insulin resistance improving agent, insulin secretagogue and biguanide can be reduced from conventional level. As a result, the side effects possibly caused by these agents can be prevented safely. In addition, the dose of the therapeutic agent for diabetic complications, anti-hyperlipidemia agent or anti-hypertensive agent can be reduced and, as a result, the side effects possibly caused by these drugs can be effectively prevented.

Since the compound of the present invention potentiates hypoglycemic action of other insulin resistance improving agents, a combined use of the compound of the present invention or a salt thereof or a prodrug thereof (particularly the compound of the present invention) and other insulin resistance improving agent (preferably, pioglitazone hydrochloride) can markedly enhance a prophylactic and/or therapeutic effect on diseases involving insulin resistance such as type 2 diabetes and the like.

In the medicament of the present invention, the compound of the present invention can be orally or parenterally administered directly or as a blend with a pharmacologically acceptable carrier.

Examples of the dosage form of the medicament of the present invention containing the compound of the present invention for oral administration include tablet (including sugar-coated tablet, film-coated tablet, sublingual tablet, orally disintegrating tablet), pill, granule, powder, capsule (including soft capsule, microcapsule), syrup, emulsion, suspension, films (e.g., orally disintegrable films) and the like. Examples of the dosage form for parenteral administration include injection, drip, infusion, suppository and the like. In addition, it is also effective to combine the compound of the present invention with a suitable base (e.g., butyric acid polymer, glycolic acid polymer, butyric acid-glycolic acid copolymer, mixture of butyric acid polymer and glycolic acid polymer, polyglycerol ester of fatty acid and the like) to give a sustained-release preparation.

As a method of producing the compound of the present invention as the above-mentioned dosage form, a known production method generally used in the art can be applied. In addition, for production of the above-mentioned dosage form, excipient, binder, disintegrant, lubricant, sweetening agent, surfactant, suspending agent, emulsifier and the like, which are generally used in the pharmaceutical field for production of the dosage form, are appropriately added in suitable amounts as necessary.

For example, when the compound of the present invention is formulated into a tablet, excipient, binder, disintegrant, lubricant and the like can be added for production, and excipient, binder, disintegrant and the like can be added for production of pill and granule. When powder and capsule are produced, excipient and the like can be added for production, and sweetening agent and the like can be added for production of syrup, and suspending agent, surfactant, emulsifier and the like can be added for production of emulsion or suspension.

Examples of the excipient include lactose, sucrose, glucose, starch, saccharose, crystalline cellulose, Glycyrrhiza uralensis, mannitol, sodium hydrogen carbonate, calcium phosphate, calcium sulfate and the like.

Examples of the binder include 5 to 10 wt % starch glue liquid, 10 to 20 wt % gum arabic liquid or gelatin liquid, 1 to 5 wt % tragacanth liquid, carboxymethylcellulose liquid, sodium alginate liquid, glycerol and the like.

Examples of the disintegrant include starch, calcium carbonate and the like.

Examples of the lubricant include magnesium stearate, stearic acid, calcium stearate, purification talc and the like.

Examples of the sweetening agent include glucose, fructose, invert sugar, sorbitol, xylitol, glycerol, simple syrup and the like.

Examples of the surfactant include sodium lauryl sulfate, polysorbate 80, sorbitan monofatty acid ester, polyoxyl 40 and the like.

Examples of the suspending agent include gum arabic, sodium alginate, sodium carboxymethylcellulose, methylcellulose, bentonite and the like.

Examples of the emulsifier include gum arabic, tragacanth, gelatin, polysorbate 80 and the like.

Furthermore, when the compound of the present invention is produced into the above-mentioned dosage form, colorant, preservative, aromatic, corrigent, stabilizer, thickening agent and the like, which are generally used in the pharmaceutical field, can be appropriately added in suitable amounts when desired.

When the compound of the present invention is parenterally administered, it is generally administered in the form of a liquid (for example, injection). While a single dose varies depending on the subject of administration, target organ, symptom, administration method and the like, for example, administration of about 0.01 mg-about 100 mg, preferably about 0.01-about 50 mg, more preferably about 0.01-about 20 mg, per 1 kg body weight by intravenous injection is generally advantageous. Injection includes intravenous injection, subcutaneous injection, intradermal injection, muscular injection, drip injection and the like, and sustainable preparation includes iontoforesis transdermal agent and the like. Such injection is prepared by a method known per se, which includes dissolving, suspending or emulsifying compound (I) in an aseptic aqueous solution or oily solution. As an aqueous solution for injection, saline, isotonic solution (e.g., D-sorbitol, D-mannitol, sodium chloride and the like) containing glucose and other auxiliary agents and the like can be mentioned, which may be used in combination with suitable solubilizing agents such as alcohol (e.g., ethanol), polyalcohol (e.g., propylene glycol, polyethylene glycol), non-ionic surfactant (for example, polysorbate 80, HCO-50) and the like. As an oily solution, sesame oil, soybean oil and the like can be mentioned, which may be used in combination with solubilizing agents such as benzyl benzoate, benzyl alcohol and the like. In addition, buffering agent (e.g., phosphate buffer, sodium acetate buffer), soothing agent (e.g., benzalkonium chloride, procaine hydrochloride and the like), stabilizer (e.g., human serum albumin, polyethylene glycol and the like), preservative (e.g., benzyl alcohol, phenol and the like) and the like may be blended. A prepared injection is generally filled in an ampoule.

Production Methods

The compound of the present invention can be produced, for example, by the method shown below or a method analogous thereto and the like.

Unless particularly indicated, the starting compounds in the following reaction scheme 1 to reaction scheme 8 are easily available from commercially available ones, or can be produced according to a method known per se or a method analogous thereto. Each starting compound can also be used in the form of a salt.

The production methods of the compound of the present invention are explained below.

The compound represented by the formula (I) of the present invention (e.g., compounds (VI), (VII), (X), (XI) in reaction scheme 1, compound (XIV) in reaction scheme 2, compound (I') in reaction scheme 3 and reaction scheme 4, compounds (XXXV) and (XXXVIII) in reaction scheme 5, compound (XXXXIII) in reaction scheme 6, compound (XXXXVI) in reaction scheme 7, and compound (XXXXX) in reaction scheme 8) can be produced by the method shown below or a method analogous thereto and the like.

is alcohol such as methanol, ethanol and the like; a water-soluble solvent such as tetrahydrofuran, dioxane and the like or a mixed solvent thereof, and treating with an aqueous alkali solution such as aqueous sodium hydroxide solution, aqueous lithium hydroxide solution and the like.

The reaction is generally performed at 0° C.-150° C., preferably 20° C.-100° C.

A preferable specific example of the method including treatment with an acid include treating compound (V) with an aqueous inorganic acid solution such as an aqueous hydrochloric acid solution, an aqueous sulfuric acid solution and the like. In this case, a solvent such as acetic acid, formic acid and the like; a water-soluble solvent such as tetrahydrofuran, dioxane and the like, and the like may be added.

The reaction is generally performed at 0° C.-150° C., preferably 20° C.-100° C.

Step B

In step B, compound (IX) is hydrolyzed to give compound (VI).

For this reaction, a method of hydrolyzing a nitrile group is generally employed, such as a method including treating Reaction scheme 1

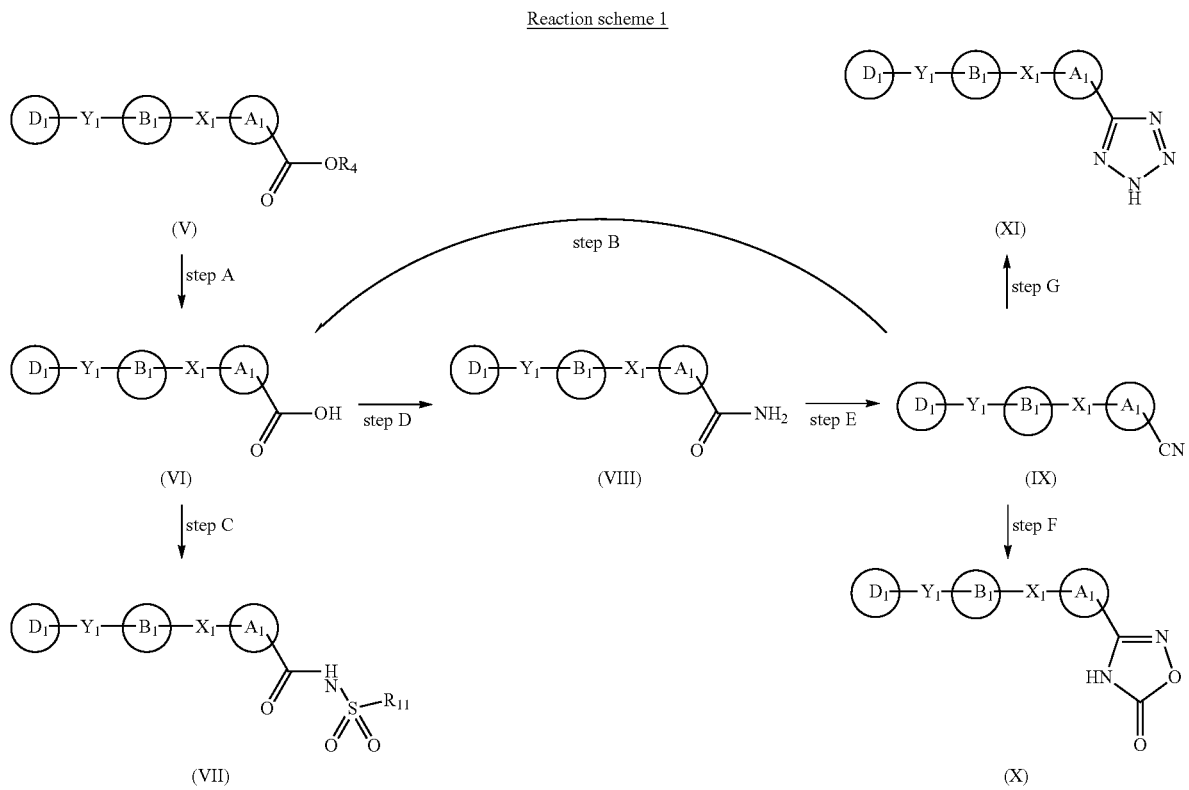

wherein each symbol is as defined above, and $R_4$ is an optionally substituted lower alkyl group.

Step A

In step A, compound (V) is hydrolyzed to give compound (VI).

For this reaction, a hydrolysis method of an ester group is generally employed and, for example, a method including treatment with an alkali such as lithium hydroxide, sodium hydroxide, potassium hydroxide and the like, or a method including treatment with an inorganic acid such as hydrochloric acid and the like is employed.

A preferable specific example of the method including treatment with an alkali include dissolving compound (V) in compound (IX) with alkali such as lithium hydroxide, sodium hydroxide, potassium hydroxide and the like, or a method including treating with inorganic acid such as hydrochloric acid and the like.

A preferable specific example of the method including treatment with alkali include dissolving compound (IX) in alcohol such as methanol, ethanol and the like; a water-soluble solvent such as tetrahydrofuran, dioxane and the like or a mixed solvent thereof, and treating with an aqueous alkali solution such as aqueous sodium hydroxide solution, aqueous lithium hydroxide solution and the like.

The reaction is generally performed at 0° C.-150° C., preferably 20° C.-100° C.

A preferable specific example of the method including treatment with an acid include treating compound (IX) with an aqueous inorganic acid solution such as an aqueous hydrochloric acid solution, an aqueous sulfuric acid solution and the like. In this case, a solvent such as acetic acid, formic acid and the like; a water-soluble solvent such as tetrahydrofuran, dioxane and the like, and the like may be added.

The reaction is generally performed at 0° C.-150° C., preferably 20° C.-100° C.

Step C

In step C, compound (VI) is reacted with a sulfoneamide derivative to give compound (VII). This reaction can be performed by using a sulfoneamide derivative and compound (VI) instead of compound (XXXIII) and compound (XXXIV) in step $L_1$ in the below-mentioned reaction scheme 5, and in the same manner as in (2) or (3) described in step $L_1$.

Examples of the sulfonamide derivative include a compound represented by the following formula

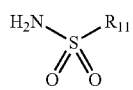

wherein the symbols are as defined above.

Step D

In step D, compound (VI) is amidated to give compound (VIII).

This reaction can be performed by using ammonia or a salt thereof and compound (VI) instead of compound (XXXIII) and compound (XXXIV) in step $L_1$ in the below-mentioned reaction scheme 5, and in the same manner as in (2) or (3) described in step $L_1$.

Examples of the ammonia salt include ammonium salt with is inorganic acid such as ammonium chloride, ammonium sulfate, ammonium carbonate and the like; ammonium salt with a lower (carbon number 1-3) organic acid such as ammonium acetate, ammonium formate, ammonium lactate and the like.

Ammonia or a salt thereof may be dissolved, before use, in an aqueous solution or other solvent that does not adversely influence the reaction.

Examples of the solvent that does not adversely influence the reaction include aromatic hydrocarbons such as benzene, toluene, xylene and the like; nitriles such as acetonitrile, propionitrile and the like; ethers such as tetrahydrofuran, 1,4-dioxane, diethyl ether and the like; halogenated hydrocarbons such as chloroform, dichloromethane and the like, and the like. Two or more kinds of these solvents may be used in combination at appropriate ratio.

The amount of ammonia or a salt thereof to be used is generally 1 mol—large excess, preferably 1-10 mol, per 1 mol of compound (VI).

Step E

In step E, compound (VIII) is subjected to a dehydrating reaction to give compound (IX).

This reaction is performed in a solvent that does not adversely influence the reaction by a method known per se, for example, by reacting 1,1'-carbonyldiimidazole with allyl bromide.

The amount of 1,1'-carbonyldiimidazole to be used is preferably about 1-about 10 mol per 1 mol of compound (VIII).

The amount of allylbromide to be used is preferably about 1-about 10 mol relative to 1,1'-carbonyldiimidazole.

Examples of the solvent that does not adversely influence the reaction include, aromatic hydrocarbons such as benzene, toluene, xylene and the like; nitriles such as acetonitrile, propionitrile and the like; ethers such as tetrahydrofuran, 1,4-dioxane, diethyl ether and the like; halogenated hydrocarbons such as chloroform, dichloromethane and the like, and the like. Two or more kinds of these solvents may be used in combination at appropriate ratio.

The reaction temperature is generally about −80° C.-about 150° C., preferably about 0-about 100° C.

The reaction time is generally about 0.5-about 20 hr.

Step E can also be performed in a solvent that does not adversely influence the reaction, for example, by a method known per se including treating compound (VIII) with a dehydrating agent such as phosphorus oxychloride, diphosphorus pentoxide, phosphorus pentachloride, N,N'-dicyclohexylcarbodiimide and the like. In the reaction, a base such as pyridine, triethylamine and the like may be added or used as a solvent.

The amount of the dehydrating agent to be used is preferably about 1-about 10 mol per 1 mol of compound (VIII).

Examples of the solvent that does not adversely influence the reaction include, aromatic hydrocarbons such as benzene, toluene, xylene and the like; nitriles such as acetonitrile, propionitrile and the like; ethers such as tetrahydrofuran, 1,4-dioxane, diethyl ether and the like; halogenated hydrocarbons such as chloroform, dichloromethane and the like, and the like. Two or more kinds of these solvents may be used in combination at appropriate ratio.

The reaction temperature is generally about −80° C.-about 150° C., preferably about 0-about 100° C.

The reaction time is generally about 0.5-about 20 hr.

Step F

In step F, cyano form (IX) is converted to amide oxime form which is subjected to ring closure reaction to give oxadiazolone form (X).

The reaction to give an amide oxime form is performed using, for example, 1-20 mol of hydroxylamine per 1 mol of compound (IX) in an organic solvent inert to the reaction.

Examples of the organic solvent include sulfoxides such as dimethyl sulfoxide and the like; amides such as N,N-dimethylformamide, N,N-dimethylacetamide and the like; alcohols such as methanol, ethanol and the like; ethers such as 1,4-dioxane, tetrahydrofuran and the like, and the like. Two or more kinds of these solvents may be used in combination at appropriate ratio.

When an inorganic acid salt such as hydroxylamine hydrochloride, hydroxylamine sulfate and the like, or an organic acid salt such as hydroxylamine oxalate and the like is used as hydroxylamine, the reaction is preferably performed in the co-presence of an equivalent amount or a small excess of a suitable base, for example, potassium carbonate, sodium hydrogen carbonate, sodium hydroxide, triethylamine, sodium methoxide, sodium hydride and the like.

When an inorganic acid salt or organic acid salt of hydroxylamine is used, the reaction may be performed using an organic solvent containing about 5-20% of water.

The reaction temperature is generally about −50° C.-about 150° C., preferably about 25° C.-about 100° C.

The reaction time is generally about 3-about 48 hr.

The reaction to obtain oxadiazolone form (X) from amide oxime form is performed using about 1-3 molar equivalents of a carbonylation reagent relative to amide oxime form in a solvent that does not adversely influence the reaction in the presence of an equivalent amount or a small excess of a base.

Examples of the carbonylation reagent include N,N'-carbonyldiimidazole, triphosgene, methyl chlorocarbonate, ethyl chlorocarbonate and the like.

Examples of the base include organic amines such as triethylamine, pyridine, diisopropylethylamine, 1,8-diazabicyclo[5.4.0]undec-7-ene and the like; inorganic salts such as potassium carbonate, sodium carbonate and the like, and the like.

Examples of the solvent include halogenated carbons such as dichloromethane, chloroform, carbon tetrachloride and the like; amides such as N,N-dimethylformamide, N,N-dimethylacetamide and the like; ethers such as diethyl ether, 1,4- dioxane, tetrahydrofuran and the like, and the like. Two or more kinds of these solvents may be used in combination at appropriate ratio.

The reaction temperature is generally about −50° C.-about 100° C., preferably about 0° C.-about 50° C.

The reaction time is generally about 0.1-about 5 hr.

Step G

In step G, compound (IX) is reacted with sodium azide to give compound (XI).

This reaction is performed in a solvent that does not adversely influence the reaction.

The amount of sodium azide to be used is preferably about 1-about 10 mol per 1 mol of compound (IX).

Examples of the solvent that does not adversely influence the reaction include aromatic hydrocarbons such as nitrobenzene and the like; amides such as N,N-dimethylformamide and the like; sulfoxides such as dimethyl sulfoxide and the like; and water. These solvents may be used in combination at appropriate ratio.

The reaction temperature is generally about −80° C.-about 180° C., preferably about 20-about 150° C.

The reaction time is generally about 0.5-about 20 hr.

Reaction scheme 2

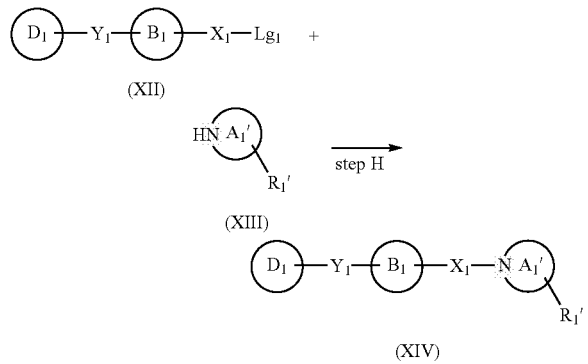

wherein each symbol is as defined above, $A_1'$ is an optionally further substituted 5-membered aromatic heterocycle containing a nitrogen atom, $Lg_1$ is a leaving group (e.g., halogen atom such as chlorine, bromine, iodine and the like; substituted sulfonic acid ester such as methanesulfonic acid ester and the like, and the like). $R_1'$ is a substituent defined for $R_1$, a group easily convertible to $R_1$ (e.g., alkoxycarbonyl group (e.g., $C_{1-6}$ alkoxy-carbonyl group such as methoxycarbonyl, ethoxycarbonyl and the like, and the like), a cyano group, a carbamoyl group, a protected tetrazolyl group (e.g., N-triphenylmethyltetrazolyl group and the like), a protected oxooxadiazolyl group (e.g., 4-[4-(tert-butoxycarbonyl)-5-oxo-4,5-dihydro-1,2,4-oxadiazol-3-yl group, 2-(tert-butoxycarbonyl)-5-oxo-2,5-dihydro-1,2,4-oxadiazol-3-yl group, 5-[(tert-butoxycarbonyl)oxy]-1,2,4-oxadiazol-3-yl group and the like) and the like).

Step H

In step H, compound (XII) is reacted with compound (XIII) to give compound (XIV). While this reaction can be performed in the absence of a base, it is generally performed in the presence of a base in a solvent that does not adversely influence the reaction.

Examples of the base include alkali metal salt such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like, and the like.

The amount of the base to be used is preferably about 1-about 5 molar equivalents relative to compound (XIII).

Examples of the solvent that does not adversely influence the reaction include aromatic hydrocarbons such as benzene, toluene, xylene and the like; nitriles such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like; and the like. Two or more kinds of these solvents may be used in combination at appropriate ratio.

This reaction is performed generally using about 0.3-3 mol of compound (XIII) per 1 mol of compound (XII).

The reaction temperature is generally about −50° C.-about 150° C., preferably about −10° C.-about 100° C.

The reaction time is generally about 0.5-about 20 hr.

Reaction scheme 3

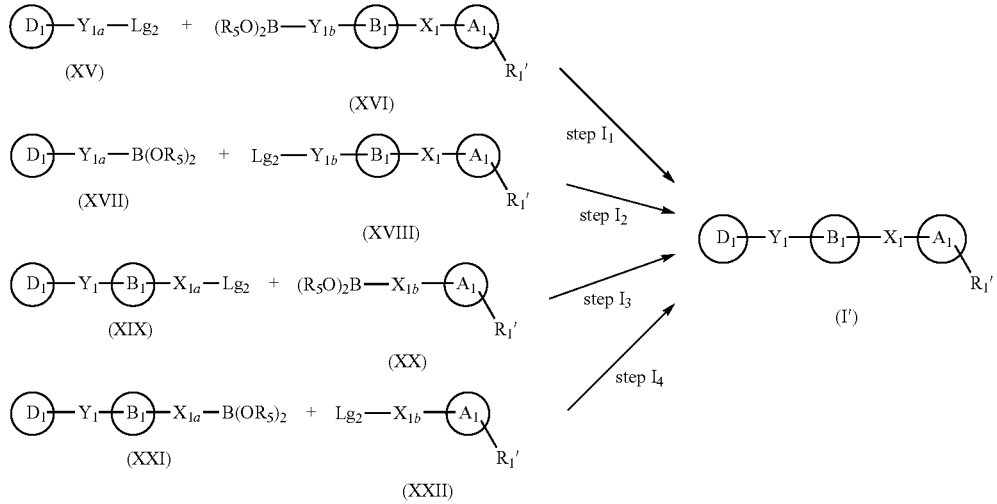

wherein each symbol is as defined above, $Lg_2$ is a leaving group (e.g., halogen atom such as chlorine, bromine, iodine and the like; substituted sulfonic acid ester such as trifluoromethanesulfonic acid ester and the like, and the like). $R_5$ is an optionally substituted lower alkyl group, and may construct a ring structure by the adjacent two $R_5$. $Y_{1a}$ and $Y_{1b}$ are the same or different and each is a bond, optionally substituted lower alkylene, or $L_{1a}$-$E_1$-$L_{1b}$, $X_{1a}$ and $X_{1b}$ are the same or different and each is a bond, or optionally substituted lower alkylene. $R_1'$ is a substituent defined for $R_1$, a group easily convertible to $R_1$ (e.g., alkoxycarbonyl group (e.g., a $C_{1-6}$ alkoxy-carbonyl group such as methoxycarbonyl, ethoxycarbonyl and the like, and the like), a cyano group, a carbamoyl group, a protected tetrazolyl group (e.g., N-triphenylmethyltetrazolyl group and the like), a protected oxooxadiazolyl group (e.g., 4-[4-(tert-butoxycarbonyl)-5-oxo-4,5-dihydro-1,2,4-oxadiazol-3-yl group, 2-(tert-butoxycarbonyl)-5-oxo-2,5-dihydro-1,2,4-oxadiazol-3-yl group, 5-[(tert-butoxycarbonyl)oxy]-1,2,4-oxadiazol-3-yl group and the like) and the like.

Step $I_1$

In step $I_1$, compound (XV) is reacted with compound (XVI) to give compound (I').

This reaction is performed by a method known per se, for example, the method described in Tetrahedron Letters, vol. 39, page 2933 (1998) and the like, or a method analogous thereto, in the presence of a base and a metal catalyst in a solvent that does not adversely influence the reaction.

Examples of the base include inorganic salts such as potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like, and the like can be mentioned. Two or more kinds of these bases may be used in combination at appropriately ratio.

The amount of the base to be used is preferably about 1-about 5 molar equivalents relative to compound (XVI).

Examples of the metal catalyst include palladium compound (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compound (e.g., tetrakis(triphenylphosphine)nickel and the like), rhodium compound (e.g., tris(triphenylphosphine)rhodium chloride and the like), platinum compound and the like.

The amount of the metal catalyst to be used is about 0.000001 mol-5 molar equivalents, preferably 0.0001 mol-1 molar equivalent, relative to compound (XVI).

Examples of the solvent that does not adversely influence the reaction include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like, sulfoxides such as dimethyl sulfoxide and the like, alcohols such as ethanol and the like, water and the like. Two or more kinds of these solvents may be used in combination at appropriate ratio.

This reaction is preferably performed under an inert gas (e.g., argon, nitrogen and the like) atmosphere.

This reaction is performed generally using about 0.3-3 mol of compound (XVI), per 1 mol of compound (XV).

The reaction temperature is generally about 0° C.-about 200° C., preferably 20° C.-about 100° C.

The reaction time is generally about 1-about 96 hr.

Step $I_2$, Step $I_3$, Step $I_4$

Step $I_2$, step $I_3$, step $I_4$ can be performed in the same manner as in step $I_1$.

Reaction scheme 4

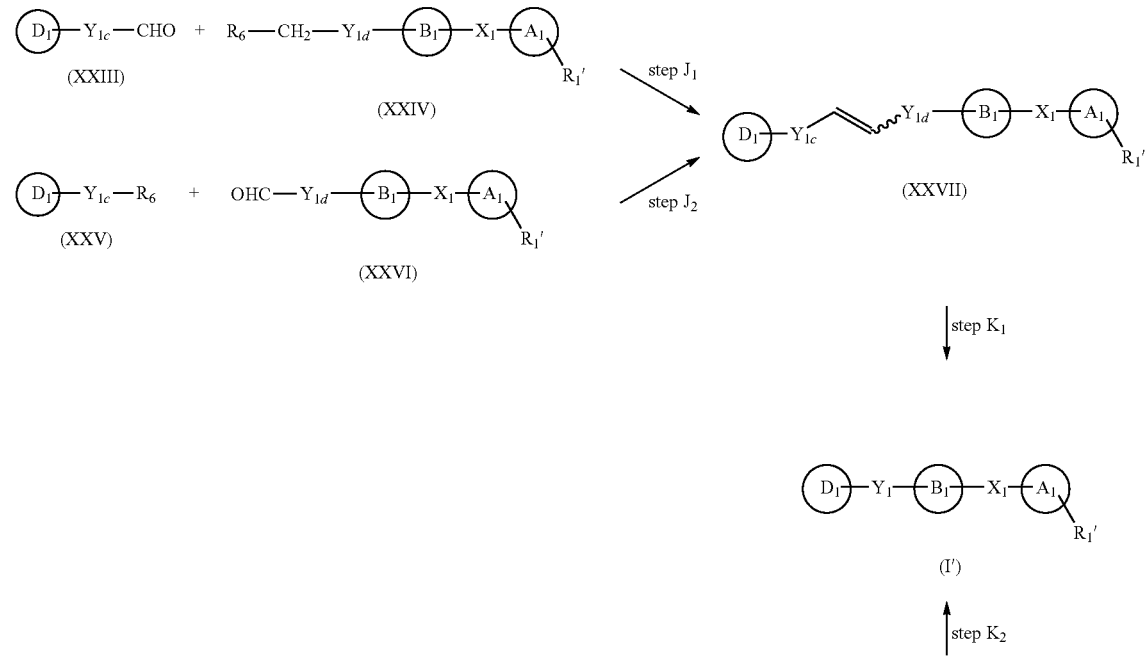

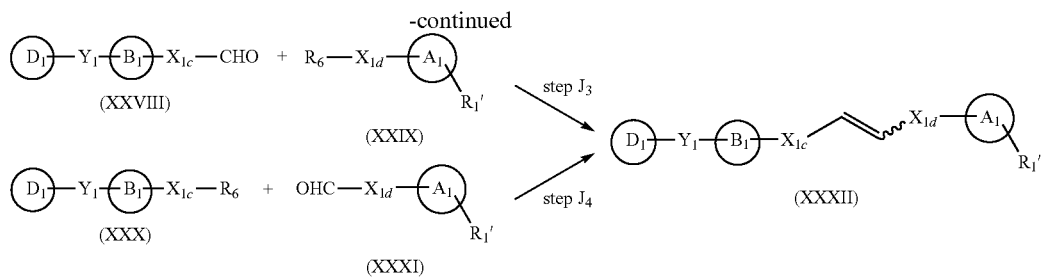

wherein each symbol is as defined above, $R_6$ is, for example, a triarylphosphonium group (e.g., a triphenylphosphonium group and the like), a dialkoxyphosphoryl group (e.g., a dimethoxyphosphoryl group and the like) and the like, compounds (XXIV), (XXV), (XXIX) and (XXX) may constitute a salt. As the form of the salt of these compounds, triphenyl phosphonium chloride, triphenyl phosphonium bromide, triphenyl phosphonium iodide and the like can be mentioned. $Y_{1c}$ and $Y_{1d}$ are the same or different and each is a bond, optionally substituted lower alkylene, or $L_{1a}$-$E_1$-$L_{1b}$, $X_{1c}$ and $X_{1d}$ are the same or different and each is a bond, or optionally substituted lower alkylene. $R_1'$ is a substituent defined for $R_1$, a group easily converted to $R_1$ (e.g., an alkoxycarbonyl group (e.g., a $C_{1-6}$ alkoxy-carbonyl group such as methoxycarbonyl, ethoxycarbonyl and the like, and the like), a cyano group, a carbamoyl group, a protected tetrazolyl group (e.g., an N-triphenylmethyltetrazolyl group and the like), a protected oxooxadiazolyl group (e.g., a 4-[4-(tert-butoxycarbonyl)-5-oxo-4,5-dihydro-1,2,4-oxadiazol-3-yl group, a 2-(tert-butoxycarbonyl)-5-oxo-2,5-dihydro-1,2,4-oxadiazol-3-yl group, a 5-[(tert-butoxycarbonyl)oxy]-1,2,4-oxadiazol-3-yl group and the like) and the like).

Step $J_1$

In step $J_1$, compound (XXIII) is reacted with compound (XXIV) to give compound (XXVII), and the reaction is performed by a method known per se, or a method analogous thereto.

Here, when $R_6$ of compound (XXIV) is a triarylphosphonium group, the reaction is generally performed in the presence of a base in a solvent that does not adversely influence the reaction.

Examples of the base include inorganic salts such as potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like, alkyl metals such as n-butyllithium and the like, and the like. Two or more kinds of these bases may be used in combination at appropriately ratio.

The amount of the base to be used is preferably about 1-about 3 molar equivalents relative to compound (XXIV).

Examples of the solvent that does not adversely influence the reaction include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; amides such as N,N-dimethylformamide and the like, sulfoxides such as dimethyl sulfoxide and the like, alcohols such as ethanol and the like, and the like. Two or more kinds of these solvents may be used in combination at appropriate ratio.

This reaction is performed generally using about 0.3-3 mol of compound (XXIII), per 1 mol of compound (XXIV).

The reaction temperature is generally about 0° C.-about 150° C., preferably 10° C.-about 100° C.

The reaction time is generally about 1-about 48 hr.

Here, when $R_6$ of compound (XXIV) is a dialkoxyphosphoryl group, the reaction is generally performed in the presence of a base in a solvent that does not adversely influence the reaction.

Examples of the base include metal hydrides such as sodium hydride and the like, metal alkoxides such as sodium methoxide, sodium ethoxide, potassium tert-butoxide and the likes, inorganic salts such as potassium carbonate, sodium carbonate, cesium carbonate and the like, and the like. Two or more kinds of these bases may be used in combination at appropriately ratio.

The amount of the base to be used is preferably about 1-about 3 molar equivalents relative to compound (XXIV).

Examples of the solvent that does not adversely influence the reaction include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; amides such as N,N-dimethylformamide and the like, sulfoxides such as dimethyl sulfoxide and the like, alcohols such as ethanol and the like, and the like. Two or more kinds of these solvents may be used in combination at appropriate ratio.

This reaction is performed generally using about 0.3-3 mol of compound (XXIII), per 1 mol of compound (XXIV).

The reaction temperature is generally about 0° C.-about 150° C., preferably 10° C.-about 100° C.

The reaction time is generally about 0.5-about 48 hr.

Step $J_2$, Step $J_3$, Step $J_4$

Step $J_2$, step $J_3$ and step $J_4$ can be performed in the same manner as in step $J_1$.

Step $K_1$

In step $K_1$, compound (XXVII) is reduced to give compound (I').

This reaction is performed, for example, according to a method including hydrogenation in the presence of a catalyst such as palladium and the like, and the like.

In a preferable example, compound (XXVII) is reacted in a solvent such as alcohols (e.g., methanol, ethanol and the like), ethers (e.g., tetrahydrofuran and the like), esters (e.g., ethyl acetate and the like), acetic acid and the like. Two or more kinds of these solvents may be used in combination at appropriate ratio. As the catalyst, a palladium catalyst such as palladium-carbon and the like, a platinum catalyst such as platinum-carbon and the like, a rhodium catalyst and the like can be mentioned.

This reaction is preferably performed under a hydrogen atmosphere at atm 1-10 generally using 5-100% (weight ratio) of a catalyst relative to compound (XXVII).

The reaction temperature is generally 0° C.-120° C.

The reaction time is generally about 0.5-about 20 hr.

Step K$_2$ step K$_2$ can be performed in the same manner as in step K$_1$.

Reaction scheme 5

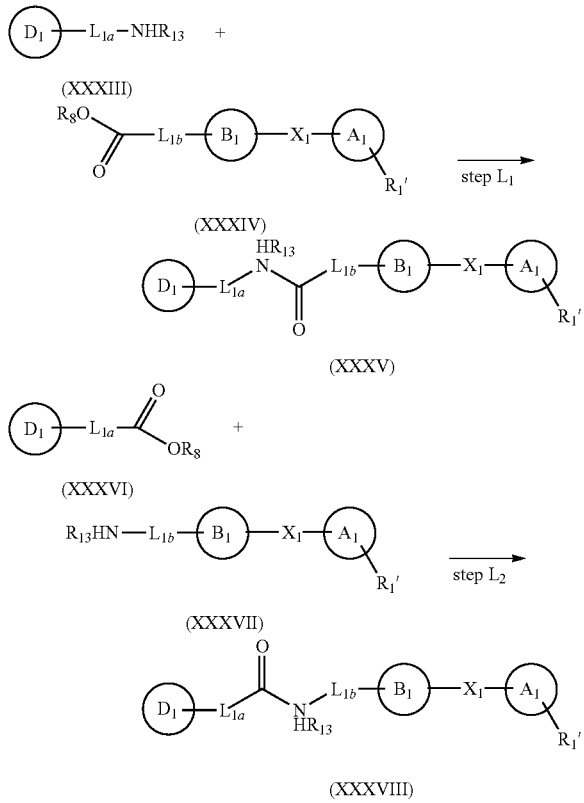

wherein each symbol is as defined above, R$_8$ is a hydrogen atom, an optionally substituted lower alkyl group and the like. R$_1$' is a substituent defined for R$_1$, a group easily converted to R$_1$ (e.g., an alkoxycarbonyl group (e.g., a C$_{1-6}$ alkoxy-carbonyl group such as methoxycarbonyl, ethoxycarbonyl and the like, and the like), a cyano group, a carbamoyl group, a protected tetrazolyl group (e.g., an N-triphenylmethyltetrazolyl group and the like), a protected oxooxadiazolyl group (e.g., 4-[4-(tert-butoxycarbonyl)-5-oxo-4,5-dihydro-1,2,4-oxadiazol-3-yl group, 2-(tert-butoxycarbonyl)-5-oxo-2,5-dihydro-1,2,4-oxadiazol-3-yl group, 5-[(tert-butoxycarbonyl)oxy]-1,2,4-oxadiazol-3-yl group and the like) and the like).

Step L$_1$

In step L$_1$, compound (XXXIII) is reacted with compound (XXXIV) to give compound (XXXV) wherein, for example, any of the following reactions is(are) performed:

(1) a method including reacting compound (XXXIII) with compound (XXXIV) when R$_8$ is an optionally substituted lower alkyl group, (2) a method including condensing compound (XXXIII) and compound (XXXIV) with a dehydrating condensing agent when R$_8$ is a hydrogen atom, (3) a method including activating carboxylic acid of compound (XXXIV) by a generally-known activation method and reacting same with compound (XXXIII) when R$_8$ is a hydrogen atom.

The amount of compound (XXXIII) to be used in the above-mentioned method (1) is preferably 0.3-3 mol per 1 mol of compound (XXXIV).

The reaction temperature of this method is generally 0-200° C. and the reaction time is generally 1-24 hr.

Examples of the dehydrating condensing agent to be used in the above-mentioned method (2) include N,N'-dicyclohexylcarbodiimide, 1-ethyl-3-(3-dimethylaminopropyl)carbodiimide, carbonyldiimidazole, N,N"-disuccinimidylcarbonate, 1H-benzotriazol-1-yloxytris(dimethylamino)phosphoniumhexafluorophosphate, O-(benzotriazol-1-yl)-N,N,N',N'-tetramethyluroniumtetrafluoroborate, diethyl cyanophosphate, diphenylphosphoryl azide and the like.

The amount of the dehydrating condensing agent to be used is generally 1-10 mol, preferably 1-5 mol, per 1 mol of compound (XXXIV).

The amount of compound (XXXIII) to be used in this method is preferably 0.3-3 mol per 1 mol of compound (XXXIV).

The reaction temperature of the method is generally 0-200° C. and the reaction time is generally 1-24 hr.

Examples of the method of activation of the carboxylic acid in the above-mentioned (3) include the following:

(a) a method including converting the carboxylic acid moiety of compound (XXXIV) to a mixed acid anhydride with chloroformate, pivaloyl chloride etc. and reacting same with compound (XXXIII), (b) a method including converting the carboxylic acid moiety of compound (XXXIV) to an acid chloride with oxalyl chloride, thionyl chloride etc. and reacting same with compound (XXXIII), and (c) a method including converting the carboxylic acid moiety of compound (XXXIV) and 1-hydroxylbenzotriazole (HOBt) to an ester with a dehydrating condensing agent etc. and reacting same with compound (XXXIII).

The amount of chloroformate, pivaloyl chloride and the like to be used in the above-mentioned method (a) is generally 1-10 mol, preferably, 1-5 mol, per 1 mol of compound (XXXIV).

The amount of compound (XXXIII) to be used in this method is preferably, 0.3-3 mol per 1 mol of compound (XXXIV).

The reaction temperature in this method is generally 0-200° C. and the reaction time is generally 1-24 hr.

The amount of oxalyl chloride, thionyl chloride and the like to be used in the above-mentioned method (b) is generally 1-10 mol, preferably 1-5 mol, per 1 mol of compound (XXXIV).

The amount of compound (XXXIII) to be used in this method is preferably 0.3-3 mol per 1 mol of compound (XXXIV).

The reaction temperature in this method is generally 0-200° C. and the reaction time is generally 0.5-24 hr.

The amount of 1-hydroxylbenzotriazole to be used in the above-mentioned method (c) is generally 1-10 mol, preferably 1-5 mol, per 1 mol of compound (XXXIV).

As the dehydrating condensing agent to be used in this method, those exemplified in the above-mentioned method (2) can be mentioned.

The amount of dehydrating condensing agent to be used is generally 1-10 mol, preferably 1-5 mol, per 1 mol of compound (XXXIV).

The amount of compound (XXXIII) to be used in this method is preferably 0.3-3 mol per 1 mol of compound (XXXIV).

The reaction temperature in this method is generally 0-200° C. and the reaction time is generally 1-24 hr.

Step $L_2$

Step $L_2$ can be performed in the same manner as in step $L_1$ except that compound (XXXVII) and compound (XXXVI) are used instead of compound (XXXIII) and compound (XXXIV).

In this method, the reaction is generally performed using about 0.3-3 mol of compound (XXXIX) per 1 mol of compound (XXXX).

The reaction time of this method is generally about 0.5-about 20 hr.

Reaction scheme 6

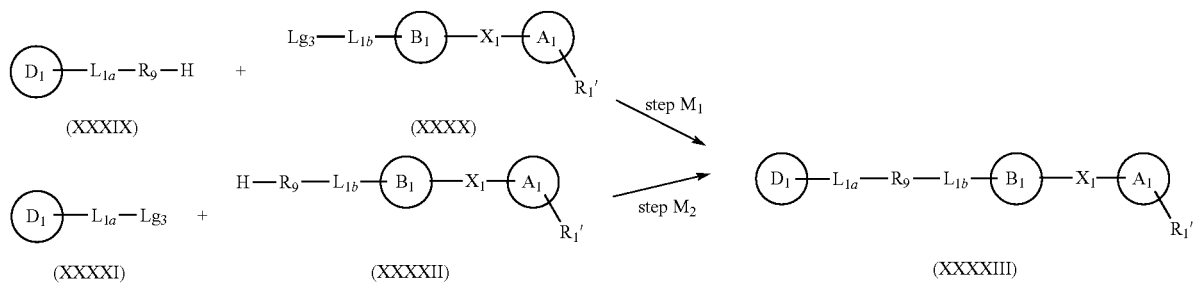

wherein each symbol is as defined above, $R_9$ is O, S or $NR_{12}$ (as defined above). $Lg_3$ is a leaving group (e.g., a halogen atom such as chlorine, bromine, iodine and the like; substituted sulfonic acid ester such as methanesulfonic acid ester and the like, and the like). $R_1'$ is a substituent defined for $R_1$, a group easily convertible to $R_1$ (e.g., an alkoxycarbonyl group (e.g., a $C_{1-6}$ alkoxy-carbonyl group such as methoxycarbonyl, ethoxycarbonyl and the like, and the like), a cyano group, a carbamoyl group, a protected tetrazolyl group (e.g., an N-triphenylmethyltetrazolyl group and the like), a protected oxooxadiazolyl group (e.g., a 4-[4-(tert-butoxycarbonyl)-5-oxo-4,5-dihydro-1,2,4-oxadiazol-3-yl group, a 2-(tert-butoxycarbonyl)-5-oxo-2,5-dihydro-1,2,4-oxadiazol-3-yl group, a 5-[(tert-butoxycarbonyl)oxy]-1,2,4-oxadiazol-3-yl group and the like) and the like).

Step $M_1$

In step $M_1$, compound (XXXIX) is reacted with compound (XXXX) to give compound (XXXXIII).

Generally, the reaction is performed according to a conventional method in the presence of a base in a solvent that does not adversely influence the reaction.

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like, and the like.

The amount of the base to be used is preferably about 1-about 5 molar equivalents relative to compound (XXXIX).

Examples of the solvent that does not adversely influence the reaction include aromatic hydrocarbons such as benzene, toluene, xylene and the like; nitriles such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like, and the like. Two or more kinds of these solvents may be used in combination at appropriate ratio.

The reaction temperature of this method is generally about −50° C.-about 150° C., preferably about −10° C.-about 100° C.

Step $M_2$

Step $M_2$ can be performed in the same manner as in step $M_1$ except that compound (XXXXII) and compound (XXXXI) are used instead of compound (XXXIX) and compound (XXXX).

Reaction scheme 7

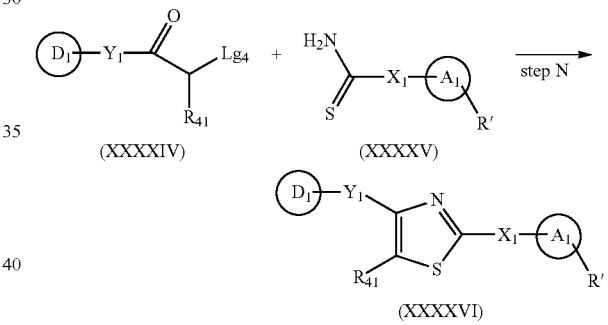

wherein each symbol is as defined above, $R_{41}$ is, for example, an optionally substituted lower alkyl group, an optionally substituted aromatic hydrocarbon ring group, or an optionally substituted 5- or 6-membered aromatic heterocyclic group and the like. $Lg_4$ is a leaving group (e.g., a halogen atom such as chlorine, bromine, iodine and the like; substituted sulfonic acid ester such as methanesulfonic acid ester and the like, and the like). $R_1'$ is a substituent defined for $R_1$, a group easily convertible to $R_1$ (e.g., a $C_{1-6}$ alkoxy-carbonyl group such as methoxycarbonyl, ethoxycarbonyl and the like, and the like, a cyano group, a carbamoyl group, a protected tetrazolyl group (e.g., N-triphenylmethyltetrazolyl group and the like), a protected oxooxadiazolyl group (e.g., a 4-[4-(tert-butoxycarbonyl)-5-oxo-4,5-dihydro-1,2,4-oxadiazol-3-yl group, a 2-(tert-butoxycarbonyl)-5-oxo-2,5-dihydro-1,2,4-oxadiazol-3-yl group, a 5-[(tert-butoxycarbonyl)oxy]-1,2,4-oxadiazol-3-yl group and the like) and the like).

Step N

In step N, compound (XXXXIV) is reacted with compound (XXXXV) to give compound (XXXXVI). This reaction is generally performed under conditions free of a base or in the presence of a base in a solvent that does not adversely influence the reaction.

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; and the like.

When the reaction is performed in the presence of a base, the amount of the base to be used is preferably about 1-about 5 molar equivalents relative to compound (XXXXIV).

Examples of the solvent that does not adversely influence the reaction include aromatic hydrocarbons such as benzene, toluene, xylene and the like; nitriles such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like, alcohols such as, ethanol and the like, and the like. Two or more kinds of these solvents may be used in combination at appropriate ratio.

This reaction is generally performed using about 0.3-3 mol of compound (XXXXV) per 1 mol of compound (XXXXIV).

The reaction temperature is generally about −50° C.-about 150° C., preferably about 0° C.-about 100° C.

The reaction time is generally about 0.5-about 48 hr.

Reaction scheme 8

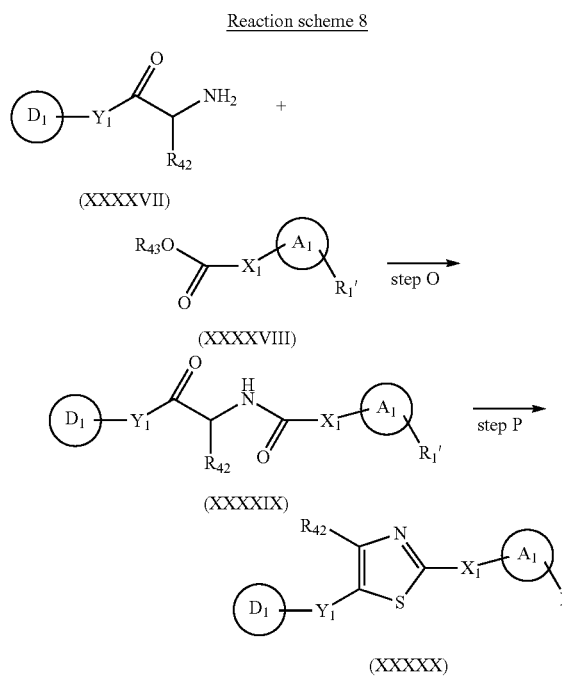

(XXXXVII)

(XXXXVIII)

(XXXXIX)

(XXXXX)

wherein each symbol is as defined above, $R_{42}$ is, for example, an optionally substituted lower alkyl group, an optionally substituted aromatic hydrocarbon ring group, or an optionally substituted 5- or 6-membered aromatic heterocyclic group and the like. $R_{43}$ is, for example, a hydrogen atom, an optionally substituted lower alkyl group and the like. $R_1'$ is a substituent defined for $R_1$, a group easily convertible to $R_1$ (e.g., a $C_{1-6}$ alkoxy-carbonyl group such as methoxycarbonyl, ethoxycarbonyl and the like, and the like, a cyano group, a carbamoyl group, a protected tetrazolyl group (e.g., an N-triphenylmethyltetrazolyl group and the like), a protected oxooxadiazolyl group (e.g., a 4-[4-(tert-butoxycarbonyl)-5-oxo-4,5-dihydro-1,2,4-oxadiazol-3-yl group, a 2-(tert-butoxycarbonyl)-5-oxo-2,5-dihydro-1,2,4-oxadiazol-3-yl group, a 5-[(tert-butoxycarbonyl)oxy]-1,2,4-oxadiazol-3-yl group and the like) and the like).

Step O

In step O, compound (XXXXVII) is reacted with compound (XXXXVIII) to give compound (XXXXIX).

Step O can be performed in the same manner as in step $L_1$ except that compound (XXXXVII) and compound (XXXXVIII) are used instead of compound (XXXIII) and compound (XXXIV).

Step P

In step P, compound (XXXXX) is obtained from compound (XXXXIX). This reaction is performed, for example, using a thiocarbonylation reagent such as 2,4-bis(4-methoxyphenyl)-1,3,2,4-dithiadiphosphetane-2,4-disulfide (Lawesson reagent) and the like in a solvent that does not adversely influence the reaction.

Examples of the solvent that does not adversely influence the reaction include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; and the like. Two or more kinds of these solvents may be used in combination at appropriate ratio.

This reaction is performed preferably using about 1-5 mol of 2,4-bis(4-methoxyphenyl)-1,3,2,4-dithiadiphosphetane-2,4-disulfide per 1 mol of compound (XXXXIV).

The reaction temperature is generally about −50° C.-about 150° C., preferably about 0° C.-about 100° C.

The reaction time is generally about 0.5-about 48 hr.

It is also possible to obtain the compound represented by the formula (I) by converting a functional group of a compound obtained in the aforementioned reaction scheme 1-reaction scheme 8 by a method known per se or a method analogous thereto (e.g., oxidation reaction, reduction reaction, hydrolysis, acylation reaction, alkylation reaction, amidation reaction, amination reaction, transfer reaction and the like).

In each reaction of the aforementioned reaction scheme 1-reaction scheme 8, when the starting material compound has a hydroxy group, an amino group, a carboxyl group or a carbonyl group as a substituent, a protecting group generally used for these groups may be introduced, and the object compound can be obtained by removing the protecting group as necessary after the reaction.

Examples of the hydroxyl-protecting group include a ($C_1$-$C_6$)alkyl group (e.g., methyl, ethyl, propyl, isopropyl, butyl, tert-butyl), a phenyl group, a trityl group, a ($C_7$-$C_{10}$)aralkyl group (e.g., benzyl), a formyl group, a ($C_1$-$C_6$)alkyl-carbonyl group (e.g., acetyl, propionyl), a benzoyl group, a ($C_7$-$C_{10}$) aralkyl-carbonyl group (e.g., benzylcarbonyl), a 2-tetrahydropyranyl group, a 2-tetrahydrofuranyl group, a silyl group (e.g., trimethylsilyl, triethylsilyl, dimethylphenylsilyl, tert-butyldimethylsilyl, tert-butyldiethylsilyl), a ($C_2$-$C_6$)alkenyl group (e.g., 1-allyl) and the like. These groups are optionally substituted by 1 to 3 substituents selected from a halogen atom (e.g., fluorine, chlorine, bromine, iodine), a ($C_1$-$C_6$) alkyl group (e.g., methyl, ethyl, propyl), a ($C_1$-$C_6$)alkoxy group (e.g., methoxy, ethoxy, propoxy), a nitro group and the like.

Examples of the amino-protecting group include a formyl group, a ($C_1$-$C_6$)alkyl-carbonyl group (e.g., acetyl, propionyl), a ($C_1$-$C_6$)alkoxy-carbonyl group (e.g., methoxycarbonyl, ethoxycarbonyl, tert-butoxycarbonyl), a benzoyl group, a ($C_7$-$C_{10}$)aralkyl-carbonyl group (e.g., benzylcarbonyl), a ($C_7$-$C_{14}$)aralkyloxy-carbonyl group (e.g., benzyloxycarbonyl, 9-fluorenylmethoxycarbonyl), a trityl group, a phthaloyl group, an N,N-dimethylaminomethylene group, a silyl group (e.g., trimethylsilyl, triethylsilyl, dimethylphenylsilyl, tert-butyldimethylsilyl, tert-butyldiethylsilyl), a $(C_2-C_6)$alkenyl group (e.g., 1-allyl) and the like. These groups are optionally substituted by 1 to 3 substituents selected from a halogen atom (e.g., fluorine, chlorine, bromine, iodine), $(C_1-C_6)$ alkoxy group (e.g., methoxy, ethoxy, propoxy), nitro group and the like.

Examples of the carboxyl group-protecting group include a $(C_1-C_6)$alkyl group (e.g., methyl, ethyl, propyl, isopropyl, butyl, tert-butyl), a $(C_7-C_{10})$aralkyl group (e.g., benzyl), a phenyl group, a trityl group, a silyl group (e.g., trimethylsilyl, triethylsilyl, dimethylphenylsilyl, tert-butyldimethylsilyl, tert-butyldiethylsilyl, tert-butyldiphenylsilyl), a $(C_2-C_6)$alkenyl group (e.g., 1-allyl) and the like can be mentioned. These groups are optionally substituted by 1 to 3 substituents selected from a halogen atom (e.g., fluorine, chlorine, bromine, iodine), a $(C_1-C_6)$alkoxy group (e.g., methoxy, ethoxy, propoxy), a nitro group and the like.

Examples of the carbonyl group-protecting group include cyclic acetal (e.g., 1,3-dioxane), non-cyclic acetal (e.g., di-$(C_{1-6})$alkylacetal) and the like.

In addition, these protecting groups may be removed according to a method known per se, for example, the method described in Protective Groups in Organic Synthesis, John Wiley and Sons (1980) and the like. For example, a method using an acid, a base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide etc.) and the like, a reduction method and the like can be used.

Compound (I) obtained by the aforementioned reaction scheme 1-reaction scheme 8 can be isolated and purified by, for example, a general separation means such as recrystallization, distillation, chromatography and the like. When compound (I) thus obtained of the present invention is a free form can be converted to a salt by a method known per se or method according thereto (e.g., neutralization etc.), and when the compound is obtained as a salt, it can be converted to a free form or other salt by a method known per se or method according thereto. When the obtained compound is a racemate, it can be separated to a d-form or an l-form by a general optical resolution means.

EXAMPLES

The eight compounds shown below are known compounds in which we have found an sGC activating action.

1-[4-(3-aminophenyl)-1,3-thiazol-2-yl]-5-(trifluoromethyl)-1H-pyrazole-4-carboxylic acid

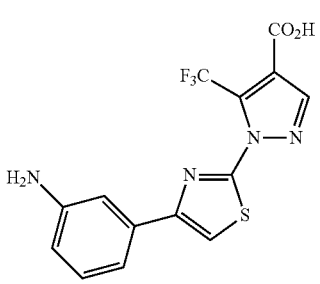

1-(4-thiophen-2-yl-1,3-thiazol-2-yl)-5-(trifluoromethyl)-1H-pyrazole-4-carboxylic acid

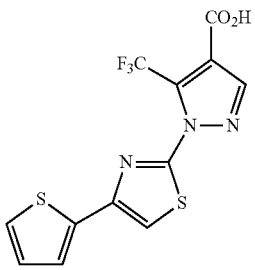 [SMILES: O=C(O)c1cnn(-c2nc(-c3cccs3)cs2)c1C(F)(F)F]

1-(4-phenyl-1,3-thiazol-2-yl)-5-(trifluoromethyl)-1H-pyrazole-4-carboxylic acid

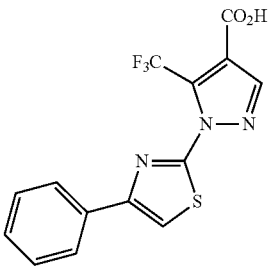 [SMILES: O=C(O)c1cnn(-c2nc(-c3ccccc3)cs2)c1C(F)(F)F]

1-[4-(4-fluorophenyl)-1,3-thiazol-2-yl]-5-(trifluoromethyl)-1H-pyrazole-4-carboxylic acid

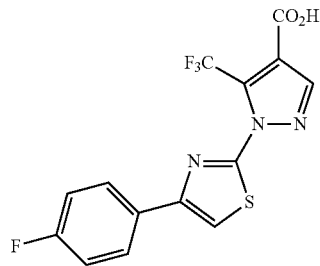 [SMILES: O=C(O)c1cnn(-c2nc(-c3ccc(F)cc3)cs2)c1C(F)(F)F]

1-[4-(3-fluorophenyl)-1,3-thiazol-2-yl]-5-(trifluoromethyl)-1H-pyrazole-4-carboxylic acid

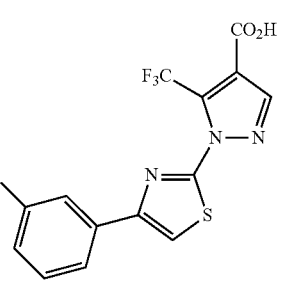

5-(trifluoromethyl)-1-{4-[3-(trifluoromethyl)phenyl]-1,3-thiazol-2-yl}-1H-pyrazole-4-carboxylic acid

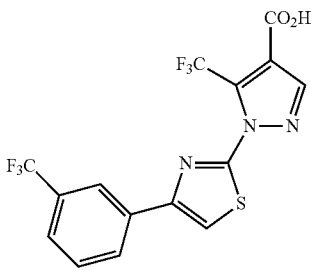 [SMILES: O=C(O)c1cnn(-c2nc(-c3cccc(C(F)(F)F)c3)cs2)c1C(F)(F)F]

1-[4-(4-chlorophenyl)-1,3-thiazol-2-yl]-5-(trifluoromethyl)-1H-pyrazole-4-carboxylic acid

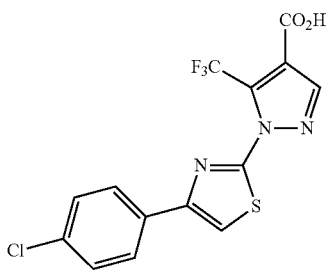 [SMILES: O=C(O)c1cnn(-c2nc(-c3ccc(Cl)cc3)cs2)c1C(F)(F)F]

1-[4-(3-nitrophenyl)-1,3-thiazol-2-yl]-5-(trifluoromethyl)-1H-pyrazole-4-carboxylic acid

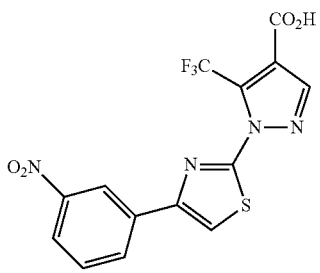 [SMILES: O=C(O)c1cnn(-c2nc(-c3cccc([N+](=O)[O-])c3)cs2)c1C(F)(F)F]

These compounds and salts thereof can be preferably included in the sGC activating agent of the present invention as active ingredients thereof.

The present invention is explained in detail in the following by referring to Reference Examples, Examples, Experimental Examples and Preparation Examples, which are mere exemplifications and do not limit the present invention. In addition, the present invention may be modified without departing from the scope of the invention. In the present specification, the Production Examples of compound (I) are described as Reference Examples and Examples, and particularly, the Production Examples of compound (II) and compound (III) are described as Examples.

$^1$H-NMR spectrum was measured using Varian Mercury 300 (300 MHz), Bruker AVANCE II300 (300 MHz), or Bruker AVANCE 400 (400 MHz) spectrometer with tetramethylsilane as the internal standard, and total δ value is shown in ppm. Unless otherwise specified, the numerical values of mixed solvents show the volume mixing ratio of each solvent. Unless otherwise specified, % means wt %. Unless otherwise specified, the ratio of elution solvents of silica gel chromatography is a volume mixing ratio. In the present specification, the room temperature (ambient temperature) means a temperature from about 10° C. to about 30° C.

Each symbol in the Reference Examples and Examples means the following.

s: singlet, d: doublet, t: triplet, q: quartet, dd: double doublet, dt: double triplet, ddd: double double doublet, m: multiplet, br.s.: broad singlet, J: coupling constant In the Reference Examples and Examples, the LC/MS analysis was performed under the following conditions.

measurement device: Waters LC/MS system
HPLC: Agilent HP1100
MS: Waters ZQ2000
column: SHISEIDO CAPCELLPAK C18 UG120 1.5 mm I.D.×35 mm S-3 µm
solvent: SOLUTION A; 0.05% aqueous trifluoroacetic acid solution, SOLUTION B; 0.04% trifluoroacetic acid acetonitrile solution
gradient cycle: 0.00 min (SOLUTION A/SOLUTION B=90/10), 0.01 min (SOLUTION A/SOLUTION B-90/10), 2.00 min (SOLUTION A/SOLUTION B=5/95), 2.75 min (SOLUTION A/SOLUTION B=5/95), 2.76 min (SOLUTION A/SOLUTION B=90/10), 3.45 min (SOLUTION A/SOLUTION B=90/10)
injection volume: 10 µL, flow rate: 0.5 mL/min, detection method: UV 220 nm, column temperature: 40° C.
MS conditions ionization method: ESI In the Reference Examples and Examples, purification by preparative HPLC was performed under the following conditions.

instrument: Waters preparative HPLC system
column: Waters SunFire Prep C18 OBD 5 µm 30×50 mm Column
solvent: SOLUTION A; 0.1% aqueous trifluoroacetic acid solution, SOLUTION B; 0.1% trifluoroacetic acid acetonitrile solution
gradient cycle: 0.00 min (SOLUTION A/SOLUTION B=90/10), 1.20 min (SOLUTION A/SOLUTION B=90/10), 5.20 min (SOLUTION A/SOLUTION B=0/100), 7.00 min (SOLUTION A/SOLUTION B=0/100), 7.01 min (SOLUTION A/SOLUTION B=90/10), 8.50 min (SOLUTION A/SOLUTION B=90/10) flow rate: 70 mL/min, detection method: UV 220 nm, column temperature: room temperature Reference Example 1

1-[4-(3,4-dichlorophenyl)-1,3-thiazol-2-yl]-5-(trifluoromethyl)-1H-pyrazole-4-carboxylic acid Reference Example 1a ethyl 1-[4-(3,4-dichlorophenyl)-1,3-thiazol-2-yl]-5-(trifluoromethyl)-1H-pyrazole-4-carboxylate

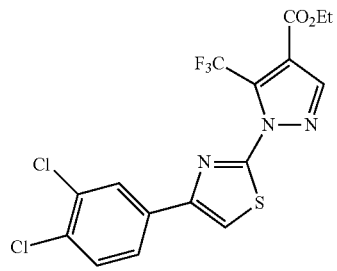 [SMILES: CCOC(=O)c1cnn(-c2nc(-c3ccc(Cl)c(Cl)c3)cs2)c1C(F)(F)F]

A mixture of ethyl 4,4,4-trifluoroacetoacetate (3.59 g, 19.5 mmol), ethyl orthoformate (4.49 mL, 27 mmol) and acetic anhydride (5.10 mL, 54 mmol) was heated under reflux for 3.5 hr, and the mixture was concentrated under reduced pressure. Ethanol (50 mL) and thiosemicarbazide (1.37 g, 15 mmol) were added, and the reaction mixture was stirred at room temperature for 2.5 hr. 2-Bromo-1-(3,4-dichlorophenyl)ethanone (4.02 g, 15 mmol) was added, and the mixture was stirred at 80° C. for 30 min, cooled to room temperature. The precipitated crystals were collected by filtration to give a crude title compound (4.73 g, 72%) as colorless crystals.

$^1$H NMR (400 MHz, CHLOROFORM-d) δ ppm 1.40 (3H, t, J=7.1 Hz), 4.40 (2H, q, J=7.3 Hz), 7.50-7.54 (2H, m), 7.73 (1H, dd, J=8.3, 2.0 Hz), 7.98 (1H, d, J=2.0 Hz), 8.11 (1H, s)

LCMS (ESI+) M+H: 436.

Reference Example 1

1-[4-(3,4-dichlorophenyl)-1,3-thiazol-2-yl]-5-(trifluoromethyl)-1H-pyrazole-4-carboxylic acid

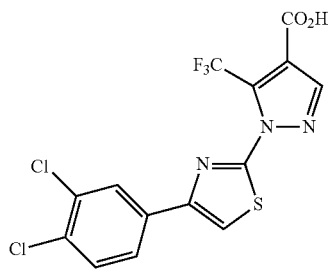 [SMILES: O=C(O)c1cnn(-c2nc(-c3ccc(Cl)c(Cl)c3)cs2)c1C(F)(F)F]

The compound (2.18 g, 5.0 mmol) obtained in Reference Example 1a was dissolved in ethanol (20 ml), 2N aqueous sodium hydroxide solution (5.0 mL, 10 mmol) was added, and the mixture was stirred at 80° C. for 30 min. The reaction mixture was extracted with water, and washed with ether. The aqueous layer was neutralized with 1N hydrochloric acid (10 mL), extracted with ethyl acetate, washed with saturated brine, dried over anhydrous sodium sulfate, and concentrated under reduced pressure. The residue was recrystallized from ethyl acetate-hexane to give the title compound (1.31 g, 64%) as colorless crystals.

$^1$H NMR (400 MHz, DMSO-d$_6$) δ ppm 7.78 (1H, d, J=8.3 Hz) 7.93 (1H, dd, J=8.3, 2.0 Hz) 8.20 (1H, d, J=2.0 Hz) 8.41 (1H, s) 8.46 (1H, s) 13.78 (1H, br. s.)

LCMS (ESI+) M+H: 408.

Reference Example 2

1-[4-(3-chlorophenyl)-1,3-thiazol-2-yl]-5-(trifluoromethyl)-1H-pyrazole-4-carboxylic acid Reference Example 2a ethyl 1-[4-(3-chlorophenyl)-1,3-thiazol-2-yl]-5-(trifluoromethyl)-1H-pyrazole-4-carboxylate

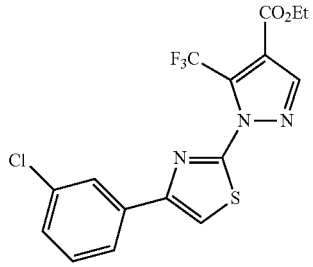 [SMILES: CCOC(=O)c1cnn(-c2nc(-c3cccc(Cl)c3)cs2)c1C(F)(F)F]

By a reaction in the same manner as in Reference Example 1a and using 2-bromo-1-(3-chlorophenyl)ethanone (0.70 g, 3.0 mmol) instead of 2-bromo-1-(3,4-dichlorophenyl)ethanone as a starting material, the title compound (714 mg, 59%) was obtained as colorless crystals.

$^1$H NMR (400 MHz, CHLOROFORM-d) δ ppm 1.40 (3H, t, J=7.1 Hz), 4.40 (2H, q, J=7.2 Hz), 7.33-7.40 (2H, m), 7.53 (1H, s), 7.77-7.80 (1H, m), 7.87 (1H, t, J=1.7 Hz), 8.11 (1H, s)

LCMS (ESI+) M+H: 402.

Reference Example 2

1-[4-(3-chlorophenyl)-1,3-thiazol-2-yl]-5-(trifluoromethyl)-1H-pyrazole-4-carboxylic acid

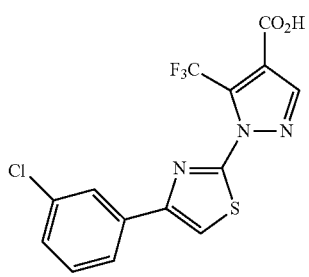 [SMILES: O=C(O)c1cnn(-c2nc(-c3cccc(Cl)c3)cs2)c1C(F)(F)F]

By a reaction in the same manner as in Reference Example 1 and using the compound (602 mg, 1.50 mmol) obtained in Reference Example 2a, the title compound (302 mg, 54%) was obtained as colorless crystals.

$^1$H NMR (400 MHz, DMSO-d$_6$) δ ppm 7.46-7.49 (1H, m) 7.54 (1H, t, J=7.8 Hz) 7.93 (1H, d, J=7.6 Hz) 8.02 (1H, t, J=1.7 Hz) 8.40 (1H, s) 8.42 (1H, s) 13.78 (1H, br. s.)

LCMS (ESI+) M+H: 374.

Reference Example 3

1-[4-(5-chlorothiophen-2-yl)-1,3-thiazol-2-yl]-5-(trifluoromethyl)-1H-pyrazole-4-carboxylic acid Reference Example 3a ethyl 1-[4-(5-chlorothiophen-2-yl)-1,3-thiazol-2-yl]-5-(trifluoromethyl)-1H-pyrazole-4-carboxylate

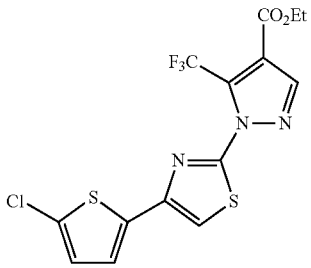 [SMILES: CCOC(=O)c1cnn(-c2nc(-c3ccc(Cl)s3)cs2)c1C(F)(F)F]

By a reaction in the same manner as in Reference Example 1a and using 2-bromo-1-(5-chlorothiophen-2-yl)ethanone (0.72 g, 3.0 mmol) instead of 2-bromo-1-(3,4-dichlorophenyl)ethanone as a starting material, the title compound (453 mg, 37%) was obtained as colorless crystals.

¹H NMR (400 MHz, CHLOROFORM-d) δ ppm 1.39 (3H, t, J=7.2 Hz), 4.39 (2H, q, J=7.2 Hz), 6.89 (1H, d, J=3.9 Hz), 7.25 (1H, t, J=3.3 Hz), 7.27-7.31 (1H, m), 8.09 (1H, s)

LCMS (ESI+) M+H: 408.

Reference Example 3

1-[4-(5-chlorothiophen-2-yl)-1,3-thiazol-2-yl]-5-(trifluoromethyl)-1H-pyrazole-4-carboxylic acid

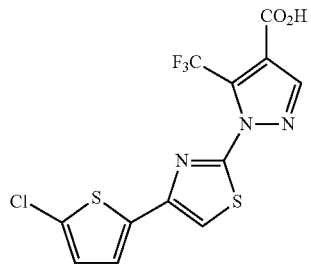 [SMILES: O=C(O)c1cnn(-c2nc(-c3ccc(Cl)s3)cs2)c1C(F)(F)F]

By a reaction in the same manner as in Reference Example 1 and using the compound (408 mg, 1.0 mmol) obtained in Reference Example 3a, the title compound (116 mg, 31%) was obtained as colorless crystals.

¹H NMR (400 MHz, DMSO-d₆) δ ppm 7.20 (1H, d, J=3.9 Hz) 7.55 (1H, d, J=3.9 Hz) 8.15 (1H, s) 8.39 (1H, s) 13.78 (1H, br. s.)

LCMS (ESI+) M+H: 380.

Reference Example 4

5-cyclopropyl-1-[4-(3,4-dichlorophenyl)-1,3-thiazol-2-yl]-1H-pyrazole-4-carboxylic acid

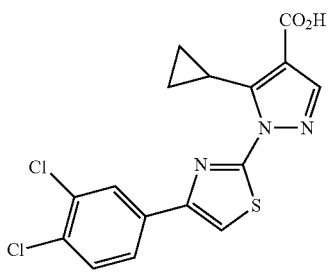 [SMILES: O=C(O)c1cnn(-c2nc(-c3ccc(Cl)c(Cl)c3)cs2)c1C1CC1]

By a reaction in the same manner as in Reference Example 1a and using methyl 3-cyclopropyl-3-oxopropanoate (1.07 g, 7.5 mmol) instead of ethyl 4,4,4-trifluoroacetoacetate as a starting material, crude methyl 5-cyclopropyl-1-[4-(3,4-dichlorophenyl)-1,3-thiazol-2-yl]-1H-pyrazole-4-carboxylate (1.61 g) was obtained. By a reaction in the same manner as in Reference Example 1 and using this, the title compound (693 mg, 36%) was obtained as colorless crystals.

¹H NMR (400 MHz, DMSO-d₆) δ ppm 0.99-1.04 (2H, m) 1.09-1.15 (2H, m) 2.60-2.68 (1H, m) 7.74 (1H, d, J=8.3 Hz) 7.98 (1H, dd, J=8.3, 2.0 Hz) 8.08 (1H, s) 8.22 (1H, d, J=2.0 Hz) 8.29 (1H, s) 12.76 (1H, br. s.)

LCMS (ESI+) M+H: 380.

Reference Example 5

1-[4-(3,4-dichlorophenyl)-1,3-thiazol-2-yl]-5-methyl-1H-pyrazole-4-carboxylic acid

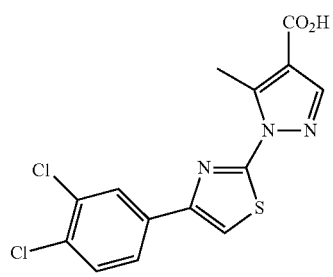 [SMILES: Cc1c(C(=O)O)cnn1-c1nc(-c2ccc(Cl)c(Cl)c2)cs1]

By a reaction in the same manner as in Reference Example 1a and using methyl 3-oxobutanoate (0.87 g, 7.5 mmol) instead of ethyl 4,4,4-trifluoroacetoacetate as a starting material, crude methyl 1-[4-(3,4-dichlorophenyl)-1,3-thiazol-2-yl]-5-methyl-1H-pyrazole-4-carboxylate (1.91 g) was obtained. By a reaction in the same manner as in Reference Example 1 and using this, the title compound (747 mg, 42%) was obtained as colorless crystals.

¹H NMR (400 MHz, DMSO-d₆) δ ppm 3.03 (3H, s) 7.73 (1H, J=8.6 Hz) 7.94 (1H, dd, J=8.4, 1.8 Hz) 8.10 (1H, s) 8.18 (1H, d, J=2.0 Hz) 8.21 (1H, s) 12.89 (1H, br. s.)

LCMS (ESI+) M+H: 354.

Reference Example 6

1-[4-(3,4-dichlorophenyl)-1,3-thiazol-2-yl]-5-(methoxymethyl)-1H-pyrazole-4-carboxylic acid

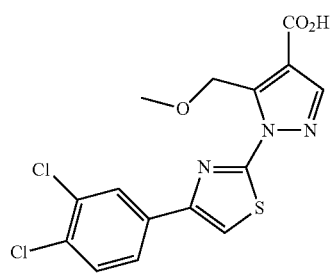 [SMILES: COCc1c(C(=O)O)cnn1-c1nc(-c2ccc(Cl)c(Cl)c2)cs1]

By a reaction in the same manner as in Reference Example 1a and using methyl 4-methoxy-3-oxobutanoate (1.10 g, 7.5 mmol) instead of ethyl 4,4,4-trifluoroacetoacetate as a starting material, crude methyl 1-[4-(3,4-dichlorophenyl)-1,3-thiazol-2-yl]-5-(methoxymethyl)-1H-pyrazole-4-carboxylate (0.90 g) was obtained. By a reaction in the same manner as in Reference Example 1 and using this, the title compound (689 mg, 36%) was obtained as colorless crystals.

¹H NMR (400 MHz, DMSO-d₆) δ ppm 3.34 (3H, s) 5.26 (2H, s) 7.75 (1H, d, J=8.3 Hz) 7.96 (1H, dd, J=8.6, 2.0 Hz) 8.19 (1H, s) 8.21 (1H, d, J=2.2 Hz) 8.25 (1H, s) 13.16 (1H, br. s.)

LCMS (ESI+) M+H: 384.

Reference Example 7

1-[4-(3,4-dichlorophenyl)-1,3-thiazol-2-yl]-5-propyl-1H-pyrazole-4-carboxylic acid

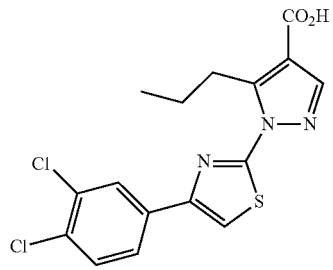 [SMILES: CCCc1c(C(=O)O)cnn1-c1nc(-c2ccc(Cl)c(Cl)c2)cs1]

By a reaction in the same manner as in Reference Example 1a and using ethyl 3-oxohexanoate (1.19 g, 7.5 mmol) instead of ethyl 4,4,4-trifluoroacetoacetate as a starting material, crude ethyl 1-[4-(3,4-dichlorophenyl)-1,3-thiazol-2-yl]-5-propyl-1H-pyrazole-4-carboxylate (1.44 g) was obtained. By a reaction in the same manner as in Reference Example 1 and using this, the title compound (202 mg, 7%) was obtained as colorless crystals.

$^1$H NMR (400 MHz, DMSO-$d_6$) δ ppm 1.04 (3H, t, J=7.3 Hz) 1.70-1.81 (2H, m) 3.49-3.55 (2H, m) 7.77 (1H, d, J=8.6 Hz) 7.93 (1H, dd, J=8.4, 2.1 Hz) 8.11 (1H, s) 8.19 (1H, d, J=2.2 Hz) 8.24 (1H, s) 12.88 (1H, br. s.)

LCMS (ESI+) M+H: 382.

Reference Example 8

5-methyl-1-{4-[3-(trifluoromethyl)phenyl]-1,3-thiazol-2-yl}-1H-pyrazole-4-carboxylic acid

Reference Example 8a ethyl 5-methyl-1-{4-[3-(trifluoromethyl)phenyl]-1,3-thiazol-2-yl}-1H-pyrazole-4-carboxylate

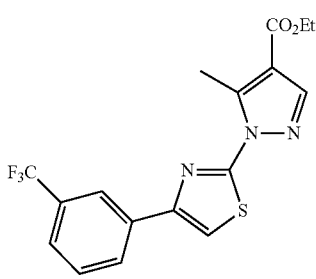 [SMILES: CCOC(=O)c1cnn(-c2nc(-c3cccc(C(F)(F)F)c3)cs2)c1C]

By a reaction in the same manner as in Reference Example 1a and using ethyl 3-oxobutanoate (364 mg, 2.8 mmol) instead of ethyl 4,4,4-trifluoroacetoacetate and 2-bromo-1-[3-(trifluoromethyl)phenyl]ethanone (0.53 g, 2.0 mmol) instead of 2-bromo-1-(3,4-dichlorophenyl)ethanone as starting materials, the title compound (607 mg, 79%) was obtained as colorless crystals.

$^1$H NMR (400 MHz, CHLOROFORM-d) δ ppm 1.40 (3H, t, J=7.1 Hz), 3.14 (3H, s), 4.35 (2H, q, J=7.2 Hz), 7.42 (1H, s), 7.54-7.63 (2H, m), 8.03 (1H, s), 8.08 (1H, d, J=7.6 Hz), 8.12 (1H, s)

LCMS (ESI+) M+H: 382.

Reference Example 8

5-methyl-1-{4-[3-(trifluoromethyl)phenyl]-1,3-thiazol-2-yl}-1H-pyrazole-4-carboxylic acid

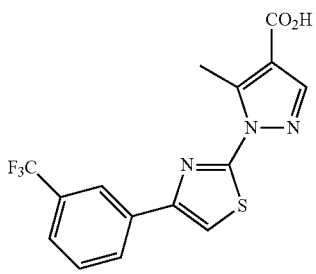 [SMILES: Cc1c(C(=O)O)cnn1-c1nc(-c2cccc(C(F)(F)F)c2)cs1]

By a reaction in the same manner as in Reference Example 1 and using the compound (607 mg, 1.59 mmol) obtained in Reference Example 8a, the title compound (339 mg, 60%) was obtained as colorless crystals.

$^1$H NMR (400 MHz, DMSO-$d_6$) δ ppm 3.05 (3H, s) 7.70-7.77 (2H, m) 8.12 (1H, s) 8.27-8.32 (3H, m) 12.88 (1H, s)

LCMS (ESI+) M+H: 354.

Reference Example 9

5-methyl-1-{4-[3-(trifluoromethoxy)phenyl]-1,3-thiazol-2-yl}-1H-pyrazole-4-carboxylic acid

Reference Example 9a ethyl 5-methyl-1-[4-[3-(trifluoromethoxy)phenyl]-1,3-thiazol-2-yl]-1H-pyrazole-4-carboxylate

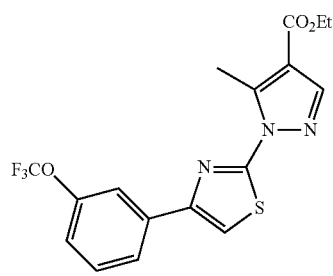 [SMILES: CCOC(=O)c1cnn(-c2nc(-c3cccc(OC(F)(F)F)c3)cs2)c1C]

By a reaction in the same manner as in Reference Example 1a and using ethyl 3-oxobutanoate (364 mg, 2.8 mmol) instead of ethyl 4,4,4-trifluoroacetoacetate and 2-bromo-1-[3-(trifluoromethoxy)phenyl]ethanone (0.56 g, 2.0 mmol) instead of 2-bromo-1-(3,4-dichlorophenyl)ethanone as starting materials, the title compound (605 mg, 76%) was obtained as colorless crystals.

$^1$H NMR (400 MHz, CHLOROFORM-d) δ ppm 1.40 (3H, t, J=7.1 Hz), 3.14 (3H, s), 4.35 (2H, q, J=7.2 Hz), 7.23 (1H, d, J=1.2 Hz), 7.38 (1H, s), 7.47 (1H, t, J=7.9 Hz), 7.75 (1H, s), 7.81 (1H, d, J=7.8 Hz), 8.03 (1H, s)

LCMS (ESI+) M+H: 398.

Reference Example 9

5-methyl-1-{4-[3-(trifluoromethoxy)phenyl]-1,3-thiazol-2-yl}-1H-pyrazole-4-carboxylic acid

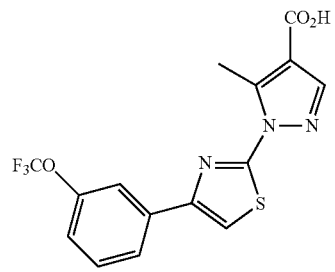 [SMILES: Cc1c(C(=O)O)cnn1-c1nc(-c2cccc(OC(F)(F)F)c2)cs1]

By a reaction in the same manner as in Reference Example 1 and using the compound (605 mg, 1.52 mmol) obtained in Reference Example 9a, the title compound (376 mg, 67%) was obtained as colorless crystals.

$^1$H NMR (400 MHz, DMSO-$d_6$) δ ppm 3.05 (3H, s) 7.39 (1H, dd, J=8.3, 1.0 Hz) 7.63 (1H, t, J=7.9 Hz) 7.93 (1H, s) 8.02 (1H, d, J=7.8 Hz) 8.12 (1H, s) 8.23 (1H, s) 12.88 (1H, br. s.)

LCMS (ESI+) M+H: 370.

Reference Example 10

1-{4-[3-(trifluoromethoxy)phenyl]-1,3-thiazol-2-yl}-5-(trifluoromethyl)-1H-pyrazole-4-carboxylic acid

Reference Example 10a ethyl 1-{4-[3-(trifluoromethoxy)phenyl]-1,3-thiazol-2-yl}-5-(trifluoromethyl)-1H-pyrazole-4-carboxylate

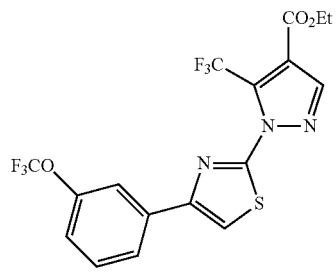 [SMILES: CCOC(=O)c1cnn(-c2nc(-c3cccc(OC(F)(F)F)c3)cs2)c1C(F)(F)F]

By a reaction in the same manner as in Reference Example 1a and using 2-bromo-1-[3-(trifluoromethoxy)phenyl]ethanone (0.28 g, 1.0 mmol) instead of 2-bromo-1-(3,4-dichlorophenyl)ethanone as a starting material, the title compound (324 mg, 71%) was obtained as an orange oil.

$^1$H NMR (400 MHz, CHLOROFORM-d) δ ppm 1.40 (3H, t, J=7.1 Hz), 4.40 (2H, q, J=7.3 Hz), 7.23 (1H, d, J=8.3 Hz), 7.48 (1H, t, J=7.9 Hz), 7.56 (1H, s), 7.77 (1H, s), 7.83 (1H, d, J=7.8 Hz), 8.11 (1H, s)

LCMS (ESI+) M+H: 452.

Reference Example 10

1-{4-[3-(trifluoromethoxy)phenyl]-1,3-thiazol-2-yl}-5-(trifluoromethyl)-1H-pyrazole-4-carboxylic acid

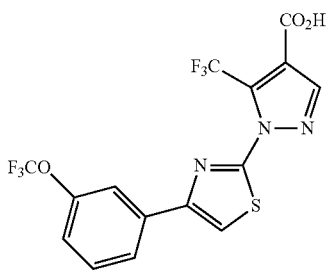 [SMILES: O=C(O)c1cnn(-c2nc(-c3cccc(OC(F)(F)F)c3)cs2)c1C(F)(F)F]

By a reaction in the same manner as in Reference Example 1 and using the compound (324 mg, 0.719 mmol) obtained in Reference Example 10a, the title compound (164 mg, 53%) was obtained as pale-orange crystals.

$^1$H NMR (400 MHz, DMSO-$d_6$) δ ppm 7.41 (1H, d, J=8.3 Hz) 7.65 (1H, t, J=8.1 Hz) 7.94 (1H, s) 8.01 (1H, d, J=7.8 Hz) 8.41 (1H, s) 8.45 (1H, s) 13.78 (1H, br. s.)

LCMS (ESI+) M+H: 424.

Reference Example 11

1-[4-(2-methoxyphenyl)-1,3-thiazol-2-yl]-5-(trifluoromethyl)-1H-pyrazole-4-carboxylic acid

Reference Example 11a ethyl 1-[4-(2-methoxyphenyl)-1,3-thiazol-2-yl]-5-(trifluoromethyl)-1H-pyrazole-4-carboxylate

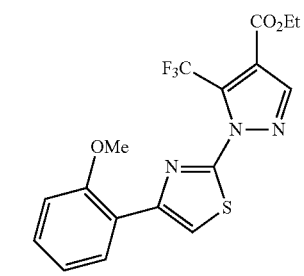 [SMILES: CCOC(=O)c1cnn(-c2nc(-c3ccccc3OC)cs2)c1C(F)(F)F]

By a reaction in the same manner as in Reference Example 1a and using 2-bromo-1-(2-methoxyphenyl)ethanone (2.29 g, 10 mmol) instead of 2-bromo-1-(3,4-dichlorophenyl)ethanone as a starting material, the title compound (2.08 g, 52%) was obtained as colorless crystals.

$^1$H NMR (400 MHz, CHLOROFORM-d) δ ppm 1.40 (3H, t, J=7.1 Hz), 3.99 (3H, s), 4.40 (2H, q, J=7.1 Hz), 7.02 (1H, d, J=8.3 Hz), 7.08 (1H, t, J=7.6 Hz), 7.34 (1H, dd, J=15.7, 1.5 Hz), 8.01 (1H, s), 8.10 (1H, s), 8.24 (1H, dd, J=7.8, 1.7 Hz)

LCMS (ESI+) M+H: 398.

Reference Example 11

1-[4-(2-methoxyphenyl)-1,3-thiazol-2-yl]-5-(trifluoromethyl)-1H-pyrazole-4-carboxylic acid

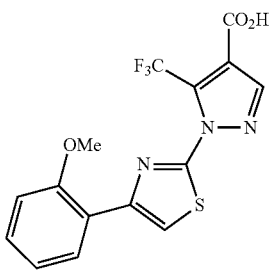 [SMILES: COc1ccccc1-c1csc(-n2ncc(C(=O)O)c2C(F)(F)F)n1]

By a reaction in the same manner as in Reference Example 1 and using the compound (298 mg, 0.75 mmol) obtained in Reference Example 11a, the title compound (227 mg, 82%) was obtained as colorless crystals.

$^1$H NMR (400 MHz, DMSO-d$_6$) δ ppm 3.96 (3H, s) 7.09 (1H, t, J=7.2 Hz) 7.20 (1H, d, J=8.3 Hz) 7.39 (1H, dd, J=15.7, 1.7 Hz) 8.05 (1H, dd, J=7.6, 1.7 Hz) 8.22 (1H, s) 8.39 (1H, s) 13.74 (1H, br. s.)

LCMS (ESI+) M+H: 370.

Reference Example 12

1-[4-(3-methoxyphenyl)-1,3-thiazol-2-yl]-5-(trifluoromethyl)-1H-pyrazole-4-carboxylic acid

Reference Example 12a ethyl 1-[4-(3-methoxyphenyl)-1,3-thiazol-2-yl]-5-(trifluoromethyl)-1H-pyrazole-4-carboxylate

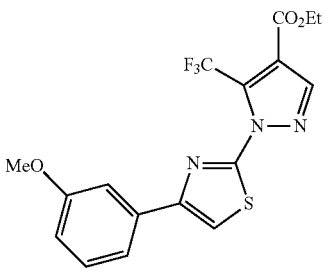 [SMILES: CCOC(=O)c1cnn(-c2nc(-c3cccc(OC)c3)cs2)c1C(F)(F)F]

By a reaction in the same manner as in Reference Example 1a and using 2-bromo-1-(3-methoxyphenyl)ethanone (2.29 g, 10 mmol) instead of 2-bromo-1-(3,4-dichlorophenyl)ethanone as a starting material, the title compound (1.80 g, 45%) was obtained as colorless crystals.

$^1$H NMR (400 MHz, CHLOROFORM-d) δ ppm 1.40 (3H, t, J=7.1 Hz), 3.88 (3H, s), 4.40 (2H, q, J=7.1 Hz), 6.93 (1H, dd, J=8.2, 2.6 Hz), 7.36 (1H, t, J=7.9 Hz), 7.47 (1H, d, J=7.8 Hz), 7.50 (2H, s), 8.11 (1H, s)

LCMS (ESI+) M+H: 398.

Reference Example 12

1-[4-(3-methoxyphenyl)-1,3-thiazol-2-yl]-5-(trifluoromethyl)-1H-pyrazole-4-carboxylic acid

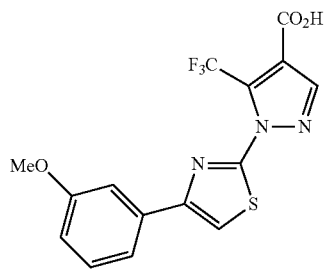 [SMILES: COc1cccc(-c2csc(-n3ncc(C(=O)O)c3C(F)(F)F)n2)c1]

By a reaction in the same manner as in Reference Example 1 and using the compound (553 mg, 1.39 mmol) obtained in Reference Example 12a, the title compound (285 mg, 56%) was obtained as colorless crystals.

$^1$H NMR (400 MHz, DMSO-d$_6$) δ ppm 3.82 (3H, s) 6.98 (1H, dd, J=8.2, 2.6 Hz) 7.41 (1H, t, J=7.9 Hz) 7.52 (1H, d, J=2.4 Hz) 7.54 (1H, d, J=7.8 Hz) 8.31 (1H, s) 8.40 (1H, s) 13.76 (1H, br. s.)

LCMS (ESI+) M+H: 370.

Reference Example 13

1-{4-[2-(cyclopropylmethoxy)phenyl]-1,3-thiazol-2-yl}-5-(trifluoromethyl)-1H-pyrazole-4-carboxylic acid

Reference Example 13a ethyl 1-[4-(2-hydroxyphenyl)-1,3-thiazol-2-yl]-5-(trifluoromethyl)-1H-pyrazole-4-carboxylate

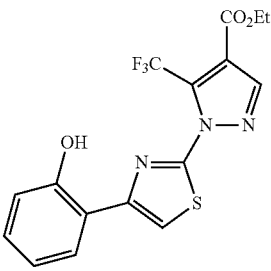 [SMILES: CCOC(=O)c1cnn(-c2nc(-c3ccccc3O)cs2)c1C(F)(F)F]

To a solution (20 mL) of the compound (1.78 g, 4.47 mmol) obtained in Reference Example 11a in toluene was added aluminum chloride(III) (1.79 g, 13.4 mmol), and the mixture was stirred at 95° C. for 3.5 hr. To the reaction mixture were added ethanol (10 mL), 6N hydrochloric acid (50 mL) and ethyl acetate (20 mL), and concentrated hydrochloric acid (2 mL) was added, and the mixture was stirred for 30 min. The reaction mixture was extracted with ethyl acetate, washed successively with water and saturated brine, dried over sodium sulfate, and concentrated under reduced pressure. To the residue were added ethanol (30 ml) and conc. sulfuric acid (1 mL), and the mixture was heated under reflux for 24 hr. The reaction mixture was diluted with water, extracted with ethyl acetate, washed successively with water and saturated brine, dried over sodium sulfate, and concentrated under reduced pressure. The residue was recrystallized from ethyl acetate-hexane to give the title compound (1.20 g, 70%) as colorless crystals.

¹H NMR (400 MHz, CHLOROFORM-d) δ ppm 1.40 (3H, t, J=7.1 Hz), 4.40 (2H, q, J=7.2 Hz), 6.89-6.97 (1H, m), 7.04 (1H, d, J=8.3 Hz), 7.23-7.33 (1H, m), 7.63 (1H, d, J=2.2 Hz), 7.67 (1H, d, J=8.1 Hz), 8.13 (1H, s), 10.04-10.21 (1H, m)
LCMS (ESI+) M+H: 384.

Reference Example 13b ethyl 1-{4-[2-(cyclopropylmethoxy)phenyl]-1,3-thiazol-2-yl}-5-(trifluoromethyl)-1H-pyrazole-4-carboxylate

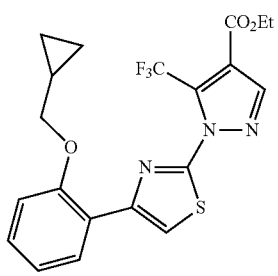 [SMILES: CCOC(=O)c1cnn(-c2nc(-c3ccccc3OCC3CC3)cs2)c1C(F)(F)F]

To the compound (0.38 g, 1.0 mmol) obtained in Reference Example 13a were added acetonitrile (4 mL), (bromomethyl)cyclopropane (0.145 mL, 1.5 mmol) and potassium carbonate (207 mg, 1.5 mmol), and the mixture was stirred at 80° C. for 17 hr. The reaction mixture was diluted with water, extracted with ethyl acetate, dried over sodium sulfate, and concentrated under reduced pressure. The residue was purified by column chromatography (carrier: silica gel, eluent: hexane-ethyl acetate) to give the title compound (418 mg, 95%) as a colorless oil.

¹H NMR (400 MHz, CHLOROFORM-d) δ ppm 0.40-0.45 (2H, m), 0.70-0.76 (2H, m), 1.37-1.46 (1H, m), 1.40 (3H, t, J=7.1 Hz), 3.97 (2H, d, J=7.1 Hz), 4.40 (2H, q, J=7.2 Hz), 6.95 (1H, d, J=8.3 Hz), 7.06 (1H, t, J=7.6 Hz), 7.30 (1H, t, J=7.8 Hz), 8.11 (1H, s), 8.21 (1H, s), 8.27 (1H, d, J=7.8 Hz)
LCMS (ESI+) M+H: 438.

Reference Example 13

1-{4-[2-(cyclopropylmethoxy)phenyl]-1,3-thiazol-2-yl}-5-(trifluoromethyl)-1H-pyrazole-4-carboxylic acid

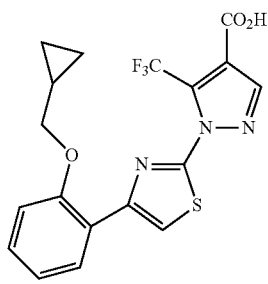 [SMILES: O=C(O)c1cnn(-c2nc(-c3ccccc3OCC3CC3)cs2)c1C(F)(F)F]

By a reaction in the same manner as in Reference Example 1 and using the compound (418 mg, 0.956 mmol) obtained in Reference Example 13b, the title compound (251 mg, 64%) was obtained as colorless crystals.

¹H NMR (400 MHz, DMSO-d₆) δ ppm 0.38-0.44 (2H, m) 0.62-0.69 (2H, m) 1.34-1.44 (1H, m) 4.02 (2H, d, J=7.1 Hz) 7.07 (1H, t, J=7.6 Hz) 7.14 (1H, d, J=8.3 Hz) 7.32-7.38 (1H, m) 8.07 (1H, dd, J=7.7, 1.3 Hz) 8.30 (1H, s) 8.40 (1H, s) 13.74 (1H, br. s.)
LCMS (ESI+) M+H: 410.

Reference Example 14

1-{4-[2-(benzyloxy)phenyl]-1,3-thiazol-2-yl}-5-(trifluoromethyl)-1H-pyrazole-4-carboxylic acid Reference Example 14a ethyl 1-{4-[2-(benzyloxy)phenyl]-1,3-thiazol-2-yl}-5-(trifluoromethyl)-1H-pyrazole-4-carboxylate

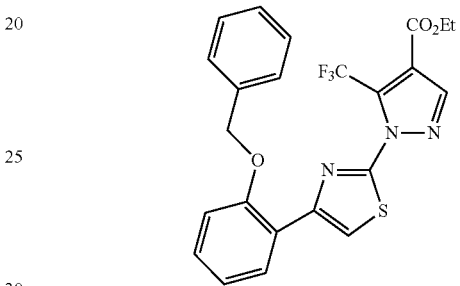

By a reaction in the same manner as in Reference Example 13b and using the compound (383 mg, 1.0 mmol) obtained in Reference Example 13a and benzyl bromide (0.18 mL, 1.5 mmol), the title compound (459 mg, 97%) was obtained as colorless crystals.

¹H NMR (400 MHz, CHLOROFORM-d) δ ppm 1.40 (3H, t, J=7.2 Hz), 4.39 (2H, q, J=7.2 Hz), 5.23 (2H, s), 7.06-7.13 (2H, m), 7.30-7.46 (4H, m), 7.47-7.51 (2H, m), 7.95 (1H, s), 8.10 (1H, s), 8.28 (1H, d, J=7.8 Hz)
LCMS (ESI+) M+H: 474.

Reference Example 14

1-{4-[2-(benzyloxy)phenyl]-1,3-thiazol-2-yl}-5-(trifluoromethyl)-1H-pyrazole-4-carboxylic acid

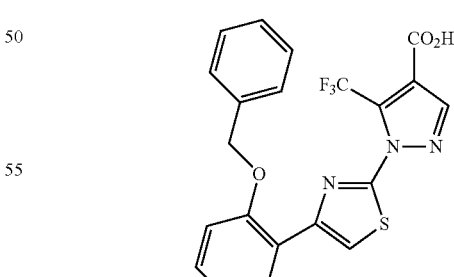

By a reaction in the same manner as in Reference Example 1 and using the compound (459 mg, 0.97 mmol) obtained in Reference Example 14a, the title compound (316 mg, 73%) was obtained as crystals ¹H NMR (400 MHz, DMSO-d₆) δ ppm 5.34 (2H, s) 7.09 (1H, t, J=7.5 Hz) 7.25-7.30 (1H, m) 7.36 (2H, t, J=7.0 Hz)

7.42 (2H, t, J=7.6 Hz) 7.54 (2H, d, J=7.3 Hz) 8.06 (1H, dd, J=7.8, 1.2 Hz) 8.15 (1H, s) 8.39 (1H, s) 13.74 (1H, br. s.)
LCMS (ESI+) M+H: 446.

Reference Example 15

1-{4-[3-(cyclopropylmethoxy)phenyl]-1,3-thiazol-2-yl}-5-(trifluoromethyl)-1H-pyrazole-4-carboxylic acid Reference Example 15a ethyl 1-[4-(3-hydroxyphenyl)-1,3-thiazol-2-yl]-5-(trifluoromethyl)-1H-pyrazole-4-carboxylate

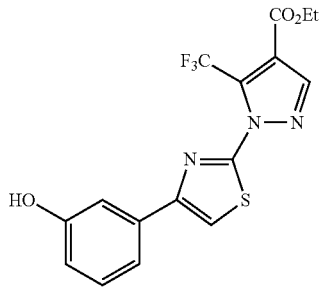 [SMILES: CCOC(=O)c1cnn(-c2nc(-c3cccc(O)c3)cs2)c1C(F)(F)F]

By a reaction in the same manner as in Reference Example 13a and using the compound (0.79 g, 2.0 mmol) obtained in Reference Example 12a, the residue was purified by column chromatography (carrier: silica gel, eluent: hexane-ethyl acetate) to give the title compound (0.46 g, 60%) as a yellow oil.
$^1$H NMR (400 MHz, CHLOROFORM-d) δ ppm 1.40 (3H, t, J=7.1 Hz), 4.40 (2H, q, J=7.2 Hz), 5.12 (1H, s), 6.86 (1H, dd, J=8.1, 2.7 Hz), 7.31 (1H, t, J=7.9 Hz), 7.40 (1H, d, J=2.4 Hz), 7.45 (1H, d, J=7.8 Hz), 7.49 (1H, s), 8.11 (1H, s)

Reference Example 15b ethyl 1-[4-[3-(cyclopropylmethoxy)phenyl]-1,3-thiazol-2-yl]-5-(trifluoromethyl)-1H-pyrazole-4-carboxylate

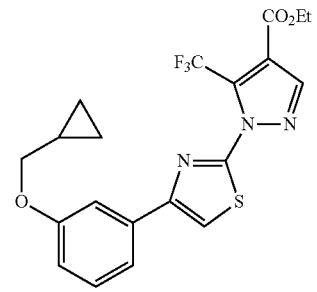 [SMILES: CCOC(=O)c1cnn(-c2nc(-c3cccc(OCC4CC4)c3)cs2)c1C(F)(F)F]

By a reaction in the same manner as in Reference Example 13b and using the compound (0.23 g, 0.61 mmol) obtained in Reference Example 15a, the title compound (0.25 g, 94%) was obtained as a colorless solid.
$^1$H NMR (400 MHz, CHLOROFORM-d) δ ppm 0.38 (2H, q, J=5.0 Hz), 0.63-0.70 (2H, m), 1.23-1.37 (1H, m), 1.40 (3H, t, J=7.1 Hz), 3.87 (2H, d, J=6.8 Hz), 4.40 (2H, q, J=7.1 Hz), 6.93 (1H, dd, J=8.1, 2.4 Hz), 7.34 (1H, t, J=7.9 Hz), 7.45-7.49 (2H, m), 7.49 (1H, s), 8.11 (1H, s)
LCMS (ESI+) M+H: 438.

Reference Example 15

1-{4-[3-(cyclopropylmethoxy)phenyl]-1,3-thiazol-2-yl}-5-(trifluoromethyl)-1H-pyrazole-4-carboxylic acid

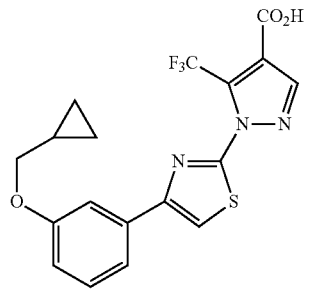 [SMILES: O=C(O)c1cnn(-c2nc(-c3cccc(OCC4CC4)c3)cs2)c1C(F)(F)F]

By a reaction in the same manner as in Reference Example 1 and using the compound (250 mg, 0.57 mmol) obtained in Reference Example 15b, the title compound (190 mg, 81%) was obtained as colorless crystals.
$^1$H NMR (400 MHz, DMSO-$d_6$) δppm 0.35 (2H, dd, J=4.8, 1.3 Hz) 0.59 (2H, dd, J=8.1, 1.7 Hz) 1.20-1.31 (1H, m) 3.88 (2H, d, J=7.1 Hz) 6.96 (1H, dd, J=7.5, 2.1 Hz) 7.38 (1H, t, J=7.9 Hz) 7.49-7.54 (2H, m) 8.31 (1H, s) 8.40 (1H, s) 13.75 (1H, br. s.)
LCMS (ESI+) M+H: 410.

Reference Example 16

1-{4-[3-(benzyloxy)phenyl]-1,3-thiazol-2-yl}-5-(trifluoromethyl)-1H-pyrazole-4-carboxylic acid Reference Example 16a ethyl 1-{4-[3-(benzyloxy)phenyl]-1,3-thiazol-2-yl}-5-(trifluoromethyl)-1H-pyrazole-4-carboxylate

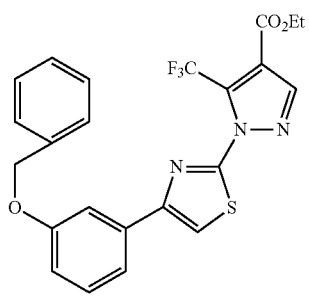 [SMILES: CCOC(=O)c1cnn(-c2nc(-c3cccc(OCc4ccccc4)c3)cs2)c1C(F)(F)F]

By a reaction in the same manner as in Reference Example 13b and using the compound (0.23 g, 0.61 mmol) obtained in Reference Example 15a and benzyl bromide (0.11 mL, 0.91 mmol), the title compound (0.27 g, 95%) was obtained as an amorphous form.

$^1$H NMR (400 MHz, CHLOROFORM-d) δ ppm 1.40 (3H, t, J=7.1 Hz), 4.40 (2H, q, J=7.1 Hz), 5.14 (2H, s), 7.00 (1H, dd, J=8.2, 2.6 Hz), 7.31-7.43 (4H, m), 7.45-7.51 (4H, m), 7.57 (1H, s), 8.11 (1H, s)

LCMS (ESI+) M+H: 474.

Reference Example 16

1-{4-[3-(benzyloxy)phenyl]-1,3-thiazol-2-yl}-5-(trifluoromethyl)-1H-pyrazole-4-carboxylic acid

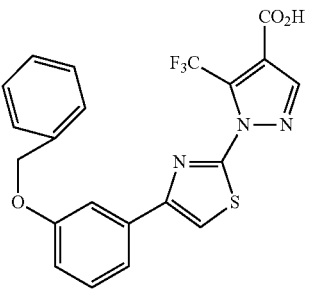 [SMILES: O=C(O)c1cnn(-c2nc(-c3cccc(OCc4ccccc4)c3)cs2)c1C(F)(F)F]

By a reaction in the same manner as in Reference Example 1 and using the compound (274 mg, 0.579 mmol) obtained in Reference Example 16a, the title compound (222 mg, 86%) was obtained as colorless crystals.

$^1$H NMR (400 MHz, DMSO-d$_6$) δ ppm 5.18 (2H, s) 7.06 (1H, dd, J=8.1, 2.4 Hz) 7.35 (1H, d, J=7.1 Hz) 7.41 (3H, t, J=7.9 Hz) 7.47-7.51 (2H, m) 7.55 (1H, d, J=7.8 Hz) 7.60 (1H, d, J=2.2 Hz) 8.31 (1H, s) 8.40 (1H, s) 13.74 (1H, br. s.)

LCMS (ESI+) M+H: 446.

Reference Example 17

1-[4-(3,4-dichlorophenyl)-1,3-thiazol-2-yl]-1H-pyrazole-4-carboxylic acid

Reference Example 17a ethyl 1-[4-(3,4-dichlorophenyl)-1,3-thiazol-2-yl]-1H-pyrazole-4-carboxylate

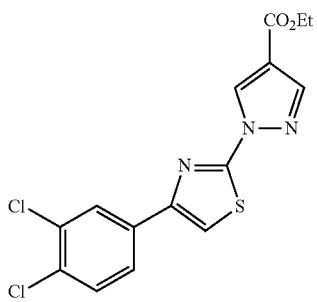 [SMILES: CCOC(=O)c1cnn(-c2nc(-c3ccc(Cl)c(Cl)c3)cs2)c1]

To a solution of ethyl 2-formyl-3-oxopropanoate (0.57 g, 3.0 mmol) in ethanol (5 mL) was added thiosemicarbazide (1.37 g, 15 mmol), and the reaction mixture was stirred at room temperature for 1 hr. 2-Bromo-1-(3,4-dichlorophenyl)-ethanone (0.54 g, 2.0 mmol) was added, and the mixture was stirred at 80° C. for 30 min, and cooled to room temperature. The precipitated crystals were collected by filtration to give the title compound (545 mg, 74%) as orange crystals.

$^1$H NMR (400 MHz, CHLOROFORM-d) δ ppm 1.40 (3H, t, J=7.2 Hz), 4.37 (2H, q, J=7.2 Hz), 7.35 (1H, s), 7.51 (1H, d, J=8.6 Hz), 7.72 (1H, dd, J=8.4, 2.1 Hz), 8.03 (1H, d, J=2.2 Hz), 8.11 (1H, d, J=0.5 Hz), 8.89 (1H, d, J=0.5 Hz)

LCMS (ESI+) M+H: 368.

Reference Example 17

1-[4-(3,4-dichlorophenyl)-1,3-thiazol-2-yl]-1H-pyrazole-4-carboxylic acid

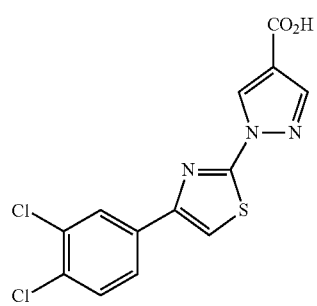 [SMILES: O=C(O)c1cnn(-c2nc(-c3ccc(Cl)c(Cl)c3)cs2)c1]

By a reaction in the same manner as in Reference Example 1 and using the compound (288 mg, 1.48 mmol) obtained in Reference Example 17a, the title compound (288 mg, 57%) was obtained as colorless crystals.

$^1$H NMR (400 MHz, DMSO-d$_6$) δ ppm 7.73 (1H, d, J=8.6 Hz) 8.02 (1H, dd, J=8.4, 2.1 Hz) 8.22 (2H, s) 8.32 (1H, d, J=2.2 Hz) 9.09 (1H, s) 13.00 (1H, br. s.)

LCMS (ESI+) M+H: 340.

Reference Example 18

5-{1-[4-(3,4-dichlorophenyl)-1,3-thiazol-2-yl]-5-(trifluoromethyl)-1H-pyrazol-4-yl}-2H-tetrazole

Reference Example 18a

1-[4-(3,4-dichlorophenyl)-1,3-thiazol-2-yl]-5-(trifluoromethyl)-1H-pyrazole-4-carboxamide

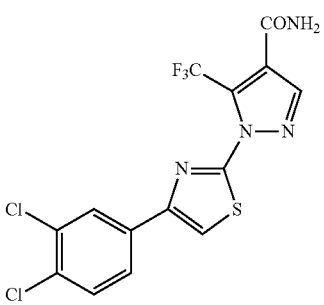 [SMILES: NC(=O)c1cnn(-c2nc(-c3ccc(Cl)c(Cl)c3)cs2)c1C(F)(F)F]

To a solution of the compound (1.0 g, 2.45 mmol) obtained in Reference Example 1 in N,N-dimethylformamide (10 mL) were added 1-ethyl-3-(3-dimethylaminopropyl)carbodiimide hydrochloride (WSC, 0.61 g, 3.18 mmol) and 1-hydroxy-1H-benzotriazole ammonium salt (0.49 g, 3.18 mmol), and the mixture was stirred for 7 hr. The reaction mixture was diluted with diluted aqueous sodium hydrogen carbonate solution, extracted with ethyl acetate, washed with saturated brine, dried over sodium sulfate, and concentrated under reduced pressure. The residue was recrystallized from ethyl acetate-hexane to give the title compound (876 mg, 88%) as colorless crystals.

$^1$H NMR (400 MHz, DMSO-$d_6$) δ ppm 7.79 (1H, d, J=8.3 Hz), 7.81 (1H, br. s.), 7.94 (1H, dd, J=8.6, 2.0 Hz), 8.15 (1H, br. s.), 8.20 (1H, d, J=2.0 Hz), 8.27 (1H, s), 8.39 (1H, s)

LCMS (ESI+) M+H: 407.

Reference Example 18b

1-[4-(3,4-dichlorophenyl)-1,3-thiazol-2-yl]-5-(trifluoromethyl)-1H-pyrazole-4-carbonitrile

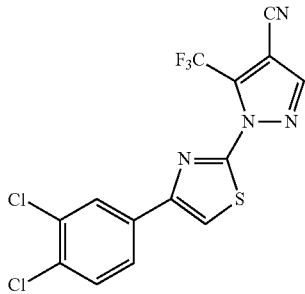 [SMILES: N#Cc1cnn(-c2nc(-c3ccc(Cl)c(Cl)c3)cs2)c1C(F)(F)F]

To a solution of the compound (821 mg, 2.02 mmol) obtained in Reference Example 18a in acetonitrile (10 mL) were added 1,1'-carbonyldiimidazole (0.65 g, 4.03 mmol) and allyl-bromide (1.37 mL, 16.1 mmol), and the mixture was stirred at 90° C. for 4 hr. The reaction mixture was diluted with water, extracted with ethyl acetate, washed with saturated brine, dried over sodium sulfate, and concentrated under reduced pressure. The residue was purified by column chromatography (carrier: silica gel, eluent: hexane-ethyl acetate) and recrystallized from ethyl acetate-hexane to give the title compound (564 mg, 72%) as colorless crystals.

$^1$H NMR (400 MHz, CHLOROFORM-d) δ ppm 7.51 (1H, s), 7.53 (1H, d, J=8.3 Hz), 7.73 (1H, dd, J=8.3, 2.0 Hz), 7.96 (1H, d, J=2.0 Hz), 8.07 (1H, s)

LCMS (ESI+) M+H: 389.

Reference Example 18

5-{1-[4-(3,4-dichlorophenyl)-1,3-thiazol-2-yl]-5-(trifluoromethyl)-1H-pyrazol-4-yl}-2H-tetrazole

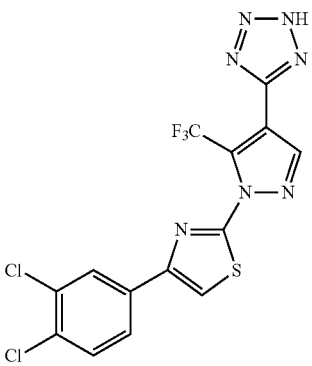 [SMILES: FC(F)(F)c1c(-c2nn[nH]n2)cnn1-c1nc(-c2ccc(Cl)c(Cl)c2)cs1]

To a solution of the compound (156 mg, 0.40 mmol) obtained in Reference Example 18b in N,N-dimethylformamide (2 mL) were added sodium azide (156 mg, 2.40 mmol) and ammonium chloride (128 mg, 2.40 mmol), and the mixture was stirred at 120° C. for 5.5 hr. 1N Hydrochloric acid (3 mL) was added to the reaction mixture, and the mixture was extracted with ethyl acetate, washed successively with water and saturated brine, dried over sodium sulfate, and concentrated under reduced pressure. The residue was recrystallized from ethyl acetate-hexane to give the title compound (126 mg, 73%) as colorless crystals.

$^1$H NMR (400 MHz, DMSO-$d_6$) δ ppm 7.80 (1H, d, J=8.6 Hz), 7.96 (1H, dd, J=8.6, 2.0 Hz), 8.23 (1H, d, J=2.0 Hz), 8.44 (1H, s), 8.54 (1H, s)

LCMS (ESI+) M+H: 432.

Reference Example 19

1-[4-(3,4-dichlorophenyl)-1,3-thiazol-2-yl]-N-(methylsulfonyl)-5-(trifluoromethyl)-1H-pyrazole-4-carboxamide

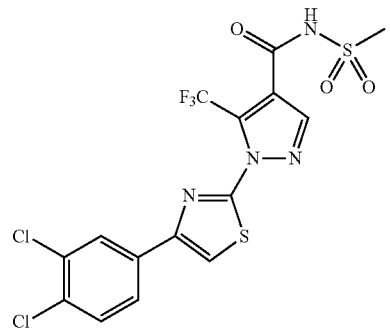 [SMILES: CS(=O)(=O)NC(=O)c1cnn(-c2nc(-c3ccc(Cl)c(Cl)c3)cs2)c1C(F)(F)F]

To a solution of the compound (289 mg, 0.71 mmol) obtained in Reference Example 1 in tetrahydrofuran (5 mL) were added 1-ethyl-3-(3-dimethylaminopropyl)carbodiimide hydrochloride (WSC, 164 mg, 0.85 mmol), methanesulfonamide (81 mg, 0.85 mmol) and 4-dimethylaminopyridine (104 mg, 0.85 mmol), and the mixture was stirred for 4 hr. 1N Hydrochloric acid (2 mL) was added to the reaction mixture, and the mixture was extracted with ethyl acetate, washed successively with water and saturated brine, dried over sodium sulfate, and concentrated under reduced pressure. The residue was recrystallized from ethyl acetate-hexane to give the title compound (83 mg, 24%) as colorless crystals.

$^1$H NMR (400 MHz, DMSO-dd δ ppm 3.37 (3H, s) 7.79 (1H, d, J=8.6 Hz) 7.94 (1H, dd, J=8.6, 2.0 Hz) 8.21 (1H, d, J=2.0 Hz) 8.43 (1H, s) 8.43 (1H, s) 12.71 (1H, br. s.)

LCMS (ESI+) M+H: 485.

Reference Example 20

1-{4-[(3-chlorophenyl)carbamoyl]-1,3-thiazol-2-yl}-5-(trifluoromethyl)-1H-pyrazole-4-carboxylic acid Reference Example 20a 2-[4-(ethoxycarbonyl)-5-(trifluoromethyl)-1H-pyrazol-1-yl]-1,3-thiazole-4-carboxylic acid

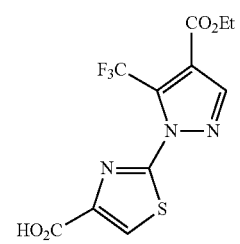 [SMILES: CCOC(=O)c1cnn(-c2nc(C(=O)O)cs2)c1C(F)(F)F]

By a reaction in the same manner as in Reference Example 1a and using bromopyruvic acid (2.50 g, 15.0 mmol) instead of 2-bromo-1-(3,4-dichlorophenyl)ethanone as a starting material, the title compound (1.11 g, 22%) was obtained as colorless crystals.

$^1$H NMR (400 MHz, DMSO-$d_6$) δ ppm 1.31 (3H, t, J=7.2 Hz) 4.34 (2H, q, J=7.1 Hz) 8.46 (1H, s) 8.59 (1H, s) 13.44 (1H, br. s.)

LCMS (ESI+) M+H: 336.

Reference Example 20b ethyl 1-[4-[(3-chlorophenyl)carbamoyl]-1,3-thiazol-2-yl]-5-(trifluoromethyl)-1H-pyrazole-4-carboxylate

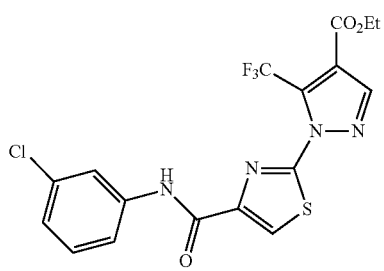 [SMILES: CCOC(=O)c1cnn(-c2nc(C(=O)Nc3cccc(Cl)c3)cs2)c1C(F)(F)F]

By a reaction in the same manner as in Reference Example 19 and using the compound (201 mg, 0.60 mmol) obtained in Reference Example 20a and 3-chloroaniline (0.069 mL, 0.66 mmol), the title compound (123 mg, 46%) was obtained as colorless crystals.

$^1$H NMR (400 MHz, DMSO-$d_6$) δ ppm 1.32 (3H, t, J=7.1 Hz), 4.35 (2H, q, J=7.1 Hz), 7.20 (1H, dd, J=7.8, 1.7 Hz), 7.39 (1H, t, J=8.2 Hz), 7.73 (1H, dd, J=8.2, 1.3 Hz), 7.98 (1H, t, J=2.0 Hz), 8.49 (1H, s), 8.68 (1H, s), 10.42 (1H, s)

LCMS (ESI+) M+H: 445.

Reference Example 20

1-{4-[(3-chlorophenyl)carbamoyl]-1,3-thiazol-2-yl}-5-(trifluoromethyl)-1H-pyrazole-4-carboxylic acid

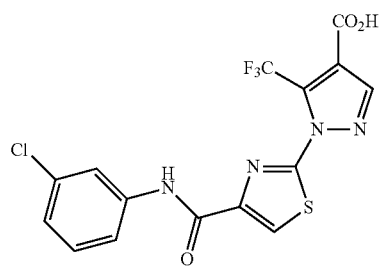 [SMILES: O=C(Nc1cccc(Cl)c1)c1csc(-n2ncc(C(=O)O)c2C(F)(F)F)n1]

By a reaction in the same manner as in Reference Example 1 and using the compound (123 mg, 0.277 mmol) obtained in Reference Example 20b, the title compound (59 mg, 51%) was obtained as colorless crystals.

$^1$H NMR (400 MHz, DMSO-$d_6$) δ ppm 7.20 (1H, dd, J=7.7, 1.8 Hz) 7.39 (1H, t, J=8.1 Hz) 7.74 (1H, dd, J=8.3, 1.2 Hz) 7.99 (1H, q, J=2.4 Hz) 8.42 (1H, s) 8.68 (1H, s) 10.42 (1H, s) 13.75 (1H, s)

LCMS (ESI+) M+H: 417.

Reference Example 21

1-(4-{[(3,4-dichlorophenyl)sulfanyl]methyl}-1,3-thiazol-2-yl)-5-(trifluoromethyl)-1H-pyrazole-4-carboxylic acid Reference Example 21a ethyl 1-[4-(chloromethyl)-1,3-thiazol-2-yl]-5-(trifluoromethyl)-1H-pyrazole-4-carboxylate

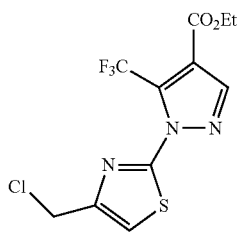 [SMILES: CCOC(=O)c1cnn(-c2nc(CCl)cs2)c1C(F)(F)F]

By a reaction in the same manner as in Reference Example 1a and using 1,3-dichloro-2-propanone (1.16 g, 9.16 mmol) instead of 2-bromo-1-(3,4-dichlorophenyl)ethanone as a starting material, the title compound (0.58 g, 17%) was obtained as colorless crystals.

$^1$H NMR (400 MHz, CHLOROFORM-d) δ ppm 1.39 (3H, t, J=7.1 Hz), 4.39 (2H, q, J=7.1 Hz), 4.69 (2H, s), 7.40 (1H, s), 8.10 (1H, s)

LCMS (ESI+) M+H: 340.

Reference Example 21b ethyl 1-(4-{[(3,4-dichlorophenyl)sulfanyl]methyl}-1,3-thiazol-2-yl)-5-(trifluoromethyl)-1H-pyrazole-4-carboxylate

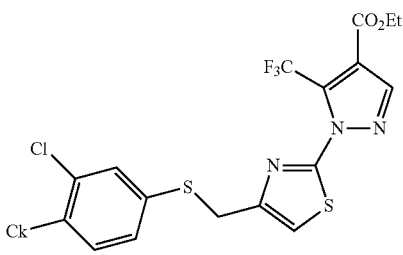

To a solution of the compound (290 mg, 0.855 mmol) obtained in Reference Example 21a in acetonitrile (5 mL) were added 3,4-dichlorothiophenol (168 mg, 0.94 mmol) and potassium carbonate (177 mg, 1.28 mmol), and the mixture was stirred at 80° C. for 4 hr. The reaction mixture was concentrated under reduced pressure, and the residue was diluted with water, extracted with ethyl acetate, washed successively with water and saturated brine, dried over sodium sulfate, and concentrated under reduced pressure. The residue was purified by column chromatography (carrier: silica gel, eluent: hexane-ethyl acetate) to give the title compound (257 mg, 62%) as a colorless oil.

¹H NMR (400 MHz, CHLOROFORM-d) δ ppm 1.39 (3H, t, J=7.2 Hz), 4.22 (2H, s), 4.39 (2H, q, J=7.3 Hz), 7.13 (1H, s), 7.18 (1H, dd, J=8.3, 2.2 Hz), 7.34 (1H, d, J=8.3 Hz), 7.43 (1H, d, J=2.2 Hz), 8.10 (1H, s)
LCMS (ESI+) M+H: 482.

Reference Example 21

1-(4-{[(3,4-dichlorophenyl)sulfanyl]methyl}-1,3-thiazol-2-yl)-5-(trifluoromethyl)-1H-pyrazole-4-carboxylic acid

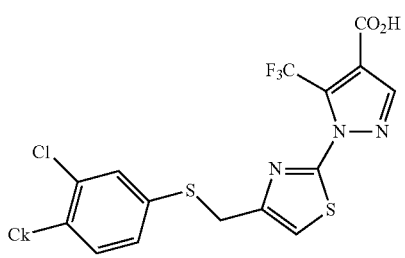

By a reaction in the same manner as in Reference Example 1 and using the compound (257 mg, 0.533 mmol) obtained in Reference Example 21b, the title compound (17 mg, 7%) was obtained as colorless crystals.
¹H NMR (400 MHz, DMSO-$d_6$) δ ppm 4.43 (2H, s) 7.36 (1H, dd, J=8.3, 2.2 Hz) 7.54 (1H, d, J=8.3 Hz) 7.66 (1H, d, J=2.2 Hz) 7.68 (1H, s) 8.35 (1H, s) 13.70 (1H, br. s.)
LCMS (ESI+) M+H: 454.

Reference Example 22

1-{4-[(3,4-dichlorophenoxy)methyl]-1,3-thiazol-2-yl}-5-(trifluoromethyl)-1H-pyrazole-4-carboxylic acid Reference Example 22a ethyl 1-(4-[(3,4-dichlorophenoxy)methyl]-1,3-thiazol-2-yl}-5-(trifluoromethyl)-1H-pyrazole-4-carboxylate

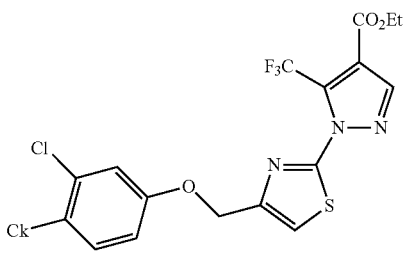

By a reaction in the same manner as in Reference Example 21b and using 3,4-dichlorophenol (153 mg, 0.94 mmol), the title compound (279 mg, 70%) was obtained as colorless crystals.
¹H NMR (400 MHz, CHLOROFORM-d) δ ppm 1.39 (3H, td, J=7.1, 2.9 Hz), 4.39 (2H, q, J=7.1 Hz), 5.18 (2H, d, J=1.0 Hz), 6.87 (1H, dd, J=9.0, 2.9 Hz), 7.12 (1H, d, J=2.9 Hz), 7.35 (1H, d, J=8.8 Hz), 7.40 (1H, t, J=1.0 Hz), 8.11 (1H, s)
LCMS (ESI+) M+H: 466.

Reference Example 22

1-[4-[(3,4-dichlorophenoxy)methyl]-1,3-thiazol-2-yl]-5-(trifluoromethyl)-1H-pyrazole-4-carboxylic acid

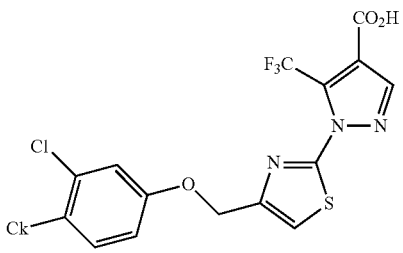

By a reaction in the same manner as in Reference Example 1 and using the compound (279 mg, 0.598 mmol) obtained in Reference Example 22a, the title compound (139 mg, 53%) was obtained as colorless crystals.
¹H NMR (400 MHz, DMSO-$d_6$) δ ppm 5.24 (2H, s) 7.08 (1H, dd, J=8.8, 2.9 Hz) 7.40 (1H, d, J=2.9 Hz) 7.54 (1H, d, J=8.8 Hz) 7.97 (1H, s) 8.37 (1H, s) 13.72 (1H, br. s.)
LCMS (ESI+) M+H: 438.

Reference Example 23

1-(4-{[(3-chlorophenyl)amino]methyl}-1,3-thiazol-2-yl)-5-(trifluoromethyl)-1H-pyrazole-4-carboxylic acid

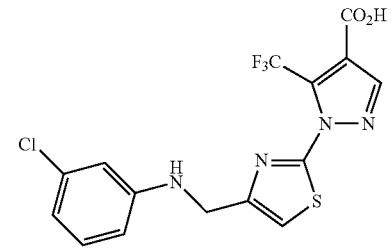 [SMILES: O=C(O)c1cnn(-c2nc(CNc3cccc(Cl)c3)cs2)c1C(F)(F)F]

To a solution of the compound (0.60 g, 1.80 mmol) obtained in Reference Example 21a in toluene (10 mL) were added 3-chloroaniline (0.568 mL, 5.41 mmol) and triethylamine (0.378 mL, 2.70 mmol), and the mixture was stirred at 85° C. for 20 hr. The reaction mixture was diluted with water, extracted with ethyl acetate, washed successively with water and saturated brine, dried over sodium sulfate, and concentrated under reduced pressure. The residue was purified by column chromatography (carrier: silica gel, eluent: hexane-ethyl acetate). The obtained compound was reacted in the same manner as in Reference Example 1 to give the title compound (57 mg, 8%) as a bister oil.
¹H NMR (400 MHz, DMSO-$d_6$) δ ppm 4.37 (2H, d, J=6.1 Hz) 6.53-6.66 (4H, m) 7.06 (1H, t, J=8.1 Hz) 7.60 (1H, s) 8.33 (1H, s) 13.68 (1H, br. s.)
LCMS (ESI+) M+H: 403.

Reference Example 24

5-(trifluoromethyl)-1-(4-[2-[3-(trifluoromethyl)phenyl]ethyl]-1,3-thiazol-2-yl)-1H-pyrazole-4-carboxylic acid

Reference Example 24a ethyl 1-[4-(chloromethyl)-1,3-thiazol-2-yl]-5-(trifluoromethyl)-1H-pyrazole-4-carboxylate

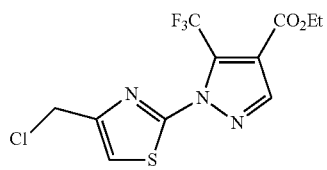 [SMILES: CCOC(=O)c1cnn(-c2nc(CCl)cs2)c1C(F)(F)F]

A mixture of ethyl 4,4,4-trifluoroacetoacetate (28.56 g), ethyl orthoformate (40 mL) and acetic anhydride (45 ml) was heated under reflux for 4 hr, and cooled to room temperature. Ethanol (240 ml) and thiosemicarbazide (10.95 g) were added, and the mixture was stirred at room temperature for 2 hr. 1,3-Dichloropropanone (15.20 g) was added, and the mixture was further heated under reflux for 16 hr, cooled to room temperature, and diluted with ethyl acetate and water. The ethyl acetate layer was separated, washed with saturated aqueous sodium hydrogen carbonate, dried over magnesium sulfate and concentrated. The residue was purified by column chromatography (carrier: silica gel, eluent: hexane-ethyl acetate) to give a crude title compound (11.4 g) as crystals $^1$H NMR (400 MHz, CHLOROFORM-d) δ ppm 1.39 (3H, t, J=7.1 Hz), 4.39 (2H, q, J=7.2 Hz), 4.68 (2H, s), 7.39 (1H, s), 8.10 (1H, s)

Reference Example 24b ({2-[4-(ethoxycarbonyl)-5-(trifluoromethyl)-1H-pyrazol-1-yl]-1,3-thiazol-4-yl}methyl)(triphenyl)phosphonium chloride

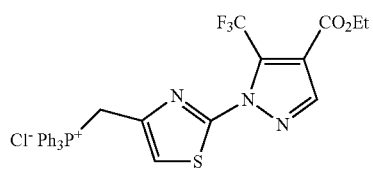

The compound (2.19 g) obtained in Reference Example 24a and triphenylphosphine (1.69 g) were heated under reflux in toluene (30 mL) for 48 hr, and cooled to room temperature. The precipitate was collected by filtration and washed with toluene and diisopropyl ether to give the title compound (1.70 g) as a colorless powder.

$^1$H NMR (300 MHz, CHLOROFORM-d) δ ppm 1.38 (3H, t, J=7.2 Hz), 4.37 (2H, q, J=7.0 Hz), 5.78 (2H, d, J=14.1 Hz), 7.59-7.92 (15H, m), 8.03 (1H, s), 8.64 (1H, d, J=3.8 Hz)

Reference Example 24c ethyl 5-(trifluoromethyl)-1-(4-{2-[3-(trifluoromethyl)phenyl]ethenyl}-1,3-thiazol-2-yl)-1H-pyrazole-4-carboxylate

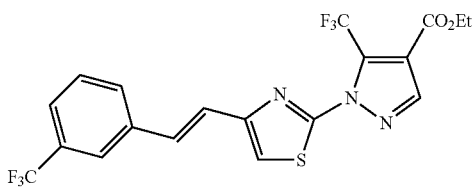

The compound (0.70 g) obtained in Reference Example 24b was suspended in tetrahydrofuran (16 mL), and cooled in an ice bath. Potassium tert-butoxide (0.16 g) was added, and the mixture was stirred for 2 min and 3-(trifluoromethyl) benzaldehyde (0.20 g) was added. The reaction mixture was stirred at room temperature for 16 hr, concentrated, and diluted with ethyl acetate and water. The ethyl acetate layer was separated, washed with saturated brine, dried over magnesium sulfate and concentrated. The residue was purified by column chromatography (carrier: silica gel, eluent: hexane-ethyl acetate) to give a crude title compound (0.40 g) as an oil. This product was used as a crude compound for the next reaction.

LCMS (ESI$^+$) M+H$^+$: 462.

Reference Example 24d ethyl 5-(trifluoromethyl)-1-(4-{2-[3-(trifluoromethyl)phenyl]ethyl}-1,3-thiazol-2-yl)-1H-pyrazole-4-carboxylate

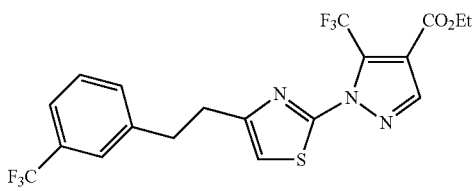 [SMILES: CCOC(=O)c1cnn(-c2nc(CCc3cccc(C(F)(F)F)c3)cs2)c1C(F)(F)F]

By a reaction in the same manner as in Reference Example 26c and using the compound (0.40 g) obtained in Reference Example 24c, and the residue was purified by column chromatography (carrier: silica gel, eluent: hexane-ethyl acetate) to give the title compound (0.16 g) as an oil.

$^1$H NMR (400 MHz, CHLOROFORM-d) δ ppm 1.39 (3H, t, J=7.2 Hz), 3.04-3.22 (4H, m), 4.39 (2H, q, J=7.2 Hz), 6.87 (1H, s), 7.30-7.55 (4H, m), 8.11 (1H, s)

Reference Example 24

5-(trifluoromethyl)-1-(4-{2-[3-(trifluoromethyl)phenyl]ethyl}-1,3-thiazol-2-yl)-1H-pyrazole-4-carboxylic acid

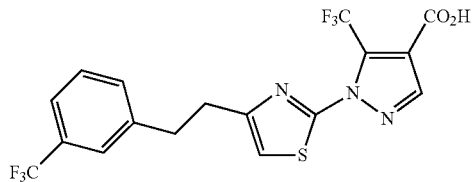 [SMILES: O=C(O)c1cnn(-c2nc(CCc3cccc(C(F)(F)F)c3)cs2)c1C(F)(F)F]

A mixture of the compound (0.16 g) obtained in Reference Example 24d, 4N sodium hydroxide (1 mL) and ethanol (3 mL) was stirred at room temperature for 16 hr, 1N hydrochloric acid (4 mL) was added, and the mixture was extracted with ethyl acetate. The ethyl acetate layer was dried over magnesium sulfate, and concentrated. The residue was recrystallized from ethanol/water to give the title compound (0.13 g) as colorless crystals.

$^1$H NMR (400 MHz, DMSO-$d_6$) δ ppm 3.08 (4H, s), 7.46 (1H, s), 7.49-7.72 (4H, m), 8.35 (1H, s), 13.68 (1H, br. s.)

Reference Example 25

5-(trifluoromethyl)-1-{4-[3-(trifluoromethyl)benzyl]-1,3-thiazol-2-yl}-1H-pyrazole-4-carboxylic acid Reference Example 25a ethyl 1-[4-(iodomethyl)-1,3-thiazol-2-yl]-5-(trifluoromethyl)-1H-pyrazole-4-carboxylate

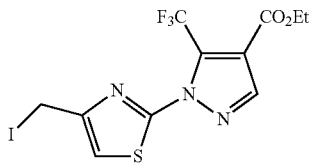 [SMILES: CCOC(=O)c1cnn(-c2nc(CI)cs2)c1C(F)(F)F]

The compound (2.05 g) obtained in Reference Example 24a was dissolved in acetone (25 mL), and sodium iodide (2.7 g) was added. The reaction mixture was heated under reflux for 4 hr, and concentrated. The residue was dissolved in ethyl acetate and 5% aqueous sodium thiosulfate solution. The ethyl acetate layer was separated, washed with saturated aqueous sodium hydrogen carbonate, dried over magnesium sulfate, and concentrated. The residue was purified by column chromatography (carrier: silica gel, eluent: hexane-ethyl acetate), and the obtained crude product was recrystallized from 2-propanol to give the title compound (0.55 g) as crystals $^1$H NMR (300 MHz, CHLOROFORM-d) δ ppm 1.39 (3H, t, J=7.2 Hz), 4.38 (2H, q, J=7.2 Hz), 4.49 (2H, s), 7.30 (1H, s), 8.09 (1H, s)

Reference Example 25b ethyl 5-(trifluoromethyl)-1-{4-[3-(trifluoromethyl)benzyl]-1,3-thiazol-2-yl}-1H-pyrazole-4-carboxylate

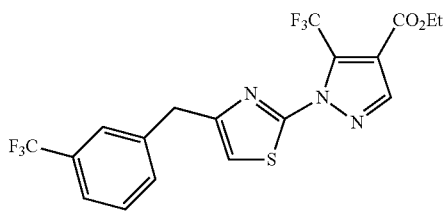 [SMILES: CCOC(=O)c1cnn(-c2nc(Cc3cccc(C(F)(F)F)c3)cs2)c1C(F)(F)F]

A mixture of the compound (0.50 g) obtained in Reference Example 25a, 3-(trifluoromethyl)phenylboronic acid (0.25 g), [1,1'-bis(diphenylphosphino)ferrocene]palladium(II) dichloride dichloromethane complex (1:1) (0.20 g), cesium carbonate (2.0 g), tetrahydrofuran (15 mL) and water (3 mL) was heated under an argon atmosphere at 85° C. for 40 hr, and cooled to room temperature. Ethyl acetate and saturated brine were added to the reaction mixture, and the ethyl acetate layer was separated. The ethyl acetate layer was dried over anhydrous magnesium sulfate, and concentrated, and the obtained crude product was purified by column chromatography (carrier: silica gel, eluent: hexane-ethyl acetate) to give the title compound (0.32 g) as colorless crystals.

$^1$H NMR (300 MHz, CHLOROFORM-d) δ ppm 1.38 (3H, t, J=7.2 Hz), 4.16 (2H, s), 4.38 (2H, q, J=7.2 Hz), 6.96 (1H, s), 7.37-7.61 (4H, m), 8.08 (1H, s)

Reference Example 25

5-(trifluoromethyl)-1-{4-[3-(trifluoromethyl)benzyl]-1,3-thiazol-2-yl}-1H-pyrazole-4-carboxylic acid

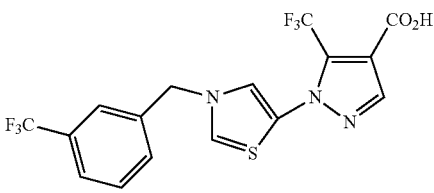

A mixture of the compound (0.32 g) obtained in Reference Example 25b, 4N sodium hydroxide (2 mL) and ethanol (3 mL) was stirred at room temperature for 60 hr, and 2N hydrochloric acid (4 mL) was added. The precipitate was collected by filtration, washed with water, and dried to give the title compound (0.25 g) as colorless crystals.

$^1$H NMR (300 MHz, DMSO-$d_6$) δ ppm 4.20 (2H, s), 7.50-7.70 (5H, m), 8.33 (1H, s), 13.65 (1H, br. s.)

Reference Example 26

5-(trifluoromethyl)-1-(4-[(4-[3-(trifluoromethyl)phenyl]butyl]-1,3-thiazol-2-yl)-1H-pyrazole-4-carboxylic acid Reference Example 26a (2E)-3-[3-(trifluoromethyl)phenyl]prop-2-enal

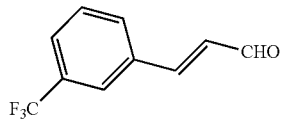

3-(Trifluoromethyl)benzaldehyde (0.70 g) was dissolved in toluene (16 mL), and (triphenylphosphoranylidene)acetoaldehyde (1.22 g) was added. The reaction mixture was heated under reflux for 40 hr and concentrated, and the residue was purified by column chromatography (carrier: silica gel, eluent: hexane-ethyl acetate) to give the title compound (0.41 g) as an oil.

$^1$H NMR (300 MHz, CHLOROFORM-d) δ ppm 6.78 (1H, dd, J=16.1, 7.4 Hz), 7.41-7.87 (5H, m), 9.75 (1H, d, J=7.5 Hz)

Reference Example 26b ethyl 5-(trifluoromethyl)-1-(4-{4-[3-(trifluoromethyl)phenyl]but-1,3-dien-1-yl}-1,3-thiazol-2-yl)-1H-pyrazole-4-carboxylate

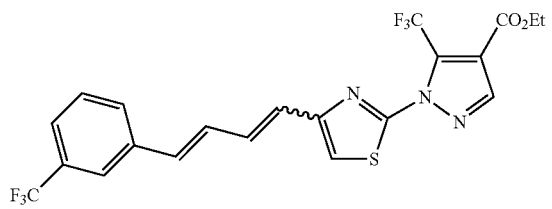 [SMILES: CCOC(=O)c1cnn(-c2nc(C=C/C=C/c3cccc(C(F)(F)F)c3)cs2)c1C(F)(F)F]

The compound (0.80 g) obtained in Reference Example 24b was suspended in tetrahydrofuran (16 mL), and potassium tert-butoxide (0.17 g) was added. The mixture was stirred at room temperature for 5 min, and a solution of the compound (0.28 g) obtained in Reference Example 26a in tetrahydrofuran (8 mL) was added dropwise. The reaction mixture was stirred at room temperature for 24 hr, concentrated, and diluted with ethyl acetate and water. The ethyl acetate layer was separated, washed with saturated brine, dried over magnesium sulfate and concentrated. The residue was purified by column chromatography (carrier: silica gel, eluent: hexane-ethyl acetate) to give the title compound (0.23 g, mixture of E form and Z form) as an oil. The next reaction was performed using this mixture.

LCMS (ESI$^+$) M+H$^+$: 492.

Reference Example 26c ethyl 5-(trifluoromethyl)-1-(4-{4-[3-(trifluoromethyl)phenyl]butyl}-1,3-thiazol-2-yl)-1H-pyrazole-4-carboxylate

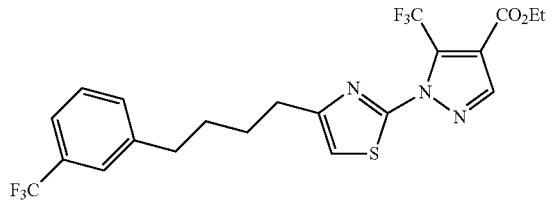 [SMILES: CCOC(=O)c1cnn(-c2nc(CCCCc3cccc(C(F)(F)F)c3)cs2)c1C(F)(F)F]

The compound (0.23 g) obtained in Reference Example 26b was dissolved in acetic acid (4 mL) and ethyl acetate (1 mL), and 10% palladium-carbon (0.23 g) was added. The reaction mixture was stirred under a hydrogen atmosphere (5 atm) at room temperature for 2.5 hr. The insoluble material was filtered off, and the filtrate was concentrated. The residue was dissolved in ethyl acetate and saturated aqueous sodium hydrogen carbonate. The ethyl acetate layer was separated, dried over magnesium sulfate, and concentrated to give the title compound (0.22 g) as an oil.

$^1$H NMR (300 MHz, CHLOROFORM-d) δ ppm 1.39 (3H, t, J=7.2 Hz), 1.50-1.83 (4H, m), 2.58-2.90 (4H, m), 4.38 (2H, q, J=7.2 Hz), 6.95 (1H, s), 7.30-7.57 (4H, m), 8.09 (1H, s)

Reference Example 26

5-(trifluoromethyl)-1-(4-{4-[3-(trifluoromethyl)phenyl]butyl}-1,3-thiazol-2-yl)-1H-pyrazole-4-carboxylic acid

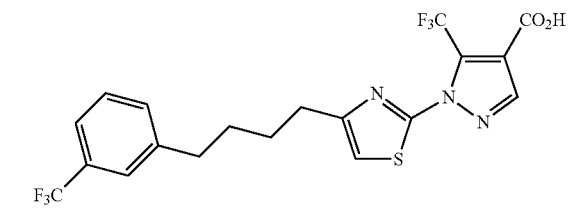 [SMILES: O=C(O)c1cnn(-c2nc(CCCCc3cccc(C(F)(F)F)c3)cs2)c1C(F)(F)F]

A mixture of the compound (0.22 g) obtained in Reference Example 26c, 4N sodium hydroxide (1.5 mL) and ethanol (2 mL) was stirred at room temperature for 60 hr, 3N hydrochloric acid (2 mL) was added, and the mixture was extracted with ethyl acetate. The ethyl acetate layer was dried over magnesium sulfate, and concentrated to give the title compound (0.22 g) as an oil.

$^1$H NMR (300 MHz, DMSO-d$_6$) δ ppm 1.46-1.78 (4H, m), 2.73 (4H, m), 7.42-7.71 (5H, m), 8.33 (1H, s), 13.62 (1H, br. s.)

Reference Example 27

5-(trifluoromethyl)-1-(4-{3-[3-(trifluoromethyl)phenyl]propyl}-1,3-thiazol-2-yl)-1H-pyrazole-4-carboxylic acid

Reference Example 27a ethyl 5-(trifluoromethyl)-1-(4-{3-[3-(trifluoromethyl)phenyl]prop-1-ene-1-yl}-1,3-thiazol-2-yl)-1H-pyrazole-4-carboxylate

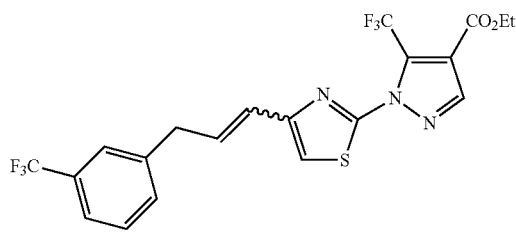 [SMILES: CCOC(=O)c1cnn(-c2nc(C=CCc3cccc(C(F)(F)F)c3)cs2)c1C(F)(F)F]

The compound (0.80 g) obtained in Reference Example 24b was suspended in tetrahydrofuran (16 mL), and potassium tert-butoxide (0.17 g) was added. The mixture was stirred at room temperature for 5 min. A solution of [3-(trifluoromethyl)phenyl]acetoaldehyde (0.52 g) in tetrahydrofuran (8 ml) was added dropwise. The reaction mixture was stirred at room temperature for 16 hr, concentrated, and diluted with ethyl acetate and water. The ethyl acetate layer was separated, washed with saturated brine, dried over magnesium sulfate and concentrated. The residue was purified by column chromatography (carrier: silica gel, eluent: hexane-ethyl acetate) to give a crude title compound (0.30 g, mixture of E form and Z form) as an oil. The next reaction was performed using this crude mixture.

Reference Example 27b ethyl 5-(trifluoromethyl)-1-(4-{3-[3-(trifluoromethyl)phenyl]propyl}-1,3-thiazol-2-yl)-1H-pyrazole-4-carboxylate

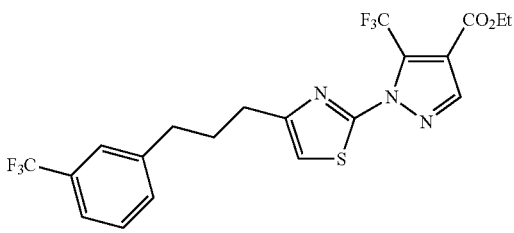 [SMILES: CCOC(=O)c1cnn(-c2nc(CCCc3cccc(C(F)(F)F)c3)cs2)c1C(F)(F)F]

The compound (0.30 g) obtained in Reference Example 27a was dissolved in acetic acid (7 mL), and 10% palladium-carbon (0.29 g) was added. The reaction mixture was stirred under a hydrogen atmosphere (5 atm) at room temperature for 4 hr. The insoluble material was filtered off, and the filtrate was concentrated. The residue was dissolved in ethyl acetate and saturated aqueous sodium hydrogen carbonate. The ethyl acetate layer was separated, dried over magnesium sulfate, and concentrated. The residue was purified by column chromatography (carrier: silica gel, eluent: hexane-ethyl acetate) to give the title compound (0.11 g) as an oil.

$^1$H NMR (300 MHz, CHLOROFORM-d) δ ppm 1.39 (3H, t, J=7.2 Hz), 2.03-2.17 (2H, m), 2.68-2.84 (4H, m), 4.38 (2H, q, J=7.2 Hz), 6.97 (1H, s), 7.34-7.50 (4H, m), 8.10 (1H, s)

Reference Example 27

5-(trifluoromethyl)-1-(4-{3-[3-(trifluoromethyl)phenyl]propyl}-1,3-thiazol-2-yl)-1H-pyrazole-4-carboxylic acid

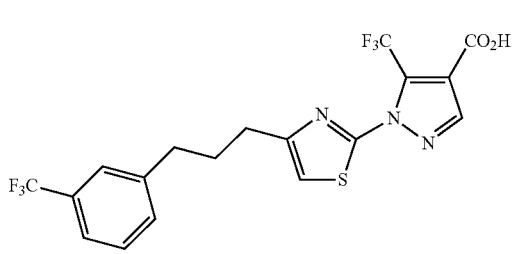 [SMILES: O=C(O)c1cnn(-c2nc(CCCc3cccc(C(F)(F)F)c3)cs2)c1C(F)(F)F]

A mixture of the compound (0.11 g) obtained in Reference Example 27b, 4N sodium hydroxide (2 mL) and ethanol (2 mL) was stirred at room temperature for 16 hr, 1N hydrochloric acid (8 mL) was added, and the mixture was extracted with ethyl acetate. The ethyl acetate layer was dried over magnesium sulfate, concentrated, and recrystallized from hexane-ethyl acetate to give the title compound (0.50 g) as colorless crystals.

$^1$H NMR (300 MHz, CHLOROFORM-d) δ ppm 2.02-2.18 (2H, m), 2.69-2.86 (4H, m), 7.00 (1H, s), 7.34-7.49 (4H, m), 8.19 (1H, s)

Example 1

1-({4-[3-(trifluoromethyl)phenyl]-1,3-thiazol-2-yl}methyl)-1H-pyrazole-4-carboxylic acid Example 1a ethyl 1-(cyanomethyl)-1H-pyrazole-4-carboxylate

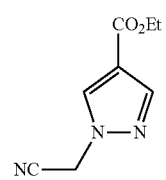 [SMILES: CCOC(=O)c1cnn(CC#N)c1]

To a solution of ethyl 1H-pyrazole-4-carboxylate (0.98 g, 7.0 mmol) in N,N-dimethylformamide (10 mL) was added 60% sodium hydride (0.42 g, 10.5 mmol) under ice-cooling, and the mixture was stirred at the same temperature for 20 min. Bromoacetonitrile (0.63 mL, 9.10 mmol) was added to the reaction mixture, the ice bath was removed and the mixture was stirred for 4.5 hr. The reaction mixture was diluted with water, extracted with ethyl acetate, washed successively with water and saturated brine, dried over sodium sulfate, and concentrated under reduced pressure. The residue was purified by column chromatography (carrier: silica gel, eluent: hexane-ethyl acetate) to give the title compound (1.14 g, 90%) as a colorless oil.

$^1$H NMR (400 MHz, CHLOROFORM-d) δ ppm 1.36 (3H, t, J=7.1 Hz), 4.32 (2H, q, J=7.3 Hz), 5.11 (2H, s), 7.99 (1H, s), 8.07 (1H, s)

Example 1b ethyl 1-(2-amino-2-thioxoethyl)-1H-pyrazole-4-carboxylate

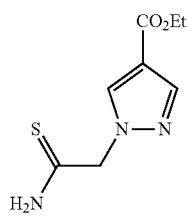 [SMILES: CCOC(=O)c1cnn(CC(N)=S)c1]

To the compound (1.14 g, 6.34 mmol) obtained in Example 1a were added 4M hydrogen chloride-ethyl acetate solution (12 mL) and diethyl dithiophosphate (1.59 mL, 9.51 mmol), and the mixture was stirred for 23 hr. The reaction mixture was alkalified with saturated aqueous sodium hydrogen carbonate solution and 8N aqueous sodium hydroxide solution, and the mixture was extracted with ethyl acetate, washed successively with water and saturated brine, dried over sodium sulfate, and concentrated under reduced pressure. The residue was purified by column chromatography (carrier:

silica gel, eluent: hexane-ethyl acetate) to give the title compound (0.98 g, 72%) as a colorless solid.

$^1$H NMR (400 MHz, CHLOROFORM-d) δ ppm 1.35 (3H, t, J=7.1 Hz), 4.31 (2H, q, J=7.1 Hz), 5.21 (2H, s), 7.77 (1H, br. s.), 7.96 (1H, br. s.), 8.01 (1H, s), 8.04 (1H, s)

LCMS (ESI+) M+H: 214.

Example 1c ethyl 1-({4-[3-(trifluoromethyl)phenyl]-1,3-thiazol-2-yl}methyl)-1H-pyrazole-4-carboxylate

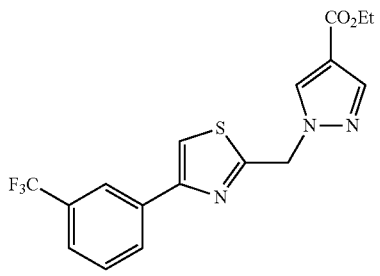 [SMILES: CCOC(=O)c1cnn(Cc2nc(-c3cccc(C(F)(F)F)c3)cs2)c1]

To a solution of the compound (2.99 g, 14.0 mmol) obtained in Example 1b in ethanol (30 mL) was added 2-bromo-1-[3-(trifluoromethyl)phenyl]ethanone (3.74 g, 14.0 mmol), and the mixture was heated under reflux for 14 hr. The reaction mixture was concentrated under reduced pressure, and the residue was extracted with ethyl acetate, washed successively with diluted aqueous sodium hydrogen carbonate solution and saturated brine, dried over sodium sulfate, and concentrated under reduced pressure. The residue was purified by column chromatography (carrier: silica gel, eluent: hexane-ethyl acetate) to give the title compound (4.90 g, 91%) as a colorless solid.

$^1$H NMR (400 MHz, CHLOROFORM-d) δ ppm 1.34 (3H, t, J=7.1 Hz), 4.30 (2H, q, J=7.3 Hz), 5.69 (2H, s), 7.52-7.59 (2H, m), 7.61 (1H, d, J=7.8 Hz), 8.01 (1H, s), 8.05 (1H, d, J=7.6 Hz), 8.11 (1H, s), 8.16 (1H, s)

LCMS (ESI+) M+H: 382.

Example 1

1-({4-[3-(trifluoromethyl)phenyl]-1,3-thiazol-2-yl}methyl)-1H-pyrazole-4-carboxylic acid

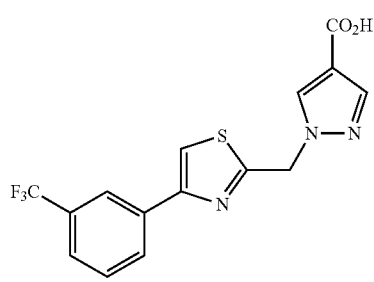 [SMILES: O=C(O)c1cnn(Cc2nc(-c3cccc(C(F)(F)F)c3)cs2)c1]

To the compound (4.80 g, 12.6 mmol) obtained in Example 1c were added ethanol (40 mL), tetrahydrofuran (10 mL) and 2N aqueous sodium hydroxide solution (12.6 mL, 25.2 mmol), and the mixture was stirred overnight. The reaction mixture was concentrated under reduced pressure, and the residue was extracted with water, and washed with ether. The aqueous layer was acidified with 6N hydrochloric acid, extracted with ethyl acetate, washed with saturated brine, dried over sodium sulfate, and concentrated under reduced pressure. The residue was recrystallized from ethyl acetate-hexane to give the title compound (3.0 g, 67%) as colorless crystals.

$^1$H NMR (400 MHz, DMSO-d$_6$) δ ppm 5.85 (2H, s) 7.66-7.76 (2H, m) 7.93 (1H, s) 8.26 (1H, d, J=6.8 Hz) 8.28 (1H, s) 8.38 (1H, s) 8.52 (1H, s) 12.52 (1H, br. s.)

LCMS (ESI+) M+H: 354.

Example 2

1-{[4-(3,4-dichlorophenyl)-1,3-thiazol-2-yl]methyl}-1H-pyrazole-4-carboxylic acid

Example 2a ethyl 1-{[4-(3,4-dichlorophenyl)-1,3-thiazol-2-yl]methyl}-1H-pyrazole-4-carboxylate

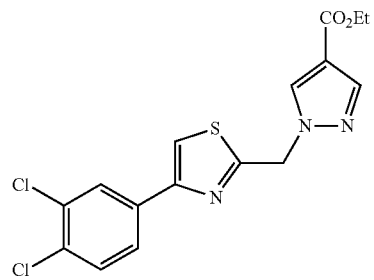 [SMILES: CCOC(=O)c1cnn(Cc2nc(-c3ccc(Cl)c(Cl)c3)cs2)c1]

By a reaction in the same manner as in Example 1c and using the compound (213 mg, 1.00 mmol) obtained in Example 1b and 2-bromo-1-(3,4-dichlorophenyl)ethanone (268 mg, 1.00 mmol) to give the title compound (290 mg, 76%) as colorless crystals.

$^1$H NMR (400 MHz, CHLOROFORM-d) δ ppm 1.34 (3H, t, J=7.1 Hz), 4.30 (2H, q, J=7.1 Hz), 5.66 (2H, s), 7.47-7.52 (2H, m), 7.70 (1H, dd, J=8.3, 2.0 Hz), 7.98-8.02 (2H, m), 8.09 (1H, s)

LCMS (ESI+) M+H: 382.

Example 2

1-{[4-(3,4-dichlorophenyl)-1,3-thiazol-2-yl]methyl}-1H-pyrazole-4-carboxylic acid

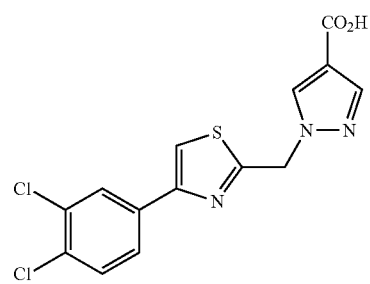 [SMILES: O=C(O)c1cnn(Cc2nc(-c3ccc(Cl)c(Cl)c3)cs2)c1]

By a reaction in the same manner as in Example 1 and using the compound (290 mg, 0.76 mmol) obtained in Example 2a, the title compound (219 mg, 81%) was obtained as colorless crystals.

¹H NMR (400 MHz, DMSO-d₆) δ ppm 5.83 (2H, s) 7.72 (1H, d, J=8.6 Hz) 7.91-7.96 (2H, m) 8.20 (1H, d, J=2.0 Hz) 8.33 (1H, s) 8.51 (1H, s) 12.51 (1H, br. s.)

LCMS (ESI+) M+H: 354.

Example 3

1-({4-[3-(trifluoromethoxy)phenyl]-1,3-thiazol-2-yl}methyl)-1H-pyrazole-4-carboxylic acid Example 3a ethyl 1-({4-[3-(trifluoromethoxy)phenyl]-1,3-thiazol-2-yl}methyl)-1H-pyrazole-4-carboxylate

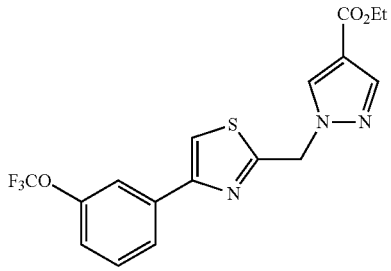 [SMILES: CCOC(=O)c1cnn(Cc2nc(-c3cccc(OC(F)(F)F)c3)cs2)c1]

By a reaction in the same manner as in Example 1c and using the compound (213 mg, 1.00 mmol) obtained in Example 1b and 2-bromo-1-[3-(trifluoromethoxy)phenyl]ethanone (283 mg, 1.00 mmol), the title compound (343 mg, 86%) was obtained as colorless crystals.

¹H NMR (300 MHz, CHLOROFORM-d) δ ppm 1.34 (3H, t, J=7.2 Hz), 4.30 (2H, q, J=6.9 Hz), 5.67 (2H, s), 7.20 (1H, d, J=8.3 Hz), 7.45 (1H, t, J=8.0 Hz), 7.52 (1H, s), 7.76 (1H, br. s.), 7.79 (1H, d, J=7.6 Hz), 8.00 (1H, s), 8.09 (1H, s)

LCMS (ESI+) M+H: 398.

Example 3

1-({4-[3-(trifluoromethoxy)phenyl]-1,3-thiazol-2-yl}methyl)-1H-pyrazole-4-carboxylic acid

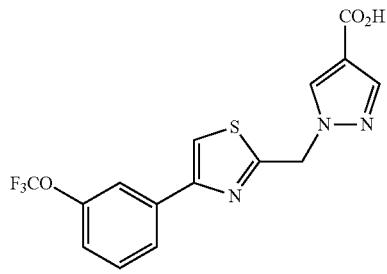 [SMILES: O=C(O)c1cnn(Cc2nc(-c3cccc(OC(F)(F)F)c3)cs2)c1]

By a reaction in the same manner as in Example 1 and using the compound (343 mg, 0.86 mmol) obtained in Example 3a, the title compound (248 mg, 78%) was obtained as colorless crystals.

¹H NMR (400 MHz, DMSO-d₆) δ ppm 5.84 (2H, s) 7.36 (1H, ddd, J=8.2, 1.2, 1.1 Hz) 7.60 (1H, t, J=7.9 Hz) 7.91 (1H, s) 7.92 (1H, s) 7.99 (1H, ddd, J=8.1, 1.2, 1.0 Hz) 8.31 (1H, s) 8.51 (1H, s) 12.51 (1H, br. s.)

LCMS (ESI+) M+H: 370.

Example 4

1-[(4-{[3-(trifluoromethyl)phenyl]carbamoyl}-1,3-thiazol-2-yl)methyl]-1H-pyrazole-4-carboxylic acid Example 4a 2-{[4-(ethoxycarbonyl)-1H-pyrazol-1-yl]methyl}-1,3-thiazole-4-carboxylic acid

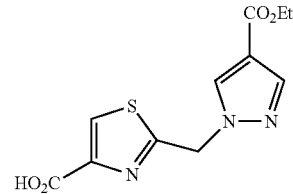 [SMILES: CCOC(=O)c1cnn(Cc2nc(C(=O)O)cs2)c1]

By a reaction in the same manner as in Example 1c and using the compound (1.07 g, 5.0 mmol) obtained in Example 1b and bromopyruvic acid (920 mg, 5.5 mmol), the title compound (814 mg, 57%) was obtained as bister crystals.

¹H NMR (400 MHz, DMSO-d₆) δ ppm 1.27 (3H, t, J=7.1 Hz) 4.22 (2H, q, J=7.1 Hz) 5.79 (2H, s) 7.97 (1H, s) 8.43 (1H, s) 8.56 (1H, s) 13.12 (1H, br. s.)

LCMS (ESI+) M+H: 282.

Example 4b ethyl 1-[(4-{[3-(trifluoromethyl)phenyl]carbamoyl}-1,3-thiazol-2-yl)methyl]-1H-pyrazole-4-carboxylate

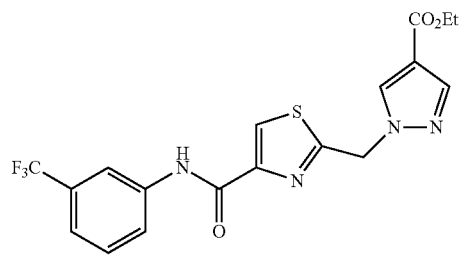 [SMILES: CCOC(=O)c1cnn(Cc2nc(C(=O)Nc3cccc(C(F)(F)F)c3)cs2)c1]

By a reaction in the same manner as in Reference Example 19 and using the compound (281 mg, 1.00 mmol) obtained in Example 4a and 3-(trifluoromethyl)aniline (0.149 mL, 1.20 mmol), the title compound (368 mg, 86%) was obtained as a colorless oil.

¹H NMR (400 MHz, CHLOROFORM-d) δ ppm 1.35 (3H, t, J=7.1 Hz), 4.31 (2H, q, J=7.1 Hz), 5.66 (2H, s), 7.40-7.44 (1H, m), 7.51 (1H, t, J=7.9 Hz), 7.94 (1H, d, J=8.1 Hz), 8.00 (1H, s), 8.02 (1H, s), 8.10 (1H, s), 8.24 (1H, s), 9.21 (1H, br. s.)

LCMS (ESI+) M+H: 425.

Example 4

1-[(4-{[3-(trifluoromethyl)phenyl]carbamoyl}-1,3-thiazol-2-yl)methyl]-1H-pyrazole-4-carboxylic acid

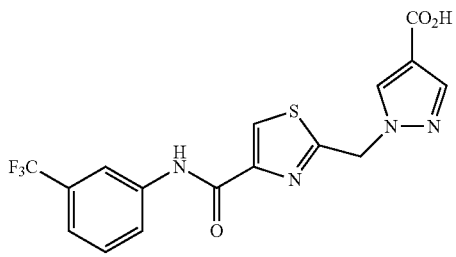 [SMILES: O=C(O)c1cnn(Cc2nc(C(=O)Nc3cccc(C(F)(F)F)c3)cs2)c1]

By a reaction in the same manner as in Example 1 and using the compound (368 mg, 0.868 mmol) obtained in Example 4b, the title compound (260 mg, 78%) was obtained as colorless crystals.

$^1$H NMR (400 MHz, DMSO-d$_6$) δ ppm 5.86 (2H, s) 7.47 (1H, d, J=7.8 Hz) 7.60 (1H, t, J=7.9 Hz) 7.95 (1H, s) 8.12 (1H, d, J=8.3 Hz) 8.34 (1H, s) 8.48 (1H, s) 8.54 (1H, s) 10.69 (1H, s) 12.56 (1H, br. s.)

LCMS (ESI+) M+H: 397.

Example 5

5-methyl-1-({4-[3-(trifluoromethyl)phenyl]-1,3-thiazol-2-yl}methyl)-1H-pyrazole-3-carboxylic acid

Example 5a

[3-(ethoxycarbonyl)-5-methyl-1H-pyrazol-1-yl]acetic acid

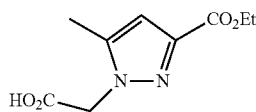

To a mixture of ethyl 2,4-dioxopentanoate (1.74 g, 11.0 mmol), ammonium acetate (1.16 g, 15.0 mmol) and ethanol (20 mL) was added benzyl hydrazinoacetate hydrochloride (2.17 g, 10.0 mmol), and the mixture was stirred at room temperature for 1 hr and at 80° C. for 3 hr. The reaction mixture was concentrated under reduced pressure, and the residue was diluted with water, extracted with ethyl acetate, washed with saturated brine, dried over sodium sulfate, and concentrated under reduced pressure. The residue was purified by column chromatography (carrier: silica gel, eluent: hexane-ethyl acetate) to give benzyl [3-(ethoxycarbonyl)-5-methyl-1H-pyrazol-1-yl]acetate (0.95 g, 31%) and benzyl [5-(ethoxycarbonyl)-3-methyl-1H-pyrazol-1-yl]acetate (1.56 g, 51%). To a solution of benzyl [3-(ethoxycarbonyl)-5-methyl-1H-pyrazol-1-yl]acetate (0.95 g, 3.14 mmol) in ethanol (10 mL) was added 5% palladium/carbon (0.30 g), and the mixture was stirred under a hydrogen stream for 21 hr. The insoluble material was filtered off, and the filtrate was concentrated. The residue was recrystallized from ethyl acetate-hexane to give the title compound (0.59 g, 88%).

$^1$H NMR (400 MHz, DMSO-d$_6$) δ ppm 1.27 (3H, t, J=7.1 Hz) 2.23 (3H, s) 4.24 (2H, q, J=7.1 Hz) 5.01 (2H, s) 6.55 (1H, s) 13.34 (1H, br. s.)

LCMS (ESI+) M+H: 213.

Example 5c ethyl 1-(2-amino-2-thioxoethyl)-5-methyl-1H-pyrazole-3-carboxylate

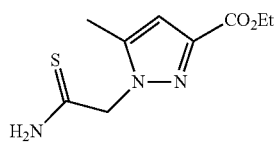

By a reaction in the same manner as in Reference Example 18a and using the compound (0.59 g, 2.77 mmol) obtained in Example 5a, ethyl 1-(2-amino-2-oxoethyl)-5-methyl-1H-pyrazole-3-carboxylate was obtained. To the obtained compound were added tetrahydrofuran (10 mL) and 2,4-bis(4-methoxyphenyl)-1,3-dithia-2,4-diphosphetane-2,4-disulfide (Lawesson reagent, 1.68 g, 4.15 mmol), and the mixture was heated under reflux overnight. A saturated aqueous sodium hydrogen carbonate solution was added to the reaction mixture until foaming ceased, and the mixture was stirred for 30 min. The reaction mixture was extracted with ethyl acetate, washed successively with water and saturated brine, dried over sodium sulfate, and concentrated under reduced pressure. The residue was purified by column chromatography (carrier: silica gel, eluent: hexane-ethyl acetate) and recrystallized from ethyl acetate-hexane to give the title compound (0.77 g, 73%) as colorless crystals.

$^1$H NMR (400 MHz, CHLOROFORM-d) δ ppm 1.39 (3H, t, J=7.1 Hz), 2.36 (3H, s), 4.39 (2H, q, J=7.1 Hz), 5.21 (2H, s), 6.64 (1H, s), 7.62 (2H, br. s.)

LCMS (ESI+) M+H: 228.

Example 5d ethyl 5-methyl-1-({4-[3-(trifluoromethyl)phenyl]-1,3-thiazol-2-yl}methyl)-1H-pyrazole-3-carboxylate

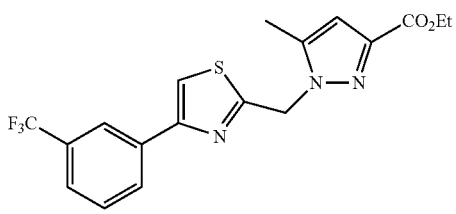 [SMILES: CCOC(=O)c1cc(C)n(Cc2nc(-c3cccc(C(F)(F)F)c3)cs2)n1]

By a reaction in the same manner as in Example 1c and using the compound (227 mg, 1.00 mmol) obtained in Example 5c and 2-bromo-1-[3-(trifluoromethoxy)phenyl]ethanone (283 mg, 1.00 mmol), the title compound (310 mg, 78%) was obtained as colorless crystals.

$^1$H NMR (400 MHz, CHLOROFORM-d) δ ppm 1.40 (3H, t, J=7.1 Hz), 2.39 (3H, s), 4.42 (2H, q, J=7.1 Hz), 5.71 (2H, s), 6.65 (1H, s), 7.52-7.57 (2H, m), 7.58-7.62 (1H, m), 8.04 (1H, d, J=7.8 Hz), 8.14 (1H, s)

LCMS (ESI+) M+H: 396.

Example 5

5-methyl-1-({4-[3-(trifluoromethyl)phenyl]-1,3-thiazol-2-yl}methyl)-1H-pyrazole-3-carboxylic acid

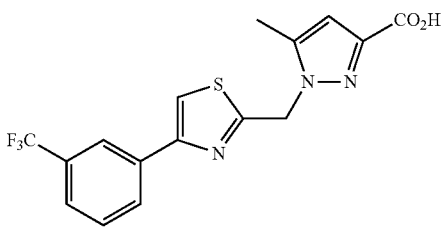 [SMILES: Cc1cc(C(=O)O)nn1Cc1nc(-c2cccc(C(F)(F)F)c2)cs1]

By a reaction in the same manner as in Example 1 and using the compound (310 mg, 0.784 mmol) obtained in Example 5d, the title compound (262 mg, 91%) was obtained as colorless crystals.

$^1$H NMR (400 MHz, DMSO-d$_6$) δ ppm 2.39 (3H, s) 5.82 (2H, s) 6.58 (1H, s) 7.67-7.75 (2H, m) 8.25 (1H, d, J=7.1 Hz) 8.28 (1H, s) 8.38 (1H, s) 12.73 (1H, br. s.)

LCMS (ESI+) M+H: 368.

Example 6

1-{[4-(3,4-dichlorophenyl)-1,3-thiazol-2-yl]methyl}-5-methyl-1H-pyrazole-3-carboxylic acid

Example 6a ethyl 1-{([4-(3,4-dichlorophenyl)-1,3-thiazol-2-yl]methyl}-5-methyl-1H-pyrazole-3-carboxylate

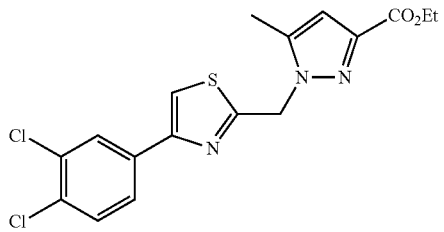 [SMILES: CCOC(=O)c1cc(C)n(Cc2nc(-c3ccc(Cl)c(Cl)c3)cs2)n1]

By a reaction in the same manner as in Example 5d and using the compound (227 mg, 1.0 mmol) obtained in Example 5c and 2-bromo-1-(3,4-dichlorophenyl)ethanone (268 mg, 1.0 mmol), the title compound (360 mg, 90%) was obtained as colorless crystals.

$^1$H NMR (400 MHz, CHLOROFORM-d) δ ppm 1.40 (3H, t, J=7.1 Hz), 2.39 (3H, s), 4.41 (2H, q, J=7.1 Hz), 5.69 (2H, s), 6.64 (1H, s), 7.46 (1H, s), 7.49 (1H, d, J=8.6 Hz), 7.68 (1H, dd, J=8.4, 2.1 Hz), 7.98 (1H, d, J=2.2 Hz)

LCMS (ESI+) M+H: 396.

Example 6

1-{[4-(3,4-dichlorophenyl)-1,3-thiazol-2-yl]methyl}-5-methyl-1H-pyrazole-3-carboxylic acid

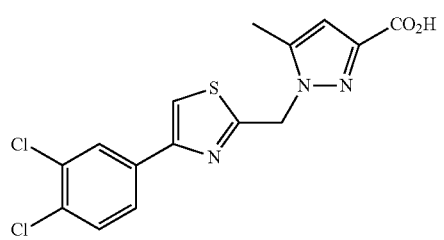 [SMILES: Cc1cc(C(=O)O)nn1Cc1nc(-c2ccc(Cl)c(Cl)c2)cs1]

By a reaction in the same manner as in Example 1 and using the compound (360 mg, 0.908 mmol) obtained in Example 6a, the title compound (308 mg, 92%) was obtained as colorless crystals.

$^1$H NMR (400 MHz, DMSO-d$_6$) δ ppm 2.38 (3H, s) 5.79 (2H, s) 6.58 (1H, d, J=1.0 Hz) 7.72 (1H, d, J=8.3 Hz) 7.93 (1H, dd, J=8.3, 2.0 Hz) 8.19 (1H, d, J=2.0 Hz) 8.33 (1H, s) 12.73 (1H, br. s.)

LCMS (ESI+) M+H: 368.

Example 7

3-methyl-1-({4-[3-(trifluoromethyl)phenyl]-1,3-thiazol-2-yl}methyl)-1H-pyrazole-5-carboxylic acid

Example 7a

[5-(ethoxycarbonyl)-3-methyl-1H-pyrazol-1-yl]acetic acid

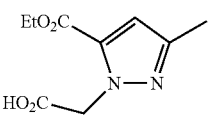

Benzyl [5-(ethoxycarbonyl)-3-methyl-1H-pyrazol-1-yl]acetate (1.56 g, 5.16 mmol) obtained in Example 5a was subjected to a catalytic reduction in the same manner as in the method described in Example 5a to give the title compound (0.98 g, 89%).

$^1$H NMR (400 MHz, DMSO-d$_6$) δ ppm 1.27 (3H, t, J=7.1 Hz) 2.19 (3H, s) 4.25 (2H, q, J=7.1 Hz) 5.11 (2H, s) 6.71 (1H, s) 13.08 (1H, br. s.)

LCMS (ESI+) M+H: 213.

Example 7b ethyl 1-(2-amino-2-thioxoethyl)-3-methyl-1H-pyrazole-5-carboxylate

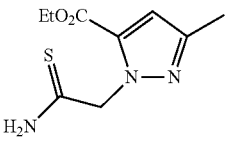

By a reaction in the same manner as in Example 5c and using the compound (0.98 g, 4.60 mmol) obtained in Example 7a, the title compound (0.77 g, 73%) was obtained as colorless crystals.

$^1$H NMR (400 MHz, CHLOROFORM-d) δ ppm 1.37 (3H, t, J=7.2 Hz), 2.31 (3H, s), 4.35 (2H, q, J=7.1 Hz), 5.57 (2H, s), 6.72 (1H, s), 7.31 (1H, br. s.), 7.51 (1H, br. s.)

LCMS (ESI+) M+H: 228.

Example 7c ethyl 3-methyl-1-({4-[3-(trifluoromethyl)phenyl]-1,3-thiazol-2-yl}methyl)-1H-pyrazole-5-carboxylate

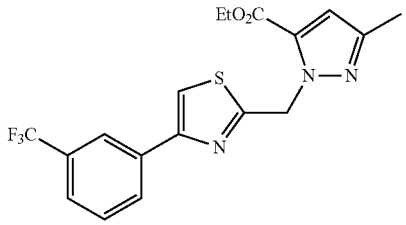 [SMILES: Cc1cc(C(=O)O)n(Cc2nc(-c3cccc(C(F)(F)F)c3)cs2)n1]

By a reaction in the same manner as in Example 1c and using the compound (227 mg, 1.00 mmol) obtained in Example 7b and 2-bromo-1-[3-(trifluoromethyl)phenyl]ethanone (283 mg, 1.00 mmol), the title compound (374 mg, 94%) was obtained as a colorless oil.

$^1$H NMR (400 MHz, CHLOROFORM-d) δ ppm 1.35 (3H, t, J=7.2 Hz), 2.32 (3H, s), 4.34 (2H, q, J=7.3 Hz), 6.07 (2H, s), 6.73 (1H, s), 7.48 (1H, s), 7.52 (1H, t, J=7.7 Hz), 7.55-7.59 (1H, m), 8.06 (1H, d, J=7.6 Hz), 8.15 (1H, s)

LCMS (ESI+) M+H: 396.

Example 7

3-methyl-1-({4-[3-(trifluoromethyl)phenyl]-1,3-thiazol-2-yl}methyl)-1H-pyrazole-5-carboxylic acid

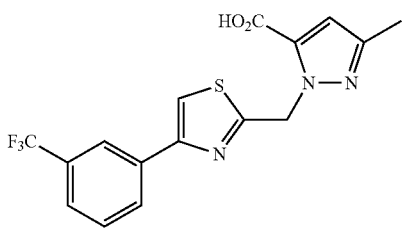

By a reaction in the same manner as in Example 1 and using the compound (374 mg, 0.946 mmol) obtained in Example 7c, the title compound (229 mg, 66%) was obtained as colorless crystals.

$^1$H NMR (400 MHz, DMSO-d$_6$) δ ppm 2.22 (3H, s) 6.02 (2H, s) 6.75 (1H, s) 7.66-7.74 (2H, m) 8.24 (1H, d, J=7.1 Hz) 8.26 (1H, s) 8.31 (1H, s) 13.57 (1H, br. s.)

LCMS (ESI+) M+H: 368.

Example 8

5-ethoxy-1-({4-[3-(trifluoromethyl)phenyl]-1,3-thiazol-2-yl}methyl)-1H-pyrazole-4-carboxylic acid

Example 8a

[5-ethoxy-4-(ethoxycarbonyl)-1H-pyrazol-1-yl]acetic acid

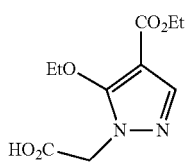

To a solution of diethyl(ethoxymethylidene)propanedioate (3.52 g, 16.3 mmol) in ethanol (35 mL) were added benzyl hydrazinoacetate hydrochloride (3.20 g, 14.8 mmol), triethylamine (2.20 ml, 16.3 mmol) and acetonitrile (15 mL), and the mixture was stirred at 80° C. for 5 hr. The reaction mixture was diluted with diluted aqueous sodium hydrogen carbonate solution, extracted with ethyl acetate, dried over sodium sulfate, and concentrated under reduced pressure. The residue was purified by column chromatography (carrier: silica gel, eluent: hexane-ethyl acetate) to give ethyl [5-ethoxy-4-(ethoxycarbonyl)-1H-pyrazol-1-yl]acetate (0.56 g, 14%) wherein benzyl ester was converted to ethyl ester. To a solution of the present compound (0.56 g, 2.07 mmol) in tetrahydrofuran (10 mL) was added 1N aqueous sodium hydroxide solution (2.07 mL, 2.07 mmol) under ice-cooling, and the mixture was stirred at the same temperature for 1 hr. The reaction mixture was extracted with water, and washed with ether. The aqueous layer was neutralized with 1N hydrochloric acid (2 mL), and the mixture was extracted with ethyl acetate, washed with saturated brine, dried over anhydrous sodium sulfate, and concentrated under reduced pressure. The residue was recrystallized from ethyl acetate-hexane to give the title compound (401 mg, 80%) as colorless crystals.

$^1$H NMR (400 MHz, DMSO-d$_6$) δ ppm 1.23 (3H, t, J=7.1 Hz) 1.30 (3H, t, J=7.1 Hz) 4.11-4.21 (4H, m) 4.81 (2H, s) 8.11 (1H, s) 13.19 (1H, br. s.)

LCMS (ESI+) M+H: 243.

Example 8b ethyl 1-(2-amino-2-thioxoethyl)-5-ethoxy-1H-pyrazole-4-carboxylate

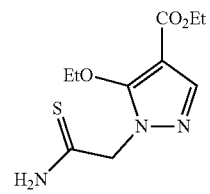

By a reaction in the same manner as in Example 5c and using the compound (401 mg, 1.66 mmol) obtained in Example 8a, the title compound (312 mg, 73%) was obtained as colorless crystals.

$^1$H NMR (400 MHz, DMSO-d$_6$) δ ppm 1.23 (3H, t, J=7.1 Hz), 1.29 (3H, t, J=7.0 Hz), 4.11-4.20 (4H, m), 4.90 (2H, s), 8.10 (1H, s), 9.20 (1H, br. s.), 9.85 (1H, br. s.)

LCMS (ESI+) M+H: 258.

Example 8c ethyl 5-ethoxy-1-({4-[3-(trifluoromethyl)phenyl]-1,3-thiazol-2-yl}methyl)-1H-pyrazole-4-carboxylate

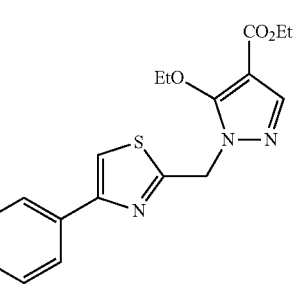

By a reaction in the same manner as in Example 1c and using the compound (200 mg, 0.78 mmol) obtained in Example 8b and 2-bromo-1-[3-(trifluoromethyl)phenyl] ethanone (0.53 g, 2.0 mmol), the title compound (275 mg, 83%) was obtained as colorless crystals.

$^1$H NMR (400 MHz, CHLOROFORM-d) δ ppm 1.32 (3H, t, J=7.1 Hz), 1.46 (3H, t, J=7.1 Hz), 4.27 (2H, q, J=7.1 Hz), 4.37 (2H, q, J=7.1 Hz), 5.48 (2H, s), 7.52-7.58 (2H, m), 7.59-7.63 (1H, m), 7.89 (1H, s), 8.05 (1H, d, J=7.8 Hz), 8.16 (1H, s)

LCMS (ESI+) M+H: 426.

Example 8

5-ethoxy-1-({4-[3-(trifluoromethyl)phenyl]-1,3-thiazol-2-yl}methyl)-1H-pyrazole-4-carboxylic acid

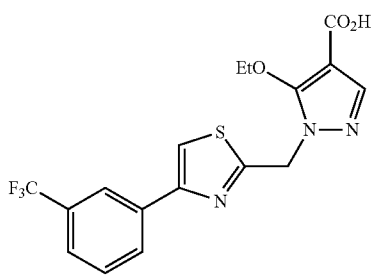 [SMILES: CCOC(=O)c1cnn(Cc2nc(-c3cccc(C(F)(F)F)c3)cs2)c1OCC]

By a reaction in the same manner as in Example 1 and using the compound (275 mg, 0.646 mmol) obtained in Example 8c, the title compound (200 mg, 78%) was obtained as colorless crystals.

$^1$H NMR (400 MHz, DMSO-$d_6$) δ ppm 1.31 (3H, t, J=7.1 Hz) 4.21 (2H, q, J=7.0 Hz) 5.66 (2H, s) 7.67-7.75 (2H, m) 8.23-8.30 (2H, m) 8.32 (1H, s) 8.37 (1H, s) 12.14 (1H, br. s.)

LCMS (ESI+) M+H: 398.

Example 9

1-{[4-(3,4-dichlorophenyl)-1,3-thiazol-2-yl]methyl}-3-(trifluoromethyl)-1H-pyrazole-4-carboxylic acid

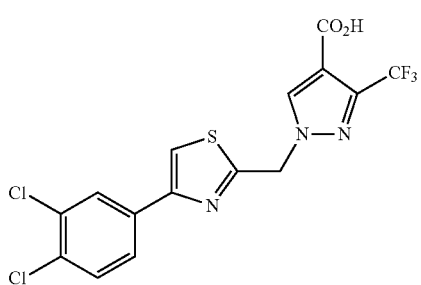 [SMILES: O=C(O)c1cn(Cc2nc(-c3ccc(Cl)c(Cl)c3)cs2)nc1C(F)(F)F]

In the same manner as in Example 1a, 1b, 1c and 1d, 4 steps were performed using ethyl 3-(trifluoromethyl)-1H-pyrazole-4-carboxylate (1.04 g, 5.0 mmol), the title compound (274 mg) was obtained as colorless crystals.

$^1$H NMR (400 MHz, CHLOROFORM-d) δ ppm 5.71 (2H, s), 7.51 (1H, d, J=8.3 Hz), 7.55 (1H, s), 7.70 (1H, dd, J=8.4, 2.1 Hz), 7.99 (1H, d, J=2.0 Hz), 8.27 (1H, s)

LCMS (ESI+) M+H: 422.

Example 10

1-{[5-(3,4-dichlorophenyl)-1,3-thiazol-2-yl]methyl}-3-(trifluoromethyl)-1H-pyrazole-4-carboxylic acid

Example 10a

[4-(ethoxycarbonyl)-3-(trifluoromethyl)-1H-pyrazol-1-yl]acetic acid

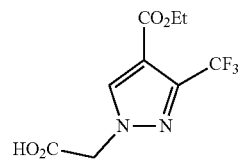

To a solution of ethyl 3-(trifluoromethyl)-1H-pyrazole-4-carboxylate (6.24 g, 30.0 mmol) in N,N-dimethylformamide (60 ml) was added under ice-cooling 60% sodium hydride (1.80 g, 45.0 mmol) by a small amount and the mixture was stirred for 30 min. tert-Butyl bromoacetate (5.32 mL, 36.0 mmol) was added to the reaction mixture under ice-cooling, and the mixture was stirred at room temperature for 4 hr. The reaction mixture was diluted with water, extracted with ethyl acetate, washed successively with water and saturated brine, dried over sodium sulfate, and concentrated under reduced pressure. The residue was purified by column chromatography (carrier: silica gel, eluent: hexane-ethyl acetate) to give tert-butyl [4-(ethoxycarbonyl)-3-(trifluoromethyl)-1H-pyrazol-1-yl]acetate (7.33 g, 75%) as a colorless oil. Trifluoroacetic acid (30 mL) was added to the present compound (3.22 g, 10.0 mmol), and the mixture was stirred under ice-cooling for 2.5 hr. The reaction mixture was concentrated under reduced pressure, and the residue was recrystallized from ethyl acetate-hexane to give the title compound (2.03 g, 76%) as colorless crystals.

$^1$H NMR (400 MHz, CHLOROFORM-d) δ ppm 1.36 (3H, t, J=7.2 Hz), 4.28 (1H, br. s.), 4.34 (2H, q, J=7.2 Hz), 5.03 (2H, s), 8.13 (1H, d, J=1.0 Hz)

LCMS (ESI+) M+H: 267.

Example 10b ethyl 1-{[5-(3,4-dichlorophenyl)-1,3-thiazol-2-yl]methyl}-3-(trifluoromethyl)-1H-pyrazole-4-carboxylate

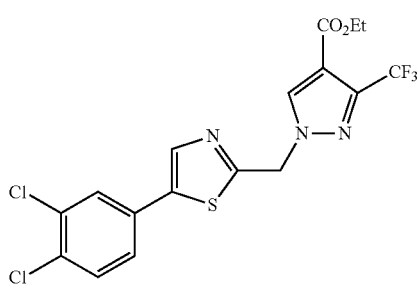 [SMILES: CCOC(=O)c1cn(Cc2ncc(-c3ccc(Cl)c(Cl)c3)s2)nc1C(F)(F)F]

To a solution of the compound (1.06 g, 4.0 mmol) obtained in Example 10a in N,N-dimethylformamide (10 mL) were added 1-ethyl-3-(3-dimethylaminopropyl)carbodiimide hydrochloride (WSC, 1.15 g, 6.0 mmol) and 1-hydroxy-1H-benzotriazole monohydrate (0.92 g, 6.0 mmol), and the mixture was stirred for 10 min. 2-Amino-1-(3,4-dichlorophenyl)ethanone hydrochloride (1.44 g, 6.0 mmol) and triethylamine (1.12 mL, 8.0 mmol) were added and the mixture was stirred for 2.5 days.

The reaction mixture was diluted with water, extracted with ethyl acetate, washed with saturated brine, dried over sodium sulfate, and concentrated under reduced pressure. The residue was purified by column chromatography (carrier: silica gel, eluent: hexane-ethyl acetate) to give ethyl 1-(2-{[2-(3,4-dichlorophenyl)-2-oxoethyl]amino}-2-oxoethyl)-3-(trifluoromethyl)-1H-pyrazole-4-carboxylate (322 mg, 17%) as colorless crystals. To a solution of the present compound (175 mg, 0.387 mmol) in tetrahydrofuran (5 mL) was added 2,4-bis(4-methoxyphenyl)-1,3-dithia-2,4-diphosphetane-2,4-disulfide (Lawesson reagent, 188 mg, 0.464 mmol), and the mixture was heated under reflux for 1 hr. A saturated aqueous sodium hydrogen carbonate solution was added to the reaction mixture until foaming ceased, and the mixture was stirred for 1 hr. The reaction mixture was extracted with ethyl acetate, washed successively with water and saturated brine, dried over sodium sulfate, and concentrated under reduced pressure. The residue was purified by column chromatography (carrier: silica gel, eluent: hexane-ethyl acetate) to give the title compound (158 mg, 90%) as a yellow oil.

$^1$H NMR (400 MHz, CHLOROFORM-d) δ ppm 1.35 (3H, t, J=7.1 Hz), 4.32 (2H, q, J=7.1 Hz), 5.65 (2H, s), 7.35 (1H, dd, J=8.3, 1.7 Hz), 7.49 (1H, d, J=8.6 Hz), 7.62 (1H, d, J=2.0 Hz), 7.93 (1H, s), 8.19 (1H, s)

LCMS (ESI+) M+H: 450.

Example 10

1-{[5-(3,4-dichlorophenyl)-1,3-thiazol-2-yl]methyl}-3-(trifluoromethyl)-1H-pyrazole-4-carboxylic acid

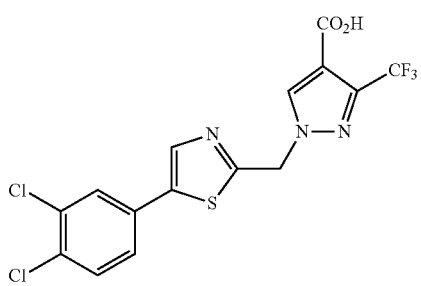 [SMILES: O=C(O)c1cn(Cc2ncc(-c3ccc(Cl)c(Cl)c3)s2)nc1C(F)(F)F]

By a reaction in the same manner as in Example 1 and using the compound (158 mg, 0.351 mmol) obtained in Example 10b, the title compound (115 mg, 77%) was obtained as colorless crystals.

$^1$H NMR (400 MHz, DMSO-$d_6$) δ ppm 5.89 (2H, s) 7.63-7.67 (1H, m) 7.68-7.72 (1H, m) 8.03 (1H, d, J=2.0 Hz) 8.34 (1H, s) 8.72 (1H, s) 13.11 (1H, s)

LCMS (ESI+) M+H: 422.

Example 11

1-{[4-(3,4-dichlorophenyl)-1,3-thiazol-2-yl]methyl}-5-methyl-1H-pyrazole-4-carboxylic acid Example 11a

[4-(tert-butoxycarbonyl)-5-methyl-1H-pyrazol-1-yl]acetic acid

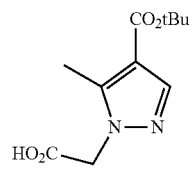

By a reaction in the same manner as in Example 5a and using tert-butyl 3-oxobutanoate (2.37 g, 15.0 mmol) and ethyl hydrazinoacetate hydrochloride (2.78 g, 18.0 mmol), tert-butyl 1-(2-ethoxy-2-oxoethyl)-5-methyl-1H-pyrazole-4-carboxylate (1.67 g, 41%) was obtained. To a solution of the present compound (1.67 g, 6.21 mmol) in tetrahydrofuran (15 ml) was added 2N aqueous sodium hydroxide solution (3.41 ml, 6.83 mmol), and the mixture was stirred under ice-cooling for 1.5 hr and at room temperature for 13 hr. The reaction mixture was extracted with water, and washed with ether. The aqueous layer was neutralized with 1N hydrochloric acid (6.9 mL), extracted with ethyl acetate, washed with saturated brine, dried over anhydrous sodium sulfate, and concentrated under reduced pressure. The residue was recrystallized from ethyl acetate-tetrahydrofuran-hexane to give the title compound (1.12 g, 75%) as colorless crystals.

$^1$H NMR (400 MHz, DMSO-$d_6$) δ ppm 1.50 (9H, s) 2.40 (3H, s) 4.97 (2H, s) 7.70 (1H, s) 13.28 (1H, br. s.)

LCMS (ESI+) M+H: 241.

Example 11b tert-butyl 1-(2-amino-2-thioxoethyl)-5-methyl-1H-pyrazole-4-carboxylate

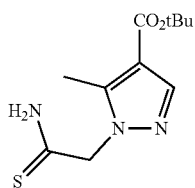

By a reaction in the same manner as in Example 5c and using the compound (0.96 g, 4.00 mmol) obtained in Example 11a, the title compound (0.64 g, 62%) was obtained as colorless crystals.

$^1$H NMR (400 MHz, CHLOROFORM-d) δ ppm 1.56 (9H, s), 2.55 (3H, s), 5.13 (2H, s), 7.51 (1H, br. s.), 7.60 (1H, br. s.), 7.90 (1H, s)

LCMS (ESI+) M+H: 256.

Example 11

1-{[4-(3,4-dichlorophenyl)-1,3-thiazol-2-yl]methyl}-5-methyl-1H-pyrazole-4-carboxylic acid

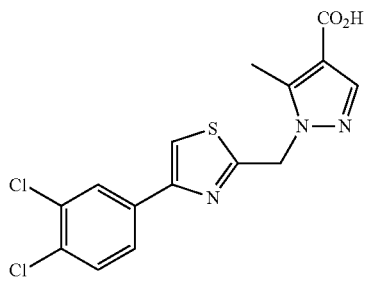 [SMILES: Cc1c(C(=O)O)cnn1Cc1nc(-c2ccc(Cl)c(Cl)c2)cs1]

A reaction similar to Example 1c was performed using the compound (200 mg, 0.783 mmol) obtained in Example 11b and 2-bromo-1-(3,4-dichlorophenyl)ethanone (210 mg, 0.783 mmol). As a result, the title compound (230 mg, 79%) wherein tert-butyl ester was hydrolyzed by hydrobromic acid produced under the reaction conditions was obtained as colorless crystals.

$^1$H NMR (400 MHz, DMSO-d$_6$) δ ppm 2.59 (3H, s) 5.77 (2H, s) 7.72 (1H, d, J=8.3 Hz) 7.85 (1H, s) 7.93 (1H, dd, J=8.3, 2.0 Hz) 8.18 (1H, d, J=2.0 Hz) 8.32 (1H, s) 12.41 (1H, br. s.)

LCMS (ESI+) M+H: 368.

Example 12

5-methyl-1-({4-[3-(trifluoromethoxy)phenyl]-1,3-thiazol-2-yl}methyl)-1H-pyrazole-4-carboxylic acid

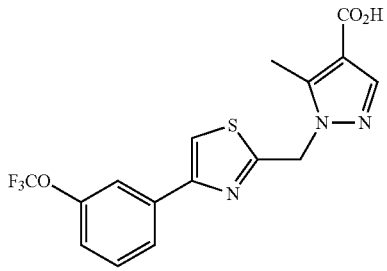 [SMILES: Cc1c(C(=O)O)cnn1Cc1nc(-c2cccc(OC(F)(F)F)c2)cs1]

A reaction similar to Example 1c was performed using the compound (200 mg, 0.783 mmol) obtained in Example 11b and 2-bromo-1-[3-(trifluoromethoxy)phenyl]ethanone (222 mg, 0.783 mmol). As a result, the title compound (224 mg, 74%) wherein tert-butyl ester was hydrolyzed by hydrobromic acid produced under the reaction conditions was obtained as colorless crystals.

$^1$H NMR (400 MHz, DMSO-d$_6$) δ ppm 2.59 (3H, s) 5.79 (2H, s) 7.36 (1H, ddd, J=8.2, 1.2, 1.1 Hz) 7.60 (1H, t, J=8.1 Hz) 7.85 (1H, s) 7.90 (1H, s) 7.98 (1H, ddd, J=7.6, 1.0, 0.7 Hz) 8.30 (1H, s) 12.41 (1H, br. s.)

LCMS (ESI+) M+H: 384.

Example 13

5-methyl-1-({4-[3-(trifluoromethyl)phenyl]-1,3-thiazol-2-yl}methyl)-1H-pyrazole-4-carboxylic acid

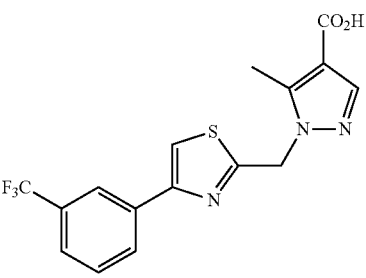 [SMILES: Cc1c(C(=O)O)cnn1Cc1nc(-c2cccc(C(F)(F)F)c2)cs1]

A reaction similar to Example 1c was performed using the compound (200 mg, 0.783 mmol) obtained in Example 11b and 2-bromo-1-[3-(trifluoromethyl)phenyl]ethanone (209 mg, 0.783 mmol). As a result, the title compound (235 mg, 81%) wherein tert-butyl ester was hydrolyzed by hydrobromic acid produced under the reaction conditions was obtained as colorless crystals.

$^1$H NMR (400 MHz, DMSO-d$_6$) δ ppm 2.59 (3H, s) 5.80 (2H, s) 7.68-7.75 (2H, m) 7.85 (1H, s) 8.25 (1H, dd, J=7.0, 1.3 Hz) 8.27 (1H, s) 8.37 (1H, s) 12.41 (1H, br. s.)

LCMS (ESI+) M+H: 368.

Example 14

1-(1-{4-[3-(trifluoromethyl)phenyl]-1,3-thiazol-2-yl}ethyl)-1H-pyrazole-4-carboxylic acid

Example 14a

2-[4-(ethoxycarbonyl)-1H-pyrazol-1-yl]propanoic acid

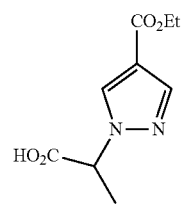

By a reaction in the same manner as in Example 10a and using ethyl 1H-pyrazole-4-carboxylate (1.40 g, 10.0 mmol) and tert-butyl 2-bromopropanate (3.14 g, 15.0 mmol), the title compound (1.85 g, 87%) was obtained as a colorless oil.

$^1$H NMR (400 MHz, CHLOROFORM-d) δ ppm 1.35 (3H, t, J=7.2 Hz), 1.84 (3H, d, J=7.3 Hz), 4.30 (2H, q, J=7.1 Hz), 5.18 (1H, q, J=7.3 Hz), 7.36 (1H, br. s.), 7.98 (1H, s), 8.08 (1H, s)

LCMS (ESI+) M+H: 213.

Example 14b ethyl 1-(2-amino-1-methyl-2-thioxoethyl)-1H-pyrazole-4-carboxylate

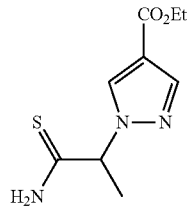

By a reaction in the same manner as in Example 5c and using the compound (1.85 g, 8.72 mmol) obtained in Example 14a, the title compound (0.79 g, 40%) was obtained as colorless crystals.

$^1$H NMR (400 MHz, CHLOROFORM-d) δ ppm 1.35 (3H, t, J=7.1 Hz), 1.94 (3H, d, J=7.1 Hz), 4.31 (2H, q, J=7.1 Hz), 5.37 (1H, q, J=7.1 Hz), 7.61 (1H, br. s.), 8.02 (1H, s), 8.03 (1H, s), 8.26 (1H, br. s.)

LCMS (ESI+) M+H: 228.

Example 14c ethyl 1-(1-{4-[3-(trifluoromethyl)phenyl]-1,3-thiazol-2-yl}ethyl)-1H-pyrazole-4-carboxylate

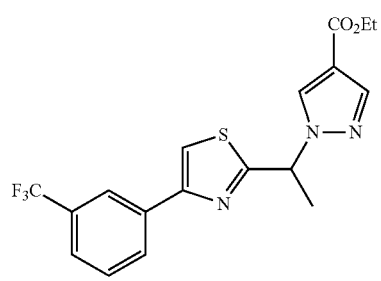 [SMILES: CCOC(=O)c1cnn(C(C)c2nc(-c3cccc(C(F)(F)F)c3)cs2)c1]

By a reaction in the same manner as in Example 1c and using the compound (227 mg, 1.00 mmol) obtained in Example 14b and 2-bromo-1-[3-(trifluoromethyl)phenyl]ethanone (267 mg, 1.00 mmol), the title compound (358 mg, 90%) was obtained as colorless crystals.

$^1$H NMR (400 MHz, CHLOROFORM-d) δ ppm 1.35 (3H, t, J=7.1 Hz), 2.11 (3H, d, J=7.1 Hz), 4.30 (2H, q, J=7.1 Hz), 5.91 (1H, q, J=7.1 Hz), 7.52-7.62 (3H, m), 8.01 (1H, s), 8.05 (1H, d, J=7.6 Hz), 8.12 (1H, s), 8.15 (1H, s)

LCMS (ESI+) M+H: 396.

Example 14

1-(1-{4-[3-(trifluoromethyl)phenyl]-1,3-thiazol-2-yl}ethyl)-1H-pyrazole-4-carboxylic acid

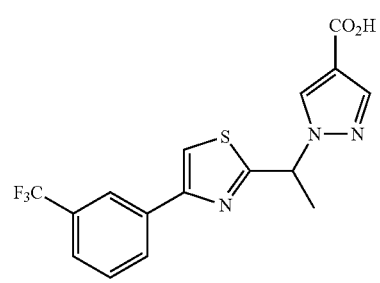

By a reaction in the same manner as in Example 1 and using the compound (358 mg, 0.905 mmol) obtained in Example 14c, the title compound (268 mg, 80%) was obtained as colorless crystals.

$^1$H NMR (400 MHz, DMSO-d$_6$) δ ppm 1.98 (3H, d, J=7.1 Hz) 6.18 (1H, q, J=7.0 Hz) 7.67-7.75 (2H, m) 7.94 (1H, s) 8.24-8.29 (2H, 8.36 (1H, s) 8.55 (1H, s) 12.50 (1H, br. s.)

LCMS (ESI+) M+H: 368.

Example 15

1-{1-[4-(3,4-dichlorophenyl)-1,3-thiazol-2-yl]ethyl}-1H-pyrazole-4-carboxylic acid

Example 15a ethyl 1-{1-[4-(3,4-dichlorophenyl)-1,3-thiazol-2-yl]ethyl}-1H-pyrazole-4-carboxylate

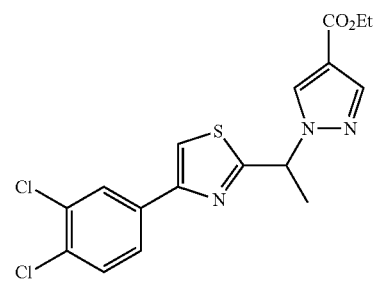 [SMILES: CCOC(=O)c1cnn(C(C)c2nc(-c3ccc(Cl)c(Cl)c3)cs2)c1]

By a reaction in the same manner as in Example 1c and using the compound (227 mg, 1.00 mmol) obtained in Example 14b and 2-bromo-1-(3,4-dichlorophenyl)ethanone (268 mg, 1.00 mmol), the title compound (359 mg, 90%) was obtained as a colorless oil.

$^1$H NMR (400 MHz, CHLOROFORM-d) δ ppm 1.35 (3H, t, J=7.2 Hz), 2.09 (3H, d, J=7.1 Hz), 4.30 (2H, q, J=7.1 Hz), 5.88 (1H, q, J=7.1 Hz), 7.47 (1H, s), 7.48 (1H, d, J=8.3 Hz), 7.70 (1H, dd, J=8.3, 2.0 Hz), 7.99-8.01 (2H, m), 8.10 (1H, s)

LCMS (ESI+) M+H: 396.

Example 15

1-{1-[4-(3,4-dichlorophenyl)-1,3-thiazol-2-yl]ethyl}-1H-pyrazole-4-carboxylic acid

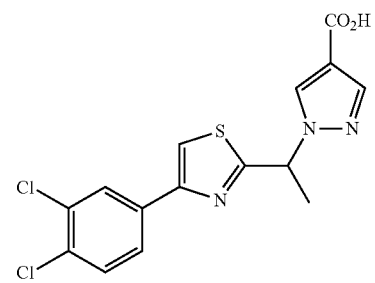 [SMILES: CC(c1nc(-c2ccc(Cl)c(Cl)c2)cs1)n1cc(C(=O)O)cn1]

By a reaction in the same manner as in Example 1 and using the compound (359 mg, 0.906 mmol) obtained in Example 15a, the title compound (287 mg, 86%) was obtained as colorless crystals.

$^1$H NMR (400 MHz, DMSO-d$_6$) δ ppm 1.97 (3H, d, J=6.8 Hz) 6.15 (1H, q, J=7.0 Hz) 7.72 (1H, d, J=8.6 Hz) 7.91-7.96 (2H, 8.20 (1H, d, J=2.0 Hz) 8.31 (1H, s) 8.54 (1H, s) 12.50 (1H, br. s.)

LCMS (ESI+) M+H: 368.

Example 16

1-(1-methyl-1-{4-[3-(trifluoromethyl)phenyl]-1,3-thiazol-2-yl}ethyl)-1H-pyrazole-4-carboxylic acid

Example 16a

2-[4-(ethoxycarbonyl)-1H-pyrazol-1-yl]-2-methyl-propanoic acid

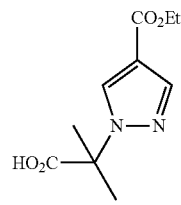 [SMILES: CCOC(=O)c1cnn(C(C)(C)C(=O)O)c1]

By a reaction in the same manner as in Example 10a and using ethyl 1H-pyrazole-4-carboxylate (1.40 g, 10.0 mmol) and tert-butyl 2-bromo-2-methylpropanate (6.70 g, 30.0 mmol), the title compound (1.88 g, 83%) was obtained as a colorless oil.

$^1$H NMR (400 MHz, CHLOROFORM-d) δ ppm 1.35 (3H, t, J=7.1 Hz), 1.89 (6H, s), 4.31 (2H, q, J=7.1 Hz), 6.22 (1H, br. s.), 8.00 (1H, s), 8.12 (1H, s)

LCMS (ESI+) M+H: 227.

Example 16b ethyl 1-(2-amino-1,1-dimethyl-2-thioxoethyl)-1H-pyrazole-4-carboxylate

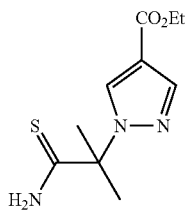

By a reaction in the same manner as in Example 5c and using the compound (1.88 g, 7.97 mmol) obtained in Example 16a, the title compound (1.22 g, 63%) was obtained as colorless crystals.

$^1$H NMR (400 MHz, CHLOROFORM-d) δ ppm 1.36 (3H, t, J=7.1 Hz), 2.05 (6H, s), 4.31 (2H, q, J=7.1 Hz), 7.55 (1H, br. s.), 7.71 (1H, br. s.), 8.04 (1H, s), 8.15 (1H, s)

LCMS (ESI+) M+H: 242.

Example 16c ethyl 1-(1-methyl-1-[4-[3-(trifluoromethyl)phenyl]-1,3-thiazol-2-yl]ethyl)-1H-pyrazole-4-carboxylate

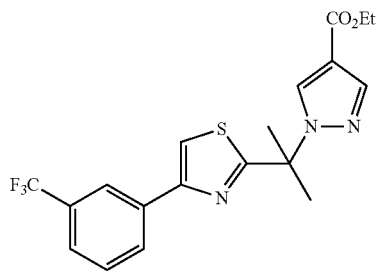 [SMILES: CCOC(=O)c1cnn(C(C)(C)c2nc(-c3cccc(C(F)(F)F)c3)cs2)c1]

By a reaction in the same manner as in Example 1c and using the compound (241 mg, 1.00 mmol) obtained in Example 16b and 2-bromo-1-[3-(trifluoromethyl)phenyl]ethanone (267 mg, 1.00 mmol), the title compound (374 mg, 91%) was obtained as a colorless oil.

$^1$H NMR (400 MHz, CHLOROFORM-d) δ ppm 1.35 (3H, t, J=7.1 Hz), 2.19 (6H, s), 4.30 (2H, q, J=7.1 Hz), 7.51 (1H, s), 7.51-7.61 (2H, m), 8.00 (1H, s), 8.06 (1H, d, J=7.6 Hz), 8.14 (1H, s), 8.16 (1H, s)

LCMS (ESI+) M+H: 410.

Example 16

1-(1-methyl-1-{4-[3-(trifluoromethyl)phenyl]-1,3-thiazol-2-yl}ethyl)-1H-pyrazole-4-carboxylic acid

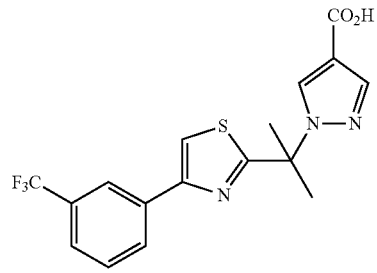 [SMILES: CC(C)(c1nc(-c2cccc(C(F)(F)F)c2)cs1)n1cc(C(=O)O)cn1]

By a reaction in the same manner as in Example 1 and using the compound (374 mg, 0.913 mmol) obtained in Example 16c, the title compound (280 mg, 73%) was obtained as colorless crystals.

$^1$H NMR (400 MHz, DMSO-d$_6$) δ ppm 2.13 (6H, s) 7.66-7.75 (2H, m) 7.94 (1H, s) 8.23-8.28 (2H, m) 8.33 (1H, s) 8.55 (1H, s) 12.51 (1H, br. s.)

LCMS (ESI+) M+H: 382.

Example 17

1-{1-[4-(3,4-dichlorophenyl)-1,3-thiazol-2-yl]-1-methylethyl}-1H-pyrazole-4-carboxylic acid

Example 17a ethyl 1-{1-[4-(3,4-dichlorophenyl)-1,3-thiazol-2-yl]-1-methylethyl}-1H-pyrazole-4-carboxylate

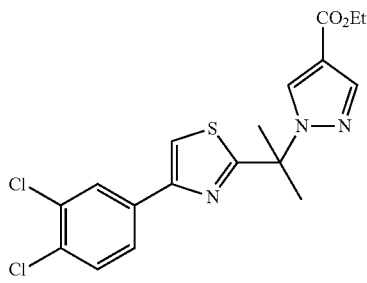 [SMILES: CCOC(=O)c1cnn(C(C)(C)c2nc(-c3ccc(Cl)c(Cl)c3)cs2)c1]

By a reaction in the same manner as in Example 1c and using the compound (241 mg, 1.00 mmol) obtained in Example 16b and 2-bromo-1-(3,4-dichlorophenyl)ethanone (268 mg, 1.00 mmol), the title compound (402 mg, 98%) was obtained as a colorless oil.

$^1$H NMR (400 MHz, CHLOROFORM-d) δ ppm 1.35 (3H, t, J=7.2 Hz), 2.17 (6H, s), 4.30 (2H, q, J=7.1 Hz), 7.44 (1H, s), 7.47 (1H, d, J=8.6 Hz), 7.69 (1H, dd, J=8.4, 2.1 Hz), 7.99-8.01 (2H, m), 8.15 (1H, s)

LCMS (ESI+) M+H: 410.

Example 17

1-{1-[4-(3,4-dichlorophenyl)-1,3-thiazol-2-yl]-1-methylethyl}-1H-pyrazole-4-carboxylic acid

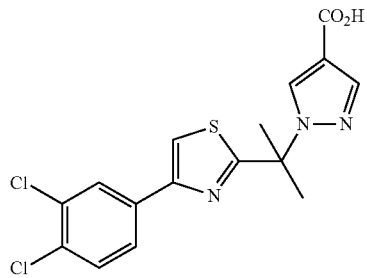 [SMILES: CC(C)(c1nc(-c2ccc(Cl)c(Cl)c2)cs1)n1cc(C(=O)O)cn1]

By a reaction in the same manner as in Example 1 and using the compound (402 mg, 0.913 mmol) obtained in Example 17a, the title compound (304 mg, 81%) was obtained as colorless crystals.

$^1$H NMR (400 MHz, DMSO-d$_6$) δ ppm 2.11 (6H, s) 7.72 (1H, d, J=8.3 Hz) 7.91-7.96 (2H, m) 8.19 (1H, d, J=2.2 Hz) 8.28 (1H, s) 8.53 (1H, s) 12.51 (1H, br. s.)

LCMS (ESI+) M+H: 382.

Example 18

5-[1-({4-[3-(trifluoromethyl)phenyl]-1,3-thiazol-2-yl}methyl)-1H-pyrazol-4-yl]-2H-tetrazole

Example 18a 1-({4-[3-(trifluoromethyl)phenyl]-1,3-thiazol-2-yl}methyl)-1H-pyrazole-4-carboxamide

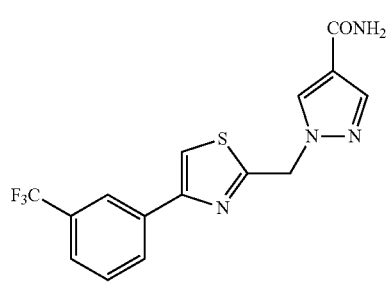 [SMILES: NC(=O)c1cnn(Cc2nc(-c3cccc(C(F)(F)F)c3)cs2)c1]

By a reaction in the same manner as in Reference Example 18a and using the compound (2.65 g, 7.50 mmol) obtained in Example 1, the title compound (2.11 g, 80%) was obtained as colorless crystals.

$^1$H NMR (400 MHz, CHLOROFORM-d) δ ppm 5.59 (2H, br. s.), 5.69 (2H, s), 7.52-7.64 (3H, m), 7.87 (1H, s), 8.05 (1H, d, J=7.8 Hz), 8.08 (1H, s), 8.15 (1H, s)

LCMS (ESI+) M+H: 353.

Example 18b 1-({4-[3-(trifluoromethyl)phenyl]-1,3-thiazol-2-yl}methyl)-1H-pyrazole-4-carbonitrile

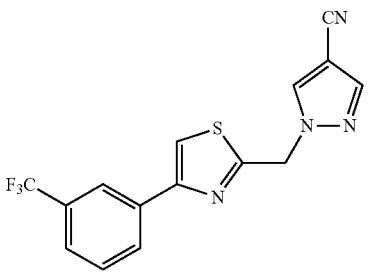 [SMILES: N#Cc1cnn(Cc2nc(-c3cccc(C(F)(F)F)c3)cs2)c1]

By a reaction in the same manner as in Reference Example 18b and using the compound (2.39 g, 6.79 mmol) obtained in Example 18a, the title compound (1.87 g, 82%) was obtained as colorless crystals.

$^1$H NMR (400 MHz, CHLOROFORM-d) δ ppm 5.71 (2H, s), 7.58 (1H, t, J=7.8 Hz), 7.60 (1H, s), 7.61-7.64 (1H, m, J=8.1 Hz), 7.89 (1H, s), 8.05 (1H, d, J=7.8 Hz), 8.07 (1H, s), 8.15 (1H, s)

LCMS (ESI+) M+H: 335.

Example 18

5-[1-({4-[3-(trifluoromethyl)phenyl]-1,3-thiazol-2-yl}methyl)-1H-pyrazol-4-yl]-2H-tetrazole

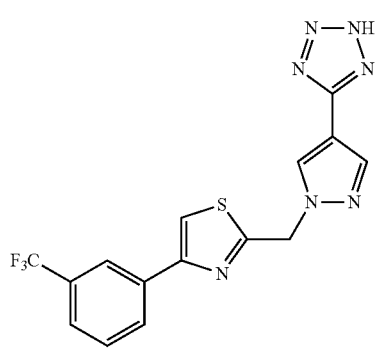 [SMILES: FC(F)(F)c1cccc(-c2csc(Cn3cc(-c4nn[nH]n4)cn3)n2)c1]

By a reaction in the same manner as in Reference Example 18 and using the compound (334 mg, 1.00 mmol) obtained in Example 18b, the title compound (314 mg, 83%) was obtained as colorless crystals.

$^1$H NMR (400 MHz, DMSO-$d_6$) δ ppm 5.95 (2H, s), 7.67-7.75 (2H, m), 8.14 (1H, s), 8.27 (1H, d, J=7.1 Hz), 8.29 (1H, s), 8.39 (1H, s), 8.66 (1H, s)

LCMS (ESI+) M+H: 378.

Example 19

3-[1-({4-[3-(trifluoromethyl)phenyl]-1,3-thiazol-2-yl}methyl)-1H-pyrazol-4-yl]-1,2,4-oxadiazole-5(4H)-one

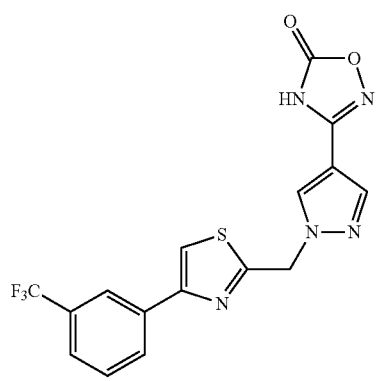 [SMILES: O=c1[nH]c(-c2cnn(Cc3nc(-c4cccc(C(F)(F)F)c4)cs3)c2)no1]

To a solution of the compound (501 mg, 1.50 mmol) obtained in Example 18b in dimethylsulfoxide (5 mL) were added hydroxyammonium chloride (1.04 g, 15.0 mmol) and sodium hydrogen carbonate (1.26 g, 15.0 mmol), and the mixture was stirred at 80° C. overnight. The reaction mixture was diluted with water, extracted with ethyl acetate, washed with saturated brine, dried over sodium sulfate, and concentrated under reduced pressure. Tetrahydrofuran (10 mL), 1,1'-carbonyldiimidazole (365 mg, 2.25 mmol) and 1,8-diazabicyclo[5.4.0]undec-7-ene (0.224 mL, 1.5 mmol) were added to the residue, and the mixture was stirred at room temperature for 2.5 hr, and further heated under reflux for 1.5 hr. The reaction mixture was extracted with ethyl acetate, washed successively with 1N hydrochloric acid and saturated brine, dried over sodium sulfate, and concentrated under reduced pressure. The residue was purified by column chromatography (carrier: silica gel, eluent: hexane-ethyl acetate) and recrystallized from ethyl acetate-hexane to give the title compound (426 mg, 72%) as colorless crystals.

$^1$H NMR (400 MHz, DMSO-$d_6$) δ ppm 5.93 (2H, s) 7.66-7.76 (2H, m) 8.04 (1H, s) 8.26 (1H, d, J=7.1 Hz) 8.29 (1H, s) 8.40 (1H, s) 8.55 (1H, s) 12.81 (1H, br. s.)

LCMS (ESI+) M+H: 394.

Example 20

N-(methylsulfonyl)-1-({4-[3-(trifluoromethyl)phenyl]-1,3-thiazol-2-yl}methyl)-1H-pyrazole-4-carboxamide

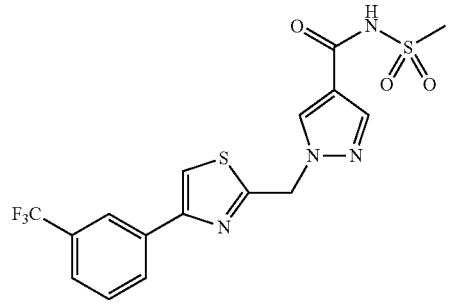 [SMILES: CS(=O)(=O)NC(=O)c1cnn(Cc2nc(-c3cccc(C(F)(F)F)c3)cs2)c1]

By a reaction in the same manner as in Reference Example 19 and using the compound (353 mg, 1.00 mmol) obtained in Example 1, the title compound (231 mg, 53%) was obtained as colorless crystals.

$^1$H NMR (400 MHz, CHLOROFORM-d) δ ppm 3.39 (3H, s), 5.70 (2H, s), 7.53-7.64 (3H, m), 8.00 (1H, s), 8.05 (1H, d, J=7.6 Hz), 8.14 (1H, s), 8.20 (1H, s), 8.74 (1H, br. s.)

LCMS (ESI+) M+H: 431.

Example 21

1-({2-[3-(trifluoromethyl)phenyl]-1,3-thiazol-4-yl}methyl)-1H-pyrazole-4-carboxylic acid

Example 21a 4-(chloromethyl)-2-[3-(trifluoromethyl)phenyl]-1,3-thiazole

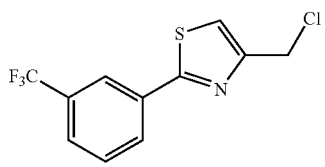 [SMILES: FC(F)(F)c1cccc(-c2nc(CCl)cs2)c1]

By a reaction in the same manner as in Example 1c and using 3-(trifluoromethyl)benzenecarbothioamide (1.38 g, 6.73 mmol) and 1,3-dichloropropa-2-none (2.56 g, 20.2 mmol), the title compound (1.52 g, 81%) was obtained as colorless crystals.

$^1$H NMR (400 MHz, CHLOROFORM-d) δ ppm 4.76 (2H, s), 7.38 (1H, s), 7.58 (1H, t, J=7.8 Hz), 7.69 (1H, d, J=7.8 Hz), 8.12 (1H, d, J=7.8 Hz), 8.22 (1H, s)

LCMS (ESI+) M+H: 278.

Example 21b ethyl 1-({2-[3-(trifluoromethyl)phenyl]-1,3-thiazol-4-yl}methyl)-1H-pyrazole-4-carboxylate

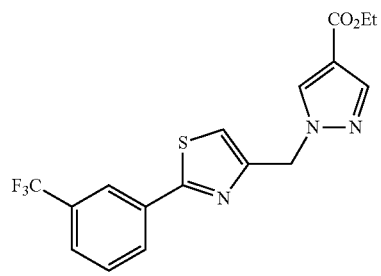 [SMILES: CCOC(=O)c1cnn(Cc2csc(-c3cccc(C(F)(F)F)c3)n2)c1]

To a solution of ethyl 1H-pyrazole-4-carboxylate (140 mg, 1.0 mmol) in tetrahydrofuran (4 mL) was added potassium tert-butoxide (146 mg, 1.30 mmol) under ice-cooling, and the mixture was stirred at the same temperature for 20 min. The compound (278 mg, 1.00 mmol) obtained in Example 21a was added to the reaction mixture, an ice bath was removed and the mixture was stirred for 13 hr. The reaction mixture was further heated under reflux for 1 hr, N,N-dimethylformamide (1 mL) was added and the mixture was stirred at 75° C. for 1.5 hr. The reaction mixture was diluted with water, extracted with ethyl acetate, washed successively with water and saturated brine, dried over sodium sulfate, and concentrated under reduced pressure. The residue was purified by column chromatography (carrier: silica gel, eluent: hexane-ethyl acetate) to give the title compound (273 mg, 71%) as colorless crystals.

$^1$H NMR (400 MHz, CHLOROFORM-d) δ ppm 1.34 (3H, t, J=7.1 Hz), 4.30 (2H, q, J=7.2 Hz), 5.50 (2H, s), 7.19 (1H, s), 7.58 (1H, t, J=7.8 Hz), 7.69 (1H, d, J=7.6 Hz), 7.97 (1H, s), 8.07-8.12 (2H, m), 8.20 (1H, s)

LCMS (ESI+) M+H: 382.

Example 21

1-({2-[3-(trifluoromethyl)phenyl]-1,3-thiazol-4-yl}methyl)-1H-pyrazole-4-carboxylic acid

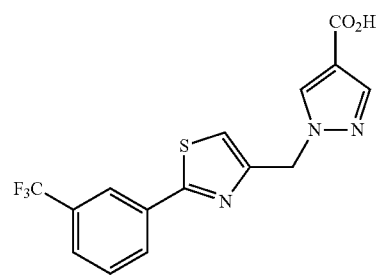

By a reaction in the same manner as in Example 1 and using the compound (273 mg, 0.716 mmol) obtained in Example 21b, the title compound (215 mg, 85%) was obtained as colorless crystals.

$^1$H NMR (400 MHz, DMSO-d$_6$) δ ppm 5.56 (2H, s) 7.67 (1H, s) 7.76 (1H, t, J=7.8 Hz) 7.85 (1H, s) 7.87 (1H, d, J=7.8 Hz) 8.18 (1H, s) 8.21 (1H, d, J=8.3 Hz) 8.40 (1H, s) 12.42 (1H, br. s.)

LCMS (ESI+) M+H: 354.

Example 22

1-{[5-(3,4-dichlorophenyl)-1,3-thiazol-2-yl]methyl}-1H-pyrazole-4-carboxylic acid

Example 22a

[5-(3,4-dichlorophenyl)-1,3-thiazol-2-yl]methanol

To a suspension of 2-amino-1-(3,4-dichlorophenyl)ethanone hydrochloride (2.18 g, 9.06 mmol) in ethyl acetate (25 mL) was added 2-chloro-2-oxoethyl acetate (0.975 mL, 9.06 mmol), and triethylamine (3.8 mL, 27.2 mmol) was added dropwise under ice-cooling. The reaction mixture was stirred under ice-cooling for 30 min, and at room temperature for 1 hr. Saturated aqueous sodium hydrogen carbonate solution (20 mL) was added and the mixture was stirred overnight. The reaction mixture was extracted with ethyl acetate, washed successively with water and saturated brine, dried over sodium sulfate, and concentrated under reduced pressure. Tetrahydrofuran (30 mL) and 2,4-bis(4-methoxyphenyl)-1,3-dithia-2,4-diphosphetane-2,4-disulfide (Lawesson reagent, 2.56 g, 6.34 mmol) was added to the residue, and the mixture was heated under reflux for 1 hr. To the reaction mixture was added saturated aqueous sodium hydrogen carbonate solution (15 mL) and the mixture was stirred for 1 hr, extracted with ethyl acetate, washed successively with water and saturated brine, dried over sodium sulfate, and concentrated under reduced pressure. The residue was purified by column chromatography (carrier: silica gel, eluent: hexane-ethyl acetate) to give [5-(3,4-dichlorophenyl)-1,3-thiazol-2-yl]methyl acetate (364 mg, 13%) as a colorless oil. The present compound was reacted in the same manner as in Example 1 to give the title compound (260 mg, 83%) as colorless crystals.

$^1$H NMR (400 MHz, CHLOROFORM-d) δ ppm 2.77 (1H, t, J=6.1 Hz), 4.97 (2H, d, J=6.1 Hz), 7.37 (1H, dd, J=8.3, 2.2 Hz), 7.48 (1H, d, J=8.3 Hz), 7.64 (1H, d, J=2.2 Hz), 7.89 (1H, s)

LCMS (ESI+) M+H: 260.

Example 22b ethyl 1-{[5-(3,4-dichlorophenyl)-1,3-thiazol-2-yl]methyl}-1H-pyrazole-4-carboxylate

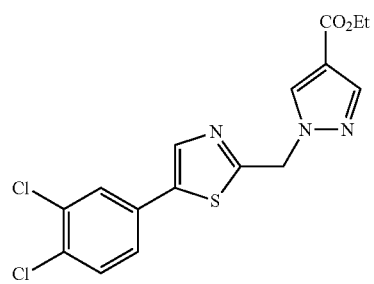 [SMILES: CCOC(=O)c1cnn(Cc2ncc(-c3ccc(Cl)c(Cl)c3)s2)c1]

To a solution of the compound (260 mg, 1.00 mmol) obtained in Example 22a and triethylamine (0.21 mL, 1.50 mmol) in tetrahydrofuran (4 ml) was added methanesulfonyl chloride (0.093 mL, 1.20 mmol), and the mixture was stirred for 30 min. The reaction mixture was filtered off, and the filtrate was concentrated under reduced pressure. The residue was dissolved in N,N-dimethylformamide (5 mL), ethyl 1H-pyrazole-4-carboxylate (140 mg, 1.00 mmol) and potassium carbonate (207 mg, 1.50 mmol) were added, and the mixture was stirred at 80° C. for 15 hr. The reaction mixture was extracted with ethyl acetate, washed successively with water and saturated brine, dried over sodium sulfate, and concentrated under reduced pressure. The residue was purified by column chromatography (carrier: silica gel, eluent: hexane-ethyl acetate) to give the title compound (85 mg, 22%) as colorless crystals.

$^1$H NMR (400 MHz, CHLOROFORM-d) δ ppm 1.34 (3H, t, J=7.2 Hz), 4.30 (2H, q, J=7.2 Hz), 5.62 (2H, s), 7.34 (1H, dd, J=8.3, 2.2 Hz), 7.47 (1H, d, J=8.3 Hz), 7.60 (1H, d, J=2.2 Hz), 7.90 (1H, s), 8.01 (1H, s), 8.08 (1H, s)

LCMS (ESI+) M+H: 382.

Example 22

1-{[5-(3,4-dichlorophenyl)-1,3-thiazol-2-yl]methyl}-1H-pyrazole-4-carboxylic acid

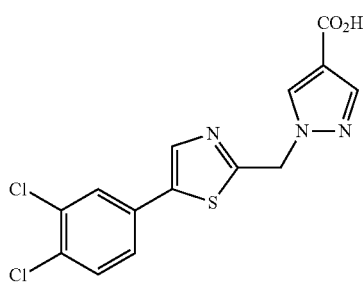 [SMILES: O=C(O)c1cnn(Cc2ncc(-c3ccc(Cl)c(Cl)c3)s2)c1]

By a reaction in the same manner as in Example 1 and using the compound (85 mg, 0.222 mmol) obtained in Example 22b, the title compound (29 mg, 37%) was obtained as colorless crystals.

$^1$H NMR (400 MHz, DMSO-$d_6$) δ ppm 5.79 (2H, s) 7.60-7.65 (1H, m) 7.66-7.70 (1H, m) 7.92 (1H, s) 8.01 (1H, d, J=2.0 Hz) 8.32 (1H, s) 8.49 (1H, s) 12.50 (1H, br. s.)

LCMS (ESI+) M+H: 354.

Example 23

1-({5-[3-(trifluoromethyl)phenyl]-1,3-thiazol-2-yl}methyl)-1H-pyrazole-4-carboxylic acid Example 23a {5-[3-(trifluoromethyl)phenyl]-1,3-thiazol-2-yl}methanol

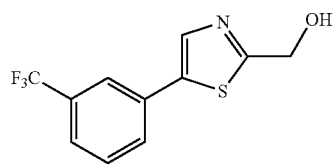 [SMILES: OCc1ncc(-c2cccc(C(F)(F)F)c2)s1]

By a reaction in the same manner as in Example 22a and using 2-amino-1-[3-(trifluoromethyl)phenyl]ethanone hydrochloride (1.68 g, 7.01 mmol) instead of 2-amino-1-(3,4-dichlorophenyl)ethanone hydrochloride as a starting material, the title compound (458 mg, 25%) was obtained as colorless crystals.

$^1$H NMR (400 MHz, CHLOROFORM-d) δ ppm 3.07 (1H, t, J=6.2 Hz), 4.98 (2H, d, J=6.1 Hz), 7.54 (1H, d, J=7.6 Hz), 7.57-7.62 (1H, m), 7.72 (1H, d, J=7.6 Hz), 7.78 (1H, s), 7.95 (1H, s)

LCMS (ESI+) M+H: 260.

Example 23b ethyl 1-({5-[3-(trifluoromethyl)phenyl]-1,3-thiazol-2-yl}methyl)-1H-pyrazole-4-carboxylate

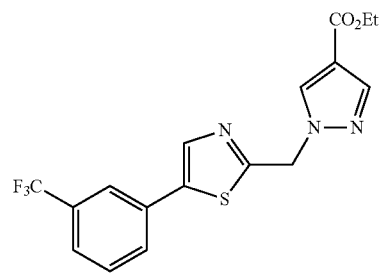 [SMILES: CCOC(=O)c1cnn(Cc2ncc(-c3cccc(C(F)(F)F)c3)s2)c1]

By a reaction in the same manner as in Example 22b and using the compound (259 mg, 1.00 mmol) obtained in Example 23a, the title compound (141 mg, 37%) was obtained as colorless crystals.

$^1$H NMR (400 MHz, CHLOROFORM-d) δ ppm 1.34 (3H, t, J=7.1 Hz), 4.30 (2H, g, J=7.1 Hz), 5.64 (2H, s), 7.50-7.56 (1H, m), 7.58-7.62 (1H, m), 7.69 (1H, d, J=7.6 Hz), 7.75 (1H, s), 7.97 (1H, s), 8.01 (1H, s), 8.09 (1H, s)

LCMS (ESI+) M+H: 382.

Example 23

1-({5-[3-(trifluoromethyl)phenyl]-1,3-thiazol-2-yl}methyl)-1H-pyrazole-4-carboxylic acid

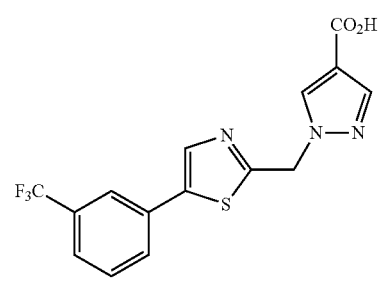 [SMILES: O=C(O)c1cnn(Cc2ncc(-c3cccc(C(F)(F)F)c3)s2)c1]

By a reaction in the same manner as in Example 1 and using the compound (141 mg, 0.370 mmol) obtained in Example 23b, the title compound (109 mg, 84%) was obtained as yellow crystals.

$^1$H NMR (400 MHz, DMSO-$d_6$) δ ppm 5.80 (2H, s) 7.64-7.69 (1H, m) 7.70-7.75 (1H, m) 7.91-7.96 (2H, m) 8.01 (1H, s) 8.38 (1H, s) 8.50 (1H, s) 12.50 (1H, br. s.)

LCMS (ESI+) M+H: 354.

Example 24

1-({2-[3-(trifluoromethyl)phenyl]-1,3-thiazol-5-yl}methyl)-1H-pyrazole-4-carboxylic acid

Example 24a

{2-[3-(trifluoromethyl)phenyl]-1,3-thiazol-5-yl}methanol

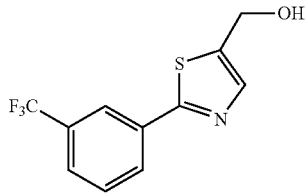 [SMILES: OCc1cnc(-c2cccc(C(F)(F)F)c2)s1]

To a solution of 3-(trifluoromethyl)benzenecarbothioamide (1.31 g, 6.37 mmol) in ethanol (15 mL) was added 2-chloropropane-1,3-dial (2.04 g, 19.1 mmol), and the mixture was heated under reflux overnight. The reaction mixture was extracted with ethyl acetate, washed successively with diluted aqueous sodium hydrogen carbonate solution and saturated brine, dried over sodium sulfate, and concentrated under reduced pressure. The residue was purified by column chromatography (carrier: silica gel, eluent: hexane-ethyl acetate) to give 2-[3-(trifluoromethyl)phenyl]-1,3-thiazole-5-carbaldehyde (423 mg) as colorless crystals. The present compound was dissolved in ethanol (5 mL), sodium borohydride (91 mg, 2.47 mmol) was added under ice-cooling, and the mixture was stirred at room temperature overnight. 1N Hydrochloric acid was added to the reaction mixture, and the mixture was extracted with ethyl acetate, washed with saturated brine, dried over sodium sulfate, and concentrated under reduced pressure. The residue was purified by column chromatography (carrier: silica gel, eluent: hexane-ethyl acetate) to give the title compound (334 mg, 78%) as a colorless oil.

$^1$H NMR (400 MHz, CHLOROFORM-d) δ ppm 2.24 (1H, t, J=5.1 Hz), 4.93 (2H, d, J=4.4 Hz), 7.57 (1H, t, J=7.8 Hz), 7.68 (1H, d, J=7.8 Hz), 7.74 (1H, s), 8.08 (1H, d, J=7.8 Hz), 8.20 (1H, s)

LCMS (ESI+) M+H: 260.

Example 24b ethyl 1-({2-[3-(trifluoromethyl)phenyl]-1,3-thiazol-5-yl}methyl)-1H-pyrazole-4-carboxylate

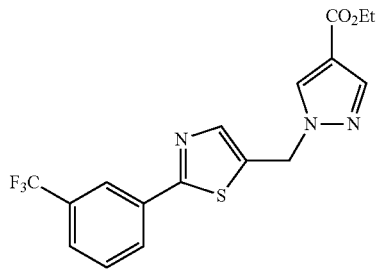 [SMILES: CCOC(=O)c1cnn(Cc2cnc(-c3cccc(C(F)(F)F)c3)s2)c1]

By a reaction in the same manner as in Example 22b and using the compound (334 mg, 1.29 mmol) obtained in Example 24a, the title compound (334 mg, 67%) was obtained as colorless crystals.

$^1$H NMR (400 MHz, CHLOROFORM-d) δ ppm 1.34 (3H, t, J=7.1 Hz), 4.29 (2H, q, J=7.1 Hz), 5.55 (2H, s), 7.57 (1H, t, J=7.8 Hz), 7.69 (1H, d, J=8.1 Hz), 7.85 (1H, s), 7.97 (2H, s), 8.06 (1H, d, J=7.6 Hz), 8.19 (1H, s)

LCMS (ESI+) M+H: 382.

Example 24

1-({2-[3-(trifluoromethyl)phenyl]-1,3-thiazol-5-yl}methyl)-1H-pyrazole-4-carboxylic acid

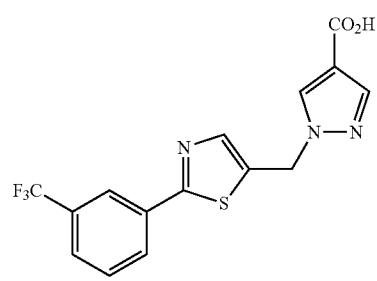 [SMILES: O=C(O)c1cnn(Cc2cnc(-c3cccc(C(F)(F)F)c3)s2)c1]

By a reaction in the same manner as in Example 1 and using the compound (332 mg, 0.871 mmol) obtained in Example 24b, the title compound (275 mg, 77%) was obtained as colorless crystals.

$^1$H NMR (400 MHz, DMSO-$d_6$) δ ppm 5.72 (2H, s) 7.74 (1H, t, J=8.2 Hz) 7.83-7.90 (2H, m) 8.00 (1H, s) 8.17-8.23 (2H, m) 8.43 (1H, s) 12.45 (1H, br. s.)

LCMS (ESI+) M+H: 354.

Example 25

1-{[4-(3-nitrophenyl)-1,3-thiazol-2-yl]methyl}-1H-pyrazole-4-carboxylic acid

Example 25a ethyl 1-{[4-(3-nitrophenyl)-1,3-thiazol-2-yl]methyl}-1H-pyrazole-4-carboxylate

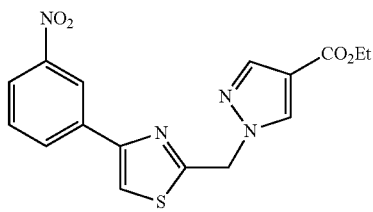 [SMILES: CCOC(=O)c1cnn(Cc2nc(-c3cccc([N+](=O)[O-])c3)cs2)c1]

A solution (24 mL) of the compound (2.2 g, 10.2 mmol) obtained in Example 1b and 2-bromo-1-(3-nitrophenyl)ethanone (3.0 g, 12.3 mmol) in ethanol was heated under reflux overnight, and the mixture was cooled to room temperature. The solvent was evaporated under reduced pressure, and the produced crude title compound was recrystallized (ethyl acetate-hexane) to give the title compound (3.4 g, 78%) as colorless crystals.

$^1$H NMR (400 MHz, DMSO-$d_6$) δ ppm 1.27 (3H, t, J=7.1 Hz), 4.23 (2H, q, J=7.0 Hz), 5.87 (2H, s), 7.76 (1H, t, J=8.1 Hz), 7.99 (1H, s), 8.21 (1H, dd, J=8.2, 2.3 Hz), 8.39 (1H, d, J=7.8 Hz), 8.45 (1H, s), 8.61 (1H, s), 8.75 (1H, br. s.)
LCMS (ESI$^+$) M+H$^+$: 359.

Example 25

1-{[4-(3-nitrophenyl)-1,3-thiazol-2-yl]methyl}-1H-pyrazole-4-carboxylic acid

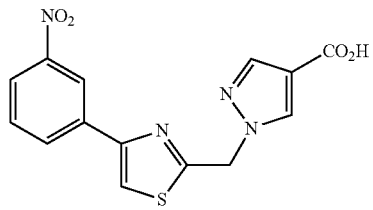 [SMILES: O=C(O)c1cnn(Cc2nc(-c3cccc([N+](=O)[O-])c3)cs2)c1]

To a mixed solution of the compound (250 mg, 0.70 mmol) obtained in Example 25a in tetrahydrofuran-ethanol (v/v=1/1, 7 ml) was added 2N aqueous sodium hydroxide solution (1.4 mL, 2.8 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure and the produced crude title compound was recrystallized (ethyl acetate-hexane) to give the title compound (227 mg, 98%) as colorless crystals.
$^1$H NMR (300 MHz, DMSO-$d_6$) δ ppm 5.86 (2H, s), 7.76 (1H, t, J=8.0 Hz), 7.92 (1H, s), 8.21 (1H, dd, J=8.1, 1.5 Hz), 8.39 (1H, d, J=7.7 Hz), 8.44 (1H, s), 8.51 (1H, s), 8.76 (1H, t, J=2.0 Hz), 12.48 (1H, br. s.)
LCMS (ESI$^+$) M+H$^+$: 331.

Example 26

1-[(4-{3-[(methoxyacetyl)amino]phenyl}-1,3-thiazol-2-yl)methyl]-1H-pyrazole-4-carboxylic acid Example 26a ethyl 1-{[4-(3-aminophenyl)-1,3-thiazol-2-yl]methyl}-1H-pyrazole-4-carboxylate

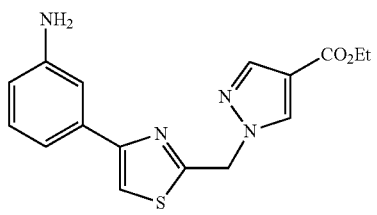

To a mixed solution of the compound (3.15 g, 8.8 mmol) obtained in Example 25a in ethanol-tetrahydrofuran (v/v=1/1, 18 ml) was added Pd—C (10% wet., 320 mg), and the mixture was stirred at room temperature for 3 hr under a hydrogen atmosphere. Pd—C was removed, and the solvent was evaporated under reduced pressure to give a crude title compound (2.9 g).

$^1$H NMR (300 MHz, DMSO-$d_6$) δ ppm 1.27 (3H, t, J=7.2 Hz), 4.23 (2H, q, J=7.1 Hz), 5.17 (2H, s), 5.80 (2H, s), 6.45-6.62 (1H, m), 6.97-7.10 (2H, m), 7.11-7.24 (1H, m), 7.87 (1H, s), 7.96 (1H, s), 8.56 (1H, s)
LCMS (ESI$^+$) M+H$^+$: 329.

Example 26b ethyl 1-[(4-{3-[(methoxyacetyl)amino]phenyl}-1,3-thiazol-2-yl)methyl]-1H-pyrazole-4-carboxylate

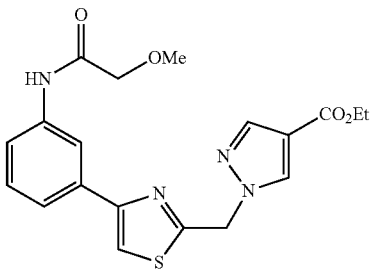 [SMILES: CCOC(=O)c1cnn(Cc2nc(-c3cccc(NC(=O)COC)c3)cs2)c1]

A solution (4 mL) of the crude compound (290 mg, 0.88 mmol) obtained in Example 26a in tetrahydrofuran was cooled in an ice bath, triethylamine (0.16 mL, 1.14 mmol) and methoxyacetylchloride (115 mg, 1.06 mmol) were added, and the mixture was stirred at room temperature overnight. After confirmation of the termination of the reaction by TLC, the resulting salt was removed. The solvent was evaporated under reduced pressure. The resulting crude title compound was purified by column chromatography (hexane-hexane/ethyl acetate=30/70-ethyl acetate) to give the title compound (339 mg, 96% in 2 steps) as a colorless oil.
$^1$H NMR (300 MHz, CHLOROFORM-d) δ ppm 1.34 (3H, t, J=7.2 Hz), 3.53 (3H, s), 4.04 (2H, s), 4.29 (2H, q, J=7.0 Hz), 5.67 (2H, s), 7.40 (1H, t, J=7.9 Hz), 7.52 (1H, s), 7.57-7.68 (2H, m), 8.00 (1H, s), 8.06 (1H, t, J=1.9 Hz), 8.08 (1H, s), 8.35 (1H, br. s.)
LCMS (ESI$^+$) M+H$^+$: 401.

Example 26

1-[(4-{3-[(methoxyacetyl)amino]phenyl}-1,3-thiazol-2-yl)methyl]-1H-pyrazole-4-carboxylic acid

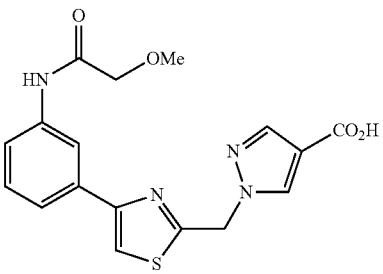 [SMILES: COCC(=O)Nc1cccc(-c2csc(Cn3cc(C(=O)O)cn3)n2)c1]

To a solution (4 mL) of the compound (339 mg, 0.85 mmol) obtained in Example 26b in ethanol was added 2N aqueous sodium hydroxide solution (1.7 mL, 3.4 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (221 mg, 70%) as colorless crystals.

$^1$H NMR (300 MHz, DMSO-d$_6$) δ ppm 3.39 (3H, s), 4.01 (2H, s), 5.82 (2H, s), 7.37 (1H, t, J=7.9 Hz), 7.52-7.74 (2H, m), 7.91 (1H, s), 8.01 (1H, s), 8.24 (1H, t, J=1.8 Hz), 8.49 (1H, s), 9.86 (1H, s), 12.46 (1H, br. s.)

Anal. Calcd. For C$_{17}$H$_{16}$N$_4$O$_4$S: C, 54.83; H, 4.33; N, 15.04. Found: C, 54.81; H, 4.34; N, 14.97.

LCMS (ESI$^+$) M+H$^+$: 373.

Example 27

1-[(4-{3-[(E)-2-phenylethenyl]phenyl}-1,3-thiazol-2-yl)methyl]-1H-pyrazole-4-carboxylic acid

Example 27a ethyl 1-{[4-(3-bromophenyl)-1,3-thiazol-2-yl]methyl}-1H-pyrazole-4-carboxylate

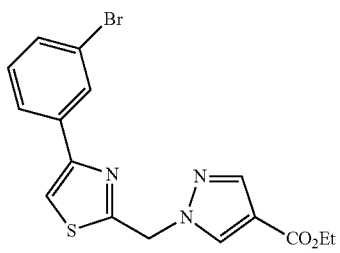 [SMILES: CCOC(=O)c1cnn(Cc2nc(-c3cccc(Br)c3)cs2)c1]

To a solution (5 mL) of the compound (1.1 g, 5.16 mmol) obtained in Example 1b in ethanol was added 2-bromo-1-(3-bromophenyl)ethanone (1.6 g, 5.67 mmol), and the mixture was heated under reflux for 3 hr. The mixture was allowed to cool to room temperature and the solvent was evaporated under reduced pressure. The obtained crude product was washed with ethyl acetate to give the title compound (1.44 g, 71%) as white crystals.

$^1$H NMR (400 MHz, DMSO-d$_6$) δ ppm 1.27 (3H, t, J=7.1 Hz), 4.23 (2H, q, J=7.2 Hz), 5.83 (2H, s), 7.42 (1H, t, J=7.8 Hz), 7.54 (1H, d, J=1.0 Hz), 7.95 (1H, d, J=7.8 Hz), 7.98 (1H, s), 8.14 (1H, s), 8.27 (1H, s), 8.59 (1H, s)

LCMS (ESI$^+$) M+H$^+$: 392, 394.

Example 27b ethyl 1-[(4-{3-[(E)-2-phenylethenyl]phenyl}-1,3-thiazol-2-yl)methyl]-1H-pyrazole-4-carboxylate

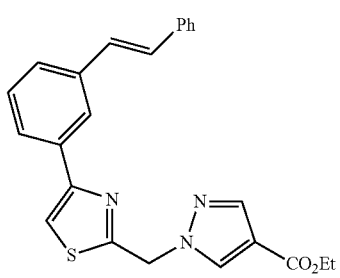 [SMILES: CCOC(=O)c1cnn(Cc2nc(-c3cccc(/C=C/c4ccccc4)c3)cs2)c1]

Example 27c ethyl 1-[(4-phenyl-1,3-thiazol-2-yl)methyl]-1H-pyrazole-4-carboxylate

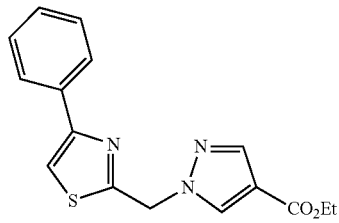 [SMILES: CCOC(=O)c1cnn(Cc2nc(-c3ccccc3)cs2)c1]

Under an argon atmosphere, a mixture of the compound (400 mg, 1.02 mmol) obtained in Example 27a, [(E)-2-phenylethenyl]boronic acid (200 mg, 1.33 mmol), tetrakistriphenylphosphinepalladium (118 mg, 0.10 mmol), potassium carbonate (282 mg, 2.04 mmol), dimethoxyethane (5 mL) and water (1 mL) was stirred under microwave conditions at 150° C. for 10 min. The mixture was allowed to cool to room temperature, water was added to the reaction mixture, and the mixture was extracted with ethyl acetate. The obtained organic layer was washed with saturated brine and dried over anhydrous sodium sulfate, and the solvent was evaporated under reduced pressure. The obtained crude product was purified by column chromatography (hexane-hexane/ethyl acetate=70/30) to give a compound (49 mg, 12%) shown in Example 27b as a pale-yellow oil and a compound (85 mg, 27%) shown in Example 27c as a pale-red oil.

Example 27b $^1$H NMR (400 MHz, CHLOROFORM-d) δ ppm 1.35 (3H, t, J=7.1 Hz), 4.31 (2H, q, J=7.2 Hz), 5.76 (2H, s), 7.06-8.33 (14H, m)

LCMS (ESI$^+$) M+H$^+$: 416.

Example 27c $^1$H NMR (400 MHz, CHLOROFORM-d) δ ppm 1.34 (3H, t, J=7.1 Hz), 4.30 (2H, q, J=7.3 Hz), 5.73 (2H, s), 7.38 (1H, d, J=7.6 Hz), 7.44 (2H, t, J=7.7 Hz), 7.48 (1H, s), 7.85 (2H, d, J=7.8 Hz), 8.03 (1H, s), 8.13 (1H, s)

LCMS (ESI$^+$) M+H$^+$: 314.

Example 27

1-[(4-[3-[(E)-2-phenylethenyl]phenyl]-1,3-thiazol-2-yl)methyl]-1H-pyrazole-4-carboxylic acid

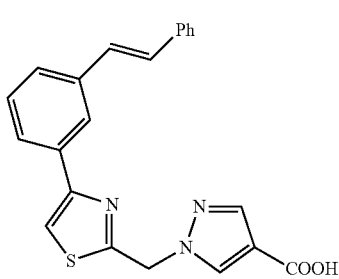 [SMILES: O=C(O)c1cnn(Cc2nc(-c3cccc(/C=C/c4ccccc4)c3)cs2)c1]

To a solution (2 mL) of the compound (49 mg, 0.12 mmol) obtained in Example 27b in ethanol was added 2N aqueous sodium hydroxide solution (0.24 ml, 0.48 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The obtained crude title compound was purified by recrystallization (ethyl acetate-hexane) to give the title compound (7 mg, 15%) as colorless crystals.

$^1$H NMR (300 MHz, DMSO-$d_6$) δ ppm 5.84 (2H, s), 7.21-7.51 (6H, m), 7.61-7.69 (3H, m), 7.85 (1H, d, J=7.7 Hz), 7.93 (1H, s), 8.18 (2H, s), 8.52 (1H, s), 12.47 (1H, br. s.)

Example 28

1-({4-[3-(2-phenylethyl)phenyl]-1,3-thiazol-2-yl}methyl)-1H-pyrazole-4-carboxylic acid

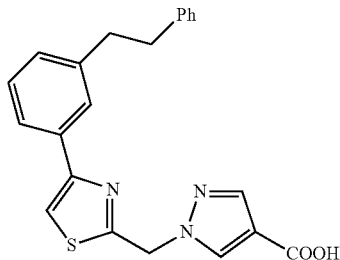 [SMILES: O=C(O)c1cnn(Cc2nc(-c3cccc(CCc4ccccc4)c3)cs2)c1]

The compound (40 mg, 0.10 mmol) obtained in Example 27 was dissolved in ethanol (2 mL), Pd—C (10% wet., ca. 1 mg) was added, and the mixture was stirred under a hydrogen atmosphere at room temperature for 6 hr. After confirmation of the termination of the reaction by TLC, Pd—C was removed. The solvent was evaporated under reduced pressure. The obtained crude product was purified by preparative high performance liquid chromatography to give the title compound (12 mg, 29%) as a colorless oil.

$^1$H NMR (300 MHz, DMSO-$d_6$) δ ppm 2.93 (4H, s), 5.81 (2H, s), 7.12-7.43 (7H, m), 7.75 (1H, d, J=7.7 Hz), 7.83 (1H, s), 7.91 (1H, s), 8.06 (1H, s), 8.49 (1H, s), 12.48 (1H, br. s.)
LCMS (ESI$^+$) M+H$^+$: 390.

Example 29

1-[(4-phenyl-1,3-thiazol-2-yl)methyl]-1H-pyrazole-4-carboxylic acid

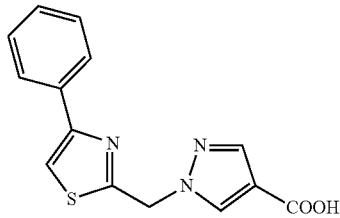 [SMILES: O=C(O)c1cnn(Cc2nc(-c3ccccc3)cs2)c1]

To a solution (2 mL) of the compound (85 mg, 0.27 mmol) obtained in Example 27c in ethanol was added 2N aqueous sodium hydroxide solution (0.54 mL, 1.08 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, dried over anhydrous sodium sulfate and the solvent was evaporated under reduced pressure. The obtained crude product was purified by recrystallization (ethyl acetate-hexane) to give the title compound (56 mg, 73%) as colorless crystals.

$^1$H NMR (300 MHz, DMSO-$d_6$) δ ppm 5.81 (2H, s), 7.36 (1H, d, J=7.3 Hz), 7.45 (2H, t, J=7.5 Hz), 7.83-7.98 (3H, m), 8.10 (1H, s), 8.49 (1H, s), 12.47 (1H, br. s.)
LCMS (ESI$^+$) M+H$^+$: 286.

Example 30

1-{[4-(3-acetylphenyl)-1,3-thiazol-2-yl]methyl}-1H-pyrazole-4-carboxylic acid

Example 30a (4-bromo-1,3-thiazol-2-yl)methanol

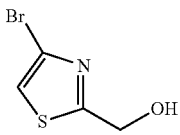

Under a nitrogen atmosphere at −78° C., to a solution (20 mL) of 2,4-dibromothiazole (5 g, 20.6 mmol) in diethyl ether was added n-butyllithium (1.6 M hexane solution, 15.4 mL, 24.7 mmol), and the mixture was stirred at the same temperature for 30 min. N,N-Dimethylformamide (2.3 g, 30.9 mmol) was added to the reaction mixture at −78° C., and the mixture was gradually warmed to room temperature. After confirmation of the termination of the reaction by TLC, hexane was added. The resulting salt was filtered and the solvent was evaporated under reduced pressure to give 4-bromo-1,3-thiazole-2-carbaldehyde as a crude product.

To a solution (20 mL) of crude 4-bromo-1,3-thiazole-2-carbaldehyde in ethanol was added sodium tetrahydroborate (935 mg, 24.7 mmol), and the mixture was stirred at room temperature for 3 hr. Water was added to the reaction mixture, and the mixture was extracted with ethyl acetate. The obtained organic layer was washed with saturated brine, and dried over anhydrous sodium sulfate. The solvent was evaporated under reduced pressure. The obtained crude product was purified by column chromatography (hexane-hexane/ethyl acetate=75/25) to give the title compound (1.8 g, 44%) as a pale-yellow oil.

$^1$H NMR (300 MHz, CHLOROFORM-d) δ ppm 2.60 (1H, t, J=6.2 Hz), 4.96 (2H, d, J=6.2 Hz), 7.22 (1H, s)

Example 30b 4-bromo-2-(chloromethyl)-1,3-thiazole

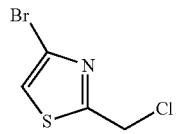

At 0° C., to a solution (9 mL) of the compound (1.77 g, 9.12 mmol) obtained in Example 30a in tetrahydrofuran was added thionyl chloride (1.3 mL, 18.2 mmol), and the mixture was stirred at room temperature for 5 hr. Saturated aqueous sodium hydrogen carbonate solution was added to the reaction mixture, and the mixture was extracted with ethyl acetate. The obtained organic layer was washed with saturated brine, and dried over anhydrous sodium sulfate. The solvent was evaporated under reduced pressure. The obtained crude product was purified by column chromatography (hexane-hexane/ethyl acetate=80/20) to give the title compound (1.57 g, 81%) as a pale-brown oil.

$^1$H NMR (400 MHz, CHLOROFORM-d) δ ppm 4.83 (2H, s), 7.29 (1H, s)

Example 30c ethyl 1-[(4-bromo-1,3-thiazol-2-yl)methyl]-1H-pyrazole-4-carboxylate

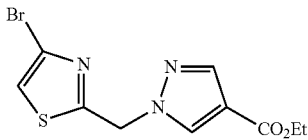

To a solution (4 mL) of the compound (1.57 g, 7.39 mmol) obtained in Example 30b in N,N-dimethylformamide were added ethyl 1H-pyrazole-4-carboxylate (1.3 g, 9.28 mmol) and potassium carbonate (1.5 g, 10.9 mmol), and the mixture was stirred at 80° C. overnight. The reaction mixture was allowed to cool to room temperature, water was added and the mixture was extracted with ethyl acetate. The obtained organic layer was washed with water and saturated brine and dried over anhydrous sodium sulfate, and the solvent was evaporated under reduced pressure. The obtained crude product was purified by column chromatography (hexane-hexane/ethyl acetate=70/30) to give the title compound (1.51 g, 66%) as a pale-brown oil.

$^1$H NMR (400 MHz, CHLOROFORM-d) δ ppm 1.34 (3H, t, J=7.2 Hz), 4.30 (2H, q, J=7.1 Hz), 5.60 (2H, s), 7.26 (1H, s), 7.99 (1H, s), 8.05 (1H, s)

LCMS (ESI$^+$) M+H$^+$: 315, 317.

Example 30d ethyl 1-{[4-(3-acetylphenyl)-1,3-thiazol-2-yl]methyl}-1H-pyrazole-4-carboxylate

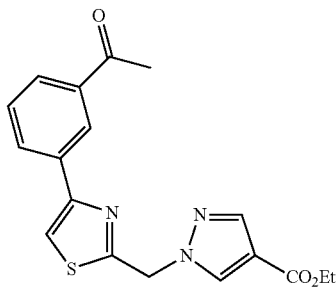 [SMILES: CCOC(=O)c1cnn(Cc2nc(-c3cccc(C(C)=O)c3)cs2)c1]

Under an argon atmosphere, to a solution (4 mL) of the compound (250 mg, 0.79 mmol) obtained in Example 30c in 1,2-dimethoxyethane were added (3-acetylphenyl)boronic acid (156 mg, 0.95 mmol), potassium carbonate (218 mg, 1.58 mmol) and tetrakistriphenylphosphinepalladium (91 mg, 0.079 mmol), and the mixture was stirred at 120° C. for 15 min under microwave conditions. The mixture was allowed to cool to room temperature, water was added to the reaction mixture, and the mixture was extracted with ethyl acetate. The obtained organic layer was washed with saturated brine, and dried over anhydrous sodium sulfate. The solvent was evaporated under reduced pressure. The obtained crude product was purified by column chromatography (hexane-hexane/ethyl acetate=1/1) to give the title compound (188 mg, 67%) as a pale-brown oil.

$^1$H NMR (400 MHz, CHLOROFORM-d) δ ppm 1.34 (3H, t, J=7.1 Hz), 2.68 (3H, s), 4.30 (2H, q, J=7.1 Hz), 5.69 (2H, s), 7.54 (1H, t, J=7.8 Hz), 7.59 (1H, s), 7.94 (1H, d, J=7.8 Hz), 8.01 (1H, s), 8.07-8.13 (2H, m), 8.47 (1H, s)

LCMS (ESI$^+$) M+H$^+$: 356.

Example 30

1-{[4-(3-acetylphenyl)-1,3-thiazol-2-yl]methyl}-1H-pyrazole-4-carboxylic acid

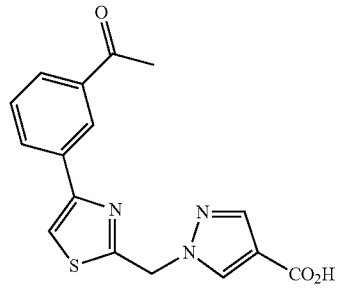 [SMILES: CC(=O)c1cccc(-c2csc(Cn3cc(C(=O)O)cn3)n2)c1]

To a mixed solution of the compound (188 mg, 0.53 mmol) obtained in Example 30d in ethanol-tetrahydrofuran (v/v=2/1) was added 2N aqueous sodium hydroxide solution (1.5 mL, 3.0 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The obtained crude product was purified by recrystallization (ethyl acetate-hexane) to give the title compound (145 mg, 84%) as colorless crystals.

$^1$H NMR (400 MHz, DMSO-d$_6$) δ ppm 2.64 (3H, s), 5.85 (2H, s), 7.62 (1H, t, J=7.7 Hz), 7.92 (1H, s), 7.95 (1H, d, J=7.6 Hz), 8.20 (1H, d, J=7.8 Hz), 8.29 (1H, s), 8.45-8.58 (2H, m), 12.50 (1H, br. s.)

LCMS (ESI$^+$) M+H$^+$: 328.

Example 31

1-{[4-(4-acetylphenyl)-1,3-thiazol-2-yl]methyl}-1H-pyrazole-4-carboxylic acid

Example 31a ethyl 1-{[4-(4-acetylphenyl)-1,3-thiazol-2-yl]methyl}-1H-pyrazole-4-carboxylate

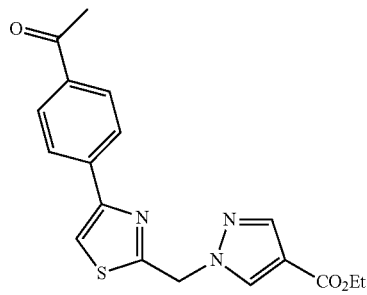 [SMILES: CCOC(=O)c1cnn(Cc2nc(-c3ccc(C(C)=O)cc3)cs2)c1]

By a method similar to that of Example 30d, the title compound (219 mg, 78%) was obtained as a pale-yellow oil from the compound (250 mg, 0.79 mmol) obtained in Example 30c and (4-acetylphenyl)boronic acid (156 mg, 0.95 mmol).

$^1$H NMR (400 MHz, CHLOROFORM-d) δ ppm 1.34 (3H, t, J=7.1 Hz), 2.64 (3H, s), 4.30 (2H, q, J=7.1 Hz), 5.69 (2H, s), 7.62 (1H, s), 7.92-8.08 (5H, m), 8.10 (1H, s)

LCMS (ESI$^+$) M+H$^+$: 356.

Example 31

1-{[4-(4-acetylphenyl)-1,3-thiazol-2-yl]methyl}-1H-pyrazole-4-carboxylic acid

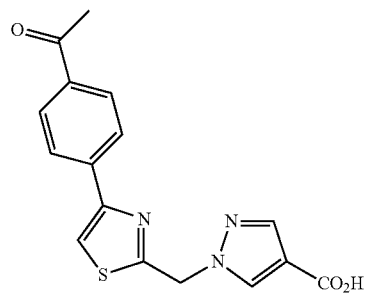 [SMILES: CC(=O)c1ccc(-c2csc(Cn3cc(C(=O)O)cn3)n2)cc1]

By a method similar to that of Example 30, the title compound (170 mg, 84%) was obtained as colorless crystals from the compound (219 mg, 0.62 mmol) obtained in Example 31a.

$^1$H NMR (400 MHz, DMSO-d$_6$) δ ppm 2.60 (3H, s), 5.84 (2H, s), 7.93 (1H, s), 8.04 (2H, d, J=7.2 Hz), 8.09 (2H, d, J=7.2 Hz), 8.34 (1H, s), 8.52 (1H, s), 12.44 (1H, br. s.)

LCMS (ESI$^+$) M+H$^+$: 328.

Example 32

1-({4-[3,5-bis(trifluoromethyl)phenyl]-1,3-thiazol-2-yl}methyl)-1H-pyrazole-4-carboxylic acid

Example 32a ethyl 1-({4-[3,5-bis(trifluoromethyl)phenyl]-1,3-thiazol-2-yl}methyl)-1H-pyrazole-4-carboxylate

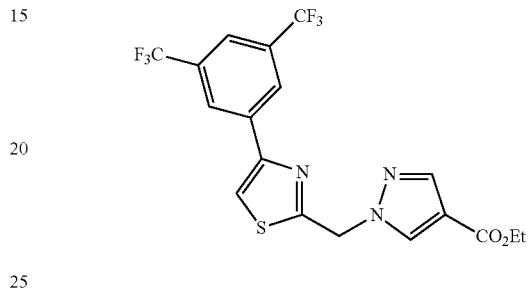

By a method similar to that of Example 30d, the title compound (143 mg, 40%) was obtained as a yellow oil from the compound (250 mg, 0.79 mmol) obtained in Example 30c and 3,5-bis(trifluoromethyl)phenylboronic acid (245 mg, 0.95 mmol).

$^1$H NMR (300 MHz, CHLOROFORM-d) δ ppm 1.35 (3H, t, J=7.2 Hz), 4.31 (2H, q, J=7.2 Hz), 5.70 (2H, s), 7.68 (1H, s), 8.02 (1H, s), 8.11 (1H, s), 8.22 (1H, s), 8.33 (2H, s)

LCMS (ESI$^+$) M+H$^+$: 450.

Example 32

1-({4-[3,5-bis(trifluoromethyl)phenyl]-1,3-thiazol-2-yl}methyl)-1H-pyrazole-4-carboxylic acid

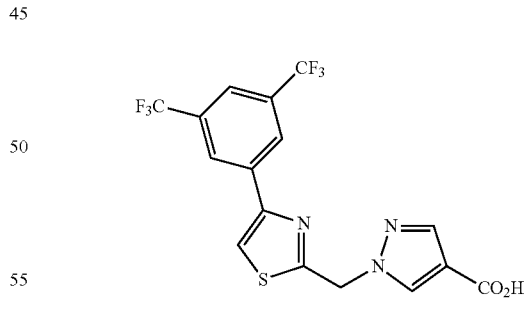

By a method similar to that of Example 30, the title compound (35 mg, 26%) was obtained as colorless crystals from the compound (143 mg, 0.32 mmol) obtained in Example 32a.

$^1$H NMR (300 MHz, DMSO-d$_6$) δ ppm 5.87 (2H, s), 7.92 (1H, s), 8.10 (1H, s), 8.51 (1H, s), 8.61 (2H, s), 8.65 (1H, s), 12.50 (1H, br. s.)

LCMS (ESI$^+$) M+H$^+$: 422:

Example 33

1-({4-[4,6-bis(trifluoromethyl)pyrimidin-2-yl]-1,3-thiazol-2-yl}methyl)-1H-pyrazole-4-carboxylic acid

Example 33a

2-{[4-(ethoxycarbonyl)-1H-pyrazol-1-yl]methyl}-1,3-thiazole-4-carboxylic acid

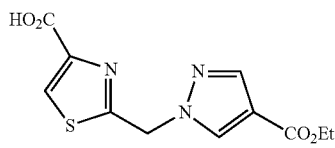

To a solution (9 mL) of the compound (2.0 g, 9.38 mmol) obtained in Example 1b in acetonitrile was added 3-bromo-2-oxopropanoic acid (1.9 g, 11.3 mmol), and the mixture was stirred at 80° C. for 2 hr. The resulting crystals were collected by filtration and washed with hexane to give the title compound (2.56 g, 97%) as pale-brown crystals.

$^1$H NMR (400 MHz, DMSO-$d_6$) δ ppm 1.27 (3H, t, J=7.1 Hz), 4.23 (2H, q, J=7.1 Hz), 5.80 (2H, s), 7.97 (1H, s), 8.43 (1H, s), 8.57 (1H, s)

LCMS (ESI$^+$) M+H$^+$: 282.

Example 33b ethyl 1-[(4-carbamoyl-1,3-thiazol-2-yl)methyl]-1H-pyrazole-4-carboxylate

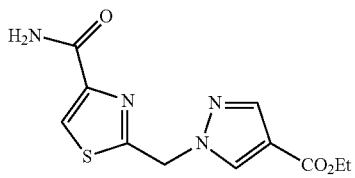 [SMILES: CCOC(=O)c1cnn(Cc2nc(C(N)=O)cs2)c1]

To a solution (7 mL) of the compound (1.0 g, 3.56 mmol) obtained in Example 33a in N,N-dimethylformamide were added 1-ethyl-3-(3-dimethylaminopropyl)carbodiimide hydrochloride (WSC, 820 mg, 4.27 mmol) and 1-hydroxy-1H-benzotriazole ammonium salt (704 mg, 4.63 mmol), and the mixture was stirred at room temperature for 4 hr. After confirmation of the termination of the reaction by TLC, saturated aqueous sodium hydrogen carbonate solution was added to the reaction mixture, and the mixture was extracted with ethyl acetate. The obtained organic layer was washed with water and saturated brine, and dried over anhydrous sodium sulfate. The solvent was evaporated under reduced pressure. The obtained crude product was purified by column chromatography (hexane-ethyl acetate) and recrystallization (ethyl acetate-hexane) to give the title compound (524 mg, 52%) as colorless crystals.

$^1$H NMR (400 MHz, DMSO-$d_6$) δ ppm 1.27 (3H, t, J=7.1 Hz), 4.23 (2H, q, J=7.1 Hz), 5.78 (2H, s), 7.62 (1H, br. s.), 7.73 (1H, br. s.), 7.97 (1H, s), 8.23 (1H, s), 8.58 (1H, s)

LCMS (ESI$^+$) M+H$^+$: 281.

Example 33c ethyl 1-[(4-carbamothioyl-1,3-thiazol-2-yl)methyl]-1H-pyrazole-4-carboxylate

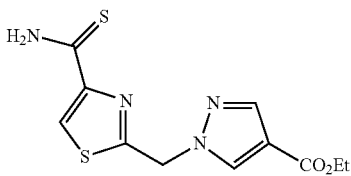

To a solution (10 mL) of the compound (524 mg, 1.87 mmol) obtained in Example 33b in toluene was added 2,4-bis(4-methoxyphenyl)-1,3-dithia-2,4-diphosphetane-2,4-disulfide (Lawesson reagent, 756 mg, 1.87 mmol), and the mixture was heated under reflux overnight. The reaction mixture was allowed to cool to room temperature, saturated aqueous sodium hydrogen carbonate solution was added, and the mixture was stirred for 30 min, and extracted with ethyl acetate. The obtained organic layer was washed with saturated brine, and dried over anhydrous sodium sulfate. The solvent was evaporated under reduced pressure. The obtained crude product was purified by column chromatography (hexane-hexane/ethyl acetate=1/1) and recrystallization (ethyl acetate-hexane) to give the title compound (200 mg, 36%) as pale-yellow crystals.

$^1$H NMR (400 MHz, DMSO-$d_6$) δ ppm 0.86 (3H, t, J=6.7 Hz), 4.23 (2H, q, J=7.1 Hz), 5.78 (2H, s), 7.97 (1H, s), 8.41 (1H, s), 8.59 (1H, s), 9.47 (1H, br. s.), 10.03 (1H, br. s.)

LCMS (ESI$^+$) M+H$^+$: 297.

Example 33d ethyl 1-({4-[4,6-bis(trifluoromethyl)pyrimidin-2-yl]-1,3-thiazol-2-yl}methyl)-1H-pyrazole-4-carboxylate

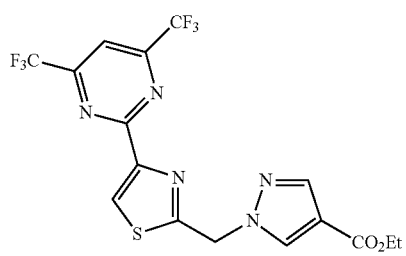 [SMILES: CCOC(=O)c1cnn(Cc2nc(-c3nc(C(F)(F)F)cc(C(F)(F)F)n3)cs2)c1]

To a solution (6 mL) of the compound (200 mg, 0.67 mmol) obtained in Example 33c in anhydrous acetone was added iodomethane (0.21 mL, 3.37 mmol), and the mixture was stirred at room temperature overnight. The solvent was evaporated under reduced pressure, and the residue was dissolved in anhydrous methanol (6 mL). Ammonium acetate (260 mg, 3.37 mmol) was added, and the mixture was stirred at room temperature overnight.

The solvent was evaporated under reduced pressure, and the residue was dissolved in anhydrous ethanol (4 mL). 1,1,1,5,5,5-Hexafluoropentane-2,4-dione (209 mg, 1.01 mmol) was added, and the mixture was heated under reflux overnight. The reaction mixture was allowed to cool to room temperature, acetic acid (1 mL) and 1,1,1,5,5,5-hexafluoropentane-2,4-dione (418 mg, 2.02 mmol) were added again, and the mixture was heated under reflux overnight. The reaction mixture was allowed to cool to room temperature, water was added and the mixture was extracted with ethyl acetate.

The obtained organic layer was washed with saturated brine, and dried over anhydrous sodium sulfate. The solvent was evaporated under reduced pressure. The resulting crystals were washed with hexane and diisopropyl ether to give a crude title compound (100 mg) as colorless crystals.

LCMS (ESI+) M+H+: 452.

Example 33

1-({4-[4,6-bis(trifluoromethyl)pyrimidin-2-yl]-1,3-thiazol-2-yl}methyl)-1H-pyrazole-4-carboxylic acid

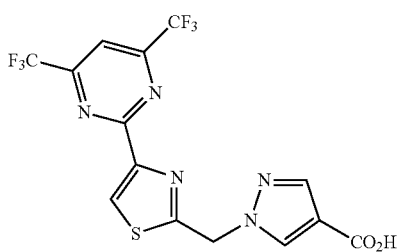 [SMILES: O=C(O)c1cnn(Cc2nc(-c3nc(C(F)(F)F)cc(C(F)(F)F)n3)cs2)c1]

The crude compound (100 mg) obtained in Example 33d was dissolved in ethanol (2 mL), 2N aqueous sodium hydroxide solution (0.44 mL, 0.88 mmol) was added, and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The obtained crude product was purified by preparative high performance liquid chromatography and then recrystallization (ethyl acetate-hexane) to give the title compound (6 mg, 7% in 2 steps) as colorless crystals.

$^1$H NMR (300 MHz, DMSO-$d_6$) δ ppm 5.91 (2H, s), 7.94 (1H, s), 8.50 (1H, s), 8.53 (1H, s), 12.47 (1H, br. s.)

LCMS (ESI+) M+H+: 424.

Example 34

1-({5-methyl-4-[3-(trifluoromethyl)phenyl]-1,3-thiazol-2-yl}methyl)-1H-pyrazole-4-carboxylic acid

Example 34a ethyl 1-({5-methyl-4-[3-(trifluoromethyl)phenyl]-1,3-thiazol-2-yl}methyl)-1H-pyrazole-4-carboxylate

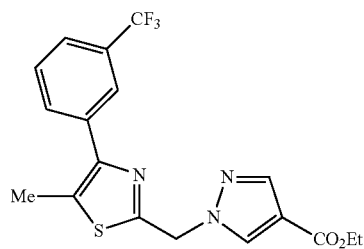

Under a nitrogen atmosphere, to a solution (10 mL) of 1-[3-(trifluoromethyl)phenyl]propan-1-one (1.0 g, 4.95 mmol) in diethyl ether was added bromine (0.15 mL, 5.94 mmol) at 0° C., and the mixture was stirred at room temperature overnight. An aqueous sodium thiosulfate solution was added to the reaction mixture, and the mixture was extracted with ethyl acetate. The obtained organic layer was washed with saturated brine, and dried over anhydrous sodium sulfate. The solvent was evaporated under reduced pressure. The residue was dissolved in ethanol (4 mL), the compound (175 mg, 0.82 mmol) obtained in Example 1b was added and the mixture was heated under reflux for 3 hr. The reaction mixture was allowed to cool and the solvent was evaporated under reduced pressure. The obtained crude product was purified by recrystallization (ethyl acetate-hexane) to give the title compound (112 mg, 35%) as colorless crystals.

$^1$H NMR (400 MHz, DMSO-$d_6$) δ ppm 1.26 (3H, t, J=7.1 Hz), 2.55 (3H, s), 4.22 (2H, q, J=7.1 Hz), 5.75 (2H, s), 7.55-7.85 (2H, m), 7.94-8.03 (3H, m), 8.57 (1H, s)

LCMS (ESI+) M+H+: 396.

Example 34

1-({5-methyl-4-[3-(trifluoromethyl)phenyl]-1,3-thiazol-2-yl}methyl)-1H-pyrazole-4-carboxylic acid

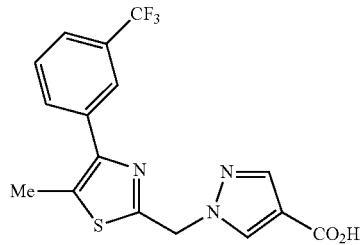 [SMILES: CCOC(=O)c1cnn(Cc2nc(-c3cccc(C(F)(F)F)c3)c(C)s2)c1]

To a solution (3 mL) of the compound (112 mg, 0.28 mmol) obtained in Example 34a in ethanol was added 2N aqueous sodium hydroxide solution (0.56 mL, 1.08 mmol), and the mixture was stirred at room temperature for 5 hr. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The obtained crude product was purified by recrystallization (ethyl acetate-hexane) to give the title compound (49 mg, 48%) as colorless crystals.

$^1$H NMR (400 MHz, DMSO-$d_6$) δ ppm 2.55 (3H, s), 5.74 (2H, s), 7.65-7.83 (2H, m), 7.90 (1H, s), 7.93-8.04 (2H, m), 8.48 (1H, s), 12.48 (1H, br. s.)

LCMS (ESI+) M+H+: 368.

Example 35

1-({5-(trifluoromethyl)-2-[3-(trifluoromethyl)phenyl]-1,3-thiazol-4-yl}methyl)-1H-pyrazole-4-carboxylic acid

Example 35a 5-iodo-4-[(tetrahydro-2H-pyran-2-yloxy)methyl]-2-[3-(trifluoromethyl)phenyl]-1,3-thiazole

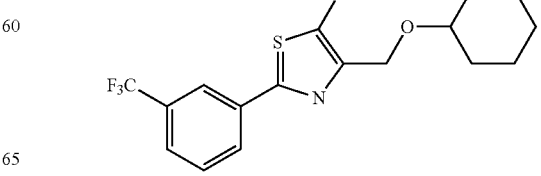

Under a nitrogen atmosphere at −78° C., to a solution (20 mL) of the compound (3.2 g, 9.3 mmol) obtained in Example 89a in tetrahydrofuran was added n-butyllithium (2.6 M hexane solution, 5.6 mL, 11 mmol), and the mixture was stirred at the same temperature for 30 min. Iodine (2.4 g, 19 mmol) was added to the reaction mixture and the mixture was stirred overnight while allowing to spontaneously warm to room temperature from −78° C. An aqueous sodium sulfite solution was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=85/15) to give the title compound (2.5 g, 57%) as a mixture with 89a in an orange oil with purity 81%.

$^1$H NMR (300 MHz, CHLOROFORM-d) δppm 1.22-1.98 (6H, m), 3.56-3.67 (1H, m), 3.94-4.08 (1H, m), 4.68 (1H, d, J=12.0 Hz), 4.81-4.93 (2H, m), 7.56 (1H, t, J=7.8 Hz), 7.68 (1H, d, J=8.0 Hz), 8.05 (1H, d, J=7.6 Hz), 8.17 (1H, s)

Example 35b

4-[(tetrahydro-2H-pyran-2-yloxy)methyl]-5-(trifluoromethyl)-2-[3-(trifluoromethyl)phenyl]-1,3-thiazole

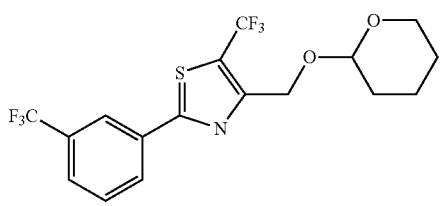

Under a nitrogen atmosphere, to a solution (10 mL) of the compound (purity 81%, 1.9 g, 3.3 mmol) obtained in Example 35a in N,N-dimethylformamide were added copper iodide(I) (720 mg, 4.0 mmol) and methyl 2,2-difluoro-2-(fluorosulfonyl)acetate (2.8 mL, 23 mmol), and the mixture was stirred at 100° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (860 mg, 63%) as an orange solid.

$^1$H NMR (300 MHz, CHLOROFORM-d) δppm 1.50-1.90 (6H, m), 3.52-3.67 (1H, m), 3.87-4.02 (1H, m), 4.74 (1H, d, J=12.1 Hz), 4.86 (1H, t, J=3.2 Hz), 4.97 (1H, d, J=12.1 Hz), 7.60 (1H, t, J=7.8 Hz), 7.74 (1H, d, J=8.0 Hz), 8.11 (1H, d, J=7.6 Hz), 8.23 (1H, s)

Example 35c ethyl 1-({5-(trifluoromethyl)-2-[3-(trifluoromethyl)phenyl]-1,3-thiazol-4-yl}methyl)-1H-pyrazole-4-carboxylate

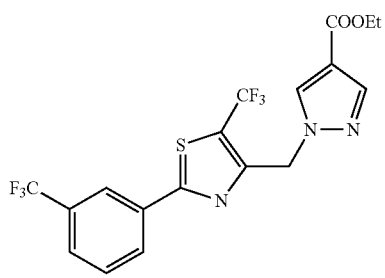

By a method similar to that in Example 89e, 89f, the title compound (910 mg, 98%) was obtained as a pale-yellow oil from the compound (860 mg, 2.1 mmol) obtained in Example 35b and p-toluenesulfonic acid monohydrate (1.2 g, 6.2 mmol), triphenylphosphine (710 mg, 2.7 mmol), ethyl 1H-pyrazole-4-carboxylate (350 mg, 2.5 mmol) and diisopropyl azodicarboxylate (1.9 M toluene solution, 1.4 mL, 2.7 mmol).

$^1$H NMR (300 MHz, CHLOROFORM-d) δppm 1.34 (3H, t, J=7.2 Hz), 4.29 (2H, q, J=6.9 Hz), 5.56 (2H, s), 7.61 (1H, t, J=7.8 Hz), 7.76 (1H, d, J=8.0 Hz), 7.94 (1H, s), 8.02-8.13 (2H, m), 8.15 (1H, s)

LCMS (ESI$^+$) M+H$^+$: 450.

Example 35

1-({5-(trifluoromethyl)-2-[3-(trifluoromethyl)phenyl]-1,3-thiazol-4-yl}methyl)-1H-pyrazole-4-carboxylic acid

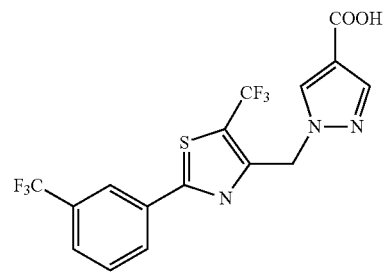

In the same manner as in Example 38, the title compound (580 mg, 68%) was obtained as colorless crystals from the compound (910 mg, 2.0 mmol) obtained in Example 35c.

$^1$H NMR (300 MHz, DMSO-d$_6$) δ ppm 5.66 (2H, s), 7.79 (1H, d, J=7.9 Hz), 7.83 (1H, s), 7.96 (1H, d, J=7.9 Hz), 8.15-8.31 (2H, m), 8.45 (1H, s), 12.42 (1H, s)

LCMS (ESI$^+$) M+H$^+$: 422.

Example 36

1-[(4-{4-[(methoxyacetyl)amino]phenyl}-1,3-thiazol-2-yl)methyl]-1H-pyrazole-4-carboxylic acid Example 36a ethyl 1-{[4-(4-nitrophenyl)-1,3-thiazol-2-yl]methyl}-1H-pyrazole-4-carboxylate

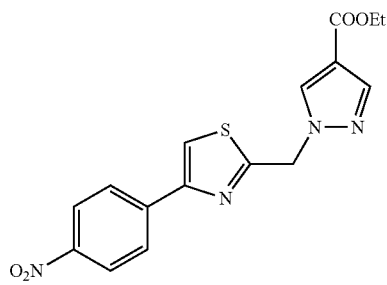 [SMILES: CCOC(=O)c1cnn(Cc2nc(-c3ccc(N)cc3)cs2)c1]

A solution (8 mL) of the compound (1.0 g, 4.7 mmol) obtained in Example 1b and 2-bromo-1-(4-nitrophenyl)ethanone (1.4 g, 5.6 mmol) in ethanol was heated under reflux overnight, and cooled to room temperature. The solvent was evaporated under reduced pressure, and the resulting crude title compound was recrystallized (ethyl acetate-hexane) to give the title compound (1.5 g, 89%) as colorless crystals.

$^1$H NMR (400 MHz, DMSO-$d_6$) δ ppm 1.27 (3H, t, J=7.1 Hz), 4.23; H, q, J=6.9 Hz), 5.87 (2H, s), 7.98 (1H, s), 8.21 (2H, m, J=8.6 Hz), 8.32 (2H, m, J=8.6 Hz), 8.48 (1H, s), 8.60 (1H, s)

LCMS (ESI$^+$) M+H$^+$: 359.

Example 36b ethyl 1-{[4-(4-aminophenyl)-1,3-thiazol-2-yl]methyl}-1H-pyrazole-4-carboxylate

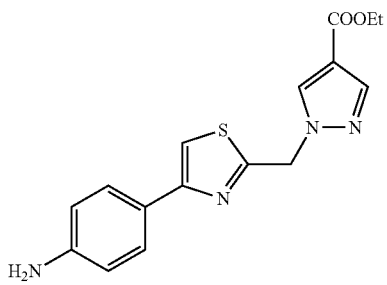

To a mixed solution of the compound (1.5 g, 4.2 mmol) obtained in Example 36a in ethanol/tetrahydrofuran (v/v=1/1, 20 mL) was added palladium-carbon (10% wet., 150 mg), and the mixture was stirred at room temperature for 3 hr under a hydrogen atmosphere (1 atm). Palladium-carbon was removed by filtration and the solvent was evaporated under reduced pressure to give a crude title compound.

$^1$H NMR (400 MHz, DMSO-$d_6$) δ ppm 1.27 (3H, t, J=7.1 Hz), 4.23 (2H, d, J=7.1 Hz), 5.78 (2H, s), 6.70 (2H, m, J=8.1 Hz), 7.65 (2H, m, J=8.3 Hz), 7.73 (1H, s), 7.96 (1H, s), 8.56 (1H, s)

LCMS (ESI$^+$) M+H$^+$: 329.

Example 36c ethyl 1-[(4-{4-[(methoxyacetyl)amino]phenyl}-1,3-thiazol-2-yl)methyl]-1H-pyrazole-4-carboxylate

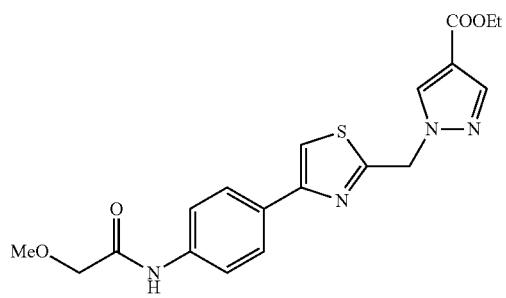 [SMILES: CCOC(=O)c1cnn(Cc2nc(-c3ccc(NC(=O)COC)cc3)cs2)c1]

In an ice-bath, to a solution (4 mL) of the crude compound (0.84 mmol) obtained in Example 36b in tetrahydrofuran were added triethylamine (0.15 mL, 1.1 mmol) and methoxyacetylchloride (110 mg, 1.0 mmol), and the mixture was stirred at room temperature overnight. After confirmation of the termination of the reaction by TLC, the resulting salt was removed. The solvent was evaporated under reduced pressure. The resulting crude title compound was recrystallized (hexane-ethyl acetate) to give the title compound (250 mg, 74% in 2 steps) as colorless crystals.

$^1$H NMR (400 MHz, DMSO-$d_6$) δ ppm 1.27 (3H, t, J=7.1 Hz), 3.38 (3H, s), 4.02 (2H, s), 4.23 (2H, q, J=7.0 Hz), 5.82 (2H, s), 7.75 (2H, m, J=8.6 Hz), 7.88 (2H, m, J=8.6 Hz), 7.97 (1H, s), 8.00 (1H, s), 8.58 (1H, s), 9.89 (1H, s)

LCMS (ESI$^+$) M+H$^+$: 401.

Example 36

1-[(4-{4-[(methoxyacetyl)amino]phenyl}-1,3-thiazol-2-yl)methyl]-1H-pyrazole-4-carboxylic acid

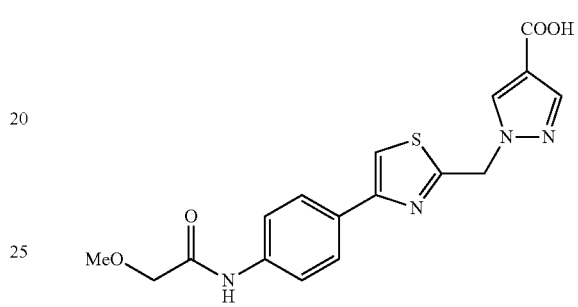

To a solution (4 mL) of the compound (250 mg, 0.62 mmol) obtained in Example 36c in ethanol was added 2N aqueous sodium hydroxide solution (1.6 mL, 3.2 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (110 mg, 49%) as colorless crystals.

1H NMR (300 MHz, DMSO-$d_6$) δ ppm 3.39 (3H, s), 4.01 (2H, s), 5.82 (2H, s), 7.37 (1H, t, J=7.9 Hz), 7.52-7.74 (2H, m), 7.91 (1H, s), 8.01 (1H, s), 8.24 (1H, t, J=1.8 Hz), 8.49 (1H, s), 9.86 (1H, s), 12.46 (1H, br. s.)

LCMS (ESI$^+$) M+H$^+$: 373.

Example 37

1-[(4-{4-[(ethoxycarbonyl)amino]phenyl}-1,3-thiazol-2-yl)methyl]-1H-pyrazole-4-carboxylic acid Example 37a ethyl 1-[(4-{4-[(ethoxycarbonyl)amino]phenyl}-1,3-thiazol-2-yl)methyl]-1H-pyrazole-4-carboxylate

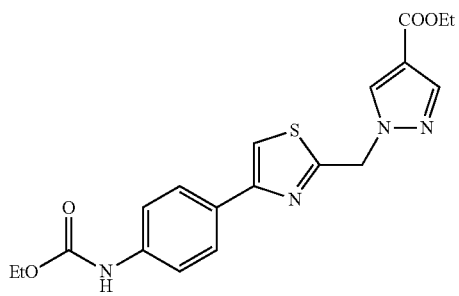 [SMILES: CCOC(=O)Nc1ccc(-c2csc(Cn3cc(C(=O)OCC)cn3)n2)cc1]

In an ice-bath, to a solution (4 mL) of the crude compound (0.84 mmol) obtained in Example 36b in tetrahydrofuran were added triethylamine (0.15 ml, 1.1 mmol) and ethyl chlorocarbonate (79 ml, 1.0 mmol), and the mixture was stirred at room temperature overnight. After confirmation of the termination of the reaction by TLC, the resulting salt was removed. The solvent was evaporated under reduced pressure. The resulting crude title compound was recrystallized (hexane-ethyl acetate) to give the title compound (180 mg, 54% in 2 steps) as colorless crystals.

$^1$H NMR (400 MHz, DMSO-d$_6$) δ ppm 1.26 (6H, q, J=6.9 Hz), 4.14 (2H, q, J=7.1 Hz), 4.23 (2H, q, J=7.1 Hz), 5.81 (2H, s), 7.53 (2H, m, J=8.6 Hz), 7.84 (2H, m, J=8.6 Hz), 7.95 (1H, s), 7.97 (1H, s), 8.58 (1H, s), 9.77 (1H, s)

LCMS (ESI$^+$) M+H$^+$: 401.

Example 37

1-[(4-{4-[(ethoxycarbonyl)amino]phenyl}-1,3-thiazol-2-yl)methyl]-1H-pyrazole-4-carboxylic acid

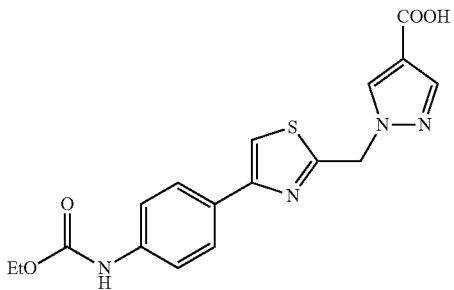

To a solution (4 mL) of the compound (180 mg, 0.45 mmol) obtained in Example 37a in ethanol was added 2N aqueous sodium hydroxide solution (1.6 mL, 3.2 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (95 mg, 57%) as colorless crystals.

$^1$H NMR (400 MHz, DMSO-d$_5$) δ ppm 1.25 (3H, t, J=7.0 Hz), 4.14 (2H, q, J=7.1 Hz), 5.80 (2H, s), 7.53 (2H, m, J=8.8 Hz), 7.84 (2H, m, J=8.6 Hz), 7.91 (1H, s), 7.95 (1H, s), 8.49 (1H, s), 9.77 (1H, s), 12.48 (1H, br. s.)

LCMS (ESI$^+$) M+H$^+$: 373.

Example 38

1-({4-[3-(2,2,2-trifluoroethoxy)phenyl]-1,3-thiazol-2-yl}methyl)-1H-pyrazole-4-carboxylic acid Example 38a 1-(3{[tert-butyl(dimethyl)silyl]oxy}phenyl)ethanone

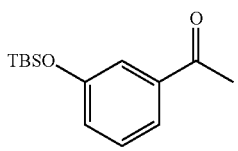 [SMILES: CC(=O)c1cccc(O[Si](C)(C)C(C)(C)C)c1]

Under a nitrogen atmosphere at 0° C., to a solution (40 mL) of 3-acetylphenol (5.0 g, 37 mmol) in tetrahydrofuran were added triethylamine (7.7 mL, 55 mmol) and tert-butyldimethylsilylchloride (6.6 g, 44 mmol), and the mixture was stirred at room temperature overnight. After confirmation of the termination of the reaction by TLC, the resulting salt was removed. The solvent was evaporated under reduced pressure. The resulting crude title compound was purified by column chromatography (hexane-hexane/ethyl acetate=9/1) to give the title compound (9.4 g, 100%) as a colorless oil.

$^1$H NMR (300 MHz, CHLOROFORM-d) δppm 0.22 (6H, s), 1.00 (9H, s), 2.58 (3H, s), 7.04 (1H, ddd, J=8.0, 2.5, 1.1 Hz), 7.32 (1H, t, J=7.9 Hz), 7.37-7.46 (1H, m), 7.54 (1H, dt, J=7.7, 1.3 Hz)

Example 38b 2-bromo-1-(3-{[tert-butyl(dimethyl)silyl]oxy}phenyl)ethanone

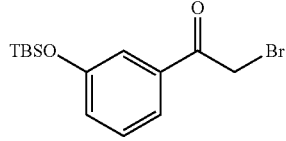 [SMILES: CC(C)(C)[Si](C)(C)Oc1cccc(C(=O)CBr)c1]

To a solution (40 mL) of the compound (9.4 g, 37 mmol) obtained in Example 38a in diethyl ether was added phenyltrimethylammonium tribromide (14 g, 37 mmol), and the mixture was stirred at room temperature for 5 hr. After confirmation of the termination of the reaction by TLC, aqueous sodium thiosulfate solution was added to the reaction mixture, and the mixture was extracted with ethyl acetate. The obtained organic layer was washed with saturated brine, and dried over anhydrous sodium sulfate. The solvent was evaporated under reduced pressure to give a crude title compound as a colorless oil.

$^1$H NMR (300 MHz, CHLOROFORM-d) δppm 0.23 (6H, s), 1.00 (9H, s), 4.43 (2H, s), 6.68-7.86 (4H, m)

LCMS (ESI$^+$) M+H$^+$: 329.

Example 38c ethyl 1-{[4-(3-hydroxyphenyl)-1,3-thiazol-2-yl]methyl}-1-pyrazole-4-carboxylate

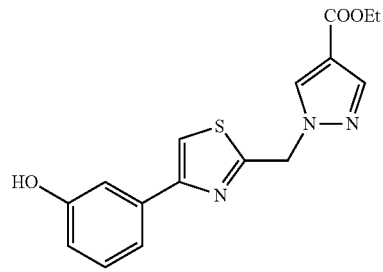 [SMILES: CCOC(=O)c1cnn(Cc2nc(-c3cccc(O)c3)cs2)c1]

To a solution (40 ml) of the crude compound (37 mmol) obtained in Example 38b in ethanol was added the compound (7.0 g, 33 mmol) obtained in Example 1b, and the mixture was stirred at 70° C. for 3 hr. After confirmation of the termination of the reaction by TLC, the solvent was evaporated under reduced pressure, and the resulting crude title compound was recrystallized (tetrahydrofuran-ethyl acetate-hexane) to give the title compound (11 g, 100% in 2 steps) as colorless crystals.

$^1$H NMR (300 MHz, DMSO-d$_6$) δ ppm 1.26 (3H, t, J=7.2 Hz), 4.23 (2H, q, J=7.2 Hz), 5.81 (2H, s), 6.74 (1H, dt, J=7.5, 1.4 Hz), 7.22 (1H, t, J=8.1 Hz), 7.29-7.40 (2H, m), 7.96 (1H, s), 8.00 (1H, s), 8.57 (1H, s)

LCMS (ESI$^+$) M+H$^+$: 330.

Example 38d ethyl 1-({4-[3-(2,2,2-trifluoroethoxy)phenyl]-1,3-thiazol-2-yl}methyl)-1H-pyrazole-4-carboxylate

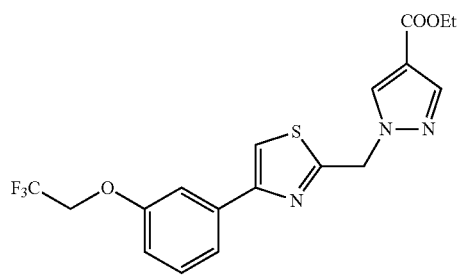 [SMILES: CCOC(=O)c1cnn(Cc2nc(-c3cccc(OCC(F)(F)F)c3)cs2)c1]

Under a nitrogen atmosphere at 0° C., to a solution (2 mL) of sodium hydride (60% in mineral oil, 44 mg, 1.1 mmol) in N,N-dimethylformamide was added dropwise a solution (2 mL) of the compound (300 mg, 0.91 mmol) obtained in Example 38c in N,N-dimethylformamide, and the mixture was stirred at room temperature for 30 min. Then, to the reaction mixture was added 2,2,2-trifluoroethyl-p-toluenesulfonate (280 mg, 1.1 mmol) and the mixture was stirred at 70° C. for 48 hr. Water was added to the reaction mixture and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=65/35) to give the title compound (24 mg, 6%) as a colorless oil.

$^1$H NMR (300 MHz, CHLOROFORM-d) δppm 1.34 (3H, t, J=7.2 Hz), 4.30 (2H, q, J=7.1 Hz), 4.43 (2H, q, J=8.2 Hz), 5.67 (2H, s), 6.88-7.01 (1H, m), 7.37 (1H, t, J=8.2 Hz), 7.44-7.58 (3H, m), 8.00 (1H, s), 8.09 (1H, s)

LCMS (ESI$^+$) M+H$^+$: 412.

Example 38

1-({4-[3-(2,2,2-trifluoroethoxy)phenyl]-1,3-thiazol-2-yl}methyl)-1H-pyrazole-4-carboxylic acid

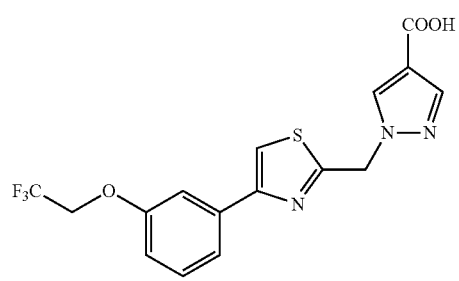 [SMILES: O=C(O)c1cnn(Cc2nc(-c3cccc(OCC(F)(F)F)c3)cs2)c1]

To a solution (2 mL) of the compound (24 mg, 0.058 mmol) obtained in Example 38d in ethanol was added 2N aqueous sodium hydroxide solution (0.12 ml, 0.24 mmol), and the mixture was stirred at room temperature overnight. Water was added to the reaction mixture, and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (11 mg, 49%) as colorless crystals.

$^1$H NMR (300 MHz, DMSO-d$_6$) δ ppm 4.83 (2H, q, J=9.1 Hz), 5.81 (2H, s), 7.05 (1H, dd, J=8.3, 1.9 Hz), 7.41 (1H, t, J=8.0 Hz), 7.53-7.71 (2H, m), 7.91 (1H, s), 8.18 (1H, s), 8.49 (1H, s), 12.43 (1H, br. s.)

LCMS (ESI$^+$) M+H$^+$: 384.

Example 39

1-({5-[3-(trifluoromethyl)phenyl]thiophen-2-yl}methyl)-1H-pyrazole-4-carboxylic acid

Example 39a ethyl 5-[3-(trifluoromethyl)phenyl]thiophene-2-carboxylate

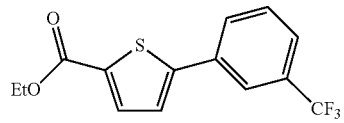 [SMILES: CCOC(=O)c1ccc(-c2cccc(C(F)(F)F)c2)s1]

Under a nitrogen atmosphere, to a mixed solvent of ethyl 5-bromothiophene-2-carboxylate (2.4 g, 10 mmol), 3-(trifluoromethyl)phenylboronic acid (2.9 g, 15 mmol) and sodium carbonate (2.1 g, 20 mmol) in water/1,4-dioxane (v/v=1/1, 10 mL) was added tetrakistriphenylphosphinepalladium (1.1 g, 1.0 mmol), and the mixture was stirred at 80° C. for 12 hr. The reaction mixture was cooled to room temperature, water was added and the mixture was extracted with ethyl acetate. The obtained organic layer was washed with saturated brine, and dried over anhydrous sodium sulfate. The solvent was evaporated under reduced pressure. The resulting crude title compound was purified by column chromatography (petroleum ether/ethyl acetate=60/1) to give the title compound (2.5 g, 83%) as colorless crystals.

$^1$H NMR (400 MHz, CHLOROFORM-d) δ ppm 1.39 (3H, t, J=7.0 Hz), 4.36 (2H, q, J=7.1 Hz), 7.33 (1H, d, J=4.0 Hz), 7.52 (1H, t, J=7.8 Hz), 7.59 (1H, d, J=4.8 Hz), 7.74-7.86 (2H, m), 7.85 (1H, s)

Example 39b

{5-[3-(trifluoromethyl)phenyl]thiophen-2-yl}methanol

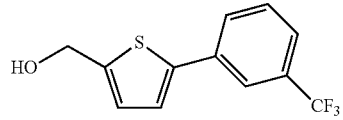 [SMILES: OCc1ccc(-c2cccc(C(F)(F)F)c2)s1]

To a mixed solution of the compound (2.5 g, 8.0 mmol) obtained in Example 39a in tetrahydrofuran/ethanol (v/v=1/2, 36 mL) were added sodium tetrahydroborate (1.8 g, 48 mmol) and calcium chloride (5.4 g, 48 mmol), and the mixture was stirred at room temperature for 12 hr. Water was added to the reaction mixture, and the mixture was extracted with ethyl acetate. The obtained organic layer was washed with saturated brine, dried over anhydrous sodium sulfate, and the solvent was evaporated under reduced pressure to give a crude title compound (1.4 g, 68%) as colorless crystals.

$^1$H-NMR (400 MHz, CHLOROFORM-d): δ 1.76 (1H, br. s.), 4.83 (2H, s), 6.99 (1H, d, J=3.6 Hz), 7.23 (1H, d, J=3.6 Hz), 7.46-7.54 (2H, m), 7.72 (1H, d, J=7.6 Hz), 7.80 (1H, s) LCMS (ESI$^+$) M+H$^+$: 258.

Example 39c ethyl 1-({5-[3-(trifluoromethyl)phenyl]thiophen-2-yl}methyl)-1H-pyrazole-4-carboxylate

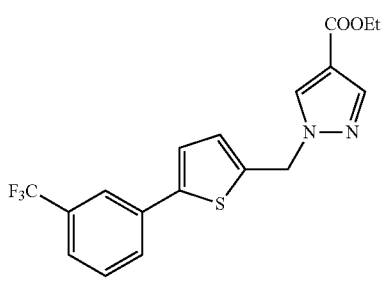 [SMILES: CCOC(=O)c1cnn(Cc2ccc(-c3cccc(C(F)(F)F)c3)s2)c1]

To a solution (3 mL) of the compound (170 mg, 0.65 mmol) obtained in Example 39b in tetrahydrofuran was added thionylchloride (0.095 mL, 1.3 mmol), and the mixture was stirred at room temperature for 48 hr. Saturated aqueous sodium hydrogen carbonate solution was added to the reaction mixture, and the mixture was extracted with ethyl acetate. The obtained organic layer was washed with saturated brine, and dried over anhydrous sodium sulfate. The solvent was evaporated under reduced pressure.

To a solution (3 mL) of the obtained residue in N,N-dimethylformamide were added ethyl 1H-pyrazole-4-carboxylate (110 mg, 0.78 mmol) and potassium carbonate (140 mg, 0.98 mmol), and the mixture was stirred at 70° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (260 mg, 100%) as pale-brown crystals.

$^1$H NMR (300 MHz, DMSO-d$_6$) δ ppm 1.26 (3H, t, J=7.1 Hz), 4.21 (2H, q, J=7.0 Hz), 5.61 (2H, s), 7.19 (1H, d, J=3.8 Hz), 7.58 (1H, d, J=3.8 Hz), 7.61-7.69 (2H, m), 7.90 (3H, m), 8.48 (1H, s)

Example 39

1-({5-[3-(trifluoromethyl)phenyl]thiophen-2-yl}methyl)-1H-pyrazole-4-carboxylic acid

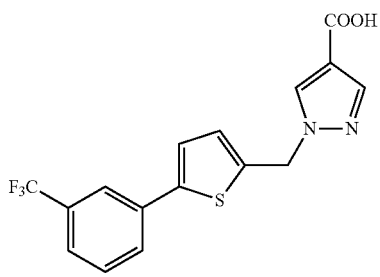

To a mixed solution of the compound (260 mg, 0.65 mmol) obtained in Example 39c in ethanol/tetrahydrofuran (v/v=1/1, 6 mL) was added 2N aqueous sodium hydroxide solution (1.3 mL, 2.6 mmol), and the mixture was stirred at room temperature overnight. Water was added to the reaction mixture and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (160 mg, 69%) as colorless crystals.

$^1$H NMR (300 MHz, DMSO-d$_6$) δ ppm 5.60 (2H, s), 7.19 (1H, d, J=3.8 Hz), 7.48-7.74 (3H, m), 7.81-8.08 (3H, m), 8.39 (1 H, s), 12.40 (1H, br. s.)

Example 40

1-({4-[4-chloro-3-(trifluoromethyl)phenyl]-1,3-thiazol-2-yl}methyl)-1H-pyrazole-4-carboxylic acid Example 40a ethyl 1-({4-[4-chloro-3-(trifluoromethyl)phenyl]-1,3-thiazol-2-yl}methyl)-1H-pyrazole-4-carboxylate

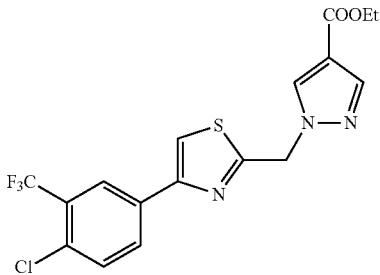 [SMILES: CCOC(=O)c1cnn(Cc2nc(-c3ccc(Cl)c(C(F)(F)F)c3)cs2)c1]

Under a nitrogen atmosphere, to a mixed solution of the compound (300 mg, 0.95 mmol) obtained in Example 30c and 4-chloro-3-(trifluoromethyl)phenylboronic acid (260 mg, 1.1 mmol) in 1,2-dimethoxyethane/ethanol (v/v=3/1, 4 mL) were added 2N aqueous sodium carbonate solution (0.57 mL, 1.1 mmol) and tetrakistriphenylphosphinepalladium (55 mg, 0.048 mmol), and the mixture was stirred at 100° C. for 12 hr. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (274 mg, 69%) as pale-yellow crystals.

¹H NMR (300 MHz, CHLOROFORM-d) δppm 1.34 (3H, t, J=7.2 Hz), 4.30 (2H, q, J=7.2 Hz), 5.67 (2H, s), 7.51-7.61 (1H, m), 7.56 (1H, s), 7.97 (1H, dd, J=8.4, 2.0 Hz), 8.00 (1H, s), 8.10 (1H, s), 8.22 (1H, d, J=2.1 Hz)

LCMS (ESI⁺) M+H⁺: 416.

Example 40

1-({4-[4-chloro-3-(trifluoromethyl)phenyl]-1,3-thiazol-2-yl}methyl)-1H-pyrazole-4-carboxylic acid

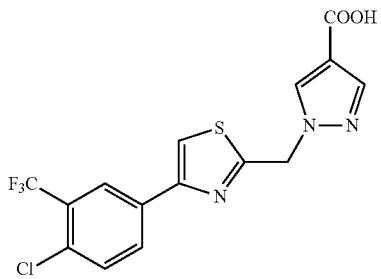

To a mixed solution of the compound (270 mg, 0.66 mmol) obtained in Example 40a in ethanol/tetrahydrofuran (v/v=1/1, 8 ml) was added 2N aqueous sodium hydroxide solution (2.0 mL, 4.0 mmol), and the mixture was stirred at room temperature overnight. Water was added to the reaction mixture, and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was recrystallized (ethanol-hexane) to give the title compound (67 mg, 18%) as pale-yellow crystals.

¹H NMR (300 MHz, DMSO-d₆) δ ppm 5.84 (2H, s), 7.82 (1H, d, J=8.3 Hz), 7.92 (1H, s), 8.25 (1H, dd, J=8.3, 1.5 Hz), 8.37 (1H, s), 8.42 (1H, s), 8.50 (1H, s), 12.49 (1H, br. s.)

LCMS (ESI⁺) M+H⁺: 388.

Example 41

1-({4-[4-fluoro-3-(trifluoromethyl)phenyl]-1,3-thiazol-2-yl}methyl)-1H-pyrazole-4-carboxylic acid Example 41a ethyl 1-({4-[4-fluoro-3-(trifluoromethyl)phenyl]-1,3-thiazol-2-yl}methyl)-1H-pyrazole-4-carboxylate

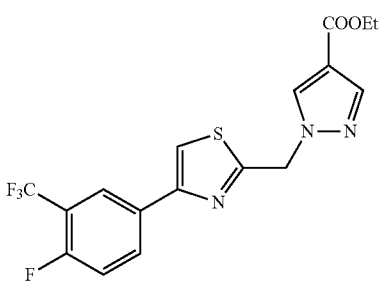 [SMILES: CCOC(=O)c1cnn(Cc2nc(-c3ccc(F)c(C(F)(F)F)c3)cs2)c1]

In the same manner as in Example 40a, the title compound (380 mg, 100%) as a brown oil from the compound (300 mg, 0.95 mmol) obtained in Example 30c, 4-fluoro-3-(trifluoromethyl)phenylboronic acid (240 mg, 1.1 mmol), 2N aqueous sodium carbonate solution (0.57 mL, 1.1 mmol) and tetrakistriphenylphosphinepalladium (55 mg, 0.048 mmol).

¹H NMR (300 MHz, CHLOROFORM-d) δppm 1.34 (3H, t, J=7.2 Hz), 4.30 (2H, q, J=7.0 Hz), 5.67 (2H, s), 7.39-8.33 (6H, m)

LCMS (ESI⁺) M+H⁺: 400.

Example 41

1-({4-[4-fluoro-3-(trifluoromethyl)phenyl]-1,3-thiazol-2-yl}methyl)-1H-pyrazole-4-carboxylic acid

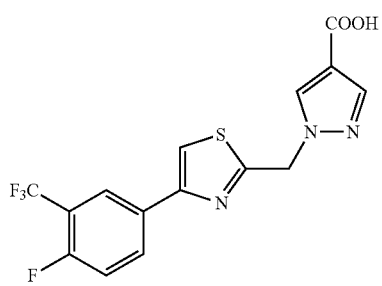 [SMILES: O=C(O)c1cnn(Cc2nc(-c3ccc(F)c(C(F)(F)F)c3)cs2)c1]

In the same manner as in Example 40, the title compound (193 mg, 55%) was obtained as pale-yellow crystals (380 mg, 0.95 mmol) from the compound of Example 41a.

¹H NMR (300 MHz, DMSO-d₆) δ ppm 5.84 (2H, s), 7.62 (1H, t, J=9.8 Hz), 7.92 (1H, s), 8.25-8.38 (3H, m), 8.50 (1H, s), 12.49 (1H, br. s.)

LCMS (ESI⁺) M+H⁺: 372.

Example 42

1-({4-[2-fluoro-5-(trifluoromethyl)phenyl]-1,3-thiazol-2-yl}methyl)-1H-pyrazole-4-carboxylic acid Example 42a ethyl 1-({4-[2-fluoro-5-(trifluoromethyl)phenyl]-1,3-thiazol-2-yl}methyl)-1H-pyrazole-4-carboxylate

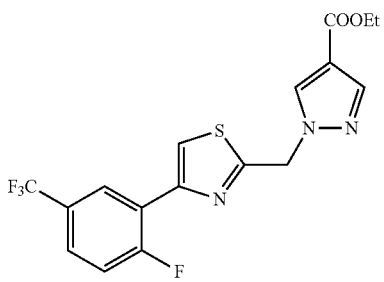 [SMILES: CCOC(=O)c1cnn(Cc2nc(-c3cc(C(F)(F)F)ccc3F)cs2)c1]

In the same manner as in Example 40a, the title compound (100 mg, 27%) as a pale-yellow solid was obtained from the compound (300 mg, 0.95 mmol) obtained in Example 30c, 2-fluoro-5-(trifluoromethyl)phenylboronic acid (240 mg, 1.1 mmol), 2N aqueous sodium carbonate solution (0.57 mL, 1.1 mmol), and tetrakistriphenylphosphinepalladium (55 mg, 0.048 mmol).

¹H NMR (300 MHz, CHLOROFORM-d) δ ppm 1.34 (3H, t, J=7.2 Hz), 4.30 (2H, q, J=7.0 Hz), 5.69 (2H, s), 7.20-7.32 (1H, m), 7.49-7.64 (1H, m), 7.84 (1H, d, J=2.1 Hz), 8.01 (1H, s), 8.10 (1H, s), 8.54 (1H, dd, J=7.0, 2.3 Hz)
LCMS (ESI⁺) M+H⁺: 400.

Example 42

1-({4-[2-fluoro-5-(trifluoromethyl)phenyl]-1,3-thiazol-2-yl}methyl)-1H-pyrazole-4-carboxylic acid

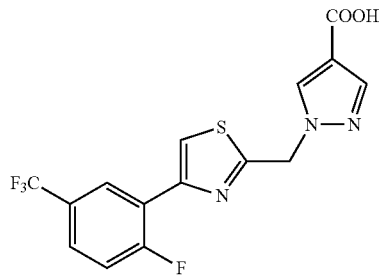 [SMILES: O=C(O)c1cnn(Cc2nc(-c3cc(C(F)(F)F)ccc3F)cs2)c1]

In the same manner as in Example 40, the title compound (38 mg, 39%) was obtained as colorless crystals from the compound (100 mg, 0.26 mmol) of Example 42a.
¹H NMR (300 MHz, DMSO-d₆) δ ppm 5.87 (2H, s), 7.62 (1H, t, J=8.9 Hz), 7.77-7.89 (1H, m), 7.93 (1H, s), 8.15 (1H, d, J=2.6 Hz), 8.41 (1H, dd, J=6.8, 2.3 Hz), 8.52 (1H, s), 12.48 (1H, br. s.)
LCMS (ESI⁺) M+H⁺: 372.

Example 43

1-({4-[3-fluoro-5-(trifluoromethyl)phenyl]-1,3-thiazol-2-yl}methyl)-1H-pyrazole-4-carboxylic acid

Example 43a ethyl 1-({4-[3-fluoro-5-(trifluoromethyl)phenyl]-1,3-thiazol-2-yl}methyl)-1H-pyrazole-4-carboxylate

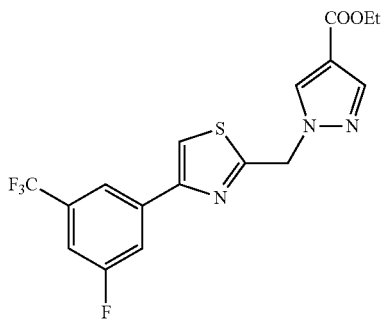

In the same manner as in Example 40a, the title compound (220 mg, 57%) was obtained as a pale-yellow solid from the compound (300 mg, 0.95 mmol) obtained in Example 30c, 3-fluoro-5-(trifluoromethyl)phenylboronic acid (240 mg, 1.1 mmol), 2N aqueous sodium carbonate solution (0.57 mL, 1.1 mmol) and tetrakistriphenylphosphinepalladium (55 mg, 0.048 mmol).

¹H NMR (300 MHz, CHLOROFORM-d) δ ppm 1.34 (3H, t, J=7.2 Hz), 4.30 (2H, q, J=7.2 Hz), 5.68 (2H, s), 7.31 (1H, d, J=8.3 Hz), 7.60 (1H, s), 7.75-7.84 (1H, m), 7.94 (1H, s), 8.01 (1H, s), 8.10 (1H, s)
LCMS (ESI⁺) M+H⁺: 400.

Example 43

1-({4-[3-fluoro-5-(trifluoromethyl)phenyl]-1,3-thiazol-2-yl}methyl)-1H-pyrazole-4-carboxylic acid

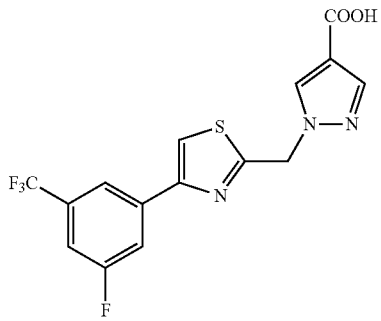 [SMILES: O=C(O)c1cnn(Cc2nc(-c3cc(F)cc(C(F)(F)F)c3)cs2)c1]

In the same manner as in Example 40, the title compound (150 mg, 75%) was obtained as colorless crystals from the compound (220 mg, 0.55 mmol) of Example 43a.
¹H NMR (300 MHz, DMSO-d₆) δ ppm 5.85 (2H, s), 7.69 (1H, d, J=8.7 Hz), 7.93 (1H, s), 8.11 (1H, d, J=9.8 Hz), 8.16 (1H, s), 8.48 (1H, s), 8.51 (1H, s), 12.49 (1H, br. s.)
LCMS (ESI⁺) M+H⁺: 372.

Example 44

1-{[4-(3,4-difluorophenyl)-1,3-thiazol-2-yl]methyl}-1H-pyrazole-4-carboxylic acid

Example 44a ethyl 1-{[4-(3,4-difluorophenyl)-1,3-thiazol-2-yl]methyl}-1H-pyrazole-4-carboxylate

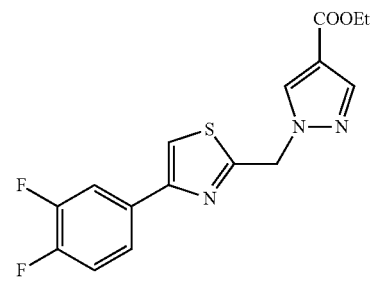 [SMILES: CCOC(=O)c1cnn(Cc2nc(-c3ccc(F)c(F)c3)cs2)c1]

In the same manner as in Example 40a, the title compound (260 mg, 79%) was obtained as a pale-yellow solid from the compound (300 mg, 0.95 mmol) obtained in Example 30c, 3,4-difluorophenylboronic acid (180 mg, 1.1 mmol), 2N aqueous sodium carbonate solution (0.57 mL, 1.1 mmol) and tetrakistriphenylphosphinepalladium (55 mg, 0.048 mmol).
¹H NMR (300 MHz, CHLOROFORM-d) δ ppm 1.34 (3H, t, J=7.0 Hz), 4.30 (2H, q, J=7.2 Hz), 5.66 (2H, s), 7.13-7.23

(1H, m), 7.43 (1H, s), 7.52-7.63 (1H, m), 7.72 (1H, ddd, J=11.4, 7.6, 2.3 Hz), 8.00 (1H, s), 8.09 (1H, s)
LCMS (ESI⁺) M+H⁺: 350.

Example 44

1-{[4-(3,4-difluorophenyl)-1,3-thiazol-2-yl]methyl}-1H-pyrazole-4-carboxylic acid

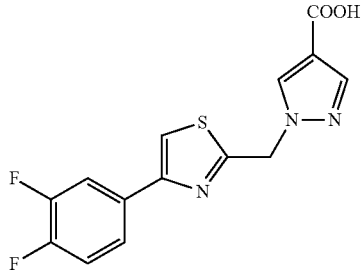 [SMILES: O=C(O)c1cnn(Cc2nc(-c3ccc(F)c(F)c3)cs2)c1]

In the same manner as in Example 40, the title compound (150 mg, 63%) was obtained as colorless crystals from the compound (260 mg, 0.75 mmol) of Example 44a.
¹H NMR (300 MHz, DMSO-d₆) δ ppm 5.81 (2H, s), 7.52 (1H, dt, J=10.6, 8.5 Hz), 7.74-7.87 (1H, m), 7.91 (1H, s), 7.97 (1H, ddd, J=12.1, 8.0, 2.3 Hz), 8.21 (1H, s), 8.50 (1H, s), 12.49 (1H, br. s.)
LCMS (ESI⁺) M+H⁺: 322.

Example 45

1-[(4-{3-[(hydroxyacetyl)amino]phenyl}-1,3-thiazol-2-yl)methyl]-1H-pyrazole-4-carboxylic acid

Example 45a ethyl 1-{[4-(3-{[(acetyloxy)acetyl]amino}phenyl)-1,3-thiazol-2-yl]methyl}-1H-pyrazole-4-carboxylate

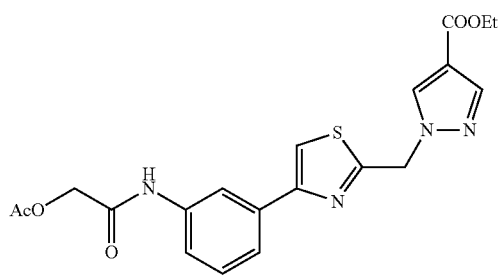 [SMILES: CCOC(=O)c1cnn(Cc2nc(-c3cccc(NC(=O)COC(C)=O)c3)cs2)c1]

To a solution (4 mL) of the crude compound (310 mg, 0.88 mmol) obtained in Example 26a in tetrahydrofuran were added triethylamine (0.16 mL, 1.1 mmol) and acetoxyacetylchloride (145 mg, 1.1 mmol), and the mixture was stirred at room temperature overnight. After confirmation of the termination of the reaction by TLC, the resulting salt was removed. The solvent was evaporated under reduced pressure. The resulting crude title compound was purified by column chromatography (hexane-hexane/ethyl acetate=7/3) to give the title compound (270 mg, 72% in 2 steps) as a colorless oil.
¹H NMR (300 MHz, CHLOROFORM-d) δppm 1.34 (3H, t, J=7.1 Hz), 2.27 (3H, s), 4.30 (2H, q, J=7.2 Hz), 4.72 (2H, s), 5.67 (2H, s), 7.42 (1H, t, J=7.9 Hz), 7.52 (1H, s), 7.64-7.69 (2H, m), 7.89 (1H, br. s.), 8.00 (1H, s), 8.02 (1H, t, J=1.8 Hz), 8.09 (1H, s)
LCMS (ESI⁺) M+H⁺: 429.

Example 45

1-[(4-{3-[(hydroxyacetyl)amino]phenyl}-1,3-thiazol-2-yl)methyl]-1H-pyrazole-4-carboxylic acid

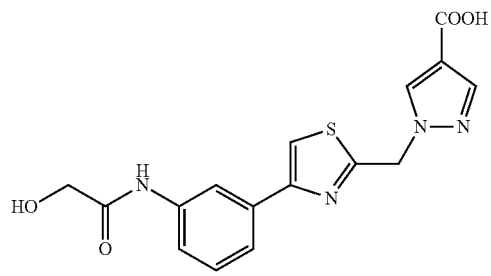 [SMILES: O=C(CO)Nc1cccc(-c2csc(Cn3cc(C(=O)O)cn3)n2)c1]

To a solution (4 mL) of the compound (270 mg, 0.63 mmol) obtained in Example 45a in ethanol was added 2N aqueous sodium hydroxide solution (1.7 mL, 3.4 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The resulting crude title compound was recrystallized (tetrahydrofuran-ethyl acetate-hexane) to give the title compound (110 mg, 33%) as colorless crystals.
¹H NMR (300 MHz, DMSO-d₆) δ ppm 4.01 (2H, br. s.), 5.63 (1H, br. s.), 5.81 (2H, s), 7.37 (1H, t, J=7.8 Hz), 7.61 (1H, d, J=6.8 Hz), 7.69 (1H, d, J=8.0 Hz), 7.91 (1H, s), 8.01 (1H, s), 8.27 (1H, s), 8.49 (1H, s), 9.75 (1H, s), 12.46 (1H, br. s.)

Example 46

1-({4-[3-(methylamino)phenyl]-1,3-thiazol-2-yl}methyl)-1H-pyrazole-4-carboxylic acid

Example 46a ethyl 1-[(4-{3-[(methoxyacetyl)(methyl)amino]phenyl}-1,3-thiazol-2-yl)methyl]-1H-pyrazole-4-carboxylate

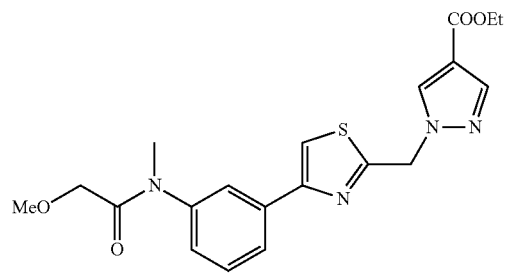

Under a nitrogen atmosphere at 0° C., to a solution (2 mL) of sodium hydride (60% in mineral oil, 93 mg, 2.3 mmol) in N,N-dimethylformamide was added dropwise a solution (2 mL) of the compound (720 mg, 1.8 mmol) obtained in Example 26b in tetrahydrofuran, and the mixture was stirred at room temperature for 30 min. Then, iodomethane (0.22 mL, 3.6 mmol) was added to the reaction mixture and the mixture was stirred at room temperature for 3 hr. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-ethyl acetate) to give the title compound (500 mg, 67%) as a colorless oil.

$^1$H NMR (300 MHz, CHLOROFORM-d) δppm 1.34 (3H, t, J=7.1 Hz), 3.27-3.42 (6H, m), 3.85 (2H, br. s.), 4.30 (2H, q, J=7.2 Hz), 5.68 (2H, s), 7.18 (1H, dd, J=7.9, 1.1 Hz), 7.49 (1H, t, J=7.9 Hz), 7.53 (1H, s), 7.77 (1H, t, J=1.8 Hz), 7.85 (1H, d, J=7.9 Hz), 8.00 (1H, s), 8.09 (1H, s)

LCMS (ESI$^+$) M+H$^+$: 415.

Example 46

1-({4-[3-(methylamino)phenyl]-1,3-thiazol-2-yl}methyl)-1H-pyrazole-4-carboxylic acid

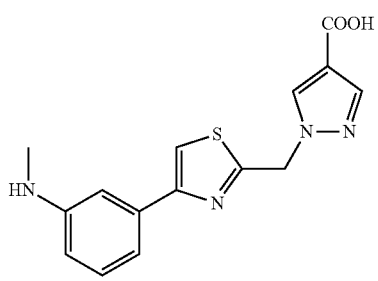 [SMILES: CNc1cccc(-c2csc(Cn3cc(C(=O)O)cn3)n2)c1]

To a solution (6 mL) of the compound (500 mg, 1.2 mmol) obtained in Example 46a in ethanol was added 2N aqueous sodium hydroxide solution (2.4 mL, 4.8 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The resulting crude title compound was purified by HPLC and recrystallization (ethyl acetate-hexane) to give the title compound (193 mg, 39%) as colorless crystals.

$^1$H NMR (300 MHz, DMSO-d$_6$) δ ppm 2.76 (3H, s), 5.80 (2H, s), 6.65 (1H, br. s.), 7.13-7.40 (3H, m), 7.91 (1H, s), 7.99 (1H, s), 8.49 (1H, s)

LCMS (ESI$^+$) M+H$^+$: 315.

Example 47

1-({4-[3-(cyclopropylmethoxy)phenyl]-1,3-thiazol-2-yl}methyl)-1H-pyrazole-4-carboxylic acid Example 47a ethyl 1-({4-[3-(cyclopropylmethoxy)phenyl]-1,3-thiazol-2-yl}methyl)-1H-pyrazole-4-carboxylate

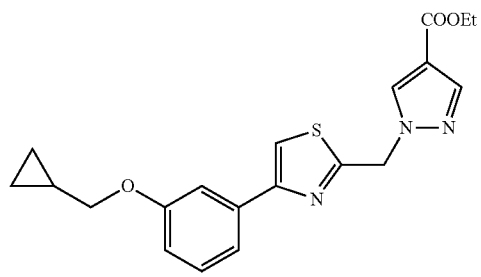 [SMILES: CCOC(=O)c1cnn(Cc2nc(-c3cccc(OCC4CC4)c3)cs2)c1]

under a nitrogen atmosphere at 0° C., to a solution (9 mL) of the compound (300 mg, 0.91 mmol) obtained in Example 38c, cyclopropylmethanol (85 mg, 1.2 mmol) and triphenylphosphine (290 mg, 1.1 mmol) in toluene was slowly added dropwise diisopropyl azodicarboxylate (220 mg, 1.1 mmol), and the mixture was stirred at room temperature overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (340 mg, 98%) as a colorless oil.

$^1$H NMR (300 MHz, CHLOROFORM-d) δppm 0.28-0.45 (2H, m), 0.57-0.75 (2H, m), 1.29-1.38 (4H, m), 3.88 (2H, d, J=7.0 Hz), 4.29 (2H, q, J=7.2 Hz), 5.66 (2H, s), 6.91 (1H, dd, J=7.7, 1.5 Hz), 7.32 (1H, t, J=8.2 Hz), 7.39-7.50 (3H, m), 7.99 (1H, s), 8.08 (1H, s)

LCMS (ESI$^+$) M+H$^+$: 384.

Example 47

1-({4-[3-(cyclopropylmethoxy)phenyl]-1,3-thiazol-2-yl}methyl)-1H-pyrazole-4-carboxylic acid

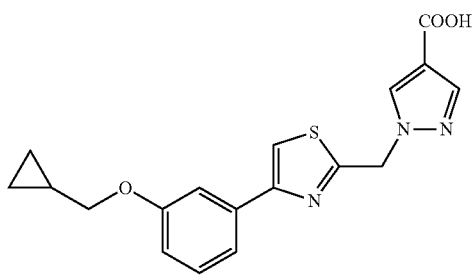 [SMILES: O=C(O)c1cnn(Cc2nc(-c3cccc(OCC4CC4)c3)cs2)c1]

To a solution (4 mL) of the compound (340 mg, 0.89 mmol) obtained in Example 47a in ethanol was added 2N aqueous sodium hydroxide solution (1.8 mL, 3.6 mmol), and the mixture was stirred at room temperature overnight. Water was added to the reaction mixture, and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (180 mg, 57%) as colorless crystals.

$^1$H NMR (300 MHz, DMSO-d$_6$) δ ppm 0.20-0.47 (2H, m), 0.47-0.72 (2H, m), 1.14-1.31 (1H, m), 3.87 (2H, d, J=7.0 Hz), 5.81 (2H, s), 6.91 (1H, dt, J=8.2, 1.3 Hz), 7.33 (1H, t, J=7.9 Hz), 7.44-7.50 (2H, m), 7.91 (1H, s), 8.13 (1H, s), 8.49 (1H, s), 12.46 (1H, br. s.)

LCMS (ESI$^+$) M+H$^+$: 356.

Example 48

1-({4-[3-(2-methoxyethoxy)phenyl]-1,3-thiazol-2-yl}methyl)-1H-pyrazole-4-carboxylic acid

Example 48a ethyl 1-({4-[3-(2-methoxyethoxy)phenyl]-1,3-thiazol-2-yl}methyl)-1H-pyrazole-4-carboxylate

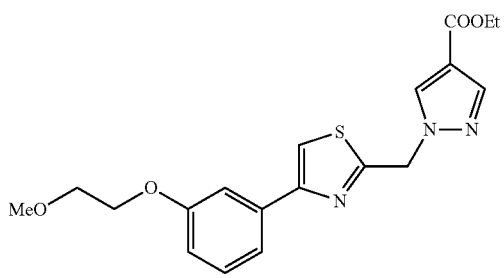 [SMILES: CCOC(=O)c1cnn(Cc2nc(-c3cccc(OCCOC)c3)cs2)c1]

In the same manner as in Example 38d, the title compound (190 mg, 53%) as a colorless oil from the compound (300 mg, 0.91 mmol) obtained in Example 38c, sodium hydride (60% in mineral oil, 40 mg, 1.0 mmol) and 2-bromoethylmethylether (250 mg, 1.8 mmol).

$^1$H NMR (300 MHz, CHLOROFORM-d) δppm 1.34 (3H, t, J=7.2 Hz), 3.47 (3H, s), 3.72-3.83 (2H, m), 4.15-4.23 (2H, m), 4.29 (2H, q, J=7.2 Hz), 5.66 (2H, s), 6.93 (1H, ddd, J=8.2, 2.5, 0.9 Hz), 7.33 (1H, t, J=7.9 Hz), 7.41-7.52 (3H, m), 7.99 (1H, s), 8.08 (1H, s)

LCMS (ESI$^+$) M+H$^+$: 388.

Example 48

1-({4-[3-(2-methoxyethoxy)phenyl]-1,3-thiazol-2-yl}methyl)-1H-pyrazole-4-carboxylic acid

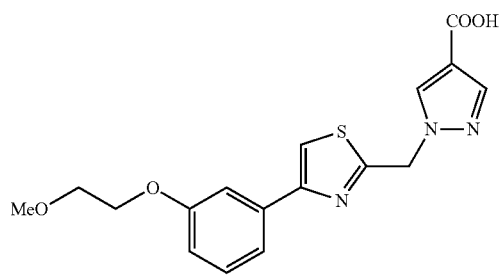 [SMILES: COCCOc1cccc(-c2csc(Cn3cc(C(=O)O)cn3)n2)c1]

In the same manner as in Example 38, the title compound (86 mg, 49%) was obtained as colorless crystals from the compound (190 mg, 0.49 mmol) obtained in Example 48a.

$^1$H NMR (300 MHz, DMSO-d$_6$) δ ppm 3.32 (3H, s), 3.59-3.76 (2H, m), 4.05-4.21 (2H, m), 5.81 (2H, s), 6.93 (1H, dd, J=7.9, 2.7 Hz), 7.35 (1H, t, J=8.0 Hz), 7.46-7.63 (2H, m), 7.91 (1H, s), 8.14 (1H, s), 8.49 (1H, s), 12.47 (1H, br. s.)

LCMS (ESI$^+$) M+H$^+$: 360.

Example 49

1-({4-[3-(trifluoromethyl)benzyl]-1,3-thiazol-2-yl}methyl)-1H-pyrazole-4-carboxylic acid

Example 49a 4,4,5,5-tetramethyl-2-[3-(trifluoromethyl)benzyl]-1,3,2-dioxaborolaneborolane

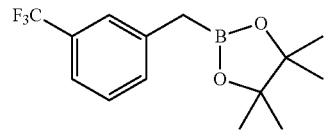 [SMILES: CC1(C)OB(Cc2cccc(C(F)(F)F)c2)OC1(C)C]

under a nitrogen atmosphere, a solution (10 ml) of 3-trifluoromethylbenzylbromide (500 mg, 2.1 mmol), bispinacholatediborane (640 mg, 2.5 mmol) and potassium acetate (620 mg, 6.3 mmol) in 1,2-dimethoxyethane was added[1,1'-bis(diphenylphosphino)ferrocene]dichloropalladium(II) dichloromethane complex (170 mg, 0.21 mmol), and the mixture was stirred at 100° C. overnight. Water was added to the reaction mixture, and the mixture was extracted with ethyl acetate. The obtained organic layer was washed with saturated brine, and dried over anhydrous sodium sulfate. The solvent was evaporated under reduced pressure to give a crude title compound.

Example 49b ethyl 1-({4-[3-(trifluoromethyl)benzyl]-1,3-thiazol-2-yl}methyl)-1H-pyrazole-4-carboxylate

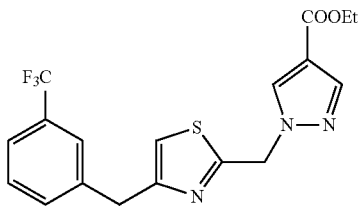 [SMILES: CCOC(=O)c1cnn(Cc2nc(Cc3cccc(C(F)(F)F)c3)cs2)c1]

Under a nitrogen atmosphere, to a mixed solution of the compound (300 mg, 0.95 mmol) obtained in Example 30c and the compound (2.1 mmol) obtained in Example 49a in 1,2-dimethoxyethane/ethanol (v/v=3/1, 4 mL) were added 2N aqueous sodium carbonate solution (0.57 ml, 1.1 mmol) and [1,1'-bis(diphenylphosphino)ferrocene]dichloropalladium(II) dichloromethane complex (78 mg, 0.095 mmol), and the mixture was stirred at 100° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-ethyl acetate) to give the title compound (63 mg, 17%) as a pale-yellow oil.

$^1$H NMR (300 MHz, CHLOROFORM-d) δppm 1.34 (3H, t, J=8.0 Hz), 4.16 (2H, s), 4.29 (2H, q, J=7.0 Hz), 5.58 (2H, s), 6.84 (1H, s), 7.32-7.57 (4H, m), 7.98 (1H, s), 8.05 (1H, s)

LCMS (ESI$^+$) M+H$^+$: 396.

Example 49

1-({4-[3-(trifluoromethyl)benzyl]-1,3-thiazol-2-yl}methyl)-1H-pyrazole-4-carboxylic acid

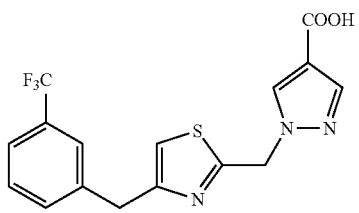 [SMILES: O=C(O)c1cnn(Cc2nc(Cc3cccc(C(F)(F)F)c3)cs2)c1]

In the same manner as in Example 40, the title compound (9 mg, 15%) was obtained as colorless crystals from the compound (63 mg, 0.16 mmol) of Example 49b.

$^1$H NMR (300 MHz, DMSO-$d_6$) δ ppm 4.16 (2H, s), 5.69 (2H, s), 7.35 (1H, s), 7.48-7.73 (4H, m), 7.87 (1H, s), 8.41 (1H, s), 12.44 (1H, br. s.)

LCMS (ESI$^+$) M+H$^+$: 368.

Example 50

1-{[4-(3-phenoxyphenyl)-1,3-thiazol-2-yl]methyl}-1H-pyrazole-4-carboxylic acid

Example 50a 4,4,5,5-tetramethyl-2-(3-phenoxyphenyl)-1,3,2-dioxaborolane

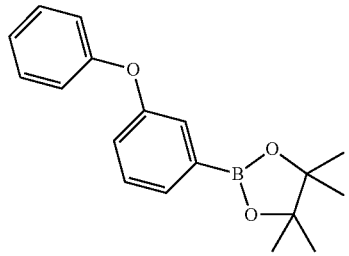 [SMILES: CC1(C)OB(c2cccc(Oc3ccccc3)c2)OC1(C)C]

In the same manner as in Example 49a, the title compound was obtained from 3-phenoxy-1-bromobenzene (300 mg, 1.2 mmol) and bispinacholatediborane (370 mg, 1.5 mmol), potassium acetate (350 mg, 3.6 mmol), [1,1'-bis(diphenylphosphino)ferrocene]dichloropalladium(II) dichloromethane complex (100 mg, 0.12 mmol).

Example 50b ethyl 1-{[4-(3-phenoxyphenyl)-1,3-thiazol-2-yl]methyl}-1H-pyrazole-4-carboxylate

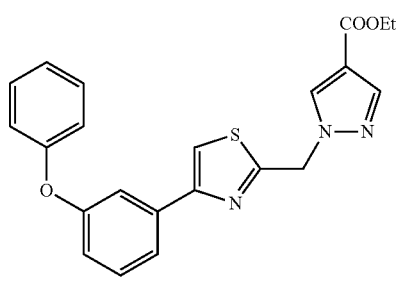 [SMILES: CCOC(=O)c1cnn(Cc2nc(-c3cccc(Oc4ccccc4)c3)cs2)c1]

In the same manner as in Example 49b, the title compound (292 mg, 76%) was obtained as a pale-yellow oil from the compound (300 mg, 0.95 mmol) obtained from Example 30c, the compound (1.2 mmol) obtained from Example 50a, 2N aqueous sodium carbonate solution (0.57 mL, 1.1 mmol), [1,1'-bis(diphenylphosphino)ferrocene]dichloropalladium (II) dichloromethane complex (78 mg, 0.095 mmol).

$^1$H NMR (300 MHz, CHLOROFORM-d) δppm 1.34 (3H, t, J=7.2 Hz), 4.29 (2H, q, J=7.2 Hz), 5.65 (2H, s), 6.96-7.18 (4H, m), 7.30-7.71 (6H, m), 7.99 (1H, s), 8.07 (1H, s)

LCMS (ESI$^+$) M+H$^+$: 406.

Example 50

1-{[4-(3-phenoxyphenyl)-1,3-thiazol-2-yl]methyl}-1H-pyrazole-4-carboxylic acid

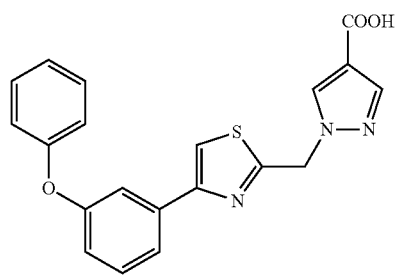 [SMILES: O=C(O)c1cnn(Cc2nc(-c3cccc(Oc4ccccc4)c3)cs2)c1]

In the same manner as in Example 40, the title compound (240 mg, 87%) was obtained as colorless crystals from the compound (290 mg, 0.72 mmol) of Example 50b.

$^1$H NMR (300 MHz, DMSO-$d_6$) δ ppm 5.79 (2H, s), 6.99 (1H, dd, J=8.1, 2.5 Hz), 7.05 (2H, d, J=8.7 Hz), 7.16 (1H, t, J=7.4 Hz), 7.35-7.51 (3H, m), 7.59 (1H, s), 7.72 (1H, d, J=7.6 Hz), 7.90 (1H, s), 8.16 (1H, s), 8.47 (1H, s), 12.47 (1H, br. s.)

LCMS (ESI$^+$) M+H$^+$: 378.

Example 51

1-({4-[3-(benzyloxy)phenyl]-1,3-thiazol-2-yl}methyl)-1H-pyrazole-4-carboxylic acid

Example 51a ethyl 1-({4-[3-(benzyloxy)phenyl]-1,3-thiazol-2-yl}methyl)-1H-pyrazole-4-carboxylate

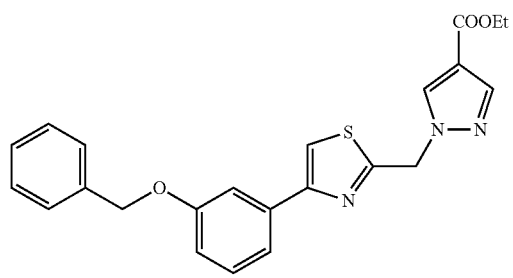 [SMILES: CCOC(=O)c1cnn(Cc2nc(-c3cccc(OCc4ccccc4)c3)cs2)c1]

In the same manner as in Example 38d, the title compound (320 mg, 62%) was obtained as a colorless oil from the compound (400 mg, 1.2 mmol) obtained in Example 38c, sodium hydride (60% in mineral oil, 73 mg, 1.8 mmol), benzyl bromide (0.22 mL, 1.8 mmol).

$^1$H NMR (300 MHz, CHLOROFORM-d) δppm 1.34 (3H, t, J=7.1 Hz), 4.29 (2H, q, J=7.2 Hz), 5.14 (2H, s), 5.67 (2H, s), 6.97 (1H, ddd, J=7.0, 1.7, 1.3 Hz), 7.29-7.62 (9H, m), 8.00 (1H, s), 8.09 (1H, s)

LCMS (ESI$^+$) M+H$^+$: 420.

Example 51

1-({4-[3-(benzyloxy)phenyl]-1,3-thiazol-2-yl}methyl)-1H-pyrazole-4-carboxylic acid

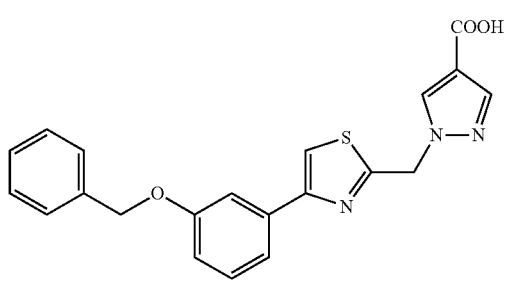 [SMILES: O=C(O)c1cnn(Cc2nc(-c3cccc(OCc4ccccc4)c3)cs2)c1]

In the same manner as in Example 38, the title compound (240 mg, 80%) was obtained as colorless crystals from the compound (320 mg, 0.75 mmol) obtained in Example 51a.

$^1$H NMR (300 MHz, DMSO-d$_6$) δ ppm 5.16 (2H, s), 5.81 (2H, s), 7.00 (1H, dd, J=8.0, 2.2 Hz), 7.30-7.63 (8H, m), 7.92 (1H, s), 8.14 (1H, s), 8.50 (1H, s), 12.45 (1H, s)

LCMS (ESI$^+$) M+H$^+$: 392.

Example 52

1-({4-[2-fluoro-3-(trifluoromethyl)phenyl]-1,3-thiazol-2-yl}methyl)-1H-pyrazole-4-carboxylic acid Example 52a ethyl 1-({4-[2-fluoro-3-(trifluoromethyl)phenyl]-1,3-thiazol-2-yl}methyl)-1H-pyrazole-4-carboxylate

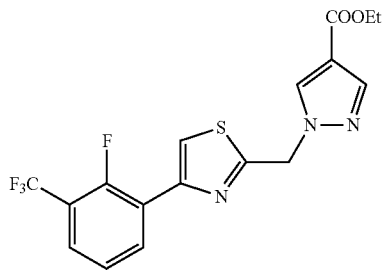 [SMILES: CCOC(=O)c1cnn(Cc2nc(-c3cccc(C(F)(F)F)c3F)cs2)c1]

Under a nitrogen atmosphere, to a mixed solution of the compound (300 mg, 0.95 mmol) obtained in Example 30c and 2-fluoro-3-(trifluoromethyl)phenylboronic acid (260 mg, 1.1 mmol) in 1,2-dimethoxyethane/ethanol (v/v=3/1, 4 mL) were added 2N aqueous sodium carbonate solution (0.57 mL, 1.1 mmol) and [1,1'-bis(diphenylphosphino)ferrocene] dichloropalladium(II) dichloromethane complex (78 mg, 0.095 mmol), and the mixture was stirred at 90° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (320 mg, 84%) as colorless crystals.

$^1$H NMR (300 MHz, CHLOROFORM-d) δppm 1.34 (3H, t, J=7.2 Hz), 4.30 (2H, q, J=6.9 Hz), 5.68 (2H, s), 7.34 (1H, t, J=7.6 Hz), 7.59 (1H, t, J=6.8 Hz), 7.83 (1H, d, J=2.3 Hz), 8.00 (1H, s), 8.10 (1H, s), 8.42 (1H, t, J=7.6 Hz)

LCMS (ESI$^+$) M+H$^+$: 400.

Example 52

1-({4-[2-fluoro-3-(trifluoromethyl)phenyl]-1,3-thiazol-2-yl}methyl)-1H-pyrazole-4-carboxylic acid

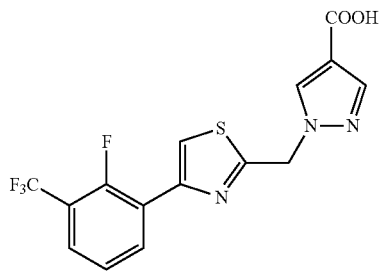

To a mixed solution of the compound (320 mg, 0.79 nmol) obtained in Example 52a in ethanol/tetrahydrofuran (v/v=1/1, 8 mL) was added 2N aqueous sodium hydroxide solution (1.6 mL, 3.2 mmol), and the mixture was stirred at room temperature overnight. Water was added to the reaction mixture, and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (250 mg, 84%) as colorless crystals.

$^1$H NMR (300 MHz, DMSO-d$_6$) δ ppm 5.85 (2H, s), 7.54 (1H, t, J=8.0 Hz), 7.81 (1H, t, J=6.8 Hz), 7.92 (1H, s), 8.15 (1H, d, J=3.0 Hz), 8.37 (1H, t, J=7.2 Hz), 8.51 (1H, s), 12.49 (1H, br. s.)

LCMS (ESI$^+$) M+H$^+$: 372.

Example 53

1-({4-[3-(1,1-difluoroethyl)phenyl]-1,3-thiazol-2-yl}methyl)-1H-pyrazole-4-carboxylic acid Example 53a ethyl 1-{[4-(3-acetylphenyl)-1,3-thiazol-2-yl]methyl}-1H-pyrazole-4-carboxylate

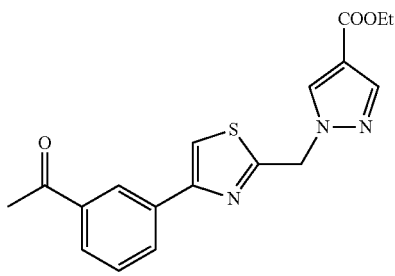 [SMILES: CCOC(=O)c1cnn(Cc2nc(-c3cccc(C(C)=O)c3)cs2)c1]

In the same manner as in Example 52a, the title compound (260 mg, 76%) was obtained as a pale-yellow oil from the compound (300 mg, 0.95 mmol) obtained in Example 30c, 3-acetylphenylboronic acid (200 mg, 1.1 mmol), 2N aqueous sodium carbonate solution (0.57 mL, 1.1 mmol), [1,1'-bis(diphenylphosphino)ferrocene]dichloropalladium(II) dichloromethane complex (78 mg, 0.095 mmol).

$^1$H NMR (300 MHz, CHLOROFORM-d) δppm 1.34 (3H, t, J=7.2 Hz), 2.67 (3H, s), 4.30 (2H, q, J=7.2 Hz), 5.69 (2H, s), 7.58 (1H, s), 7.54 (1H, t, J=7.8 Hz), 7.94 (1H, d, J=6.8 Hz), 8.01 (1H, s), 8.04-8.20 (2H, m), 8.37-8.55 (1H, m)

LCMS (ESI$^+$) M+H$^+$: 356.

Example 53b ethyl 1-({4-[3-(1,1-difluoroethyl)phenyl]-1,3-thiazol-2-yl}methyl)-1H-pyrazole-4-carboxylate

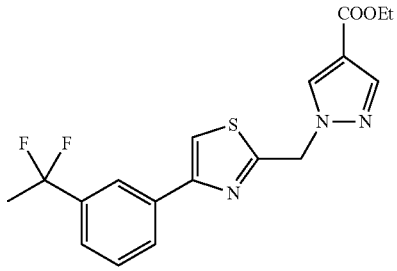 [SMILES: CCOC(=O)c1cnn(Cc2nc(-c3cccc(C(C)(F)F)c3)cs2)c1]

To a solution (4 mL) of the compound (260 mg, 0.72 mmol) obtained in Example 53a in toluene was added diethylaminosulfur trifluoride (460 mg, 2.9 mmol), and the mixture was stirred at room temperature overnight. To the reaction mixture was added saturated aqueous sodium hydrogen carbonate solution, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (130 mg, 46%) as a brown oil.

$^1$H NMR (300 MHz, CHLOROFORM-d) δppm 1.34 (3H, t, J=7.2 Hz), 1.97 (3H, t, J=18.2 Hz), 4.30 (2H, q, J=7.0 Hz), 5.68 (2H, s), 7.45-7.52 (2H, m), 7.53 (1H, s), 7.86-7.97 (1H, m), 7.97-8.07 (2H, m), 8.10 (1H, s)

LCMS (ESI$^+$) M+H$^+$: 378.

Example 53

1-({4-[3-(1,1-difluoroethyl)phenyl]-1,3-thiazol-2-yl}methyl)-1H-pyrazole-4-carboxylic acid

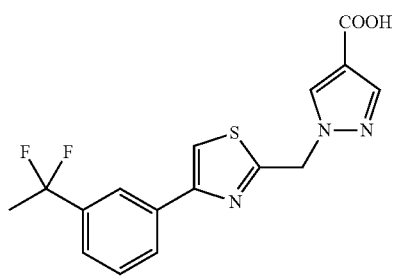 [SMILES: CC(F)(F)c1cccc(-c2csc(Cn3cc(C(=O)O)cn3)n2)c1]

In the same manner as in Example 38, the title compound (46 mg, 40%) was obtained as colorless crystals from the compound (130 mg, 0.33 mmol) obtained in Example 53b.

$^1$H NMR (300 MHz, DMSO-d$_6$) δ ppm 2.01 (3H, t, J=18.9 Hz), 5.84 (2H, s), 7.48-7.65 (2H, m), 7.92 (1H, s), 8.06 (1H, d, J=6.8 Hz), 8.12 (1H, s), 8.26 (1H, s), 8.51 (1H, s), 12.47 (1H, br. s.)

LCMS (ESI$^+$) M+H$^+$: 350.

Example 54

1-({4-[3-(methylsulfonyl)phenyl]-1,3-thiazol-2-yl}methyl)-1H-pyrazole-4-carboxylic acid Example 54a ethyl 1-({4-[3-(methylsulfonyl)phenyl]-1,3-thiazol-2-yl}methyl)-1H-pyrazole-4-carboxylate

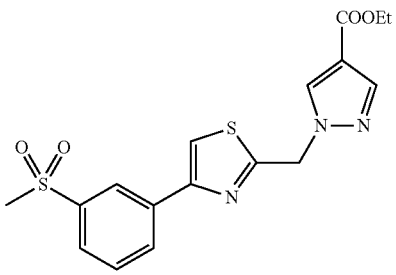 [SMILES: CCOC(=O)c1cnn(Cc2nc(-c3cccc(S(C)(=O)=O)c3)cs2)c1]

In the same manner as in Example 52a, the title compound (350 mg, 94%) was obtained as a pale-yellow oil from the compound (300 mg, 0.95 mmol) obtained in Example 30c, 3-(methylsulfonyl)phenylboronic acid (260 mg, 1.2 mmol), 2N aqueous sodium carbonate solution (0.57 mL, 1.1 mmol), [1,1'-bis(diphenylphosphino)ferrocene]dichloropalladium(II) dichloromethane complex (78 mg, 0.095 mmol).

$^1$H NMR (300 MHz, CHLOROFORM-d) δppm 1.34 (3H, t, J=7.2 Hz), 3.12 (3H, s), 4.30 (2H, q, J=6.9 Hz), 5.68 (2H, s), 7.65 (1H, t, J=7.8 Hz), 7.63 (1H, s), 7.92 (1H, d, J=8.0 Hz), 8.00 (1H, s), 8.10 (1H, s), 8.18 (1H, d, J=8.0 Hz), 8.36-8.54 (1H, m)

LCMS (ESI$^+$) M+H$^+$: 392.

Example 54

1-({4-[3-(methylsulfonyl)phenyl]-1,3-thiazol-2-yl}methyl)-1H-pyrazole-4-carboxylic acid

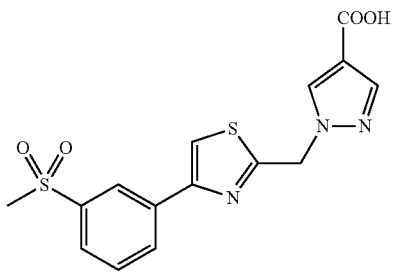 [SMILES: CS(=O)(=O)c1cccc(-c2csc(Cn3cc(C(=O)O)cn3)n2)c1]

In the same manner as in Example 38, the title compound (220 mg, 68%) was obtained as colorless crystals from the compound (350 mg, 0.89 mmol) obtained in Example 54a.

$^1$H NMR (300 MHz, DMSO-d$_6$) δ ppm 3.27 (3H, s), 5.86 (2H, s), 7.74 (1H, t, J=7.8 Hz), 7.87-7.91 (1H, m), 7.93 (1H, s), 8.28 (1H, dd, J=7.8, 1.4 Hz), 8.36 (1H, s), 8.48 (1H, t, J=1.6 Hz), 8.52 (1H, s), 12.48 (1H, br. s.)
LCMS (ESI+) M+H+: 364.

Example 55

1-({4-[2-(trifluoromethoxy)phenyl]-1,3-thiazol-2-yl}methyl)-1H-pyrazole-4-carboxylic acid Example 55a ethyl 1-({4-[2-(trifluoromethoxy)phenyl]-1,3-thiazol-2-yl}methyl)-1H-pyrazole-4-carboxylate

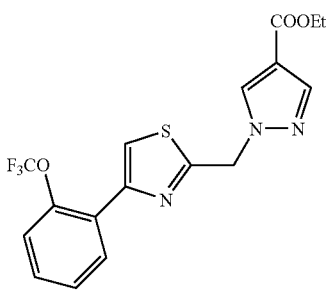 [SMILES: CCOC(=O)c1cnn(Cc2nc(-c3ccccc3OC(F)(F)F)cs2)c1]

In the same manner as in Example 52a, the title compound (320 mg, 86%) was obtained as an orange oil from the compound (300 mg, 0.95 mmol) obtained in Example 30c, 2-trifluoromethoxyphenylboronic acid (240 mg, 1.1 mmol), 2N aqueous sodium carbonate solution (0.57 mL, 1.1 mmol), [1,1'-bis(diphenylphosphino)ferrocene]dichloropalladium (II) dichloromethane complex (78 mg, 0.095 mmol).

¹H NMR (300 MHz, CHLOROFORM-d) δppm 1.34 (3H, t, J=7.2 Hz), 4.30 (2H, q, J=7.2 Hz), 5.68 (2H, s), 7.31-7.40 (3H, m), 7.74 (1H, s), 8.00 (1H, s), 8.09 (1H, s), 8.17 (1H, dd, J=5.4, 4.1 Hz)
LCMS (ESI+) M+H+: 398.

Example 55

1-({4-[2-(trifluoromethoxy)phenyl]-1,3-thiazol-2-yl}methyl)-1H-pyrazole-4-carboxylic acid

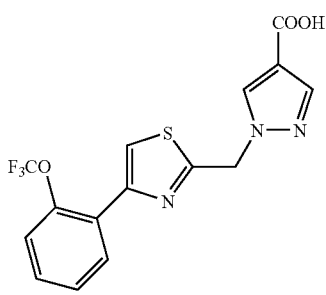 [SMILES: O=C(O)c1cnn(Cc2nc(-c3ccccc3OC(F)(F)F)cs2)c1]

In the same manner as in Example 38, the title compound (230 mg, 68%) was obtained as colorless crystals from the compound (320 mg, 0.82 mmol) obtained in Example 55a.

¹H NMR (300 MHz, DMSO-d₆) δ ppm 5.83 (2H, s), 7.37-7.59 (3H, m), 7.92 (1H, s), 7.95 (1H, s), 8.00-8.14 (1H, m), 8.49 (1H, s), 12.48 (1H, br. s.)
LCMS (ESI+) M+H+: 370.

Example 56

1-({4-[2-(benzyloxy)phenyl]-1,3-thiazol-2-yl}methyl)-1H-pyrazole-4-carboxylic acid Example 56a ethyl 1-({4-[2-(benzyloxy)phenyl]-1,3-thiazol-2-yl}methyl)-1H-pyrazole-4-carboxylate

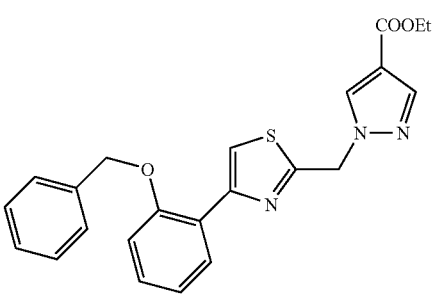 [SMILES: CCOC(=O)c1cnn(Cc2nc(-c3ccccc3OCc3ccccc3)cs2)c1]

In the same manner as in Example 52a, the title compound (300 mg, 76%) was obtained as a pale-yellow oil from the compound (300 mg, 0.95 mmol) obtained in Example 30c, 2-benzyloxyphenylboronic acid (260 mg, 1.1 mmol), 2N aqueous sodium carbonate solution (0.57 mL, 1.1 mmol), [1,1'-bis(diphenylphosphino)ferrocene]dichloropalladium (II) dichloromethane complex (78 mg, 0.095 mmol).

¹H NMR (300 MHz, CHLOROFORM-d) δppm 1.32 (3H, q, J=7.5 Hz), 4.29 (2H, q, J=7.0 Hz), 5.19 (2H, s), 5.66 (2H, s), 7.09 (2 H, td, J=7.5, 1.1 Hz), 7.27-7.51 (6H, m), 7.89 (1H, s), 7.98 (1H, s), 8.08 (1H, s), 8.26 (1H, dd, J=7.6, 1.8 Hz)
LCMS (ESI+) M+H+: 420.

Example 56

1-({4-[2-(benzyloxy)phenyl]-1,3-thiazol-2-yl}methyl)-1H-pyrazole-4-carboxylic acid

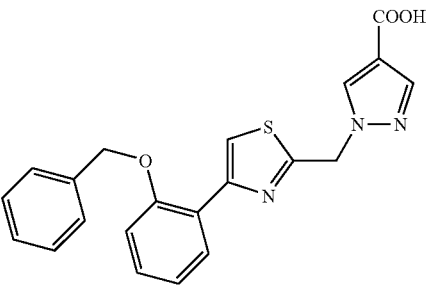 [SMILES: O=C(O)c1cnn(Cc2nc(-c3ccccc3OCc3ccccc3)cs2)c1]

In the same manner as in Example 38, the title compound (190 mg, 68%) was obtained as colorless crystals from the compound (300 mg, 0.72 mmol) obtained in Example 56a.

¹H NMR (300 MHz, DMSO-d₆) δ ppm 5.29 (2H, s), 5.81 (2H, s), 7.05 (1H, t, J=7.4 Hz), 7.18-7.26 (1H, m), 7.26-7.57 (6 H, m), 7.91 (1H, s), 8.00 (1H, s), 8.12 (1H, dd, J=7.8, 1.7 Hz), 8.49 (1H, s), 12.47 (1H, br. s.)
LCMS (ESI+) M+H+: 392.

Example 57

1-({4-[2-chloro-3-(trifluoromethyl)phenyl]-1,3-thiazol-2-yl}methyl)-1H-pyrazole-4-carboxylic acid

Example 57a ethyl 1-({4-[2-chloro-3-(trifluoromethyl)phenyl]-1,3-thiazol-2-yl}methyl)-1H-pyrazole-4-carboxylate

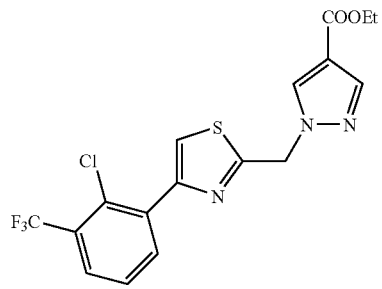 [SMILES: CCOC(=O)c1cnn(Cc2nc(-c3cccc(C(F)(F)F)c3Cl)cs2)c1]

In the same manner as in Example 52a, the title compound (260 mg, 78%) was obtained as orange crystals from the compound (250 mg, 0.79 mmol) obtained in Example 30c, 2-chloro-3-trifluoromethylphenylboronic acid (210 mg, 1.0 mmol), 2N aqueous sodium carbonate solution (0.48 mL, 0.96 mmol), [1,1'-bis(diphenylphosphino)ferrocene]dichloropalladium(II) dichloromethane complex (65 mg, 0.079 mmol).

$^1$H NMR (300 MHz, CHLOROFORM-d) δppm 1.34 (3H, t, J=7.1 Hz), 4.30 (2H, q, J=7.2 Hz), 5.68 (2H, s), 7.41-7.51 (1H, m), 7.74 (1H, dd, J=7.8, 1.6 Hz), 7.79 (1H, s), 7.93-8.06 (2H, m), 8.10 (1H, s)

LCMS (ESI$^+$) M+H$^+$: 416.

Example 57

1-({4-[2-chloro-3-(trifluoromethyl)phenyl]-1,3-thiazol-2-yl}methyl)-1H-pyrazole-4-carboxylic acid

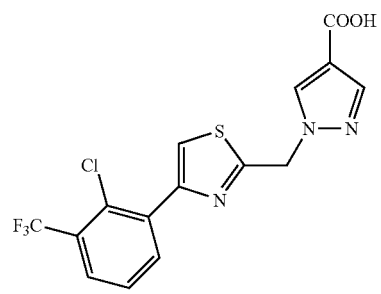 [SMILES: O=C(O)c1cnn(Cc2nc(-c3cccc(C(F)(F)F)c3Cl)cs2)c1]

In the same manner as in Example 38, the title compound (190 mg, 77%) was obtained as pale-yellow crystals from the compound (260 mg, 0.62 mmol) obtained in Example 57a.

$^1$H NMR (300 MHz, DMSO-d$_6$) δ ppm 5.83 (2H, s), 7.66 (1H, t, J=8.0 Hz), 7.88-7.97 (2H, m), 8.03 (1H, d, J=7.6 Hz), 8.14 (1H, s), 8.49 (1H, s), 12.48 (1H, br. s.)

LCMS (ESI$^+$) M+H$^+$: 388.

Example 58

1-({4-[2-chloro-5-(trifluoromethyl)phenyl]-1,3-thiazol-2-yl}methyl)-1H-pyrazole-4-carboxylic acid

Example 58a ethyl 1-({4-[2-chloro-5-(trifluoromethyl)phenyl]-1,3-thiazol-2-yl}methyl)-1H-pyrazole-4-carboxylate

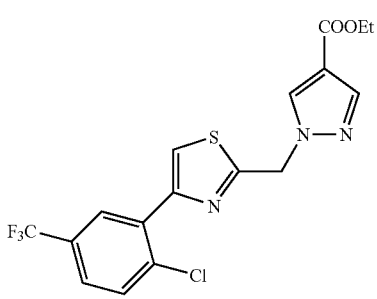 [SMILES: CCOC(=O)c1cnn(Cc2nc(-c3cc(C(F)(F)F)ccc3Cl)cs2)c1]

In the same manner as in Example 52a, the title compound (290 mg, 74%) was obtained as pale-yellow crystals from the compound (300 mg, 0.95 mmol) obtained in Example 30c, 2-chloro-5-trifluoromethylphenylboronic acid (260 mg, 1.1 mmol), 2N aqueous sodium carbonate solution (0.57 mL, 1.1 mmol), [1,1'-bis(diphenylphosphino)ferrocene]dichloropalladium(II) dichloromethane complex (78 mg, 0.095 mmol).

$^1$H NMR (300 MHz, CHLOROFORM-d) δppm 1.34 (3H, t, J=7.2 Hz), 4.30 (2H, q, J=7.0 Hz), 5.69 (2H, s), 7.47-7.66 (2H, m), 7.95 (1H, s), 8.01 (1H, s), 8.10 (1H, s), 8.27 (1H, d, J=2.3 Hz)

LCMS (ESI$^+$) M+H$^+$: 416.

Example 58

1-({4-[2-chloro-5-(trifluoromethyl)phenyl]-1,3-thiazol-2-yl}methyl)-1H-pyrazole-4-carboxylic acid

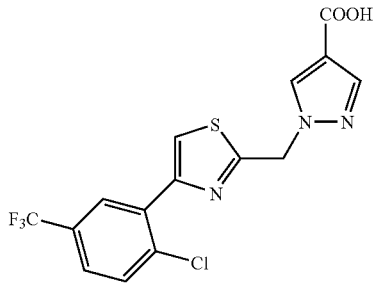 [SMILES: O=C(O)c1cnn(Cc2nc(-c3cc(C(F)(F)F)ccc3Cl)cs2)c1]

In the same manner as in Example 38, the title compound (220 mg, 80%) was obtained as colorless crystals from the compound (290 mg, 0.70 mmol) obtained in Example 58a.

$^1$H NMR (300 MHz, DMSO-d$_6$) δ ppm 5.85 (2H, s), 7.72-7.89 (2H, m), 7.93 (1H, s), 8.21 (1H, d, J=1.5 Hz), 8.29 (1H, s), 8.51 (1H, s), 12.47 (1H, br. s)

LCMS (ESI$^+$) M+H$^+$: 388.

Example 59

1-[(4-naphthalen-2-yl-1,3-thiazol-2-yl)methyl]-1H-pyrazole-4-carboxylic acid

Example 59a ethyl 1-[(4-naphthalen-2-yl-1,3-thiazol-2-yl)methyl]-1H-pyrazole-4-carboxylate

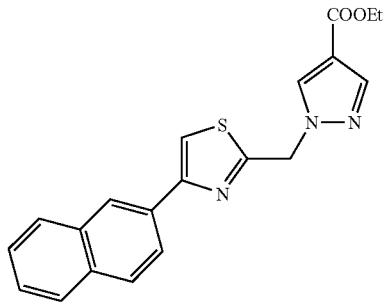 [SMILES: CCOC(=O)c1cnn(Cc2nc(-c3ccc4ccccc4c3)cs2)c1]

In the same manner as in Example 52a, the title compound (83 mg, 71%) was obtained as a pale-yellow oil from the compound (100 mg, 0.32 mmol) obtained in Example 30c, 2-naphthalenylboronic acid (62 mg, 0.38 mmol), 2N aqueous sodium carbonate solution (0.19 mL, 0.38 mmol), [1,1'-bis(diphenylphosphino)ferrocene]dichloropalladium(II) dichloromethane complex (26 mg, 0.032 mmol).

$^1$H NMR (300 MHz, CHLOROFORM-d) δppm 1.34 (3H, t, J=7.1 Hz), 4.30 (2H, q, J=7.2 Hz), 5.72 (2H, s), 7.50 (1H, t, J=5.6 Hz), 7.50 (1H, d, J=7.7 Hz), 7.60 (1H, s), 7.81-7.97 (4H, m), 8.01 (1H, s), 8.12 (1H, s), 8.42 (1H, s)

LCMS (ESI$^+$) M+H$^+$: 364.

Example 59

1-[(4-naphthalen-2-yl-1,3-thiazol-2-yl)methyl]-1H-pyrazole-4-carboxylic acid

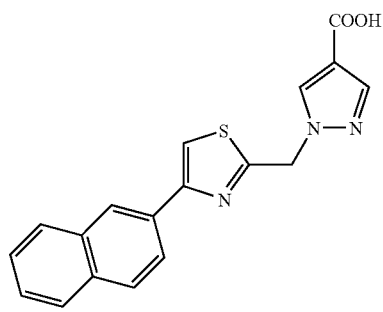 [SMILES: O=C(O)c1cnn(Cc2nc(-c3ccc4ccccc4c3)cs2)c1]

In the same manner as in Example 38, the title compound (44 mg, 57%) was obtained as colorless crystals from the compound (83 mg, 0.23 mmol) obtained in Example 59a.

$^1$H NMR (300 MHz, DMSO-d$_6$) δ ppm 5.86 (2H, s), 7.39-7.66 (2H, m), 7.85-8.04 (4H, m), 8.04-8.14 (1H, m), 8.25 (1H, s), 8.52 (2H, s), 12.49 (1H, br. s.)

LCMS (ESI$^+$) M+H$^+$: 336.

Example 60

1-[(4-(biphenyl-3-yl)-1,3-thiazol-2-yl)methyl]-1H-pyrazole-4-carboxylic acid

Example 60a ethyl 1-[(4-(biphenyl-3-yl)-1,3-thiazol-2-yl)methyl]-1H-pyrazole-4-carboxylate

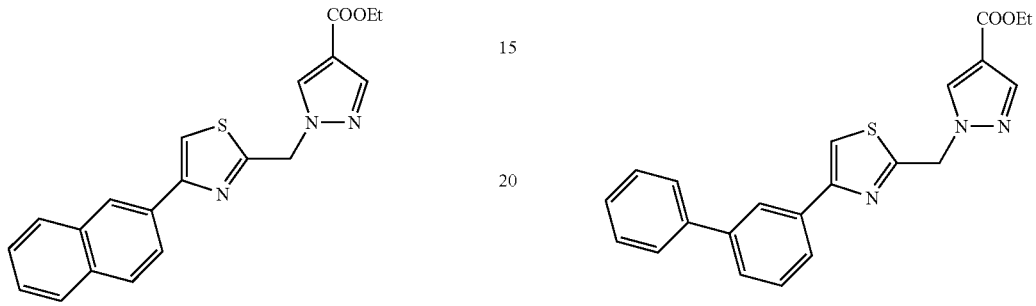

In the same manner as in Example 52a, the title compound (90 mg, 72%) was obtained as a pale-yellow oil from the compound (100 mg, 0.32 mmol) obtained in Example 30c, 3-biphenylboronic acid (76 mg, 0.38 mmol), 2N aqueous sodium carbonate solution (0.19 mL, 0.38 mmol), [1,1'-bis(diphenylphosphino)ferrocene]dichloropalladium(II) dichloromethane complex (26 mg, 0.032 mmol).

$^1$H NMR (300 MHz, CHLOROFORM-d) δppm 1.34 (3H, t, J=7.0 Hz), 4.29 (2H, q, J=7.2 Hz), 5.69 (2H, s), 7.32-7.74 (8H, m), 7.85 (1H, d, J=7.6 Hz), 8.00 (1H, s), 8.06-8.19 (2H, m)

LCMS (ESI$^+$) M+H$^+$: 390.

Example 60

1-[(4-(biphenyl-3-yl)-1,3-thiazol-2-yl)methyl]-1H-pyrazole-4-carboxylic acid

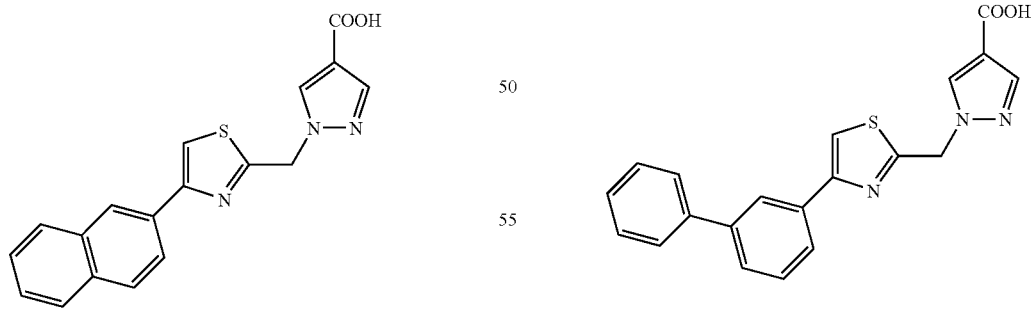

In the same manner as in Example 38, the title compound (60 mg, 72%) was obtained as colorless crystals from the compound (90 mg, 0.23 mmol) obtained in Example 60a.

$^1$H NMR (300 MHz, DMSO-d$_5$) δ ppm 5.84 (2H, s), 7.31-7.59 (4H, m), 7.65 (1H, d, J=7.6 Hz), 7.73 (2H, d, J=7.2 Hz), 7.88-8.02 (2H, m), 8.22 (1H, s), 8.26 (1H, s), 8.51 (1H, s), 12.47 (1H, br. s.)

LCMS (ESI$^+$) M+H$^+$: 362.

Example 61

1-{[4-(1-benzothiophen-3-yl)-1,3-thiazol-2-yl]methyl}-1H-pyrazole-4-carboxylic acid

Example 61a ethyl 1-{[4-(1-benzothiophen-3-yl)-1,3-thiazol-2-yl]methyl}-1H-pyrazole-4-carboxylate

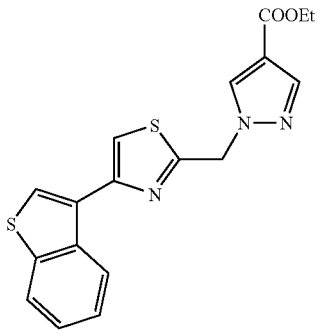 [SMILES: CCOC(=O)c1cnn(Cc2nc(-c3csc4ccccc34)cs2)c1]

In the same manner as in Example 52a, the title compound (86 mg, 73%) was obtained as a pale-yellow oil from the compound (100 mg, 0.32 mmol) obtained in Example 30c, benzothiophene-3-boronic acid (68 mg, 0.38 mmol), 2N aqueous sodium carbonate solution (0.19 mL, 0.38 mmol), [1,1'-bis(diphenylphosphino)ferrocene]dichloropalladium (II) dichloromethane complex (26 mg, 0.032 mmol).

$^1$H NMR (300 MHz, CHLOROFORM-d) δppm 1.34 (3H, t, J=7.2 Hz), 4.30 (2H, q, J=6.9 Hz), 5.72 (2H, s), 7.34-7.51 (2H, m), 7.54 (1H, s), 7.84 (1H, s), 7.91 (1H, d, J=6.8 Hz), 8.02 (1H, s), 8.12 (1H, s), 8.25 (1H, d, J=7.2 Hz)

LCMS (ESI$^+$) M+H$^+$: 370.

Example 61

1-{[4-(1-benzothiophen-3-yl)-1,3-thiazol-2-yl]methyl}-1H-pyrazole-4-carboxylic acid

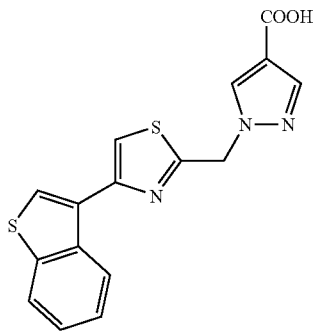 [SMILES: O=C(O)c1cnn(Cc2nc(-c3csc4ccccc34)cs2)c1]

In the same manner as in Example 38, the title compound (58 mg, 74%) was obtained as colorless crystals from the compound (86 mg, 0.23 mmol) obtained in Example 61a.

$^1$H NMR (300 MHz, DMSO-d$_6$) δ ppm 5.88 (2H, s), 7.37-7.54 (2H, m), 7.93 (1H, s), 8.01-8.12 (2H, m), 8.18 (1H, s), 8.35-8.47 (1H, m), 8.53 (1H, s), 12.45 (1H, br. s.)

LCMS (ESI$^+$) M+H$^+$: 342.

Example 62

1-{[4-(5-chlorothiophen-2-yl)-1,3-thiazol-2-yl]methyl}-1H-pyrazole-4-carboxylic acid

Example 62a ethyl 1-{[4-(5-chlorothiophen-2-yl)-1,3-thiazol-2-yl]methyl}-1H-pyrazole-4-carboxylate

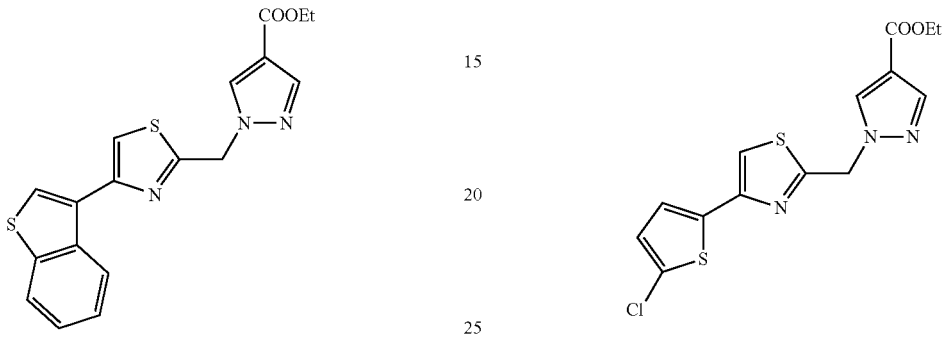

In the same manner as in Example 52a, the title compound (85 mg, 75%) was obtained as a pale-yellow oil from the compound (100 mg, 0.32 mmol) obtained in Example 30c, 5-chlorothiophene-2-boronic acid (62 mg, 0.38 mmol), 2N aqueous sodium carbonate solution (0.19 mL, 0.38 mmol), [1,1'-bis(diphenylphosphino)ferrocene]dichloropalladium (II) dichloromethane complex (26 mg, 0.032 mmol).

$^1$H NMR (300 MHz, CHLOROFORM-d) δppm 1.34 (3H, t, J=7.2 Hz), 4.30 (2H, q, J=7.2 Hz), 5.63 (2H, s), 6.88 (1H, d, J=4.2 Hz), 7.19 (1H, d, J=4.2 Hz), 7.28 (1H, s), 7.99 (1H, s), 8.07 (1H, s)

LCMS (ESI$^+$) M+H$^+$: 354.

Example 62

1-{[4-(5-chlorothiophen-2-yl)-1,3-thiazol-2-yl]methyl}-1H-pyrazole-4-carboxylic acid

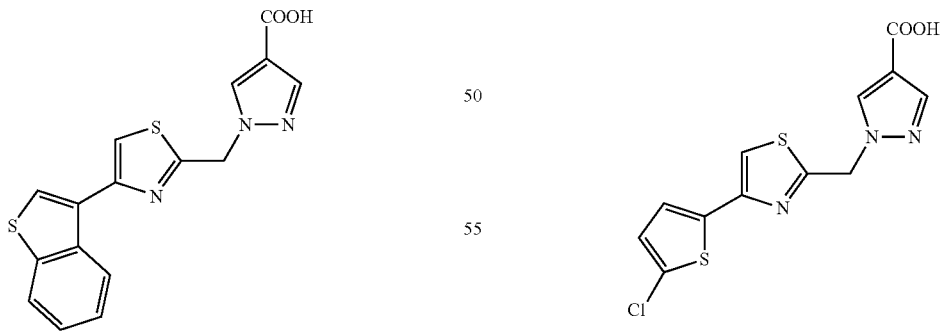

In the same manner as in Example 38, the title compound (62 mg, 79%) was obtained as colorless crystals from the compound (85 mg, 0.24 mmol) obtained in Example 62a.

$^1$H NMR (300 MHz, DMSO-d$_6$) δ ppm 5.78 (2H, s), 7.15 (1H, d, J=4.2 Hz), 7.46 (1H, d, J=4.2 Hz), 7.91 (1H, s), 8.01 (1H, s), 8.48 (1H, s), 12.48 (1H, br. s)

LCMS (ESI$^+$) M+H$^+$: 326.

Example 63

1-({5-ethyl-2-[3-(trifluoromethyl)phenyl]-1,3-thiazol-4-yl}methyl)-1H-pyrazole-4-carboxylic acid

Example 63a 5-ethyl-2-[3-(trifluoromethyl)phenyl]-1,3-thiazole-4-carboxylic acid

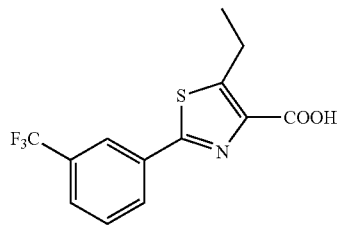 [SMILES: CCc1sc(-c2cccc(C(F)(F)F)c2)nc1C(=O)O]

By a method similar to that in Example 71a, the title compound (490 mg, 33%) was obtained as a pale-red solid from 2-oxopropionic acid (1.0 g, 8.6 mmol), bromine (760 mg, 9.5 mmol), 3-trifluoromethylphenylthioamide (1.0 g, 4.9 mmol).

$^1$H NMR (300 MHz, DMSO-$d_6$) δ ppm 1.31 (3H, t, J=7.5 Hz), 3.26 (2H, q, J=7.5 Hz), 7.77 (1H, t, J=7.7 Hz), 7.84-7.93 (1H, m), 8.15-8.27 (2H, m), 13.13 (1H, br. s.)

Example 63b

{5-ethyl-2-[3-(trifluoromethyl)phenyl]-1,3-thiazol-4-yl}methanol

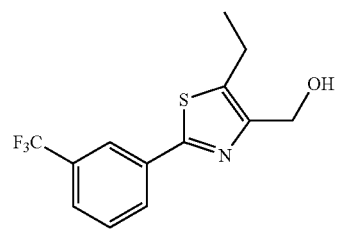 [SMILES: CCc1sc(-c2cccc(C(F)(F)F)c2)nc1CO]

Under a nitrogen atmosphere at 0° C., to a solution (5 mL) of the compound (490 mg, 1.6 mmol) obtained in Example 63a in tetrahydrofuran were added ethyl chlorocarbonate (0.19 mL, 2.0 mmol) and triethylamine (0.27 mmol, 2.0 mmol), and the mixture was stirred at room temperature for 1 hr. After confirmation of the termination of the reaction by TLC, the resulting salt was removed. The solvent was evaporated under reduced pressure.

Under a nitrogen atmosphere at 0° C., to a solution (4 mL) of the residue in tetrahydrofuran was added sodium tetrahydroborate (190 mg, 4.9 mmol), ethanol (4 mL) was slowly added dropwise, and the mixture was stirred at room temperature overnight. 1N Hydrochloric acid was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=65/35) to give the title compound (370 mg, 78%) as a colorless solid.

$^1$H NMR (300 MHz, CHLOROFORM-d) δppm 1.34 (3H, t, J=7.6 Hz), 2.89 (2H, q, J=7.3 Hz), 4.73 (2H, s), 7.54 (1H, t, J=7.8 Hz), 7.65 (1H, d, J=8.0 Hz), 8.05 (1H, d, J=7.6 Hz), 8.16 (1H, s)

Example 63c ethyl 1-({5-ethyl-2-[3-(trifluoromethyl)phenyl]-1,3-thiazol-4-yl}methyl)-1H-pyrazole-4-carboxylate

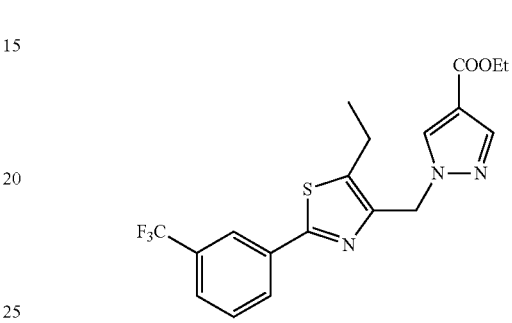

By a method similar to that in Example 71c, the title compound (420 mg, 80%) was obtained as colorless crystals from the compound (370 mg, 1.3 mmol) obtained in Example 63b, oxalyl chloride (0.20 mL, 2.5 mmol), ethyl 1H-pyrazole-4-carboxylate (200 mg, 1.4 mmol) and potassium carbonate (230 mg, 1.7 mmol).

$^1$H NMR (300 MHz, CHLOROFORM-d) δppm 1.27-1.40 (6H, m), 2.95 (2H, q, J=7.4 Hz), 4.27 (2H, q, J=7.2 Hz), 5.41 (2H, s), 7.55 (1H, t, J=7.8 Hz), 7.66 (1H, d, J=7.7 Hz), 7.91 (1H, s), 7.97-8.10 (2H, m), 8.14 (1H, s)

LCMS (ESI$^+$) M+H$^+$: 410.

Example 63

1-({5-ethyl-2-[3-(trifluoromethyl)phenyl]-1,3-thiazol-4-yl}methyl)-1H-pyrazole-4-carboxylic acid

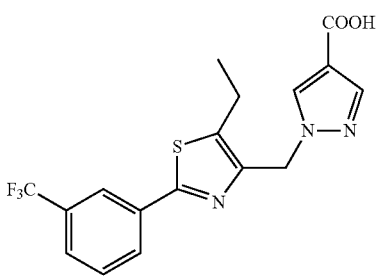 [SMILES: CCc1sc(-c2cccc(C(F)(F)F)c2)nc1Cn1cc(C(=O)O)cn1]

By a method similar to that in Example 71, the title compound (330 mg, 85%) was obtained as colorless crystals from the compound (420 mg, 1.0 mmol) obtained in Example 63c.

$^1$H NMR (300 MHz, DMSO-$d_6$) δ ppm 1.25 (3H, t, J=7.4 Hz), 3.00 (2H, q, J=7.4 Hz), 5.49 (2H, s), 7.67-7.77 (1H, m), 7.79 (1H, s), 7.80-7.88 (1H, m), 8.07-8.17 (2H, m), 8.34 (1H, s), 12.39 (1H, br. s.)

LCMS (ESI$^+$) M+H$^+$: 382.

Example 64

1-({5-bromo-2-[3-(trifluoromethyl)phenyl]-1,3-thiazol-4-yl}methyl)-1H-pyrazole-4-carboxylic acid

Example 64a ethyl 2-[3-(trifluoromethyl)phenyl]-1,3-thiazole-4-carboxylate

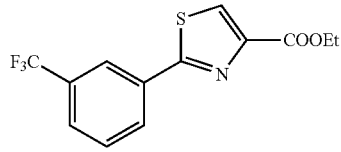 [SMILES: CCOC(=O)c1csc(-c2cccc(C(F)(F)F)c2)n1]

To a solution (33 mL) of ethyl bromopyruvate (8.8 g, 36 mmol) in ethanol was added 3-trifluoromethylphenylthioamide (10 g, 33 mmol), and the mixture was stirred at 80° C. for 3 hr. Saturated aqueous sodium hydrogen carbonate solution was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was recrystallized (hexane-ethyl acetate) to give the title compound (7.4 g, 75%) as colorless crystals.

$^1$H NMR (300 MHz, DMSO-$d_6$) δ ppm 1.35 (3H, t, J=7.2 Hz), 4.36 (2H, q, J=7.2 Hz), 7.79 (1H, t, J=7.8 Hz), 7.92 (1H, d, J=8.0 Hz), 8.21-8.36 (2H, m), 8.67 (1H, s)

LCMS (ESI$^+$) M+H$^+$: 302.

Example 64b

{2-[3-(trifluoromethyl)phenyl]-1,3-thiazol-4-yl}methanol

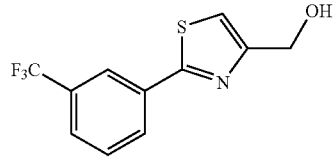 [SMILES: OCc1csc(-c2cccc(C(F)(F)F)c2)n1]

Under a nitrogen atmosphere at 0° C., to a solution (4 mL) of the compound (7.4 g, 25 mmol) obtained in Example 64a in tetrahydrofuran was added lithium tetrahydroborate (2.6 g, 49 mmol), and the mixture was stirred at 80° C. for 5 hr. 1N Hydrochloric acid was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=50/50) to give the title compound (5.4 g, 85%) as a colorless solid.

$^1$H NMR (300 MHz, CHLOROFORM-d) δppm 2.31 (1H, t, J=5.9 Hz), 4.85 (2H, d, J=5.7 Hz), 7.24 (1H, s), 7.57 (1H, t, J=7.8 Hz), 7.68 (1H, d, J=7.9 Hz), 8.11 (1H, d, J=7.7 Hz), 8.23 (1H, s)

LCMS (ESI$^+$) M+H$^+$: 260.

Example 64c

{2-[3-(trifluoromethyl)phenyl]-1,3-thiazol-4-yl}methyl acetate

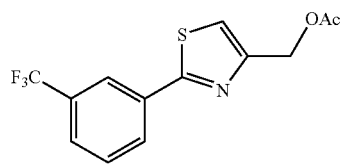 [SMILES: CC(=O)OCc1csc(-c2cccc(C(F)(F)F)c2)n1]

Under a nitrogen atmosphere at 0° C., to a solution (21 mL) of the compound (5.4 g, 21 mmol) obtained in Example 64b in tetrahydrofuran were added acetyl chloride (2.0 g, 25 mmol) and triethylamine (3.8 mL, 27 mmol), and the mixture was stirred at room temperature for 30 min. The resulting salt was removed and the solvent was evaporated under reduced pressure to give a crude title compound as a colorless solid.

$^1$H NMR (300 MHz, CHLOROFORM-d) δppm 2.15 (3H, s), 5.28 (2H, s), 7.35 (1H, s), 7.57 (1H, t, J=7.8 Hz), 7.68 (1H, d, J=7.6 Hz), 8.11 (1H, d, J=8.0 Hz), 8.23 (1H, s)

LCMS (ESI$^+$) M+H$^+$: 302.

Example 64d

{5-bromo-2-[3-(trifluoromethyl)phenyl]-1,3-thiazol-4-yl}methyl acetate

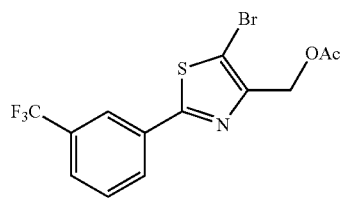 [SMILES: CC(=O)OCc1nc(-c2cccc(C(F)(F)F)c2)sc1Br]

Under a nitrogen atmosphere at 0° C., to a solution (10 mL) of the crude compound (21 mmol) obtained in Example 64c in acetic acid was slowly added dropwise a solution (10 mL) of bromine (2.5 g, 31 mmol) in acetic acid, and the mixture was stirred at 0-10° C. overnight. An aqueous sodium thiosulfate solution was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=80/20) to give the title compound (4.0 g, 51%) as a colorless solid.

$^1$H NMR (300 MHz, CHLOROFORM-d) δppm 2.15 (3H, s), 5.23 (2H, s), 7.58 (1H, t, J=7.8 Hz), 7.70 (1H, d, J=7.9 Hz), 8.02 (1H, d, J=7.7 Hz), 8.15 (1H, s)

LCMS (ESI$^+$) M+H$^+$: 380.

Example 64e

{5-bromo-2-[3-(trifluoromethyl)phenyl]-1,3-thiazol-4-yl}methanol

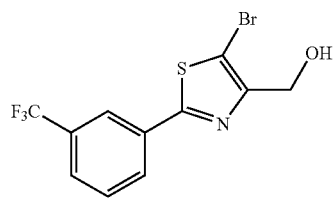 [SMILES: OCc1nc(-c2cccc(C(F)(F)F)c2)sc1Br]

To a mixed solution of the compound (2.0 g, 5.3 mmol) obtained in Example 64d in ethanol/tetrahydrofuran (v/v=1/1, 20 mL) was added 2N aqueous sodium hydroxide solution (5.3 mL, 11 mmol), and the mixture was stirred at room temperature overnight. The reaction mixture was neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (1.6 g, 89%) as colorless crystals.

$^1$H NMR (300 MHz, CHLOROFORM-d) δppm 2.43 (1H, t, J=6.0 Hz), 4.77 (2H, d, J=5.8 Hz), 7.58 (1H, t, J=7.8 Hz), 7.70 (1H, d, J=7.9 Hz), 8.02 (1H, d, J=7.9 Hz), 8.15 (1H, s)

LCMS (ESI$^+$) M+H$^+$: 338.

Example 64f ethyl 1-({5-bromo-2-[3-(trifluoromethyl)phenyl]-1,3-thiazol-4-yl}methyl)-1H-pyrazole-4-carboxylate

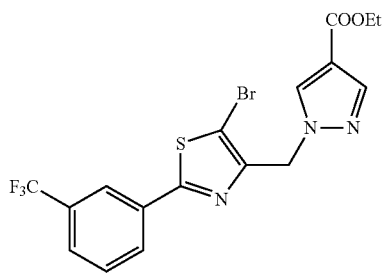 [SMILES: CCOC(=O)c1cnn(Cc2nc(-c3cccc(C(F)(F)F)c3)sc2Br)c1]

By a method similar to that in Example 71c, the title compound (600 mg, 75%) was obtained as colorless crystals from the compound (590 mg, 1.7 mmol) obtained in Example 64e, oxalyl chloride (0.25 mL, 3.5 mmol), ethyl 1H-pyrazole-4-carboxylate (270 mg, 1.9 mmol) and potassium carbonate (310 mg, 2.3 mmol).

$^1$H NMR (300 MHz, CHLOROFORM-d) δppm 1.33 (3H, t, J=7.2 Hz), 4.29 (2H, q, J=6.9 Hz), 5.46 (2H, s), 7.57 (1H, t, J=7.8 Hz), 7.70 (1H, d, J=8.0 Hz), 7.93 (1H, s), 8.00 (1H, d, J=7.6 Hz), 8.07 (1H, s), 8.10 (1H, s)

LCMS (ESI$^+$) M+H$^+$: 460.

Example 64

1-({5-bromo-2-[3-(trifluoromethyl)phenyl]-1,3-thiazol-4-yl}methyl)-1H-pyrazole-4-carboxylic acid

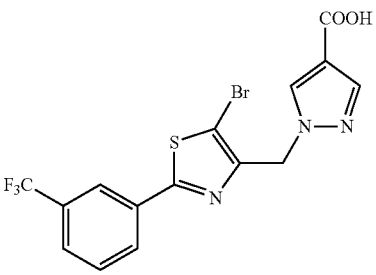 [SMILES: O=C(O)c1cnn(Cc2nc(-c3cccc(C(F)(F)F)c3)sc2Br)c1]

By a method similar to that in Example 71, the title compound (89 mg, 94%) was obtained as colorless crystals from the compound (100 mg, 0.22 mmol) obtained in Example 64f.

$^1$H NMR (300 MHz, DMSO-d$_6$) δ ppm 5.51 (2H, s), 7.68-7.83 (2H, m), 7.83-7.93 (1H, m), 8.06-8.19 (2H, m), 8.38 (1H, s), 12.37 (1H, br. s.)

LCMS (ESI$^+$) M+H$^+$: 432.

Example 65

1-({5-ethenyl-2-[3-(trifluoromethyl)phenyl]-1,3-thiazol-4-yl}methyl)-1H-pyrazole-4-carboxylic acid

Example 65a ethyl 1-({5-ethenyl-2-[3-(trifluoromethyl)phenyl]-1,3-thiazol-4-yl}methyl)-1H-pyrazole-4-carboxylate

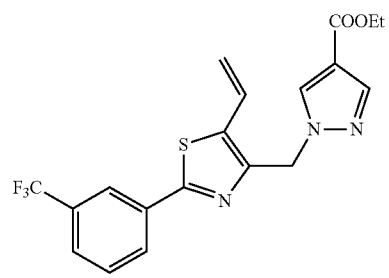 [SMILES: C=Cc1sc(-c2cccc(C(F)(F)F)c2)nc1Cn1cc(C(=O)OCC)cn1]

Under a nitrogen atmosphere, to a mixed solution of the compound (1.3 g, 2.7 mmol) obtained in Example 64f, vinyl tri-n-butyltin (0.95 ml, 3.3 mmol) and lithium chloride (170 mg, 4.1 mmol) in toluene/N,N-dimethylformamide (v/v=4/1, 10 mL) was added tetrakistriphenylphosphinepalladium (310 mg, 0.27 mmol), and the mixture was stirred at 100° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=65/35) to give a crude title compound (560 mg, 50%) as pale-yellow crystals.

LCMS (ESI$^+$) M+H$^+$: 408.

Example 65

1-({5-ethenyl-2-[3-(trifluoromethyl)phenyl]-1,3-thiazol-4-yl}methyl)-1H-pyrazole-4-carboxylic acid

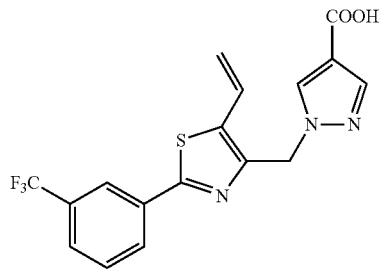

By a method similar to that in Example 71, the title compound (130 mg, 94%) was obtained as colorless crystals from the compound (150 mg, 0.37 mmol) obtained in Example 65a.

$^1$H NMR (300 MHz, DMSO-$d_6$) δ ppm 5.49 (1H, d, J=11.0 Hz), 5.60 (2H, s), 5.70 (1H, d, J=17.0 Hz), 7.22 (1H, dd, J=17.0, 11.0 Hz), 7.68-7.83 (2H, m), 7.83-7.94 (1H, m), 8.09-8.24 (2H, m), 8.36 (1H, s), 12.35 (1H, br. s.)

LCMS (ESI$^+$) M+H$^+$: 380.

Example 66

1-({4-[3-chloro-5-(trifluoromethyl)phenyl]-1,3-thiazol-2-yl}methyl)-1H-pyrazole-4-carboxylic acid

Example 66a ethyl 1-({4-[3-chloro-5-(trifluoromethyl)phenyl]-1,3-thiazol-2-yl}methyl)-1H-pyrazole-4-carboxylate

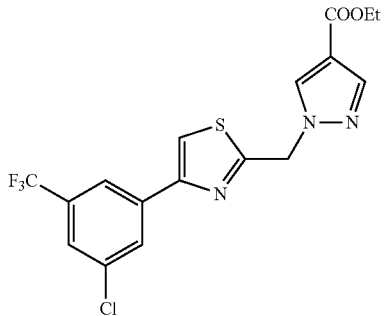 [SMILES: CCOC(=O)c1cnn(Cc2nc(-c3cc(Cl)cc(C(F)(F)F)c3)cs2)c1]

In the same manner as in Example 52a, the title compound (1.1 g, 83%) was obtained as a colorless solid from the compound (1.0 g, 3.2 mmol) obtained in Example 30c, 3-chloro-5-trifluoromethylphenylboronic acid (850 mg, 3.8 mmol), 2N aqueous sodium carbonate solution (1.9 mL, 3.8 mmol), [1,1'-bis(diphenylphosphino)ferrocene]dichloropalladium (II) dichloromethane complex (130 mg, 0.16 mmol).

$^1$H NMR (300 MHz, CHLOROFORM-d) δppm 1.34 (3H, t, J=7.2 Hz), 4.30 (2H, q, J=7.2 Hz), 5.68 (2H, s), 7.55-7.64 (2H, m), 7.98-8.04 (2H, m), 8.06 (1H, s), 8.10 (1H, s)

LCMS (ESI$^+$) M+H$^+$: 416.

Example 66

1-({4-[3-chloro-5-(trifluoromethyl)phenyl]-1,3-thiazol-2-yl}methyl)-1H-pyrazole-4-carboxylic acid

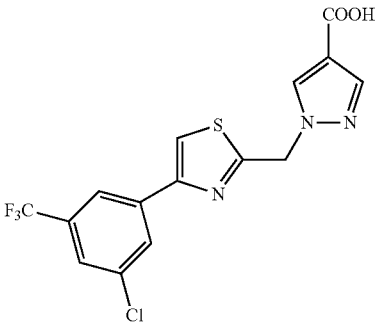 [SMILES: O=C(O)c1cnn(Cc2nc(-c3cc(Cl)cc(C(F)(F)F)c3)cs2)c1]

In the same manner as in Example 38, the title compound (890 mg, 88%) was obtained as colorless crystals from the compound (1.1 g, 2.6 mmol) obtained in Example 66a.

$^1$H NMR (300 MHz, DMSO-$d_6$) δ ppm 5.84 (2H, s), 7.85 (1H, s), 7.92 (1H, s), 8.26 (1H, s), 8.33 (1H, s), 8.50 (1H, s), 8.51 (1H, s), 12.49 (1H, br. s.)

LCMS (ESI$^+$) M+H$^+$: 388.

Example 67

1-({4-[3-chloro-4-(trifluoromethyl)phenyl]-1,3-thiazol-2-yl}methyl)-1H-pyrazole-4-carboxylic acid

Example 67a ethyl 1-({4-[3-chloro-4-(trifluoromethyl)phenyl]-1,3-thiazol-2-yl}methyl)-1H-pyrazole-4-carboxylate

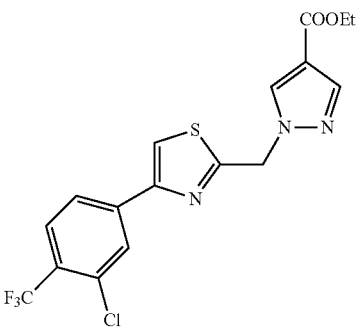 [SMILES: CCOC(=O)c1cnn(Cc2nc(-c3ccc(C(F)(F)F)c(Cl)c3)cs2)c1]

In the same manner as in Example 52a, the title compound (350 mg, 88%) was obtained as a colorless solid from the compound (300 mg, 0.95 mmol) obtained in Example 30c, 3-chloro-4-trifluoromethylphenylboronic acid (260 mg, 1.1 mmol), 2N aqueous sodium carbonate solution (0.57 mL, 1.1 mmol), [1,1'-bis(diphenylphosphino)ferrocene]dichloropalladium(II) dichloromethane complex (78 mg, 0.095 mmol).

$^1$H NMR (300 MHz, CHLOROFORM-d) δppm 1.34 (3H, t, J=7.2 Hz), 4.30 (2H, q, J=7.0 Hz), 5.67 (2H, s), 7.62 (1H, s), 7.70-7.77 (1H, m), 7.81-7.88 (1H, m), 8.01 (1H, s), 8.05 (1H, s), 8.10 (1H, s)

LCMS (ESI$^+$) M+H$^+$: 416.

Example 67

1-({4-[3-chloro-4-(trifluoromethyl)phenyl]-1,3-thiazol-2-yl}methyl)-1H-pyrazole-4-carboxylic acid

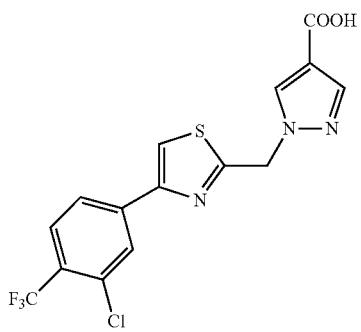 [SMILES: O=C(O)c1cnn(Cc2nc(-c3ccc(C(F)(F)F)c(Cl)c3)cs2)c1]

In the same manner as in Example 38, the title compound (270 mg, 83%) was obtained as colorless crystals from the compound (350 mg, 0.83 mmol) obtained in Example 67a.

$^1$H NMR (300 MHz, DMSO-$d_6$) δ ppm 5.85 (2H, s), 7.94 (1H, d, J=8.3 Hz), 7.92 (1H, s), 8.11 (1H, d, J=8.9 Hz), 8.27 (1H, s), 8.49 (1H, s), 8.51 (1H, s), 12.45 (1H, br. s.)

LCMS (ESI$^+$) M+H$^+$: 388.

Example 68

1-({4-[3-bromo-5-(trifluoromethyl)phenyl]-1,3-thiazol-2-yl}methyl)-1H-pyrazole-4-carboxylic acid

Example 68a 2-bromo-1-[3-bromo-5-(trifluoromethyl)phenyl]ethanone

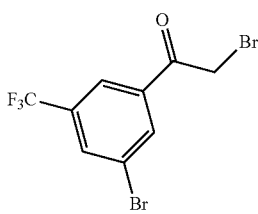 [SMILES: O=C(CBr)c1cc(Br)cc(C(F)(F)F)c1]

Under a nitrogen atmosphere, to a solution (20 mL) of 3-bromo-5-(trifluoromethyl)benzoic acid (5.0 g, 19 mmol) in tetrahydrofuran was added oxalyl chloride (1.9 mL, 22 mmol), and the mixture was stirred at room temperature for 5 hr. The solvent was evaporated under reduced pressure, and to a solution of the residue in acetonitrile was added trimethylsilyldiazomethane (2M diethyl ether solution, 20 mL, 39 mmol), and the mixture was stirred at room temperature for 12 hr. The reaction mixture was cooled to 0° C., 25% bromic acid-acetic acid solution (6.6 mL, 28 mmol) was added, and the mixture was stirred for 30 min at the same temperature. The solvent was evaporated under reduced pressure and the resulting crude title compound was purified by column chromatography (hexane-hexane/ethyl acetate=80/20) to give the title compound (5.3 g, 80%) as a brown oil.

$^1$H NMR (300 MHz, CHLOROFORM-d) δppm 4.42 (2H, s), 8.00 (1H, s), 8.15 (1H, s), 8.29 (1H, s)

Example 68b ethyl 1-({4-[3-bromo-5-(trifluoromethyl)phenyl]-1,3-thiazol-2-yl}methyl)-1H-pyrazole-4-carboxylate

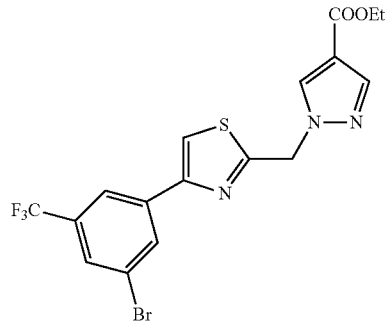 [SMILES: CCOC(=O)c1cnn(Cc2nc(-c3cc(Br)cc(C(F)(F)F)c3)cs2)c1]

In the same manner as in Example 36a, the title compound (1.7 g, 81%) was obtained as colorless crystals from the compound (1.6 g, 4.7 mmol) obtained in Example 1b and the compound (1.6 g, 4.7 mmol) obtained in Example 68a.

$^1$H NMR (300 MHz, CHLOROFORM-d) δppm 1.34 (3H, t, J=7.2 Hz), 4.30 (2H, q, J=7.2 Hz), 5.67 (2H, s), 7.60 (1H, s), 7.73 (1H, s), 8.01 (1H, s), 8.07 (1H, s), 8.09 (1H, s), 8.22 (1H, s)

Example 68

1-({4-[3-bromo-5-(trifluoromethyl)phenyl]-1,3-thiazol-2-yl}methyl)-1H-pyrazole-4-carboxylic acid

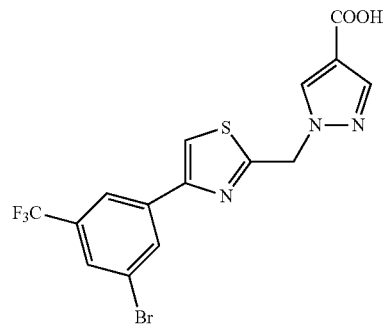 [SMILES: O=C(O)c1cnn(Cc2nc(-c3cc(Br)cc(C(F)(F)F)c3)cs2)c1]

In the same manner as in Example 38, the title compound (340 mg, 90%) was obtained as colorless crystals from the compound (400 mg, 0.87 mmol) obtained in Example 68b.

$^1$H NMR (300 MHz, DMSO-$d_6$) δ ppm 5.85 (2H, s), 7.92 (1H, s), 7.96 (1H, s), 8.30 (1H, s), 8.47 (1H, s), 8.49-8.55 (2H, m), 12.47 (1H, br. s.)

Example 69

1-({4-[3-cyano-5-(trifluoromethyl)phenyl]-1,3-thiazol-2-yl}methyl)-1H-pyrazole-4-carboxylic acid

Example 69a ethyl 1-({4-[3-cyano-5-(trifluoromethyl)phenyl]-1,3-thiazol-2-yl}methyl)-1H-pyrazole-4-carboxylate

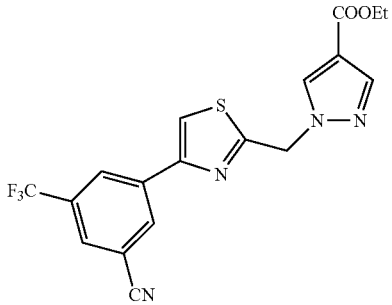 [SMILES: CCOC(=O)c1cnn(Cc2nc(-c3cc(C#N)cc(C(F)(F)F)c3)cs2)c1]

Under a nitrogen atmosphere, to a solution (4 mL) of the compound (200 mg, 0.43 mmol) obtained in Example 68b and zinc cyanide (77 mg, 0.65 mmol) in N,N-dimethylformamide was added tetrakistriphenylphosphinepalladium (50 mg, 0.043 mmol), and the mixture was stirred at 90° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by HPLC to give the title compound (52 mg, 30%) as a white solid.

$^1$H NMR (300 MHz, CHLOROFORM-d) δppm 1.36 (3H, t, J=7.2 Hz), 4.32 (2H, d, J=7.0 Hz), 5.70 (2H, s), 7.69 (1H, s), 7.88 (1H, s), 8.03 (1H, s), 8.12 (1H, s), 8.37 (2. H, s)

LCMS (ESI$^+$) M+H$^+$: 407.

Example 69

1-({4-[3-cyano-5-(trifluoromethyl)phenyl]-1,3-thiazol-2-yl}methyl)-1H-pyrazole-4-carboxylic acid

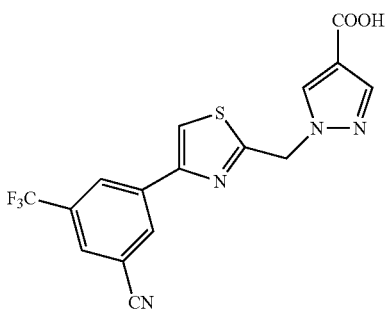 [SMILES: N#Cc1cc(-c2csc(Cn3cc(C(=O)O)cn3)n2)cc(C(F)(F)F)c1]

In the same manner as in Example 38, the title compound (2 mg, 4%) was obtained as colorless crystals from the compound (52 mg, 0.13 mmol) obtained in Example 69a.

$^1$H NMR (300 MHz, DMSO-d$_6$) δ ppm 5.85 (2H, s), 7.92 (1H, s), 8.34 (1H, s), 8.51 (1H, s), 8.54-8.60 (2H, m), 8.72 (1H, s), 12.45 (1H, br. s.)

LCMS (ESI$^+$) M+H$^+$: 379.

Example 70

1-({4-methyl-2-[3-(trifluoromethyl)phenyl]-1,3-thiazol-5-yl}methyl)-1H-pyrazole-4-carboxylic acid Example 70a ethyl 4-methyl-2-[3-(trifluoromethyl)phenyl]-1,3-thiazole-5-carboxylate

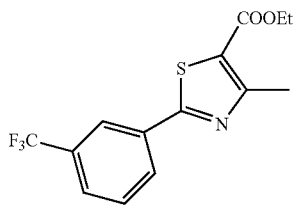 [SMILES: CCOC(=O)c1sc(-c2cccc(C(F)(F)F)c2)nc1C]

To a solution (6 mL) of ethyl 2-chloroacetoacetate (220 mg, 1.3 mmol) in ethanol was added 3-trifluoromethylphenylthioamide (250 mg, 1.2 mmol), and the mixture was stirred at 80° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=80/20) to give the title compound (380 mg, 100%) as a colorless solid.

$^1$H NMR (300 MHz, CHLOROFORM-d) δppm 1.40 (3H, t, J=7.2 Hz), 2.80 (3H, s), 4.37 (2H, q, J=7.2 Hz), 7.59 (1H, t, J=7.8 Hz), 7.72 (1H, d, J=7.7 Hz), 8.13 (1H, d, J=7.9 Hz), 8.25 (1H, s)

LCMS (ESI$^+$) M+H$^+$: 316.

Example 70b

{4-methyl-2-[3-(trifluoromethyl)phenyl]-1,3-thiazol-5-yl}methanol

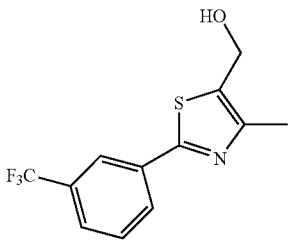 [SMILES: Cc1nc(-c2cccc(C(F)(F)F)c2)sc1CO]

Under a nitrogen atmosphere at 0° C., to a mixed solution of the compound (380 mg, 1.2 mmol) obtained in Example 70a in ethanol/tetrahydrofuran (v/v=1/1, 6 mL) were added calcium chloride (500 mg, 4.5 mmol) and sodium tetrahydroborate (170 mg, 4.5 mmol), and the mixture was stirred at room temperature overnight. 1N Hydrochloric acid was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=65/35) to give the title compound (160 mg, 50%) as a colorless solid.

2.41 (1H, t, J=5.9 Hz), 2.49 (3H, s), 4.73 (2H, d, J=5.3 Hz), 7.54 (1H, t, J=7.8 Hz), 7.65 (1H, d, J=7.0 Hz), 8.04 (1H, d, J=8.0 Hz), 8.16 (1H, s)

LCMS (ESI$^+$) M+H$^+$: 274.

Example 70c ethyl 1-({4-methyl-2-[3-(trifluoromethyl)phenyl]-1,3-thiazol-5-yl}methyl)-1H-pyrazole-4-carboxylate

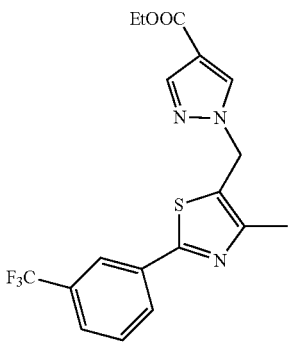 [SMILES: CCOC(=O)c1cnn(Cc2sc(-c3cccc(C(F)(F)F)c3)nc2C)c1]

Under a nitrogen atmosphere at 0° C., to a solution (5 mL) of the compound (160 mg, 0.60 mmol) obtained in Example 70b in tetrahydrofuran was added oxalyl chloride (0.10 mL, 1.2 mmol), and the mixture was stirred at room temperature for 4 hr. After confirmation of the termination of the reaction by TLC, saturated aqueous sodium hydrogen carbonate solution was added, and the mixture was extracted with ethyl acetate. The obtained organic layer was washed with saturated brine, and dried over anhydrous sodium sulfate. The solvent was evaporated under reduced pressure.

To a solution (3 mL) of the residue in N,N-dimethylformamide were added ethyl 1H-pyrazole-4-carboxylate (130 mg, 0.90 mmol) and potassium carbonate (170 mg, 1.2 mmol), and the mixture was stirred at 80° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (70 mg, 29%) as colorless crystals.

$^1$H NMR (300 MHz, CHLOROFORM-d) δppm 1.33 (3H, t, J=7.2 Hz), 2.55 (3H, s), 4.28 (2H, q, J=7.2 Hz), 5.47 (2H, s), 7.50-7.63 (1H, m), 7.63-7.75 (1H, m), 7.90 (1H, s), 7.95 (1H, s), 8.00-8.09 (1H, m), 8.17 (1H, s)

LCMS (ESI$^+$) M+H$^+$: 396.

Example 70

1-({4-methyl-2-[3-(trifluoromethyl)phenyl]-1,3-thiazol-5-yl}methyl)-1H-pyrazole-4-carboxylic acid

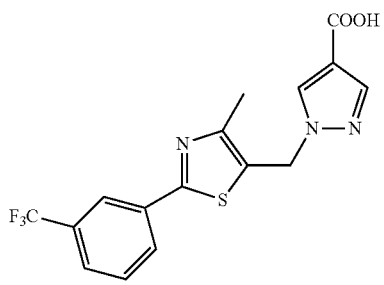 [SMILES: Cc1nc(-c2cccc(C(F)(F)F)c2)sc1Cn1cc(C(=O)O)cn1]

To a mixed solution of the compound (70 mg, 0.18 mmol) obtained in Example 70c in ethanol/tetrahydrofuran (v/v=1/1, 4 mL) was added 2N aqueous sodium hydroxide solution (0.71 mL, 1.4 mmol), and the mixture was stirred at room temperature overnight. Water was added to the reaction mixture, and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (44 mg, 67%) as colorless crystals.

$^1$H NMR (300 MHz, DMSO-d$_6$) δ ppm 2.52 (3H, s), 5.65 (2H, s), 7.72 (1H, t, J=8.0 Hz), 7.79-7.90 (2H, m), 8.08-8.25 (2 H, m), 8.43 (1H, s), 12.37 (1H, br. s.)

LCMS (ESI$^+$) M+H$^+$: 368.

Example 71

1-({5-methyl-2-[3-(trifluoromethyl)phenyl]-1,3-thiazol-4-yl}methyl)-1H-pyrazole-4-carboxylic acid Example 71a 5-methyl-2-[3-(trifluoromethyl)phenyl]-1,3-thiazole-4-carboxylic acid

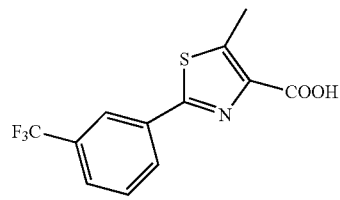 [SMILES: Cc1sc(-c2cccc(C(F)(F)F)c2)nc1C(=O)O]

Under a nitrogen atmosphere at 0° C., to a solution (5 mL) of 2-oxobutyric acid (500 mg, 4.9 mmol) in diethyl ether was slowly added dropwise a solution (5 mL) of bromine (430 mg, 5.4 mmol) in diethyl ether over 30 min, and the mixture was stirred at room temperature for 3 hr. The solvent was evaporated under reduced pressure, to a solution (10 mL) of the residue in acetonitrile was added 3-trifluoromethylphenylthioamide (400 mg, 2.0 mmol), and the mixture was stirred at 80° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane/ethyl acetate=80/20-hexane/ethyl acetate=50/50) to give the title compound (310 mg, 56%) as a colorless solid.

$^1$H NMR (300 MHz, DMSO-d$_6$) δ ppm 2.77 (3H, s), 7.77 (1H, t, J=7.8 Hz), 7.83-7.92 (1H, m), 8.08-8.28 (2H, m), 13.08 (1H, br. s.)

LCMS (ESI$^+$) M+H$^+$: 288.

Example 71b

{5-methyl-2-[3-(trifluoromethyl)phenyl]-1,3-thiazol-4-yl}methanol

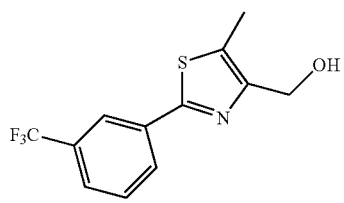 [SMILES: Cc1sc(-c2cccc(C(F)(F)F)c2)nc1CO]

Under a nitrogen atmosphere at 0° C., to a solution (5 mL) of the compound (310 mg, 1.1 mmol) obtained in Example 71a in tetrahydrofuran was added borane-tetrahydrofuran complex (1.1 M tetrahydrofuran solution, 3.0 mL, 3.3 mmol), and the mixture was stirred at room temperature overnight. 1N Hydrochloric acid was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=65/35) to give the title compound (82 mg, 27%) as a colorless oil.

$^1$H NMR (300 MHz, CHLOROFORM-d) δppm 2.48 (3H, s), 4.85 (2H, s), 7.55 (1H, t, J=7.8 Hz), 7.65 (1H, d, J=7.0 Hz), 8.06 (1H, d, J=8.0 Hz), 8.19 (1H, s)

LCMS (ESI$^+$) M+H$^+$: 274.

Example 71c ethyl 1-({5-methyl-2-[3-(trifluoromethyl)phenyl]-1,3-thiazol-4-yl}methyl)-1H-pyrazole-4-carboxylate

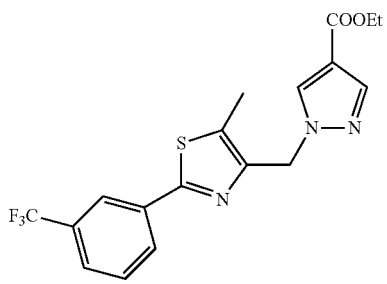 [SMILES: CCOC(=O)c1cnn(Cc2nc(-c3cccc(C(F)(F)F)c3)sc2C)c1]

Under a nitrogen atmosphere at 0° C., to a solution (5 mL) of the compound (82 mg, 0.30 mmol) obtained in Example 71b in tetrahydrofuran was added oxalyl chloride (0.051 mL, 0.60 mmol), and the mixture was stirred at room temperature for 4 hr. After confirmation of the termination of the reaction by TLC, saturated aqueous sodium hydrogen carbonate solution was added, and the mixture was extracted with ethyl acetate. The obtained organic layer was washed with saturated brine, and dried over anhydrous sodium sulfate. The solvent was evaporated under reduced pressure.

To a solution (3 mL) of the residue in N,N-dimethylformamide were added ethyl 1H-pyrazole-4-carboxylate (65 mg, 0.45 mmol) and potassium carbonate (85 mg, 0.60 mmol). The mixture was stirred at 80° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (31 mg, 26%) as colorless crystals.

$^1$H NMR (300 MHz, CHLOROFORM-d) δppm 1.33 (3H, t, J=7.2 Hz), 2.55 (3H, s), 4.28 (2H, q, J=7.1 Hz), 5.40 (2H, s), 7.49-7.60 (1H, m), 7.62-7.71 (1H, m), 7.91 (1H, s), 7.97-8.08 (2H, m), 8.13 (1H, s)

LCMS (ESI$^+$) M+H$^+$: 396.

Example 71

1-({5-methyl-2-[3-(trifluoromethyl)phenyl]-1,3-thiazol-4-yl}methyl)-1H-pyrazole-4-carboxylic acid

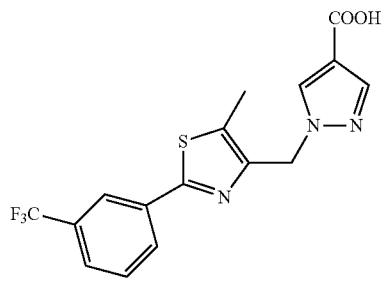 [SMILES: Cc1sc(-c2cccc(C(F)(F)F)c2)nc1Cn1cc(C(=O)O)cn1]

To a mixed solution of the compound (31 mg, 0.078 mmol) obtained in Example 71c in ethanol/tetrahydrofuran (v/v=1/1, 4 mL) was added 2N aqueous sodium hydroxide solution (0.31 mL, 0.62 mmol), and the mixture was stirred at room temperature overnight. Water was added to the reaction mixture, and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (21 mg, 72%) as colorless crystals.

$^1$H NMR (300 MHz, DMSO-d$_6$) δ ppm 2.56 (3H, s), 5.48 (2H, s), 7.73 (1H, t, J=7.9 Hz), 7.79-7.89 (2H, m), 8.02-8.22 (2H, m), 8.34 (1H, s), 12.21 (1H, br. s.)

LCMS (ESI$^+$) M+H$^+$: 368.

Example 72

1-({5-cyclopropyl-2-[3-(trifluoromethyl)phenyl]-1,3-thiazol-4-yl}methyl)-1H-pyrazole-4-carboxylic acid

Example 72a methyl 2-amino-3-cyclopropyl-3-oxopropanoate hydrochloride

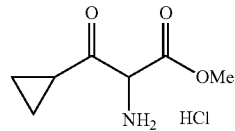 [SMILES: COC(=O)C(N)C(=O)C1CC1 ; Cl]

To a solution (15 mL) of methyl 3-cyclopropyl-3-oxopropionate (10 g, 70 mmol) in acetic acid was slowly added dropwise aqueous solution (15 mL) of sodium nitrate (5.8 g, 84 mmol) at 0° C., and the mixture was stirred at 0-10° C. for 5 hr. To the reaction mixture was added saturated sodium hydrogen carbonate, and the mixture was extracted with ethyl acetate. The obtained organic layer was washed with saturated brine, and dried over anhydrous sodium sulfate. The solvent was evaporated under reduced pressure to give residue.

$^1$H NMR (300 MHz, CHLOROFORM-d) δppm 0.97-1.09 (2H, m), 1.15-1.24 (2H, m), 2.59-2.83 (1H, m), 3.91 (3H, s)

To a solution (30 mL) of residue in ethanol were added 6N hydrochloric acid (20 mL) and palladium-carbon (1.0 g), and the mixture was stirred at room temperature for 6 hr under a hydrogen atmosphere (3.5 pressure). Palladium-carbon was filtered, 4N hydrogen chloride ethyl acetate solution was added, and the mixture was stirred for 30 min. The solvent was evaporated under reduced pressure. The resulting crude title compound was recrystallized (acetone-ethyl acetate) to give the title compound (9.7 g, 71%) as a white solid.

$^1$H NMR (300 MHz, DMSO-d$_6$) δ ppm 0.90-1.24 (4H, m), 2.36-2.50 (1H, m), 3.82 (3H, s), 5.52 (1H, s), 9.03 (3H, br. s.)

Example 72b methyl 3-cyclopropyl-3-oxo-2-({[3-(trifluoromethyl)phenyl]carbonyl}amino)propanoate

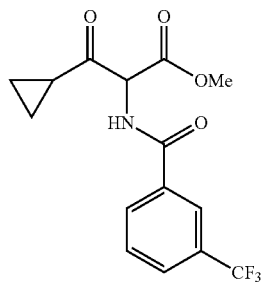 [SMILES: COC(=O)C(NC(=O)c1cccc(C(F)(F)F)c1)C(=O)C1CC1]

To a solution (16 mL) of the compound (3.0 g, 16 mmol) obtained in Example 72a in N,N-dimethylformamide were added 3-trifluoromethylbenzoic acid (3.2 g, 17 mmol), N-[3-(dimethylamino)propyl]-N'-ethylcarbodiimide (3.6 g, 19 mmol), 1-hydroxybenzotriazole (2.9 g, 19 mmol) and triethylamine (4.3 mL, 31 mmol), and the mixture was stirred at room temperature overnight. Saturated aqueous sodium hydrogen carbonate solution was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (4.0 g, 66%) as a colorless oil.

$^1$H NMR (300 MHz, CHLOROFORM-d) δppm 1.04-1.35 (4H, m), 2.35-2.50 (1H, m), 3.87 (3H, s), 5.63 (1H, d, J=6.4 Hz), 7.43 (1H, br. s.), 7.61 (1H, t, J=7.8 Hz), 7.80 (1H, d, J=7.9 Hz), 8.03 (1H, d, J=7.7 Hz), 8.12 (1H, s)

LCMS (ESI$^+$) M+H$^+$: 330.

Example 72c methyl 5-cyclopropyl-2-[3-(trifluoromethyl)phenyl]-1,3-thiazole-4-carboxylate

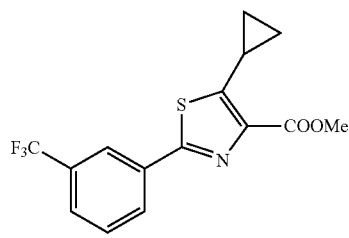 [SMILES: COC(=O)c1nc(-c2cccc(C(F)(F)F)c2)sc1C1CC1]

To a solution (12 mL) of the compound (4.0 g, 12 mmol) obtained in Example 72b in tetrahydrofuran was added 2,4-bis(4-methoxyphenyl)-1,3,2,4-dithiadiphosphetane 2,4-disulfide (4.9 g, 12 mmol), and the mixture was stirred at 80° C. overnight. Saturated aqueous sodium hydrogen carbonate was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=90/10) to give the title compound (3.4 g, 86%) as a colorless solid.

$^1$H NMR (300 MHz, CHLOROFORM-d) δppm 0.79-0.90 (2H, m), 1.29-1.41 (2H, m), 2.97-3.22 (1H, m), 4.00 (3H, s), 7.55 (1H, t, J=7.8 Hz), 7.67 (1H, d, J=7.6 Hz), 8.06 (1H, d, J=7.6 Hz), 8.14 (1H, s)

LCMS (ESI$^+$) M+H$^+$: 328.

Example 72d

{5-cyclopropyl-2-[3-(trifluoromethyl)phenyl]-1,3-thiazol-4-yl}methanol

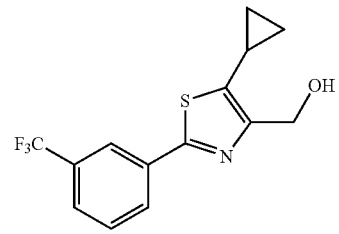 [SMILES: OCc1nc(-c2cccc(C(F)(F)F)c2)sc1C1CC1]

By a method similar to that in Example 64b, the title compound (2.5 g, 80%) was obtained as a colorless solid from the compound (3.4 g, 10 mmol) obtained in Example 72c and lithium tetrahydroborate (1.1 g, 21 mmol).

$^1$H NMR (300 MHz, CHLOROFORM-d) δppm 0.66-0.84 (2H, m), 1.04-1.22 (2H, m), 1.95-2.21 (1H, m), 2.59 (1H, t, J=5.7 Hz), 4.83 (2H, d, J=5.7 Hz), 7.52 (1H, t, J=7.8 Hz), 7.63 (1H, d, J=7.7 Hz), 8.01 (1H, d, J=7.7 Hz), 8.12 (1H, s)

LCMS (ESI$^+$) M+H$^+$: 300.

Example 72e ethyl 1-({5-cyclopropyl-2-[3-(trifluoromethyl)phenyl]-1,3-thiazol-4-yl}methyl)-1H-pyrazole-4-carboxylate

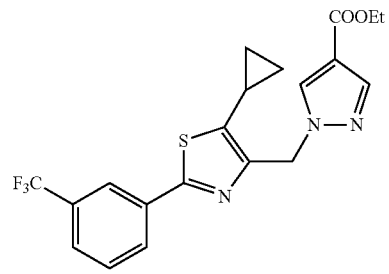 [SMILES: CCOC(=O)c1cnn(Cc2nc(-c3cccc(C(F)(F)F)c3)sc2C2CC2)c1]

By a method similar to that in Example 71c, the title compound (660 mg, 94%) was obtained as a colorless oil from the compound (500 mg, 1.7 mmol) obtained in Example 72d, oxalyl chloride (0.24 mL, 3.3 mmol), ethyl 1H-pyrazole-4-carboxylate (260 mg, 1.8 mmol) and potassium carbonate (300 mg, 2.2 mmol).

¹H NMR (300 MHz, CHLOROFORM-d) δppm 0.69-0.86 (2H, m), 1.08-1.22 (2H, m), 1.33 (3H, t, J=7.2 Hz), 2.06-2.19 (1H, m), 4.28 (2H, q, J=7.2 Hz), 5.50 (2H, s), 7.53 (1H, t, J=8.0 Hz), 7.64 (1H, d, J=8.0 Hz), 7.92 (1H, s), 7.96-8.07 (2H, m), 8.10 (1H, s)

LCMS (ESI⁺) M+H⁺: 422.

Example 72

1-({5-cyclopropyl-2-[3-(trifluoromethyl)phenyl]-1,3-thiazol-4-yl}methyl)-1H-pyrazole-4-carboxylic acid

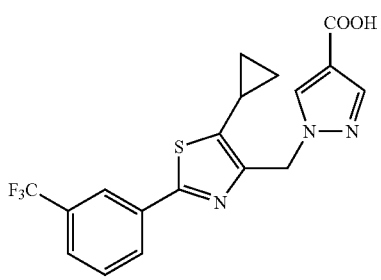

By a method similar to that in Example 71, the title compound (510 mg, 83%) was obtained as colorless crystals from the compound (660 mg, 1.6 mmol) obtained in Example 72e.

¹H NMR (300 MHz, DMSO-d₆) δ ppm 0.62-0.86 (2H, m), 1.02-1.31 (2H, m), 2.22-2.44 (1H, m), 5.56 (2H, s), 7.65-7.76 (1H, m), 7.78-7.87 (2H, m), 8.05-8.14 (2H, m), 8.35 (1H, s), 12.33 (1H, s)

LCMS (ESI⁺) M+H⁺: 394.

Example 73

1-({4-[3-(hydroxymethyl)-5-(trifluoromethyl)phenyl]-1,3-thiazol-2-yl}methyl)-1H-pyrazole-4-carboxylic acid

Example 73a 3-(4,4,5,5-tetramethyl-1,3,2-dioxaborolan-2-yl)-5-(trifluoromethyl)benzaldehyde

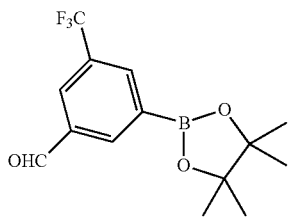 [SMILES: CC1(C)OB(c2cc(C=O)cc(C(F)(F)F)c2)OC1(C)C]

In the same manner as in Example 49a, the title compound was obtained from 3-bromo-5-(trifluoromethyl)benzaldehyde (3.7 g, 15 mmol), bispinacholatediborane (4.4 g, 17 mmol), potassium acetate (4.3 g, 44 mmol), and [1,1'-bis(diphenylphosphino)ferrocene]dichloropalladium(II) dichloromethane complex (1.2 g, 1.5 mmol).

Example 73b ethyl 1-({4-[3-formyl-5-(trifluoromethyl)phenyl]-1,3-thiazol-2-yl}methyl)-1H-pyrazole-4-carboxylate

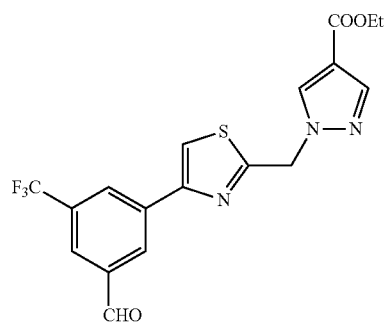 [SMILES: CCOC(=O)c1cnn(Cc2nc(-c3cc(C=O)cc(C(F)(F)F)c3)cs2)c1]

In the same manner as in Example 52a, the title compound (4.5 g, 100%) was obtained as a brown oil from the compound (3.5 g, 11 mmol) obtained in Example 30c, the compound (15 mmol) obtained in Example 73a, 2N aqueous sodium carbonate solution (6.7 mL, 13 mmol) and [1,1-r-bis(diphenylphosphino)ferrocene]dichloropalladium(II) dichloromethane complex (560 mg, 0.56 mmol).

¹H NMR (300 MHz, CHLOROFORM-d) δppm 1.34 (3H, t, J=6.9 Hz), 4.30 (2H, q, J=6.9 Hz), 5.70 (2H, s), 7.71 (1H, s), 8.01 (1H, s), 8.11 (2H, s), 8.42 (1H, s), 8.56 (1H, s), 10.14 (1H, s)

LCMS (ESI⁺) M+H⁺: 410.

Example 73c ethyl 1-({4-[3-(hydroxymethyl)-5-(trifluoromethyl)phenyl]-1,3-thiazol-2-yl}methyl)-1H-pyrazole-4-carboxylate

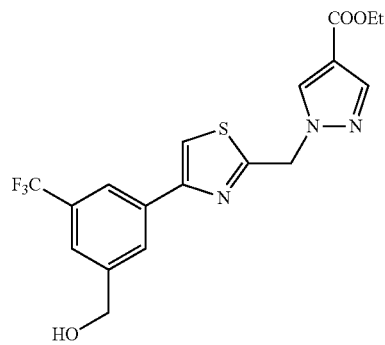 [SMILES: CCOC(=O)c1cnn(Cc2nc(-c3cc(CO)cc(C(F)(F)F)c3)cs2)c1]

Under a nitrogen atmosphere at 0° C., to a solution (2 mL) of the compound (700 mg, 1.7 mmol) obtained in Example 73b in tetrahydrofuran were added sodium tetrahydroborate (130 mg, 3.4 mmol) and ethanol (2 mL), and the mixture was stirred at the same temperature for 2 hr. 1N Hydrochloric acid was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=50/50) to give the title compound (680 mg, 96%) as a colorless solid.

¹H NMR (300 MHz, CHLOROFORM-d) δppm 1.34 (3H, t, J=7.0 Hz), 4.30 (2H, q, J=7.2 Hz), 4.83 (2H, s), 5.68 (2H, s), 7.58 (1H, s), 7.62 (1H, s), 8.00 (1H, s), 8.07 (2H, s), 8.10 (1H, s)

Example 73

1-({4-[3-(hydroxymethyl)-5-(trifluoromethyl)phenyl]-1,3-thiazol-2-yl}methyl)-1H-pyrazole-4-carboxylic acid

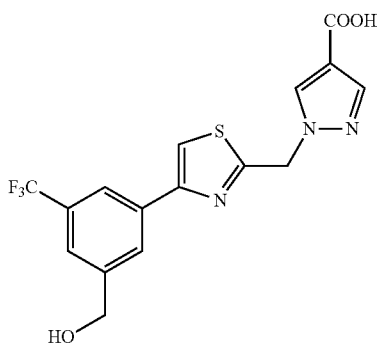

In the same manner as in Example 38, the title compound (160 mg, 79%) was obtained as colorless crystals from the compound (210 mg, 0.52 mmol) obtained in Example 73c.

¹H NMR (300 MHz, DMSO-d₆) δ ppm 4.65 (2H, br. s.), 5.49 (1H, br. s.), 5.84 (2H, s), 7.65 (1H, s), 7.92 (1H, s), 8.14 (1H, s), 8.21 (1H, s), 8.35 (1H, s), 8.51 (1H, s), 12.47 (1H, br. s.)

LCMS (ESI⁺) M+H⁺: 384.

Example 74

1-({4-[3-(2-phenylethyl)-5-(trifluoromethyl)phenyl]-1,3-thiazol-2-yl}methyl)-1H-pyrazole-4-carboxylic acid

Example 74a ethyl 1-[(4-{3-[(E/Z)-2-phenylethenyl]-5-(trifluoromethyl)phenyl}-1,3-thiazol-2-yl)methyl]-1H-pyrazole-4-carboxylate

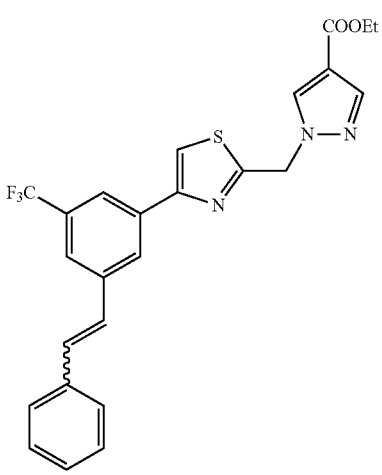 [SMILES: CCOC(=O)c1cnn(Cc2nc(-c3cc(C=Cc4ccccc4)cc(C(F)(F)F)c3)cs2)c1]

Under a nitrogen atmosphere at 0° C., to a solution (3 mL) of benzyltriphenylphosphoniumbromide (700 mg, 2.0 mmol) in tetrahydrofuran was added tert-butoxy potassium (240 mg, 2.2 mmol), and the mixture was stirred at the same temperature for 30 min. To the resulting orange reaction solution was added the compound (400 mg, 0.98 mmol) obtained in Example 73b, and the mixture was stirred at 0° C. for 2 hr. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (230 mg, E/Z=ca. 1/1, 48%) as a colorless solid.

¹H NMR (300 MHz, CHLOROFORM-d) δppm 1.34 (3H, t, J=7.0 Hz), 4.30 (2H, q, J=6.9 Hz), 5.35-5.91 (2H, m), 6.29-8.48 (13H, m)

LCMS (ESI⁺) M+H⁺: 484.

Example 74

1-({4-[3-(2-phenylethyl)-5-(trifluoromethyl)phenyl]-1,3-thiazol-2-yl}methyl)-1H-pyrazole-4-carboxylic acid

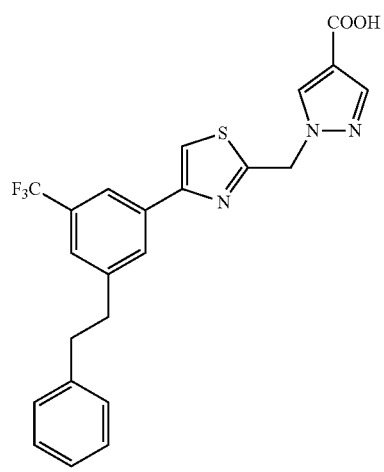

To a mixed solution of the compound (230 mg, 0.47 mmol) obtained in Example 74a in ethanol/tetrahydrofuran (v/v=1/1, 4 mL) was added 2N aqueous sodium hydroxide solution (0.93 mL, 1.9 mmol), and the mixture was stirred at room temperature overnight. Water was added to the reaction mixture, and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure.

To a solution (4 mL) of the residue in ethanol was added palladium-carbon (20 mg), and the mixture was stirred under a hydrogen atmosphere (1 atm) at room temperature overnight. Palladium-carbon was removed and the solvent was evaporated under reduced pressure. The resulting crude title compound was recrystallized (hexane-ethyl acetate) to give the title compound (120 mg, 56% in 2 steps) as colorless crystals.

201

¹H NMR (300 MHz, DMSO-d₆) δ ppm 2.81-3.16 (4H, m), 5.83 (2H, s), 7.08-7.35 (5H, m), 7.54 (1H, s), 7.91 (1H, s), 8.09 (1H, s), 8.13 (1H, s), 8.31 (1H, s), 8.49 (1H, s), 12.47 (1H, br. s.)

LCMS (ESI⁺) M+H⁺: 458.

Example 75

1-({4-[3-(phenoxymethyl)-5-(trifluoromethyl)phenyl]-1,3-thiazol-2-yl}methyl)-1H-pyrazole-4-carboxylic acid Example 75a ethyl 1-({4-[(3-(phenoxymethyl)-5-(trifluoromethyl)phenyl]-1,3-thiazol-2-yl}methyl)-1H-pyrazole-4-carboxylate

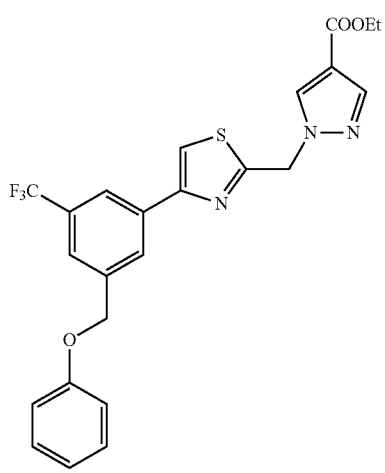 [SMILES: CCOC(=O)c1cnn(Cc2nc(-c3cc(COc4ccccc4)cc(C(F)(F)F)c3)cs2)c1]

Under a nitrogen atmosphere at 0° C., to a solution (4 mL) of the compound (160 mg, 0.39 mmol) obtained in Example 73c, triphenylphosphine (150 mg, 0.58 mmol) and phenol (73 mg, 0.78 mmol) in tetrahydrofuran was slowly added dropwise diethyl azodicarboxylate (0.25 mL, 0.58 mmol), and the mixture was stirred at the same temperature for 5 hr. Water was added to the reaction mixture, and the mixture was extracted with ethyl acetate. The obtained organic layer was washed with saturated brine, and dried over anhydrous sodium sulfate. The solvent was evaporated under reduced pressure. The residue was purified by column chromatography (hexane-hexane/ethyl acetate=75/25) to give the title compound (62 mg, 33%) as a colorless oil.

¹H NMR (300 MHz, CHLOROFORM-d) δppm 1.34 (3H, t, J=7.6 Hz), 4.29 (2H, q, J=7.6 Hz), 5.16 (2H, s), 5.68 (2H, s), 6.89-7.08 (3H, m), 7.28-7.37 (2H, m), 7.59 (1H, d, J=1.3 Hz), 7.69 (1H, br. s.), 8.00 (1H, br. s.), 8.05-8.20 (3H, m)

LCMS (ESI⁺) M+H⁺: 488.

202

Example 75

1-({4-[3-(phenoxymethyl)-5-(trifluoromethyl)phenyl]-1,3-thiazol-2-yl}methyl)-1H-pyrazole-4-carboxylic acid

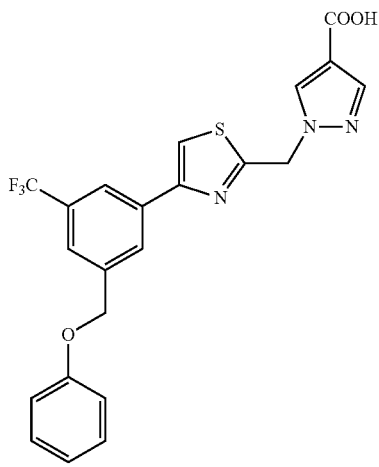

In the same manner as in Example 38, the title compound (40 mg, 67%) was obtained as colorless crystals from the compound (62 mg, 0.13 mmol) obtained in Example 75a.

¹H NMR (300 MHz, DMSO-d₆) δ ppm 5.27 (2H, s), 5.85 (2H, s), 6.97 (1H, t, J=7.9 Hz), 7.06 (2H, d, J=8.0 Hz), 7.32 (2H, t, J=8.1 Hz), 7.80 (1H, s), 7.92 (1H, s), 8.24 (1H, s), 8.35 (1H, s), 8.40 (1H, s), 8.51 (1H, s), 12.47 (1H, br. s.)

LCMS (ESI⁺) M+H⁺: 460.

Example 76

1-({4-[3-methoxy-5-(trifluoromethyl)phenyl]-1,3-thiazol-2-yl}methyl)-1H-pyrazole-4-carboxylic acid Example 76a 2-bromo-1-[3-methoxy-5-(trifluoromethyl)phenyl]ethanone

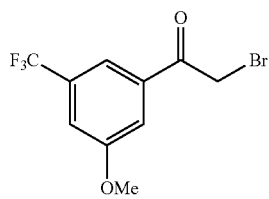 [SMILES: COc1cc(C(=O)CBr)cc(C(F)(F)F)c1]

In the same manner as in Example 38b, the title compound (6.8 g, 100%) was obtained as a colorless solid from 3-trifluoromethyl-5-methoxyacetophenone (5.0 g, 23 mmol) and phenyltrimethylammonium tribromide (9.5 g, 25 mmol).

¹H NMR (300 MHz, CHLOROFORM-d) δppm 3.92 (3H, s), 4.44 (2H, s), 7.36 (1H, s), 7.67 (1H, s), 7.78 (1H, s)

Example 76b ethyl 1-({4-[3-methoxy-5-(trifluoromethyl)phenyl]-1,3-thiazol-2-yl}methyl)-1H-pyrazole-4-carboxylate

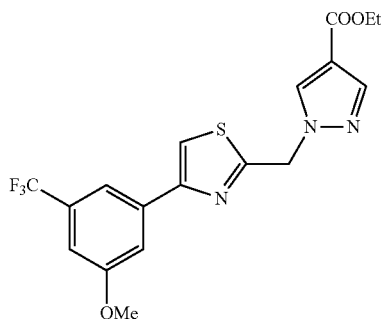 [SMILES: CCOC(=O)c1cnn(Cc2nc(-c3cc(OC)cc(C(F)(F)F)c3)cs2)c1]

In the same manner as in Example 38c, the title compound (7.5 g, 80%) was obtained as colorless crystals from the crude compound (6.8 g, 23 mmol) obtained in Example 76a and the compound (4.9 g, 23 mmol) obtained in Example 1b.

$^1$H NMR (300 MHz, CHLOROFORM-d) δppm 1.34 (3H, t, J=7.1 Hz), 3.91 (3H, s), 4.30 (2H, q, J=7.1 Hz), 5.68 (2H, s), 7.11 (1 H, s), 7.55 (1H, s), 7.61 (1H, s), 7.71 (1H, s), 8.00 (1H, s), 8.09 (1H, s)

LCMS (ESI$^+$) M+H$^+$: 412.

Example 76

1-({4-[3-methoxy-5-(trifluoromethyl)phenyl]-1,3-thiazol-2-yl}methyl)-1H-pyrazole-4-carboxylic acid

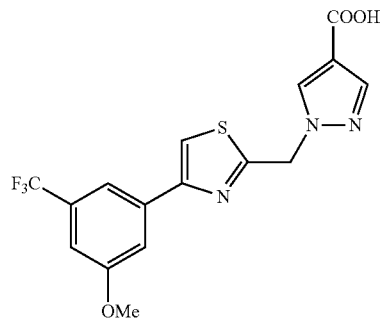 [SMILES: COc1cc(-c2csc(Cn3cc(C(=O)O)cn3)n2)cc(C(F)(F)F)c1]

In the same manner as in Example 38, the title compound (330 mg, 89%) was obtained as colorless crystals from the compound (400 mg, 0.97 mmol) obtained in Example 76b.

$^1$H NMR (300 MHz, DMSO-d$_6$) δ ppm 3.90 (3H, s), 5.84 (2H, s), 7.23 (1H, s), 7.79 (1H, s), 7.87 (1H, s), 7.92 (1H, s), 8.40 (1H, s), 8.51 (1H, s), 12.47 (1H, br. s.)

LCMS (ESI$^+$) M+H$^+$: 384.

Example 77

1-({2-[3-bromo-5-(trifluoromethyl)phenyl]-5-methyl-1,3-thiazol-4-yl}methyl)-1H-pyrazole-4-carboxylic acid

Example 77a 3-bromo-5-(trifluoromethyl)benzamide

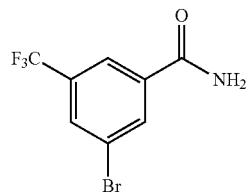 [SMILES: NC(=O)c1cc(Br)cc(C(F)(F)F)c1]

To a solution (18 mL) of 3-trifluoromethyl-5-bromobenzoic acid (5.0 g, 19 mmol) in N,N-dimethylformamide were added N-[3-(dimethylamino)propyl]-N'-ethylcarbodiimide (4.3 g, 22 mmol), 1-hydroxybenzotriazole (3.4 g, 22 mmol) and 28% aqueous ammonia (1.7 mL, 28 mmol), and the mixture was stirred at room temperature overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was to recrystallized (hexane-ethyl acetate) to give the title compound (3.7 g, 74%) as colorless crystals.

$^1$H NMR (300 MHz, DMSO-d$_6$) δ ppm 7.76 (1H, br. s.), 8.17 (1H, s), 8.20 (1H, s), 8.31 (1H, br. s.), 8.36 (1H, s)

Example 77b 3-bromo-5-(trifluoromethyl)benzenecarbothioamide

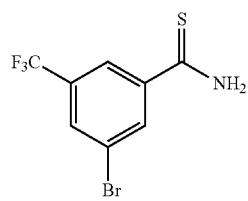 [SMILES: NC(=S)c1cc(Br)cc(C(F)(F)F)c1]

To a solution (30 mL) of the compound (3.7 g, 14 mmol) obtained in Example 77a in tetrahydrofuran was added 2,4-bis(4-methoxyphenyl)-1,3,2,4-dithiadiphosphetane 2,4-disulfide (5.5 g, 14 mmol), and the mixture was stirred at 80° C. for 5 hr. Saturated aqueous sodium hydrogen carbonate was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was recrystallized (hexane-ethyl acetate) to give the title compound (3.2 g, 83%) as pale-yellow crystals.

$^1$H NMR (300 MHz, DMSO-d$_6$) δ ppm 8.14 (1H, s), 8.19 (1H, s), 8.32 (1H, s), 9.84 (1H, br. s.), 10.24 (1H, br. s.)

LCMS (ESI$^+$) M+H$^+$: 282.

Example 77c ethyl 2-[3-bromo-5-(trifluoromethyl)phenyl]-5-methyl-1,3-thiazole-4-carboxylate

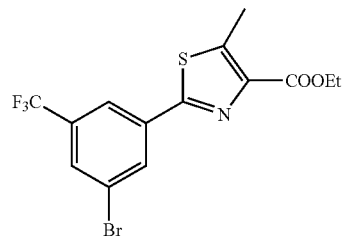 [SMILES: CCOC(=O)c1nc(-c2cc(Br)cc(C(F)(F)F)c2)sc1C]

Under a nitrogen atmosphere at 0° C., to a solution (30 mL) of 2-oxobutyric acid (3.0 g, 29 mmol) in diethyl ether was slowly added dropwise a solution (20 mL) of bromine (2.6 g, 33 mmol) in diethyl ether over 30 min, and the mixture was stirred at the same temperature for 3 hr. The solvent was evaporated under reduced pressure, and to a solution (50 mL) of the residue in ethanol was added the compound (3.2 g, 11 mmol) obtained in Example 77b, and the mixture was stirred at 80° C. overnight. Saturated aqueous sodium hydrogen carbonate was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=90/10) to give a crude title compound (5.9 g) as a pale-yellow solid.

$^1$H NMR (300 MHz, CHLOROFORM-d) δppm 1.46 (3H, t, J=7.2 Hz), 2.83 (3H, s), 4.46 (2H, q, J=7.1 Hz), 7.80 (1H, s), 8.08 (1H, s), 8.28 (1H, s)

LCMS (ESI$^+$) M+H$^+$: 394.

Example 77d

{2-[3-bromo-5-(trifluoromethyl)phenyl]-5-methyl-1,3-thiazol-4-yl}methanol

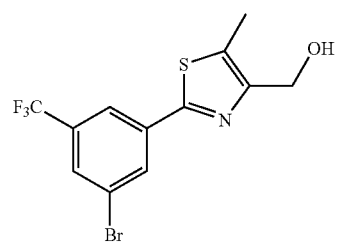 [SMILES: Cc1sc(-c2cc(Br)cc(C(F)(F)F)c2)nc1CO]

In the same manner as in Example 64b, the title compound (2.9 g, 73% in 2 steps) was obtained as a pale-yellow solid from the compound (5.9 g) obtained in Example 77c and lithium tetraborate (1.8 g, 34 mmol).

$^1$H NMR (300 MHz, CHLOROFORM-d) δppm 2.51 (3H, s), 4.73 (2H, s), 7.76 (1H, s), 8.04 (1H, s), 8.20 (1H, s)

LCMS (ESI$^+$) M+H$^+$: 352.

Example 77e ethyl 1-({2-[3-bromo-5-(trifluoromethyl)phenyl]-5-methyl-1,3-thiazol-4-yl}methyl)-1H-pyrazole-4-carboxylate

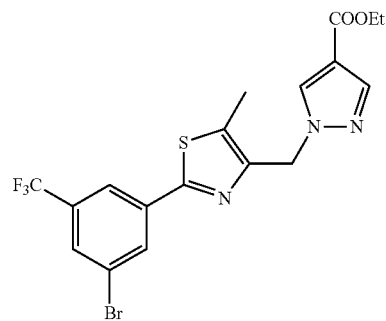

By a method similar to that in Example 71c, the title compound (2.4 g, 60%) was obtained as colorless crystals from the compound (2.9 g, 1.3 mmol) obtained in Example 77d, oxalyl chloride (1.2 mL, 17 mmol), ethyl 1H-pyrazole-4-carboxylate (1.1 g, 9.1 mmol) and potassium carbonate (1.3 g, 11 mmol).

$^1$H NMR (300 MHz, CHLOROFORM-d) δppm 1.33 (3H, t, J=7.2 Hz), 2.56 (3H, s), 4.28 (2H, q, J=7.2 Hz), 5.40 (2H, s), 7.78 (1H, s), 7.91 (1H, s), 8.02 (2H, s), 8.19 (1H, s)

LCMS (ESI$^+$) M+H$^+$: 474.

Example 77

1-({2-[3-bromo-5-(trifluoromethyl)phenyl]-5-methyl-1,3-thiazol-4-yl}methyl)-1H-pyrazole-4-carboxylic acid

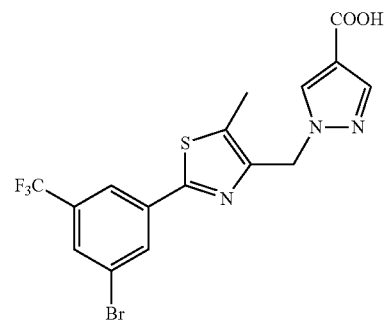

In the same manner as in Example 38, the title compound (69 mg, 91%) was obtained as colorless crystals from the compound (80 mg, 0.17 mmol) obtained in Example 77e.

$^1$H NMR (300 MHz, DMSO-d$_6$) δ ppm 2.57 (3H, s), 5.48 (2H, s), 7.80 (1H, s), 8.08 (2H, s), 8.27 (1H, s), 8.35 (1H, s), 12.23 (1H, br. s.)

LCMS (ESI$^+$) M+H$^+$: 446.

Example 78

1-[(5-methyl-2-[3-[(E)-2-phenylethenyl]-5-(trifluoromethyl)phenyl]-1,3-thiazol-4-yl)methyl]-1H-pyrazole-4-carboxylic acid

Example 78a ethyl 1-[(5-methyl-2-{3-[(E)-2-phenylethenyl]-5-(trifluoromethyl)phenyl}-1,3-thiazol-4-yl)methyl]-1H-pyrazole-4-carboxylate

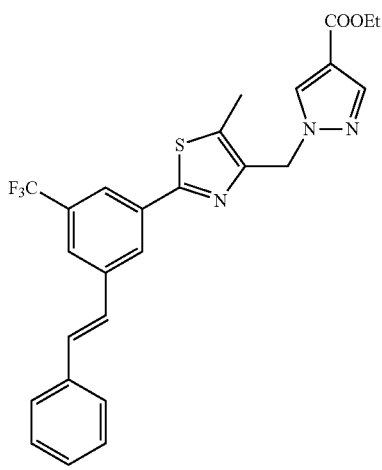 [SMILES: CCOC(=O)c1cnn(Cc2nc(-c3cc(/C=C/c4ccccc4)cc(C(F)(F)F)c3)sc2C)c1]

Under a nitrogen atmosphere, to a mixed solution of the compound (220 mg, 0.46 mmol) obtained in Example 77e, (E)-2-phenylvinylboronic acid (100 mg, 0.70 mmol) and 2N aqueous sodium carbonate solution (0.28 mL, 0.55 mmol) in 1,2-dimethoxyethane/ethanol (v/v=3/1, 4 mL) was added [1,1'-bis(diphenylphosphino)ferrocene]dichloropalladium (II) dichloromethane complex (38 mg, 0.046 mmol), and the mixture was stirred at 90° C. overnight. The solvent was evaporated under reduced pressure and the resulting crude title compound was purified by column chromatography (hexane-hexane/ethyl acetate=80/20) to give the title compound (210 mg, 92%) as a pale-yellow solid.

$^1$H NMR (300 MHz, CHLOROFORM-d) δppm 1.32 (3H, t, J=7.2 Hz), 2.56 (3H, s), 4.28 (2H, q, J=6.9 Hz), 5.42 (2H, s), 7.09-7.46 (5H, m), 7.56 (2H, d, J=7.2 Hz), 7.78 (1H, s), 7.92 (1H, s), 7.97 (1H, s), 8.04 (1H, s), 8.14 (1H, s)

LCMS (ESI$^+$) M+H$^+$: 498.

Example 78

1-[(5-methyl-2-{3-[(E)-2-phenylethenyl]-5-(trifluoromethyl)phenyl}-1,3-thiazol-4-yl)methyl]-1H-pyrazole-4-carboxylic acid

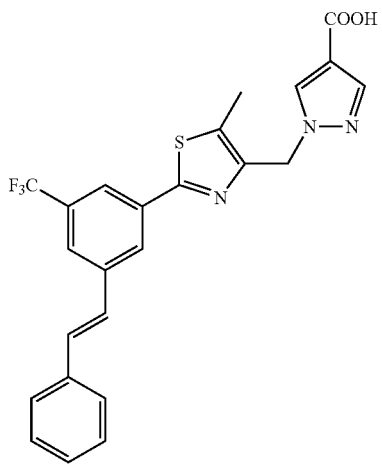 [SMILES: Cc1sc(-c2cc(/C=C/c3ccccc3)cc(C(F)(F)F)c2)nc1Cn1cc(C(=O)O)cn1]

In the same manner as in Example 38, the title compound (143 mg, 71%) was obtained as colorless crystals from the compound (210 mg, 0.42 mmol) obtained in Example 78a.

$^1$H NMR (300 MHz, DMSO-d$_6$) δ ppm 2.57 (3H, s), 5.50 (2H, s), 7.24-7.62 (5H, m), 7.68 (2H, d, J=7.2 Hz), 7.81 (1H, s), 7.98 (1H, s), 8.09 (1H, s), 8.26 (1H, s), 8.34 (1H, s), 12.36 (1H, br. s.)

LCMS (ESI$^+$) M+H$^+$: 470.

Example 79

1-({5-methyl-2-[3-(2-phenylethyl)-5-(trifluoromethyl)phenyl]-1,3-thiazol-4-yl}methyl)-1H-pyrazole-4-carboxylic acid

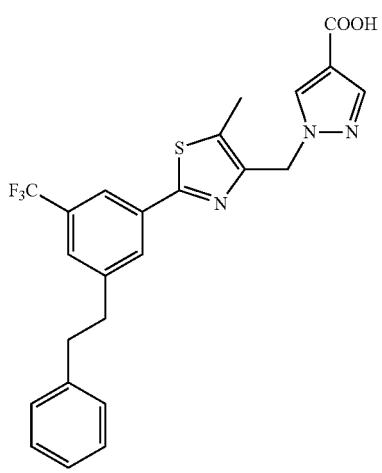 [SMILES: Cc1sc(-c2cc(CCc3ccccc3)cc(C(F)(F)F)c2)nc1Cn1cc(C(=O)O)cn1]

To a solution (4 mL) of the compound (95 mg, 0.20 mmol) obtained in Example 78 in ethanol was added palladium-carbon (10 mg), and the mixture was stirred under a hydrogen atmosphere (1 atm) at room temperature overnight. Palladium-carbon was removed and the solvent was evaporated under reduced pressure. The resulting crude title compound was recrystallized (hexane-ethyl acetate) to give the title compound (61 mg, 66%) as colorless crystals.

$^1$H NMR (300 MHz, DMSO-$d_6$) δ ppm 2.55 (3H, s), 2.85-2.99 (2H, m), 3.00-3.12 (2H, m), 5.47 (2H, s), 7.10-7.33 (5H, m), 7.65 (1H, s), 7.80 (1H, s), 7.91 (2H, s), 8.32 (1H, s), 12.36 (1H, br. s.)

LCMS (ESI$^+$) M+H$^+$: 472.

Example 80

1-({2-[2-fluoro-3-(trifluoromethyl)phenyl]-5-methyl-1,3-thiazol-4-yl}methyl)-1H-pyrazole-4-carboxylic acid

Example 80a methyl 2-amino-5-methyl-1,3-thiazole-4-carboxylate

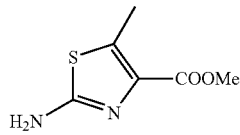

Under a nitrogen atmosphere at 0° C., to a solution of 2-oxobutyric acid (12 g, 120 mmol) in methanol was added thionyl chloride (40 mL, 330 mmol), and the mixture was stirred at the same temperature for 3 hr. The solvent was evaporated under reduced pressure. Under a nitrogen atmosphere at 0° C., to a solution (50 mL) of the residue in diethyl ether was slowly added dropwise a solution (50 mL) of bromine (10 g, 130 mmol) in diethyl ether, and the mixture was stirred overnight while allowing the mixture to spontaneously warm. The solvent was evaporated under reduced pressure. An aqueous solution (120 mL) of the residue and thiourea (6.3 g, 83 mmol) was heated under reflux for 3 hr, and cooled to room temperature. The reaction mixture was neutralized with 20% aqueous ammonia solution. The resulting crude title compound was collected by filtration, washed with water to give the title compound (3.3 g, 23%) as a colorless solid.

$^1$H NMR (300 MHz, DMSO-$d_6$) δ ppm 2.47 (3H, s), 3.71 (3H, s), 6.94 (2H, s)

Example 80b methyl 2-bromo-5-methyl-1,3-thiazole-4-carboxylate

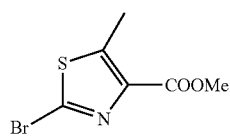

To a solution (60 mL) of copper(II) bromide (13 g, 58 mmol) in acetonitrile was slowly added dropwise tert-butyl nitrate (3.0 g, 29 mmol), and the mixture was stirred at 60° C. for 5 min. To the reaction mixture was added dropwise a solution (60 ml) of the compound (3.3 g, 19 mmol) obtained in Example 80a in acetonitrile, and the mixture was stirred at 60° C. for 4 hr. To the reaction mixture was added a 1N aqueous sodium hydroxide solution, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (3.8 g, 84%) as a green solid.

$^1$H NMR (300 MHz, DMSO-$d_6$) δ ppm 2.68 (3H, s), 3.32 (3H, s)

Example 80c (2-bromo-5-methyl-1,3-thiazol-4-yl)methyl acetate

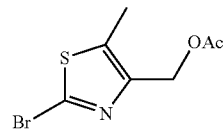

Under a nitrogen atmosphere at 0° C., to a solution (20 mL) of lithium aluminum hydride (2.3 g, 61 mmol) in tetrahydrofuran was slowly added dropwise a solution (30 mL) of the compound (3.6 g, 15 mmol) obtained in Example 80b in tetrahydrofuran, and the mixture was stirred at the same temperature for 30 min. To the reaction mixture was added sodium sulfate decahydrate and the mixture was stirred at room temperature for 30 min. The resulting salt was removed by filtration, and the solvent was evaporated under reduced pressure.

To a solution of the residue in tetrahydrofuran solution (30 mL) was added acetyl chloride (1.6 g, 20 mmol) and triethylamine (3.2 mL, 23 mmol), and the mixture was stirred at 0° C. for 30 min. The resulting salt was removed by filtration and the solvent was evaporated under reduced pressure.

To a solution (20 mL) of the residue in acetonitrile was added N-bromosuccinimide (3.3 g, 18 mmol), and the mixture was stirred at 70° C. for 2 hr. An aqueous sodium thiosulfate solution was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (1.2 g, 32%) as a yellow oil.

$^1$H NMR (300 MHz, CHLOROFORM-d) δppm 2.09 (3H, s), 2.45 (3H, s), 5.07 (2H, s)

LCMS (ESI$^+$) M+H$^+$: 250.

Example 80d (2-bromo-5-methyl-1,3-thiazol-4-yl)methanol

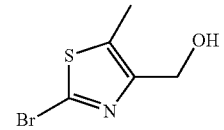

To a mixed solution of the compound (1.2 g, 4.8 mmol) obtained in Example 80c in ethanol/tetrahydrofuran (v/v=1/1, 4 mL) was added 2N aqueous sodium hydroxide solution (4.8 mL, 9.6 mmol), and the mixture was stirred at room temperature overnight. The reaction mixture was neutralized with 1N hydrochloric acid, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=50/50) to give the title compound (590 mg, 59%) as a colorless solid.

$^1$H NMR (300 MHz, CHLOROFORM-d) δ ppm 2.41 (3H, s), 4.63 (2H, s)

LCMS (ESI$^+$) M+H$^+$: 208.

Example 80e ethyl 1-[(2-bromo-5-methyl-1,3-thiazol-4-yl)methyl]-1H-pyrazole-4-carboxylate

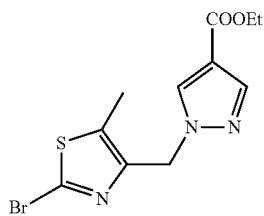 [SMILES: CCOC(=O)c1cnn(Cc2nc(Br)sc2C)c1]

Under a nitrogen atmosphere at 0° C., to a solution (10 mL) of the compound (590 mg, 2.8 mmol) obtained in Example 80d, triphenylphosphine (970 mg, 3.7 mmol) and ethyl 1H-pyrazole-4-carboxylate (480 mg, 3.4 mmol) in tetrahydrofuran was added diisopropyl azodicarboxylate (1.9 M toluene solution, 1.9 mL, 3.7 mmol), and the mixture was stirred at the same temperature for 2 hr. Saturated aqueous ammonium chloride solution was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (940 mg, 100%) as a yellow oil.

$^1$H NMR (300 MHz, CHLOROFORM-d) δ ppm 1.34 (3H, t, J=7.1 Hz), 2.46 (3H, s), 4.28 (2H, q, J=7.1 Hz), 5.29 (2H, s), 7.89 (1H, s), 7.99 (1H, s)

LCMS (ESI$^+$) M+H$^+$: 330.

Example 80f ethyl 1-({2-[2-fluoro-3-(trifluoromethyl)phenyl]-5-methyl-1,3-thiazol-4-yl}methyl)-1H-pyrazole-4-carboxylate

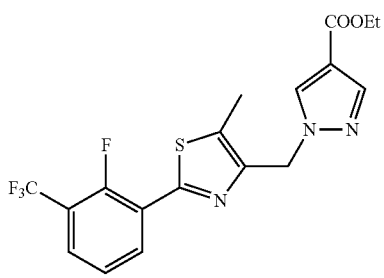 [SMILES: CCOC(=O)c1cnn(Cc2nc(-c3cccc(C(F)(F)F)c3F)sc2C)c1]

Under a nitrogen atmosphere, to a mixed solution of the compound (230 mg, 0.71 mmol) obtained in Example 80e and 2-fluoro-3-(trifluoromethyl)phenylboronic acid (190 mg, 0.92 mmol) in 1,2-dimethoxyethane/ethanol (v/v=3/1, 4 mL) were added 2N aqueous sodium carbonate solution (0.71 mL, 1.4 mmol) and [1,1'-bis(diphenylphosphino)ferrocene]dichloropalladium(II) dichloromethane complex (60 mg, 0.071 mmol), and the mixture was stirred at 90° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=75/25) to give the title compound (200 mg, 68%) as colorless crystals.

$^1$H NMR (300 MHz, CHLOROFORM-d) δ ppm 1.32 (3H, t, J=7.2 Hz), 2.56 (3H, s), 4.27 (2H, q, J=7.2 Hz), 5.43 (2H, s), 7.35 (1H, t, J=8.0 Hz), 7.65 (1H, t, J=7.2 Hz), 7.91 (1H, s), 8.01 (1H, s), 8.44 (1H, t, J=7.3 Hz)

LCMS (ESI$^+$) M+H$^+$: 414.

Example 80

1-({2-[2-fluoro-3-(trifluoromethyl)phenyl]-5-methyl-1,3-thiazol-4-yl}methyl)-1H-pyrazole-4-carboxylic acid

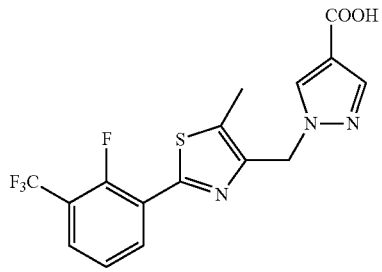

To a mixed solution of the compound (200 mg, 0.48 mmol) obtained in Example 80f in ethanol/tetrahydrofuran (v/v=1/1, 4 mL) was added 2N aqueous sodium hydroxide solution (0.97 mL, 1.9 mmol), and the mixture was stirred at room temperature overnight. Water was added to the reaction mixture, and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (150 mg, 81%) as colorless crystals.

$^1$H NMR (300 MHz, DMSO-d$_6$) δ ppm 2.58 (3H, s), 5.50 (2H, s), 7.56 (1H, t, J=7.7 Hz), 7.77 (1H, s), 7.89 (1H, t, J=6.8 Hz), 8.29 (1H, s), 8.40 (1H, t, J=7.7 Hz), 12.39 (1H, br. s.)

LCMS (ESI$^+$) M+H$^+$: 386.

Example 81

1-({2-[4-fluoro-3-(trifluoromethyl)phenyl]-5-methyl-1,3-thiazol-4-yl}methyl)-1H-pyrazole-4-carboxylic acid

Example 81a ethyl 1-({2-[4-fluoro-3-(trifluoromethyl)phenyl]-5-methyl-1,3-thiazol-4-yl}methyl)-1H-pyrazole-4-carboxylate

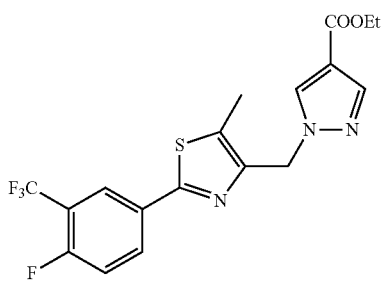 [SMILES: CCOC(=O)c1cnn(Cc2nc(-c3ccc(F)c(C(F)(F)F)c3)sc2C)c1]

In the same manner as in Example 80f, the title compound (160 mg, 40%) was obtained as a colorless solid from the compound (230 mg, 0.71 mmol) obtained in Example 80e, 4-fluoro-3-trifluoromethylphenylboronic acid (190 mg, 0.92 mmol), 2N aqueous sodium carbonate solution (0.71 mL, 1.4 mmol), [1,1'-bis(diphenylphosphino)ferrocene]dichloropalladium(II) dichloromethane complex (60 mg, 0.071 mmol).

$^1$H NMR (300 MHz, CHLOROFORM-d) δppm 1.33 (3H, t, J=7.2 Hz), 2.54 (3H, s), 4.28 (2H, q, J=6.9 Hz), 5.39 (2H, s), 7.20-7.32 (1H, m), 7.91 (1H, s), 7.97-8.07 (2H, m), 8.11 (1H, dd, J=6.4, 1.9 Hz)

LCMS (ESI$^+$) M+H$^+$: 414.

Example 81

1-({2-[4-fluoro-3-(trifluoromethyl)phenyl]-5-methyl-1,3-thiazol-4-yl}methyl)-1H-pyrazole-4-carboxylic acid

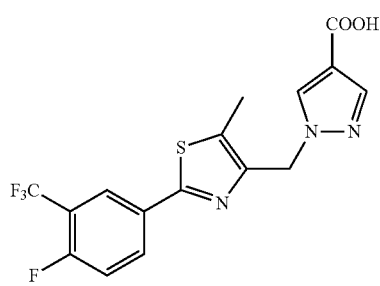 [SMILES: Cc1sc(-c2ccc(F)c(C(F)(F)F)c2)nc1Cn1cc(C(=O)O)cn1]

In the same manner as in Example 38, the title compound (110 mg, 69%) was obtained as colorless crystals from the compound (160 mg, 0.40 mmol) obtained in Example 81a.

$^1$H NMR (300 MHz, DMSO-d$_6$) δ ppm 2.55 (3H, s), 5.47 (2H, s), 7.64 (1H, t, J=9.7 Hz), 7.80 (1H, s), 8.07-8.24 (2H, m), 8.33 (1H, s), 12.36 (1H, br. s.)

LCMS (ESI$^+$) M+H$^+$: 386.

Example 82

1-({2-[3-fluoro-5-(trifluoromethyl)phenyl]-5-methyl-1,3-thiazol-4-yl}methyl)-1H-pyrazole-4-carboxylic acid

Example 82a ethyl 1-({2-[3-fluoro-5-(trifluoromethyl)phenyl]-5-methyl-1,3-thiazol-4-yl}methyl)-1H-pyrazole-4-carboxylate

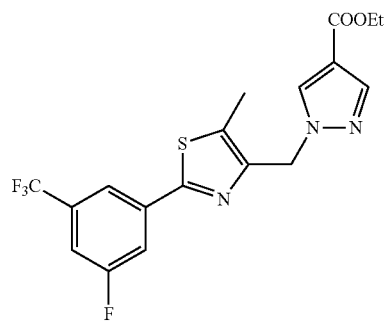 [SMILES: CCOC(=O)c1cnn(Cc2nc(-c3cc(F)cc(C(F)(F)F)c3)sc2C)c1]

In the same manner as in Example 52a, the title compound (210 mg, 72%) was obtained as colorless crystals from the compound (230 mg, 0.71 mmol) obtained in Example 80e, 3-fluoro-5-trifluoromethylphenylboronic acid (190 mg, 0.92 mmol), 2N aqueous sodium carbonate solution (0.71 mL, 1.4 mmol), and [1,1'-bis(diphenylphosphino)ferrocene]dichloropalladium(II) dichloromethane complex (60 mg, 0.071 mmol).

$^1$H NMR (300 MHz, CHLOROFORM-d) δppm 1.33 (3H, t, J=6.9 Hz), 2.56 (3H, s), 4.28 (2H, q, J=6.9 Hz), 5.40 (2H, s), 7.35 (1H, d, J=8.3 Hz), 7.77 (1H, d, J=9.1 Hz), 7.84-7.94 (2H, m), 8.02 (1H, s)

LCMS (ESI$^+$) M+H$^+$: 414.

Example 82

1-({2-[3-fluoro-5-(trifluoromethyl)phenyl]-5-methyl-1,3-thiazol-4-yl}methyl)-1H-pyrazole-4-carboxylic acid

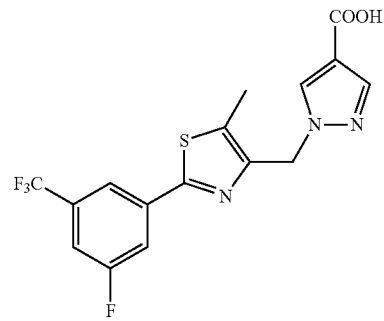 [SMILES: Cc1sc(-c2cc(F)cc(C(F)(F)F)c2)nc1Cn1cc(C(=O)O)cn1]

In the same manner as in Example 38, the title compound (160 mg, 82%) was obtained as colorless crystals from the compound (210 mg, 0.51 mmol) obtained in Example 82a.

$^1$H NMR (300 MHz, DMSO-d$_6$) δ ppm 2.57 (3H, s), 5.49 (2H, s), 7.76-7.86 (2H, m), 7.93-8.02 (2H, m), 8.35 (1H, s), 12.21 (1H, br. s.)

LCMS (ESI$^+$) M+H$^+$: 386.

Example 83

1-({2-[3-chloro-5-(trifluoromethyl)phenyl]-5-methyl-1,3-thiazol-4-yl}methyl)-1H-pyrazole-4-carboxylic acid

Example 83a ethyl 1-({2-[3-chloro-5-(trifluoromethyl)phenyl]-5-methyl-1,3-thiazol-4-yl}methyl)-1H-pyrazole-4-carboxylate

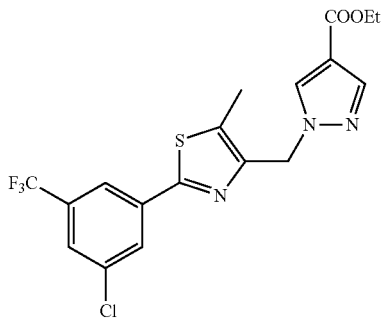 [SMILES: CCOC(=O)c1cnn(Cc2nc(-c3cc(Cl)cc(C(F)(F)F)c3)sc2C)c1]

Under a nitrogen atmosphere, to a solution of the compound (230 mg, 0.71 mmol) obtained in Example 80e and 3-chloro-5-trifluoromethylphenylboronic acid (210 mg, 0.92 mmol) in 1,2-dimethoxyethane/ethanol (v/v=3/1, 4 mL) were added 2N aqueous sodium carbonate solution (0.71 mL, 1.4 mmol) and [1,1'-bis(diphenylphosphino)ferrocene]dichloropalladium(II) dichloromethane complex (60 mg, 0.071 mmol), and the mixture was stirred at 90° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=75/25) to give the title compound (230 mg, 76%) as colorless crystals.

$^1$H NMR (300 MHz, CHLOROFORM-d) δppm 1.33 (3H, t, J=7.2 Hz), 2.56 (3H, s), 4.28 (2H, q, J=7.2 Hz), 5.40 (2H, s), 7.63 (1H, s), 7.91 (1H, s), 7.98 (1H, s), 8.02 (1H, s), 8.03 (1H, s)

LCMS (ESI$^+$) M+H$^+$: 430.

Example 83

1-({2-[3-chloro-5-(trifluoromethyl)phenyl]-5-methyl-1,3-thiazol-4-yl}methyl)-1H-pyrazole-4-carboxylic acid

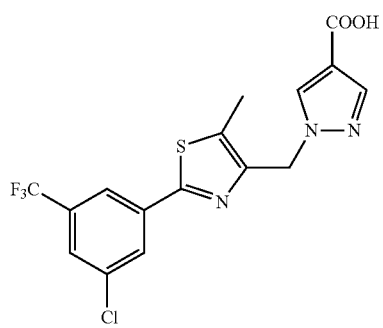 [SMILES: Cc1sc(-c2cc(Cl)cc(C(F)(F)F)c2)nc1Cn1cc(C(=O)O)cn1]

To a solution of the compound (230 mg, 0.54 mmol) obtained in Example 83a in ethanol/tetrahydrofuran (v/v=1/1, 4 mL) was added 2N aqueous sodium hydroxide solution (1.1 mL, 2.2 mmol), and the mixture was stirred at room temperature overnight. Water was added to the reaction mixture, and the aqueous layer was washed with diethyl ether, neutralized with 1N aqueous hydrochloric acid solution, and the mixture was extracted with ethyl acetate. The obtained organic layer was washed with saturated brine, and dried over anhydrous sodium sulfate. The solvent was evaporated under reduced pressure. The resulting crude title compound was recrystallized (ethyl acetate-hexane) to give the title compound (150 mg, 70%) as colorless crystals.

$^1$H NMR (300 MHz, DMSO-d$_6$) δ ppm 2.57 (3H, s), 5.48 (2H, s), 7.79 (1H, s), 7.98 (1H, s), 8.06 (1H, s), 8.15 (1H, s), 8.33 (1H, s), 12.37 (1H, br. s.)

LCMS (ESI$^+$) M+H$^+$: 402.

Example 84

1-({4-[3-cyclopropyl-5-(trifluoromethyl)phenyl]-1,3-thiazol-2-yl}methyl)-1H-pyrazole-4-carboxylic acid

Example 84a ethyl 1-({4-[3-cyclopropyl-5-(trifluoromethyl)phenyl]-1,3-thiazol-2-yl}methyl)-1H-pyrazole-4-carboxylate

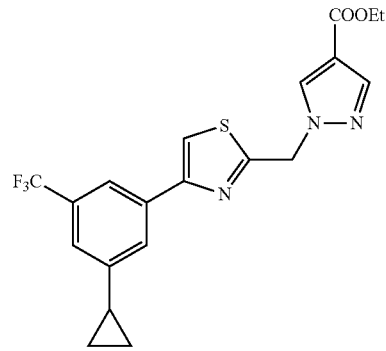 [SMILES: CCOC(=O)c1cnn(Cc2nc(-c3cc(C4CC4)cc(C(F)(F)F)c3)cs2)c1]

Under a nitrogen atmosphere, to a mixed solution of the compound (400 mg, 0.87 mmol) obtained in Example 77e, potassium cyclopropyltrifluoroborate (140 mg, 0.96 mmol), cesium carbonate (850 mg, 2.6 mmol) and di-(1-adamantyl)-n-butylphosphine (20 mg, 0.050 mmol) in toluene/water (v/v=10/1, 11 mL) was added palladium acetate (II) (8 mg, 0.030 mmol), and the mixture was stirred at 100° C. overnight. The palladium catalyst was removed by filtration and the solvent was evaporated under reduced pressure. The resulting crude title compound was purified by column chromatography (hexane-hexane/ethyl acetate=70/30) to give the title compound (240 mg, 65%) as a pale-brown solid.

$^1$H NMR (300 MHz, CHLOROFORM-d) δppm 0.74-0.88 (2H, m), 1.00-1.14 (2H, m), 1.34 (3H, t, J=7.0 Hz), 1.94-2.12 (1H, m), 4.30 (2H, q, J=7.2 Hz), 5.68 (2H, s), 7.28 (1H, s), 7.54 (1H, s), 7.77 (1H, s), 7.89 (1H, s), 8.00 (1H, s), 8.09 (1H, s)

LCMS M+H$^+$: 422.

Example 84

1-({4-[3-cyclopropyl-5-(trifluoromethyl)phenyl]-1,3-thiazol-2-yl}methyl)-1H-pyrazole-4-carboxylic acid

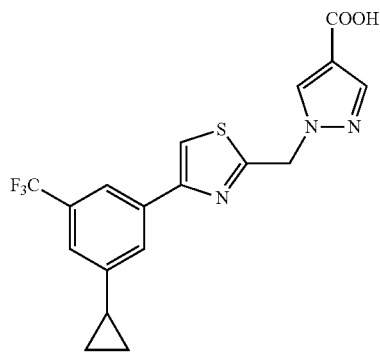 [SMILES: O=C(O)c1cnn(Cc2nc(-c3cc(C4CC4)cc(C(F)(F)F)c3)cs2)c1]

In the same manner as in Example 38, the title compound (200 mg, 89%) was obtained as colorless crystals from the compound (240 mg, 0.57 mmol) obtained in Example 84a.

$^1$H NMR (300 MHz, DMSO-$d_6$) δ ppm 0.74-0.92 (2H, m), 0.97-1.12 (2H, m), 2.02-2.22 (1H, m), 5.84 (2H, s), 7.42 (1H, s), 7.83-7.96 (2H, m), 8.03 (1H, s), 8.37 (1H, s), 8.50 (1H, s), 12.48 (1H, br. s.)

LCMS (ESI$^+$) M+H$^+$: 394.

Example 85

1-{[2-(3-bromo-5-methylphenyl)-5-methyl-1,3-thiazol-4-yl]methyl}-1H-pyrazole-4-carboxylic acid

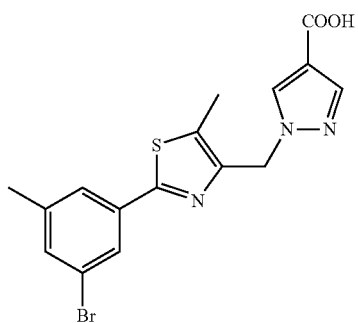 [SMILES: Cc1cc(Br)cc(-c2nc(Cn3cc(C(=O)O)cn3)c(C)s2)c1]

In the step of Example 77d, a byproduct wherein the trifluoromethyl group was reduced to a methyl group was confirmed. The title compound (93 mg) derived from the byproduct was purified by HPLC after the steps of Example 77e and Example 77 to give colorless crystals.

$^1$H NMR (300 MHz, DMSO-$d_6$) δ ppm 2.36 (3H, s), 2.54 (3H, s), 5.45 (2H, s), 7.50 (1H, s), 7.63 (1H, s), 7.78 (1H, s), 7.80 (1H, s), 8.31 (1H, s), 12.36 (1H, br. s.)

LCMS (ESI$^+$) M+H$^+$: 392.

Example 86

1-({4-[3-(pyridin-3-ylmethoxy)-5-(trifluoromethyl)phenyl]-1,3-thiazol-2-yl}methyl)-1H-pyrazole-4-carboxylic acid

Example 86a ethyl 1-({4-[3-hydroxy-5-(trifluoromethyl)phenyl]-1,3-thiazol-2-yl}methyl)-1H-pyrazole-4-carboxylate

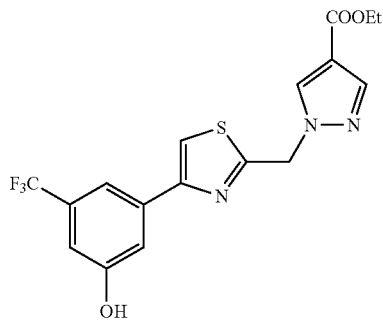 [SMILES: CCOC(=O)c1cnn(Cc2nc(-c3cc(O)cc(C(F)(F)F)c3)cs2)c1]

Under a nitrogen atmosphere at 0° C., to a solution (6 mL) of the compound (500 mg, 1.2 mmol) obtained in Example 76b in p-chlorobenzene was added boron tribromide (1 M dichloromethane solution, 3.7 mL, 3.7 mmol), and the mixture was stirred at room temperature overnight. 1N Hydrochloric acid was added to the reaction mixture, and the mixture was extracted with ethyl acetate. The obtained organic layer was washed with saturated brine, and dried over anhydrous sodium sulfate. The solvent was evaporated under reduced pressure. A solution (3 mL) of the residue in ethanol was added conc. sulfuric acid (1 drop), and the mixture was stirred at 80° C. for 3 hr. Saturated aqueous sodium hydrogen carbonate was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=50/50) to give the title compound (180 mg, 37%) as a colorless solid.

$^1$H NMR (300 MHz, CHLOROFORM-d) δppm 1.35 (3H, t, J=7.2 Hz), 4.31 (2H, q, J=6.9 Hz), 5.67 (2H, s), 6.09 (1H, s), 7.05 (1H, s), 7.45-7.56 (2H, m), 7.64 (1H, s), 8.01 (1H, s), 8.12 (1H, s)

LCMS (ESI$^+$) M+H$^+$: 398.

Example 86b ethyl 1-({4-[3-(pyridin-3-ylmethoxy)-5-(trifluoromethyl)phenyl]-1,3-thiazol-2-yl}methyl)-1H-pyrazole-4-carboxylate

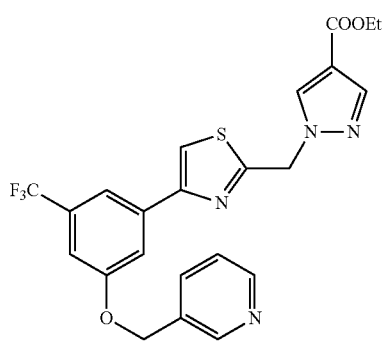 [SMILES: CCOC(=O)c1cnn(Cc2nc(-c3cc(OCc4cccnc4)cc(C(F)(F)F)c3)cs2)c1]

Under a nitrogen atmosphere at 0° C., to a solution (7 mL) of the compound (300 mg, 0.75 mmol) obtained in Example 86a, 3-pyridinemethanol (0.088 mL, 0.91 mmol) and triphenylphosphine (260 mg, 0.98 mmol) in tetrahydrofuran was added diisopropyl azodicarboxylate (1.9M toluene solution, 0.51 mL, 0.98 mmol), and the mixture was stirred at room temperature overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=50/50) to give the title compound (370 mg, 100%) as a colorless solid.

$^1$H NMR (300 MHz, CHLOROFORM-d) δppm 1.34 (3H, t, J=7.2 Hz), 4.30 (2H, q, J=7.2 Hz), 5.32 (2H, s), 5.69 (2H, s), 7.21 (1H, br. s.), 7.61 (1H, br. s.), 7.77 (3H, br. s.), 8.00 (1H, br. s.), 8.12 (1H, br. s.), 8.26 (1H, br. s.), 8.78 (1H, br. s.), 8.97 (1H, br. s.)

LCMS (ESI$^+$) M+H$^+$: 489.

Example 86

1-({4-[3-(pyridin-3-ylmethoxy)-5-(trifluoromethyl)phenyl]-1,3-thiazol-2-yl}methyl)-1H-pyrazole-4-carboxylic acid

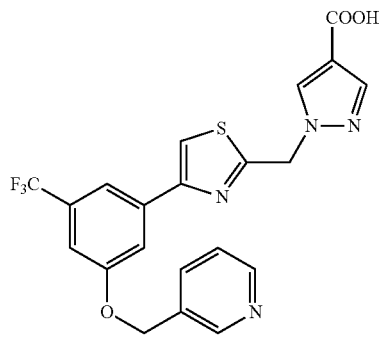 [SMILES: O=C(O)c1cnn(Cc2nc(-c3cc(OCc4cccnc4)cc(C(F)(F)F)c3)cs2)c1]

In the same manner as in Example 38, the title compound (110 mg, 32%) was obtained as colorless crystals from the compound (370 mg, 0.75 mmol) obtained in Example 86b.

$^1$H NMR (400 MHz, DMSO-d$_6$+DCl in D$_2$O) δ ppm 5.57 (2H, s), 5.86 (2H, s), 7.43 (1H, s), 7.89-8.05 (3H, m), 8.10-8.26 (1H, m), 8.45 (1H, s), 8.54 (1H, s), 8.80 (1H, d, J=8.1 Hz), 8.97 (1H, d, J=5.6 Hz), 9.14 (1H, s)

LCMS (ESI$^+$) M+H$^+$: 461.

Example 87

1-[(4-{3-[(Z)-2-pyridin-3-ylethenyl]-5-(trifluoromethyl)phenyl}-1,3-thiazol-2-yl)methyl]-1H-pyrazole-4-carboxylic acid Example 87a ethyl 1-({4-[3-(pyridin-3-ylethynyl)-5-(trifluoromethyl)phenyl]-1,3-thiazol-2-yl}methyl)-1H-pyrazole-4-carboxylate

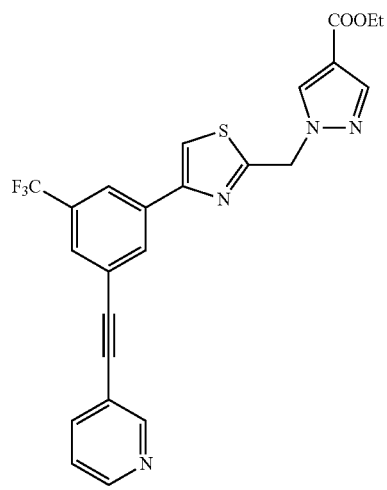 [SMILES: CCOC(=O)c1cnn(Cc2nc(-c3cc(C#Cc4cccnc4)cc(C(F)(F)F)c3)cs2)c1]

Under a nitrogen atmosphere, to a solution (2 mL) of the compound (500 mg, 1.1 mmol) obtained in Example 68b, 3-ethenylpyridine (170 mg, 1.6 mmol), triethylamine (0.30 mL, 2.2 mmol) and copper iodide(I) (42 mg, 0.22 mmol) in N,N-dimethylformamide was added tetrakistriphenylphosphinepalladium (22 mg, 0.11 mmol), and the mixture was stirred at 100° C. overnight. The palladium catalyst was removed by filtration and the solvent was evaporated under reduced pressure. The resulting crude title compound was purified by column chromatography (hexane-hexane/ethyl acetate=70/30) to give the title compound (250 mg, 47%) as a colorless solid.

$^1$H NMR (300 MHz, CHLOROFORM-d) δppm 1.34 (3H, t, J=7.2 Hz), 4.30 (2H, q, J=6.9 Hz), 5.69 (2H, s), 7.33 (1H, dd, J=8.0, 4.9 Hz), 7.63 (1H, s), 7.78 (1H, s), 7.85 (1H, dt, J=8.0, 1.9 Hz), 8.01 (1H, s), 8.11 (1H, s), 8.14 (1H, s), 8.23 (1H, s), 8.60 (1H, d, J=3.8 Hz), 8.81 (1H, s)

LCMS (ESI$^+$) M+H$^+$: 483.

Example 87b ethyl 1-[(4-{3-[(Z)-2-pyridin-3-ylethenyl]-5-(trifluoromethyl)phenyl}-1,3-thiazol-2-yl)methyl]-1H-pyrazole-4-carboxylate

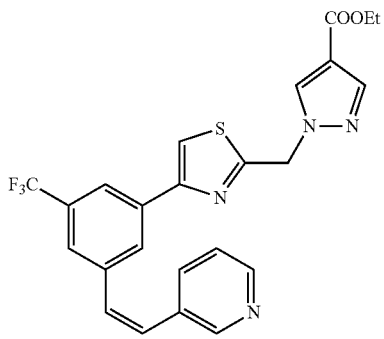 [SMILES: CCOC(=O)c1cnn(Cc2nc(-c3cc(/C=C\c4cccnc4)cc(C(F)(F)F)c3)cs2)c1]

To a solution (10 mL) of the compound (980 mg, 2.0 mmol) obtained in Example 87a in ethanol were added pyridine (480 mg, 6.1 mmol) and palladium-barium sulfate (490 mg), and the mixture was stirred at room temperature for 5 hr under a hydrogen atmosphere (1 atm). Palladium-carbon was removed and the solvent was evaporated under reduced pressure. The resulting crude title compound was purified by column chromatography (hexane-hexane/ethyl acetate=35/65) to give the title compound (450 mg, 46%) as colorless crystals.

$^1$H NMR (300 MHz, CHLOROFORM-d) δppm 1.34 (3H, t, J=7.2 Hz), 4.30 (2H, q, J=7.2 Hz), 5.64 (2H, s), 6.64-6.86 (2H, m), 7.15 (1H, dd, J=7.6, 4.9 Hz), 7.37 (1H, s), 7.42 (1H, s), 7.52 (1H, d, J=8.0 Hz), 7.87 (1H, s), 7.96-8.03 (2H, m), 8.07 (1H, s), 8.43-8.57 (2H, m)

LCMS (ESI$^+$) M+H$^{30}$: 485.

Example 87

1-[(4-{3-[(Z)-2-pyridin-3-ylethenyl]-5-(trifluoromethyl)phenyl}-1,3-thiazol-2-yl)methyl]-1H-pyrazole-4-carboxylic acid

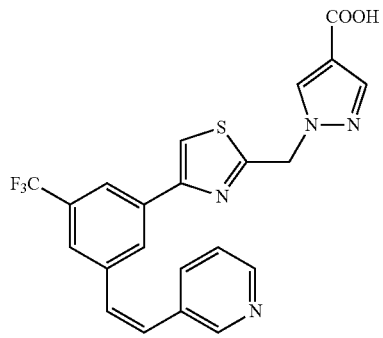 [SMILES: O=C(O)c1cnn(Cc2nc(-c3cc(/C=C\c4cccnc4)cc(C(F)(F)F)c3)cs2)c1]

In the same manner as in Example 38, the title compound (130 mg, 94%) was obtained as colorless crystals from the compound (150 mg, 0.31 mmol) obtained in Example 87b.

$^1$H NMR (300 MHz, DMSO-d$_6$) δ ppm 5.79 (2H, s), 6.77-7.05 (2H, m), 7.30 (1H, dd, 3=7.8, 4.7 Hz), 7.42 (1H, s), 7.60 (1H, d, J=8.0 Hz), 7.91 (1H, s), 8.14 (1H, s), 8.10 (1H, s), 8.25 (1H, s), 8.36-8.54 (3H, m), 12.48 (1H, br. s.)

LCMS (ESI$^+$) M+H$^+$: 457.

Example 88

1-[(4-[3-[(2,4-difluorobenzyl)oxy]-5-(trifluoromethyl)phenyl]-1,3-thiazol-2-yl)methyl]-1H-pyrazole-4-carboxylic acid

Example 88a ethyl 1-[(4-{3-[(2,4-difluorobenzyl)oxy]-5-(trifluoromethyl)phenyl}-1,3-thiazol-2-yl)methyl]-1H-pyrazole-4-carboxylate

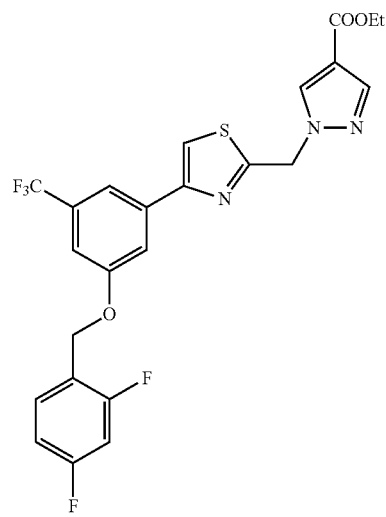 [SMILES: CCOC(=O)c1cnn(Cc2nc(-c3cc(OCc4ccc(F)cc4F)cc(C(F)(F)F)c3)cs2)c1]

By a method similar to that in Example 86b, the title compound (390 mg, 100%) was obtained as a colorless solid from the compound (300 mg, 0.75 mmol) obtained in Example 86a, 2,4-difluorobenzylalcohol (130 mg, 0.91 mmol), triphenylphosphine (260 mg, 0.98 mmol), diisopropyl azodicarboxylate (1.9M toluene solution, 0.51 mL, 0.98 mmol).

$^1$H NMR (300 MHz, CHLOROFORM-d) δppm 1.34 (3H, t, J=7.0 Hz), 4.30 (2H, q, J=7.2 Hz), 5.17 (2H, s), 5.71 (2H, s), 6.79-7.02 (2H, m), 7.20 (1H, s), 7.43-7.55 (1H, m), 7.56 (1H, s), 7.68 (1H, s), 7.73 (1H, s), 8.03 (1H, s), 8.12 (1H, s)

LCMS (ESI$^+$) M+H$^+$: 524.

Example 88

1-[(4-{3-[(2,4-difluorobenzyl)oxy]-5-(trifluoromethyl)phenyl}-1,3-thiazol-2-yl)methyl]-1H-pyrazole-4-carboxylic acid

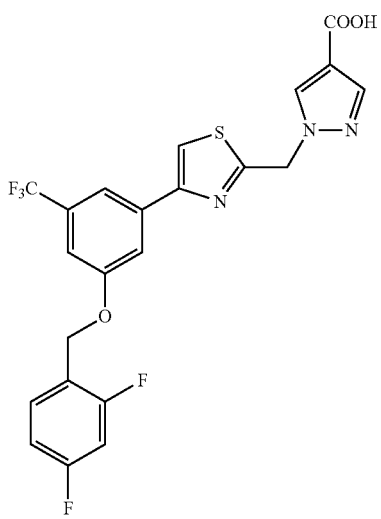 [SMILES: O=C(O)c1cnn(Cc2nc(-c3cc(OCc4ccc(F)cc4F)cc(C(F)(F)F)c3)cs2)c1]

In the same manner as in Example 38, the title compound (300 mg, 80%) was obtained as colorless crystals from the compound (390 mg, 0.75 mmol) obtained in Example 88a.

$^1$H NMR (300 MHz, DMSO-$d_6$) δ ppm 5.28 (2H, s), 5.83 (2H, s), 7.09-7.22 (1H, m), 7.27-7.40 (2H, m), 7.62-7.75 (1H, m), 7.90 (2H, s), 7.92 (1H, s), 8.41 (1H, s), 8.50 (1H, s), 12.47 (1H, br. s.)

LCMS (ESI$^+$) M+H$^+$: 496.

Example 89

1-({5-(fluoromethyl)-2-[3-(trifluoromethyl)phenyl]-1,3-thiazol-4-yl}methyl)-1H-pyrazole-4-carboxylic acid

Example 89a

4-[(tetrahydro-2H-pyran-2-yloxy)methyl]-2-[3-(trifluoromethyl)phenyl]-1,3-thiazole

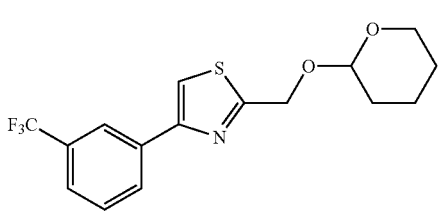 [SMILES: FC(F)(F)c1cccc(-c2csc(COC3CCCCO3)n2)c1]

To a solution (50 mL) of the compound (7.0 g, 27 mmol) obtained in Example 64b in toluene were added dihydropyran (4.9 mL, 54 mmol) and conc. sulfuric acid (3 drops), and the mixture was stirred at room temperature overnight. The reaction mixture was neutralized with saturated aqueous sodium hydrogen carbonate, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=80/20) to give the title compound (9.2 g, 99%) as a pale-yellow oil.

$^1$H NMR (300 MHz, CHLOROFORM-d) δppm 1.53-1.93 (6H, m), 3.42-3.67 (1H, m), 3.82-4.00 (1H, m), 4.73 (1H, d, J=14.0 Hz), 4.82 (1H, t, J=3.4 Hz), 4.95 (1H, d, J=12.1 Hz), 7.31 (1H, s), 7.56 (1H, t, J=7.8 Hz), 7.67 (1H, d, J=8.0 Hz), 8.12 (1H, d, J=7.6 Hz), 8.23 (1H, s)

LCMS (ESI$^+$) M+H$^+$: 344.

Example 89b

4-[(tetrahydro-2H-pyran-2-yloxy)methyl]-2-[3-(trifluoromethyl)phenyl]-1,3-thiazole-5-carbaldehyde

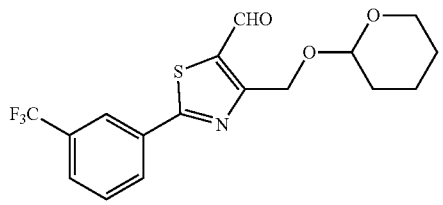 [SMILES: O=Cc1sc(-c2cccc(C(F)(F)F)c2)nc1COC1CCCCO1]

Under a nitrogen atmosphere at -78° C., to a solution (100 mL) of the compound (8.0 g, 23 mmol) obtained in Example 89a in tetrahydrofuran was added n-butyllithium (1.6M hexane solution, 18 mL, 28 mmol), and the mixture was stirred at the same temperature for 1 hr. Anhydrous N,N-dimethylformamide (2.3 mL, 30 mmol) was added to the reaction mixture, and the mixture was stirred at -78° C. for 3 hr. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=80/20) to give the title compound (5.5 g, 64%) as a pale-yellow solid.

$^1$H NMR (300 MHz, CHLOROFORM-d) δppm 1.52-1.91 (6H, m), 3.52-3.69 (1H, m), 3.81-3.99 (1H, m), 4.86 (1H, t, J=3.0 Hz), 4.99 (1H, d, J=14.0 Hz), 5.25 (1H, d, J=13.6 Hz), 7.62 (1H, t, J=7.8 Hz), 7.76 (1H, d, J=7.6 Hz), 8.16 (1H, d, J=8.0 Hz), 8.30 (1H, s), 10.42 (1H, s)

Example 89c

{4-[(tetrahydro-2H-pyran-2-yloxy)methyl]-2-[3-(trifluoromethyl)phenyl]-1,3-thiazol-5-yl}methanol

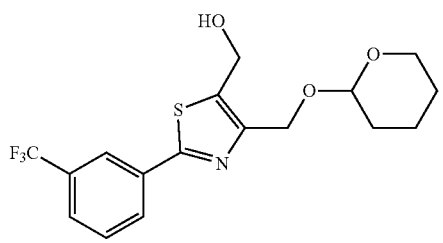 [SMILES: OCc1sc(-c2cccc(C(F)(F)F)c2)nc1COC1CCCCO1]

To a mixed solution of the compound (2.2 g, 5.9 mmol) obtained in Example 89b in tetrahydrofuran/ethanol (v/v=1/1, 10 mL) was added sodium tetrahydroborate (340 mg, 8.9 mmol), and the mixture was stirred at 0° C. for 5 hr. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=50/50) to give the title compound (2.0 g, 92%) as a colorless oil.

$^1$H NMR (300 MHz, CHLOROFORM-d) δppm 1.51-1.90 (6H, m), 3.43 (1H, t, J=6.4 Hz), 3.53-3.69 (1H, m), 3.79-3.97 (1H, m), 4.69-5.00 (4H, m), 7.55 (1H, t, J=8.0 Hz), 7.66 (1H, d, J=7.2 Hz), 8.07 (1H, d, J=7.6 Hz), 8.21 (1H, s)

LCMS (ESI$^+$) M+H$^+$: 374.

Example 89d 5-(fluoromethyl)-4-[(tetrahydro-2H-pyran-2-yloxy)methyl]-2-[3-(trifluoromethyl)phenyl]-1,3-thiazole

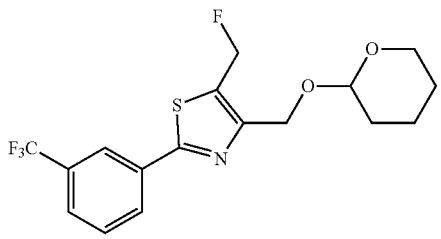 [SMILES: FCc1sc(-c2cccc(C(F)(F)F)c2)nc1COC1CCCCO1]

Under a nitrogen atmosphere at 0° C., to a solution (7 mL) of the compound (500 mg, 1.3 mmol) obtained in Example 89c in toluene was added diethylaminosulfur trifluoride (DAST) (650 mg, 4.0 mmol), and the mixture was stirred at room temperature overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=50/50) to give the title compound (350 mg, 70%) as a colorless oil.

$^1$H NMR (300 MHz, CHLOROFORM-d) δppm 1.51-1.90 (6H, m), 3.46-3.68 (1H, m), 3.84-3.99 (1H, m), 4.67-4.83 (2H, m), 4.96 (1H, dd, J=12.8, 2.3 Hz), 5.69 (2H, d, J=48.0 Hz), 7.57 (1H, t, J=7.9 Hz), 7.69 (1H, d, J=7.5 Hz), 8.10 (1H, d, J=7.5 Hz), 8.23 (1H, s)

LCMS (ESI$^+$) M+H$^+$: 376.

Example 89e

{5-(fluoromethyl)-2-[3-(trifluoromethyl)phenyl]-1,3-thiazol-4-yl}methanol

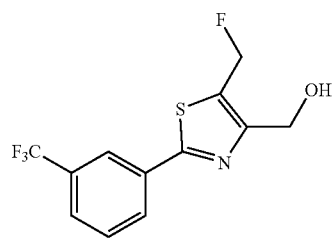 [SMILES: OCc1nc(-c2cccc(C(F)(F)F)c2)sc1CF]

To a solution (10 mL) of the compound (350 mg, 0.93 mmol) obtained in Example 89d in methanol was added p-toluenesulfonic acid monohydrate (530 mg, 2.8 mmol), and the mixture was stirred at 70° C. for 4 hr. The reaction mixture was neutralized with saturated aqueous sodium hydrogen carbonate, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=75/25) to give the title compound (150 mg, 56%) as a colorless oil.

$^1$H NMR (300 MHz, CHLOROFORM-d) δppm 2.41 (1H, t, J=5.9 Hz), 4.86 (2H, dd, J=5.7, 2.7 Hz), 5.62 (2H, d, J=49.0 Hz), 7.59 (1H, t, J=8.0 Hz), 7.71 (1H, d, J=8.0 Hz), 8.09 (1H, d, J=8.0 Hz), 8.22 (1H, s)

LCMS (ESI$^+$) M+H$^+$: 292.

Example 89f ethyl 1-({5-(fluoromethyl)-2-[3-(trifluoromethyl)phenyl]-1,3-thiazol-4-yl}methyl)-1H-pyrazole-4-carboxylate

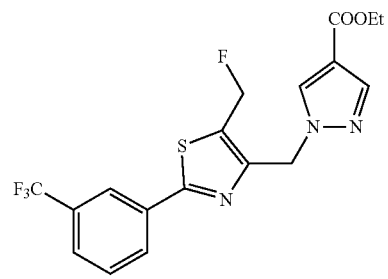 [SMILES: CCOC(=O)c1cnn(Cc2nc(-c3cccc(C(F)(F)F)c3)sc2CF)c1]

By a method similar to that of Example 80e, the title compound (210 mg, 91%) was obtained as a colorless solid from the compound (150 mg, 0.56 mmol) obtained in Example 89g and triphenylphosphine (190 mg, 0.73 mmol), ethyl 1H-pyrazole-4-carboxylate (94 mg, 0.67 mmol), and diisopropyl azodicarboxylate (1.9M toluene solution, 0.38 mL, 0.73 mmol).

$^1$H NMR (300 MHz, CHLOROFORM-d) δppm 1.33 (3H, t, J=7.1 Hz), 4.28 (2H, q, J=7.1 Hz), 5.49 (2H, d, J=1.5 Hz), 5.66 (2H, d, J=49.0 Hz), 7.58 (1H, t, J=7.8 Hz), 7.71 (1H, d, J=8.0 Hz), 7.91 (1H, s), 8.02-8.12 (2H, m), 8.18 (1H, s)

LCMS (ESI$^+$) M+H$^+$: 414.

Example 89

1-({5-(fluoromethyl)-2-[3-(trifluoromethyl)phenyl]-1,3-thiazol-4-yl}methyl)-1H-pyrazole-4-carboxylic acid

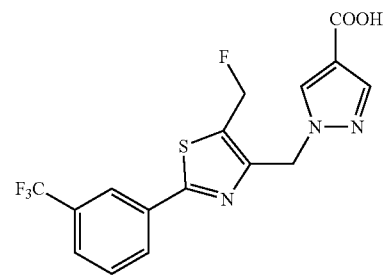 [SMILES: O=C(O)c1cnn(Cc2nc(-c3cccc(C(F)(F)F)c3)sc2CF)c1]

In the same manner as in Example 38, the title compound (140 mg, 70%) was obtained as colorless crystals from the compound (210 mg, 0.51 mmol) obtained in Example 89f.

$^1$H NMR (300 MHz, DMSO-$d_6$) δ ppm 5.62 (2H, d, J=1.5 Hz), 5.86 (2H, d, J=49.0 Hz), 7.70-7.80 (1H, m), 7.81 (1H, s), 7.90 (1H, d, J=7.9 Hz), 8.12-8.27 (2H, m), 8.38 (1H, s), 12.33 (1H, br. s.)

LCMS (ESI$^+$) M+H$^+$: 386.

Example 90

1-({5-(difluoromethyl)-2-[3-(trifluoromethyl)phenyl]-1,3-thiazol-4-yl}methyl)-1H-pyrazole-4-carboxylic acid

Example 90a 5-(difluoromethyl)-4-[(tetrahydro-2H-pyran-2-yloxy)methyl]-2-[3-(trifluoromethyl)phenyl]-1,3-thiazole

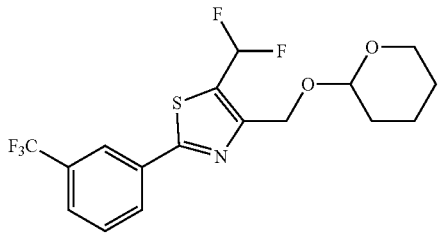 [SMILES: FC(F)c1sc(-c2cccc(C(F)(F)F)c2)nc1COC1CCCCO1]

By a method similar to that of Example 89d, the title compound (220 mg, 69%) as a colorless oil from the compound (300 mg, 0.81 mmol) obtained in Example 89b and diethylaminosulfur trifluoride (DAST) (390 mg, 2.4 mmol).

$^1$H NMR (300 MHz, CHLOROFORM-d) δppm 1.51-1.91 (6H, m), 3.48-3.68 (1H, m), 3.78-3.99 (1H, m), 4.73-4.88 (2H, m), 5.06 (1H, dt, J=13.5, 1.9 Hz), 7.33 (1H, t, J=55.0 Hz), 7.59 (1H, t, J=8.0 Hz), 7.72 (1H, d, J=8.0 Hz), 8.10 (1H, J=8.0 Hz), 8.23 (1H, s)

Example 90b ethyl 1-({5-(difluoromethyl)-2-[3-(trifluoromethyl)phenyl]-1,3-thiazol-4-yl}methyl)-1H-pyrazole-4-carboxylate

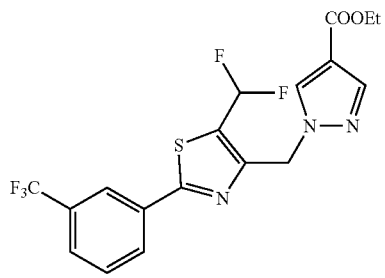 [SMILES: CCOC(=O)c1cnn(Cc2nc(-c3cccc(C(F)(F)F)c3)sc2C(F)F)c1]

By a method similar to that in Example 89e, 89f, the title compound (220 mg, 91%) as a colorless oil from the compound (220 mg, 0.56 mmol) obtained in Example 90a p-toluenesulfonic acid monohydrate (320 mg, 1.7 mmol), triphenylphosphine (190 mg, 0.73 mmol), ethyl 1H-pyrazole-4-carboxylate (94 mg, 0.67 mmol), and diisopropyl azodicarboxylate (1.9M toluene solution, 0.38 mL, 0.73 mmol).

$^1$H NMR (300 MHz, CHLOROFORM-d) δppm 1.33 (3H, t, J=7.0 Hz), 4.29 (2H, q, J=7.2 Hz), 5.51 (2H, s), 7.14 (1H, t, J=55.0 Hz), 7.60 (1H, t, J=7.7 Hz), 7.74 (1H, d, J=7.9 Hz), 7.93 (1H, s), 8.01-8.13 (2H, m), 8.19 (1H, s)

LCMS (ESI$^+$) M+H$^+$: 432.

Example 90

1-({5-(difluoromethyl)-2-[3-(trifluoromethyl)phenyl]-1,3-thiazol-4-yl}methyl)-1H-pyrazole-4-carboxylic acid

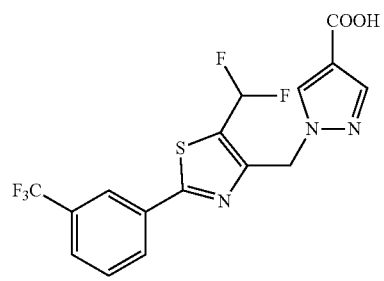

In the same manner as in Example 38, the title compound (120 mg, 60%) was obtained as colorless crystals from the compound (220 mg, 0.51 mmol) obtained in Example 90b.

$^1$H NMR (300 MHz, DMSO-$d_6$) δ ppm 5.69 (2H, s), 7.46-7.89 (3H, m), 7.93 (1H, d, J=7.9 Hz), 8.16-8.30 (2H, m), 8.41 (1H, s), 12.43 (1H, br. s.)

LCMS (ESI$^+$) M+H$^+$: 404.

Example 91

1-({2-[2-chloro-3-(trifluoromethyl)phenyl]-5-methyl-1,3-thiazol-4-yl}methyl)-1H-pyrazole-4-carboxylic acid

Example 91a ethyl 1-({2-[2-chloro-3-(trifluoromethyl)phenyl]-5-methyl-1,3-thiazol-4-yl}methyl)-1H-pyrazole-4-carboxylate

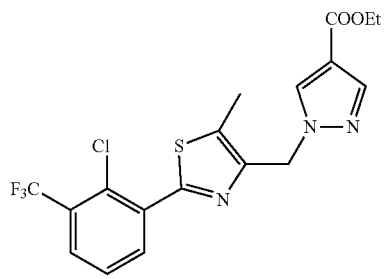 [SMILES: CCOC(=O)c1cnn(Cc2nc(-c3cccc(C(F)(F)F)c3Cl)sc2C)c1]

In the same manner as in Example 80f, the title compound (280 mg, 72%) was obtained as a colorless solid from the compound (300 mg, 0.91 mmol) obtained in Example 80e, 2-chloro-3-trifluoromethylphenylboronic acid (270 mg, 1.2

Example 91

1-({2-[2-chloro-3-(trifluoromethyl)phenyl]-5-methyl-1,3-thiazol-4-yl}methyl)-1H-pyrazole-4-carboxylic acid

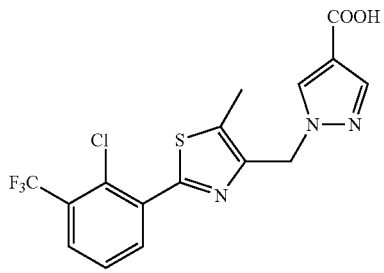 [SMILES: Cc1sc(-c2cccc(C(F)(F)F)c2Cl)nc1Cn1cc(C(=O)O)cn1]

In the same manner as in Example 80, the title compound (210 mg, 82%) was obtained as colorless crystals from the compound (280 mg, 0.65 mmol) obtained in Example 91a.
$^1$H NMR (300 MHz, DMSO-d$_6$) δ ppm 2.58 (3H, s), 5.50 (2H, s), 7.69 (1H, t, J=7.9 Hz), 7.78 (1H, s), 7.93-8.04 (1H, m), 8.14-8.38 (2H, m), 12.19 (1H, br. s.)
LCMS (ESI$^+$) M+H$^+$: 402.

Example 92

1-({2-[4-chloro-3-(trifluoromethyl)phenyl]-5-methyl-1,3-thiazol-4-yl}methyl)-1H-pyrazole-4-carboxylic acid

Example 92a ethyl 1-({2-[4-chloro-3-(trifluoromethyl)phenyl]-5-methyl-1,3-thiazol-4-yl}methyl)-1H-pyrazole-4-carboxylate

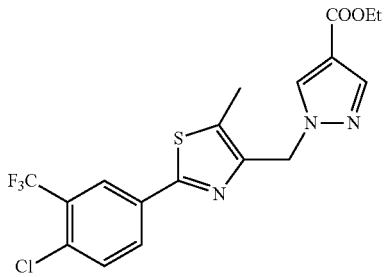 [SMILES: CCOC(=O)c1cnn(Cc2nc(-c3ccc(Cl)c(C(F)(F)F)c3)sc2C)c1]

In the same manner as in Example 80f, the title compound (270 mg, 69%) was obtained as a colorless solid from the compound (300 mg, 0.91 mmol) obtained in Example 80e and 4-chloro-3-trifluoromethylphenylboronic acid (270 mg, 1.2 mmol), 2N aqueous sodium carbonate solution (0.91 mL, 1.8 mmol), and [1,1'-bis(diphenylphosphino)ferrocene]dichloropalladium(II) dichloromethane complex (74 mg, 0.091 mmol).
$^1$H NMR (300 MHz, CHLOROFORM-d) δppm 1.33 (3H, t, J=7.0 Hz), 2.56 (3H, s), 4.28 (2H, q, J=7.2 Hz), 5.40 (2H, s), 7.72 (1H, d, J=8.3 Hz), 7.81 (1H, d, J=8.3 Hz), 7.91 (1H, s), 8.00-8.08 (2H, m)
LCMS (ESI$^+$) M+H$^+$: 430.

Example 92

1-({2-[4-chloro-3-(trifluoromethyl)phenyl]-5-methyl-1,3-thiazol-4-yl}methyl)-1H-pyrazole-4-carboxylic acid

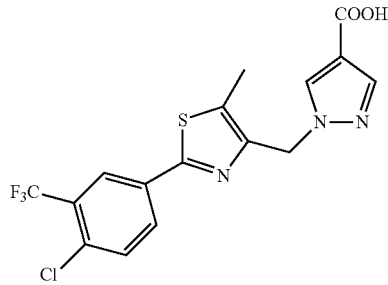 [SMILES: Cc1sc(-c2ccc(Cl)c(C(F)(F)F)c2)nc1Cn1cc(C(=O)O)cn1]

In the same manner as in Example 38, the title compound (210 mg, 82%) was obtained as colorless crystals from the compound (270 mg, 0.64 mmol) obtained in Example 92a.
$^1$H NMR (300 MHz, DMSO-d$_6$) δ ppm 2.57 (3H, s), 5.49 (2H, s), 7.79 (1H, s), 7.89-8.01 (2H, m), 8.10 (1H, s), 8.33 (1H, s), 12.35 (1H, br. s.)

Example 93

1-({4-[3-(pyridin-3-ylethynyl)-5-(trifluoromethyl)phenyl]-1,3-thiazol-2-yl}methyl)-1H-pyrazole-4-carboxylic acid

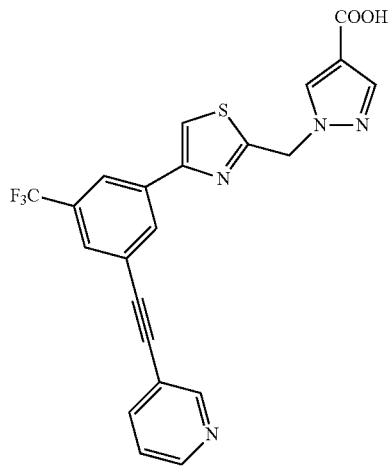 [SMILES: O=C(O)c1cnn(Cc2nc(-c3cc(C#Cc4cccnc4)cc(C(F)(F)F)c3)cs2)c1]

In the same manner as in Example 38, the title compound (130 mg, 99%) was obtained as colorless crystals from the compound (250 mg, 0.52 mmol) obtained in Example 87a.
$^1$H NMR (300 MHz, DMSO-d$_6$) δ ppm 5.86 (2H, s), 7.52 (1H, dd, J=8.0, 4.9 Hz), 7.86-7.99 (2H, m), 7.99-8.12 (1H, m), 8.34 (1H, s), 8.47 (1H, s), 8.52 (2H, s), 8.59-8.74 (1H, m), 8.84 (1H, s), 12.47 (1H, s)
LCMS (ESI$^+$) M+H$^+$: 455

Example 94

1-({4-[3-(2-pyridin-3-ylethyl)-5-(trifluoromethyl)phenyl]-1,3-thiazol-2-yl}methyl)-1H-pyrazole-4-carboxylic acid

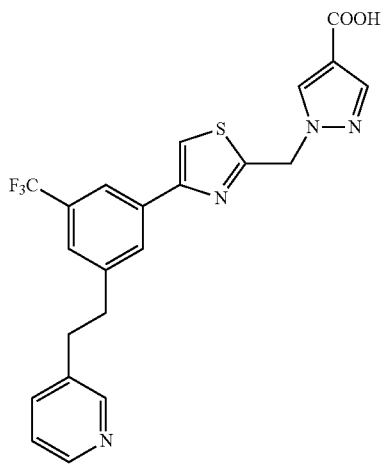 [SMILES: O=C(O)c1cnn(Cc2nc(-c3cc(CCc4cccnc4)cc(C(F)(F)F)c3)cs2)c1]

To a mixed solution of the compound (200 mg, 0.44 mmol) obtained in Example 93 in tetrahydrofuran/ethanol (v/v=3/1, 8 mL) was added palladium-carbon (20 mg), and the mixture was stirred overnight under a hydrogen atmosphere (1 atm) at room temperature. Palladium-carbon was removed and the solvent was evaporated under reduced pressure. The resulting crude title compound was recrystallized (hexane-ethyl acetate) to give the title compound (160 mg, 61%) as colorless crystals.

$^1$H NMR (300 MHz, DMSO-d$_6$) δ ppm 2.87-3.17 (4H, m), 5.84 (2H, s), 7.31 (1H, dd, J=7.7, 4.7 Hz), 7.57 (1H, s), 7.68 (1H, d, J=7.9 Hz), 7.93 (1H, s), 8.14 (1H, s), 8.10 (1H, s), 8.32 (1H, s), 8.36-8.43 (1H, m), 8.46 (1H, br. s.), 8.51 (1H, s), 12.46 (1H, br. s.)

LCMS (ESI$^+$) M+H$^+$: 459.

Example 95

1-({5-methyl-2-[3-{[(pyridin-2-ylcarbonyl)amino]methyl}-5-(trifluoromethyl)phenyl]-1,3-thiazol-4-yl}methyl)-1H-pyrazole-4-carboxylic acid

Example 95a

2-[3-bromo-5-(trifluoromethyl)phenyl]-5-methyl-4-[(tetrahydro-2H-pyran-2-yloxy)methyl]-1,3-thiazole

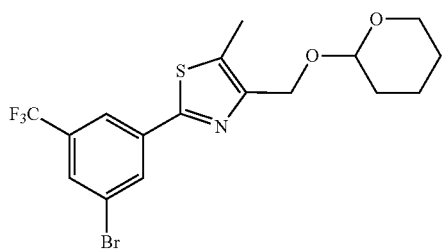 [SMILES: Cc1sc(-c2cc(Br)cc(C(F)(F)F)c2)nc1COC1CCCCO1]

To a solution (50 mL) of the compound (6.2 g, 18 mmol) obtained in Example 77d in toluene were added dihydropyran (2.1 mL, 23 mmol) and p-toluenesulfonic acid monohydrate (340 mg, 1.8 mmol), and the mixture was stirred at room temperature overnight. The reaction mixture was neutralized with saturated aqueous sodium hydrogen carbonate, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=85/15) to give the title compound (7.3 g, 95%) as a colorless oil.

$^1$H NMR (300 MHz, CHLOROFORM-d) δppm 1.58-1.96 (6H, m), 2.56 (3H, s), 3.54-3.66 (1H, m), 3.89-4.01 (1H, m), 4.64 (1H, d, J=11.7 Hz), 4.76 (1H, t, J=3.4 Hz), 4.84 (1H, d, J=11.7 Hz), 7.75 (1H, s), 8.06 (1H, s), 8.23 (1H, s)

LCMS (ESI$^+$) M+H$^+$: 436.

Example 95b

3-{5-methyl-4-[(tetrahydro-2H-pyran-2-yloxy)methyl]-1,3-thiazol-2-yl}-5-(trifluoromethyl)benzaldehyde

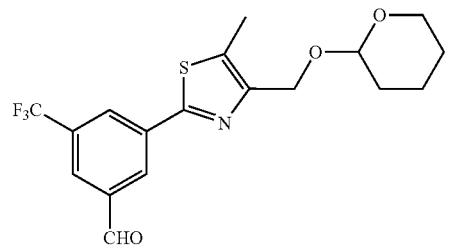 [SMILES: Cc1sc(-c2cc(C=O)cc(C(F)(F)F)c2)nc1COC1CCCCO1]

Under a nitrogen atmosphere at −78° C., to a solution (80 mL) of the compound (7.3 g, 17 mmol) obtained in Example 95a in tetrahydrofuran was added n-butyllithium (1.6M hexane solution, 16 mL, 25 mmol), and the mixture was stirred at the same temperature for 1 hr. Anhydrous N,N-dimethylformamide (2.6 mL, 33 mmol) was added to the reaction mixture, and the mixture was stirred overnight while allowing to spontaneously warm to room temperature from −78° C. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=80/20) to give the title compound (1.6 g, 24%) as an orange oil.

$^1$H NMR (300 MHz, CHLOROFORM-d) δppm 1.57-1.96 (6H, m), 2.58 (3H, s), 3.47-3.68 (1H, m), 3.85-4.04 (1H, m), 4.66 (1H, d, J=11.7 Hz), 4.78 (1H, t, J=3.4 Hz), 4.87 (1H, d, J=11.7 Hz), 8.13 (1H, s), 8.43 (1H, s), 8.53 (1H, s), 10.12 (1H, s)

LCMS (ESI$^+$) M+H$^+$: 386.

Example 95c

[3-{5-methyl-4-[(tetrahydro-2H-pyran-2-yloxy)methyl]-1,3-thiazol-2-yl}-5-(trifluoromethyl)phenyl]methanol

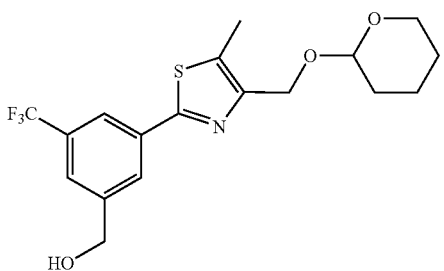 [SMILES: Cc1sc(-c2cc(CO)cc(C(F)(F)F)c2)nc1COC1CCCCO1]

To a mixed solution of the compound (1.6 g, 4.1 mmol) obtained in Example 95b in tetrahydrofuran/ethanol (v/v=1/1, 8 mL) was added sodium tetrahydroborate (230 mg, 6.1 mmol), and the mixture was stirred overnight while allowing to spontaneously warm to room temperature from 0° C. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=65/35) to give the title compound (1.3 g, 84%) as a pale-orange oil.

$^1$H NMR (300 MHz, CHLOROFORM-d) δppm 1.49-1.89 (6H, m), 2.55 (3H, s), 3.48-3.67 (1H, m), 3.87-4.05 (1H, m), 4.64 (1H, d, J=12.1 Hz), 4.72-4.92 (4H, m), 7.64 (1H, s), 8.04 (2H, s)

LCMS (ESI$^+$) M+H$^+$: 388.

Example 95d

2-[3-(azidomethyl)-5-(trifluoromethyl)phenyl]-5-methyl-4-[(tetrahydro-2H-pyran-2-yloxy)methyl]-1,3-thiazole

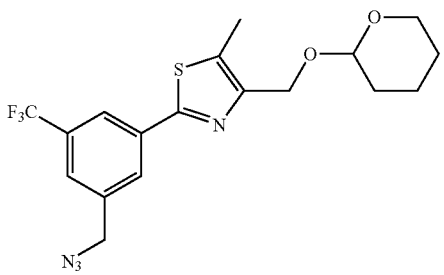 [SMILES: Cc1sc(-c2cc(CN=[N+]=[N-])cc(C(F)(F)F)c2)nc1COC1CCCCO1]

To a solution (7 mL) of the compound (1.3 g, 3.4 mmol) obtained in Example 95c in tetrahydrofuran were added 1,8-diazabicyclo[5.4.0]undec-7-ene (0.61 mL, 4.1 mmol) and diphenylphosphoryl azide (1.1 g, 4.1 mmol), and the mixture was stirred at room temperature overnight. The solvent was evaporated under reduced pressure and the resulting crude title compound was purified by column chromatography (hexane-hexane/ethyl acetate=85/15) to give the title compound (1.1 g, 80%) as a colorless oil.

$^1$H NMR (300 MHz, CHLOROFORM-d) δppm 1.55-1.92 (6H, m), 2.56 (3H, s), 3.48-3.71 (1H, m), 3.87-4.03 (1H, m), 4.49 (2 H, s), 4.65 (1H, d, J=11.7 Hz), 4.77 (1H, t, J=3.4 Hz), 4.85 (1H, d, J=12.1 Hz), 7.58 (1H, s), 8.04 (1H, s), 8.10 (1H, s)

LCMS (ESI$^+$) M+H$^+$: 413.

Example 95e ethyl 1-({2-[3-(azidomethyl)-5-(trifluoromethyl)phenyl]-5-methyl-1,3-thiazol-4-yl}methyl)-1H-pyrazole-4-carboxylate

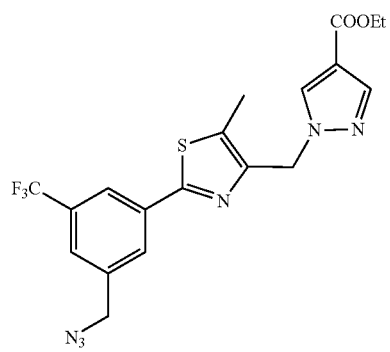 [SMILES: CCOC(=O)c1cnn(Cc2nc(-c3cc(CN=[N+]=[N-])cc(C(F)(F)F)c3)sc2C)c1]

By a method similar to that in Example 89e, 89f, the title compound (1.2 g, 100%) as a colorless oil from the compound (1.1 g, 2.7 mmol) obtained in Example 95d and p-toluenesulfonic acid monohydrate (570 mg, 3.0 mmol), triphenylphosphine (930 mg, 3.6 mmol), ethyl 1H-pyrazole-4-carboxylate (460 mg, 3.3 mmol), and diisopropyl azodicarboxylate (1.9M toluene solution, 1.9 ml, 3.6 mmol).

$^1$H NMR (300 MHz, CHLOROFORM-d) δppm 1.33 (3H, t, J=7.2 Hz), 2.56 (3H, s), 4.28 (2H, q, J=7.2 Hz), 4.51 (2H, s), 5.41 (2 H, s), 7.61 (1H, s), 7.91 (1H, s), 8.00 (1H, s), 8.02 (1H, s), 8.06 (1H, s)

LCMS (ESI$^+$) M+H$^+$: 451.

Example 95f ethyl 1-({2-[3-(aminomethyl)-5-(trifluoromethyl)phenyl]-5-methyl-1,3-thiazol-4-yl}methyl)-1H-pyrazole-4-carboxylate hydrochloride

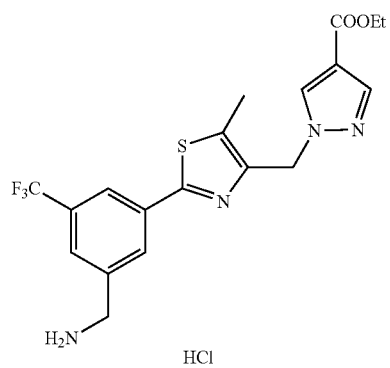 [SMILES: CCOC(=O)c1cnn(Cc2nc(-c3cc(CN)cc(C(F)(F)F)c3)sc2C)c1 ; Cl]

To a solution (6 mL) of the compound (1.2 g, 2.7 mmol) obtained in Example 95e in ethanol was added palladium-carbon (150 mg), and the mixture was stirred at room temperature overnight under a hydrogen atmosphere (1 atm). Palladium-carbon was removed and the solvent was evaporated under reduced pressure. To the resulting crude title compound was added 4N hydrogen chloride ethyl acetate solution (4 mL) and the mixture was at room temperature for 10 min. The resulting crystals were collected by filtration to give the title compound (1.1 g, 88%) as colorless crystals.

LCMS (ESI$^+$) M+H$^+$: 425.

Example 95g ethyl 1-({5-methyl-2-[3-{[(pyridin-2-ylcarbonyl) amino]methyl}-5-(trifluoromethyl)phenyl]-1,3-thiazol-4-yl}methyl)-1H-pyrazole-4-carboxylate

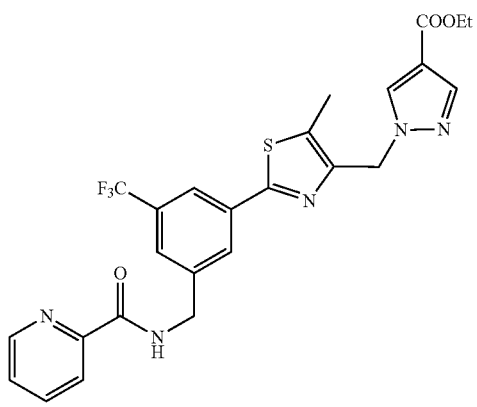 [SMILES: CCOC(=O)c1cnn(Cc2nc(-c3cc(CNC(=O)c4ccccn4)cc(C(F)(F)F)c3)sc2C)c1]

To a solution (3 mL) of the compound (200 mg, 0.43 mmol) obtained in Example 95f in N,N-dimethylformamide were added 2-pyridinecarboxylic acid (64 mg, 0.52 mmol), N-[3-(dimethylamino)propyl]-N'-ethylcarbodiimide (99 mg, 0.52 mmol), 1-hydroxybenzotriazole (80 mg, 0.52 mmol) and triethylamine (0.12 mL, 0.86 mmol), and the mixture was stirred at room temperature overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=30/70) to give the title compound (79 mg, 35%) as a pale-orange oil.

$^1$H NMR (300 MHz, CHLOROFORM-d) δppm 1.29-1.36 (3H, m), 2.53 (3H, s), 4.27 (2H, q, J=7.2 Hz), 4.78 (2H, d, J=6.1 Hz), 5.39 (2H, s), 7.42-7.51 (1H, m), 7.65 (1H, s), 7.80-7.95 (2H, m), 7.95-8.06 (3H, m), 8.24 (1H, d, J=7.6 Hz), 8.44-8.55 (1H, m), 8.56 (1H, d, J=4.2 Hz)

LCMS (ESI$^+$) M+H$^+$: 530.

Example 95

1-({5-methyl-2-[3-{[(pyridin-2-ylcarbonyl)amino] methyl}-5-(trifluoromethyl)phenyl]-1,3-thiazol-4-yl}methyl)-1H-pyrazole-4-carboxylic acid

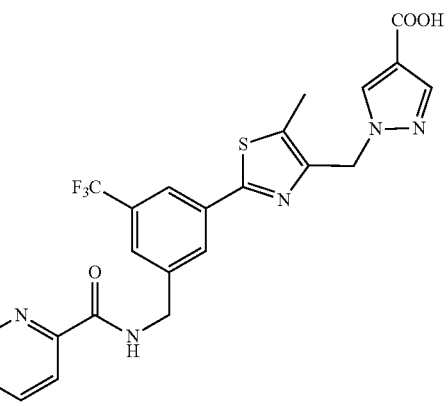

In the same manner as in Example 38, the title compound (56 mg, 74%) was obtained as colorless crystals from the compound (79 mg, 0.15 mmol) obtained in Example 95g.

$^1$H NMR (300 MHz, DMSO-d$_6$) δ ppm 2.54 (3H, s), 4.62 (2H, d, J=6.4 Hz), 5.47 (2H, s), 7.63 (1H, ddd, J=7.0, 4.9, 1.7 Hz), 7.72-7.84 (2H, m), 7.92-8.13 (4H, m), 8.31 (1H, s), 8.68 (1H, d, J=4.5 Hz), 9.60 (1H, t, J=6.4 Hz), 12.32 (1H, br. s.)

LCMS (ESI$^+$) M+H$^+$: 502.

Example 96

1-[(4-{3-[2-(5-methyl-4H-1,2,4-triazol-3-yl)ethyl]-5-(trifluoromethyl)phenyl}-1,3-thiazol-2-yl)methyl]-1H-pyrazole-4-carboxylic acid

Example 96a ethyl 1-[(4-{3-[(E/Z)-2-cyanoethenyl]-5-(trifluoromethyl)phenyl}-1,3-thiazol-2-yl)methyl]-1H-pyrazole-4-carboxylate

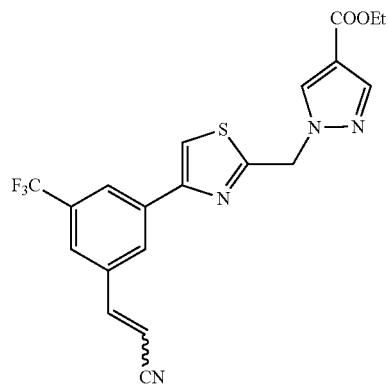 [SMILES: CCOC(=O)c1cnn(Cc2nc(-c3cc(C=CC#N)cc(C(F)(F)F)c3)cs2)c1]

Under a nitrogen atmosphere, to a solution (9 mL) of the compound (4.0 g, 8.7 mmol) obtained in Example 68b, cyanoacrylate (0.86 mL, 13 mmol), triethylamine (3.6 mL, 26 mmol) and tri(o-tolyl)phosphine (390 mg, 1.3 mmol) in N,N-dimethylformamide was added palladium acetate (100 mg, 0.43 mmol), and the mixture was stirred at 130° C. overnight. The palladium catalyst was removed by filtration and the solvent was evaporated under reduced pressure. The resulting crude title compound was purified by column chromatography (hexane-hexane/ethyl acetate=70/30) to give the title compound (3.3 g, 87%, E/Z=ca. 3/1) as a colorless solid.

$^1$H NMR (300 MHz, CHLOROFORM-d) δppm 1.35 (3H, t, J=7.0 Hz), 4.30 (2H, q, J=7.2 Hz), 5.69 (2H, s), 6.07 (1H, d, J=17.0 Hz), 7.49 (1H, d, J=16.6 Hz), 7.64 (1H, s), 7.66 (1H, s), 8.01 (1H, s), 8.10 (1H, s), 8.15 (1H, s), 8.18 (1H, s)

LCMS (ESI$^+$) M+H$^+$: 433.

Example 96b ethyl 1-({4-[3-(2-cyanoethyl)-5-(trifluoromethyl)phenyl]-1,3-thiazol-2-yl}methyl)-1H-pyrazole-4-carboxylate

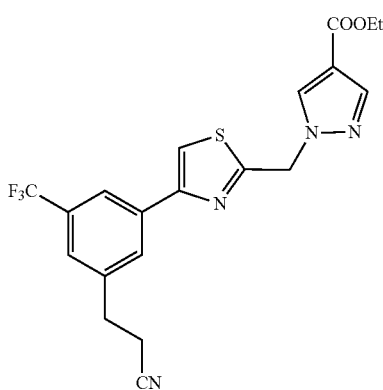 [SMILES: CCOC(=O)c1cnn(Cc2nc(-c3cc(CCC#N)cc(C(F)(F)F)c3)cs2)c1]

To a mixed solution of the compound (3.3 g, 7.5 mmol) obtained in Example 96a in ethanol/tetrahydrofuran (v/v=1/1, 16 mL) was added palladium-carbon (330 mg), and the mixture was stirred at room temperature overnight under a hydrogen atmosphere (1 atm). Palladium-carbon was removed and the solvent was evaporated under reduced pressure. The resulting crude title compound was purified by column chromatography (hexane-hexane/ethyl acetate=70/30) to give the title compound (2.8 g, 86%) was colorless crystals.

$^1$H NMR (300 MHz, CHLOROFORM-d) δppm 1.34 (3H, t, J=7.2 Hz), 2.72 (2H, t, J=7.4 Hz), 3.10 (2H, t, J=7.4 Hz), 4.30 (2H, q, J=7.2 Hz), 5.68 (2H, s), 7.46 (1H, s), 7.59 (1H, s), 7.98 (1H, s), 8.00 (1H, s), 8.04 (1H, s), 8.10 (1H, s)

LCMS (ESI$^+$) M+H$^{30}$: 435.

Example 96c ethyl 1-({4-[3-(3-amino-3-thioxopropyl)-5-(trifluoromethyl)phenyl]-1,3-thiazol-2-yl}methyl)-1H-pyrazole-4-carboxylate

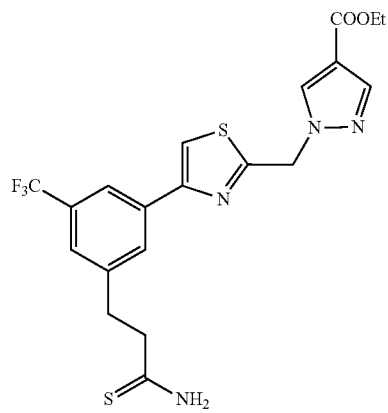 [SMILES: CCOC(=O)c1cnn(Cc2nc(-c3cc(CCC(N)=S)cc(C(F)(F)F)c3)cs2)c1]

To a solution (13 mL) of the compound (2.8 g, 6.5 mmol) obtained in Example 96b in 4N hydrogen chloride ethyl acetate was added O,O-diethyl dithiophosphate (1.8 g, 9.7 mmol), and the mixture was stirred at room temperature overnight. The reaction mixture was neutralized with saturated aqueous sodium hydrogen carbonate, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=50/50) to give the title compound (2.0 g, 66%) as a colorless amorphous form.

$^1$H NMR (300 MHz, DMSO-d$_6$) δ ppm 1.27 (3H, t, J=7.0 Hz), 2.84 (2H, t, J=7.8 Hz), 3.14 (2H, t, J=7.6 Hz), 4.23 (2H, q, J=6.9 Hz), 5.85 (2H, s), 7.58 (1H, s), 7.98 (1H, s), 8.10 (1H, s), 8.13 (1H, s), 8.33 (1H, s), 8.60 (1H, s), 9.21 (1H, br. s.), 9.42 (1H, br. s.)

LCMS (ESI$^+$) M+H$^+$: 469.

Example 96

1-[(4-{3-[2-(5-methyl-4H-1,2,4-triazol-3-yl)ethyl]-5-(trifluoromethyl)phenyl}-1,3-thiazol-2-yl)methyl]-1H-pyrazole-4-carboxylic acid

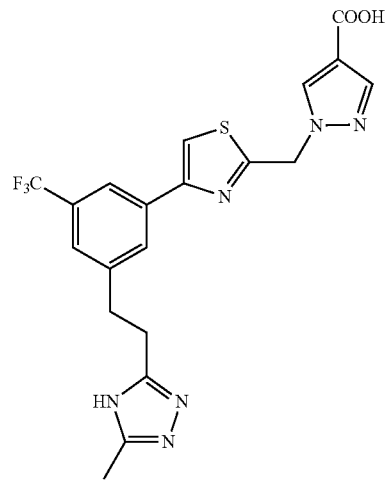 [SMILES: Cc1nnc(CCc2cc(-c3csc(Cn4cc(C(=O)O)cn4)n3)cc(C(F)(F)F)c2)[nH]1]

To a solution (3 mL) of the compound (300 mg, 0.64 mmol) obtained in Example 96c in acetone was added iodomethane (0.20 mL, 3.2 mmol), and the mixture was stirred at room temperature overnight. The solvent was evaporated under reduced pressure, and to a solution (4 mL) of the residue in ethanol was added acetylhydrazine (240 mg, 3.2 mmol), and the mixture was stirred at 80° C. for 6 hr. The solvent was evaporated under reduced pressure, and a solution (6 mL) of the residue in xylene was stirred at 150° C. overnight. The solvent was evaporated under reduced pressure, and to an ethanol/tetrahydrofuran mixed solution (v/v=1/1, 4 mL) of the residue was added 2N aqueous sodium hydroxide solution (0.45 mL, 0.91 mmol), and the mixture was stirred at room temperature overnight. Water was added to the reaction mixture, and the aqueous layer was washed with diethyl ether. The obtained aqueous layer was neutralized with 1N hydrochloric acid, and the mixture was extracted with ethyl acetate. The obtained organic layer was washed with saturated brine, and dried over anhydrous sodium sulfate. The solvent was evaporated under reduced pressure. The resulting crude title compound was purified by HPLC and recrystallization (hexane-ethyl acetate) to give the title compound (2 mg, 0.7%) as colorless crystals.

$^1$H NMR (300 MHz, DMSO-$d_6$) δ ppm 2.27 (3H, s), 2.98 (2H, t, J=7.5 Hz), 3.13 (2H, t, J=7.5 Hz), 5.84 (2H, s), 7.55 (1H, s), 7.92 (1H, s), 8.09 (1H, s), 8.12 (1H, s), 8.33 (1H, s), 8.51 (1H, s), 12.52 (1H, br. s.)

LCMS (ESI$^+$) M+H$^+$: 463.

Example 97

1-({2-[3-(1,1-difluoroethyl)-2-fluorophenyl]-5-methyl-1,3-thiazol-4-yl}methyl)-1H-pyrazole-4-carboxylic acid Example 97a ethyl 1-{[2-(3-acetyl-2-fluorophenyl)-5-methyl-1,3-thiazol-4-yl]methyl}-1H-pyrazole-4-carboxylate

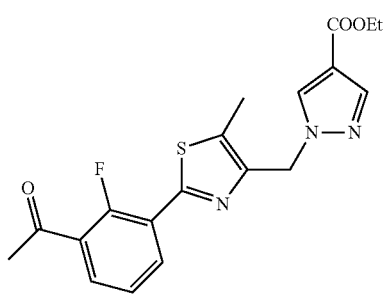 [SMILES: CCOC(=O)c1cnn(Cc2nc(-c3cccc(C(C)=O)c3F)sc2C)c1]

In the same manner as in Example 52a, the title compound (1.6 g, 81%) was obtained as a colorless solid from the compound (1.7 g, 5.0 mmol) obtained in Example 80e, 3-acetyl-2-fluorophenylboronic acid (1.1 g, 6.0 mmol), 2N aqueous sodium carbonate solution (5.0 mL, 10 mmol), [1,1'-bis(diphenylphosphino)ferrocene]dichloropalladium(II) dichloromethane complex (410 mg, 0.50 mmol).

$^1$H NMR (300 MHz, CHLOROFORM-d) δ ppm 1.33 (3H, t, J=7.0 Hz), 2.56 (3H, s), 2.71 (3H, d, J=4.9 Hz), 4.28 (2H, q, J=7.1 Hz), 5.43 (2H, s), 7.33 (1H, t, J=7.8 Hz), 7.83-7.95 (2H, m), 8.01 (1H, s), 8.33-8.47 (1H, m)

LCMS (ESI$^{30}$) M+H$^+$: 388.

Example 97b ethyl 1-({2-[3-(1,1-difluoroethyl)-2-fluorophenyl]-5-methyl-1,3-thiazol-4-yl}methyl)-1H-pyrazole-4-carboxylate

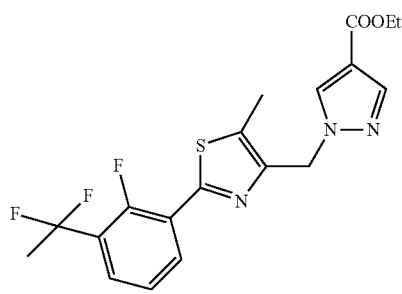 [SMILES: CCOC(=O)c1cnn(Cc2nc(-c3cccc(C(C)(F)F)c3F)sc2C)c1]

Under a nitrogen atmosphere, to the compound (250 mg, 0.65 mmol) obtained in Example 97a were added bis(2-methoxymethyl)aminosulfur trifluoride (1.5 mL, 6.8 mmol) and ethanol (0.0070 mL, 0.13 mmol), and the mixture was stirred at 90° C. overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=60/40) to give the title compound (140 mg, 53%) as brown crystals.

$^1$H NMR (300 MHz, CHLOROFORM-d) δppm 1.32 (3H, t, J=7.2 Hz), 2.05 (3H, t, J=18.6 Hz), 2.55 (3H, s), 4.27 (2H, q, J=7.2 Hz), 5.43 (2H, s), 7.27-7.34 (1H, m), 7.52-7.65 (1H, m), 7.91 (1H, s), 8.00 (1H, s), 8.23-8.36 (1H, m)

LCMS (ESI$^+$) M+H$^+$: 410.

Example 97

1-({2-[3-(1,1-difluoroethyl)-2-fluorophenyl]-5-methyl-1,3-thiazol-4-yl}methyl)-1H-pyrazole-4-carboxylic acid

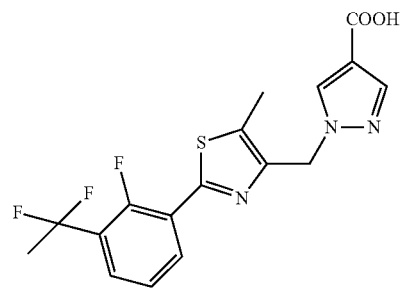 [SMILES: Cc1sc(-c2cccc(C(C)(F)F)c2F)nc1Cn1cc(C(=O)O)cn1]

In the same manner as in Example 38, the title compound (68 mg, 51%) was obtained as colorless crystals from the compound (140 mg, 0.35 mmol) obtained in Example 97b.

$^1$H NMR (300 MHz, DMSO-$d_6$) δ ppm 2.06 (3H, t, J=19.2 Hz), 2.57 (3H, s), 5.50 (2H, s), 7.45 (1H, t, J=7.8 Hz), 7.67 (1H, t, J=6.8 Hz), 7.80 (1H, s), 8.23 (1H, t, J=6.8 Hz), 8.33 (1H, s), 12.35 (1H, br. s.)

LCMS (ESI$^+$) M+H$^+$: 382.

Example 98

1-[(4-{3-[2-(3-acetylphenyl)ethyl]-5-(trifluoromethyl)phenyl}-1,3-thiazol-2-yl)methyl]-1H-pyrazole-4-carboxylic acid

Example 98a ethyl 1-[(4-{3-(trifluoromethyl)-5-[(trimethylsilyl)ethynyl]phenyl}-1,3-thiazol-2-yl)methyl]-1H-pyrazole-4-carboxylate

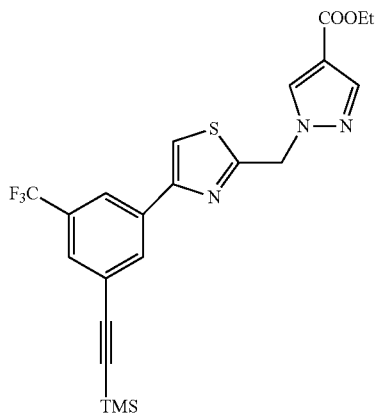 [SMILES: CCOC(=O)c1cnn(Cc2nc(-c3cc(C#C[Si](C)(C)C)cc(C(F)(F)F)c3)cs2)c1]

Under a nitrogen atmosphere, to a solution (8 mL) of the compound (2.0 g, 4.4 mmol) obtained in Example 68b, trimethylsilylacetylene (3.1 mL, 22 mmol), triethylamine (1.2 ml, 87 mmol) and copper iodide(I) (170 mg, 0.87 mmol) in N,N-dimethylformamide was added tetrakistriphenylphosphinepalladium (250 mg, 0.22 mmol), and the mixture was stirred at 70° C. overnight. The palladium catalyst was removed by filtration and the solvent was evaporated under reduced pressure. The resulting crude title compound was purified by column chromatography (hexane-hexane/ethyl acetate=75/25) to give the title compound (2.1 g, 100%) as an orange oil.

$^1$H NMR (300 MHz, CHLOROFORM-d) δppm 0.28 (9H, s), 1.34 (3H, t, J=6.9 Hz), 4.30 (2H, q, J=6.9 Hz), 5.68 (2H, s), 7.59 (1H, s), 7.69 (1H, s), 8.00 (1H, s), 8.04-8.18 (3H, m)

LCMS (ESI$^+$) M+H$^+$: 478.

Example 98b ethyl 1-({4-[3-ethynyl-5-(trifluoromethyl)phenyl]-1,3-thiazol-2-yl}methyl)-1H-pyrazole-4-carboxylate

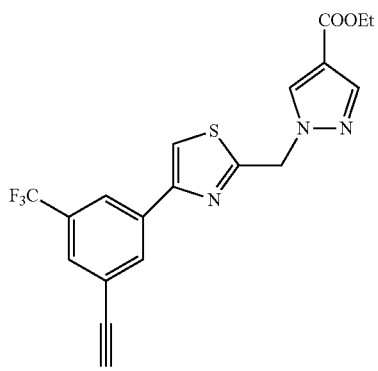 [SMILES: C#Cc1cc(-c2csc(Cn3cc(C(=O)OCC)cn3)n2)cc(C(F)(F)F)c1]

Under a nitrogen atmosphere at 0° C., to a solution (20 mL) of the compound (2.1 g, 4.4 mmol) obtained in Example 98a in tetrahydrofuran was added tetrabutylammonium fluoride (1M tetrahydrofuran solution, 6.5 mL, 6.5 mmol), and the mixture was stirred at room temperature overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (940 mg, 53%) as orange crystals.

$^1$H NMR (300 MHz, CHLOROFORM-d) δppm 1.34 (3H, t, J=7.2 Hz), 3.19 (1H, s), 4.30 (2H, q, J=7.2 Hz), 5.68 (2H, s), 7.59 (1H, s), 7.71 (1H, s), 8.00 (1H, s), 8.10 (1H, s), 8.13 (1H, s), 8.16 (1H, s)

LCMS (ESI$^+$) M+H$^+$: 406.

Example 98c ethyl 1-[(4-[(3-[(3-acetylphenyl)ethynyl]-5-(trifluoromethyl)phenyl]-1,3-thiazol-2-yl)methyl]-1H-pyrazole-4-carboxylate

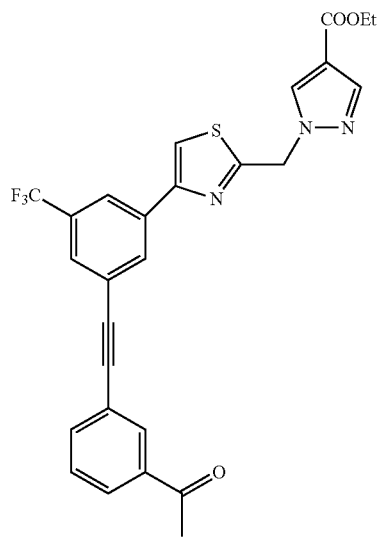 [SMILES: CCOC(=O)c1cnn(Cc2nc(-c3cc(C#Cc4cccc(C(C)=O)c4)cc(C(F)(F)F)c3)cs2)c1]

Under a nitrogen atmosphere, to a solution (3 ml) of the compound (200 mg, 0.49 mmol) obtained in Example 98b, 3-bromoacetophenone (150 mg, 0.74 mmol), triethylamine (0.14 mL, 0.98 mmol) and copper iodide(I) (19 mg, 0.10 mmol) in N,N-dimethylformamide was added tetrakistriphenylphosphinepalladium (58 mg, 0.050 mmol), and the mixture was stirred at 90° C. overnight. The palladium catalyst was removed by filtration and the solvent was evaporated under reduced pressure. The resulting crude title compound was purified by column chromatography (hexane-hexane/ethyl acetate=75/25) to give a crude title compound (100 mg, mixture with 3-bromoacetophenone) as an orange oil.

LCMS (ESI$^+$) M+H$^+$: 524.

Example 98

1-[(4-{3-[2-(3-acetylphenyl)ethyl]-5-(trifluoromethyl)phenyl}-1,3-thiazol-2-yl)methyl]-1H-pyrazole-4-carboxylic acid

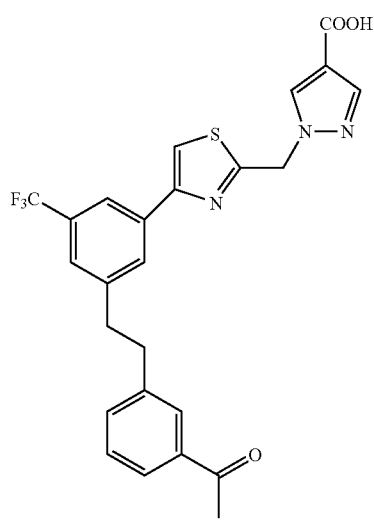 [SMILES: CC(=O)c1cccc(CCc2cc(-c3csc(Cn4cc(C(=O)O)cn4)n3)cc(C(F)(F)F)c2)c1]

To a mixed solution of the compound (100 mg) obtained in Example 98c in tetrahydrofuran/ethanol (v/v=1/1, 4 mL) was added palladium-carbon (10 mg), and the mixture was stirred at room temperature overnight under a hydrogen atmosphere (1 atm). Palladium-carbon was removed and the solvent was evaporated under reduced pressure. To the residue in tetrahydrofuran/ethanol mixed solution (v/v=1/2, 3 mL) was added 2N aqueous sodium hydroxide solution (0.38 mL, 0.76 mmol), and the mixture was stirred at room temperature overnight. Water was added to the reaction mixture, and the aqueous layer was washed with diethyl ether. The obtained aqueous layer was neutralized with 1N hydrochloric acid, and the mixture was extracted with ethyl acetate. The obtained organic layer was washed with saturated brine, and dried over anhydrous sodium sulfate. The solvent was evaporated under reduced pressure. The resulting crude title compound was recrystallized (hexane-ethyl acetate) to give the title compound (42 mg, 45%) as colorless crystals.

$^1$H NMR (300 MHz, DMSO-$d_6$) δ ppm 2.55 (3H, s), 2.85-3.19 (4H, m), 5.84 (2H, s), 7.44 (1H, t, J=7.5 Hz), 7.51-7.67 (2H, m), 7.79 (1H, d, J=7.6 Hz), 7.86 (1H, s), 7.92 (1H, s), 8.09 (1H, s), 8.17 (1H, s), 8.33 (1H, s), 8.51 (1H, s), 12.47 (1H, br. s.)

LCMS (ESI$^+$) M+H$^+$: 500.

Example 99

1-[(4-[3-[2-(4-acetylphenyl)ethyl]-5-(trifluoromethyl)phenyl]-1,3-thiazol-2-yl)methyl]-1H-pyrazole-4-carboxylic acid

Example 99a ethyl 1-[(4-[3-[(4-acetylphenyl)ethynyl]-5-(trifluoromethyl)phenyl]-1,3-thiazol-2-yl)methyl]-1H-pyrazole-4-carboxylate

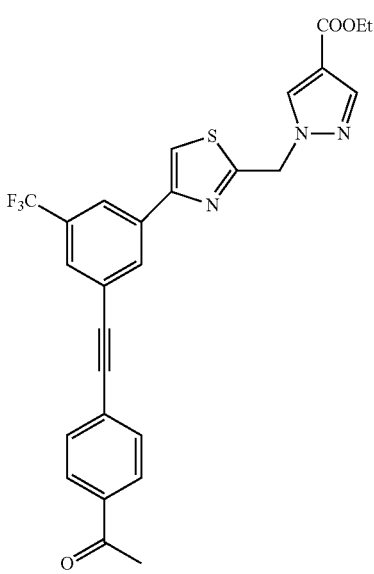 [SMILES: CCOC(=O)c1cnn(Cc2nc(-c3cc(C#Cc4ccc(C(C)=O)cc4)cc(C(F)(F)F)c3)cs2)c1]

In the same manner as in Example 98c, to a solution (3 mL) of the compound (200 mg, 0.49 mmol) obtained in Example 98b, 4-bromoacetophenone (150 mg, 0.74 mmol), triethylamine (0.14 mL, 0.98 mmol) and copper iodide(I) (19 mg, 0.10 mmol) in N,N-dimethylformamide was added tetrakistriphenylphosphinepalladium (58 mg, 0.050 mmol), and the mixture was stirred at 90° C. overnight. The palladium catalyst was removed by filtration and the solvent was evaporated under reduced pressure. The resulting crude title compound was purified by column chromatography (hexane-hexane/ethyl acetate=75/25) to give the title compound (97 mg, 38%) as a pale-yellow solid.

$^1$H NMR (300 MHz, CHLOROFORM-d) δppm 1.34 (3H, t, J=7.0 Hz), 2.63 (3H, s), 4.30 (2H, q, J=7.2 Hz), 5.69 (2H, s), 7.58-7.68 (3H, m), 7.78 (1H, s), 7.93-8.04 (3H, m), 8.11 (1H, s), 8.14 (1H, s), 8.23 (1H, s)

LCMS (ESI$^+$) M+H$^+$: 524.

Example 99

1-[(4-{3-[2-(4-acetylphenyl)ethyl]-5-(trifluoromethyl)phenyl}-1,3-thiazol-2-yl)methyl]-1H-pyrazole-4-carboxylic acid

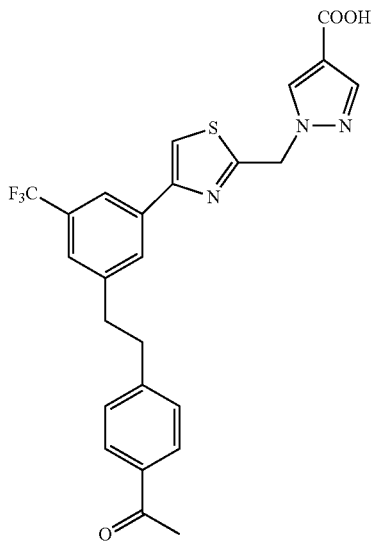 [SMILES: CC(=O)c1ccc(CCc2cc(-c3csc(Cn4cc(C(=O)O)cn4)n3)cc(C(F)(F)F)c2)cc1]

In the same manner as in Example 98, the title compound (71 mg, 75%) was obtained as colorless crystals from the compound (97 mg, 0.19 mmol) obtained in Example 99a.

$^1$H NMR (300 MHz, DMSO-$d_6$) δ ppm 2.55 (3H, s), 3.06 (4H, br. s.), 5.84 (2H, s), 7.42 (2H, m, J=8.3 Hz), 7.58 (1H, s), 7.88 (2H, m, J=8.3 Hz), 7.93 (1H, s), 8.09 (1H, s), 8.16 (1H, s), 8.33 (1H, s), 8.51 (1H, s), 12.46 (1H, br. s.)

LCMS (ESI$^+$) M+H$^+$: 500.

Example 100

1-[(4-{3-[2-(2-methylpyridin-3-yl)ethyl]-5-(trifluoromethyl)phenyl}-1,3-thiazol-2-yl)methyl]-1H-pyrazole-4-carboxylic acid

Example 100a ethyl 1-[(4-{(3-[(2-methylpyridin-3-yl)ethynyl]-5-(trifluoromethyl)phenyl}-1,3-thiazol-2-yl)methyl]-1H-pyrazole-4-carboxylate

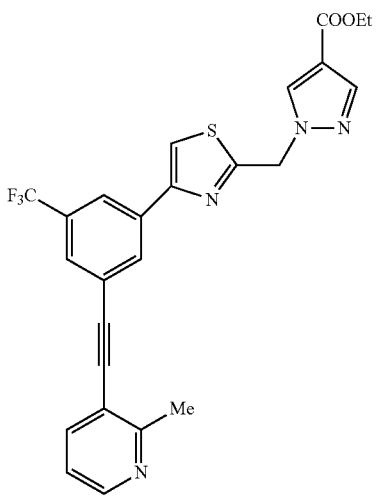 [SMILES: CCOC(=O)c1cnn(Cc2nc(-c3cc(C#Cc4cccnc4C)cc(C(F)(F)F)c3)cs2)c1]

In the same manner as in Example 98c, to a solution (3 mL) of the compound (160 mg, 0.39 mmol) obtained in Example 98b, 2-methyl-3-bromopyridine (100 mg, 0.59 mmol), triethylamine (0.11 mL, 0.78 mmol) and copper iodide(I) (15 m 0.080 mmol) in N,N-dimethylformamide was added tetrakistriphenylphosphinepalladium (45 mg, 0.040 mmol), and the mixture was stirred at 90° C. overnight. The palladium catalyst was removed by filtration and the solvent was evaporated under reduced pressure. The resulting crude title compound was purified by column chromatography (hexane-hexane/ethyl acetate=70/30) to give a crude title compound (29 mg) as an orange oil.

Example 100

1-[(4-{3-[2-(2-methylpyridin-3-yl)ethyl]-5-(trifluoromethyl)phenyl}-1,3-thiazol-2-yl)methyl]-1H-pyrazole-4-carboxylic acid

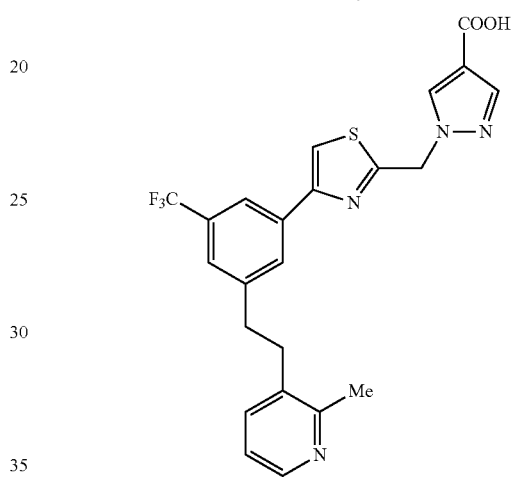

In the same manner as in Example 98, the title compound (19 mg, 69%) was obtained as colorless crystals from the compound (29 mg) obtained in Example 100a.

$^1$H NMR (300 MHz, DMSO-$d_6$) δ ppm 2.47 (3H, s), 2.85-3.07 (4H, m), 5.84 (2H, s), 7.13 (1H, dd, J=7.8, 4.7 Hz), 7.49-7.60 (2H, m), 7.93 (1H, s), 8.12 (2H, d, J=9.8 Hz), 8.24-8.30 (1H, m), 8.33 (1H, s), 8.51 (1H, s), 12.39 (1H, br. s.)

LCMS (ESI$^+$) M+H$^+$: 473.

Reference Example 101

5-(trifluoromethyl)-1-(4-{[3-(trifluoromethyl)phenyl]carbamoyl}-1,3-thiazol-2-yl)-1H-pyrazole-4-carboxylic acid

Reference Example 101a ethyl 5-(trifluoromethyl)-1-(4-{[3-(trifluoromethyl)phenyl]carbamoyl}-1,3-thiazol-2-yl)-1H-pyrazole-4-carboxylate

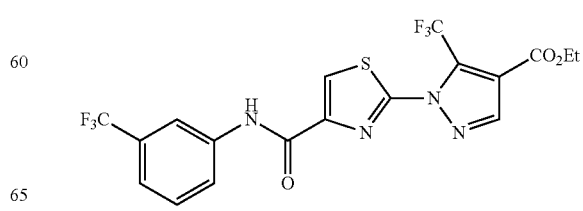

By a reaction in the same manner as in Reference Example 19 and using the compound (335 mg, 1.00 mmol) obtained in Reference Example 20a and 3-(trifluoromethyl)aniline (0.149 ml, 1.20 mmol), the title compound (394 mg, 82%) was obtained as colorless crystals.

¹H NMR (300 MHz, CHLOROFORM-d) δ ppm 1.41 (3H, t, J=7.2 Hz), 4.42 (2H, q, J=7.2 Hz), 7.43 (1H, d, J=8.0 Hz), 7.51 (1H, t, J=8.0 Hz), 7.81 (1H, d, J=8.0 Hz), 8.02 (1H, s), 8.14 (1H, s), 8.25 (1H, s), 9.05 (1H, s)

LCMS (ESI+) M+H: 479.

Reference Example 101

5-(trifluoromethyl)-1-(4-{[3-(trifluoromethyl)phenyl]carbamoyl}-1,3-thiazol-2-yl)-1H-pyrazole-4-carboxylic acid

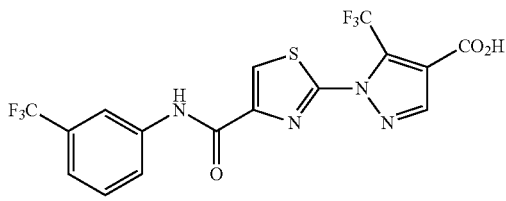 [SMILES: O=C(Nc1cccc(C(F)(F)F)c1)c1csc(-n2ncc(C(=O)O)c2C(F)(F)F)n1]

By a reaction in the same manner as in Reference Example 1 and using the compound (394 mg, 0.824 mmol) obtained in Reference Example 101a, the title compound (289 mg, 78%) was obtained as colorless crystals.

¹H NMR (300 MHz, DMSO-d₆) δppm 7.48 (1H, d, J=7.6 Hz) 7.61 (1H, t, J=8.0 Hz) 8.07 (1H, d, J=8.7 Hz) 8.28 (1H, s) 8.37-8.45 (1H, m) 8.69 (1H, s) 10.56 (1H, s) 13.69 (1H, br. s.)

LCMS (ESI+) M+H: 451.

Reference Example 102

1-[4-(3,4-dichlorobenzyl)-1,3-thiazol-2-yl]-5-(trifluoromethyl)-1H-pyrazole-4-carboxylic acid Reference Example 102a ethyl 1-[4-(3,4-dichlorobenzyl)-1,3-thiazol-2-yl]-5-(trifluoromethyl)-1H-pyrazole-4-carboxylate

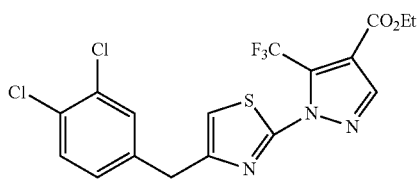 [SMILES: CCOC(=O)c1cnn(-c2nc(Cc3ccc(Cl)c(Cl)c3)cs2)c1C(F)(F)F]

By a reaction in the same manner as in Reference Example 25b and using the compound (0.56 g) obtained in Reference Example 25a and 3,4-dichlorophenylboronic acid (0.28 g), the title compound (0.23 g) was obtained as a colorless oil.

¹H NMR (300 MHz, CDCl₃) δ ppm 1.38 (3H, t, J=7.2 Hz), 4.05 (2H, s), 4.37 (2H, q, J=7.2 Hz), 6.95 (1H, s), 7.14 (1H, d, J=8.4 Hz), 7.36-7.40 (2H, m), 8.07 (1H, s)

Reference Example 102

1-[4-(3,4-dichlorobenzyl)-1,3-thiazol-2-yl]-5-(trifluoromethyl)-1H-pyrazole-4-carboxylic acid

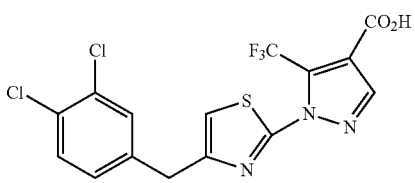 [SMILES: O=C(O)c1cnn(-c2nc(Cc3ccc(Cl)c(Cl)c3)cs2)c1C(F)(F)F]

By a reaction in the same manner as in Reference Example and using the compound (0.23 g) obtained in Reference Example 102a, the title compound (0.18 g) was obtained as colorless crystals.

¹H NMR (300 MHz, DMSO-d₆) δ ppm 4.10 (2H, s), 7.29 (1H, dd, J=8.3, 2.1 Hz), 7.53-7.61 (3H, m), 8.34 (1H, s), 13.66 (1H, br. s.)

Example 103

5-(trifluoromethyl)-1-({4-[3-(trifluoromethyl)phenyl]-1,3-thiazol-2-yl}methyl)-1H-pyrazole-4-carboxylic acid Example 103a {4-[3-(trifluoromethyl)phenyl]-1,3-thiazol-2-yl}methanol

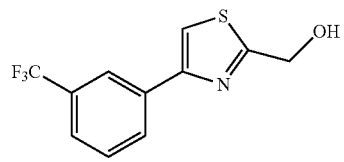 [SMILES: OCc1nc(-c2cccc(C(F)(F)F)c2)cs1]

A mixture of 2-amino-2-thioxoethyl 2,2-dimethylpropanoate (7.38 g), 2-bromo-1-[3-(trifluoromethyl)phenyl]ethanone (7.50 g) and ethanol (150 ml) was heated under reflux for 16 hr. The reaction mixture was concentrated under reduced pressure, and the residue was extracted with ethyl acetate, washed successively with diluted aqueous sodium hydrogen carbonate solution and saturated brine, dried over sodium sulfate, and concentrated under reduced pressure. The residue was purified by column chromatography (carrier: silica gel, eluent: hexane-ethyl acetate) to give crude {4-[3-(trifluoromethyl)phenyl]-1,3-thiazol-2-yl}methyl 2,2-dimethylpropanoate (about 10 g) as a colorless solid. The solid was dissolved in ethanol (100 mL) and tetrahydrofuran (100 mL), 2N aqueous sodium hydroxide solution (80 mL) was added, and the mixture was stirred at room temperature for 16 hr. The reaction mixture was concentrated under reduced pressure, and the residue was extracted with ethyl acetate, washed successively with diluted aqueous citric acid solution and saturated brine, dried over sodium sulfate, and concentrated under reduced pressure. The residue was washed with hexane to give the title compound (4.90 g) as pale-yellow crystals.

$^1$H NMR (300 MHz, CHLOROFORM-d) δ ppm 2.43-2.65 (1H, m), 5.03 (2H, d, J=4.1 Hz), 7.45-7.68 (3H, m), 8.06 (1H, d, J=7.2 Hz), 8.16 (0.1H, s)

Example 103b 2-(chloromethyl)-4-[3-(trifluoromethyl)phenyl]-1,3-thiazole

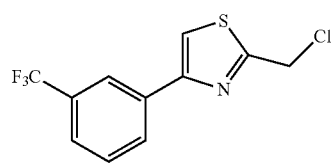 [SMILES: FC(F)(F)c1cccc(-c2csc(CCl)n2)c1]

The compound (4.14 g) obtained in Example 103a was dissolved in tetrahydrofuran (100 mL), and thionyl chloride (3.5 mL) was added. The reaction mixture was stirred at room temperature for 24 hr, and heated under reflux for 2 hr. The reaction mixture was concentrated under reduced pressure, and the residue was extracted with ethyl acetate, washed successively with saturated aqueous sodium hydrogen carbonate solution and saturated brine, dried over sodium sulfate, and concentrated under reduced pressure. The residue was purified by column chromatography (carrier: silica gel, eluent: hexane-ethyl acetate) to give the title compound (3.19 g) as a colorless solid.

$^1$H NMR (300 MHz, CHLOROFORM-d) δ ppm 4.91 (2H, s), 7.51-7.61 (3H, m), 8.05 (1H, d, J=7.5 Hz), 8.15 (1H, s)

Example 103c 2-(hydrazinomethyl)-4-[3-(trifluoromethyl)phenyl]-1,3-thiazole hydrochloride

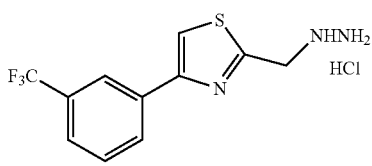 [SMILES: NNCc1nc(-c2cccc(C(F)(F)F)c2)cs1 ; Cl]

The compound (0.60 g) obtained in Example 103b was dissolved in N,N-dimethylformamide (3 mL), and tert-butyl hydrazinecarboxylate (1.45 g) and triethylamine (0.61 mL) were added. The reaction mixture was stirred at room temperature for 96 hr, and diluted with ethyl acetate and water. The ethyl acetate layer was separated, washed with saturated brine, dried over sodium sulfate, and concentrated under reduced pressure. The residue was purified by column chromatography (carrier: silica gel, eluent: hexane-ethyl acetate) to give tert-butyl 2-({4-[3-(trifluoromethyl)phenyl]-1,3-thiazol-2-yl}methyl)hydrazinecarboxylate (0.54 g) as a colorless solid. The solid was dissolved in 10% hydrogen chloride-ethanol (30 mL), and the mixture was stirred at room temperature for 16 hr. The reaction mixture was concentrated under reduced pressure, and the residue was washed with diisopropyl ether to give the title compound (0.45 g) as colorless crystals.

$^1$H NMR (300 MHz, DMSO-d$_6$) δ ppm 4.43 (2H, s), 7.63-7.80 (2H, m), 8.22-8.34 (2H, m), 8.39 (1H, s), 9.26 (2H, br. s.)

Example 103d ethyl 5-(trifluoromethyl)-1-({4-[3-(trifluoromethyl)phenyl]-1,3-thiazol-2-yl}methyl)-1H-pyrazole-4-carboxylate

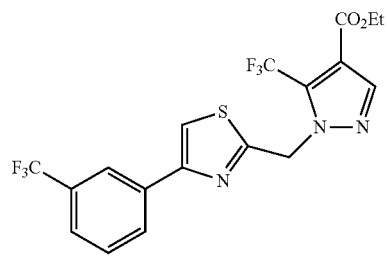 [SMILES: CCOC(=O)c1cnn(Cc2nc(-c3cccc(C(F)(F)F)c3)cs2)c1C(F)(F)F]

A mixture of the compound (0.16 g) obtained in Example 103c, ethyl 2-[(dimethylamino)methylidene]-4,4,4-trifluoro-3-oxobutanoate (0.10 g), triethylamine (0.21 mL) and ethanol (4 mL) was heated under reflux for 16 hr. The reaction mixture was concentrated under reduced pressure, and the residue was dissolved in ethyl acetate and saturated brine. The ethyl acetate layer was separated, dried over sodium sulfate, and concentrated under reduced pressure. The residue was purified by column chromatography (carrier: silica gel, eluent: hexane-ethyl acetate) to give the title compound (0.13 g) as a colorless oil.

$^1$H NMR (300 MHz, CHLOROFORM-d) δ ppm 1.37 (3H, t, J=7.2 Hz), 4.35 (2H, q, J=7.0 Hz), 5.90 (2H, s), 7.45-7.67 (3H, m), 7.94-8.20 (3H, m)

Example 103

5-(trifluoromethyl)-1-({4-[3-(trifluoromethyl)phenyl]-1,3-thiazol-2-yl}methyl)-1H-pyrazole-4-carboxylic acid

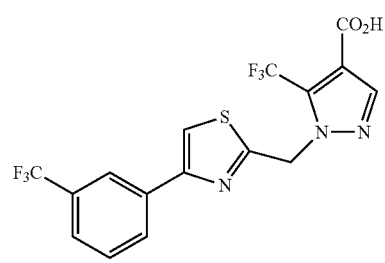

A mixture of the compound (0.13 g) obtained in Example 103d, 4N sodium hydroxide (1 mL), ethanol (2 mL) and tetrahydrofuran (0.5 mL) was stirred at room temperature for 20 hr. The reaction mixture was adjusted to pH 5 with 1N hydrochloric acid, and ethyl acetate and water were added. The ethyl acetate layer was separated, dried over sodium sulfate, and concentrated under reduced pressure to give the title compound (0.12 g) as colorless crystals.

$^1$H NMR (300 MHz, DMSO-d$_6$) δ ppm 6.05 (2H, s), 7.56-7.82 (2H, m), 8.08-8.32 (3H, m), 8.39 (1H, s), 13.24 (1H, br. s.)

Example 104

5-cyclopropyl-1-({4-[3-(trifluoromethyl)phenyl]-1,3-thiazol-2-yl}methyl)-1H-pyrazole-4-carboxylic acid Example 104a methyl 5-cyclopropyl-1-({4-[3-(trifluoromethyl)phenyl]-1,3-thiazol-2-yl}methyl)-1H-pyrazole-4-carboxylate

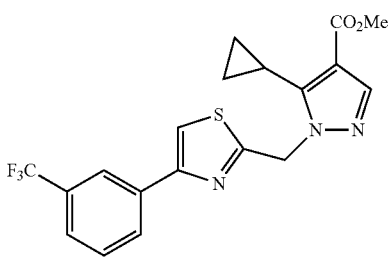 [SMILES: COC(=O)c1cnn(Cc2nc(-c3cccc(C(F)(F)F)c3)cs2)c1C1CC1]

By a method similar to that in Example 103d, the title compound (0.12 g) as colorless crystals from the compound (0.16 g) obtained in Example 103c and methyl 2-(cyclopropylcarbonyl)-3-(dimethylamino)prop-2-enoate (0.13 g).

$^1$H NMR (300 MHz, CHLOROFORM-d) δ ppm 0.86-0.98 (2H, m), 1.09-1.23 (2H, m), 1.78-1.98 (1H, m), 3.84 (3H, s), 5.81 (2H, s), 7.44-7.66 (3H, m), 7.95 (1H, s), 8.04 (1H, d, J=7.5 Hz), 8.15 (1H, s)

Example 104

5-cyclopropyl-1-({4-[3-(trifluoromethyl)phenyl]-1,3-thiazol-2-yl}methyl)-1H-pyrazole-4-carboxylic acid

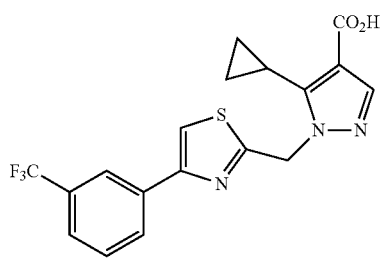 [SMILES: O=C(O)c1cnn(Cc2nc(-c3cccc(C(F)(F)F)c3)cs2)c1C1CC1]

By a method similar to that in Example 103, the title compound (0.09 g) as colorless crystals from the compound (0.12 g) obtained in Example 104a.

$^1$H NMR (300 MHz, DMSO-d$_6$) δ ppm 0.79-1.18 (4H, m), 1.84-2.08 (1H, m), 5.86 (2H, s), 7.56-7.79 (2H, m), 7.84 (1H, s), 8.15-8.32 (2H, m), 8.36 (1H, s), 12.24 (1H, br. s.)

Example 105

1-({2-[2-fluoro-3-(trifluoromethyl)phenyl]-1,3-oxazol-4-yl}methyl)-1H-pyrazole-4-carboxylic acid Example 105a 4-(chloromethyl)-2-[2-fluoro-3-(trifluoromethyl)phenyl]-1,3-oxazole

A mixture of 2-fluoro-3-(trifluoromethyl)benzamide (1.02 g), 1,3-dichloropropanone (1.27 g) and toluene (4 mL) was heated at 130° C. for 40 hr. The reaction mixture was purified by column chromatography (carrier: silica gel, eluent: hexane-ethyl acetate) to give the title compound (0.81 g) as colorless crystals.

$^1$H NMR (300 MHz, CHLOROFORM-d) δ ppm 4.60 (2H, s), 7.37 (1H, t, J=8.0 Hz), 7.73 (1H, t, J=7.0 Hz), 7.81 (1H, s), 8.19-8.33 (1H, m)

Example 105b ethyl 1-({2-[2-fluoro-3-(trifluoromethyl)phenyl]-1,3-oxazol-4-yl}methyl)-1H-pyrazole-4-carboxylate

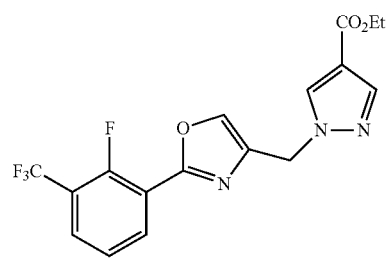 [SMILES: CCOC(=O)c1cnn(Cc2coc(-c3cccc(C(F)(F)F)c3F)n2)c1]

To a suspension of sodium hydride (60% in mineral oil, 0.08 g) in N,N-dimethylformamide (2 ml) was added ethyl 1H-pyrazole-4-carboxylate (0.21 g). After stirring at room temperature for 30 min, the compound (0.42 g) obtained in Example 105a was added to the reaction mixture. After stirring at room temperature for 2 hr, 10% aqueous citric acid solution and ethyl acetate were added to the reaction mixture. The ethyl acetate layer was separated, washed with saturated brine, dried over sodium sulfate, and concentrated under reduced pressure. The residue was purified by column chromatography (carrier: silica gel, eluent: hexane-ethyl acetate) to give the title compound (0.44 g) as colorless crystals.

$^1$H NMR (300 MHz, CHLOROFORM-d) δ ppm 1.34 (3H, t, J=7.2 Hz), 4.29 (2H, q, J=7.2 Hz), 5.34 (2H, s), 7.36 (1H, t, J=8.0 Hz), 7.73 (1H, t, J=7.2 Hz), 7.78 (1H, s), 7.95 (1H, s), 8.08 (1H, s), 8.17-8.29 (1H, m)

Example 105

1-({2-[2-fluoro-3-(trifluoromethyl)phenyl]-1,3-oxazol-4-yl}methyl)-1H-pyrazole-4-carboxylic acid

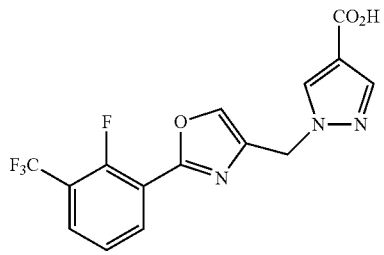 [SMILES: O=C(O)c1cnn(Cc2coc(-c3cccc(C(F)(F)F)c3F)n2)c1]

A mixture of the compound (0.44 g) obtained in Example 105b, 4N sodium hydroxide (3 mL), ethanol (8 mL) and tetrahydrofuran (2 mL) was stirred at room temperature for 16 hr. The reaction mixture was adjusted to pH 5 with 1N hydrochloric acid, and the precipitate was collected by filtration, dried under reduced pressure and recrystallized from ethanol-hexane to give the title compound (0.32 g) as colorless crystals.

$^1$H NMR (300 MHz, DMSO-$d_6$) δ ppm 5.40 (2H, s), 7.57 (1H, t, J=7.9 Hz), 7.83 (1H, s), 7.97 (1H, t, J=7.3 Hz), 8.22-8.43 (3H, m), 12.33 (1H, br. s.)

Example 106

1-{[4-(4-chlorophenyl)-1,3-thiazol-2-yl]methyl}-1H-pyrazole-4-carboxylic acid

Example 106a ethyl 1-{[4-(4-chlorophenyl)-1,3-thiazol-2-yl]methyl}-1H-pyrazole-4-carboxylate

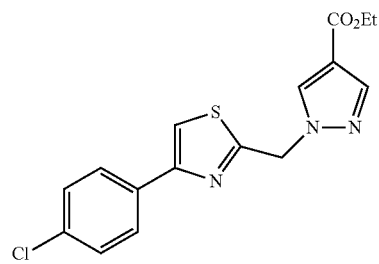 [SMILES: CCOC(=O)c1cnn(Cc2nc(-c3ccc(Cl)cc3)cs2)c1]

To a solution of the compound (500 mg) obtained in Example 1b in ethanol (5 mL) was added 2-bromo-1-[4-chlorophenyl]ethanone (546 mg), and the mixture was heated under reflux for 1 hr. The reaction mixture was concentrated under reduced pressure, and the residue was washed with ether to give the title compound (660 mg) as a colorless solid.

$^1$H NMR (DMSO, Varian 400 MHz) δ ppm 1.24 (3H, t, J=7.2 Hz), 4.20 (2H, q, J=7.2 Hz), 5.81 (2H, s), 7.45-7.50 (2H, m), 7.90-7.95 (3H, m), 8.15 (1H, s), 8.56 (1H, d, J=0.8 Hz)

Example 106

1-{[4-(4-chlorophenyl)-1,3-thiazol-2-yl]methyl}-1H-pyrazole-4-carboxylic acid

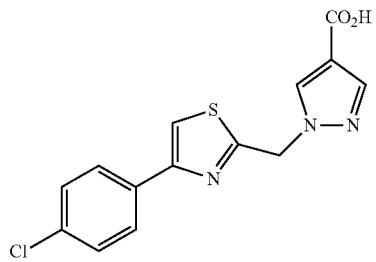 [SMILES: O=C(O)c1cnn(Cc2nc(-c3ccc(Cl)cc3)cs2)c1]

To a solution of the compound (660 mg) obtained in Example 106a in tetrahydrofuran (5 ml) was added 2N lithium hydroxide aqueous solution (5 mL), and the mixture was heated under reflux overnight. The reaction mixture was concentrated under reduced pressure, and the residue was diluted with water, and adjusted to pH 5-6 with 3N hydrochloric acid. The resulting precipitate was collected by filtration. The obtained solid was dissolved in tetrahydrofuran and dried over anhydrous sodium sulfate, and the solvent was evaporated. The residue was recrystallized from ethanol to give the title compound (150 mg) as colorless crystals.

$^1$H NMR (DMSO, Varian 400 MHz) δ ppm 5.79 (2H, s), 7.49 (2H, d, J=8.4 Hz), 7.89 (1H, s), 7.94 (2H, d, J=8.8 Hz), 8.15 (1H, s), 8.46 (1H, s)

Example 107

1-{[4-(2-methoxyphenyl)-1,3-thiazol-2-yl]methyl}-1H-pyrazole-4-carboxylic acid

Example 107a ethyl 1-{[4-(2-methoxyphenyl)-1,3-thiazol-2-yl]methyl}-1H-pyrazole-4-carboxylate

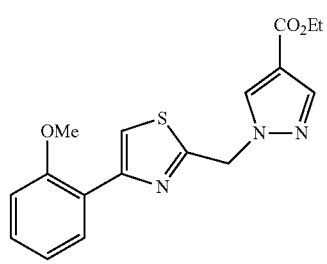 [SMILES: CCOC(=O)c1cnn(Cc2nc(-c3ccccc3OC)cs2)c1]

By a method similar, to that in Example 106a, the title compound was obtained from the compound obtained in Example 1b and 2-bromo-1-(2-methoxyphenyl)ethanone.

$^1$H NMR (DMSO, Varian 400 MHz) δ ppm 1.23 (3H, t, J=7.2 Hz), 3.87 (3H, s), 4.19 (2H, q, J=7.2 Hz), 5.78 (2H, s), 7.00 (1H, d, J=8.2 Hz), 7.10 (1H, d, J=6.8 Hz), 7.26-7.34 (1H, m), 7.92 (1H, s), 8.01 (1H, s), 8.06 (1H, dd, J=7.8, 1.4 Hz), 8.54 (1H, s)

Example 107

1-{[4-(2-methoxyphenyl)-1,3-thiazol-2-yl]methyl}-1H-pyrazole-4-carboxylic acid

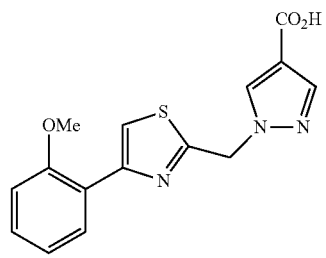 [SMILES: COc1ccccc1-c1csc(Cn2cc(C(=O)O)cn2)n1]

By a method similar to that in Example 106, the title compound was obtained from the compound obtained in Example 107a.

$^1$H NMR (DMSO, Varian 400 MHz) δ ppm 3.88 (3H, s), 5.75 (2H, s), 6.98-7.04 (1H, m), 7.11 (1H, d, J=8.0 Hz), 7.30 (1H, td, J=7.8, 1.4 Hz), 7.82 (1H, s), 8.01 (1H, s), 8.08 (1H, dd, J=7.6, 2.0 Hz), 8.36 (1H, s)

Example 108

1-{[4-(3-chlorophenyl)-1,3-thiazol-2-yl]methyl}-1H-pyrazole-4-carboxylic acid

Example 108a ethyl 1-{[4-(3-chlorophenyl)-1,3-thiazol-2-yl]methyl}-1H-pyrazole-4-carboxylate

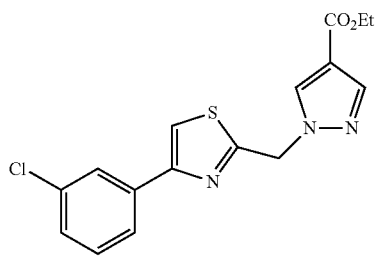 [SMILES: CCOC(=O)c1cnn(Cc2nc(-c3cccc(Cl)c3)cs2)c1]

By a method similar to that in Example 106a, the title compound was obtained from the compound obtained in Example 1b and 2-bromo-1-[3-chlorophenyl]ethanone.

$^1$H NMR (DMSO, Varian 400 MHz) δ ppm 1.22 (3H, t, J=7.2 Hz), 4.18 (2H, q, J=7.2 Hz), 5.79 (2H, s), 7.34-7.40 (1H, m), 7.44 (1H, t, J=7.8 Hz), 7.86 (1H, d, J=7.6 Hz), 7.91-8.00 (2H, m), 8.21 (1H, s), 8.54 (1H, s)

Example 108

1-{[4-(3-chlorophenyl)-1,3-thiazol-2-yl]methyl}-1H-pyrazole-4-carboxylic acid

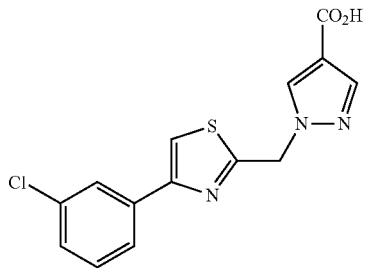 [SMILES: O=C(O)c1cnn(Cc2nc(-c3cccc(Cl)c3)cs2)c1]

By a method similar to that in Example 106, the title compound was obtained from the compound obtained in Example 108a.

$^1$H NMR (DMSO, Varian 400 MHz) δ ppm 5.77 (2H, s), 7.38 (1H, d, J=8.4 Hz), 7.44 (1H, t, J=8.0 Hz), 7.84 (1H, s), 7.87 (1H, d, J=7.6 Hz), 7.96 (1H, s), 8.21 (1H, s), 8.40 (1H, s)

Example 109

1-{[4-(4-methoxyphenyl)-1,3-thiazol-2-yl]methyl}-1H-pyrazole-4-carboxylic acid

Example 109a ethyl 1-{[4-(4-methoxyphenyl)-1,3-thiazol-2-yl]methyl}-1H-pyrazole-4-carboxylate

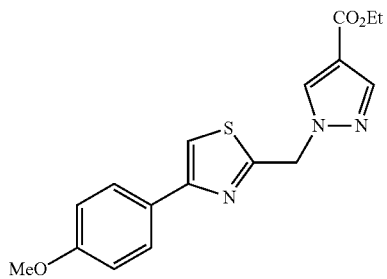 [SMILES: CCOC(=O)c1cnn(Cc2nc(-c3ccc(OC)cc3)cs2)c1]

By a method similar to that in Example 106a, the title compound was obtained from the compound obtained in Example 1b and 2-bromo-1-(4-methoxyphenyl)ethanone.

$^1$H NMR (DMSO, Varian 400 MHz) δ ppm 1.22 (3H, t, J=7.2 Hz), 3.75 (3H, s), 4.18 (2H, q, J=7.2 Hz), 5.76 (2H, s), 6.96 (2H, d, J=8.8 Hz), 7.82 (2H, d, J=8.8 Hz), 7.88 (1H, s), 7.92 (1H, s), 8.53 (1H, s)

Example 109

1-{[4-(4-methoxyphenyl)-1,3-thiazol-2-yl]methyl}-1H-pyrazole-4-carboxylic acid

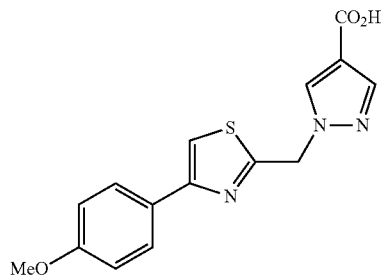 [SMILES: COc1ccc(-c2csc(Cn3cc(C(=O)O)cn3)n2)cc1]

By a method similar to that in Example 106, the title compound was obtained from the compound obtained in Example 109a.

¹H NMR (DMSO, Varian 400 MHz) δ ppm 3.77 (3H, s), 5.78 (2H, s), 6.96-7.00 (2H, m), 7.82-7.87 (2H, m), 7.89 (1H, s), 7.91 (1H, s), 8.47 (1H, s)

Example 110

1-({4-[4-(trifluoromethyl)phenyl]-1,3-thiazol-2-yl}methyl)-1H-pyrazole-4-carboxylic acid

Example 110a ethyl 1-({4-[4-(trifluoromethyl)phenyl]-1,3-thiazol-2-yl}methyl)-1H-pyrazole-4-carboxylate

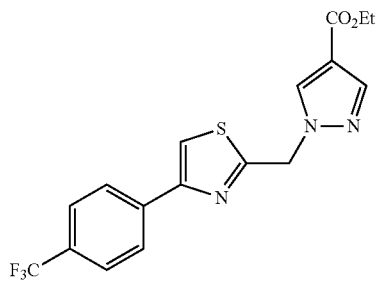 [SMILES: CCOC(=O)c1cnn(Cc2nc(-c3ccc(C(F)(F)F)cc3)cs2)c1]

By a method similar to that in Example 106a, the title compound was obtained from the compound obtained in Example 1b and 2-bromo-1-[4-(trifluoromethyl)phenyl]ethanone.

¹H NMR (DMSO, Varian 400 MHz) δ ppm 1.23 (3H, t, J=7.2 Hz), 4.19 (2H, q, J=7.2 Hz), 5.81 (2H, s), 7.78 (2H, d, J=8.0 Hz), 7.94 (1H, s), 8.12 (2H, d, J=8.4 Hz), 8.30 (1H, s), 8.55 (1H, s)

Example 110

1-({4-[4-(trifluoromethyl)phenyl]-1,3-thiazol-2-yl}methyl)-1H-pyrazole-4-carboxylic acid

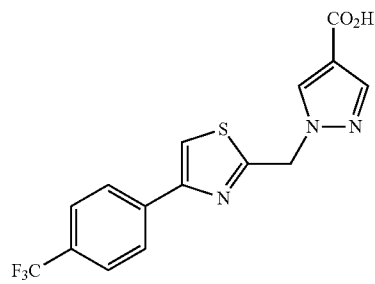 [SMILES: O=C(O)c1cnn(Cc2nc(-c3ccc(C(F)(F)F)cc3)cs2)c1]

By a method similar to that in Example 106, the title compound was obtained from the compound obtained in Example 110a.

¹H NMR (DMSO, Varian 400 MHz) δ ppm 5.86 (2H, s), 7.83 (1H, s), 7.88 (2H, d, J=8.4 Hz), 8.23 (2H, d, J=8.4 Hz), 8.32 (1H, s), 8.40 (1H, s)

Example 111

1-{[4-(4-fluorophenyl)-1,3-thiazol-2-yl]methyl}-1H-pyrazole-4-carboxylic acid

Example 111a ethyl 1-{[4-(4-fluorophenyl)-1,3-thiazol-2-yl]methyl}-1H-pyrazole-4-carboxylate

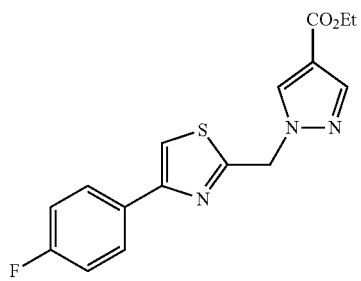 [SMILES: CCOC(=O)c1cnn(Cc2nc(-c3ccc(F)cc3)cs2)c1]

By a method similar to that in Example 106a, the title compound was obtained from the compound obtained in Example 1b and 2-bromo-1-(4-fluorophenyl)ethanone.

¹H NMR (DMSO, Varian 400 MHz) δ ppm 1.23 (3H, t, J=7.2 Hz), 4.19 (2H, q, J=7.2 Hz), 5.78 (2H, s), 7.24 (2H, d, J=9.0 Hz), 7.90-7.98 (3H, m), 8.05 (1H, s), 8.54 (1H, s)

Example 111

1-{[4-(4-fluorophenyl)-1,3-thiazol-2-yl]methyl}-1H-pyrazole-4-carboxylic acid

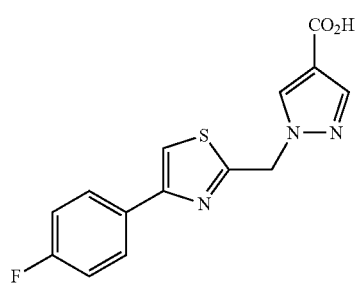 [SMILES: O=C(O)c1cnn(Cc2nc(-c3ccc(F)cc3)cs2)c1]

By a method similar to that in Example 106, the title compound was obtained from the compound obtained in Example 111a.

¹H NMR (DMSO, Varian 400 MHz) δ ppm 5.76 (2H, s), 7.24 (2H, t, J=9.0 Hz), 7.84 (1H, s), 7.94 (2H, dd, J=8.6, 5.4 Hz), 8.04 (1H, s), 8.40 (1H, s)

Example 112

1-{[4-(2-fluorophenyl)-1,3-thiazol-2-yl]methyl}-1H-pyrazole-4-carboxylic acid

Example 112a ethyl 1-{[4-(2-fluorophenyl)-1,3-thiazol-2-yl]methyl}-1H-pyrazole-4-carboxylate

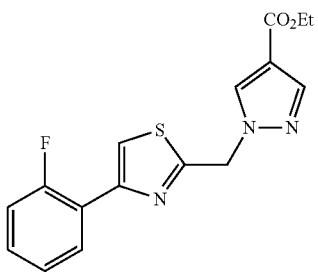 [SMILES: CCOC(=O)c1cnn(Cc2nc(-c3ccccc3F)cs2)c1]

By a method similar to that in Example 106a, the title compound was obtained from the compound obtained in Example 1b and 2-bromo-1-(2-fluorophenyl)ethanone.

¹H NMR (DMSO, Varian 400 MHz) δ ppm 1.25 (3H, t, J=7.2 Hz), 4.20 (2H, q, J=7.2 Hz), 5.83 (2H, s), 7.28-7.35 (2H, m), 7.36-7.45 (1H, m), 7.96 (2H, s), 8.05 (1H, dt, J=8.0, 2.0 Hz), 8.58 (1H, s)

Example 112

1-{[4-(2-fluorophenyl)-1,3-thiazol-2-yl]methyl}-1H-pyrazole-4-carboxylic acid

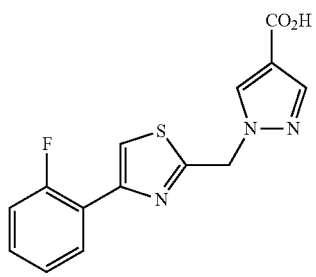 [SMILES: O=C(O)c1cnn(Cc2nc(-c3ccccc3F)cs2)c1]

By a method similar to that in Example 106, the title compound was obtained from the compound obtained in Example 112a.

¹H NMR (DMSO, Varian 400 MHz) δ ppm 5.76 (2H, s), 7.21-7.32 (2H, m), 7.33-7.44 (1H, m), 7.82 (1H, s), 7.92 (1H, d, J=2.4 Hz), 8.04 (1H, t, J=8.0 Hz), 8.35 (1H, s)

Example 113

1-{[4-(3-fluorophenyl)-1,3-thiazol-2-yl]methyl}-1H-pyrazole-4-carboxylic acid

Example 113a ethyl 1-{[4-(3-fluorophenyl)-1,3-thiazol-2-yl]methyl}-1H-pyrazole-4-carboxylate

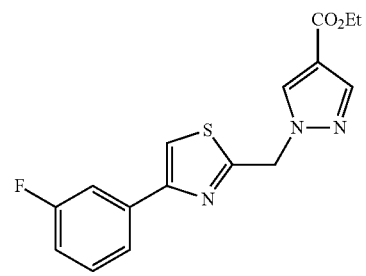 [SMILES: CCOC(=O)c1cnn(Cc2nc(-c3cccc(F)c3)cs2)c1]

By a method similar to that in Example 106a, the title compound was obtained from the compound obtained in Example 1b and 2-bromo-1-(3-fluorophenyl)ethanone.

¹H NMR (DMSO, Varian 400 MHz) δ ppm 1.23 (3H, t, J=7.2 Hz), 4.19 (2H, q, J=7.2 Hz), 5.79 (2H, s), 7.11-7.19 (1H, m), 7.45 (1H, dd, J=14.4, 8.0 Hz), 7.70 (1H, d, J=10 Hz), 7.75 (1H, d, J=8.0 Hz), 7.93 (1H, s), 8.19 (1H, s), 8.55 (1H, s)

Example 113

1-{[4-(3-fluorophenyl)-1,3-thiazol-2-yl]methyl}-1H-pyrazole-4-carboxylic acid

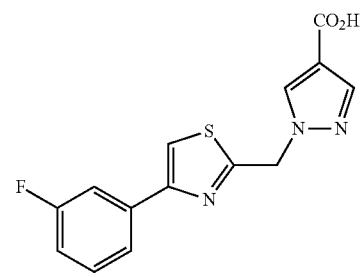 [SMILES: O=C(O)c1cnn(Cc2nc(-c3cccc(F)c3)cs2)c1]

By a method similar to that in Example 106, the title compound was obtained from the compound obtained in Example 113a.

$^1$H NMR (DMSO, Varian 400 MHz) δ ppm 5.77 (2H, s), 7.14 (1H, t, J=7.6 Hz), 7.45 (1H, dd, J=14.2, 7.4 Hz), 7.69 (1H, d, J=10.0 Hz), 7.75 (1H, d, J=7.6 Hz), 7.87 (1H, s), 8.17 (1H, s), 8.44 (1H, s)

Example 114

1-({5-[3-(trifluoromethyl)phenyl]-1,2,4-oxadiazol-3-yl}methyl)-1H-pyrazole-4-carboxylic acid

Example 114a ethyl 1-[(2Z)-2-amino-2-(hydroxyimino)ethyl]-1H-pyrazole-4-carboxylate

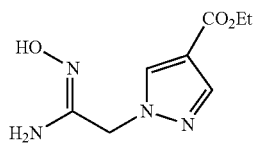

The compound (1.6 g) obtained in Example 1a was suspended in ethanol (20 mL), and potassium carbonate (10.4 g) and hydroxylamine hydrochloride (5.2 g) were added. The reaction mixture was heated under reflux for 12 hr, and the insoluble material was removed by filtration. The solvent was evaporated under reduced pressure from the obtained filtrate to give the title compound as a bister solid.

$^1$H NMR (DMSO-d$_6$, Varian 400 MHz) δ ppm 1.26 (3H, t, J=7.2 Hz), 4.20 (2H, q, J=6.8 Hz), 4.69 (2H, s), 5.57 (2H, br. s.), 7.84 (1H, s), 8.31 (1H, s), 9.33 (1H, br. s.)

Example 114b ethyl 1-({5-[3-(trifluoromethyl)phenyl]-1,2,4-oxadiazol-3-yl}methyl)-1H-pyrazole-4-carboxylate

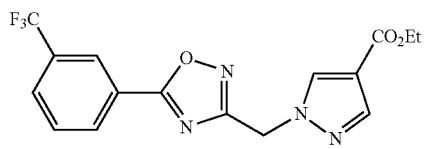

A solution of the compound (2.2 g) obtained in Example 114a in pyridine (40 mL) was cooled in an ice bath and 3-(trifluoromethyl)benzoyl chloride (4.16 g) was added. The reaction mixture was heated to 110-120° C. overnight, cooled to room temperature, and poured into water. The mixture was extracted with ethyl acetate. The ethyl acetate layer was separated, washed successively with 1N aqueous hydrochloric acid solution, and saturated aqueous sodium hydrogen carbonate, dried over sodium sulfate, and concentrated under reduced pressure. The residue was purified by column chromatography (carrier: silica gel, eluent: hexane-petroleum ether) to give the title compound (0.85 g) as a colorless solid.

$^1$H NMR (CDCl$_3$, Varian 400 MHz) δ ppm 1.27 (3H, t, J=7.2 Hz), 4.23 (2H, q, J=7.2 Hz), 5.46 (2H, s), 7.62 (1H, t, J=7.8 Hz), 7.80 (1H, d, J=8.0 Hz), 7.90 (1H, s), 8.06 (1H, s), 8.23 (1H, d, J=8.0 Hz), 8.32 (1H, s)

Example 114

1-({5-[3-(trifluoromethyl)phenyl]-1,2,4-oxadiazol-3-yl}methyl)-1H-pyrazole-4-carboxylic acid

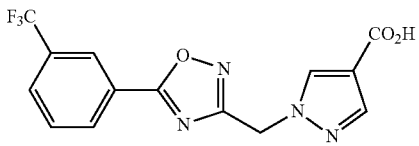 [SMILES: CCOC(=O)c1cnn(Cc2noc(-c3cccc(C(F)(F)F)c3)n2)c1]

The compound (0.85 g) obtained in Example 114b was dissolved in ethanol (8 mL) and water (2 ml), and lithium hydroxide (0.42 g) was added. The reaction mixture was stirred at room temperature overnight and concentrated under reduced pressure. The residue was diluted with water and adjusted to pH 5-6 with 1N hydrochloric acid. The resulting precipitate was collected by filtration and the obtained solid was recrystallized from ethyl acetate-petroleum ether to give the title compound (0.22 g) as a colorless solid.

$^1$H NMR (DMSO-d$_6$, Varian 400 MHz) δ ppm 5.67 (2H, s), 7.72-7.91 (2H, m), 8.06 (1H, d, J=8.0 Hz), 8.27 (1H, s), 8.34 (1H, d, J=8.0 Hz), 8.43 (1H, s)

Example 115

1-({3-[3-(trifluoromethyl)phenyl]-1,2,4-oxadiazol-5-yl}methyl)-1H-pyrazole-4-carboxylic acid

Example 115a ethyl 1-(2-tert-butoxy-2-oxoethyl)-1H-pyrazole-4-carboxylate

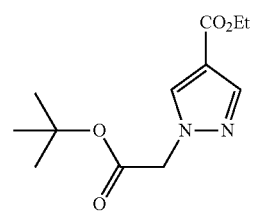 [SMILES: CCOC(=O)c1cnn(CC(=O)OC(C)(C)C)c1]

Ethyl 1H-pyrazole-4-carboxylate (20.0 g) was dissolved in N,N-dimethylformamide (200 mL), and sodium hydride (60% in mineral oil, 8.6 g) was added by small portions under cooling in an ice bath. The reaction mixture was stirred at the same temperature for 30 min, and tert-butyl 2-bromoacetate (33 g) was added dropwise. The mixture was stirred at room temperature for 10 min, heated at 50° C. overnight. The reaction mixture was poured into ice water, and the mixture was extracted with ethyl acetate. The ethyl acetate layer was separated, washed with saturated brine, dried over sodium sulfate, and concentrated under reduced pressure. The residue was purified by column chromatography (carrier: silica gel, eluent: hexane-petroleum ether) to give the title compound (17.6 g) as a colorless solid.

Example 115b

[4-(ethoxycarbonyl)-1H-pyrazol-1-yl]acetic acid

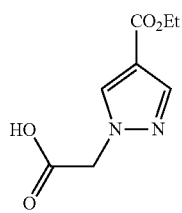 [SMILES: CCOC(=O)c1cnn(CC(=O)O)c1]

The compound (17.5 g) obtained in Example 115a was added to trifluoroacetic acid (280 mL), and the mixture was stirred at room temperature for 30 min. The reaction mixture was concentrated under reduced pressure, and the residue was washed with hexane, and dried to give the title compound (15.0 g) as a colorless solid.

$^1$H NMR (DMSO, Varian 400 MHz) δ ppm 1.32 (3H, t, J=7.2 Hz), 4.27 (2H, q, J=7.2 Hz), 4.99 (2H, s), 7.87 (1H, s), 8.18 (1H, s)

Example 115c ethyl 1-(2-chloro-2-oxoethyl)-1H-pyrazole-4-carboxylate

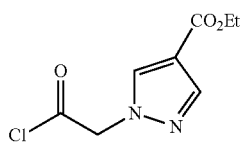 [SMILES: CCOC(=O)c1cnn(CC(=O)Cl)c1]

A solution of the compound (2.0 g) obtained in Example 115b in dichloromethane (20 mL) was cooled in an ice bath, and oxalyl chloride (2.5 g) and N,N-dimethylformamide (2 drops) were added. The reaction mixture was stirred at room temperature overnight and the solvent was evaporated under reduced pressure to give the title compound.

Example 115d ethyl 1-({3-[3-(trifluoromethyl)phenyl]-1,2,4-oxadiazol-5-yl}methyl)-1H-pyrazole-4-carboxylate

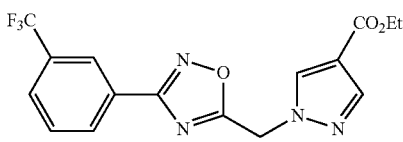 [SMILES: CCOC(=O)c1cnn(Cc2nc(-c3cccc(C(F)(F)F)c3)no2)c1]

A solution of N'-hydroxy-3-(trifluoromethyl)benzenecarboximidamide (2.1 g) in pyridine (20 mL) was cooled in an ice bath, and the compound (2.3 g) obtained in Example 115c was added. The reaction mixture was stirred overnight with heating at 110-120° C. The mixture was poured into water, and the mixture was extracted with ethyl acetate. The ethyl acetate layer was separated, washed successively with 1N hydrochloric acid and saturated brine, dried over sodium sulfate, and concentrated under reduced pressure. The residue was purified by column chromatography (carrier: silica gel, eluent: petroleum ether-ethyl acetate) to give the title compound (0.38 g) as a solid.

$^1$H NMR (CDCl$_3$, Varian 400 MHz) δ ppm 1.29 (3H, t, J=7.0 Hz), 4.23 (2H, q, J=7.2 Hz), 5.59 (2H, s), 7.55 (1H, t, J=7.8 Hz), 7.71 (1H, d, J=8.0 Hz), 7.93 (1H, s), 8.09 (1H, s), 8.18 (1H, d, J=7.6 Hz), 8.27 (1H, s)

Example 115

1-({3-[3-(trifluoromethyl)phenyl]-1,2,4-oxadiazol-5-yl}methyl)-1H-pyrazole-4-carboxylic acid

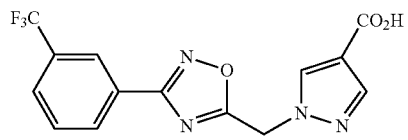 [SMILES: O=C(O)c1cnn(Cc2nc(-c3cccc(C(F)(F)F)c3)no2)c1]

By a method similar to that in Example 114, the title compound (0.22 g) was obtained as a colorless solid from the compound (0.38 g) obtained in Example 115d.

$^1$H NMR (CDCl$_3$, Varian 400 MHz) δ ppm 5.67 (2H, s), 7.61 (1H, t, J=7.8 Hz), 7.74-7.80 (1H, m), 8.05 (1H, s), 8.22 (1H, s), 8.24 (1H, d, J=8.0 Hz), 8.32 (1H, s)

Example 116

1-{[4-(2,4-dichlorophenyl)-1,3-thiazol-2-yl]methyl}-1H-pyrazole-4-carboxylic acid

Example 116a ethyl 1-{[4-(2,4-dichlorophenyl)-1,3-thiazol-2-yl]methyl}-1H-pyrazole-4-carboxylate

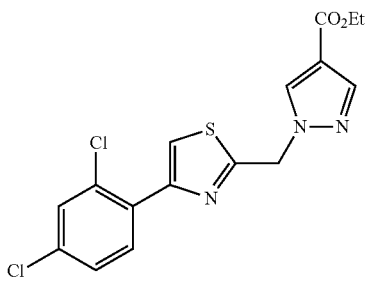 [SMILES: CCOC(=O)c1cnn(Cc2nc(-c3ccc(Cl)cc3Cl)cs2)c1]

By a method similar to that in Example 106a, the title compound was obtained from the compound obtained in Example 1b and 2-bromo-1-(2,4-dichlorophenyl)ethanone.

$^1$H NMR (DMSO, Varian 400 MHz) δ ppm 1.23 (3H, t, J=7.2 Hz), 4.19 (2H, q, J=7.2 Hz), 5.79 (2H, s), 7.50 (1H, dd, J=8.4, 2.0 Hz), 7.70 (1H, d, J=2.0 Hz), 7.83 (1H, d, J=8.4 Hz), 7.93 (1H, s), 8.10 (1H, s), 8.54 (1H, s)

Example 116

1-{[4-(2,4-dichlorophenyl)-1,3-thiazol-2-yl]methyl}-1H-pyrazole-4-carboxylic acid

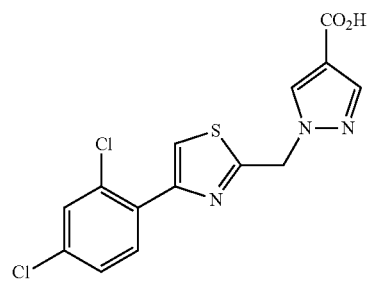 [SMILES: O=C(O)c1cnn(Cc2nc(-c3ccc(Cl)cc3Cl)cs2)c1]

By a method similar to that in Example 106, the title compound was obtained from the compound obtained in Example 116a.

$^1$H NMR (DMSO, Varian 400 MHz) δ ppm 5.80 (2H, s), 7.52 (1H, dd, J=8.4, 2.0 Hz), 7.72 (1H, d, J=2.0 Hz), 7.86 (1H, d, J=8.4 Hz), 7.90 (1H, d, J=0.4 Hz), 8.11 (1H, s), 8.47 (1H, d, J=0.4 Hz)

Example 117

1-{[4-(3-methoxyphenyl)-1,3-thiazol-2-yl]methyl}-1H-pyrazole-4-carboxylic acid

Example 117a)

ethyl 1-{[4-(3-methoxyphenyl)-1,3-thiazol-2-yl]methyl}-1H-pyrazole-4-carboxylate

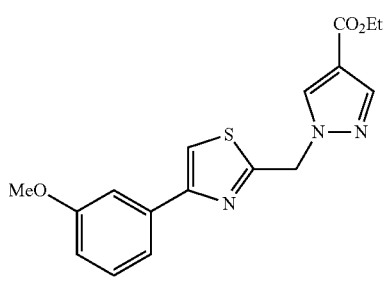 [SMILES: CCOC(=O)c1cnn(Cc2nc(-c3cccc(OC)c3)cs2)c1]

By a method similar to that in Example 106a, the title compound was obtained from the compound obtained in Example 1b and 2-bromo-1-(3-methoxyphenyl)ethanone.

$^1$H NMR (DMSO, Varian 400 MHz) δ ppm 1.25 (3H, t, J=7.2 Hz), 3.79 (3H, s), 4.20 (2H, q, J=7.2 Hz), 5.81 (2H, s), 6.88-6.93 (1H, m), 7.33 (1H, t, J=8.0 Hz), 7.45-7.52 (2H, m), 7.95 (1H, s), 8.12 (1H, s), 8.57 (1H, s)

Example 117

1-{[4-(3-methoxyphenyl)-1,3-thiazol-2-yl]methyl}-1H-pyrazole-4-carboxylic acid

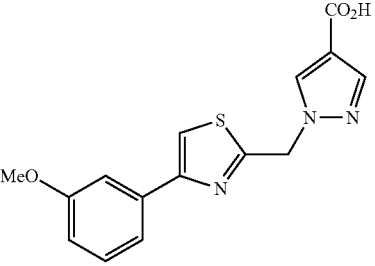 [SMILES: COc1cccc(-c2csc(Cn3cc(C(=O)O)cn3)n2)c1]

By a method similar to that in Example 106, the title compound was obtained from the compound obtained in Example 117a.

$^1$H NMR (DMSO, Varian 400 MHz) δ ppm 3.80 (3H, s), 5.66 (2H, s), 6.88-6.92 (1H, m), 7.33 (1H, t, J=8.0 Hz), 7.47-7.56 (3H, m), 7.85 (1H, s), 8.07 (1H, s)

Example 118

1-{[4-(2,3-dichlorophenyl)-1,3-thiazol-2-yl]methyl}-1H-pyrazole-4-carboxylic acid Example 118a ethyl 1-{[4-(2,3-dichlorophenyl)-1,3-thiazol-2-yl]methyl}-1H-pyrazole-4-carboxylate

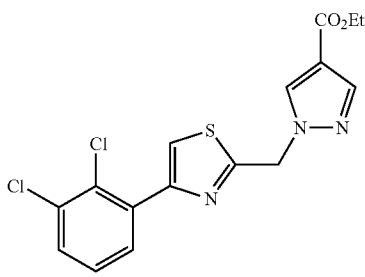 [SMILES: CCOC(=O)c1cnn(Cc2nc(-c3cccc(Cl)c3Cl)cs2)c1]

By a method similar to that in Example 106a, the title compound was obtained from the compound obtained in Example 1b and 2-bromo-1-(2,3-dichlorophenyl)ethanone.

$^1$H NMR (DMSO, Varian 400 MHz) δ ppm 1.23 (3H, t, J=7.2 Hz), 4.18 (2H, q, J=7.2 Hz), 5.80 (2H, s), 7.42 (1H, t, J=8.0 Hz), 7.65 (1H, dd, J=8.0, 1.2 Hz), 7.70 (1H, dd, J=8.0, 1.2 Hz), 7.93 (1H, s), 8.08 (1H, s), 8.54 (1H, s)

Example 118

1-{[4-(2,3-dichlorophenyl)-1,3-thiazol-2-yl]methyl}-1H-pyrazole-4-carboxylic acid

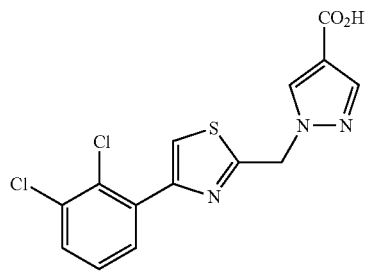 [SMILES: O=C(O)c1cnn(Cc2nc(-c3cccc(Cl)c3Cl)cs2)c1]

By a method similar to that in Example 106, the title compound was obtained from the compound obtained in Example 118a.

$^1$H NMR (DMSO, Varian 400 MHz) δ ppm 5.78 (2H, s), 7.43 (1H, t, J=7.8 Hz), 7.66 (1H, dd, J=8.0, 1.6 Hz), 7.71 (1H, dd, J=8.0, 1.6 Hz), 7.88 (1H, s), 8.08 (1H, s), 8.45 (1H, s)

Example 119

1-{[4-(2,5-dichlorophenyl)-1,3-thiazol-2-yl]methyl}-1H-pyrazole-4-carboxylic acid Example 119a ethyl 1-{[4-(2,5-dichlorophenyl)-1,3-thiazol-2-yl]methyl}-1H-pyrazole-4-carboxylate

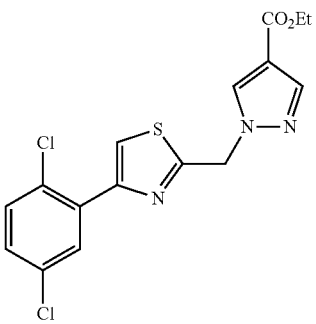 [SMILES: CCOC(=O)c1cnn(Cc2nc(-c3cc(Cl)ccc3Cl)cs2)c1]

By a method similar to that in Example 106a, the title compound was obtained from the compound obtained in Example 1b and 2-bromo-1-(2,5-dichlorophenyl)ethanone.

$^1$H NMR (DMSO, Varian 400 MHz) δ ppm 1.23 (3H, t, J=7.2 Hz), 4.19 (2H, q, J=7.2 Hz), 5.80 (2H, s), 7.45 (1H, dd, J=8.6, 2.6 Hz), 7.58 (1H, d, J=8.4 Hz), 7.87 (1H, d, J=2.8 Hz), 7.94 (1H, d, J=0.4 Hz), 8.17 (1H, s), 8.55 (1H, d, J=0.8 Hz)

Example 119

1-{[4-(2,5-dichlorophenyl)-1,3-thiazol-2-yl]methyl}-1H-pyrazole-4-carboxylic acid

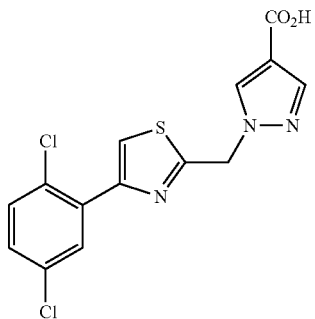 [SMILES: O=C(O)c1cnn(Cc2nc(-c3cc(Cl)ccc3Cl)cs2)c1]

By a method similar to that in Example 106, the title compound was obtained from the compound obtained in Example 119a.

$^1$H NMR (DMSO, Varian 400 MHz) δ ppm 5.79 (2H, s), 7.46 (1H, dd, J=8.4, 2.8 Hz), 7.59 (1H, d, J=8.4 Hz), 7.88 (2H, s), 8.18 (1H, s), 8.46 (1H, s)

Example 120

1-{[4-(2-chlorophenyl)-1,3-thiazol-2-yl]methyl}-1H-pyrazole-4-carboxylic acid

Example 120a ethyl 1-{[4-(2-chlorophenyl)-1,3-thiazol-2-yl]methyl}-1H-pyrazole-4-carboxylate

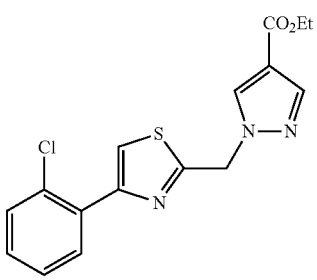 [SMILES: CCOC(=O)c1cnn(Cc2nc(-c3ccccc3Cl)cs2)c1]

By a method similar to that in Example 106a, the title compound was obtained from the compound obtained in Example 1b and 2-bromo-1-[2-chlorophenyl]ethanone.

¹H NMR (DMSO, Varian 400 MHz) δ ppm 1.25 (3H, t, J=7.2 Hz), 4.21 (2H, q, J=7.2 Hz), 5.81 (2H, s), 7.34-7.45 (2H, m), 7.51-7.56 (1H, m), 7.79-7.84 (1H, m), 7.95 (1H, s), 8.06 (1H, s), 8.56 (1H, s)

Example 120

1-{[4-(2-chlorophenyl)-1,3-thiazol-2-yl]methyl}-1H-pyrazole-4-carboxylic acid

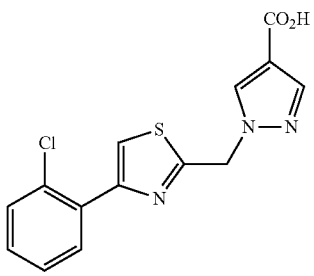 [SMILES: O=C(O)c1cnn(Cc2nc(-c3ccccc3Cl)cs2)c1]

By a method similar to that in Example 106, the title compound was obtained from the compound obtained in Example 120a.

¹H NMR (DMSO, Varian 400 MHz) δ ppm 5.74 (2H, s), 7.43-7.55 (2H, m), 7.63 (1H, dd, J=7.6, 1.6 Hz), 7.91 (1H, dd, J=7.6, 2.0 Hz), 7.86 (1H, s), 8.14 (1H, s), 8.53 (1H, s)

Example 121

1-{([4-(3,5-dichlorophenyl)-1,3-thiazol-2-yl]methyl}-1H-pyrazole-4-carboxylic acid Example 121a ethyl 1-{[4-(3,5-dichlorophenyl)-1,3-thiazol-2-yl]methyl}-1H-pyrazole-4-carboxylate

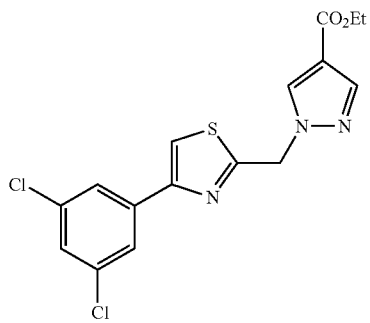 [SMILES: CCOC(=O)c1cnn(Cc2nc(-c3cc(Cl)cc(Cl)c3)cs2)c1]

By a method similar to that in Example 106a, the title compound was obtained from the compound obtained in Example 1b and 2-bromo-1-(3,5-dichlorophenyl)ethanone.

¹H NMR (DMSO, Varian 400 MHz) δ ppm 1.25 (3H, t, J=7.0 Hz), 4.21 (2H, q, J=7.0 Hz), 5.81 (2H, s), 7.57 (1H, t, J=1.8 Hz), 7.94-7.98 (3H, m), 8.38 (1H, s), 8.57 (1H, s)

Example 121

1-{[4-(3,5-dichlorophenyl)-1,3-thiazol-2-yl]methyl}-1H-pyrazole-4-carboxylic acid

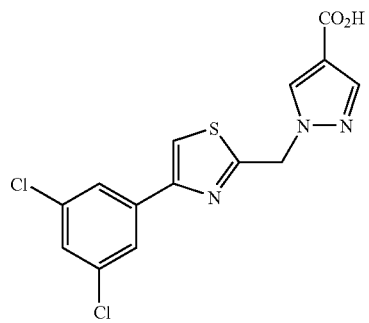 [SMILES: O=C(O)c1cnn(Cc2nc(-c3cc(Cl)cc(Cl)c3)cs2)c1]

By a method similar to that in Example 106, the title compound was obtained from the compound obtained in Example 121a.

¹H NMR (DMSO, Varian 400 MHz) δ ppm 5.79 (2H, s), 7.54 (1H, t, J=1.8 Hz), 7.88 (1H, s), 7.95 (2H, d, J=2.0 Hz), 8.35 (1H, s), 8.47 (1H, s)

Example 122

1-({5-[3-(trifluoromethyl)phenyl]-1,3,4-oxadiazol-2-yl}methyl)-1H-pyrazole-4-carboxylic acid Example 122a ethyl 1-({5-[3-(trifluoromethyl)phenyl]-1,3,4-oxadiazol-2-yl}methyl)-1H-pyrazole-4-carboxylate

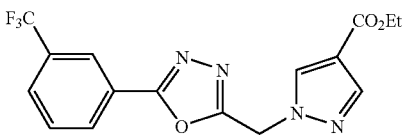

A solution of the compound (1.0 g) obtained in Example 115b in dichloromethane (15 ml) was cooled in an ice bath, N,N'-carbonyldiimidazole (0.81 g) was added and the mixture was stirred for 30 min. 3-(Trifluoromethyl)benzohydrazide hydrochloride (1.2 g) was added, and the mixture was stirred at the same temperature for 45 min. Then, carbon tetrabromide (3.32 g) and triphenylphosphine (2.6 g) were added, and the mixture was further stirred at the same temperature for 2 hr. The solvent was evaporated under reduced pressure, and the residue was purified by column chromatography (carrier: silica gel, eluent: petroleum ether-ethyl acetate) to give the title compound (0.64 g) as a colorless oil.

¹H NMR (CDCl₃, Varian 400 MHz) δ ppm 1.27 (3H, t, J=7.2 Hz), 4.23 (2H, q, J=7.2 Hz), 5.59 (2H, s), 7.60 (1H, t, J=7.8 Hz), 7.75 (1H, d, J=8.0 Hz), 7.92 (1H, s), 8.05 (1H, s), 8.16 (1H, d, J=7.6 Hz), 8.22 (1H, s)

Example 122b benzyl 1-({5-[3-(trifluoromethyl)phenyl]-1,3,4-oxadiazol-2-yl}methyl)-1H-pyrazole-4-carboxylate

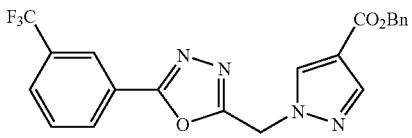 [SMILES: O=C(OCc1ccccc1)c1cnn(Cc2nnc(-c3cccc(C(F)(F)F)c3)o2)c1]

Benzyl alcohol (4 mL) was cooled in an ice bath, sodium hydride (60% in mineral oil, 30 mg) was added and the mixture was stirred for 30 min. The compound (0.40 g) obtained in Example 115c in benzyl alcohol (1 mL) was added to the reaction mixture, and the mixture was stirred under an argon atmosphere at 80° C. overnight with heating, and cooled to room temperature. Benzyl alcohol was evaporated under reduced pressure, and the residue was purified by column chromatography (carrier: silica gel, eluent: petroleum ether-ethyl acetate) to give the title compound (0.29 g) as a colorless solid.

$^1$H NMR (CDCl$_3$, Varian 400 MHz) δ ppm 5.22 (2H, s), 5.58 (2H, s), 7.26-7.34 (5H, m), 7.59 (1H, t, J=8.4 Hz), 7.75 (1H, d, J=8.0 Hz), 7.94 (1H, s), 8.06 (1H, s), 8.15 (1H, d, J=7.6 Hz), 8.22 (1H, s)

Example 122

1-({5-[3-(trifluoromethyl)phenyl]-1,3,4-oxadiazol-2-yl}methyl)-1H-pyrazole-4-carboxylic acid

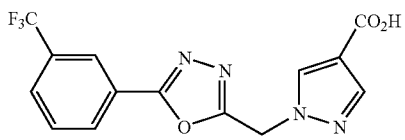

The compound (0.08 g) obtained in Example 122b was dissolved in ethyl acetate (2 ml), palladium carbon (5 mg) was added, and the mixture was stirred under a hydrogen atmosphere at room temperature overnight. Palladium carbon was removed by filtration, and the solvent was evaporated from the filtrate under reduced pressure to give the title compound (0.06 g) as a colorless solid.

$^1$H NMR (CDCl$_3$, Varian 400 MHz) δ ppm 5.68 (2H, s), 7.65 (1H, t, J=8.0 Hz), 7.81 (1H, d, J=7.6 Hz), 8.03 (1H, s), 8.19 (1H, s), 8.22 (1H, d, J=7.6 Hz), 8.28 (1H, s)

Example 123

1-({5-[3-(trifluoromethyl)phenyl]-1,3,4-thiadiazol-2-yl}methyl)-1H-pyrazole-4-carboxylic acid

Example 123a ethyl 1-(2-hydrazino-2-oxoethyl)-1H-pyrazole-4-carboxylate

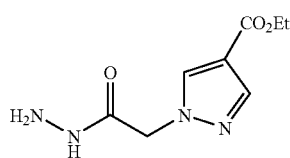 [SMILES: CCOC(=O)c1cnn(CC(=O)NN)c1]

A solution of the compound (9.4 g) obtained in Example 115b, N-[3-(dimethylamino)propyl]-N'-ethylcarbodiimide (18.1 g) and 1-hydroxybenzotriazole (6.5 g) in dichloromethane (100 mL) was cooled to −20° C., and a solution of tert-butyl hydrazinecarboxylate (9.5 g) in dichloromethane (20 mL) was added dropwise. The reaction mixture was stirred at room temperature overnight, poured into water, and the mixture was extracted with ethyl acetate. The ethyl acetate layer was washed with saturated brine, dried over sodium sulfate, and concentrated under reduced pressure. The residue was purified by column chromatography (carrier: silica gel, eluent: petroleum ether/ethyl acetate/triethylamine=10/1/0.001) to give ethyl 1-{2-[2-(tert-butoxycarbonyl)hydrazino]-2-oxoethyl}-1H-pyrazole-4-carboxylate (9.2 g) as a colorless solid. The solid was dissolved in ethyl acetate (50 mL), and hydrogen chloride-ethyl acetate (50 mL) was added. The mixture was stirred at room temperature for 1 hr, and the precipitate was collected by filtration to give the title compound (6.0 g) as a colorless solid.

$^1$H NMR (DMSO-d$_6$, Varian 400 MHz): δ 1.23 (3H, t, J=7.0 Hz), 4.19 (2H, q, J=7.2 Hz), 5.04 (2H, s), 7.85 (1H, s), 8.33 (1H, s)

Example 123b ethyl 1-[2-oxo-2-(2-{[3-(trifluoromethyl)phenyl]carbonyl}hydrazino)ethyl]-1H-pyrazole-4-carboxylate

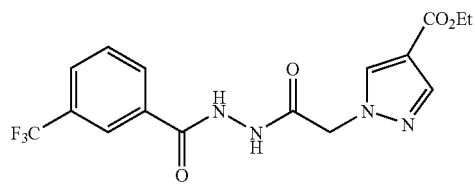 [SMILES: CCOC(=O)c1cnn(CC(=O)NNC(=O)c2cccc(C(F)(F)F)c2)c1]

The compound (6.0 g) obtained in Example 123a and triethylamine (8.33 g) were dissolved in dichloromethane (100 mL), and a solution of 3-(trifluoromethyl)benzoylchloride (10.0 g) in dichloromethane (20 ml) was added. The reaction mixture was stirred at room temperature overnight, an insoluble material was removed by filtration, and the filtrate was washed with saturated brine, dried over sodium sulfate, and concentrated under reduced pressure. The residue was purified by column chromatography (carrier: silica gel, eluent: petroleum ether/ethyl acetate/triethylamine=5/1/0.001) to give the title compound (4.1 g) as an oil.

¹H-NMR (CDCl₃, Varian 400 MHz) δ ppm 1.34 (3H, t, J=7.2 Hz), 4.29 (2H, q, J=7.2 Hz), 5.01 (2H, s), 7.52 (1H, t, J=7.8 Hz), 7.71 (1H, d, J=7.6 Hz), 7.96 (1H, s), 8.0 (1H, s), 8.03 (1H, d, J=7.6 Hz), 8.11 (1H, s)

Example 123c ethyl 1-({5-[3-(trifluoromethyl)phenyl]-1,3,4-thiadiazol-2-yl}methyl)-1H-pyrazole-4-carbonxylate

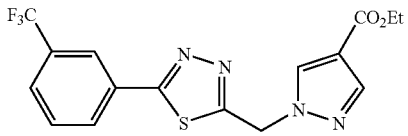 [SMILES: CCOC(=O)c1cnn(Cc2nnc(-c3cccc(C(F)(F)F)c3)s2)c1]

To a solution of the compound (2.1 g) obtained in Example 123b in toluene (25 ml) was added 2,4-bis(4-methoxyphenyl)-1,3,2,4-dithiadiphosphetane 2,4-disulfide (2.65 g), and the reaction mixture was heated under reflux overnight. The solvent was evaporated under reduced pressure and the residue was purified by column chromatography (carrier: silica gel, eluent: petroleum ether-ethyl acetate) to give the title compound (0.45 g) as an oil.

¹H-NMR (CDCl₃, Varian 400 MHz): δ 1.34 (3H, t, J=7.0 Hz), 4.30 (2H, q, J=7.2 Hz), 5.66 (2H, s), 7.66 (1H, t, J=8.0 Hz), 7.82 (1H, d, J=8.0 Hz), 7.99 (1H, s), 8.12 (1H, s), 8.23 (1H, d, J=7.6 Hz), 8.29 (1H, s)

Example 123

1-({5-[3-(trifluoromethyl)phenyl]-1,3,4-thiadiazol-2-yl}methyl)-1H-pyrazole-4-carboxylic acid

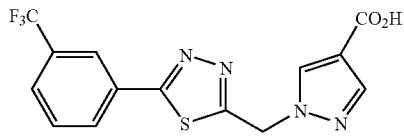

By a method similar to that in Example 114, the title compound (0.13 g) was obtained as a colorless solid from the compound (0.45 g) obtained in Example 123c.

¹H NMR (DMSO-ds, Varian 400 MHz) δ ppm 5.97 (2H, s), 7.76 (1H, t, J=8.2 Hz), 7.83-7.97 (2H, m) 8.21-8.29 (2H, m), 8.50 (1H, s)

Example 124

1-({5-[3-(trifluoromethyl)phenyl]-1,3-oxazol-2-yl}methyl)-1H-pyrazole-4-carboxylic acid Example 124a ethyl 1-[2-oxo-2-({2-oxo-2-[3-(trifluoromethyl)phenyl]ethyl}amino)ethyl]-1H-pyrazole-4-carboxylate

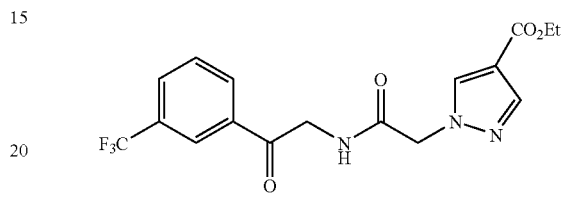

The compound (3.2 g) obtained in Example 115c and 2-amino-1-[3-(trifluoromethyl)phenyl]ethanone (2.88 g) were dissolved in dichloromethane (120 mL) and water (40 ml), and an aqueous solution (40 mL) of sodium acetate (2.46 g) was added dropwise under cooling in an ice bath. The reaction mixture was stirred at room temperature overnight, and the organic layer was separated, dried over sodium sulfate and concentrated under reduced pressure. The residue was purified by column chromatography (carrier: silica gel, eluent: petroleum ether-ethyl acetate) to give the title compound (0.92 g) as a colorless solid.

¹H NMR (DMSO-d₆, Varian 400 MHz) δ ppm 1.24 (3H, t, J=7.2 Hz), 4.19 (2H, q, J=7.2 Hz), 4.74 (2H, d, J=5.2 Hz), 4.98 (2H, s), 7.78 (1H, t, J=7.8 Hz), 7.84 (1H, s), 8.02 (1H, d, J=8.0 Hz), 8.21 (1H, s), 8.24-8.35 (2H, m), 8.59 (1H, t, J=4.8 Hz)

Example 124b ethyl 1-({5-[3-(trifluoromethyl)phenyl]-1,3-oxazol-2-yl}methyl)-1H-pyrazole-4-carboxylate

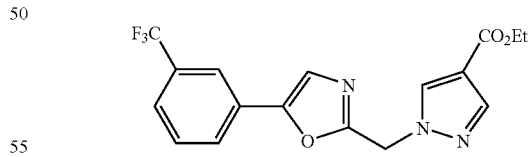

The compound (0.73 g) obtained in Example 124a was dissolved in phosphorus oxychloride (10 mL), and the mixture was stirred at 110-130° C. overnight with heating. The reaction mixture was cooled to room temperature, slowly poured into water, and the mixture was extracted with ethyl acetate. The ethyl acetate layer was dried over sodium sulfate, and concentrated under reduced pressure. The residue was purified by column chromatography (carrier: silica gel, eluent: petroleum ether-ethyl acetate) to give the title compound (0.50 g) as a colorless solid.

¹H NMR (CDCl₃, Varian 400 MHz) δ ppm 1.27 (3H, t, J=7.0 Hz), 4.22 (2H, q, J=7.2 Hz), 5.45 (2H, s), 7.35 (1H, s), 7.44-7.56 (2H, m), 7.71 (1H, d, J=8.0 Hz), 7.78 (1H, s), 7.91 (1H, s), 8.03 (1H, s)

Example 124

1-({5-[3-(trifluoromethyl)phenyl]-1,3-oxazol-2-yl}methyl)-1H-pyrazole-4-carboxylic acid

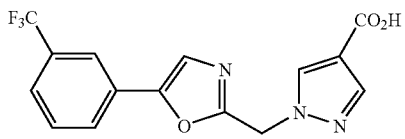 [SMILES: O=C(O)c1cnn(Cc2ncc(-c3cccc(C(F)(F)F)c3)o2)c1]

By a method similar to that in Example 114, the title compound (0.12 g) was obtained as a colorless solid from the compound (0.40 g) obtained in Example 124b.

¹H NMR (CDCl₃, Varian 400 MHz) δ ppm 5.49 (2H, s), 7.36 (1H, s), 7.45-7.59 (2H, m), 7.72 (1H, d, J=7.6 Hz), 7.78 (1H, s), 7.97 (1H, s), 8.10 (1H, s)

Example 125

1-({4-[2-(trifluoromethyl)phenyl]-1,3-thiazol-2-yl}methyl)-1H-pyrazole-4-carboxylic acid

Example 125a ethyl 1-({4-[2-(trifluoromethyl)phenyl]-1,3-thiazol-2-yl}methyl)-1H-pyrazole-4-carboxylate

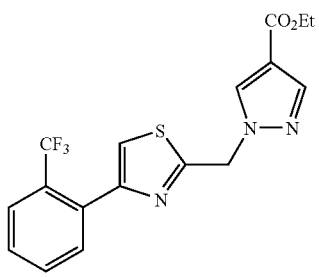 [SMILES: CCOC(=O)c1cnn(Cc2nc(-c3ccccc3C(F)(F)F)cs2)c1]

By a method similar to that in Example 106a, the title compound was obtained from the compound obtained in Example 1b and 2-bromo-1-[2-(trifluoromethyl)phenyl]ethanone.

¹H NMR (DMSO, Varian 400 MHz) δ ppm 1.23 (3H, t, J=7.2 Hz), 4.18 (2H, q, J=7.2 Hz), 5.78 (2H, s), 7.56-7.65 (2H, m), 7.66-7.78 (2H, m), 7.81 (1H, d, J=7.6 Hz), 7.93 (1H, s), 8.50 (1H, s)

Example 125

1-({4-[2-(trifluoromethyl)phenyl]-1,3-thiazol-2-yl}methyl)-1H-pyrazole-4-carboxylic acid

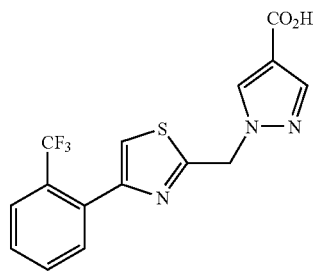

By a method similar to that in Example 106, the title compound was obtained from the compound obtained in Example 125a.

¹H NMR (CDCl₃, Varian 400 MHz) δ ppm 5.86 (2H, s), 7.66-7.75 (2H, m), 7.76-7.85 (2H, m), 7.86-8.00 (2H, m), 8.46 (1H, s)

Example 126

1-({5-methyl-4-[3-(trifluoromethyl)phenyl]thiophen-2-yl}methyl)-1H-pyrazole-4-carboxylic acid

Example 126a 4-bromo-5-methylthiophene-2-carbaldehyde

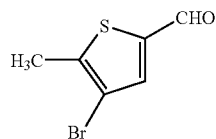

To a solution of 5-methylthiophene-2-carbaldehyde (2.00 g) in acetic acid (20 mL) was added dropwise bromine (0.90 mL). The reaction mixture was stirred at room temperature for 8 hr, saturated aqueous sodium hydrogen carbonate was added by small portions, and the mixture was extracted with ethyl acetate. The ethyl acetate layer was washed successively with saturated aqueous sodium hydrogen carbonate, saturated sodium thiosulfate aqueous solution, dried over magnesium sulfate, and concentrated under reduced pressure. The residue was purified by column chromatography (carrier: silica gel, eluent: hexane-ethyl acetate) to give the title compound (2.11 g).

¹H NMR (CDCl₃, Varian 400 MHz) δ ppm 2.49 (3H, s), 7.60 (1H, s), 9.78 (1H, s)

Example 126b (4-bromo-5-methylthiophen-2-yl)methanol

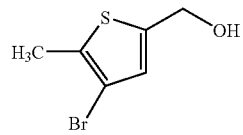

A solution of the compound (1.00 g) obtained in Example 126a in ethanol (20 mL) was cooled in an ice bath, and sodium borohydride (0.28 g) was added. The reaction mixture was stirred at room temperature for 1 hr and cooled in an ice bath. Aqueous saturated ammonium chloride was added, and the mixture was extracted with ethyl acetate. The ethyl acetate layer was washed successively with aqueous saturated ammonium chloride and saturated brine, dried over magnesium sulfate, and concentrated under reduced pressure. The residue was purified by column chromatography (carrier: silica gel, eluent: hexane-ethyl acetate) to give the title compound (0.79 g) as an oil.

$^1$H NMR (CDCl$_3$, Varian 400 MHz) δ ppm 1.77 (1H, t, J=5.6 Hz), 2.38 (3H, s), 4.71 (2H, d, J=5.6 Hz), 6.81 (1H, s)

Example 126c

{5-methyl-4-[3-(trifluoromethyl)phenyl]thiophen-2-yl}methanol[3-(trifluoromethyl)phenyl]boronic acid

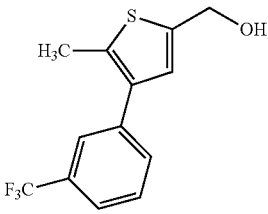

Under a nitrogen atmosphere, to a mixture of the compound (1.21 g) obtained in Example 126b, 3-(trifluoromethyl)phenylboronic acid (1.34 g), cesium carbonate (3.82 g) and tetrahydrofuran (15 ml) was added [1,1'-bis(diphenylphosphino)ferrocene]dichloropalladium(II) (0.14 g), and the mixture was heated under reflux for 15 hr. The reaction mixture was cooled to room temperature, water was added, and the mixture was extracted with ethyl acetate. The ethyl acetate layer was washed with saturated brine, dried over magnesium sulfate, and concentrated under reduced pressure. The residue was purified by column chromatography (carrier: silica gel, eluent: hexane-ethyl acetate) to give the title compound (1.20 g) as a solid.

$^1$H NMR (CDCl$_3$, Varian 400 MHz) δ ppm 1.79 (1H, t, J=6.0 Hz), 2.48 (3H, s), 4.79 (2H, d, J=6.0 Hz), 6.96 (1H, s), 7.50-7.61 (3H, m), 7.62 (1H, s)

Example 126d 5-(chloromethyl)-2-methyl-3-[3-(trifluoromethyl)phenyl]thiophene

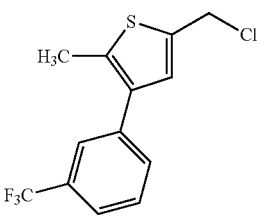

To a solution of the compound (1.00 g) obtained in Example 126c in dichloromethane (8 mL) were added carbon tetrachloride (1.8 mL) and triphenylphosphine (1.44 g). The reaction mixture was stirred at room temperature for 18 hr and the solvent was evaporated under reduced pressure. To the residue were added hexane and ethyl acetate (v/v=1/1), and the insoluble material was filtered off. The filtrate was concentrated under reduced pressure, and the residue was purified by column chromatography (carrier: silica gel, eluent: hexane-ethyl acetate) to give the title compound (0.78 g) as an oil.

$^1$H NMR (CDCl$_3$, Varian 400 MHz) δ ppm 2.48 (3H, s), 4.77 (2H, s), 7.03 (1H, s), 7.52-7.58 (3H, m), 7.61 (1H, s)

Example 126e ethyl 1-({5-methyl-4-[3-(trifluoromethyl)phenyl]thiophen-2-yl}methyl)-1H-pyrazole-4-carboxylate

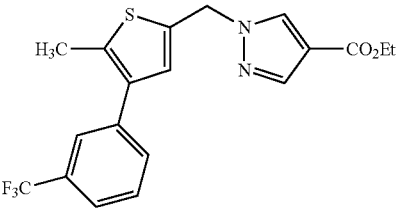

A suspension of sodium hydride (55% in mineral oil, 0.11 g) in tetrahydrofuran (4 mL) was cooled in an ice bath, and a solution of ethyl 1H-pyrazole-4-carboxylate (0.29 g) in tetrahydrofuran (2 mL) was added dropwise. The mixture was stirred at room temperature for 30 min, and a solution of the compound obtained in Example 126d in tetrahydrofuran (2 mL) was added dropwise. After stirring at room temperature for 6 hr, saturated aqueous ammonium chloride solution was added, and the mixture was extracted with ethyl acetate. The ethyl acetate layer was washed with saturated brine, dried over magnesium sulfate, and concentrated under reduced pressure. The residue was purified by column chromatography (carrier: silica gel, eluent: hexane-ethyl acetate) to give the title compound (0.20 g) as a solid.

$^1$H NMR (CDCl$_3$, Varian 400 MHz) δ ppm 1.34 (3H, t, J=7.2 Hz), 2.46 (3H, s), 4.28 (2H, q, J=7.2 Hz), 5.42 (2H, s), 7.02 (1H, s), 7.52-7.55 (2H, m), 7.56-7.60 (1H, m), 7.60 (1H, s), 7.95 (2H, s)

Example 126

1-({5-methyl-4-[3-(trifluoromethyl)phenyl]thiophen-2-yl}methyl)-1H-pyrazole-4-carboxylic acid

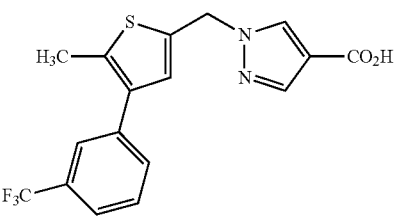 [SMILES: CCOC(=O)c1cnn(Cc2cc(-c3cccc(C(F)(F)F)c3)c(C)s2)c1]

The compound (0.20 g) obtained in Example 126e was dissolved in ethanol (2 mL), and 6N aqueous sodium hydroxide solution (0.83 mL) was added. The reaction mixture was heated under reflux for 2 hr, cooled in an ice bath, adjusted to pH 2 with 6N hydrochloric acid, and the mixture was extracted with ethyl acetate. The ethyl acetate layer was dried over magnesium sulfate, concentrated under reduced pressure, and the residue was washed with ether to give the title compound (0.16 g) as a colorless solid.

$^1$H NMR (DMSO-$d_6$, Varian 400 MHz) δ ppm 2.43 (3H, s), 5.51 (2H, s), 7.25 (1H, s), 7.68-7.74 (4H, s), 7.83 (1H, s), 8.37 (1H, s)

Example 127

1-({2-methyl-5-[3-(trifluoromethyl)phenyl]furan-3-yl}methyl)-1H-pyrazole-4-carboxylic acid Example 127a methyl 2-methyl-5-[3-(trifluoromethyl)phenyl]furan-3-carboxylate

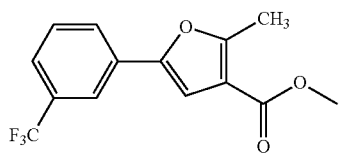 [SMILES: COC(=O)c1cc(-c2cccc(C(F)(F)F)c2)oc1C]

A solution of acetomethyl acetate (4.3 mL) and DBU (2.0 ml) in toluene (20 mL) was cooled in an ice bath, and a solution of 2-bromo-1-[3-(trifluoromethyl)phenyl]ethanone (3.50 g) in toluene (20 mL) was added. The reaction mixture was stirred at room temperature for 4 hr, and purified by column chromatography (carrier: silica gel, eluent: hexane-ethyl acetate). The obtained compound was dissolved in toluene (40 mL), p-toluenesulfonic acid (0.23 g) was added, and the mixture was heated at 100° C. for 2 hr. The reaction mixture was cooled to room temperature, saturated aqueous sodium hydrogen carbonate was added, and the mixture was extracted with ethyl acetate. The ethyl acetate layer was washed with saturated brine, dried over magnesium sulfate, and concentrated under reduced pressure. The residue was purified by column chromatography (carrier: silica gel, eluent: hexane-ethyl acetate) to give the title compound (2.00 g) as a solid.

$^1$H NMR (CDCl$_3$, Varian 400 MHz) δ ppm 2.67 (3H, s), 3.86 (3H, s), 6.98 (1H, s), 7.48-7.53 (2H, m), 7.77-7.80 (1H, m), 7.88 (1H, s)

Example 127b

{2-methyl-5-[3-(trifluoromethyl)phenyl]furan-3-yl}methanol

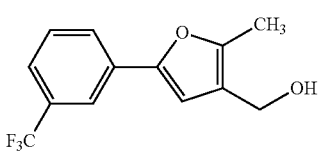

By a method similar to that in Example 128d, the title compound (1.59 g) was obtained as an oil from the compound obtained in Example 127a.

$^1$H NMR (CDCl$_3$, Varian 400 MHz) δ ppm 1.43 (1H, br. s.), 2.38 (3H, s), 4.53 (2H, s), 6.73 (1H, s), 7.46-7.47 (2H, m), 7.75-7.78 (1H, m), 7.86 (1H, s)

Example 127c ethyl 1-({2-methyl-5-[3-(trifluoromethyl)phenyl]furan-3-yl}methyl)-1H-pyrazole-4-carboxylate

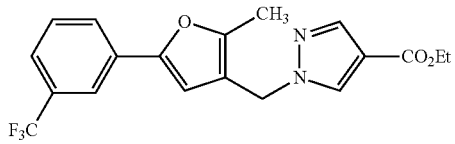 [SMILES: CCOC(=O)c1cnn(Cc2cc(-c3cccc(C(F)(F)F)c3)oc2C)c1]

A solution of the compound (0.40 g) obtained in Example 127b, ethyl 1H-pyrazole-4-carboxylate (0.26 g) and triphenylphosphine (0.49 g) in tetrahydrofuran (8 mL) was cooled in an ice bath, diethyl azodicarboxylate (0.30 mL) was added, and the mixture was stirred at the same temperature for 1 hr. Saturated aqueous ammonium chloride solution was added to the reaction mixture, and the mixture was extracted with ethyl acetate. The obtained organic layer was washed with saturated brine, and dried over anhydrous magnesium sulfate. The solvent was evaporated under reduced pressure and the residue was purified by column chromatography (carrier: silica gel, eluent: hexane/ethyl acetate) to give the title compound (0.35 g) as a solid.

$^1$H NMR (CDCl$_3$, Varian 400 MHz) δ ppm 1.33 (3H, t, J=7.2 Hz), 2.42 (3H, s), 4.28 (2H, q, J=7.2 Hz), 5.13 (2H, s), 6.62 (1H, s), 7.47-7.49 (2H, m), 7.75-7.76 (1H, m), 7.85 (1H, s), 7.86 (1H, s), 7.94 (1H, s)

Example 127

1-({2-methyl-5-[3-(trifluoromethyl)phenyl]furan-3-yl}methyl)-1H-pyrazole-4-carboxylic acid

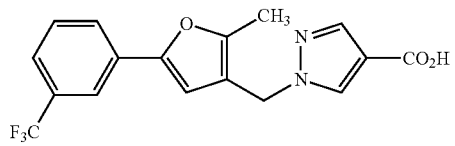 [SMILES: Cc1oc(-c2cccc(C(F)(F)F)c2)cc1Cn1cc(C(=O)O)cn1]

The compound (0.35 g) obtained in Example 127c was dissolved in ethanol (3 mL), and 6N aqueous sodium hydroxide solution (0.77 mL) was added. The reaction mixture was heated under reflux for 2 hr, cooled in an ice bath, adjusted to pH 2 with 6N hydrochloric acid, and the mixture was extracted with ethyl acetate. The ethyl acetate layer was dried over magnesium sulfate, concentrated under reduced pressure, and the residue was purified by column chromatography (carrier: silica gel, eluent: dichloromethane/methanol) to give the title compound (0.25 g) as a colorless solid.

¹H NMR (DMSO-d₆, Varian 400 MHz) δ ppm 2.42 (3H, s), 5.20 (2H, s), 7.06 (1H, s), 7.59-7.65 (2H, r), 7.80 (1H, s), 7.92-7.93 (2H, m), 8.29 (1H, s) 12.45 (1H, br. s.)

Example 128

1-({5-methyl-4-[3-(trifluoromethyl)phenyl]furan-2-yl}methyl)-1H-pyrazole-4-carboxylic acid Example 128a methyl 4,5-dibromofuran-2-carboxylate

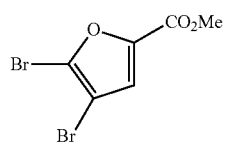 [SMILES: COC(=O)c1cc(Br)c(Br)o1]

A mixture of 4,5-dibromofuran-2-carboxylic acid (2.00 g) and thionyl chloride (10.7 mL) was heated under reflux for 2 hr, and concentrated under reduced pressure. Methanol (40 ml) was added, and the reaction mixture was stirred at room temperature for 2 hr and the solvent was evaporated under reduced pressure. The residue was purified by column chromatography (carrier: silica gel, eluent: hexane-ethyl acetate) to give the title compound (2.11 g) as a colorless solid.

¹H NMR (CDCl₃, Varian 400 MHz) δ ppm 3.91 (3H, s), 7.18 (1H, s)

Example 128b methyl 4-bromo-5-methylfuran-2-carboxylate

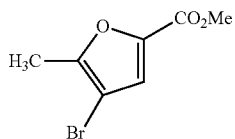

To a mixture of the compound (1.80 g) obtained in Example 128a, palladium chloride(II) (0.02 g), triphenylphosphine (0.07 g) and tetrahydrofuran (30 mL) was added MeZnCl (2M tetrahydrofuran solution, 9.5 ml), and the mixture was heated under reflux for 4 hr under a nitrogen atmosphere. The reaction mixture was cooled to room temperature, saturated aqueous ammonium chloride was added, and the mixture was extracted with ethyl acetate. The ethyl acetate layer was washed with saturated brine, dried over magnesium sulfate, and concentrated under reduced pressure. The residue was purified by column chromatography (carrier: silica gel, eluent: hexane ethyl acetate) to give the title compound (1.07 g) as a colorless solid.

¹H NMR (CDCl₃, Varian 400 MHz) δ ppm 2.38 (3H, s), 3.88 (3H, s), 7.12 (1H, s)

Example 128c methyl 5-methyl-4-[3-(trifluoromethyl)phenyl]furan-2-carboxylate

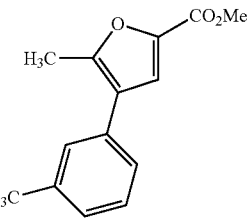

By a method similar to that in Example 126c and using the compound (1.00 g) obtained in Example 128b, 3-(trifluoromethyl)phenylboronic acid (1.04 g), cesium carbonate (2.98 g, 3.6 mmol), [1,1'-bis(diphenylphosphino)ferrocene]dichloropalladium(II) (0.19 g), the title compound (0.80 g) was obtained as a solid.

¹H NMR (CDCl₃, Varian 400 MHz) δ ppm 2.54 (3H, s), 3.92 (3H, s), 7.33 (1H, s), 7.55-7.58 (3H, m), 7.63 (1H, s)

Example 128d

{5-methyl-4-[3-(trifluoromethyl)phenyl]furan-2-yl}methanol

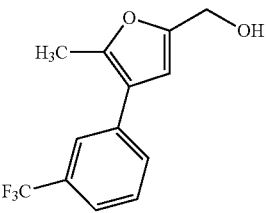 [SMILES: Cc1oc(CO)cc1-c1cccc(C(F)(F)F)c1]

A solution (4 mL) of the compound (0.80 g) obtained in Example 128c in tetrahydrofuran was cooled in an ice bath, and lithium aluminum hydride (0.16 g) was added by small portions. The reaction mixture was stirred at the same temperature for 1 hr, water (0.16 mL), 15% sodium hydroxide (0.16 ml) and water (0.48 mL) were successively added, and the mixture was stirred at room temperature for 15 min. The insoluble material was filtered off through celite, and the filtrate was concentrated under reduced pressure. The residue was purified by column chromatography (carrier: silica gel, eluent: hexane-ethyl acetate) to give the title compound (0.64 g) as a solid.

$^1$H NMR (CDCl$_3$, Varian 400 MHz) δ ppm 1.76 (1H, br. s.), 2.46 (3H, s), 4.62 (2H, d, J=3.6 Hz), 6.45 (1H, s), 7.48-7.56 (3H, m), 7.60 (1H, s)

Example 128e ethyl 1-({5-methyl-4-[3-(trifluoromethyl)phenyl]furan-2-yl}methyl)-1H-pyrazole-4-carboxylate

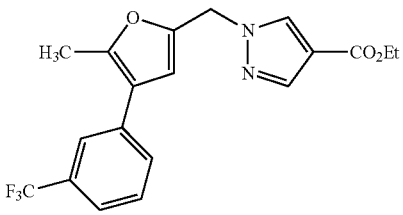 [SMILES: CCOC(=O)c1cnn(Cc2cc(-c3cccc(C(F)(F)F)c3)c(C)o2)c1]

A solution of the compound (0.40 g) obtained in Example 128d, ethyl 1H-pyrazole-4-carboxylate (0.26 g) and triphenylphosphine (0.49 g) in tetrahydrofuran (5 mL) was cooled in an ice bath, diisopropyl azodicarboxylate (0.36 mL) was added, and the mixture was stirred at the same temperature for 1 hr. Saturated aqueous ammonium chloride solution was added to the reaction mixture, and the mixture was extracted with ethyl acetate. The obtained organic layer was washed with saturated brine, and dried over anhydrous magnesium sulfate. The solvent was evaporated under reduced pressure. The residue was purified by column chromatography (carrier: silica gel, eluent: hexane/ethyl acetate) to give the title compound (0.20 g) as a yellow oil.

$^1$H NMR (CDCl$_3$, Varian 400 MHz) δ ppm 1.34 (3H, t, J=7.2 Hz), 2.43 (3H, s), 4.29 (2H, q, J=7.2 Hz), 5.29 (2H, s), 6.57 (1H, s), 7.51-7.54 (3H, m), 7.60 (1H, s), 7.94 (1H, s), 7.97 (1H, s)

Example 128

1-({5-methyl-4-[3-(trifluoromethyl)phenyl]furan-2-yl}methyl)-1H-pyrazole-4-carboxylic acid

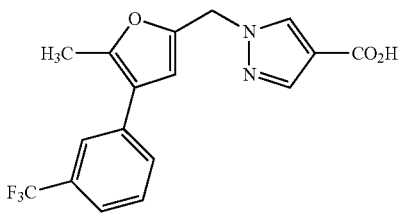

By a method similar to that in Example 126, the title compound (0.17 g) was obtained as a solid from the compound (0.20 g) obtained in Example 128e.

$^1$H NMR (DMSO-d$_6$, Varian 400 MHz) δ ppm 2.40 (3H, s), 5.37 (2H, s), 6.84 (1H, s), 7.62-7.64 (2H, m), 7.70-7.73 (2H, s), 7.80 (1H, s), 8.29 (1H, s)

Example 129

1-({2-methyl-5-[3-(trifluoromethyl)phenyl]thiophen-3-yl}methyl)-1H-pyrazole-4-carboxylic acid Example 129a 3-bromo-2-methyl-5-[3-(trifluoromethyl)phenyl]thiophene

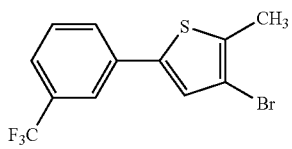 [SMILES: Cc1sc(-c2cccc(C(F)(F)F)c2)cc1Br]

Under a nitrogen atmosphere, a mixture of 3,5-dibromo-2-methylthiophene (2.00 g), 3-(trifluoromethyl)phenylboronic acid (2.23 g), tetrakis(triphenylphosphine)palladium (0.45 g), cesium carbonate (5.09 g) and tetrahydrofuran (40 mL) was heated under reflux for 16 hr. The reaction mixture was cooled, water was added, and the mixture was extracted with ethyl acetate. The ethyl acetate layer was washed with saturated brine, dried over magnesium sulfate, and concentrated under reduced pressure. The residue was purified by column chromatography (carrier: silica gel, eluent: hexane-ethyl acetate) to give the title compound (2.15 g) as a solid.

$^1$H NMR (CDCl$_3$, Varian 400 MHz) δ ppm 2.44 (3H, s), 7.18 (1H, s), 7.49 (1H, dd, J=8.4, 7.6 Hz), 7.53 (1H, d, J=8.4 Hz), 7.67 (1H, d, J=7.6 Hz), 7.74 (1H, s)

Example 129b 2-methyl-5-[3-(trifluoromethyl)phenyl]thiophene-3-carbaldehyde

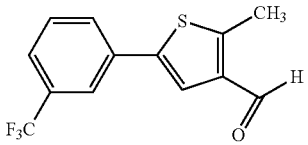 [SMILES: Cc1sc(-c2cccc(C(F)(F)F)c2)cc1C=O]

The compound (0.83 g) obtained in Example 129a was dissolved in tetrahydrofuran (15 mL), cooled to −78° C., and n-butyllithium (2.5M hexane solution, 1.24 mL) was added. The mixture was stirred at the same temperature for 1 hr, N,N-dimethylformamide (1.0 mL) was added, the reaction mixture was warmed to room temperature and stirred for 1 hr. 1N Hydrochloric acid (20 mL) was added to the reaction mixture, and the mixture was extracted with ethyl acetate. The obtained organic layer was washed with saturated brine, and dried over anhydrous magnesium sulfate. The solvent was evaporated under reduced pressure. The residue was purified by column chromatography (carrier: silica gel, eluent: hexane/ethyl acetate) to give the title compound (0.45 g) as a solid.

¹H NMR (CDCl₃, Varian 400 MHz) δ ppm 2.83 (3H, s), 7.50 (1H, dd, J=8.4, 7.6 Hz), 7.57 (1H, d, J=7.6H), 7.63 (1H, d, J=7.6 Hz), 7.73 (1H, d, J=8.4 Hz), 7.79 (1H, s), 10.1 (1H, s)

Example 129c

{2-methyl-5-[3-(trifluoromethyl)phenyl]thiophen-3-yl}methanol

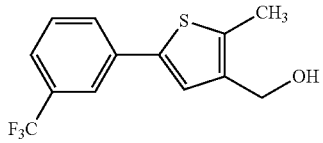

By a method similar to that in Example 126b and using the compound (1.00 g) obtained in Example 129b, the title compound (0.79 g) was obtained.
¹H NMR (CDCl₃, Varian 400 MHz) δ ppm 1.62 (1H, br. s.), 2.48 (3H, s), 4.62 (2H, d, J=4.8 Hz), 7.29 (1H, s), 7.44-7.50 (2H, m), 7.69 (1H, d, J=7.2 Hz), 7.77 (1H, s)

Example 129d ethyl 1-({2-methyl-5-[3-(trifluoromethyl)phenyl]thiophen-3-yl}methyl)-1H-pyrazole-4-carboxylate

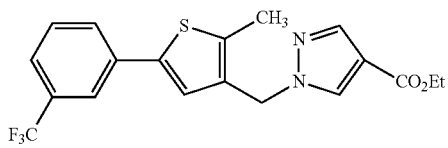 [SMILES: CCOC(=O)c1cnn(Cc2cc(-c3cccc(C(F)(F)F)c3)sc2C)c1]

By a method similar to that in Example 128e and using the compound (0.44 g) obtained in Example 129c, the title compound (0.48 g) was obtained as an oil.
¹H NMR (CDCl₃, Varian 400 MHz) δ ppm 1.33 (3H, t, J=7.2 Hz), 2.50 (3H, s), 4.28 (2H, t, J=7.2 Hz), 5.27 (2H, s), 7.13 (1H, s), 7.46 (1H, dd, J=8.0, 7.2 Hz), 7.51 (1H, d, J=8.0 Hz), 7.67 (1H, d, J=7.2 Hz), 7.74 (1H, s), 7.83 (1H, s), 7.94 (1H, s)

Example 129

1-({2-methyl-5-[3-(trifluoromethyl)phenyl]thiophen-3-yl}methyl)-1H-pyrazole-4-carboxylic acid

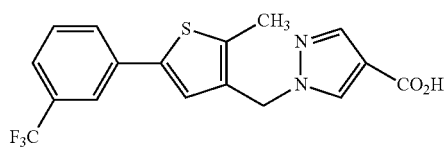 [SMILES: Cc1sc(-c2cccc(C(F)(F)F)c2)cc1Cn1cc(C(=O)O)cn1]

By a method similar to that in Example 126 and using the compound (0.48 g) obtained in Example 129d, the title compound (0.35 g) was obtained as a colorless solid.

¹H NMR (DMSO-d₆, Varian 400 MHz) δ ppm 2.48 (3H, s), 5.27 (2H, s), 7.55 (1H, s), 7.60-7.61 (2H, m), 7.79-7.83 (3H, m), 8.33 (1H, s), 12.3 (1H, br. s.)

Example 130

1-({5-[3-(trifluoromethyl)phenyl]furan-2-yl}methyl)-1H-pyrazole-4-carboxylic acid Example 130a methyl 5-[3-(trifluoromethyl)phenyl]furan-2-carboxylate

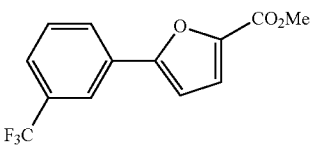 [SMILES: COC(=O)c1ccc(-c2cccc(C(F)(F)F)c2)o1]

By a method similar to that in Example 126c and using methyl 5-bromofuran-2-carboxylate (1.50 g), the title compound (1.64 g) was obtained as a colorless solid.
¹H NMR (CDCl₃, Varian 400 MHz) δ ppm 3.94 (3H, s), 6.84 (1H, d, J=3.6 Hz), 7.27 (1H, d, J=3.6 Hz), 7.55 (1H, t, J=8.0 Hz), 7.60 (1H, d, J=8.0 Hz), 7.96 (1H, d, J=8.0 Hz), 8.01 (1H, s)

Example 130b

{5-[3-(trifluoromethyl)phenyl]furan-2-yl}methanol

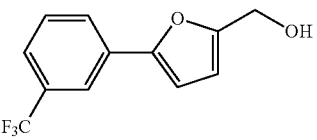

By a method similar to that in Example 128d and using the compound (1.64 g) obtained in Example 130a, the title compound (1.31 g) was obtained as an oil.
¹H NMR (CDCl₃, Varian 400 MHz) δ ppm 1.84 (1H, t, J=6.4 Hz), 4.69 (2H, d, J=6.4 Hz), 6.42 (1H, d, J=3.6 Hz), 6.69 (1H, d, J=3.6 Hz), 7.49-7.51 (2H, m), 7.82-7.84 (1H, m), 7.91 (1H, s)

Example 130c ethyl 1-({5-[3-(trifluoromethyl)phenyl]furan-2-yl}methyl)-1H-pyrazole-4-carboxylate

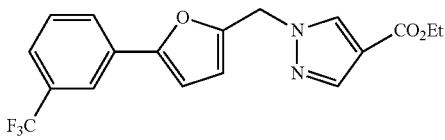

By a method similar to that in Example 127c and using the compound obtained in Example 130b, the title compound (0.16 g) was obtained as an oil.

¹H NMR (CDCl₃, Varian 400 MHz) δ ppm 1.33 (3H, t, J=7.2 Hz), 4.28 (2H, q, J=7.2 Hz), 5.37 (2H, s), 6.53 (1H, d, J=3.6 Hz), 6.72 (1H, d, J=3.6 Hz), 7.48-7.54 (2H, m), 7.80 (1H, J=2.8 Hz), 7.87 (1H, s), 7.95 (1H, s) 7.97 (1H, s)

Example 130

1-({5-[3-(trifluoromethyl)phenyl]furan-2-yl}methyl)-1H-pyrazole-4-carboxylic acid

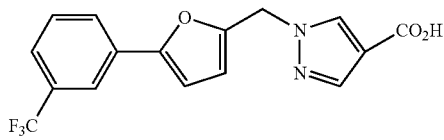 [SMILES: O=C(O)c1cnn(Cc2ccc(-c3cccc(C(F)(F)F)c3)o2)c1]

By a method similar to that in Example 126 and using the compound (0.29 g) obtained in Example 130c, the title compound (0.22 g) was obtained as a solid.

¹H NMR (DMSO-d₆, Varian 400 MHz) δ ppm 5.50 (2H, s), 6.64 (1H, d, J=3.6 Hz), 7.18 (1H, d, J=3.6 Hz), 7.65-7.67 (2H, m), 7.84 (1H, s), 7.96-7.97 (2H, m), 8.38 (1H, s), 12.35 (1H, s)

Examples 131-177

Phenol derivative (100 μmol) powder was measured in a reaction container, an alcohol reagent (130 μmol, 1.3 eq.)/0.5 mL dry toluene solution, triphenylphosphine (52 mg, 200 μmol, 2.0 eq)/0.5 mL dry toluene solution, finally, diisopropyl azodicarboxylate (130 μmol, 1.3 eq, 66 μL, 40 wt % toluene solution) was added. The mixture was shaken at room temperature overnight. The liquid phase was extracted with ethyl acetate and water, the organic layer was evaporated and the residue was separated and purified. After drying, the residue was dissolved in THF/MeOH=1/1 solvent (1.5 mL), 1N—NaOH 0.5 mL (500 μL, 5.0 eq) was added and the mixture was stirred at room temperature for one day. The mixture was neutralized with 1N—HCl (0.5 mL), and purified by preparative HPLC after liquid phase extraction to give the title compound.

The preparative HPLC purification in Examples 131-177 was performed under the following conditions.
instrument: Gilson Inc. High-Throughput Purification System
column: YMC CombiPrep, ProC18 RS
S-5 μm, 20×50 mm (YMC)
solvent: SOLUTION A; 0.1%-TFA containing water,
SOLUTION B; 0.1%-TFA containing water-acetonitrile
gradient cycle: 0.00 min (SOLUTION A/SOLUTION B=95/5), 2.00 min (SOLUTION A/SOLUTION B=95/5), 4.02 min (SOLUTION A/SOLUTION B=5/95), 6.40 min (SOLUTION A/SOLUTION B=5/95), 6.50 min (SOLUTION A/SOLUTION B=95/5), 8.00 min (SOLUTION A/SOLUTION B=95/5)
injection volume: 500 μl, flow rate: 20 ml/min, detection method: UV 220 nm, 254 nm The LC-MS (liquid chromatography-mass spectrometry spectrum) analysis in Examples 131-177 was measured under the following conditions.
measurement device: Waters 4-ch LC/MS system with MUX
column: CAPCELL PAK C18 UG-120, S-3 μm, 1.5×35 mm (Shiseido Co., Ltd.)
solvent: SOLUTION A; 5 mM ammonium acetate containing water,
SOLUTION B; 5 mM ammonium acetate containing acetonitrile
gradient cycle: gradient: 0.00 min (SOLUTION A/SOLUTION B=100/0), 2.00 min (SOLUTION A/SOLUTION B=0/100), 3.00 min (SOLUTION A/SOLUTION B=0/100), 3.01 min (SOLUTION A/SOLUTION B=100/0), 3.30 min (SOLUTION A/SOLUTION B=100/0)
injection volume: 2 μl, flow rate: 0.5 mL/min, detection method: UV 220 nm
ionization method: electrospray method (ESI method)
measurement mode: fullscan (positive+negative ion)
measurement mass value range: m/z=150-750

TABLE 1

| | compound name | molecular weight | LCMS, molecular ion peak ES+ | LCMS, molecular ion peak ES- | retention time (min) | phenol derivative used for reaction |
|---|---|---|---|---|---|---|
| Ex. 131 | 1-({4-[3-propoxy-5-(trifluoromethyl)phenyl]-1,3-thiazol-2-yl}methyl)-1H-pyrazole-4-carboxylic acid | 411.09 | 411.99 | | 1.74 | compound obtained in Ex. 86a |
| Ex. 132 | 1-({4-[3-(1-methylethoxy)-5-(trifluoromethyl)phenyl]-1,3-thiazol-2-yl}methyl)-1H-pyrazole-4-carboxylic acid | 411.09 | 411.97 | | 1.71 | compound obtained in Ex. 86a |
| Ex. 133 | 1-({4-[3-(cyclopropylmethoxy)-5-(trifluoromethyl)phenyl]-1,3-thiazol-2-yl}methyl)-1H-pyrazole-4-carboxylic acid | 423.09 | 423.98 | | 1.73 | compound obtained in Ex. 86a |
| Ex. 134 | 1-({4-[3-(2-methoxyethoxy)-5-(trifluoromethyl)phenyl]-1,3-thiazol-2-yl}methyl)-1H-pyrazole-4-carboxylic acid | 427.08 | 428.00 | | 1.57 | compound obtained in Ex. 86a |

TABLE 1-continued

| | compound name | molecular weight | LCMS, molecular ion peak ES+ | LCMS, molecular ion peak ES- | retention time (min) | phenol derivative used for reaction |
|---|---|---|---|---|---|---|
| Ex. 135 | 1-({4-[3-(cyclopentyloxy)-5-(trifluoromethyl)phenyl]-1,3-thiazol-2-yl}methyl)-1H-pyrazole-4-carboxylic acid | 437.1 | 437.99 | | 1.82 | compound obtained in Ex. 86a |
| Ex. 136 | 1-({4-[3-(furan-2-ylmethoxy)-5-(trifluoromethyl)phenyl]-1,3-thiazol-2-yl}methyl)-1H-pyrazole-4-carboxylic acid | 449.07 | 449.98 | | 1.71 | compound obtained in Ex. 86a |
| Ex. 137 | 1-({4-[3-(benzyloxy)-5-(trifluoromethyl)phenyl]-1,3-thiazol-2-yl}methyl)-1H-pyrazole-4-carboxylic acid | 459.09 | 460.00 | | 1.80 | compound obtained in Ex. 86a |
| Ex. 138 | 1-({4-[3-(pyridine-2-ylmethoxy)-5-(trifluoromethyl)phenyl]-1,3-thiazol-2-yl}methyl)-1H-pyrazole-4-carboxylic acid trifluoroacetate | 460.08 | 460.99 | | 1.62 | compound obtained in Ex. 86a |
| Ex. 139 | 1-({4-[3-(pyridin-3-ylmethoxy)-5-(trifluoromethyl)phenyl]-1,3-thiazol-2-yl}methyl)-1H-pyrazole-4-carboxylic acid trifluoro acetate | 460.08 | 460.98 | | 1.60 | compound obtained in Ex. 86a |
| Ex. 140 | 1-({4-[3-(2-phenylethoxy)-5-(trifluoromethyl)phenyl]-1,3-thiazol-2-yl}methyl)-1H-pyrazole-4-carboxylic acid | 473.1 | 474.00 | | 1.85 | compound obtained in Ex. 86a |
| Ex. 141 | 1-[(4-{3-[2-(2-oxopyrrolidine-1-yl)ethoxy]-5-(trifluoromethyl)phenyl}-1,3-thiazol-2-yl)methyl]-1H-pyrazole-4-carboxylic acid | 480.11 | 480.97 | | 1.53 | compound obtained in Ex. 86a |
| Ex. 142 | 1-[(4-{3-[(2,4-dimethyl-1,3-thiazole-5-yl)methoxy]-5-(trifluoromethyl)phenyl}-1,3-thiazol-2-yl)methyl]-1H-pyrazole-4-carboxylic acid | 494.07 | 494.92 | | 1.67 | compound obtained in Ex. 86a |
| Ex. 143 | 1-[(4-{3-[(1,3-dimethyl-1H-pyrazole-5-yl)methoxy]-5-(trifluoromethyl)phenyl}-1,3-thiazol-2-yl)methyl]-1H-pyrazole-4-carboxylic acid | 477.11 | 477.99 | | 1.63 | compound obtained in Ex. 86a |
| Ex. 144 | 1-[(4-{3-[(1,5-dimethyl-1H-pyrazole-3-yl)methoxy]-5-(trifluoromethyl)phenyl}-1,3-thiazol-2-yl)methyl]-1H-pyrazole-4-carboxylic acid | 477.11 | 477.96 | | 1.62 | compound obtained in Ex. 86a |
| Ex. 145 | 1-({4-[3-(1-methylpropoxy)-5-(trifluoromethyl)phenyl]-1,3-thiazol-2-yl}methyl)-1H-pyrazole-4-carboxylic acid | 425.1 | 426.02 | | 1.78 | compound obtained in Ex. 86a |
| Ex. 146 | 1-[(4-{3-[(3-fluorobenzyl)oxy]-5-(trifluoromethyl)phenyl}-1,3-thiazol-2-yl)methyl]-1H-pyrazole-4-carboxylic acid | 477.08 | 477.95 | | 1.82 | compound obtained in Ex. 86a |
| Ex. 147 | 1-[(4-{3-[(4-fluorobenzyl)oxy]-5-(trifluoromethyl)phenyl}-1,3-thiazol-2-yl)methyl]-1H-pyrazole-4-carboxylic acid | 477.08 | 477.94 | | 1.82 | compound obtained in Ex. 86a |

TABLE 1-continued

|  | compound name | molecular weight | LCMS, molecular ion peak ES+ | LCMS, molecular ion peak ES- | retention time (min) | phenol derivative used for reaction |
|---|---|---|---|---|---|---|
| Ex. 148 | 1-({4-[3-(2-thiophen-3-ylethoxy)-5-(trifluoromethyl)phenyl]-1,3-thiazol-2-yl}methyl)-1H-pyrazole-4-carboxylic acid | 479.06 | 479.93 | | 1.83 | compound obtained in Ex. 86a |
| Ex. 149 | 1-({4-[3-{2-[methyl(phenyl)amino]ethoxy}-5-(trifluoromethyl)phenyl]-1,3-thiazol-2-yl}methyl)-1H-pyrazole-4-carboxylic acid | 502.13 | 503.00 | | 1.87 | compound obtained in Ex. 86a |
| Ex. 150 | 1-({5-methyl-2-[3-propoxy-5-(trifluoromethyl)phenyl]-1,3-thiazol-4-yl}methyl)-1H-pyrazole-4-carboxylic acid | 425.1 | 279.07 | 423.91 | 1.79 | compound obtained in Ex. 223 |
| Ex. 151 | 1-({5-methyl-2-[3-(1-methylethoxy)-5-(trifluoromethyl)phenyl]-1,3-thiazol-4-yl}methyl)-1H-pyrazole-4-carboxylic acid | 425.1 | 426.02 | | 1.76 | compound obtained in Ex. 223 |
| Ex. 152 | 1-({2-[3-(2-methoxyethoxy)-5-(trifluoromethyl)phenyl]-5-methyl-1,3-thiazol-4-yl}methyl)-1H-pyrazole-4-carboxylic acid | 441.1 | 441.98 | | 1.62 | compound obtained in Ex. 223 |
| Ex. 153 | 1-({2-[3-(cyclopentyloxy)-5-(trifluoromethyl)phenyl]-5-methyl-1,3-thiazol-4-yl}methyl)-1H-pyrazole-4-carboxylic acid | 451.12 | 279.07 | 449.84 | 1.88 | compound obtained in Ex. 223 |
| Ex. 154 | 1-({2-[3-(benzyloxy)-5-(trifluoromethyl)phenyl]-5-methyl-1,3-thiazol-4-yl}methyl)-1H-pyrazole-4-carboxylic acid | 473.1 | 361.99 | 471.87 | 1.85 | compound obtained in Ex. 223 |
| Ex. 155 | 1-({5-methyl-2-[3-(pyridin-2-ylmethoxy)-5-(trifluoromethyl)phenyl]-1,3-thiazol-4-yl}methyl)-1H-pyrazole-4-carboxylic acid trifluoroacetate | 474.1 | 474.97 | | 1.66 | compound obtained in Ex. 223 |
| Ex. 156 | 1-({5-methyl-2-[3-(pyridine-3-ylmethoxy)-5-(trifluoromethyl)phenyl]-1,3-thiazol-4-yl}methyl)-1H-pyrazole-4-carboxylic acid | 474.1 | 456.96 | | 1.64 | compound obtained in Ex. 223 |
| Ex. 157 | 1-({5-methyl-2-[3-(2-phenylethoxy)-5-(trifluoromethyl)phenyl]-1,3-thiazol-4-yl}methyl)-1H-pyrazole-4-carboxylic acid | 487.12 | 488.00 | | 1.90 | compound obtained in Ex. 223 |
| Ex. 158 | 1-[(5-methyl-2-{3-[2-(2-oxopyrrolidin-1-yl)ethoxy]-5-(trifluoromethyl)phenyl}-1,3-thiazol-4-yl)methyl]-1H-pyrazole-4-carboxylic acid | 494.12 | 494.98 | | 1.58 | compound obtained in Ex. 223 |
| Ex. 159 | 1-[(2-{3-[(1-benzylpyrrolidin-3-yl)oxy]-5-(trifluoromethyl)phenyl}-5-methyl-1,3-thiazol-4-yl)methyl]-1H-pyrazole-4-carboxylic acid | 542.16 | 543.01 | | 1.83 | compound obtained in Ex. 223 |
| Ex. 160 | 1-[(2-{3-[(2,4-dimethyl-1,3-thiazol-5-yl)methoxy]-5-(trifluoromethyl)phenyl}-5-methyl-1,3-thiazol-4-yl)methyl]-1H-pyrazole-4-carboxylic acid | 508.09 | 508.94 | | 1.71 | compound obtained in Ex. 223 |

TABLE 1-continued

| | compound name | molecular weight | LCMS, molecular ion peak ES+ | LCMS, molecular ion peak ES- | retention time (min) | phenol derivative used for reaction |
|---|---|---|---|---|---|---|
| Ex. 161 | 1-[(2-(3-[(1,3-dimethyl-1H-pyrazol-5-yl)methoxy]-5-(trifluoromethyl)phenyl)-5-methyl-1,3-thiazol-4-yl)methyl]-1H-pyrazole-4-carboxylic acid | 491.12 | 491.99 | | 1.67 | compound obtained in Ex. 223 |
| Ex. 162 | 1-[(2-(3-[(1,5-dimethyl-1H-pyrazol-3-yl)methoxy]-5-(trifluoromethyl)phenyl)-5-methyl-1,3-thiazol-4-yl)methyl]-1H-pyrazole-4-carboxylic acid | 491.12 | 492.00 | | 1.66 | compound obtained in Ex. 223 |
| Ex. 163 | 1-({5-methyl-2-[3-(1-methylpropoxy)-5-(trifluoromethyl)phenyl]-1,3-thiazol-4-yl}methyl)-1H-pyrazole-4-carboxylic acid | 439.12 | 369.04 | 437.89 | 1.84 | compound obtained in Ex. 223 |
| Ex. 164 | 1-[(2-{3-[(2-fluorobenzyl)oxy]-5-(trifluoromethyl)phenyl}-5-methyl-1,3-thiazol-4-yl)methyl]-1H-pyrazole-4-carboxylic acid | 491.09 | 279.07 | 489.82 | 1.85 | compound obtained in Ex. 223 |
| Ex. 165 | 1-[(2-{3-[(3-fluorobenzyl)oxy]-5-(trifluoromethyl)phenyl}-5-methyl-1,3-thiazol-4-yl)methyl]-1H-pyrazole-4-carboxylic acid | 491.09 | 379.99 | 489.87 | 1.87 | compound obtained in Ex. 223 |
| Ex. 166 | 1-[ (2-{3-[(4-fluorobenzyl)oxy]-5-(trifluoromethyl)phenyl}-5-methyl-1,3-thiazol-4-yl)methyl]-1H-pyrazole-4-carboxylic acid | 491.09 | 379.99 | 489.86 | 1.87 | compound obtained in Ex. 223 |
| Ex. 167 | 1-({5-methyl-2-[3-(2-thiophen-3-ylethoxy)-5-(trifluoromethyl)phenyl]-1,3-thiazol-4-yl}methyl)-1H-pyrazole-4-carboxylic acid | 493.07 | 381.97 | 491.85 | 1.87 | compound obtained in Ex. 223 |
| Ex. 168 | 1-((2-(3-[(2,4-difluorobenzyl)oxy]-5-(trifluoromethyl)phenyl}-5-methyl-1,3-thiazol-4-yl)methyl]-1H-pyrazole-4-carboxylic acid | 509.08 | 279.07 | 507.86 | 1.88 | compound obtained in Ex. 223 |
| Ex. 169 | 1-({5-methyl-2-[3-(2-[methyl(phenyl)amino]ethoxy}-5-(trifluoromethyl)phenyl]-1,3-thiazol-4-yl]methyl)-1H-pyrazole-4-carboxylic acid | 516.14 | 516.99 | | 1.92 | compound obtained in Ex. 223 |
| Ex. 170 | 1-{[4-(3-propoxyphenyl)-1,3-thiazol-2-ylimethyl}-1H-pyrazole-4-carboxylic acid | 343.1 | 190.08 | 341.95 | 1.55 | compound obtained in Ex. 38c |
| Ex. 171 | 1-({4-[3-(2-phenylethoxy)phenyl]-1,3-thiazol-2-yl}methyl)-1H-pyrazole-4-carboxylic acid | 405.11 | 406.04 | | 1.69 | compound obtained in Ex. 38c |
| Ex. 172 | 1-[(4-(3-[(2-fluorobenzyl)oxy]phenyl}-1,3-thiazol-2-yl)methyl]-1H-pyrazole-4-carboxylic acid | 409.09 | 410.00 | | 1.65 | compound obtained in Ex. 38c |
| Ex. 173 | 1-[(4-(3-[(3-fluorobenzyl)oxy]phenyl}-1,3-thiazol-2-yl)methyl]-1H-pyrazole-4-carboxylic acid | 409.09 | 409.99 | | 1.66 | compound obtained in Ex. 38c |

TABLE 1-continued

| | compound name | molecular weight | LCMS, molecular ion peak ES+ | LCMS, molecular ion peak ES- | retention time (min) | phenol derivative used for reaction |
|---|---|---|---|---|---|---|
| Ex. 174 | 1-[(4-{3-[(4-fluorobenzyl)oxy]phenyl}-1,3-thiazol-2-yl)methyl]-1H-pyrazole-4-carboxylic acid | 409.09 | 409.99 | | 1.66 | compound obtained in Ex. 38c |
| Ex. 175 | 1-({4-[3-(2-thiophen-3-ylethoxy)phenyl]-1,3-thiazol-2-yl}methyl)-1H-pyrazole-4-carboxylic acid | 411.07 | 411.97 | | 1.66 | compound obtained in Ex. 38c |
| Ex. 176 | 1-[(4-{3-[(2,4-difluorobenzyl)oxy]phenyl}-1,3-thiazol-2-yl)methyl]-1H-pyrazole-4-carboxylic acid | 427.08 | 428.00 | | 1.68 | compound obtained in Ex. 38c |
| Ex. 177 | 1-[(4-{3-[2-(phenylsulfanil)ethoxy]phenyl}-1,3-thiazol-2-yl)methyl]-1H-pyrazole-4-carboxylic acid | 437.09 | 437.96 | | 1.72 | compound obtained in Ex. 38c |

Example 131

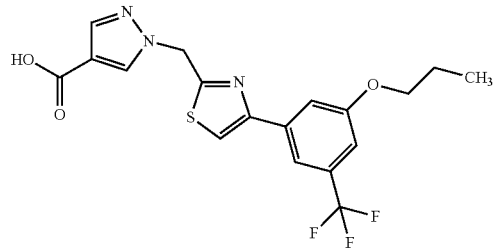 [SMILES: CCCOc1cc(-c2csc(Cn3cc(C(=O)O)cn3)n2)cc(C(F)(F)F)c1]

Example 132

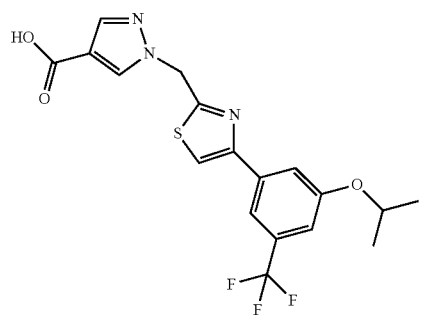 [SMILES: CC(C)Oc1cc(-c2csc(Cn3cc(C(=O)O)cn3)n2)cc(C(F)(F)F)c1]

Example 133

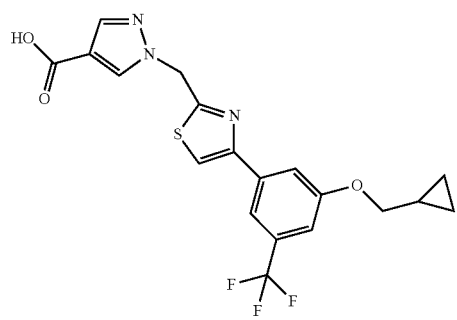 [SMILES: O=C(O)c1cnn(Cc2nc(-c3cc(OCC4CC4)cc(C(F)(F)F)c3)cs2)c1]

TABLE 1-continued
| compound name | molecular weight | LCMS, molecular ion peak | | retention time (min) | phenol derivative used for reaction |
|---|---|---|---|---|---|
| | | ES+ | ES- | | |
Example 134
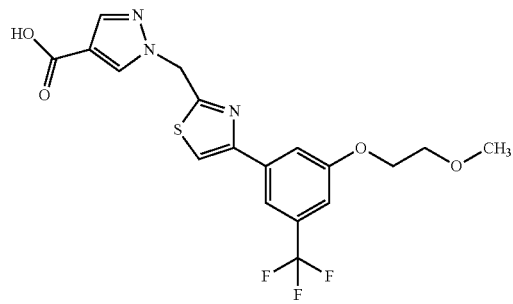 [SMILES: COCCOc1cc(-c2csc(Cn3cc(C(=O)O)cn3)n2)cc(C(F)(F)F)c1]
Example 135
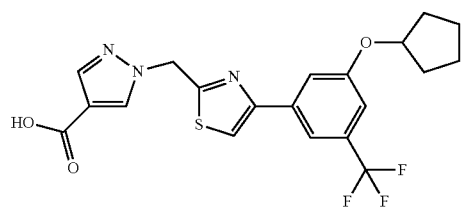 [SMILES: O=C(O)c1cnn(Cc2nc(-c3cc(OC4CCCC4)cc(C(F)(F)F)c3)cs2)c1]
Example 136
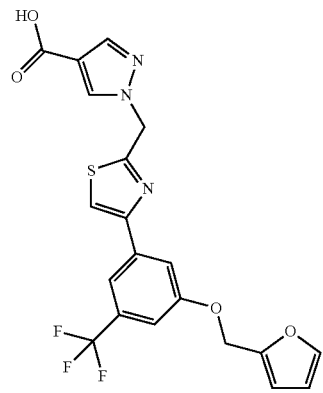 [SMILES: O=C(O)c1cnn(Cc2nc(-c3cc(OCc4ccco4)cc(C(F)(F)F)c3)cs2)c1]
Example 137
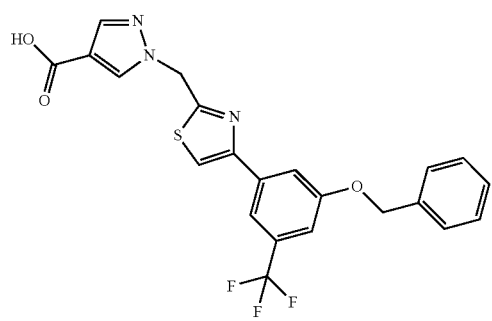 [SMILES: O=C(O)c1cnn(Cc2nc(-c3cc(OCc4ccccc4)cc(C(F)(F)F)c3)cs2)c1]

TABLE 1-continued
| compound name | molecular weight | LCMS, molecular ion peak | | retention time (min) | phenol derivative used for reaction |
| --- | --- | --- | --- | --- | --- |
| | | ES+ | ES- | | |
Example 138
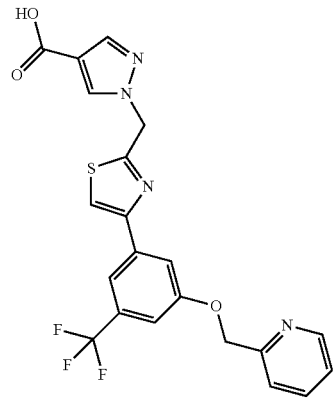 [SMILES: O=C(O)c1cnn(Cc2nc(-c3cc(OCc4ccccn4)cc(C(F)(F)F)c3)cs2)c1]
Example 139
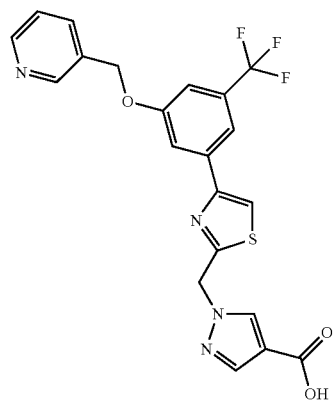 [SMILES: O=C(O)c1cnn(Cc2nc(-c3cc(OCc4cccnc4)cc(C(F)(F)F)c3)cs2)c1]
Example 140
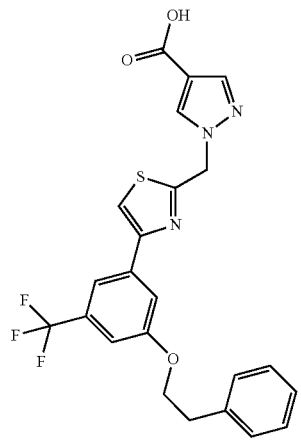 [SMILES: O=C(O)c1cnn(Cc2nc(-c3cc(OCCc4ccccc4)cc(C(F)(F)F)c3)cs2)c1]

TABLE 1-continued
| compound name | molecular weight | LCMS, molecular ion peak | | retention time (min) | phenol derivative used for reaction |
|---|---|---|---|---|---|
| | | ES+ | ES- | | |
Example 141
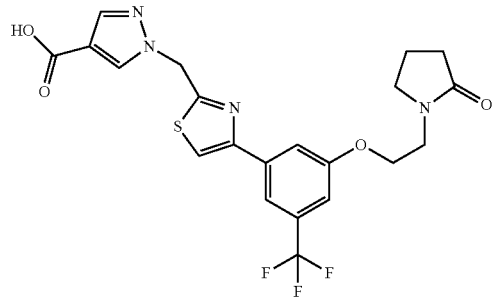 [SMILES: O=C(O)c1cnn(Cc2nc(-c3cc(OCCN4CCCC4=O)cc(C(F)(F)F)c3)cs2)c1]
Example 142
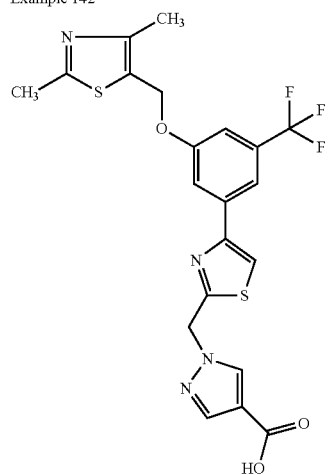
Example 143
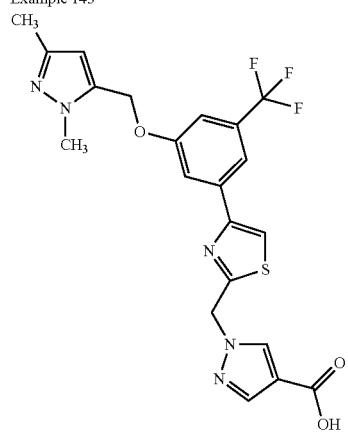
Example 144
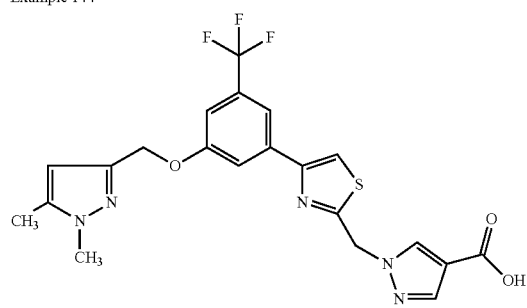

TABLE 1-continued
| compound name | molecular weight | LCMS, molecular ion peak | | retention time (min) | phenol derivative used for reaction |
| --- | --- | --- | --- | --- | --- |
| | | ES+ | ES- | | |
Example 145
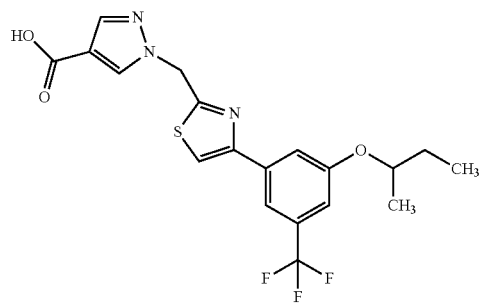 [SMILES: CCC(C)Oc1cc(-c2csc(Cn3cc(C(=O)O)cn3)n2)cc(C(F)(F)F)c1]
Example 146
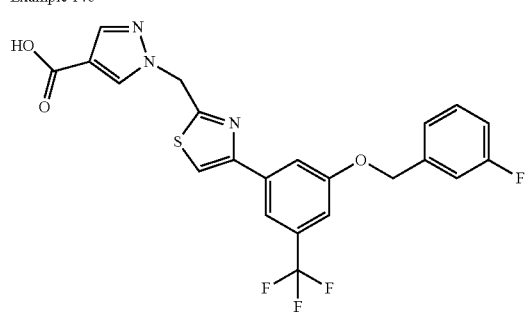
Example 147
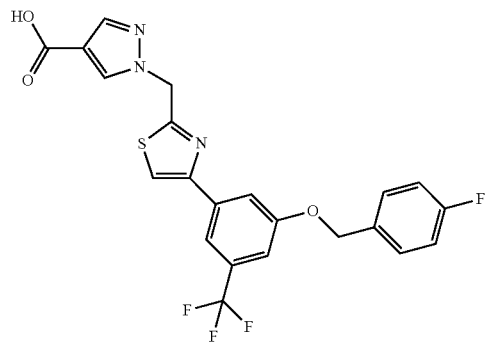 [SMILES: O=C(O)c1cnn(Cc2nc(-c3cc(OCc4ccc(F)cc4)cc(C(F)(F)F)c3)cs2)c1]
Example 148
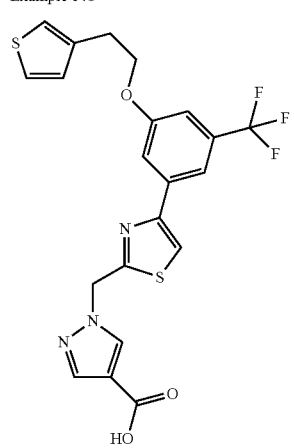

TABLE 1-continued
| compound name | molecular weight | LCMS, molecular ion peak | | retention time (min) | phenol derivative used for reaction |
|---|---|---|---|---|---|
| | | ES+ | ES- | | |
Example 149
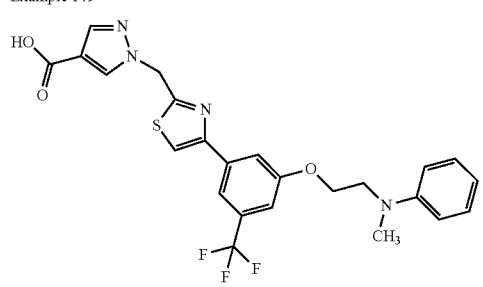
Example 150
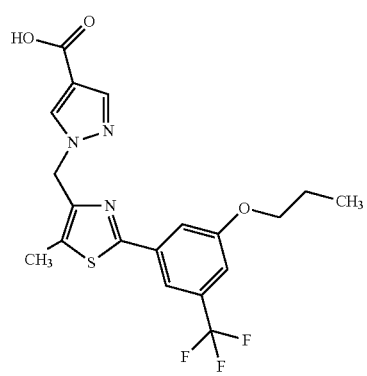 [SMILES: CCCOc1cc(-c2nc(Cn3cc(C(=O)O)cn3)c(C)s2)cc(C(F)(F)F)c1]
Example 151
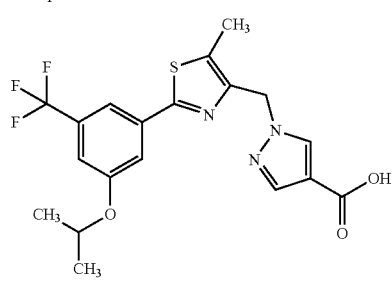
Example 152
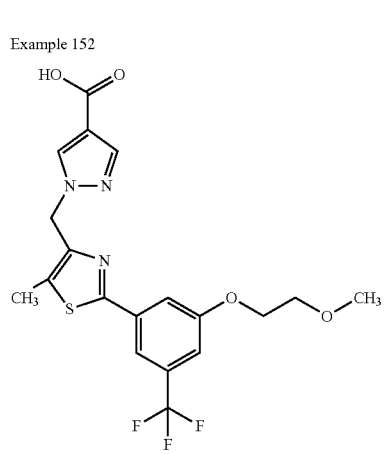

TABLE 1-continued

| compound name | molecular weight | LCMS, molecular ion peak | | retention time (min) | phenol derivative used for reaction |
| --- | --- | --- | --- | --- | --- |
| | | ES+ | ES− | | |

Example 153

Example 154

Example 155

Example 156

TABLE 1-continued
| compound name | molecular weight | LCMS, molecular ion peak | | retention time (min) | phenol derivative used for reaction |
|---|---|---|---|---|---|
| | | ES+ | ES- | | |
Example 157
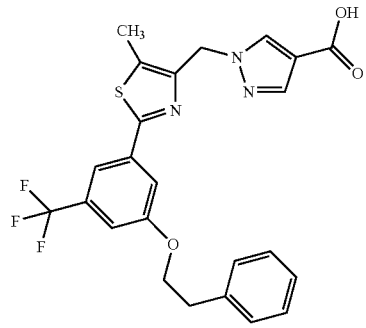 [SMILES: Cc1sc(-c2cc(OCCc3ccccc3)cc(C(F)(F)F)c2)nc1Cn1cc(C(=O)O)cn1]
Example 158
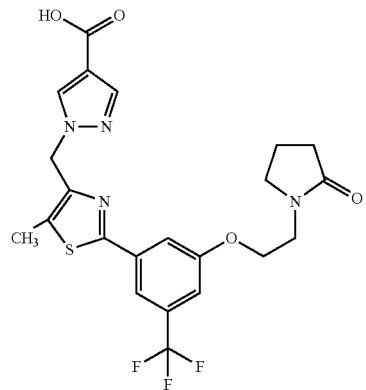 [SMILES: Cc1sc(-c2cc(OCCN3CCCC3=O)cc(C(F)(F)F)c2)nc1Cn1cc(C(=O)O)cn1]
Example 159
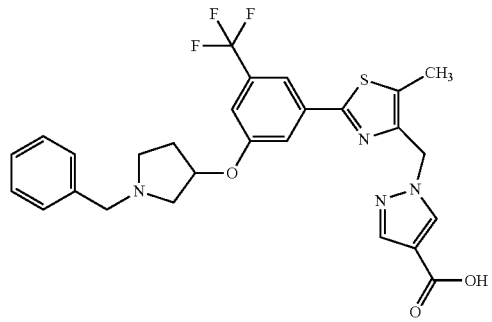 [SMILES: Cc1sc(-c2cc(OC3CCN(Cc4ccccc4)C3)cc(C(F)(F)F)c2)nc1Cn1cc(C(=O)O)cn1]
Example 160
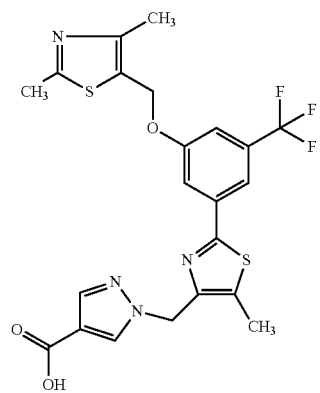 [SMILES: Cc1nc(C)c(COc2cc(-c3nc(Cn4cc(C(=O)O)cn4)c(C)s3)cc(C(F)(F)F)c2)s1]

TABLE 1-continued
| compound name | molecular weight | LCMS, molecular ion peak ES+ | LCMS, molecular ion peak ES- | retention time (min) | phenol derivative used for reaction |
|---|---|---|---|---|---|
Example 161
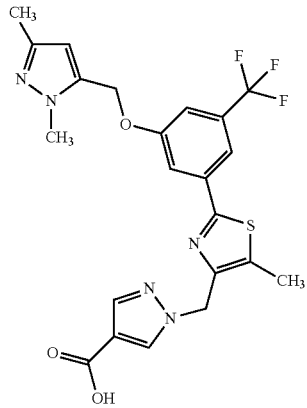 [SMILES: Cc1cc(COc2cc(-c3nc(Cn4cc(C(=O)O)cn4)c(C)s3)cc(C(F)(F)F)c2)n(C)n1]
Example 162
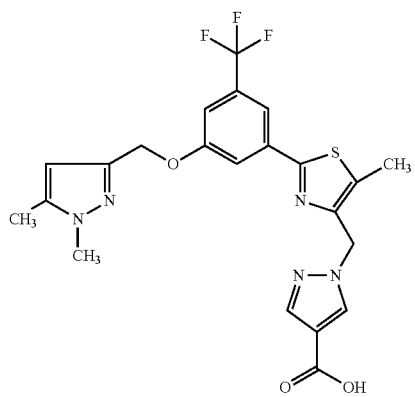
Example 163
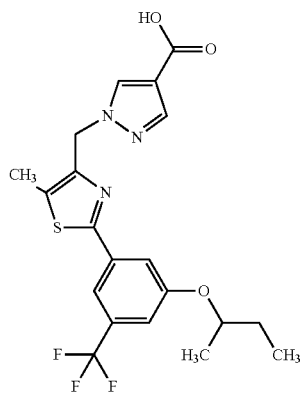 [SMILES: CCC(C)Oc1cc(-c2nc(Cn3cc(C(=O)O)cn3)c(C)s2)cc(C(F)(F)F)c1]

TABLE 1-continued
| compound name | molecular weight | LCMS, molecular ion peak | | retention time (min) | phenol derivative used for reaction |
|---|---|---|---|---|---|
| | | ES+ | ES- | | |
Example 164
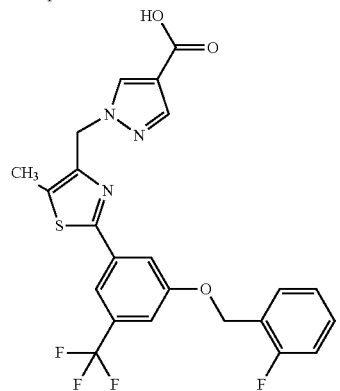
Example 165
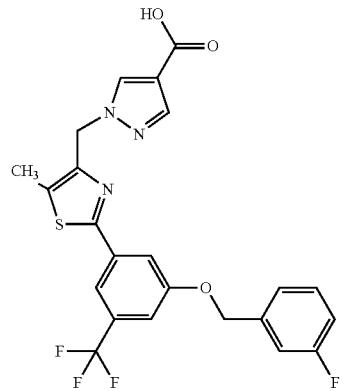 [SMILES: Cc1sc(-c2cc(OCc3cccc(F)c3)cc(C(F)(F)F)c2)nc1Cn1cc(C(=O)O)cn1]
Example 166
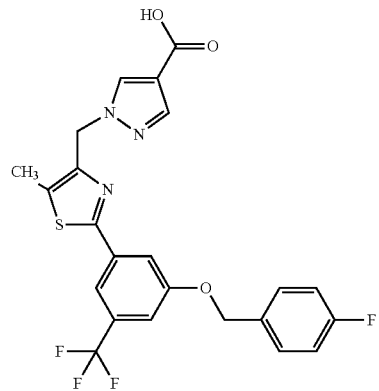 [SMILES: Cc1sc(-c2cc(OCc3ccc(F)cc3)cc(C(F)(F)F)c2)nc1Cn1cc(C(=O)O)cn1]
Example 167
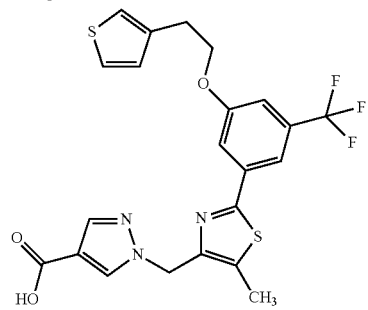 [SMILES: Cc1sc(-c2cc(OCCc3ccsc3)cc(C(F)(F)F)c2)nc1Cn1cc(C(=O)O)cn1]

TABLE 1-continued

| compound name | molecular weight | LCMS, molecular ion peak ES+ | ES- | retention time (min) | phenol derivative used for reaction |
|---|---|---|---|---|---|

Example 168

Example 169

Example 170

Example 171

TABLE 1-continued
| compound name | molecular weight | LCMS, molecular ion peak | | retention time (min) | phenol derivative used for reaction |
| --- | --- | --- | --- | --- | --- |
| | | ES+ | ES- | | |
Example 172
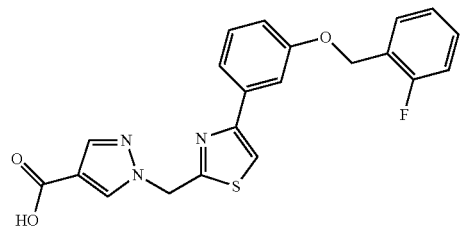 [SMILES: O=C(O)c1cnn(Cc2nc(-c3cccc(OCc4ccccc4F)c3)cs2)c1]
Example 173
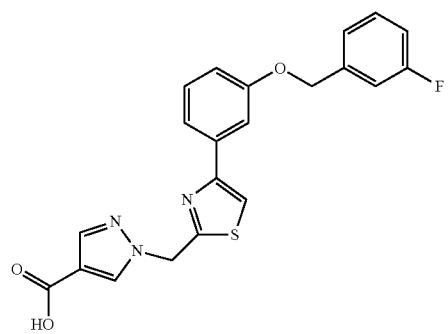 [SMILES: O=C(O)c1cnn(Cc2nc(-c3cccc(OCc4cccc(F)c4)c3)cs2)c1]
Example 174
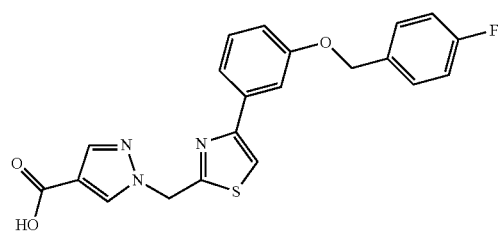 [SMILES: O=C(O)c1cnn(Cc2nc(-c3cccc(OCc4ccc(F)cc4)c3)cs2)c1]
Example 175
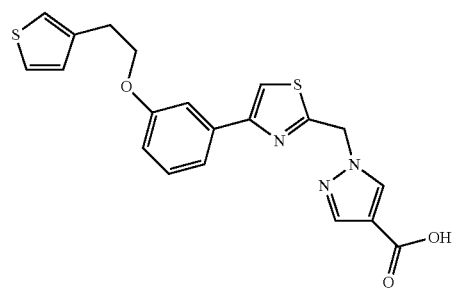 [SMILES: O=C(O)c1cnn(Cc2nc(-c3cccc(OCCc4ccsc4)c3)cs2)c1]
Example 176
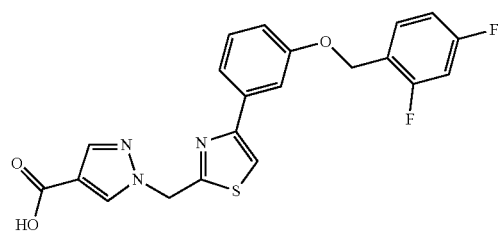 [SMILES: O=C(O)c1cnn(Cc2nc(-c3cccc(OCc4ccc(F)cc4F)c3)cs2)c1]

TABLE 1-continued

| compound name | molecular weight | LCMS, molecular ion peak ES+ | ES- | retention time (min) | phenol derivative used for reaction |
|---|---|---|---|---|---|

Example 177

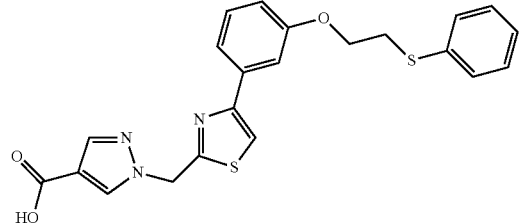 [SMILES: O=C(O)c1cnn(Cc2nc(-c3cccc(OCCSc4ccccc4)c3)cs2)c1]

Example 178

4-({4-[3-(trifluoromethyl)phenyl]-1,3-thiazol-2-yl}methyl)benzoic acid

Example 178a methyl 4-(2-amino-2-thioxoethyl)benzoate

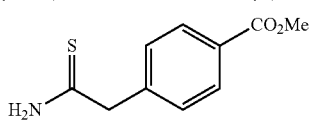

To methyl 4-(cyanomethyl)benzoate (5.0 g, 28.5 mmol) were added 4M hydrogen chloride-ethyl acetate solution (50 mL) and O,O-diethyl dithiophosphate (6.70 mL, 40.0 mmol), and the mixture was stirred overnight. The reaction mixture was alkalified with saturated aqueous sodium hydrogen carbonate solution and 8N aqueous sodium hydroxide solution, and extracted with ethyl acetate. The extract was washed successively with water and saturated brine, dried over sodium sulfate, and filtered by basic silica gel. The filtrate was concentrated under reduced pressure and recrystallized from ethyl acetate-tetrahydrofuran-hexane to give the title compound (4.46 g, 75%) as a colorless solid.

$^1$H NMR (300 MHz, CHLOROFORM-d) δppm 3.92 (3H, s), 4.14 (2H, s), 6.67 (1H, br. s.), 7.34-7.41 (2H, m), 7.59 (1H, br. s.), 8.01-8.08 (2H, m)

LCMS (ESI+) M+H: 210.

Example 178b methyl 4-({4-[3-(trifluoromethyl)phenyl]-1,3-thiazol-2-yl}methyl)benzoate

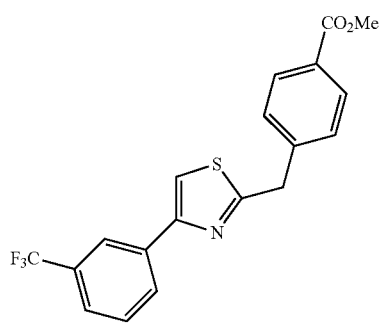 [SMILES: COC(=O)c1ccc(Cc2nc(-c3cccc(C(F)(F)F)c3)cs2)cc1]

To a solution of the compound (209 mg, 1.0 mmol) obtained in Example 178a in ethanol (4 mL) was added 2-bromo-1-[3-(trifluoromethyl)phenyl]ethanone (267 mg, 1.0 mmol), and the mixture was heated under reflux for 1.5 hr. The reaction mixture was concentrated under reduced pressure, the residue was diluted with diluted aqueous sodium hydrogen carbonate solution, and the mixture was extracted with ethyl acetate. The extract was washed with saturated brine, dried over sodium sulfate, and concentrated under reduced pressure. The residue was purified by column chromatography (carrier: silica gel, eluent: hexane-ethyl acetate) to give the title compound (346 mg, 92%) as a colorless oil.

$^1$H NMR (400 MHz, CHLOROFORM-d) δ ppm 3.92 (3H, s), 4.45 (2H, s), 7.44 (2H, d, J=8.6 Hz), 7.46 (1H, s), 7.51-7.56 (1H, m), 7.57-7.61 (1H, m), 8.01-8.09 (3H, m), 8.16 (1H, s)

LCMS (ESI+) M+H: 378.

Example 178

4-({4-[3-(trifluoromethyl)phenyl]-1,3-thiazol-2-yl}methyl)benzoic acid

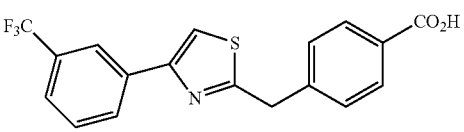 [SMILES: O=C(O)c1ccc(Cc2nc(-c3cccc(C(F)(F)F)c3)cs2)cc1]

To the compound (346 mg, 0.917 mmol) obtained in Example 178b were added ethanol (4 mL) and 2N aqueous sodium hydroxide solution (0.915 mL, 1.83 mmol), and the mixture was stirred overnight. The reaction mixture was concentrated under reduced pressure, and the residue was extracted with water, and washed with ether. The aqueous layer was acidified with 6N hydrochloric acid, and extracted with ethyl acetate. The extract was washed with saturated brine, dried over sodium sulfate, and concentrated under reduced pressure. The residue was recrystallized from ethyl acetate-hexane to give the title compound (237 mg, 71%) as colorless crystals.

$^1$H NMR (400 MHz, DMSO-$d_6$) δppm 4.52 (2H, s), 7.48-7.55 (2H, m), 7.66-7.74 (2H, m), 7.91-7.96 (2H, m), 8.23-8.30 (3 H, m), 12.94 (1H, br. s.)

LCMS (ESI+) M+H: 364.

Example 179

4-{[4-(3,4-dichlorophenyl)-1,3-thiazol-2-yl]methyl}benzoic acid

Example 179a methyl 4-{[4-(3,4-dichlorophenyl)-1,3-thiazol-2-yl]methyl}benzoate

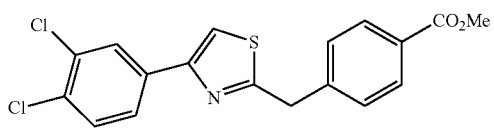 [SMILES: COC(=O)c1ccc(Cc2nc(-c3ccc(Cl)c(Cl)c3)cs2)cc1]

To a solution of the compound (209 mg, 1.0 mmol) obtained in Example 178a in ethanol (4 ml) was added 2-bromo-1-(3,4-dichlorophenyl)ethanone (268 mg, 1.00 mmol), and the mixture was heated under reflux for 1.5 hr. The reaction mixture was concentrated under reduced pressure, and the residue was diluted with diluted aqueous sodium hydrogen carbonate solution, and extracted with ethyl acetate. The extract was washed with saturated brine, dried over sodium sulfate, and concentrated under reduced pressure. The residue was purified by column chromatography (carrier: silica gel, eluent: hexane-ethyl acetate) to give the title compound (352 mg, 93%) as a yellow solid.

$^1$H NMR (400 MHz, CHLOROFORM-d) δ ppm 3.92 (3H, s), 4.43 (2H, s), 7.39 (1H, s), 7.43 (2H, d, J=8.6 Hz), 7.48 (1H, d, J=8.3 Hz), 7.70 (1H, dd, J=8.3, 2.2 Hz), 8.01 (1H, d, J=2.2 Hz), 8.02-8.05 (2H, m)

LCMS (ESI+) M+H: 378.

Example 179

4-{[4-(3,4-dichlorophenyl)-1,3-thiazol-2-yl]methyl}benzoic acid

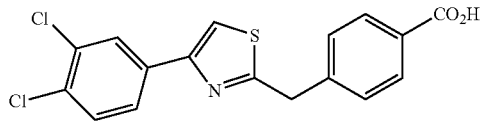 [SMILES: O=C(O)c1ccc(Cc2nc(-c3ccc(Cl)c(Cl)c3)cs2)cc1]

To the compound (352 mg, 0.931 mmol) obtained in Example 179a were added ethanol (4 mL), tetrahydrofuran (1 mL) and 2N aqueous sodium hydroxide solution (0.93 mL, 1.86 mmol), and the mixture was stirred overnight. The reaction mixture was extracted with water, and washed with ether. The aqueous layer was acidified with 6N hydrochloric acid, and extracted with ethyl acetate. The extract was washed with saturated brine, dried over sodium sulfate, and concentrated under reduced pressure. The residue was recrystallized from ethyl acetate-hexane to give the title compound (261 mg, 77%) as colorless crystals.

$^1$H NMR (400 MHz, DMSO-d$_6$) δppm 4.50 (2H, s), 7.51 (2H, d, J=8.3 Hz), 7.71 (1H, d, J=8.6 Hz), 7.90-7.97 (3H, m), 8.19 (1H, d, J=2.0 Hz), 8.22 (1H, s) 12.97 (1H, br. s.)

LCMS (ESI+) M+H: 364.

Example 180

3-({4-[3-(trifluoromethyl)phenyl]-1,3-thiazol-2-yl}methyl)benzoic acid

Example 180a ethyl 3-(cyanomethyl)benzoate

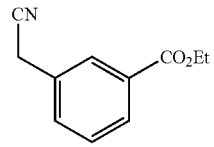 [SMILES: CCOC(=O)c1cccc(CC#N)c1]

To a solution of ethyl 3-(chloromethyl)benzoate (5.0 g, 25.1 mmol) in dimethylsulfide (50 mL) was added sodium cyanide (1.85 g, 37.8 mmol), and the mixture was stirred at room temperature for 15 hr. The reaction mixture was diluted with water, extracted with ethyl acetate, and the extract was washed successively with water and saturated brine, dried over sodium sulfate, and concentrated under reduced pressure. The residue was purified by silica gel column chromatography (carrier: silica gel, eluent: hexane-ethyl acetate) to give the title compound (4.23 g, 89%) as a colorless oil.

$^1$H NMR (300 MHz, CHLOROFORM-d) δ ppm 1.41 (3H, t, J=7.2 Hz), 3.81 (2H, s), 4.40 (2H, q, J=7.1 Hz), 7.49 (1H, d, J=7.9 Hz), 7.53-7.58 (1H, m), 7.98-8.05 (2H, m)

LCMS (ESI+) M+H: 190.

Example 180b ethyl 3-(2-amino-2-thioxoethyl)benzoate

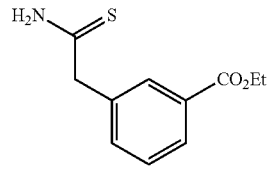 [SMILES: CCOC(=O)c1cccc(CC(N)=S)c1]

By a method similar to that in Example 178a and using the compound (4.23 g, 22.4 mmol) obtained in Example 180a, 4M hydrogen chloride-ethyl acetate solution (42 mL) and O,O-diethyl dithiophosphate (4.50 mL, 26.8 mmol), the title compound (3.94 g, 79%) was obtained as colorless crystals.

$^1$H NMR (300 MHz, CHLOROFORM-d) δ ppm 1.41 (3H, t, J=7.2 Hz), 4.14 (2H, s), 4.39 (2H, q, J=7.2 Hz), 6.68 (1H, br. s.), 7.43-7.68 (3H, m), 7.95 (1H, s), 8.01 (1H, dt, J=7.4, 1.6 Hz)

LCMS (ESI+) M+H: 224.

Example 180c methyl 3-({4-[3-(trifluoromethyl)phenyl]-1,3-thiazol-2-yl}methyl)benzoate

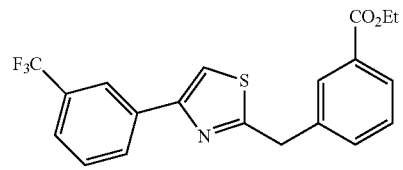 [SMILES: CCOC(=O)c1cccc(Cc2nc(-c3cccc(C(F)(F)F)c3)cs2)c1]

By a reaction in the same manner as in Example 178b and using the compound (223 mg, 1.00 mmol) obtained in Example 180b and 2-bromo-1-[3-(trifluoromethyl)phenyl]ethanone (267 mg, 1.0 mmol), the title compound (377 mg, 96%) was obtained as a yellow oil.

¹H NMR (300 MHz, CHLOROFORM-d) δ ppm 1.40 (3H, t, J=7.2 Hz), 4.38 (2H, q, J=7.2 Hz), 4.45 (2H, s), 7.40-7.47 (2H, m), 7.50-7.61 (3H, m), 7.99 (1H, dt, J=7.7, 1.4 Hz), 8.04-8.10 (2H, m), 8.17 (1H, s)

LCMS (ESI+) M+H: 392.

Example 180

3-({4-[3-(trifluoromethyl)phenyl]-1,3-thiazol-2-yl}methyl)benzoic acid

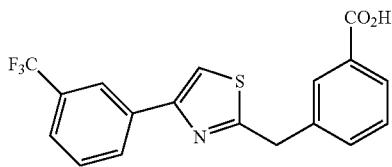 [SMILES: O=C(O)c1cccc(Cc2nc(-c3cccc(C(F)(F)F)c3)cs2)c1]

By a reaction in the same manner as in Example 178 and using the compound (377 mg, 0.96 mmol) obtained in Example 180c, the title compound (257 mg, 73%) was obtained as colorless crystals.

¹H NMR (300 MHz, DMSO-d₆) δppm 4.52 (2H, s) 7.50 (1H, t, J=7.6 Hz) 7.62-7.73 (3H, m) 7.86 (1H, d, J=7.7 Hz) 7.98 (1H, s) 8.22-8.30 (3H, m) 13.00 (1H, br. s.)

LCMS (ESI+) M+H: 364.

Example 181

4-[3-(3-bromophenyl)-1-{4-[3-(trifluoromethyl)phenyl]-1,3-thiazol-2-yl}propyl]benzoic acid Example 181a methyl 4-[3-(3-bromophenyl)-1-cyanopropyl]benzoate

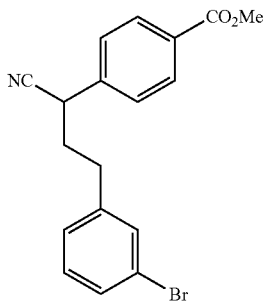 [SMILES: COC(=O)c1ccc(C(C#N)CCc2cccc(Br)c2)cc1]

To a mixed solution of methyl 4-(cyanomethyl)benzoate (3.50 g, 20.0 mmol), tetrahydrofuran (25 mL) and N,N-dimethylformamide (10 ml) was added tert-butoxy potassium (2.69 g, 24.0 mmol) at −78° C., and the mixture was stirred for 30 min. To the reaction mixture was added 1-bromo-3-(2-bromoethyl)benzene (3.37 mL, 22.0 mmol) at the same temperature, and the mixture was stirred under ice-cooling for 4 hr. The reaction mixture was diluted with water, extracted with ethyl acetate, washed successively with water and saturated brine, dried over sodium sulfate, and concentrated under reduced pressure. The residue was purified by silica gel column chromatography (carrier: silica gel, eluent: hexane-ethyl acetate) to give the title compound (3.94 g, 55%) as a colorless oil.

¹H NMR (300 MHz, CHLOROFORM-d) δ ppm 2.10-2.33 (2H, m), 2.71-2.88 (2H, m), 3.82 (1H, dd, J=8.9, 6.0 Hz), 3.93 (3H, s), 7.09-7.14 (1H, m), 7.18 (1H, t, J=7.6 Hz), 7.31-7.44 (4H, m), 8.03-8.10 (2H, Example 181b methyl 4-[3-(3-bromophenyl)-1-carbamothioylpropyl]benzoate

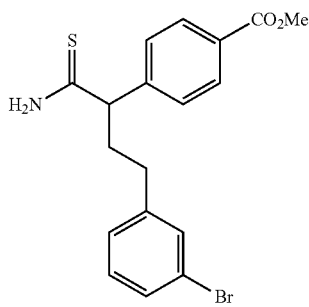 [SMILES: COC(=O)c1ccc(C(CCc2cccc(Br)c2)C(N)=S)cc1]

By a reaction in the same manner as in Example 178a and using the compound (3.94 g, 11.0 mmol) obtained in Example 181a, 4M hydrogen chloride-ethyl acetate solution (40 mL) and O,O-diethyl dithiophosphate (2.43 mL, 14.5 mmol), the title compound (3.15 g, 73%) was obtained as a colorless oil.

¹H NMR (300 MHz, CHLOROFORM-d) δ ppm 2.18-2.32 (1H, m), 2.48-2.76 (3H, m), 3.76 (1H, t, J=7.3 Hz), 3.92 (3H, s), 6.75 (1H, br. s.), 7.04-7.09 (1H, m), 7.15 (1H, t, J=7.7 Hz), 7.27-7.35 (2H, m), 7.41-7.47 (2H, m), 7.50 (1H, br. s.), 8.00-8.05 (2H, m)

LCMS (ESI+) M+H: 394.

Example 181c methyl 4-[3-(3-bromophenyl)-1-{4-[3-(trifluoromethyl)phenyl]-1,3-thiazol-2-yl}propyl]benzoate

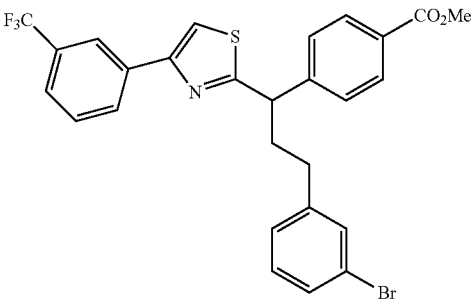 [SMILES: COC(=O)c1ccc(C(CCc2cccc(Br)c2)c2nc(-c3cccc(C(F)(F)F)c3)cs2)cc1]

By a reaction in the same manner as in Example 178b and using the compound (3.15 g, 8.03 mmol) obtained in Example 181b and 2-bromo-1-[3-(trifluoromethyl)phenyl]ethanone (3.22 g, 12.0 mmol), the title compound (4.03 g, 90%) was obtained as a yellow oil.

¹H NMR (300 MHz, CHLOROFORM-d) δ ppm 2.38-2.51 (1H, m), 2.60-2.67 (2H, m), 2.68-2.81 (1H, m), 3.91 (3H, s), 4.38 (1H, t, J=7.4 Hz), 7.06-7.11 (1H, m), 7.15 (1H, t, J=7.6 Hz), 7.30-7.36 (2H, m), 7.44-7.49 (3H, m), 7.50-7.61 (2H, m), 8.01-8.06 (2H, m), 8.09 (1H, d, J=7.2 Hz), 8.17 (1H, s)

Example 181

4-[3-(3-bromophenyl)-1-{4-[3-(trifluoromethyl)phenyl]-1,3-thiazol-2-yl}propyl]benzoic acid

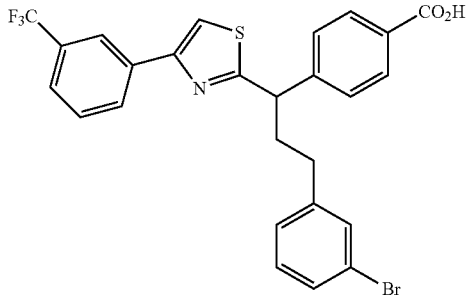 [SMILES: O=C(O)c1ccc(C(CCc2cccc(Br)c2)c2nc(-c3cccc(C(F)(F)F)c3)cs2)cc1]

By a reaction in the same manner as in Example 178 and using the compound (280 mg, 0.50 mmol) obtained in Example 181c, the title compound (263 mg, 96%) was obtained as a colorless oil.

¹H NMR (300 MHz, DMSO-d₆) δppm 2.35-2.51 (1H, m) 2.56-2.73 (3H, m) 4.53-4.64 (1H, m) 7.17-7.29 (2H, m) 7.35-7.45 (2H, m) 7.55-7.64 (2H, m) 7.66-7.75 (2H, m) 7.94-8.05 (2H, m) 8.23-8.36 (3H, m) 12.95 (1H, br. s.)

Example 182

4-({4-[2-methoxy-5-(trifluoromethyl)phenyl]-1,3-thiazol-2-yl}methyl)benzoic acid Example 182a 2-bromo-1-[2-methoxy-5-(trifluoromethyl)phenyl]ethanone

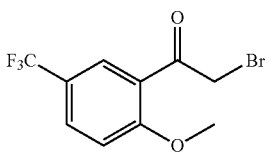 [SMILES: COc1ccc(C(F)(F)F)cc1C(=O)CBr]

To a solution of 1-[2-methoxy-5-(trifluoromethyl)phenyl]ethanone (1.00 g, 4.60 mmol) in diethyl ether (15 mL) was added phenyltrimethylammonium tribromide (1.78 g, 4.60 mmol), and the mixture was stirred overnight. The reaction mixture was diluted with diluted aqueous sodium hydrogen carbonate solution, and extracted with ethyl acetate. The extract was washed with saturated brine, dried over sodium sulfate, and concentrated under reduced pressure. The residue was purified by silica gel column chromatography (carrier: silica gel, eluent: hexane-ethyl acetate) to give the title compound (1.35 g, 98%) as a colorless solid.

¹H NMR (300 MHz, CHLOROFORM-d) δ ppm 4.02 (3H, s), 4.57 (2H, s), 7.10 (1H, d, J=8.7 Hz), 7.77 (1H, dd, J=8.7, 2.3 Hz), 8.10 (1H, d, J=2.3 Hz)

Example 182b methyl 4-({4-[2-methoxy-5-(trifluoromethyl)phenyl]-1,3-thiazol-2-yl}methyl)benzoate

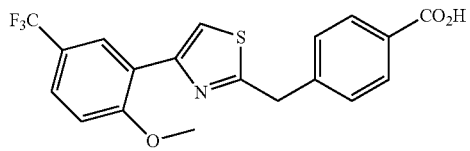 [SMILES: COc1ccc(C(F)(F)F)cc1-c1csc(Cc2ccc(C(=O)O)cc2)n1]

By a reaction in the same manner as in Example 178b and using the compound (297 mg, 1.00 mmol) obtained in Example 182a and the compound (209 mg, 1.00 mmol) obtained in Example 178a, the title compound (374 mg, 92%) was obtained as colorless crystals.

¹H NMR (300 MHz, CHLOROFORM-d) δ ppm 3.91 (3H, s), 3.99 (3H, s), 4.44 (2H, s), 7.05 (1H, d, J=8.7 Hz), 7.41-7.47 (2H, m), 7.55 (1H, dd, J=8.7, 1.9 Hz), 7.86 (1H, s), 8.00-8.05 (2H, m), 8.57 (1H, d, J=2.3 Hz)

LCMS (ESI+) M+H: 408.

Example 182

4-({4-[2-methoxy-5-(trifluoromethyl)phenyl]-1,3-thiazol-2-yl}methyl)benzoic acid By a reaction in the same manner as in Example 178 and using the compound (374 mg, 0.918 mmol) obtained in Example 182b, the title compound (247 mg, 68%) was obtained as colorless crystals.

¹H NMR (300 MHz, DMSO-d₆) δppm 4.01 (3H, s) 4.52 (2H, s) 7.35 (1H, d, J=8.7 Hz) 7.48-7.54 (2H, m) 7.70 (1H, dd, J=8.7, 1.9 Hz) 7.91-7.96 (2H, m) 8.12 (1H, s) 8.47 (1H, d, J=2.3 Hz) 12.93 (1H, br. s.)

LCMS (ESI+) M+H: 394.

Example 183

4-({5-methyl-4-[3-(trifluoromethyl)phenyl]-1,3-thiazol-2-yl}methyl)benzoic acid

Example 183a 2-bromo-1-[3-(trifluoromethyl)phenyl]propane-1-one

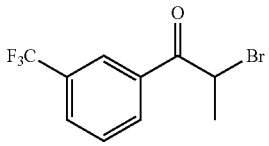

By a reaction in the same manner as in Example 182a and using 1-[3-(trifluoromethyl)phenyl]propan-1-one (1.01 g, 5.0 mmol), the title compound (1.28 g, 91%) was obtained as a colorless oil.

$^1$H NMR (300 MHz, CHLOROFORM-d) δ ppm 1.93 (3H, d, J=6.8 Hz), 5.27 (1H, q, J=6.8 Hz), 7.64 (1H, t, J=7.7 Hz), 7.85 (1H, d, J=7.9 Hz), 8.21 (1H, d, J=7.9 Hz), 8.28 (1H, s)

Example 183b methyl 4-({5-methyl-4-[3-(trifluoromethyl)phenyl]-1,3-thiazol-2-yl}methyl)benzoate

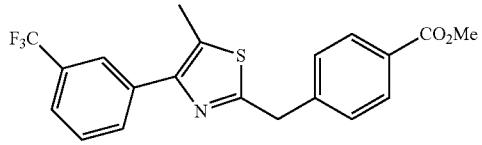 [SMILES: COC(=O)c1ccc(Cc2nc(-c3cccc(C(F)(F)F)c3)c(C)s2)cc1]

By a reaction in the same manner as in Example 178b and using the compound (314 mg, 1.00 mmol) obtained in Example 183a and the compound (422 mg, 1.50 mmol) obtained in Example 178a, the title compound (528 mg, 90%) was obtained as a colorless oil.

$^1$H NMR (400 MHz, CHLOROFORM-d) δ ppm 2.51 (3H, s), 3.92 (3H, s), 4.36 (2H, s), 7.40-7.45 (2H, m), 7.53-7.62 (2H, m), 7.82 (1H, d, J=7.6 Hz), 7.92 (1H, s), 8.00-8.05 (2H, m)

LCMS (ESI+) M+H: 392.

Example 183

4-({5-methyl-4-[3-(trifluoromethyl)phenyl]-1,3-thiazol-2-yl}methyl)benzoic acid

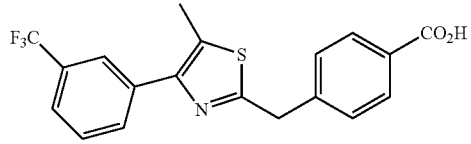 [SMILES: Cc1sc(Cc2ccc(C(=O)O)cc2)nc1-c1cccc(C(F)(F)F)c1]

By a reaction in the same manner as in Example 178 and using the compound (528 mg, 1.35 mmol) obtained in Example 183b, the title compound (242 mg, 48%) was obtained as colorless crystals.

$^1$H NMR (300 MHz, DMSO-d$_6$) δ ppm 2.52 (3H, s), 4.41 (2H, s), 7.45-7.52 (2H, m), 7.66-7.77 (2H, m), 7.88-8.00 (4H, m), 12.93 (1H, br. s.)

LCMS (ESI+) M+H: 378.

Example 184

4-(1-{4-[3-(trifluoromethyl)phenyl]-1,3-thiazol-2-yl}ethyl)benzoic acid

Example 184a methyl 4-(1-{4-[3-(trifluoromethyl)phenyl]-1,3-thiazol-2-yl}ethyl)benzoate

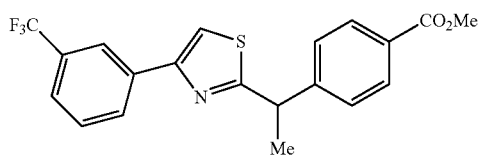 [SMILES: COC(=O)c1ccc(C(C)c2nc(-c3cccc(C(F)(F)F)c3)cs2)cc1]

To a solution of the compound (641 mg, 1.70 mmol) obtained in Example 178b in tetrahydrofuran (10 mL) was slowly added dropwise a solution (1.85 mL, 2.041 mmol) of 1.1M lithium hexamethyldisilazide in tetrahydrofuran under ice-cooling. The reaction mixture was stirred under ice-cooling for 5 min, iodomethane (0.16 mL, 2.55 mmol) was added dropwise at the same temperature, and the mixture was further stirred for 5 min. The reaction mixture was acidified with 1N aqueous hydrochloric acid solution, and extracted with ethyl acetate. The extract was washed with saturated brine, dried over magnesium sulfate, and concentrated under reduced pressure. The residue was purified by silica gel column chromatography (carrier: silica gel, eluent: hexane-ethyl acetate) to give the title compound (378 mg, 57%) as a colorless oil.

$^1$H NMR (300 MHz, CHLOROFORM-d) δ ppm 1.86 (3H, d, J=7.2 Hz), 3.91 (3H, s), 4.60 (1H, q, J=7.2 Hz), 7.43-7.48 (3H, m), 7.49-7.60 (2H, m), 8.00-8.04 (2H, m), 8.07 (1H, d, J=7.6 Hz), 8.16 (1H, s)

LCMS (ESI+) M+H: 392.

Example 184

4-(1-{4-[3-(trifluoromethyl)phenyl]-1,3-thiazol-2-yl}ethyl)benzoic acid

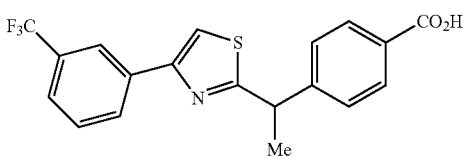 [SMILES: CC(c1ccc(C(=O)O)cc1)c1nc(-c2cccc(C(F)(F)F)c2)cs1]

By a reaction in the same manner as in Example 178 and using the compound (378 mg, 0.966 mmol) obtained in Example 184a, the title compound (275 mg, 76%) was obtained as colorless crystals.

$^1$H NMR (300 MHz, DMSO-d$_6$) ppm 1.77 (3H, d, J=6.8 Hz), 4.74 (1H, q, J=7.2 Hz), 7.46-7.56 (2H, m), 7.62-7.74 (2H, m), 7.85-7.97 (2H, m), 8.27 (3H, s), 12.93 (1H, br. s.)

LCMS (ESI+) M+H: 378.

Example 185

4-({4-[3-fluoro-5-(trifluoromethyl)phenyl]-1,3-thiazol-2-yl}methyl)benzoic acid

Example 185a 2-bromo-1-[3-fluoro-5-(trifluoromethyl)phenyl]ethanone

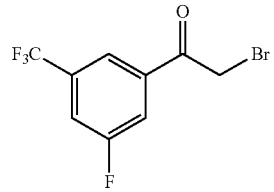 [SMILES: O=C(CBr)c1cc(F)cc(C(F)(F)F)c1]

By a reaction in the same manner as in Example 182a and using 1-[3-fluoro-5-(trifluoromethyl)phenyl]ethanone (1.96 g, 9.51 mmol), the title compound (2.58 g, 95%) was obtained as a colorless solid.

$^1$H NMR (300 MHz, CHLOROFORM-d) δ ppm 4.43 (2H, s), 7.58 (1H, d, J=7.6 Hz), 7.88 (1H, d, J=8.7 Hz), 8.04 (1H, s)

Example 185b methyl 4-({4-[3-fluoro-5-(trifluoromethyl)phenyl]-1,3-thiazol-2-yl}methyl)benzoate

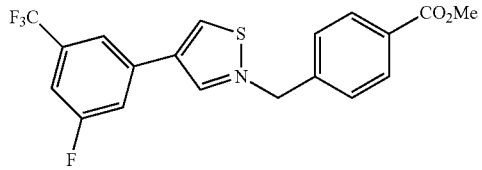

By a reaction in the same manner as in Example 178b and using the compound (285 mg, 1.00 mmol) obtained in Example 185a and the compound (209 mg, 1.00 mmol) obtained in Example 178a, the title compound (339 mg, 86%) was obtained as a colorless solid.

$^1$H NMR (300 MHz, CHLOROFORM-d) δ ppm 3.92 (3H, s), 4.44 (2H, s), 7.25-7.31 (1H, m), 7.41-7.46 (2H, m), 7.48 (1H, s), 7.77-7.83 (1H, m), 7.94 (1H, s), 8.01-8.06 (2H, m)
LCMS (ESI+) M+H: 396.

Example 185

4-({4-[3-fluoro-5-(trifluoromethyl)phenyl]-1,3-thiazol-2-yl}methyl)benzoic acid

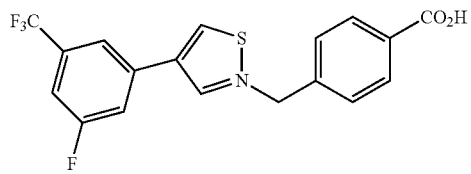

By a reaction in the same manner as in Example 178 and using the compound (339 mg, 0.857 mmol) obtained in Example 185b, the title compound (225 mg, 69%) was obtained as colorless crystals.

$^1$H NMR (300 MHz, DMSO-d$_6$) δppm 4.52 (2H, s), 7.46-7.55 (2H, m), 7.66 (1H, d, J=8.0 Hz), 7.88-7.97 (2H, m), 8.10 (1H, d, J=10.2 Hz), 8.15 (1H, s), 8.34-8.39 (1H, m), 12.96 (1H, br. s.)
LCMS (ESI+) M+H: 382.

Example 186

4-({4-[2-fluoro-3-(trifluoromethyl)phenyl]-1,3-thiazol-2-yl}methyl)benzoic acid

Example 186a 2-bromo-1-[2-fluoro-3-(trifluoromethyl)phenyl]ethanone

To a solution of 1-[2-fluoro-3-(trifluoromethyl)phenyl]ethanone (5.07 g, 24.6 mmol) in diethyl ether (15 mL) was added phenyltrimethylammonium tribromide (9.62 g, 25.6 mmol), and the mixture was stirred overnight. The reaction mixture was diluted with diluted aqueous sodium hydrogen carbonate solution, and extracted with ethyl acetate. The extract was washed with saturated brine, dried over sodium sulfate, and concentrated under reduced pressure to give the title compound (6.95 g, 99%) as a yellow oil.

$^1$H NMR (300 MHz, CHLOROFORM-d) δ ppm 4.52 (2H, s), 7.40 (1H, t, J=8.1 Hz), 7.85 (1H, t, J=8.1 Hz), 8.12 (1H, t, J=8.1 Hz)

Example 186b methyl 4-({4-[2-fluoro-3-(trifluoromethyl)phenyl]-1,3-thiazol-2-yl}methyl)benzoate

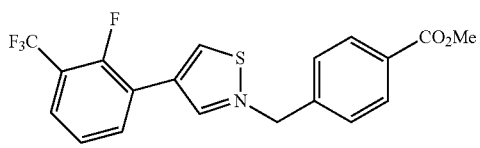

To a solution of the compound (285 mg, 1.0 mmol) obtained in Example 186a in methanol (5 mL) was added the compound (209 mg, 1.00 mmol) obtained in Example 178a, and the mixture was heated under reflux for 3 hr. The reaction mixture was concentrated under reduced pressure, and the residue was diluted with diluted aqueous sodium hydrogen carbonate solution, and the mixture was extracted with ethyl acetate. The extract was washed with saturated brine, dried over sodium sulfate, and concentrated under reduced pressure. The residue was purified by column chromatography (carrier: silica gel, eluent: hexane-ethyl acetate) to give the title compound (300 mg, 76%) as a colorless solid.

$^1$H NMR (300 MHz, CHLOROFORM-d) δ ppm 3.92 (3H, s), 4.44 (2H, s), 7.33 (1H, t, J=8.0 Hz), 7.40-7.47 (2H, m), 7.52-7.62 (1H, m), 7.72 (1H, d, J=2.7 Hz), 7.98-8.08 (2H, m), 8.40-8.48 (1H, m)
LCMS (ESI+) M+H: 396.

Example 186

4-({4-[2-fluoro-3-(trifluoromethyl)phenyl]-1,3-thiazol-2-yl}methyl)benzoic acid

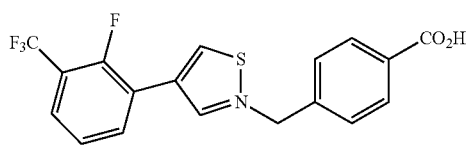

To the compound (300 mg, 0.759 mmol) obtained in Example 186b were added ethanol (4 mL), tetrahydrofuran (2 mL) and 2N aqueous sodium hydroxide solution (0.76 mL, 1.52 mmol), and the mixture was stirred overnight. The reaction mixture was extracted with water, and washed with ether. The aqueous layer was acidified with 6N hydrochloric acid, and extracted with ethyl acetate. The extract was washed with saturated brine, dried over sodium sulfate, and concentrated under reduced pressure. The residue was purified by column chromatography (carrier: silica gel, eluent: hexane-ethyl acetate), and recrystallized from ethanol-hexane to give the title compound (186 mg, 64%) as colorless crystals.

$^1$H NMR (300 MHz, DMSO-d$_6$) δppm 4.52 (2H, s), 7.48-7.56 (3H, m), 7.79 (1H, t, J=6.8 Hz), 7.90-7.96 (2H, m), 8.05 (1H, d, J=3.0 Hz), 8.41 (1H, t, J=7.0 Hz), 12.94 (1H, br. s.)

LCMS (ESI+) M+H: 382.

Example 187

4-({4-[2-chloro-5-(trifluoromethyl)phenyl]-1,3-thiazol-2-yl}methyl)benzoic acid

Example 187a 2-bromo-1-[2-chloro-5-(trifluoromethyl)phenyl]ethanone

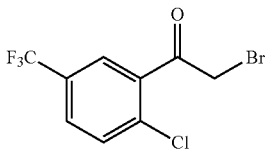 [SMILES: O=C(CBr)c1cc(C(F)(F)F)ccc1Cl]

By a reaction in the same manner as in Example 182a and using 1-[2-chloro-5-(trifluoromethyl)phenyl]ethanone (4.97 g, 22.3 mmol), the title compound (6.23 g, 93%) was obtained as a yellow oil.

$^1$H NMR (300 MHz, CHLOROFORM-d) δ ppm 4.51 (2H, s), 7.60 (1H, d, J=8.7 Hz), 7.70 (1H, dd, J=8.5, 2.1 Hz), 7.82 (1H, d, J=1.9 Hz)

Example 187b methyl 4-({4-[2-chloro-5-(trifluoromethyl)phenyl]-1,3-thiazol-2-yl}methyl)benzoate

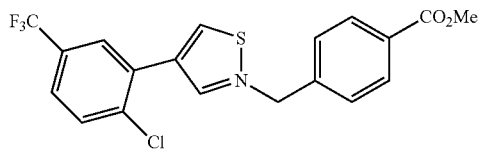

By a reaction in the same manner as in Example 178b and using the compound (301 mg, 1.00 mmol) obtained in Example 187a and the compound (209 mg, 1.00 mmol) obtained in Example 178a, the title compound (368 mg, 89%) was obtained as a colorless solid.

$^1$H NMR (300 MHz, CHLOROFORM-d) δ ppm 3.92 (3H, s), 4.45 (2H, s), 7.42-7.47 (2H, m), 7.48-7.54 (1H, m), 7.59 (1H, d, J=8.7 Hz), 7.81 (1H, s), 8.01-8.07 (2H, m), 8.29 (1H, d, J=2.3 Hz)

LCMS (ESI+) M+H: 412.

Example 187

4-({4-[2-chloro-5-(trifluoromethyl)phenyl]-1,3-thiazol-2-yl}methyl)benzoic acid

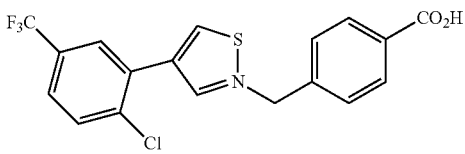

By a reaction in the same manner as in Example 178 and using the compound (368 mg, 0.894 mmol) obtained in Example 187b, the title compound (176 mg, 50%) was obtained as colorless crystals.

$^1$H NMR (300 MHz, DMSO-d$_6$) δppm 4.53 (2H, s), 7.49-7.55 (2H, m), 7.74-7.79 (1H, m), 7.84 (1H, d, J=8.3 Hz), 7.91-7.96 (2H, m), 8.18 (1H, s), 8.23 (1H, d, J=1.9 Hz), 12.96 (1H, br. s.)

LCMS (ESI+) M+H: 398.

Example 188

3-bromo-4-({4-[3-(trifluoromethyl)phenyl]-1,3-thiazol-2-yl}methyl)benzoic acid

Example 188a methyl 4-(bromomethyl)-3-bromobenzoate

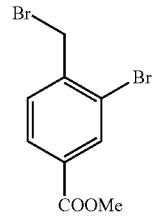

By a method similar to that in Example 189b, the crude title compound (6.4 g, 95%) was obtained as a colorless oil from methyl 4-methyl-3-bromobenzoate (5.0 g, 22 mmol), N-bromosuccinimide (5.8 g, 33 mmol) and 2,2'-azobisbutyronitrile (AIBN) (360 mg, 2.2 mmol).

$^1$H NMR (300 MHz, CHLOROFORM-d) δppm 3.93 (3H, s), 4.61 (2H, s), 7.53 (1H, d, J=8.0 Hz), 7.95 (1H, dd, J=8.0, 1.5 Hz), 8.25 (1H, d, J=1.5 Hz)

Example 188b methyl 4-(2-amino-2-thioxoethyl)-3-bromobenzoate

By a method similar to that in Example 189c, the title compound (1.7 g, 28% in 2 steps) was obtained as colorless crystals from the crude compound (6.4 g, 21 mmol) obtained in Example 189a, sodium cyanide (1.2 g, 25 mmol) and O,O-diethyl dithiophosphate (1.9 g, 10 mmol).

¹H NMR (300 MHz, DMSO-d₆) δ ppm 3.86 (3H, s), 4.02 (2H, s), 7.51 (1H, d, J=8.0 Hz), 7.91 (1H, dd, J=8.0, 1.9 Hz), 8.07 (1H, d, J=1.5 Hz), 9.42 (1H, br. s.), 9.67 (1H, br. s.)

LCMS (ESI⁺) M+H⁺: 288.

Example 188c methyl 3-bromo-4-({4-[3-(trifluoromethyl)phenyl]-1,3-thiazol-2-yl}methyl)benzoate

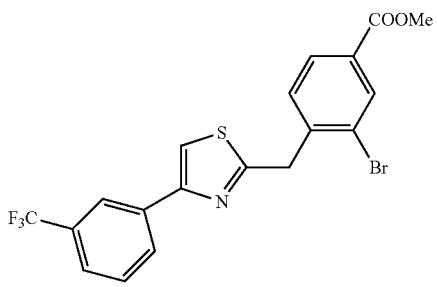 [SMILES: COC(=O)c1ccc(Cc2nc(-c3cccc(C(F)(F)F)c3)cs2)c(Br)c1]

By a method similar to that in Example 189d, the title compound (1.6 g, 69%) was obtained as colorless crystals from the compound (1.7 g, 5.8 mmol) obtained in Example 188b and 2-bromo-1-[3-(trifluoromethyl)phenyl]ethanone (1.7 g, 5.6 mmol).

¹H NMR (300 MHz, DMSO-d₆) δ ppm 3.87 (3H, s), 4.63 (2H, s), 7.53-8.37 (8H, m)

LCMS (ESI⁺) M+H⁺: 456.

Example 188

3-bromo-4-({4-[3-(trifluoromethyl)phenyl]-1,3-thiazol-2-yl}methyl)benzoic acid

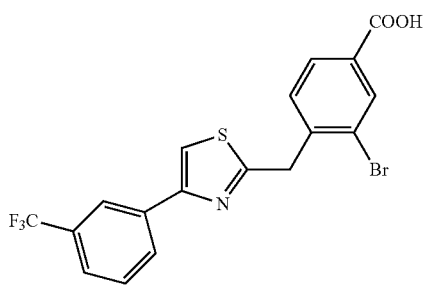 [SMILES: O=C(O)c1ccc(Cc2nc(-c3cccc(C(F)(F)F)c3)cs2)c(Br)c1]

By a method similar to that in Example 189, the title compound (66 mg, 68%) was obtained as colorless crystals from the compound (100 mg, 0.22 mmol) obtained in Example 188c.

¹H NMR (300 MHz, DMSO-d₆) δ ppm 4.62 (2H, s), 7.59-7.77 (3H, m), 7.96 (1H, d, J=8.0 Hz), 8.14 (1H, s), 8.19-8.35 (3H, m), 13.35 (1H, br. s.)

LCMS (ESI⁺) M+H⁺: 442.

Example 189

3-fluoro-4-({4-[3-(trifluoromethyl)phenyl]-1,3-thiazol-2-yl}methyl)benzoic acid

Example 189a ethyl 3-fluoro-4-methylbenzoate

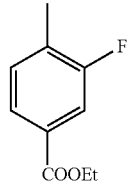

To a solution (50 mL) of 3-fluoro-4-methylbenzoic acid (5.0 g, 32 mmol) in ethanol was added conc. sulfuric acid (0.25 mL), and the mixture was heated under reflux overnight. The reaction mixture was allowed to cool to room temperature, and neutralized with saturated aqueous sodium hydrogen carbonate, and extracted with ethyl acetate. The obtained organic layer was washed with saturated brine, and dried over anhydrous sodium sulfate. The solvent was evaporated under reduced pressure. The obtained crude product was purified by column chromatography (hexane-hexane/ethyl acetate=80/20) to give the title compound as a colorless oil.

¹H NMR (300 MHz, CHLOROFORM-d) δ ppm 1.39 (3H, t, J=7.0 Hz), 2.33 (3H, d, J=1.9 Hz), 4.36 (2H, q, J=7.2 Hz), 7.23 (1H, d, J=7.7 Hz), 7.66 (1H, d, J=9.8 Hz), 7.73 (1H, dd, J=7.8, 1.7 Hz)

Example 189b ethyl 4-(bromomethyl)-3-fluorobenzoate

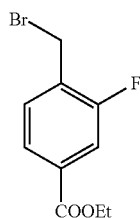

To a solution (11 ml) of the compound (2.0 g, 11 mmol) obtained in Example 189a in ethyl acetate were added N-bromosuccinimide (2.9 g, 17 mmol) and 2,2'-azobisbutyronitrile (AIBN) (180 mg, 1.1 mmol), and the mixture was heated under reflux for 5 hr under light irradiation. An aqueous sodium thiosulfate solution was added to the reaction mixture, and the mixture was extracted with ethyl acetate. The obtained organic layer was washed with saturated brine, and dried over anhydrous sodium sulfate. The solvent was evaporated under reduced pressure. The obtained crude product was purified by column chromatography (hexane-hexane/ethyl acetate=90/10) to give a crude title compound (2.3 g, 81%) as a colorless oil.

¹H NMR (300 MHz, CHLOROFORM-d) δppm 1.40 (3H, t, J=7.1 Hz), 4.39 (2H, q, J=7.2 Hz), 4.52 (2H, s), 7.47 (1H, t, J=7.6 Hz), 7.73 (1H, dd, J=10.2, 1.5 Hz), 7.82 (1H, dd, J=7.9, 1.5 Hz)

Example 189c ethyl 4-(2-amino-2-thioxoethyl)-3-fluorobenzoate

To a solution (20 mL) of crude Example 189b (2.3 g, 8.8 mmol) in dimethyl sulfoxide was added sodium cyanide (520 mg, 11 mmol), and the mixture was stirred at room temperature overnight. After confirmation of the termination of the reaction by TLC, water was added and the mixture was extracted with ethyl acetate. The obtained organic layer was washed with water and saturated brine, and the solvent was evaporated under reduced pressure.

The obtained crude product was dissolved in 4M hydrogen chloride-ethyl acetate solution (5 mL), O,O-diethyl dithiophosphate (1.8 g, 9.4 mmol) was added, and the mixture was stirred at room temperature for 5 hr. Saturated aqueous sodium hydrogen carbonate was added to the reaction mixture, and the mixture was stirred overnight and extracted with ethyl acetate. The obtained organic layer was washed with saturated brine, and dried over anhydrous sodium sulfate. The solvent was evaporated under reduced pressure. The obtained crude product was purified by column chromatography (hexane-hexane/ethyl acetate=70/30) to give the title compound (400 mg, 19% in 2 steps) as colorless crystals.

¹H NMR (300 MHz, DMSO-d₆) δ ppm 1.32 (3H, t, J=7.1 Hz), 3.92 (2H, s), 4.32 (2H, q, J=7.1 Hz), 7.50 (1H, t, J=7.7 Hz), 7.64 (1H, dd, J=10.4, 1.7 Hz), 7.75 (1H, dd, J=7.9, 1.7 Hz), 9.45 (1H, br. s.), 9.64 (1H, br. s.)

LCMS (ESI⁺) M+H⁺: 242.

Example 189d ethyl 3-fluoro-4-({4-[3-(trifluoromethyl)phenyl]-1,3-thiazol-2-yl}methyl)benzoate

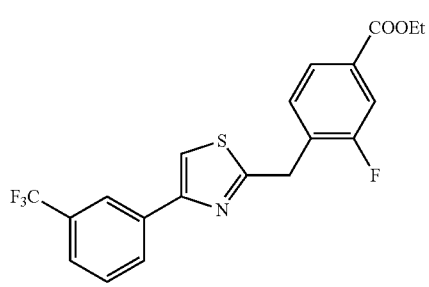 [SMILES: CCOC(=O)c1ccc(Cc2nc(-c3cccc(C(F)(F)F)c3)cs2)c(F)c1]

To a solution (4 mL) of the compound (400 mg, 1.7 mmol) obtained in Example 189c in ethanol was added 2-bromo-1-[3-(trifluoromethyl)phenyl]ethanone (530 mg, 2.0 mmol), and the mixture was heated under reflux overnight. The reaction mixture was allowed to cool to room temperature and the solvent was evaporated under reduced pressure. The obtained crude product was purified by recrystallization (ethyl acetate-hexane) to give the title compound (540 mg, 80%) as colorless crystals.

¹H NMR (300 MHz, DMSO-d₆) δ ppm 1.32 (3H, t, J=7.2 Hz), 4.33 (2H, q, J=7.2 Hz), 4.55 (2H, s), 7.58-7.88 (5H, m), 8.18-8.27 (2H, m), 8.27 (1H, s)

LCMS (ESI⁺) M+H⁺: 410.

Example 189

3-fluoro-4-({4-[3-(trifluoromethyl)phenyl]-1,3-thiazol-2-yl}methyl)benzoic acid

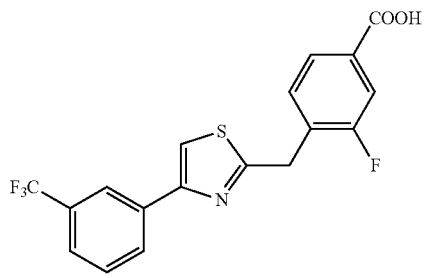 [SMILES: O=C(O)c1ccc(Cc2nc(-c3cccc(C(F)(F)F)c3)cs2)c(F)c1]

To a solution (4 mL) of the compound (540 mg, 1.3 mmol) obtained in Example 189d in ethanol was added 2N aqueous sodium hydroxide solution (2.6 mL, 5.3 mmol), and the mixture was stirred at room temperature overnight. The reaction mixture was neutralized with 1N aqueous hydrochloric acid solution, saturated brine was added, and the mixture was extracted with ethyl acetate. The obtained organic layer was washed with saturated brine, and dried over anhydrous sodium sulfate. The solvent was evaporated under reduced pressure. The obtained crude product was purified by recrystallization (ethyl acetate-hexane) to give the title compound (380 mg, 76%) as colorless crystals.

¹H NMR (300 MHz, DMSO-d₆) δ ppm 4.54 (2H, s), 7.61 (1H, t, J=7.7 Hz), 7.65-7.74 (3H, m), 7.79 (1H, dd, J=7.9, 1.5 Hz), 8.15-8.32 (3H, m), 13.27 (1H, br. s.)

LCMS (ESI⁺) M+H⁺: 382.

Example 190

2-fluoro-4-({4-[3-(trifluoromethyl)phenyl]-1,3-thiazol-2-yl}methyl)benzoic acid

Example 190a ethyl 4-[3-(trifluoromethyl)phenyl]-1,3-thiazole-2-carboxylate

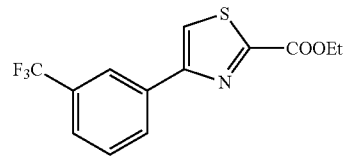 [SMILES: CCOC(=O)c1nc(-c2cccc(C(F)(F)F)c2)cs1]

To 2-bromo-1-[3-(trifluoromethyl)phenyl]ethanone (14 g, 41 mmol) was added ethyl amino(thioxo)acetate (5.0 g, 38 mmol), and the mixture was stirred at 80° C. for 3 hr. The solvent was evaporated under reduced pressure, and the obtained crude product was purified by recrystallization (ethyl acetate) to give the title compound (5.6 g, 49%) as colorless crystals.

$^1$H NMR (300 MHz, DMSO-$d_6$) δ ppm 1.37 (3H, t, J=7.2 Hz), 4.44 (2H, q, J=7.1 Hz), 7.65-7.87 (2H, m), 8.33 (2H, br. s.), 8.79 (1H, s)

LCMS (ESI$^+$) M+H$^+$: 302.

Example 190b

{4-[3-(trifluoromethyl)phenyl]-1,3-thiazol-2-yl}methanol

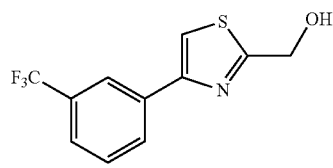

Under a nitrogen atmosphere at 0° C., to a solution (50 mL) of lithium aluminum hydride (710 mg, 19 mmol) in tetrahydrofuran was added dropwise a solution (40 mL) of the compound (5.6 g, 19 mmol) obtained in Example 190a in tetrahydrofuran, and the mixture was stirred at 0° C. for 3 hr. After confirmation of the termination of the reaction by TLC, sodium sulfate 10 hydrate was added to the reaction mixture, and the mixture was stirred at room temperature overnight. The resulting salt was removed and the solvent was evaporated under reduced pressure. The obtained crude product was purified by column chromatography (hexane-hexane/ethyl acetate=70/30) to give the title compound (1.2 g, 25%) as an orange oil.

$^1$H NMR (300 MHz, CHLOROFORM-d) δppm 2.57 (1H, br. s.), 5.03 (2 H, d, J=3.2 Hz), 7.48-7.64 (3H, m), 8.06 (1H, d, J=7.5 Hz), 8.16 (1H, s)

Example 190c 2-(iodomethyl)-4-[3-(trifluoromethyl)phenyl]-1,3-thiazole

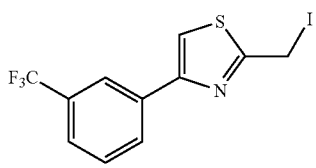 [SMILES: FC(F)(F)c1cccc(-c2csc(CI)n2)c1]

To a solution (5 mL) of the compound (1.2 g, 4.6 mmol) obtained in Example 190b in tetrahydrofuran was added oxalyl chloride (0.68 mL, 9.3 mmol), and the mixture was stirred at room temperature overnight. The reaction mixture was neutralized with saturated aqueous sodium hydrogen carbonate, and the mixture was extracted with ethyl acetate. The obtained organic layer was washed with saturated brine, and dried over anhydrous sodium sulfate. The solvent was evaporated under reduced pressure. To a solution (20 mL) of the residue in acetone was added sodium iodide (2.1 g, 14 mmol), and the mixture was stirred at 70° C. for 3 hr. Water was added to the reaction mixture, and the mixture was extracted with ethyl acetate. The obtained organic layer was washed with saturated brine, and dried over anhydrous sodium sulfate. The solvent was evaporated under reduced pressure. The obtained crude product was purified by column chromatography (hexane-hexane/ethyl acetate=90/10) to give the title compound (530 mg, 31% in 2 steps) as colorless crystals.

$^1$H NMR (300 MHz, CHLOROFORM-d) δppm 4.78 (2H, s), 7.42-7.67 (3H, m), 8.05 (1H, d, J=7.5 Hz), 8.14 (1H, s)

LCMS (ESI$^+$) M+H$^+$: 370.

Example 190d methyl 2-fluoro-4-({4-[3-(trifluoromethyl)phenyl]-1,3-thiazol-2-yl}methyl)benzoate

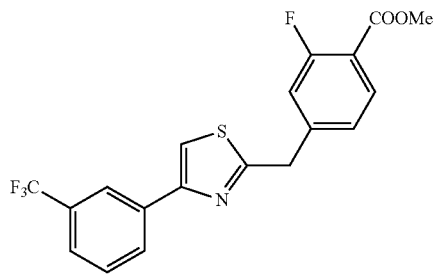 [SMILES: COC(=O)c1ccc(Cc2nc(-c3cccc(C(F)(F)F)c3)cs2)cc1F]

Under a nitrogen atmosphere, to a mixed solvent of the compound (270 mg, 0.72 mmol) obtained in Example 190c, 3-fluoro-4-methoxycarbonylphenylboronic acid (170 mg, 0.86 mmol) and cesium carbonate (1.2 g, 3.6 mmol) in tetrahydrofuran-water (v/v=5/1, 6 mL) was added [1,1'-bis(diphenylphosphino)ferrocene]dichloropalladium(II) dichloromethane complex (120 mg, 0.14 mmol), and the mixture was stirred at 90° C. overnight. The resulting salt was filtered and removed, and the solvent was evaporated under reduced pressure. The obtained crude product was purified by column chromatography (hexane-hexane/ethyl acetate=75/25) to give the title compound as colorless crystals.

$^1$H NMR (300 MHz, CHLOROFORM-d) δppm 3.93 (3H, s), 4.42 (2H, s), 7.18 (2H, dd, J=16.7, 10.6 Hz), 7.33-8.28 (6H, m)

LCMS M+H$^+$: 396.

Example 190

2-fluoro-4-({4-[3-(trifluoromethyl)phenyl]-1,3-thiazol-2-yl}methyl)benzoic acid

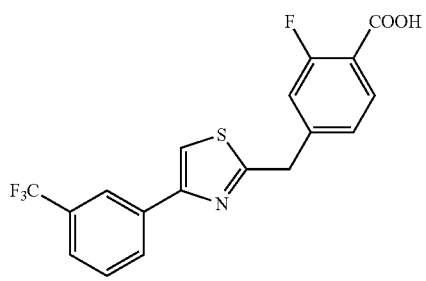 [SMILES: O=C(O)c1ccc(Cc2nc(-c3cccc(C(F)(F)F)c3)cs2)cc1F]

By a method similar to that in Example 189, the title compound (12 mg, 10%) was obtained as colorless crystals from the compound (120 mg, 0.30 mmol) obtained in Example 190d.

$^1$H NMR (300 MHz, DMSO-$d_6$) δ ppm 4.53 (2H, s), 7.27-7.44 (2H, m), 7.63-7.74 (2H, m), 7.86 (1H, t, J=7.9 Hz), 8.18-8.45 (3H, m), 13.22 (1H, br. s.)

LCMS (ESI$^+$) M+H$^+$: 382.

Example 191

4-({4-[2-(benzyloxy)phenyl]-1,3-thiazol-2-yl}methyl)benzoic acid

Example 191a

{4-[2-(benzyloxy)phenyl]-1,3-thiazol-2-yl}methanol

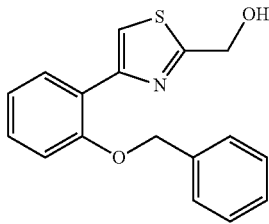 [SMILES: OCc1nc(-c2ccccc2OCc2ccccc2)cs1]

To a mixed solution of the compound (900 mg, 4.6 mmol) obtained in Example 30a, 2-benzyloxyphenylboronic acid (1.3 g, 5.6 mmol) and 2M aqueous sodium carbonate solution (2.8 mL, 5.6 mmol) in 1,2-dimethoxyethane-ethanol (v/v=3/1, 12 mL) was added [1,1'-bis(diphenylphosphino)ferrocene]dichloropalladium(II) dichloromethane complex (380 mg, 0.46 mmol), and the mixture was stirred at 90° C. overnight. The resulting salt was filtered and removed, and the solvent was evaporated under reduced pressure. The obtained crude product was purified by column chromatography (hexane-hexane/ethyl acetate=60/40) to give the title compound (1.2 g, 88%) as colorless crystals.

$^1$H NMR (300 MHz, CHLOROFORM-d) δppm 2.63 (1H, t, J=6.0 Hz), 5.00 (2H, d, J=6.0 Hz), 5.20 (2H, s), 7.02-7.13 (2H, m), 7.28-7.52 (6H, m), 7.88 (1H, s), 8.25 (1H, dd, J=8.1, 1.7 Hz)

LCMS (ESI$^+$) M+H$^+$: 298.

Example 191b methyl-4-({4-[2-(benzyloxy)phenyl]-1,3-thiazol-2-yl}methyl)benzoate

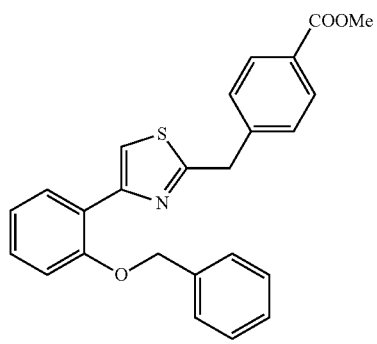 [SMILES: COC(=O)c1ccc(Cc2nc(-c3ccccc3OCc3ccccc3)cs2)cc1]

To a solution (8 mL) of the compound (1.2 g, 4.0 mmol) obtained in Example 191a in tetrahydrofuran were added triethylamine (0.73 mL, 5.3 mmol) and methanesulfonylchloride (0.38 mL, 4.8 mmol), and the mixture was stirred at room temperature for 3 hr. The resulting salt was filtered and removed, and the solvent was evaporated under reduced pressure. To a solution (40 mL) of the residue in acetone was added sodium iodide (1.8 g, 12 mmol), and the mixture was stirred at room temperature overnight. Water was added to the reaction mixture, the mixture was extracted with ethyl acetate, and the solvent was evaporated under reduced pressure. To a mixed solution of the residue, 4-methoxycarbonylphenylboronic acid (870 mg, 4.8 mmol) and 2M aqueous sodium carbonate solution (2.4 mL, 4.8 mmol) in 1,2-dimethoxyethane/ethanol (v/v=3/1, 12 mL) was added [1,1'-bis(diphenylphosphino)ferrocene]dichloropalladium(II) dichloromethane complex (330 mg, 0.40 mmol), and the mixture was stirred at 90° C. overnight. The resulting salt was filtered and removed, and the solvent was evaporated under reduced pressure. The obtained crude product was purified by column chromatography (hexane-hexane/ethyl acetate=85/15) to give the title compound (360 mg, 21% in 3 steps) as colorless crystals.

$^1$H NMR (300 MHz, DMSO-$d_6$) δ ppm 3.89 (3H, s), 4.49 (2H, s), 5.28 (2H, s), 6.79-8.36 (14H, m)

LCMS (ESI$^+$) M+H$^+$: 416.

Example 191

4-({4-[2-(benzyloxy)phenyl]-1,3-thiazol-2-yl}methyl)benzoic acid

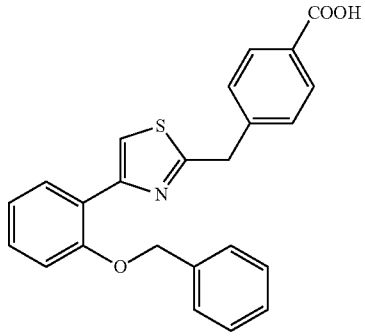 [SMILES: O=C(O)c1ccc(Cc2nc(-c3ccccc3OCc3ccccc3)cs2)cc1]

By a method similar to that in Example 189, the title compound (85 mg, 32%) was obtained as colorless crystals from the compound (270 mg, 0.65 mmol) obtained in Example 191b.

$^1$H NMR (300 MHz, DMSO-$d_6$) δ ppm 4.48 (2H, s), 5.28 (2H, s), 7.04 (1H, t, J=7.0 Hz), 7.17-7.25 (1H, m), 7.25-7.44 (4 H, m), 7.44-7.54 (4H, m), 7.84-7.99 (3H, m), 8.15 (1H, dd, J=8.0, 1.9 Hz), 12.92 (1H, br. s.)

LCMS (ESI$^+$) M+H$^+$: 402.

Example 192

4-({4-[2-fluoro-5-(trifluoromethyl)phenyl]-1,3-thiazol-2-yl}methyl)benzoic acid

Example 192a

{4-[2-fluoro-5-(trifluoromethyl)phenyl]-1,3-thiazol-2-yl}methanol

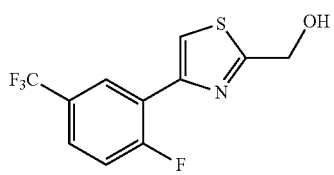 [SMILES: OCc1nc(-c2cc(C(F)(F)F)ccc2F)cs1]

By a method similar to that in Example 191b, the title compound (550 mg, 43%) was obtained as a colorless oil from the compound (900 mg, 4.6 mmol) obtained in Example 30a, 5-trifluoromethyl-2-fluorophenylboronic acid (1.2 g, 5.6 mmol), 2M aqueous sodium carbonate solution (2.8 mL, 5.6 mmol), and [1,1'-bis(diphenylphosphino)ferrocene]dichloropalladium(II) dichloromethane complex (380 mg, 0.46 mmol).

$^1$H NMR (300 MHz, CHLOROFORM-d) δppm 2.56 (1H, t, J=6.1 Hz), 5.04 (2H, d, J=6.1 Hz), 7.21-7.32 (1H, m), 7.45-7.66 (1H, m), 7.83 (1H, d, J=2.3 Hz), 8.53 (1H, dd, J=7.2, 2.3 Hz)

LCMS (ESI$^+$) M+H$^+$: 278.

Example 192b

4-[2-fluoro-5-(trifluoromethyl)phenyl]-2-(iodomethyl)-1,3-thiazole

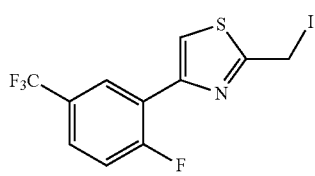 [SMILES: Fc1ccc(C(F)(F)F)cc1-c1csc(CI)n1]

By a method similar to that in Example 190c, the title compound (360 mg, 47% in 2 steps) was obtained as a pale-yellow solid from the compound (550 mg, 2.0 mmol) obtained in Example 192a.

$^1$H NMR (300 MHz, CHLOROFORM-d) δppm 4.79 (2H, s), 7.17-7.34 (1H, m), 7.57 (1H, m), 7.77-7.97 (1H, m), 8.52 (1H, dd, J=6.8, 1.9 Hz)

LCMS (ESI$^+$) M+H$^+$: 388.

Example 192c methyl4-({4-[2-fluoro-5-(trifluoromethyl)phenyl]-1,3-thiazol-2-yl}methyl)benzoate

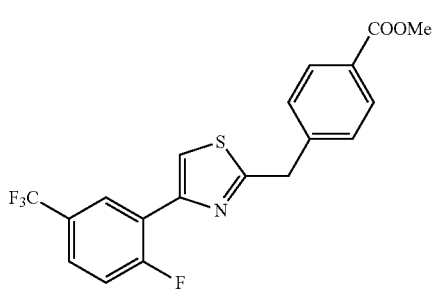 [SMILES: COC(=O)c1ccc(Cc2nc(-c3cc(C(F)(F)F)ccc3F)cs2)cc1]

By a method similar to that in Example 190d, the crude title compound (135 mg, 36%) was obtained as a colorless solid from the compound (360 mg, 0.92 mmol) obtained in Example 192b, 4-methoxycarbonylphenylboronic acid (200 mg, 1.1 mmol), 2M aqueous sodium carbonate solution (0.56 mL, 1.1 mmol), and [1,1'-bis(diphenylphosphino)ferrocene]dichloropalladium(II) dichloromethane complex (77 mg, 0.094 mmol).

LCMS (ESI$^+$) M+H$^+$: 396.

Example 192

4-({4-[2-fluoro-5-(trifluoromethyl)phenyl]-1,3-thiazol-2-yl}methyl)benzoic acid

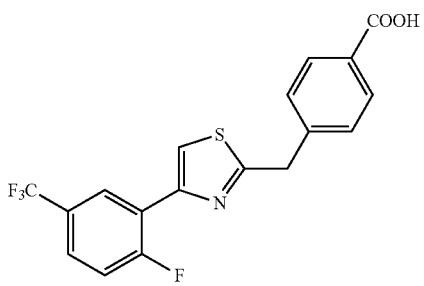 [SMILES: O=C(O)c1ccc(Cc2nc(-c3cc(C(F)(F)F)ccc3F)cs2)cc1]

By a method similar to that in Example 189, the title compound (13 mg, 10%) was obtained as colorless crystals from the compound (135 mg, 0.34 mmol) obtained in Example 192c.

$^1$H NMR (300 MHz, DMSO-d$_6$) δ ppm 4.54 (2H, s), 7.51 (2H, m, J=8.0 Hz), 7.56-7.66 (1H, m), 7.75-7.86 (1H, m), 7.93 (2H, m, J=8.0 Hz), 8.05 (1H, d, J=2.7 Hz), 8.43 (1H, dd, J=7.0, 2.1 Hz), 12.93 (1H, br. s.)

LCMS (ESI$^+$) M+H$^+$: 382.

Example 193

4-({5-cyclopropyl-2-[3-(trifluoromethyl)phenyl]-1,3-thiazol-4-yl}methyl)benzoic acid Example 193a 5-cyclopropyl-4-(iodomethyl)-2-[3-(trifluoromethyl)phenyl]-1,3-thiazole

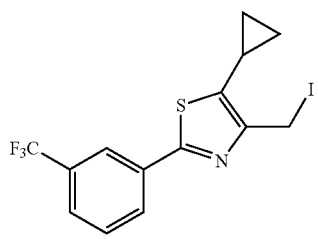 [SMILES: FC(F)(F)c1cccc(-c2nc(CI)c(C3CC3)s2)c1]

By a method similar to that in Example 190c, the title compound (1.1 g, 79% in 2 steps) was obtained as a pale-yellow solid from the compound (1.0 g, 3.3 mmol) obtained in Example 72d.

$^1$H NMR (300 MHz, CHLOROFORM-d) δppm 0.65-0.91 (2H, m), 1.08-1.33 (2H, m), 1.85-2.12 (1H, m), 4.64 (2H, s), 7.53 (1H, t, J=7.8 Hz), 7.64 (1H, d, J=8.0 Hz), 8.02 (1H, d, J=8.0 Hz), 8.11 (1H, s)

LCMS (ESI$^+$) M+H$^+$: 410.

Example 193b methyl 4-({5-cyclopropyl-2-[3-(trifluoromethyl)phenyl]-1,3-thiazol-4-yl}methyl)benzoate

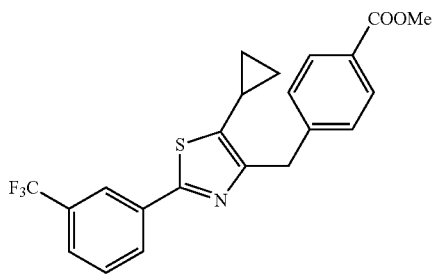 [SMILES: COC(=O)c1ccc(Cc2nc(-c3cccc(C(F)(F)F)c3)sc2C2CC2)cc1]

By a method similar to that in Example 190d, the crude title compound (650 mg) was obtained as a pale-yellow solid from the compound (1.1 g, 2.7 mmol) obtained in Example 193a, 4-methoxycarbonylphenylboronic acid (580 mg, 3.2 mmol), cesium carbonate (4.3 g, 13 mmol), and [1,1'-bis(diphenylphosphino)ferrocene]dichloropalladium(II) dichloromethane complex (430 mg, 0.53 mmol).

$^1$H NMR (300 MHz, CHLOROFORM-d) δ ppm 0.65-0.76 (2H, m), 1.02-1.13 (2H, m), 1.88-2.01 (1H, m), 3.89 (3H, s), 4.27 (2H, s), 7.30-8.21 (8H, m)

LCMS (ESI$^+$) M+H$^+$: 418.

Example 193

4-({5-cyclopropyl-2-[3-(trifluoromethyl)phenyl]-1,3-thiazol-4-yl}methyl)benzoic acid

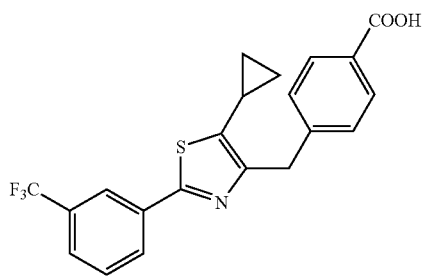 [SMILES: O=C(O)c1ccc(Cc2nc(-c3cccc(C(F)(F)F)c3)sc2C2CC2)cc1]

By a method similar to that in Example 189, the title compound (310 mg, 29% in 2 steps) was obtained as colorless crystals from the compound (650 mg) obtained in Example 193b.

$^1$H NMR (300 MHz, DMSO-d$_6$) δ ppm 0.58-0.80 (2H, m), 1.01-1.26 (2H, m), 2.13-2.35 (1H, m), 4.27 (2H, s), 7.41 (2H, m, J=8.3 Hz), 7.70 (1H, t, J=7.8 Hz), 7.80 (1H, d, J=8.1 Hz), 7.88 (2H, m, J=8.3 Hz), 8.02-8.16 (2H, m), 12.84 (1H, br. s.)

LCMS (ESI$^+$) M+H$^+$: 404.

Example 194

4-({2-[3-(trifluoromethyl)phenyl]-1,3-thiazol-4-yl}methyl)benzoic acid

Example 194a 4-(iodomethyl)-2-[3-(trifluoromethyl)phenyl]-1,3-thiazole

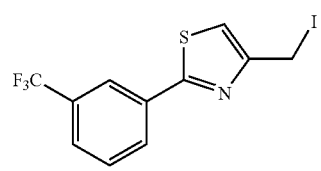 [SMILES: FC(F)(F)c1cccc(-c2nc(CI)cs2)c1]

To a solution (10 mL) of the compound (1.0 g, 3.6 mmol) obtained in Example 21a in acetone was added sodium iodide (1.6 g, 11 mmol), and the mixture was stirred at room temperature overnight. Water was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=70/30) to give the title compound (370 mg, 28%) as a colorless solid.

$^1$H NMR (300 MHz, CHLOROFORM-d) δ ppm 4.58 (2H, s), 7.31 (1H, s), 7.57 (1H, t, J=7.7 Hz), 7.69 (1H, d, J=7.5 Hz), 8.12 (1H, d, J=7.9 Hz), 8.21 (1H, s)

Example 194b

Methyl 4-({2-[3-(trifluoromethyl)phenyl]-1,3-thiazol-4-yl}methyl)benzoate

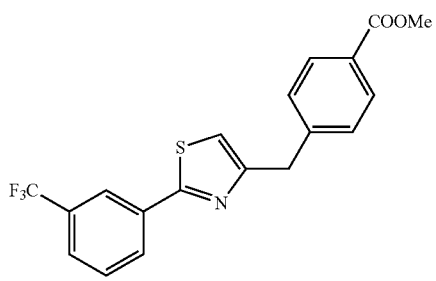 [SMILES: COC(=O)c1ccc(Cc2csc(-c3cccc(C(F)(F)F)c3)n2)cc1]

By a method similar to that in Example 190d, the crude title compound (210 mg) was obtained as a pale-yellow solid from the compound (370 mg, 2.7 mmol) obtained in Example 194a, 4-methoxycarbonylphenylboronic acid (220 mg, 1.2 mmol), 2M aqueous sodium carbonate solution (1.0 ml, 2.0 mmol), and [1,1'-bis(diphenylphosphino)ferrocene]dichloropalladium(II) dichloromethane complex (160 mg, 0.20 mmol).

LCMS (ESI$^+$) M+H$^+$: 378.

Example 194

4-({2-[3-(trifluoromethyl)phenyl]-1,3-thiazol-4-yl}methyl)benzoic acid

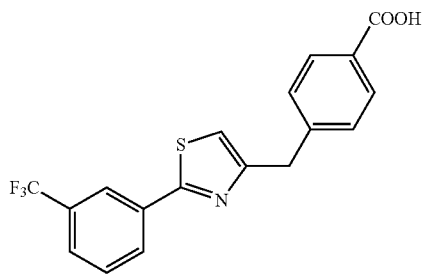 [SMILES: O=C(O)c1ccc(Cc2csc(-c3cccc(C(F)(F)F)c3)n2)cc1]

By a method similar to that in Example 189, the title compound (97 mg, 48% in 2 steps) was obtained as colorless crystals from the compound (210 mg) obtained in Example 194b.

$^1$H NMR (300 MHz, DMSO-d$_6$) δ ppm 4.24 (2H, s), 7.44 (2H, d, J=8.3 Hz), 7.52 (1H, s), 7.66-7.80 (1H, m), 7.81-7.96 (3 H, m), 8.13-8.26 (2H, m), 12.75 (1H, br. s.)

LCMS (ESI$^+$) M+H$^+$: 364.

Example 195

4-({5-methyl-2-[3-(trifluoromethyl)phenyl]-1,3-thiazol-4-yl}methyl)benzoic acid

Example 195a 4-(iodomethyl)-5-methyl-2-[3-(trifluoromethyl)phenyl]-1,3-thiazole

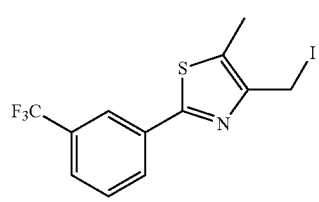 [SMILES: Cc1sc(-c2cccc(C(F)(F)F)c2)nc1CI]

By a method similar to that in Example 190c, the title compound (1.4 g, 67% in 2 steps) was obtained as a brown solid from the compound (1.5 g, 5.4 mmol) obtained in Example 71b.

$^1$H NMR (300 MHz, CHLOROFORM-d) δppm 2.41 (3H, s), 4.53 (2H, s), 7.54 (1H, t, J=7.7 Hz), 7.65 (1H, d, J=7.9 Hz), 8.04 (1H, d, J=7.5 Hz), 8.14 (1H, s)

LCMS (ESI$^+$) M+H$^+$: 384.

Example 195b

Methyl 4-({5-methyl-2-[3-(trifluoromethyl)phenyl]-1,3-thiazol-4-yl}methyl)benzoate

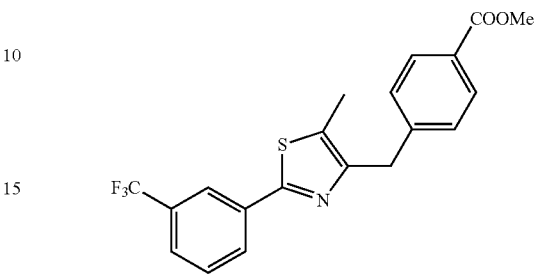

By a method similar to that in Example 190d, the crude title compound (540 mg) was obtained as a pale-yellow solid from the compound (900 mg, 2.4 mmol) obtained in Example 195a, 4-methoxycarbonylphenylboronic acid (510 mg, 2.8 mmol), 2M aqueous sodium carbonate solution (2.4 mL, 4.8 mmol), and [1,1'-bis(diphenylphosphino)ferrocene]dichloropalladium(II) dichloromethane complex (380 mg, 0.47 mmol).

$^1$H NMR (300 MHz, CHLOROFORM-d) δppm 2.43 (3H, s), 3.89 (3H, s), 4.17 (2H, s), 7.29-8.28 (8H, m)

LCMS (ESI$^+$) M+H$^+$: 392.

Example 195

4-({5-methyl-2-[3-(trifluoromethyl)phenyl]-1,3-thiazol-4-yl}methyl)benzoic acid

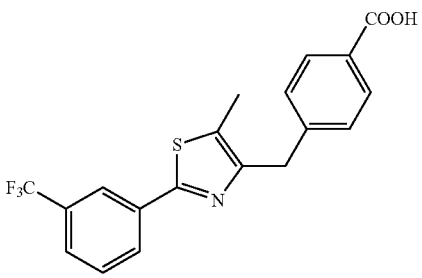 [SMILES: Cc1sc(-c2cccc(C(F)(F)F)c2)nc1Cc1ccc(C(=O)O)cc1]

By a method similar to that in Example 189, the title compound (150 mg, 30% in 2 steps) was obtained as colorless crystals from the compound (540 mg) obtained in Example 195b.

$^1$H NMR (300 MHz, DMSO-d$_6$) δ ppm 2.51 (3H, s), 4.18 (2H, s), 7.38 (2H, d, J=8.3 Hz), 7.72 (1H, t, J=7.8 Hz), 7.81 (1H, d, J=7.6 Hz), 7.87 (2H, d, J=8.3 Hz), 8.04-8.17 (2H, m), 12.71 (1H, br. s.)

LCMS (ESI$^+$) M+H$^+$: 378.

Example 196

4-({4-[3-bromo-5-(trifluoromethyl)phenyl]-1,3-thiazol-2-yl}methyl)benzoic acid

Example 196a

Methyl 4-({4-[3-bromo-5-(trifluoromethyl)phenyl]-1,3-thiazol-2-yl}methyl)benzoate

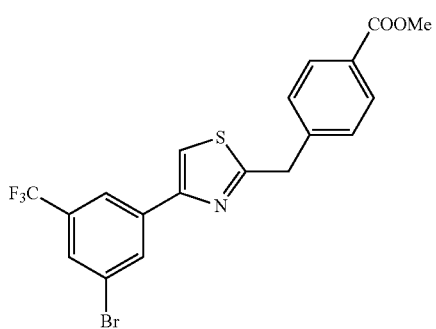 [SMILES: COC(=O)c1ccc(Cc2nc(-c3cc(Br)cc(C(F)(F)F)c3)cs2)cc1]

By a method similar to that in Example 36a, the title compound (1.5 g, 66%) was obtained as a yellow solid from the compound (1.7 g, 5.0 mmol) obtained in Example 68a and the compound (1.0 g, 5.0 mmol) obtained in Example 178a.

$^1$H NMR (300 MHz, CHLOROFORM-d) δppm 3.92 (3H, s), 4.44 (2H, s), 7.43 (2H, d, J=8.7 Hz), 7.48 (1H, s), 7.71 (1H, s), 7.98-8.10 (3H, m), 8.23 (1H, s)

LCMS (ESI$^+$) M+H$^+$: 456.

Example 196

4-({4-[3-bromo-5-(trifluoromethyl)phenyl]-1,3-thiazol-2-yl}methyl)benzoic acid

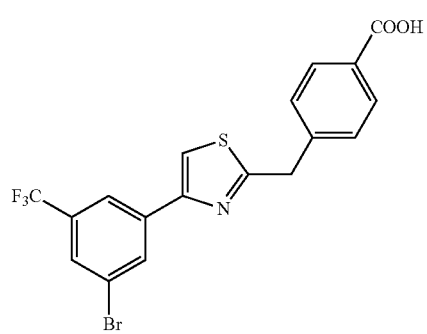 [SMILES: O=C(O)c1ccc(Cc2nc(-c3cc(Br)cc(C(F)(F)F)c3)cs2)cc1]

By a method similar to that in Example 189, the title compound (280 mg, 72%) was obtained as colorless crystals from the compound (400 mg, 0.88 mmol) obtained in Example 196a.

$^1$H NMR (300 MHz, DMSO-d$_6$) δ ppm 4.52 (2H, s), 7.51 (2H, d, J=8.3 Hz), 7.84-7.98 (3H, m), 8.29 (1H, s), 8.41 (1H, s), 8.46 (1H, s), 12.92 (1H, br. s.)

LCMS (ESI$^+$) M−H$^+$: 440.

Example 197

4-({4-[3-cyclopropyl-5-(trifluoromethyl)phenyl]-1,3-thiazol-2-yl}methyl)benzoic acid

Example 197a methyl 4-({4-[3-cyclopropyl-5-(trifluoromethyl)phenyl]-1,3-thiazol-2-yl}methyl)benzoate

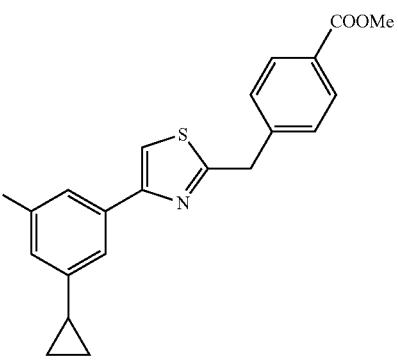

By a method similar to that in Example 84a, the title compound (390 mg, 85%) was obtained as a pale-orange solid from the compound (500 mg, 1.1 mmol) obtained in Example 196a, potassium cyclopropyl trifluoroborate (180 mg, 1.2 mmol), cesium carbonate (1.1 g, 3.3 mmol), di(1-adamantyl)-n-butylphosphine (24 mg, 0.070 mmol) and palladium acetate (II) (10 mg, 0.040 mmol).

$^1$H NMR (300 MHz, CHLOROFORM-d) δppm 0.73-0.88 (2H, m), 0.98-1.11 (2H, m), 1.92-2.12 (1H, m), 3.92 (3H, s), 4.44 (2 H, s), 7.22-7.28 (2H, m), 7.37-7.49 (2H, m), 7.79 (1H, s), 7.90 (1H, s), 8.03 (2H, d, J=8.3 Hz)

LCMS (ESI$^+$) M+H$^+$: 418.

Example 197

4-({4-[3-cyclopropyl-5-(trifluoromethyl)phenyl]-1,3-thiazol-2-yl}methyl)benzoic acid

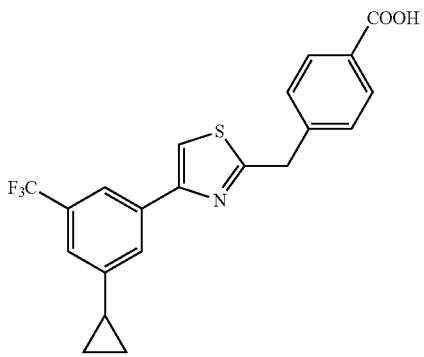 [SMILES: O=C(O)c1ccc(Cc2nc(-c3cc(C4CC4)cc(C(F)(F)F)c3)cs2)cc1]

By a method similar to that in Example 189, the title compound (250 mg, 67%) was obtained as colorless crystals from the compound (390 mg, 0.92 mmol) obtained in Example 197a.

$^1$H NMR (300 MHz, DMSO-d$_6$) δ ppm 0.74-0.91 (2H, m), 0.92-1.14 (2H, m), 2.03-2.23 (1H, m), 4.51 (2H, s), 7.39 (1H, s), 7.51 (2H, d, J=8.3 Hz), 7.86-7.98 (3H, m), 8.03 (1H, s), 8.26 (1H, s), 12.95 (1H, br. s.)

LCMS (ESI$^+$) M+H$^+$: 404.

Example 198, 199

4-(hydroxy{4-[3-(trifluoromethyl)phenyl]-1,3-thiazol-2-yl}methyl)benzoic acid

Example 198a 2-bromo-4-[3-(trifluoromethyl)phenyl]-1,3-thiazole

A solution of 2-bromo-1-[3-(trifluoromethyl)phenyl]ethanone (20 g) in ethanol (100 mL) was heated to 60-70° C., and aqueous solution (10 mL) of potassium thiocyanate (8 g) was added dropwise. The reaction mixture was heated at 80° C. for 10 min, and the mixture was stirred at room temperature for 4 hr and diluted with water. The precipitate was collected by filtration, dissolved in ethyl acetate and dried over anhydrous sodium sulfate. The solvent was evaporated to give 2-oxo-2-[3-(trifluoromethyl)phenyl]ethyl thiocyanate (14 g) as a solid. This solid (10 g) was dissolved in acetic acid (50 mL), and 48% hydrogen bromide-acetic acid solution (10 mL) was added. The reaction mixture was heated at 70-80° C. for 3 hr, and the solvent was evaporated under reduced pressure. The residue was dissolved in ethyl acetate and water, sodium bicarbonate was added, and the mixture was adjusted to pH 7. The ethyl acetate layer was separated, washed with saturated brine and dried over sodium sulfate, and the solvent was evaporated. The residue was purified by column chromatography (carrier: silica gel, eluent: hexane-ethyl acetate) to give the title compound (4.2 g) as a colorless solid.

$^1$H NMR (CDCl$_3$, Varian 400 MHz) δ ppm 7.51 (1H, s), 7.55 (1H, t, J=7.8 Hz), 7.61 (1H, d, J=8.4 Hz), 8.04 (1H, dd, J=7.6, 4.0 Hz), 8.13 (1H, s)

Example 198b methyl 1-(hydroxy{4-[3-(trifluoromethyl)phenyl]-1,3-thiazol-2-yl}methyl)-1H-pyrazole-4-carboxylate

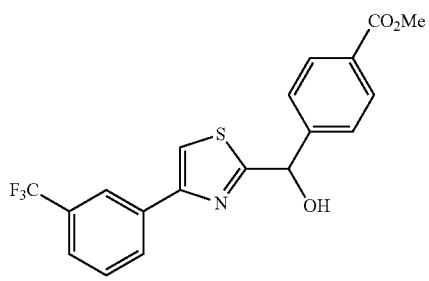 [SMILES: COC(=O)c1ccc(C(O)c2nc(-c3cccc(C(F)(F)F)c3)cs2)cc1]

A solution of the compound (0.80 g) obtained in Example 198a in tetrahydrofuran was cooled to −78° C., and a solution of isopropylmagnesium chloride in 2M tetrahydrofuran (1.5 mL) was added dropwise. After stirring at the same temperature for 30 min, a solution of methyl 4-formylbenzoate (0.51 g) in tetrahydrofuran (1 mL) was added, and the mixture was stirred at −78° C. for 3 hr. The mixture was warmed to room temperature, and water and ethyl acetate were added. The ethyl acetate layer was separated, washed successively with aqueous ammonium chloride solution and saturated brine, and dried over sodium sulfate. The solvent was evaporated and the residue was purified by column chromatography (carrier: silica gel, eluent: hexane-ethyl acetate) to give the title compound (0.65 g).

$^1$H NMR (CDCl$_3$, Varian 400 MHz) δ ppm 3.92 (3H, s), 6.19 (1H, s), 7.51-7.64 (5H, m), 8.03-8.11 (3H, m), 8.14 (1H, s)

Example 198

4-(hydroxy{4-[3-(trifluoromethyl)phenyl]-1,3-thiazol-2-yl}methyl)benzoic acid

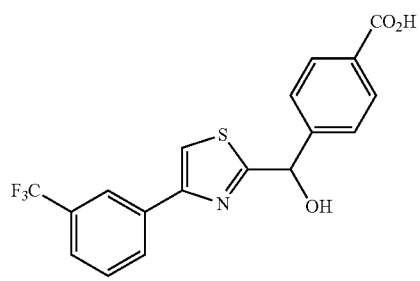 [SMILES: O=C(O)c1ccc(C(O)c2nc(-c3cccc(C(F)(F)F)c3)cs2)cc1]

A mixture of the compound (0.65 g) obtained in Example 198b, 2N aqueous sodium hydroxide solution (10 mL) and ethanol (10 mL) was stirred at room temperature for 4 hr. To the reaction mixture was added 1N hydrochloric acid, and the mixture was adjusted to pH 2-3 and extracted with ethyl acetate. The ethyl acetate layer was washed with saturated brine, dried over sodium sulfate, and concentrated under reduced pressure. The residue was purified by preparative liquid chromatography to give the title compound (0.21 g) as a colorless solid.

$^1$H NMR (DMSO-d$_6$, Bruker Avance 400 MHz) δ ppm 6.11 (1H, d, J=4.4 Hz), 7.07 (1H, d, J=4.4 Hz), 7.60-7.75 (4H, m), 7.93 (2H, d, J=8.0 Hz), 8.15-8.25 (2H, m), 8.30 (1H, s), 12.93 (1H, br. s.)

Example 199

4-({4-[3-(trifluoromethyl)phenyl]-1,3-thiazol-2-yl}carbonyl)benzoic acid

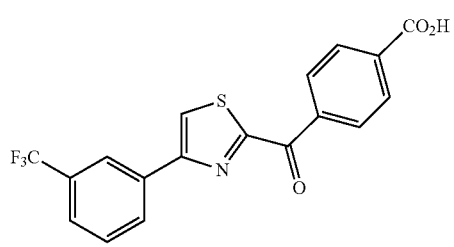 [SMILES: O=C(O)c1ccc(C(=O)c2nc(-c3cccc(C(F)(F)F)c3)cs2)cc1]

By the purification by preparative liquid chromatography in Example 198, the title compound (0.21 g) produced during hydrolysis in Example 198 was obtained.

$^1$H NMR (DMSO-$d_6$, Varian 400 MHz) δ ppm 7.70-7.80 (2H, m), 8.14 (2H, d, J=8.4 Hz), 8.35-8.45 (2H, m), 8.49 (2H, d, J=8.4 Hz), 8.94 (1H, s), 13.45 (1H, br. s.)

Example 200

4-{[4-(4-chlorophenyl)-1,3-thiazol-2-yl]methyl}benzoic acid

Example 200a methyl 4-{[4-(4-chlorophenyl)-1,3-thiazol-2-yl]methyl}benzoate

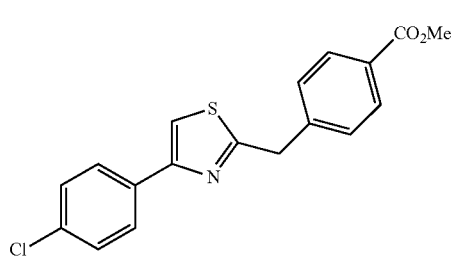 [SMILES: COC(=O)c1ccc(Cc2nc(-c3ccc(Cl)cc3)cs2)cc1]

By a method similar to that in Example 106a, the title compound was obtained from the compound obtained in Example 178a and 2-bromo-1-[4-chlorophenyl]ethanone.

$^1$H NMR (DMSO, Varian 400 MHz) δ ppm 3.82 (3H, s), 4.47 (2H, s), 7.46 (2H, d, J=8.4 Hz), 7.50 (2H, d, J=8.4 Hz), 7.89-7.95 (4H, m), 7.94 (1H, s)

Example 200

4-{[4-(4-chlorophenyl)-1,3-thiazol-2-yl]methyl}benzoic acid

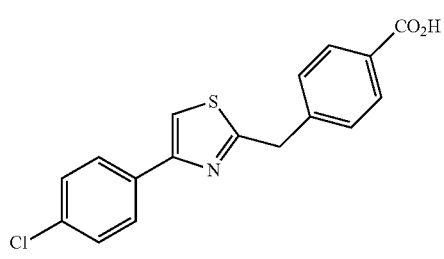 [SMILES: O=C(O)c1ccc(Cc2nc(-c3ccc(Cl)cc3)cs2)cc1]

By a method similar to that in Example 106, the title compound was obtained from the compound obtained in Example 200a.

$^1$H NMR (DMSO, Varian 400 MHz) δ ppm 4.46 (2H, s), 7.44-7.52 (4H, m), 7.88-7.97 (4H, m), 8.03 (1H, s)

Example 201

4-({5-[3-(trifluoromethyl)phenyl]-1,2,4-oxadiazol-3-yl}methyl)benzoic acid

Example 201a methyl 4-[2-amino-2-(hydroxyimino)ethyl]benzoate

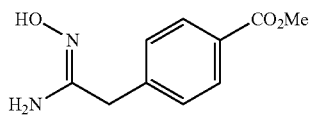

Methyl 4-(cyanomethyl)benzoate (2.0 g) was suspended in methanol (30 mL), and sodium hydrogen carbonate (0.96 g) and hydroxylamine hydrochloride (0.80 g) were added. The reaction mixture was heated under reflux for 12 hr, and the insoluble material was removed by filtration. The solvent was evaporated under reduced pressure from the obtained filtrate to give the title compound as a bister solid.

Example 201b

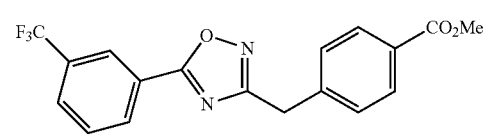 [SMILES: COC(=O)c1ccc(Cc2noc(-c3cccc(C(F)(F)F)c3)n2)cc1]

methyl 4-({5-[3-(trifluoromethyl)phenyl]-1,2,4-oxadiazol-3-yl}methyl)benzoate

By a reaction in the same manner as in Example 114b and using the compound (2.0 g) obtained in Example 201a, the title compound (1.29 g) was obtained as a solid.

$^1$H NMR (CDCl$_3$, Varian 400 MHz) δ ppm 3.88 (3H, s), 4.19 (2H, s), 7.43 (2H, d, J=8.4 Hz), 7.64 (1H, t, J=8.0 Hz), 7.81 (1H, dd, J=7.8, 0.6 Hz), 8.00 (2H, dd, J=6.6, 1.8 Hz), 8.26 (1H, d, J=8.0 Hz), 8.35 (1H, s)

Example 201

4-({5-[3-(trifluoromethyl)phenyl]-1,2,4-oxadiazol-3-yl}methyl)benzoic acid

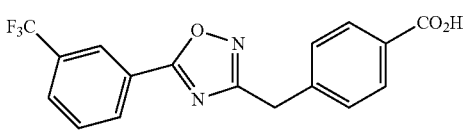 [SMILES: O=C(O)c1ccc(Cc2noc(-c3cccc(C(F)(F)F)c3)n2)cc1]

The compound (1.2 g) obtained in Example 201b was dissolved in tetrahydrofuran (32 mL) and water (8 mL), and lithium hydroxide (0.56 g) was added. The reaction mixture was heated at 40-60° C. for 48 hr, stirred and concentrated under reduced pressure. The residue was diluted with water and adjusted with 2.5N hydrochloric acid to pH 5-6. The resulting precipitate was collected by filtration and dried. The obtained solid was recrystallized from ethyl acetate to give the title compound (0.60 g) as a colorless solid.

$^1$H NMR (DMSO-$d_6$, Varian 400 MHz) δ ppm 4.26 (2H, s), 7.44 (2H, d, J=8.4 Hz), 7.83 (1H, t, J=7.8 Hz), 7.87 (2H, d, J=8.4 Hz), 8.04 (1H, d, J=8.0 Hz), 8.27 (1H, s), 8.34 (1H, d, J=8.0 Hz)

Example 202

4-{[4-(3-fluorophenyl)-1,3-thiazol-2-yl]methyl}benzoic acid

Example 202a methyl 4-{[4-(3-fluorophenyl)-1,3-thiazol-2-yl]methyl}benzoate

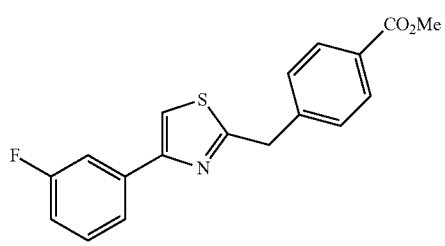 [SMILES: COC(=O)c1ccc(Cc2nc(-c3cccc(F)c3)cs2)cc1]

By a method similar to that in Example 106a, the title compound was obtained from the compound obtained in Example 178a and 2-bromo-1-(3-fluorophenyl)ethanone.

$^1$H NMR (DMSO, Varian 400 MHz) δ ppm 3.82 (3H, s), 4.48 (2H, s), 7.11-7.19 (1H, m), 7.42-7.48 (1H, m), 7.52 (2H, d, J=8.4 Hz), 7.72 (1H, dt, J=10.8, 2.0 Hz), 7.77 (1H, dd, J=8.0, 0.8 Hz), 7.93 (2H, d, J=8.4 Hz), 8.11 (1H, s)

Example 202

4-{[4-(3-fluorophenyl)-1,3-thiazol-2-yl]methyl}benzoic acid

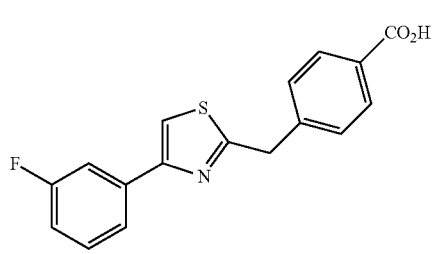 [SMILES: O=C(O)c1ccc(Cc2nc(-c3cccc(F)c3)cs2)cc1]

By a method similar to that in Example 106, the title compound was obtained from the compound obtained in Example 202a.

$^1$H NMR (DMSO, Varian 400 MHz) δ ppm 4.34 (2H, s), 7.13 (1H, t, J=7.6 Hz), 7.23 (2H, d, J=7.6 Hz), 7.44 (1H, q, J=7.8 Hz), 7.66-7.83 (4H, m), 8.05 (1H, s)

Example 203

4-{[4-(4-fluorophenyl)-1,3-thiazol-2-yl]methyl}benzoic acid

Example 203a methyl 4-{[4-(4-fluorophenyl)-1,3-thiazol-2-yl]methyl}benzoate

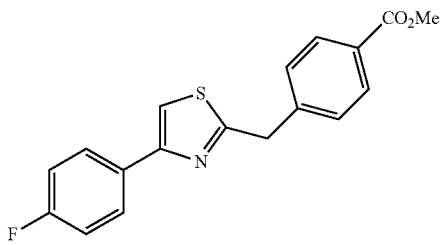 [SMILES: COC(=O)c1ccc(Cc2nc(-c3ccc(F)cc3)cs2)cc1]

By a method similar to that in Example 106a, the title compound was obtained from the compound obtained in Example 178a and 2-bromo-1-(4-fluorophenyl)ethanone.

$^1$H NMR (DMSO, Varian 400 MHz) δ ppm 3.82 (3H, s), 4.47 (2H, s), 7.24 (2H, d, J=8.8 Hz), 7.51 (2H, d, J=8.0 Hz), 7.87-8.04 (5H, m)

Example 203

4-{[4-(4-fluorophenyl)-1,3-thiazol-2-yl]methyl}benzoic acid

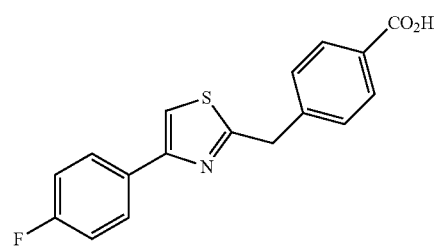 [SMILES: O=C(O)c1ccc(Cc2nc(-c3ccc(F)cc3)cs2)cc1]

By a method similar to that in Example 106, the title compound was obtained from the compound obtained in Example 203a.

$^1$H NMR (DMSO, Varian 400 MHz) δ ppm 4.34 (2H, s), 7.18-7.31 (4H, m), 7.80 (2H, d, J=8.0 Hz), 7.91-8.02 (3H, m)

Example 204

4-{[4-(2,4-dichlorophenyl)-1,3-thiazol-2-yl]methyl}benzoic acid

Example 204a methyl 4-{[4-(2,4-dichlorophenyl)-1,3-thiazol-2-yl]methyl}benzoate

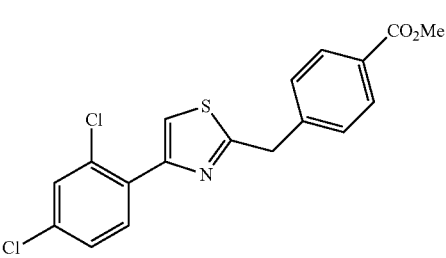 [SMILES: COC(=O)c1ccc(Cc2nc(-c3ccc(Cl)cc3Cl)cs2)cc1]

By a method similar to that in Example 106a, the title compound was obtained from the compound obtained in Example 178a and 2-bromo-1-(2,4-dichlorophenyl)ethanone.

¹H NMR (DMSO, Varian 400 MHz) δ ppm 3.80 (3H, s), 4.46 (2H, s), 7.41-7.61 (3H, m), 7.68 (1H, d, J=2.0 Hz), 7.83-7.97 (3H, m), 7.99 (1H, s)

Example 204

4-{[4-(2,4-dichlorophenyl)-1,3-thiazol-2-yl]methyl}benzoic acid

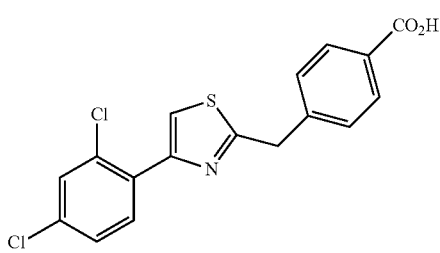 [SMILES: O=C(O)c1ccc(Cc2nc(-c3ccc(Cl)cc3Cl)cs2)cc1]

By a method similar to that in Example 106, the title compound was obtained from the compound obtained in Example 204a.

¹H NMR (DMSO, Bruker Avance 400 MHz) δ ppm 4.47 (2H, s), 7.47 (2H, d, J=8.0 Hz), 7.52 (1H, dd, J=8.6, 2.2 Hz), 7.73 (1H, d, J=2.0 Hz), 7.91 (3H, d, J=7.6 Hz), 8.02 (1H, s)

Example 205

4-[(4-phenyl-1,3-thiazol-2-yl)methyl]benzoic acid

Example 205a methyl 4-[(4-phenyl-1,3-thiazol-2-yl)methyl]benzoate

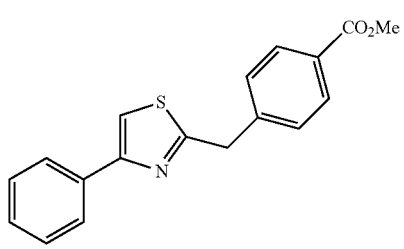 [SMILES: COC(=O)c1ccc(Cc2nc(-c3ccccc3)cs2)cc1]

By a method similar to that in Example 106a, the title compound was obtained from the compound obtained in Example 178a and 2-bromo-1-phenylethanone.

¹H NMR (DMSO, Varian 400 MHz) δ ppm 3.82 (3H, s), 4.48 (2H, s), 7.28-7.34 (1H, m), 7.41 (2H, t, J=7.6 Hz), 7.52 (2H, d, J=8.4 Hz), 7.88-7.96 (4H, m), 7.97 (1H, s)

Example 205

4-[(4-phenyl-1,3-thiazol-2-yl)methyl]benzoic acid

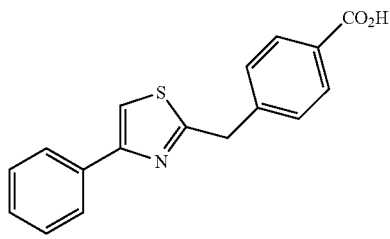 [SMILES: O=C(O)c1ccc(Cc2nc(-c3ccccc3)cs2)cc1]

By a method similar to that in Example 106, the title compound was obtained from the compound obtained in Example 205a.

¹H NMR (DMSO, Varian 400 MHz) δ ppm 4.33 (2H, s), 7.22 (2H, d, J=8.0 Hz), 7.29 (1H, t, J=7.2 Hz), 7.39 (2H, t, J=7.6 Hz), 7.79 (2H, d, J=8.0 Hz), 7.85-7.96 (3H, m)

Example 206

4-({3-[3-(trifluoromethyl)phenyl]-1,2,4-oxadiazol-5-yl}methyl)benzoic acid

Example 206a

[4-(methoxycarbonyl)phenyl]acetic acid

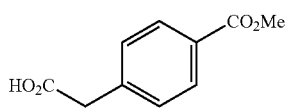 [SMILES: COC(=O)c1ccc(CC(=O)O)cc1]

Methyl 4-(2-methoxy-2-oxoethyl)benzoate (13.6 g) was dissolved in tetrahydrofuran (180 mL) and water (60 mL), and lithium hydroxide (2.75 g) was added. The reaction mixture was heated at room temperature for 24 hr, stirred and concentrated under reduced pressure. The residue was diluted with water, and washed with ethyl acetate. The aqueous layer was adjusted with 2.5N hydrochloric acid to pH 5-6, and the mixture was extracted with ethyl acetate. The ethyl acetate layer was dried over sodium sulfate and the solvent was evaporated under reduced pressure to give the title compound (13.0 g) as a colorless solid.

¹H NMR (DMSO-d₆, Varian 400 MHz) δ ppm 3.66 (2H, s), 3.83 (3H, s), 7.39 (2H, d, J=8.4 Hz), 7.89 (2H, d, J=8.0 Hz)

Example 206b methyl 4-(2-chloro-2-oxoethyl)benzoate

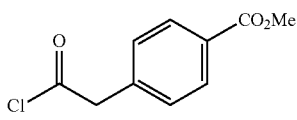 [SMILES: COC(=O)c1ccc(CC(=O)Cl)cc1]

A solution of the compound (3.0 g) obtained in Example 206a in dichloromethane (50 mL) was cooled in an ice bath, and oxalyl chloride (3.93 g) and N,N-dimethylformamide (2 drops) were added. The reaction mixture was stirred at room temperature overnight, and the solvent was evaporated under reduced pressure to give the title compound.

Example 206c methyl 4-({3-[3-(trifluoromethyl)phenyl]-1,2,4-oxadiazol-5-yl}methyl)benzoate

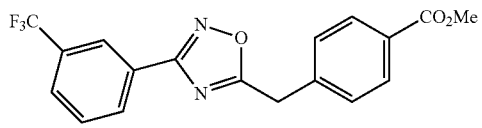 [SMILES: COC(=O)c1ccc(Cc2nc(-c3cccc(C(F)(F)F)c3)no2)cc1]

By a method similar to that in Example 115d and using the compound (3.3 g) obtained in Example 206b, the title compound (1.0 g) was obtained as a solid.
$^1$H NMR (CDCl$_3$, Varian 400 MHz) δ ppm 3.85 (3H, s), 4.30 (2H, s), 7.39 (2H, d, J=8.4 Hz), 7.55 (1H, t, J=7.8 Hz), 7.69 (1H, d, J=7.6 Hz), 7.98 (2H, d, J=8.4 Hz), 8.19 (1H, d, J=7.6 Hz), 8.28 (1H, s)

Example 206

4-({3-[3-(trifluoromethyl)phenyl]-1,2,4-oxadiazol-5-yl}methyl)benzoic acid

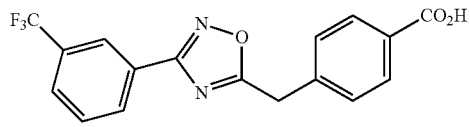 [SMILES: O=C(O)c1ccc(Cc2nc(-c3cccc(C(F)(F)F)c3)no2)cc1]

By a method similar to that in Example 114 and using the compound (0.80 g) obtained in Example 206c, the title compound (0.32 g) was obtained as a colorless solid.
$^1$H NMR (DMSO-d$_6$, Varian 400 MHz) δ ppm 4.54 (2H, s), 7.49 (2H, d, J=8.0 Hz), 7.78 (1H, t, J=7.8 Hz), 7.85-8.00 (3H, m), 8.18 (1H, s), 8.25 (1H, d, J=8.0 Hz)

Example 207

4-{[4-(2-methoxyphenyl)-1,3-thiazol-2-yl]methyl}benzoic acid

Example 207a methyl 4-{[4-(2-methoxyphenyl)-1,3-thiazol-2-yl]methyl}benzoate

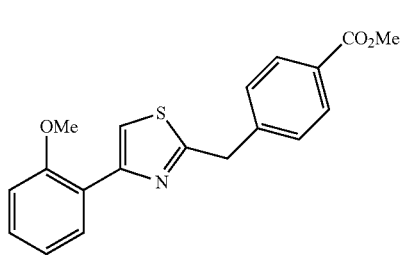 [SMILES: COC(=O)c1ccc(Cc2nc(-c3ccccc3OC)cs2)cc1]

By a method similar to that in Example 106a, the title compound was obtained from the compound obtained in Example 178a and 2-bromo-1-(2-methoxyphenyl)ethanone.

$^1$H NMR (DMSO, Varian 400 MHz) δ ppm 3.82 (3H, s), 3.88 (3H, s), 4.46 (2H, s), 7.12 (1H, td, J=7.2, 0.8 Hz), 7.11 (1H, d, J=8.0 Hz), 7.27-7.34 (1H, m), 7.51 (2H, d, J=8.4 Hz), 7.89-7.95 (3H, m), 8.10 (1H, dd, J=7.6, 2.0 Hz)

Example 207

4-{[4-(2-methoxyphenyl)-1,3-thiazol-2-yl]methyl}benzoic acid

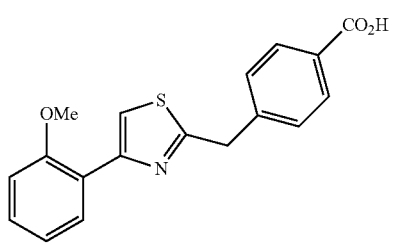 [SMILES: COc1ccccc1-c1csc(Cc2ccc(C(=O)O)cc2)n1]

By a method similar to that in Example 106, the title compound was obtained from the compound obtained in Example 207a.
$^1$H NMR (DMSO, Varian 400 MHz) δ ppm 3.89 (3H, s), 4.45 (2H, s), 7.02 (1H, dt, J=7.8, 0.8 Hz), 7.12 (1H, d, J=8.0 Hz), 7.27-7.33 (1H, m), 7.47 (2H, d, J=8.4 Hz), 7.90 (2H, d, J=8.0 Hz), 7.94 (1H, s), 8.13 (1H, dd, J=7.8, 1.8 Hz)

Example 208

4-{[4-(3-methoxyphenyl)-1,3-thiazol-2-yl]methyl}benzoic acid

Example 208a methyl 4-{[4-(3-methoxyphenyl)-1,3-thiazol-2-yl]methyl}benzoate

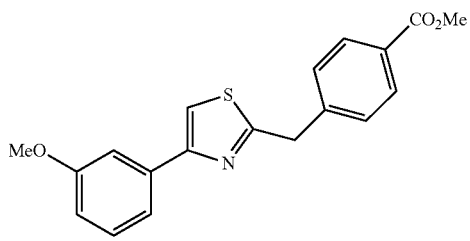 [SMILES: COC(=O)c1ccc(Cc2nc(-c3cccc(OC)c3)cs2)cc1]

By a method similar to that in Example 106a, the title compound was obtained from the compound obtained in Example 178a and 2-bromo-1-(3-methoxyphenyl)ethanone.

¹H NMR (DMSO, Varian 400 MHz) δ ppm 3.78 (3H, s), 3.82 (3H, s), 4.47 (2H, s), 6.87-6.92 (1H, m), 7.33 (1H, td, J=8.0, 1.0 Hz), 7.44-7.55 (4H, m), 7.93 (2H, d, J=8.4 Hz), 7.99 (1H, s)

Example 208

4-{[4-(3-methoxyphenyl)-1,3-thiazol-2-yl]methyl}benzoic acid

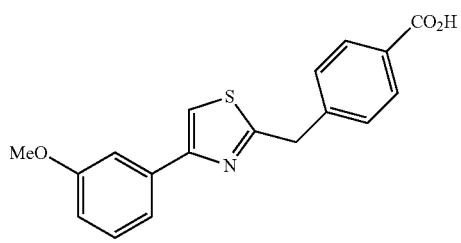 [SMILES: COc1cccc(-c2csc(Cc3ccc(C(=O)O)cc3)n2)c1]

By a method similar to that in Example 106, the title compound was obtained from the compound obtained in Example 208a.

¹H NMR (DMSO, Varian 400 MHz) δ ppm 3.79 (3H, s), 4.38 (2H, s), 6.87-6.92 (1H, m), 7.28-7.33 (3H, m), 7.45-7.53 (2H, m), 7.87 (2H, d, J=8.0 Hz), 7.98 (1H, s)

Example 209

4-{[4-(3-chlorophenyl)-1,3-thiazol-2-yl]methyl}benzoic acid

Example 209a methyl 4-{[4-(3-chlorophenyl)-1,3-thiazol-2-yl]methyl}benzoate

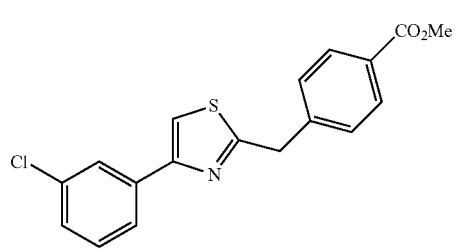 [SMILES: COC(=O)c1ccc(Cc2nc(-c3cccc(Cl)c3)cs2)cc1]

By a method similar to that in Example 106a, the title compound was obtained from the compound obtained in Example 178a and 2-bromo-1-[3-chlorophenyl]ethanone.

¹H NMR (DMSO, Varian 400 MHz) δ ppm 3.82 (3H, s), 4.49 (2H, s), 7.37 (1H, dt, J=8.0, 1.0 Hz), 7.46 (1H, d, J=7.6 Hz), 7.51 (2H, d, J=8.4 Hz), 7.89 (1H, d, J=7.6 Hz), 7.93 (2H, d, J=8.4 Hz), 7.97 (1H, t, J=1.8 Hz), 8.14 (1H, s)

Example 209

4-{[4-(3-chlorophenyl)-1,3-thiazol-2-yl]methyl}benzoic acid

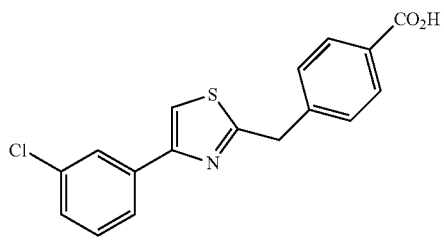 [SMILES: O=C(O)c1ccc(Cc2nc(-c3cccc(Cl)c3)cs2)cc1]

By a method similar to that in Example 106, the title compound was obtained from the compound obtained in Example 209a.

¹H NMR (DMSO, Varian 400 MHz) δ ppm 4.35 (2H, s), 7.23 (2H, d, J=8.0 Hz), 7.35-7.39 (1H, m), 7.45 (1H, t, J=7.8 Hz), 7.80 (2H, d, J=8.4 Hz), 7.90 (1H, td, J=7.6, 1.4 Hz), 7.98 (1H, t, J=1.8 Hz), 8.11 (1H, s)

Example 210

4-{[4-(4-methoxyphenyl)-1,3-thiazol-2-yl]methyl}benzoic acid

Example 210a methyl 4-{[4-(4-methoxyphenyl)-1,3-thiazol-2-yl]methyl}benzoate

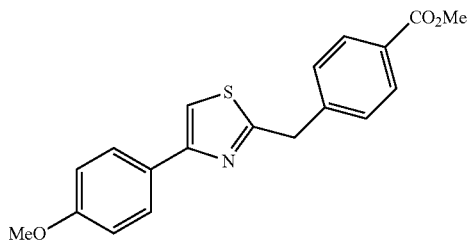 [SMILES: COC(=O)c1ccc(Cc2nc(-c3ccc(OC)cc3)cs2)cc1]

By a method similar to that in Example 106a, the title compound was obtained from the compound obtained in Example 178a and 2-bromo-1-(4-methoxyphenyl)ethanone.

¹H NMR (DMSO, Varian 400 MHz) δ ppm 3.74 (3H, s), 3.80 (3H, s), 4.44 (2H, s), 6.95 (2H, dd, J=6.8, 2.0 Hz), 7.49 (2H, d, J=8.4 Hz), 7.77 (1H, s), 7.83 (2H, dd, J=6.8, 2.0 Hz), 7.90 (2H, d, J=8.4 Hz)

Example 210

4-{[4-(4-methoxyphenyl)-1,3-thiazol-2-yl]methyl}benzoic acid

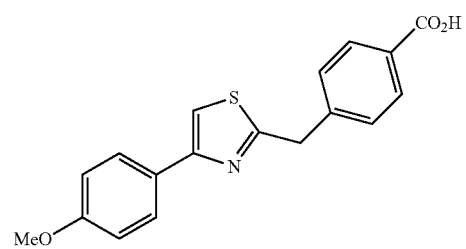 [SMILES: COc1ccc(-c2csc(Cc3ccc(C(=O)O)cc3)n2)cc1]

By a method similar to that in Example 106, the title compound was obtained from the compound obtained in Example 210a.

$^1$H NMR (DMSO, Bruker Avance 400 MHz) δ ppm 3.78 (3H, s), 4.33 (2H, s), 6.97 (2H, d, J=8.8 Hz), 7.23 (2H, d, J=8.0 Hz), 7.71 (1H, s), 7.80 (2H, d, J=8.0 Hz), 7.86 (2H, d, J=8.4 Hz)

Example 211

4-{[4-(2-fluorophenyl)-1,3-thiazol-2-yl]methyl}benzoic acid

Example 211a methyl 4-{[4-(2-fluorophenyl)-1,3-thiazol-2-yl]methyl}benzoate

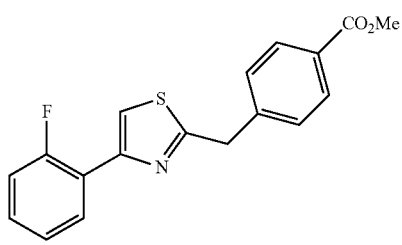 [SMILES: COC(=O)c1ccc(Cc2nc(-c3ccccc3F)cs2)cc1]

By a method similar to that in Example 106a, the title compound was obtained from the compound obtained in Example 178a and 2-bromo-1-(2-fluorophenyl)ethanone.

$^1$H NMR (DMSO, Varian 400 MHz) δ ppm 3.80 (3H, s), 4.47 (2H, s), 7.21-7.41 (3H, m), 7.50 (2H, d, J=8.4 Hz), 7.83 (1H, d, J=2.4 Hz), 7.91 (2H, d, J=8.0 Hz), 8.06 (1H, dt, J=7.8, 1.6 Hz)

Example 211

4-{[4-(2-fluorophenyl)-1,3-thiazol-2-yl]methyl}benzoic acid

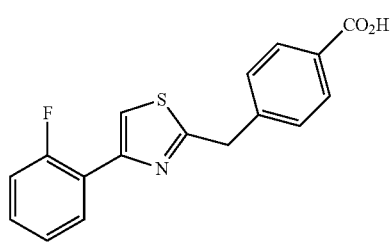 [SMILES: O=C(O)c1ccc(Cc2nc(-c3ccccc3F)cs2)cc1]

By a method similar to that in Example 106, the title compound was obtained from the compound obtained in Example 211a.

$^1$H NMR (DMSO, Bruker Avance 400 MHz) δ ppm 4.49 (2H, s), 7.27-7.43 (3H, m), 7.50 (2H, d, J=8.4 Hz), 7.86 (1H, d, J=2.4Hz), 7.92 (2H, d, J=8.4 Hz), 8.10 (1H, td, J=7.8, 2.0 Hz), 12.93 (1H, br. s.)

Example 212

4-({5-[3-(trifluoromethyl)phenyl]-1,3,4-thiadiazol-2-yl}methyl)benzoic acid

Example 212a methyl 4-({5-[3-(trifluoromethyl)phenyl]-1,3,4-thiadiazol-2-yl}methyl)benzoate

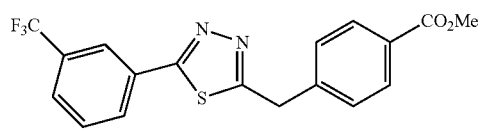 [SMILES: COC(=O)c1ccc(Cc2nnc(-c3cccc(C(F)(F)F)c3)s2)cc1]

By a method similar to that in Example 123c and using the compound (0.80 g) obtained in Example 221a, the title compound (0.63 g) was obtained as a colorless solid.

$^1$H NMR (CDCl$_3$, Varian 400 MHz) δ ppm 3.85 (3H, s), 4.47 (2H, s), 7.36 (2H, d, J=8.0 Hz), 7.53 (1H, t, J=7.8 Hz), 7.66 (1H, d, J=8.0 Hz), 7.97 (2H, dd, J=6.6, 1.8 Hz), 8.02 (1H, dd, J=7.6, 0.4 Hz), 8.09 (1H, s)

Example 212

4-({5-[3-(trifluoromethyl)phenyl]-1,3,4-thiadiazol-2-yl}methyl)benzoic acid

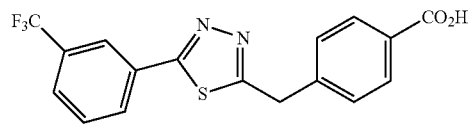

By a method similar to that in Example 114 and using the compound (0.70 g) obtained in Example 212a, the title compound (0.30 g) was obtained as a colorless solid.

$^1$H NMR (DMSO-d$_6$, Varian 400 MHz) δ ppm 4.61 (2H, s), 7.48 (2H, d, J=8.4 Hz), 7.74 (1H, t, J=8.2 Hz), 7.85-7.97 (3H, m), 8.16-8.24 (2H, m)

Example 213

4-{[4-(2,3-dichlorophenyl)-1,3-thiazol-2-yl]methyl}benzoic acid

Example 213a methyl 4-{[4-(2,3-dichlorophenyl)-1,3-thiazol-2-yl]methyl}benzoate

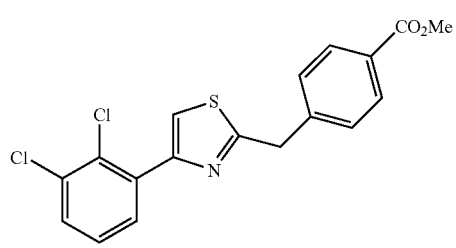 [SMILES: COC(=O)c1ccc(Cc2nc(-c3cccc(Cl)c3Cl)cs2)cc1]

By a method similar to that in Example 106a, the title compound was obtained from the compound obtained in Example 178a and 2-bromo-1-(2,3-dichlorophenyl)ethanone.

$^1$H NMR (DMSO, Varian 400 MHz) δ ppm 3.80 (3H, s), 4.47 (2H, s), 7.41 (1H, t, J=7.8 Hz), 7.50 (2H, d, J=8.4 Hz), 7.63 (1H, dd, J=8.0, 1.6 Hz), 7.73 (1H, dd, J=7.6, 1.6 Hz), 7.91 (2H, d, J=8.4 Hz), 7.97 (1H, s)

Example 213

4-{[4-(2,3-dichlorophenyl)-1,3-thiazol-2-yl]methyl}benzoic acid

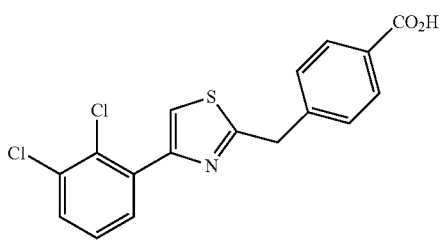 [SMILES: O=C(O)c1ccc(Cc2nc(-c3cccc(Cl)c3Cl)cs2)cc1]

By a method similar to that in Example 106, the title compound was obtained from the compound obtained in Example 213a.

$^1$H NMR (DMSO, Varian 400 MHz) δ ppm 4.41 (2H, s), 7.26-7.49 (3H, m), 7.65 (1H, d, J=7.2 Hz), 7.76 (1H, d, J=7.6 Hz), 7.90 (2H, d, J=7.2 Hz), 7.97 (1H, s)

Example 214

4-{[4-(2,5-dichlorophenyl)-1,3-thiazol-2-yl]methyl}benzoic acid

Example 214a methyl 4-{[4-(2,5-dichlorophenyl)-1,3-thiazol-2-yl]methyl}benzoate

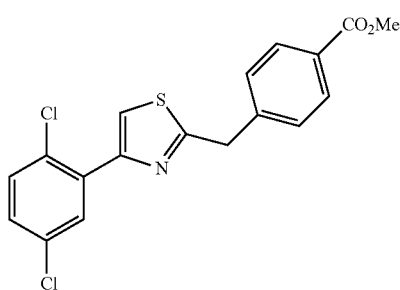 [SMILES: COC(=O)c1ccc(Cc2nc(-c3cc(Cl)ccc3Cl)cs2)cc1]

By a method similar to that in Example 106a, the title compound was obtained from the compound obtained in Example 178a and 2-bromo-1-(2,5-dichlorophenyl)ethanone.

$^1$H NMR (DMSO, Varian 400 MHz) δ ppm 3.81 (3H, s), 4.47 (2H, s), 7.43 (1H, dd, J=8.4, 2.8 Hz), 7.50 (2H, d, J=8.4 Hz), 7.56 (1H, d, J=8.8 Hz), 7.88-7.94 (3H, m), 8.07 (1H, s)

Example 214

4-{[4-(2,5-dichlorophenyl)-1,3-thiazol-2-yl]methyl}benzoic acid

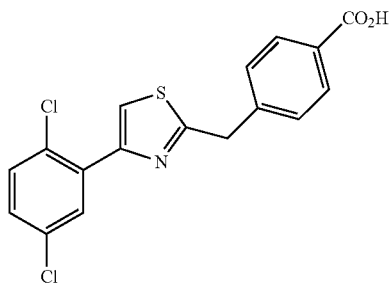 [SMILES: O=C(O)c1ccc(Cc2nc(-c3cc(Cl)ccc3Cl)cs2)cc1]

By a method similar to that in Example 106, the title compound was obtained from the compound obtained in Example 214a.

$^1$H NMR (DMSO, Varian 400 MHz) δ ppm 4.42 (2H, s), 7.38 (2H, d, J=8.4 Hz), 7.43 (1H, dd, J=8.6, 2.6 Hz), 7.56 (1H, d, J=8.4 Hz), 7.87 (2H, d, J=8.0 Hz), 7.91 (1H, d, J=2.8 Hz), 8.06 (1H, s)

Example 215

4-{[4-(3,5-dichlorophenyl)-1,3-thiazol-2-yl]methyl}benzoic acid

Example 215a methyl 4-{[4-(3,5-dichlorophenyl)-1,3-thiazol-2-yl]methyl}benzoate

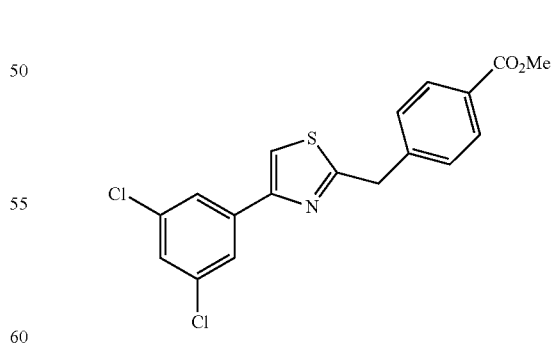

By a method similar to that in Example 106a, the title compound was obtained from the compound obtained in Example 178a and 2-bromo-1-(3,5-dichlorophenyl)ethanone.

$^1$H NMR (DMSO, Varian 400 MHz) δ ppm 3.82 (3H, s), 4.49 (2H, s), 7.51 (2H, d, J=8.0 Hz), 7.54 (1H, t, J=2.0 Hz), 7.93 (2H, d, J=8.4 Hz), 7.96 (2H, d, J=2.0 Hz), 8.28 (1H, s)

Example 215

4-{[4-(3,5-dichlorophenyl)-1,3-thiazol-2-yl]methyl}benzoic acid

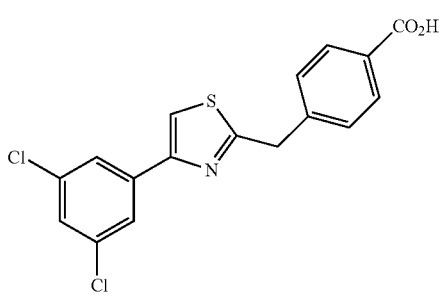 [SMILES: O=C(O)c1ccc(Cc2nc(-c3cc(Cl)cc(Cl)c3)cs2)cc1]

By a method similar to that in Example 106, the title compound was obtained from the compound obtained in Example 215a.

$^1$H NMR (DMSO, Varian 400 MHz) δ ppm 4.44 (2H, s), 7.38-7.58 (3H, m), 7.75-8.00 (4H, m), 8.25 (1H, s)

Example 216

4-({5-[3-(trifluoromethyl)phenyl]-1,3-oxazol-2-yl}methyl)benzoic acid

Example 216a 2-amino-1-[3-(trifluoromethyl)phenyl]ethanone hydrochloride

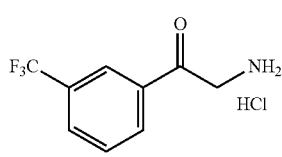 [SMILES: NCC(=O)c1cccc(C(F)(F)F)c1 ; Cl]

A mixture of 2-bromo-1-[3-(trifluoromethyl)phenyl]ethanone (22 g), NaN(CHO)$_2$ (9.5 g) and acetonitrile (50 mL) was stirred at room temperature for 3 hr and at 70° C. overnight, and the insoluble material was removed by filtration. The filtrate was concentrated to give an oil. The oil was dissolved in hydrogen chloride-ethanol, and the mixture was stirred at room temperature for 48 hr. The resulting precipitate was collected by filtration, and washed with ether to give the title compound (2.7 g) as a solid. The filtrate was concentrated, and the residue was dissolved in water. The aqueous layer was washed with ether, and the solvent was evaporated under reduced pressure to give the title compound (7.0 g).

$^1$H NMR (DMSO-d$_6$, Varian 400 MHz) δ ppm 4.59-4.73 (2H, m), 7.81 (1H, t, J=7.8 Hz), 8.06 (1H, d, J=8.0 Hz), 8.25 (1H, s), 8.28 (1H, d, J=8.0 Hz), 8.60 (3H, br. s.)

Example 216b methyl 4-[2-oxo-2-({2-oxo-2-[3-(trifluoromethyl)phenyl]ethyl}amino)ethyl]benzoate

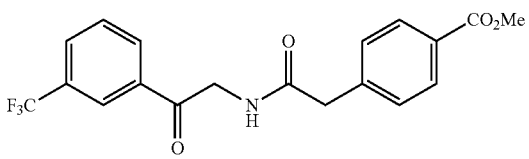 [SMILES: COC(=O)c1ccc(CC(=O)NCC(=O)c2cccc(C(F)(F)F)c2)cc1]

By a method similar to that in Example 124a and using the compound (3.2 g) obtained in Example 216a and the compound (3.0 g) obtained in Example 206b, the title compound (2.5 g) was obtained as a colorless solid.

$^1$H NMR (CDCl$_3$, Varian 400 MHz) δ ppm 3.72 (2H, s), 3.90 (3H, s), 4.75 (2H, d, J=4.4 Hz), 6.48 (1H, br. s.), 7.39 (2H, d, J=8.4 Hz), 7.63 (1H, t, J=7.8 Hz), 7.85 (1H, d, J=8.0 Hz), 8.03 (2H, d, J=8.4 Hz), 8.09 (1H, d, J=8.0 Hz), 8.18 (1H, s)

Example 216c methyl 4-({5-[3-(trifluoromethyl)phenyl]-1,3-oxazol-2-yl}methyl)benzoate

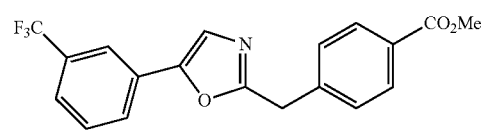 [SMILES: COC(=O)c1ccc(Cc2ncc(-c3cccc(C(F)(F)F)c3)o2)cc1]

By a method similar to that in Example 124b and using the compound (1.2 g) obtained in Example 216b, the title compound (0.99 g) was obtained as a solid.

$^1$H NMR (CDCl$_3$, Varian 400 MHz) δ ppm 3.91 (3H, s), 4.25 (2H, s), 7.35 (1H, s), 7.42 (2H, d, J=8.0 Hz), 7.49-7.60 (2H, m), 7.75 (1H, d, J=7.6 Hz), 7.82 (1H, d, J=0.4 Hz), 8.03 (2H, d, J=8.4 Hz)

Example 216

4-({5-[3-(trifluoromethyl)phenyl]-1,3-oxazol-2-yl}methyl)benzoic acid

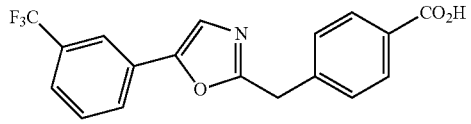 [SMILES: O=C(O)c1ccc(Cc2ncc(-c3cccc(C(F)(F)F)c3)o2)cc1]

By a method similar to that in Example 114 and using the compound (0.99 g) obtained in Example 216c, the title compound (0.18 g) was obtained as a colorless solid.

$^1$H NMR (DMSO-d$_6$, Varian 400 MHz) δ ppm 4.19 (2H, s), 7.22 (2H, d, J=7.2 Hz), 7.59-7.73 (2H, m), 7.74-7.89 (3H, m), 7.90-8.04 (2H, m)

Example 217

4-({5-[3-(trifluoromethyl)phenyl]-1,3-thiazol-2-yl}methyl)benzoic acid

Example 217a methyl 4-({5-[3-(trifluoromethyl)phenyl]-1,3-thiazol-2-yl}methyl)benzoate

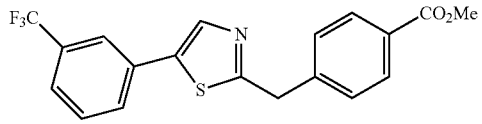

By a method similar to that in Example 123c and using the compound (1.0 g) obtained in Example 216b, the title compound (0.90 g) was obtained as a solid.

$^1$H NMR (CDCl$_3$, Varian 400 MHz) δ ppm 3.84 (3H, s), 4.33 (2H, s), 7.36 (2H, d, J=8.4 Hz), 7.42 (1H, t, J=8.2 Hz), 7.48 (1H, d, J=7.6 Hz), 7.59 (1H, d, J=7.6 Hz), 7.64 (1H, s), 7.84 (1H, s), 7.97 (2H, d, J=8.4 Hz)

Example 217

4-({5-[3-(trifluoromethyl)phenyl]-1,3-thiazol-2-yl}methyl)benzoic acid

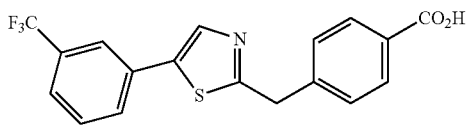

By a method similar to that in Example 114 and using the compound (0.90 g) obtained in Example 217a, the title compound (0.13 g) was obtained as a colorless solid.

$^1$H NMR (DMSO-d$_6$, Varian 400 MHz) δ ppm 4.42 (2H, s), 7.44 (2H, d, J=8.4 Hz), 7.58-7.70 (2H, m), 7.82-7.97 (4H, m), 8.27 (1H, s)

Example 218

4-({4-[2-(trifluoromethyl)phenyl]-1,3-thiazol-2-yl}methyl)benzoic acid

Example 218a methyl 4-({4-[2-(trifluoromethyl)phenyl]-1,3-thiazol-2-yl}methyl)benzoate

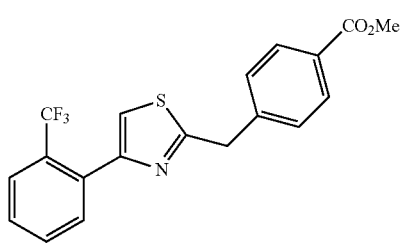

By a method similar to that in Example 106a, the title compound was obtained from the compound obtained in Example 178a and 2-bromo-1-[2-(trifluoromethyl)phenyl]ethanone.

$^1$H NMR (DMSO, Varian 400 MHz) δ ppm 3.82 (3H, s), 4.47 (2H, s), 7.49 (2H, d, J=8.0 Hz), 7.57-7.67 (3H, m), 7.71 (1H, t, J=7.6 Hz), 7.81 (1H, d, J=7.6 Hz), 7.92 (2H, d, J=8.0 Hz)

Example 218

4-({4-[2-(trifluoromethyl)phenyl]-1,3-thiazol-2-yl}methyl)benzoic acid

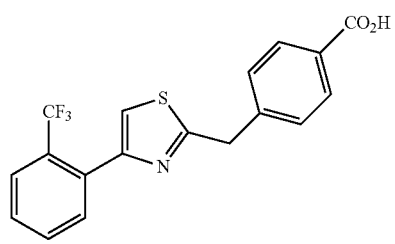

By a method similar to that in Example 106, the title compound was obtained from the compound obtained in Example 218a.

$^1$H NMR (DMSO, Bruker Avance 400 MHz) δ ppm 4.46 (2H, s), 7.48 (2H, d, J=8.0 Hz), 7.58-7.67 (3H, m), 7.68-7.76 (1H, m), 7.83 (1H, d, J=7.6 Hz), 7.91 (2H, d, J=8.0 Hz)

Example 219

4-({4-[4-(trifluoromethyl)phenyl]-1,3-thiazol-2-yl}methyl)benzoic acid

Example 219a methyl 4-({4-[4-(trifluoromethyl)phenyl]-1,3-thiazol-2-yl}methyl)benzoate

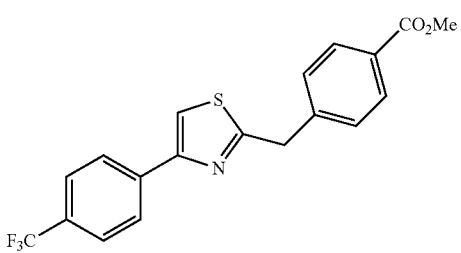 [SMILES: COC(=O)c1ccc(Cc2nc(-c3ccc(C(F)(F)F)cc3)cs2)cc1]

By a method similar to that in Example 106a, the title compound was obtained from the compound obtained in Example 178a and 2-bromo-1-[4-(trifluoromethyl)phenyl]ethanone.

$^1$H NMR (DMSO, Varian 400 MHz) δ ppm 3.94 (3H, s), 4.62 (2H, s), 7.64 (2H, d, J=8.4 Hz), 7.89 (2H, d, J=8.0 Hz), 8.05 (2H, d, J=8.0 Hz), 8.26 (2H, d, J=8.0 Hz), 8.33 (1H, s)

Example 219

4-({4-[4-(trifluoromethyl)phenyl]-1,3-thiazol-2-yl}methyl)benzoic acid

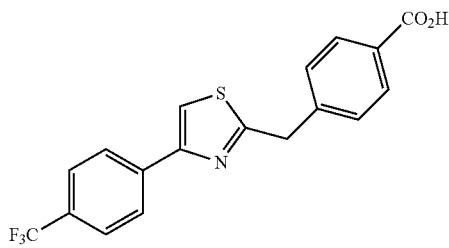 [SMILES: O=C(O)c1ccc(Cc2nc(-c3ccc(C(F)(F)F)cc3)cs2)cc1]

By a method similar to that in Example 106, the title compound was obtained from the compound obtained in Example 219a.

$^1$H NMR (DMSO, Varian 400 MHz) δ ppm 4.41 (2H, s), 7.34 (2H, d, J=8.0 Hz), 7.76 (2H, d, J=8.4 Hz), 7.86 (2H, d, J=8.0 Hz), 8.13 (2H, d, J=8.0 Hz), 8.18 (1H, s)

Example 220

4-{[4-(2-chlorophenyl)-1,3-thiazol-2-yl]methyl}benzoic acid

Example 220a methyl 4-{[4-(2-chlorophenyl)-1,3-thiazol-2-yl]methyl}benzoate

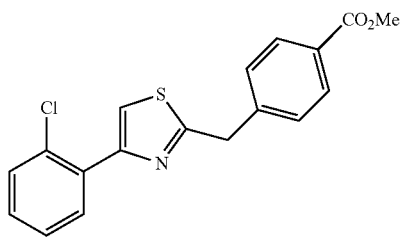 [SMILES: COC(=O)c1ccc(Cc2nc(-c3ccccc3Cl)cs2)cc1]

By a method similar to that in Example 106a, the title compound was obtained from the compound obtained in Example 178a and 2-bromo-1-[2-chlorophenyl]ethanone.

$^1$H NMR (DMSO, Varian 400 MHz) δ ppm 3.82 (3H, s), 4.48 (2H, s), 7.32-7.45 (2H, m), 7.47-7.58 (3H, m), 7.84 (1H, dd, J=7.6, 1.6 Hz), 7.88-8.00 (3H, m)

Example 220

4-{[4-(2-chlorophenyl)-1,3-thiazol-2-yl]methyl}benzoic acid

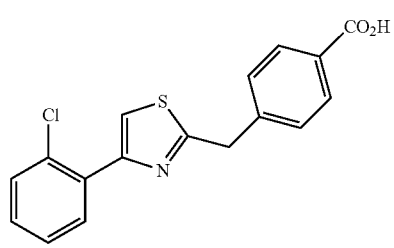

By a method similar to that in Example 106, the title compound was obtained from the compound obtained in Example 220a.

$^1$H NMR (DMSO, Varian 400 MHz) δ ppm 4.45 (2H, s), 7.31-7.42 (2H, m), 7.43-7.56 (3H, m), 7.84 (1H, dd, J=7.6, 2.0 Hz), 7.86-7.97 (3H, m)

Example 221

4-({5-[3-(trifluoromethyl)phenyl]-1,3,4-oxadiazol-2-yl}methyl)benzoic acid

Example 221a methyl 4-[2-oxo-2-(2-{[3-(trifluoromethyl)phenyl]carbonyl}hydrazino)ethyl]benzoate

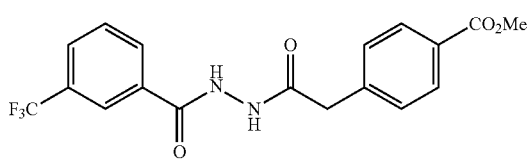 [SMILES: COC(=O)c1ccc(CC(=O)NNC(=O)c2cccc(C(F)(F)F)c2)cc1]

To a solution of 3-(trifluoromethyl)benzohydrazide hydrochloride (2.3 g) in N,N-dimethylformamide (20 mL) were added the compound (1.8 g) obtained in Example 206a, N-[3-(dimethylamino)propyl]-N'-ethylcarbodiimide (3.50 g), 1-hydroxybenzotriazole (1.25 g) and triethylamine (4.68 g). The reaction mixture was stirred at room temperature overnight, poured into water, and the mixture was extracted with ethyl acetate. The ethyl acetate layer was washed with saturated aqueous sodium hydrogen carbonate and then saturated brine, and dried over sodium sulfate. The solvent was evaporated under reduced pressure to give the title compound (1.0 g) as a colorless solid.

¹H NMR (DMSO-d₆, Varian 400 MHz) δ ppm 3.63 (2H, s), 3.82 (3H, s), 7.46 (2H, d, J=8.0 Hz), 7.72 (1H, t, J=8.0 Hz), 7.85-7.97 (3H, m), 8.13 (1H, d, J=8.0 Hz), 8.17 (1H, s), 10.34 (1H, br. s.), 10.67 (1H, br. s.)

Example 221b methyl 4-({5-[3-(trifluoromethyl)phenyl]-1,3,4-oxadiazol-2-yl}methyl)benzoate

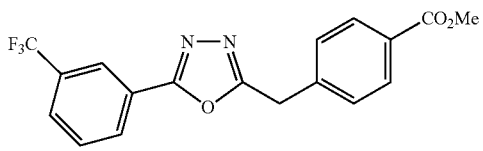 [SMILES: COC(=O)c1ccc(Cc2nnc(-c3cccc(C(F)(F)F)c3)o2)cc1]

By a method similar to that in Example 124b and using the compound (1.0 g) obtained in Example 221a, the title compound (0.50 g) was obtained as a solid.
¹H NMR (CDCl₃, Varian 400 MHz) δ ppm 3.85 (3H, s), 4.30 (2H, s), 7.37 (2H, d, J=8.4 Hz), 7.57 (1H, t, J=8.0 Hz), 7.71 (1H, d, J=8.0 Hz), 7.98 (2H, d, J=8.0 Hz), 8.14 (1H, d, J=8.0 Hz), 8.18 (1H, s)

Example 221

4-({5-[3-(trifluoromethyl)phenyl]-1,3,4-oxadiazol-2-yl}methyl)benzoic acid

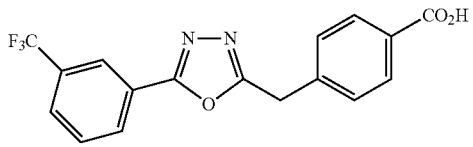 [SMILES: O=C(O)c1ccc(Cc2nnc(-c3cccc(C(F)(F)F)c3)o2)cc1]

By a method similar to that in Example 114 and using the compound (0.42 g) obtained in Example 221b, the title compound (0.34 g) was obtained as a colorless solid.
¹H NMR (DMSO-d₆, Varian 400 MHz) δ ppm 4.46 (2H, s), 7.49 (2H, d, J=8.0 Hz), 7.81 (1H, t, J=8.0 Hz), 7.91 (2H, d, J=8.0 Hz), 7.97 (1H, d, J=8.4 Hz), 8.17 (1H, s), 8.23 (1H, d, J=7.6 Hz)

Example 222

4-({5-[3-(trifluoromethyl)phenyl]furan-2-yl}methyl)benzoic acid

Example 222a

5-[3-(trifluoromethyl)phenyl]furan-2-carbaldehyde

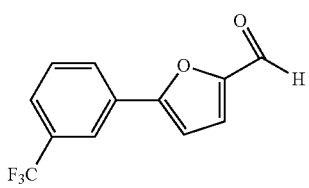 [SMILES: O=Cc1ccc(-c2cccc(C(F)(F)F)c2)o1]

A solution of the compound (0.45 g) obtained in Example 130b in dichloromethane (4 mL) was cooled in an ice bath, and Dess-martin reagent (0.94 g) was added. After stirring at room temperature for 1 hr, water was added to the reaction mixture, and the mixture was extracted with dichloromethane. The organic layer was washed with saturated aqueous sodium thiosulfate solution, dried over magnesium sulfate, and concentrated under reduced pressure to give a crude title compound.

Example 222b ethyl 4-(hydroxy{5-[3-(trifluoromethyl)phenyl]furan-2-yl}methyl)benzoate

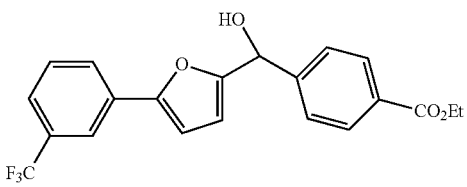 [SMILES: CCOC(=O)c1ccc(C(O)c2ccc(-c3cccc(C(F)(F)F)c3)o2)cc1]

Ethyl 4-iodobenzoate (0.55 g) was dissolved in tetrahydrofuran (5 mL), and the mixture was cooled to −40° C. Isopropylmagnesium chloride (2M tetrahydrofuran solution, 1.0 mL) was added dropwise, and the mixture was stirred at the same temperature for 30 min to prepare Grignard reagent. A solution of the compound (0.40 g) obtained in Example 222a in tetrahydrofuran (5 mL) was cooled to −40° C., and the prepared Grignard reagent solution was added. After stirring at −40° C. for 30 min, saturated aqueous ammonium chloride solution was added to the reaction mixture, and the mixture was extracted with ethyl acetate. The organic layer was washed with saturated brine, dried over magnesium sulfate, and the solvent was evaporated under reduced pressure. The residue was purified by column chromatography (carrier: silica gel, eluent: hexane-ethyl acetate) to give the title compound (0.26 g) as an oil.
¹H NMR (CDCl₃, Varian 400 MHz) δ ppm 1.40 (3H, t, J=7.2 Hz), 2.59 (1H, d, J=4.8 Hz), 4.38 (2H, q, J=7.2 Hz), 5.97 (1H, d, J=4.8 Hz), 6.20 (1H, d, J=3.2 Hz), 6.67 (1H, d, J=3.2 Hz), 7.49 (2H, m), 7.57 (2H, d, J=7.2 Hz), 7.78 (1H, m), 7.86 (1H, s), 8.08 (2H, d, J=7.2 Hz)

Example 222c ethyl 4-({5-[3-(trifluoromethyl)phenyl]furan-2-yl}methyl)benzoate

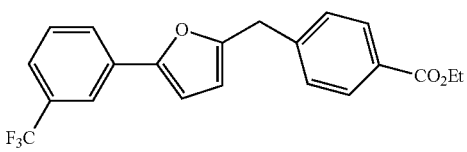

Sodium iodide (0.49 g) was suspended in acetonitrile (2 mL), and the suspension was cooled in an ice bath. Chlorotrimethylsilane (0.42 mL), and then a solution of the compound (0.26 g) obtained in Example 222b in acetonitrile (2 mL) were added. The reaction mixture was stirred at the same temperature for 30 min, water was added, and the mixture was extracted with ethyl acetate. The organic layer was washed with saturated brine, dried over magnesium sulfate, and the solvent was evaporated under reduced pressure. The residue was purified by column chromatography (carrier: silica gel, eluent: hexane-ethyl acetate) to give the title compound (0.22 g) as an oil.

$^1$H NMR (CDCl$_3$, Varian 400 MHz) δ ppm 1.39 (3H, t, J=7.2 Hz), 4.10 (2H, s), 4.37 (2H, q, J=7.2 Hz), 6.12 (1H, d, J=3.6 Hz), 6.66 (1H, d, J=3.6 Hz), 7.35 (2H, d, J=8.0 Hz), 7.46 (2H, d, J=8.0 Hz), 7.75-7.78 (1H, m), 7.84 (1H, s), 8.00-8.03 (2H, m)

Example 222

4-({5-[3-(trifluoromethyl)phenyl]furan-2-yl}methyl)benzoic acid

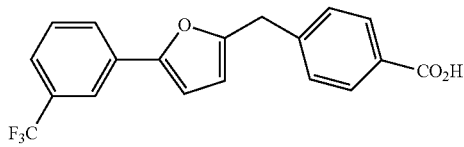 [SMILES: CCOC(=O)c1ccc(Cc2ccc(-c3cccc(C(F)(F)F)c3)o2)cc1]

By a method similar to that in Example 126 and using the compound (0.22 g) obtained in Example 222c, the title compound (0.15 g) was obtained as a solid.

$^1$H NMR (DMSO-d$_6$, Varian 400 MHz) δ ppm 4.15 (2H, s), 6.32 (1H, d, J=3.6 Hz), 7.09 (1H, d, J=3.6 Hz), 7.41 (2H, d, J=8.4 Hz), 7.57-7.63 (2H, m), 7.88-7.91 (4H, m), 12.87 (1H, br. s.)

Compound 223 ethyl 1-({2-[3-hydroxy-5-(trifluoromethyl)phenyl]-5-methyl-1,3-thiazol-4-yl}methyl)-1H-pyrazole-4-carboxylate

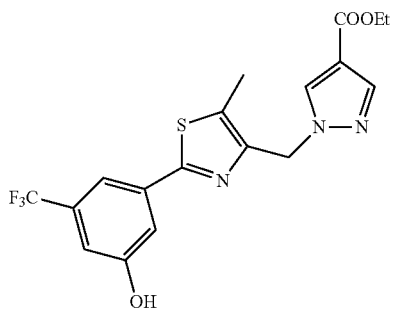 [SMILES: CCOC(=O)c1cnn(Cc2nc(-c3cc(O)cc(C(F)(F)F)c3)sc2C)c1]

Under a nitrogen atmosphere, to a solution (10 mL) of the compound (2.0 g) obtained in Example 77e, bispinacholatediborane (1.3 g) and potassium acetate (1.2 g) in N,N-dimethylformamide was added palladium acetate (II) (95 mg), and the mixture was stirred at 90° C. overnight. Ethyl acetate was added to the reaction mixture, and the resulting salt was filtered. Water was added to the organic layer, and the mixture was extracted with ethyl acetate. The obtained organic layer was washed with saturated brine, and dried over anhydrous sodium sulfate. The solvent was evaporated under reduced pressure. To a mixed solution of the obtained residue in tetrahydrofuran/acetone/water (v/v/v=1/1/1) was added Oxone™ (2.9 g), and the mixture was stirred at room temperature overnight. An aqueous sodium sulfite solution was added to the reaction mixture, and the mixture was extracted with ethyl acetate. The obtained organic layer was washed with saturated brine, and dried over anhydrous sodium sulfate. The solvent was evaporated under reduced pressure. The resulting crude title compound was purified by column chromatography (hexane-hexane/ethyl acetate=1/9) to give the title compound (0.92 g) as colorless crystals.

$^1$H NMR (300 MHz, CHLOROFORM-d) δppm 1.34 (3H, t, J=7.2 Hz), 2.47 (3H, s), 4.30 (2H, q, J=7.2 Hz), 5.36 (2H, s), 7.06 (1H, s), 7.25 (1H, s), 7.38 (1H, br. s.), 7.50 (1H, s), 7.96 (1H, s), 8.14 (1H, s)

LCMS (ESI$^+$) M+H$^+$: 412.

Experimental Example

Measurement of sGC Activation In Vitro

To evaluate sGC activation of each compound, the following in vitro tests were performed.

A test compound was diluted with a reaction buffer (50 mM HEPES, 5 mM MgCl$_2$, 2 mM DTT, 0.5 mM IBMX (isobutylmethylxanthine), 0.01% BSA) to 30 μM (3% DMSO), and dispensed to a 384 well plate (manufactured by REMP) at 10 μL/well. Purified sGC was diluted with the reaction buffer to 240 ng/mL and added to the plate at 10 μL/well. Then, 120 μM GTP prepared with the reaction buffer was added to the reaction plate at 10 μL/well to initiate an enzyme reaction. After stirring at room temperature for 20 min to allow reaction, 125 mM Na$_2$CO$_3$ was added at 15 μL/well to quench the reaction. Thereafter, 125 mM Zn Acetate (zinc acetate) was added at 15 μL/well to allow precipitation of unreacted GTP. Then, the amount of the resulting cGMP contained in the supernatant was quantified using a CatchPoint cGMP assay kit (molecular devices). The method followed the protocol attached to the assay kit. For detection, Super Signal ELISA Femto (Thermo) was used, and the amount of luminescence was measured with ARVO (Perkinelmer). The sGC activity with addition of the compound was calculated using the amount of cGMP produced without addition of the compound (in the presence of 1% DMSO) as 100%.

TABLE 2

| Ref. Ex. No./<br>Ex. No. of<br>compound tested | cGMP amount (%) in<br>experiment system |
| --- | --- |
| Ref. Ex. 1 | >1000 |
| Ref. Ex. 3 | >1000 |
| Ref. Ex. 4 | >1000 |
| Ref. Ex. 5 | >1000 |
| Ref. Ex. 10 | >1000 |
| Ref. Ex. 17 | >1000 |
| Ref. Ex. 18 | >1000 |
| Ref. Ex. 19 | >1000 |
| Ref. Ex. 20 | >1000 |
| Ref. Ex. 22 | 766 |
| Ref. Ex. 24 | >1000 |
| Ref. Ex. 25 | >1000 |
| Ex. 1 | >1000 |
| Ex. 6 | 420 |
| Ex. 13 | >1000 |

TABLE 2-continued

| Ref. Ex. No./<br>Ex. No. of<br>compound tested | cGMP amount (%) in<br>experiment system |
|---|---|
| Ex. 18 | 503 |
| Ex. 21 | >1000 |
| Ex. 23 | 996 |
| Ex. 52 | >1000 |
| Ex. 80 | >1000 |
| Ex. 83 | >1000 |
| Ex. 178 | >1000 |
| Ex. 179 | >1000 |
| Ex. 186 | >1000 |

Measurement of Hypotensive Action In Vivo

Animal used was male SHR (32- to 40-week-old, SHR/Izm, Japan SLC, Inc.). Two days before drug administration, a cannula (SP10+SP45, Natsume Seisakusho Co., Ltd.) filled with heparin physiological saline (200 U/mL, Ajinomoto Pharma Co., Ltd.) was inserted from the femoral artery under anesthesia with pentobarbital Na (50 mg/kg, i.p., Kyoritsu Seiyaku Corporation) and dwelled. The other end of the cannula was subcutaneously passed and exposed on the back of the neck where it was fixed. After a recovery period, the artery dwelling cannula was connected to a pressure transducer (DTX Plus DT-XXAD, Japan Becton Dickinson) and output on a pen recorder (linear recorder WR3320-4□L, Graphtec Corporation) via a polygraph (AP-641G, Nihon Kohden Co.), and the blood pressure waveform was recorded. The heart rate was calculated from the blood pressure waveform. After stable blood pressure was obtained, a solvent or a drug was orally administered once, and average blood pressure and average heart rate were measured over time. The blood pressure was measured under fasting, and the rats were reared under free ingestion of feed and water except the blood pressure measurement day. The drug was suspended in 0.5% methylcellulose aqueous solution. The administration dose was 2 mL/kg.

As a result, the Example 1 compound (30 mg/kg), the Example 52 compound (30 mg/kg), the Example 80 compound (10 mg/kg), the Example 83 compound (10 mg/kg) and the Example 178 compound (30 mg/kg) showed hypotension of 15.5, 29.4, 14.7, 14.5 and 15.8 mmHg, respectively, after 5 hr from the administration.

Formulation Example 1

An sGC activating agent containing compound (I) as an active ingredient, and the like, can be produced, for example, by the following formulations.

In the following formulations, components (additives) other than the active ingredient can be the products listed in the Japanese Pharmacopoeia, the Japanese Pharmacopoeia Japanese Pharmaceutical Codex or Japanese Pharmaceutical Excipients, and the like.

1. Capsule

| (1) compound obtained in Example 1 | 10 mg |
|---|---|
| (2) lactose | 90 mg |
| (3) microcrystalline cellulose | 70 mg |
| (4) magnesium stearate | 10 mg |
| 1 capsule | 180 mg |

(1), (2), (3) and ½ of (4) are blended and granulated. The rest of (4) is added thereto, and the whole is filled in a gelatin capsule.

2. Tablet

| (1) compound obtained in Example 2 | 10 mg |
|---|---|
| (2) lactose | 35 mg |
| (3) cornstarch | 150 mg |
| (4) microcrystalline cellulose | 30 mg |
| (5) magnesium stearate | 5 mg |
| 1 tablet | 230 mg |

(1), (2), (3), ⅔ of (4) and ½ of (5) are blended and granulated. The rest of (4) and (5) are added to the granules and the mixture is compression molded to give tablets.

INDUSTRIAL APPLICABILITY

Since the compound of the present invention shows an sGC activating action, it is highly useful as an sGC activating agent, or an agent for the prophylaxis and/or treatment of diseases such as hypertension, ischemic cardiac disease, cardiac failure, kidney disease, arteriosclerotic disease, atrial fibrillation, pulmonary hypertension, diabetes, diabetic complications, metabolic syndrome, peripheral arterial obstruction, erectile dysfunction and the like.

This application is based on patent application No. 2008-098622 filed in Japan, the contents of which are encompassed in full herein.

The invention claimed is:

1. A compound represented by formula (II):

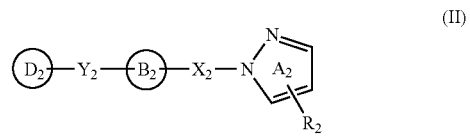

(II)

wherein:

ring $A_2$ is an optionally further substituted pyrazole ring;

ring $B_2$ is an optionally substituted 5-membered aromatic heterocycle, or an optionally substituted fused heterocycle wherein a 5-membered aromatic heterocycle is fused with a 5- or 6-membered hydrocarbon ring or heterocycle, wherein the 5-membered aromatic heterocycle (fused or mono-cyclic) has one sulfur atom and one nitrogen atom and at least 3 carbon atoms;

ring $D_2$ is an optionally substituted aromatic hydrocarbon ring;

$R_2$ is a carboxyl group, a tetrazolyl group, an oxooxadiazolyl group, or a group represented by —C(=O)NH—S(=O)$_2R_{21}$ wherein $R_{21}$ is an optionally substituted lower alkyl group, an acyl group, an optionally substituted aromatic hydrocarbon ring group, or an optionally substituted 5- or 6-membered aromatic heterocyclic group;

$X_2$ is an optionally substituted lower alkylene group; and $Y_2$ is a bond, or an optionally substituted lower alkylene group, provided that the substituent of ring $D_2$ is not a [4-(1-propylbutyl)phenoxy]methyl group when ring $B_2$ is a thiazole ring and ring $D_2$ is a benzene ring;

or a salt thereof or a prodrug thereof.

2. The compound according to claim 1, wherein the ring $A_2$ is a pyrazole ring optionally further substituted by a substituent selected from the group consisting of a $C_{1-6}$ alkyl group optionally substituted by a halogen atom, and a $C_{1-6}$ alkoxy group.

3. The compound according to claim 1, wherein the ring $A_2$ is pyrazole substituted by $R_2$ and not further substituted.

4. The compound according to claim 1, wherein the ring $B_2$ is an optionally substituted 5-membered aromatic heterocycle.

5. The compound according to claim 1, wherein the ring $B_2$ is an optionally substituted thiazole ring.

6. The compound according to claim 1, wherein the ring $D_2$ is an optionally substituted benzene ring.

7. The compound according to claim 1, wherein the ring $D_2$ is an optionally further substituted benzene ring substituted by a $C_{1-6}$ alkyl group optionally substituted by a halogen atom.

8. The compound according to claim 1, wherein the ring $D_2$ is a benzene ring substituted by substituent selected from the group consisting of a halogen atom and a $C_{1-6}$ alkyl group optionally substituted by a halogen atom.

9. The compound according to claim 1, wherein $R_2$ is a carboxyl group.

10. The compound according to claim 1, wherein $R_2$ is present at the 4-position on the pyrazole ring.

11. The compound according to claim 1, wherein $X_2$ is a $C_{1-6}$ alkylene group.

12. The compound according to claim 1, wherein $Y_2$ is a bond or an optionally substituted $C_{1-6}$ alkylene group.

13. The compound according to claim 1, wherein $Y_2$ is a bond.

14. The compound according to claim 1, wherein the ring $A_2$ is a pyrazole ring optionally further substituted by a substituent selected from the group consisting of a $C_{1-6}$ alkyl group optionally substituted by a halogen atom, and a $C_{1-6}$ alkoxy group;

$R_2$ is a carboxyl group;

ring $D_2$ is a benzene ring substituted by a halogen atom, or a $C_{1-6}$ alkyl group optionally substituted by a halogen atom.

15. 1-({-4-[3-(Trifluoromethyl)phenyl]-1,3-thiazol-2-yl}methyl)-1H-pyrazole-4-carboxylic acid or a salt thereof.

16. 1-({4-[2-Fluoro-3-(trifluoromethyl)phenyl]-1,3-thiazol-2-yl}methyl)-1H-pyrazole-4-carboxylic acid or a salt thereof.

17. 1-({2-[2-Fluoro-3-(trifluoromethyl)phenyl]-5-methyl-1,3-thiazol-4-yl}methyl)-1H-pyrazole-4-carboxylic acid or a salt thereof.

18. 1-({2-[3-Chloro-5-(trifluoromethyl)phenyl]-5-methyl-1,3-thiazol-4-yl}methyl)-1H-pyrazole-4-carboxylic acid or a salt thereof.

19. A prodrug of the compound as in any one of claims 1 to 4, 5 and 6 to 14.

20. A pharmaceutical composition comprising the compound according to claim 1 or a salt thereof or a prodrug thereof, and a pharmacologically acceptable carrier.

21. A method for activating sGC in a mammal, comprising administering an effective amount of the compound according to any one of claims 1 to 4, 5 and 6 to 18 or a salt thereof or a prodrug thereof to the mammal.

22. A method for the treatment of hypertension in a mammal, comprising administering an effective amount of the compound according to any one of claims 1 to 4, 5 and 6 to 18 or a salt thereof or a prodrug thereof to the mammal.

* * * * *